United States Patent
Bamberg et al.

(10) Patent No.: US 8,008,298 B2
(45) Date of Patent: Aug. 30, 2011

(54) PYRROLOPYRAZINE KINASE INHIBITORS

(75) Inventors: Joe Timothy Bamberg, East Palo Alto, CA (US); Daisy Joe DuBois, Palo Alto, CA (US); Todd Richard Elworthy, Los Altos, CA (US); Robert Than Hendricks, San Carlos, CA (US); Johannes Cornelius Hermann, San Francisco, CA (US); Alam Jahangir, San Jose, CA (US); Rama K. Kondru, Sunnyvale, CA (US); Remy Lemoine, San Francisco, CA (US); Yan Lou, San Jose, CA (US); Timothy D. Owens, Mountain View, CA (US); David Bernard Smith, San Mateo, CA (US); Michael Soth, Milpitas, CA (US); Hanbiao Yang, Sunnyvale, CA (US)

(73) Assignee: Roche Palo Alto, Palo Alto, CA (US)

( * ) Notice: Subject to any disclaimer, the term of this patent is extended or adjusted under 35 U.S.C. 154(b) by 0 days.

(21) Appl. No.: 12/378,977

(22) Filed: Feb. 20, 2009

(65) Prior Publication Data
US 2010/0267666 A1 Oct. 21, 2010

Related U.S. Application Data

(60) Provisional application No. 61/031,035, filed on Feb. 25, 2008, provisional application No. 61/205,729, filed on Jan. 22, 2009.

(51) Int. Cl.
*A61K 31/495* (2006.01)

(52) U.S. Cl. .......... 514/249; 544/61; 544/143; 544/333; 544/350; 544/373; 546/200; 546/276.7; 548/143; 548/235; 548/240; 548/335.1; 548/373.1; 548/460; 548/518; 548/560; 548/950; 548/361.1; 549/14; 549/59; 549/356; 549/429; 549/510

(58) Field of Classification Search .......... 514/249; 544/61, 143, 333, 350, 373; 546/200, 276.7; 548/143, 235, 240, 335.1, 361.1, 373.1, 460, 548/518, 560, 950; 549/14, 59, 356, 429, 549/510
See application file for complete search history.

(56) References Cited

U.S. PATENT DOCUMENTS

| | | |
|---|---|---|
| 2006/0148801 A1 | 7/2006 | Hsieh et al. |
| 2007/0049615 A1 | 3/2007 | Ibrahim et al. |
| 2009/0215750 A1 * | 8/2009 | Bamberg et al. ......... 514/217.05 |

FOREIGN PATENT DOCUMENTS

| | | |
|---|---|---|
| WO | 0147922 A2 | 7/2001 |
| WO | 03000688 A1 | 1/2003 |
| WO | 03082868 A1 | 10/2003 |
| WO | 2008033798 A2 | 3/2008 |
| WO | 2008063888 A2 | 5/2008 |
| WO | 2008079903 A1 | 7/2008 |

* cited by examiner

*Primary Examiner* — James O Wilson
*Assistant Examiner* — Douglas M Willis
(74) *Attorney, Agent, or Firm* — George W. Johnston; Dennis P. Tramaloni; Jennifer Kisko

(57) ABSTRACT

The present invention relates to the use of novel pyrrolopyrazine derivatives of Formula I,

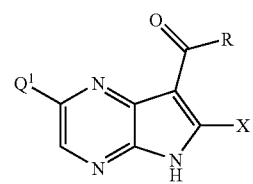

wherein the variables $Q^1$, R, and X are defined as described herein, which inhibit JAK and SYK and are useful for the treatment of auto-immune and inflammatory diseases.

42 Claims, No Drawings

PYRROLOPYRAZINE KINASE INHIBITORS

CROSS-REFERENCE TO RELATED APPLICATIONS

This application is entitled to the benefit of U.S. provisional patent application Ser. No. 61/031,035 filed on Feb. 25, 2008 and Ser. No. 61/205,729 filed on Jan. 22, 2009, the disclosures of which are incorporated herein by reference.

FIELD OF THE INVENTION

The present invention relates to the use of novel pyrrolopyrazine derivatives which are JAK and SYK inhibitors and selectively inhibit JAK3 and are useful for the treatment of auto-immune and inflammatory diseases.

BACKGROUND OF THE INVENTION

Protein kinases constitute one of the largest families of human enzymes and regulate many different signaling processes by adding phosphate groups to proteins; particularly tyrosine kinases phosphorylate proteins on the alcohol moiety of tyrosine residues. The tyrosine kinase family includes members that control cell growth, migration, and differentiation. Abnormal kinase activity has been implicated in a variety of human diseases including cancers, autoimmune and inflammatory diseases. Since protein kinases are among the key regulators of cell signaling they provide a means to modulate cellular function with small molecule inhibitors of kinase activity and thus make good drug design targets. In addition to treatment of kinase-mediated disease processes, selective and efficacious inhibitors of kinase activity are also useful for investigation of cell signaling processes and identification of other cellular targets of therapeutic interest.

The JAKs (JAnus Kinases) are a family of cytoplasmic protein tyrosine kinases including JAK1, JAK2, JAK3 and TYK2. Each of the JAKs is preferentially associated with the intracytoplasmic portion of discrete cytokine receptors (*Annu. Rev. Immunol.* 16 (1998), pp. 293-322). The JAKs are activated following ligand binding and initiate signaling by phosphorylating cytokine receptors that, per se, are devoid of intrinsic kinase activity. This phosphorylation creates docking sites on the receptors for other molecules known as STAT proteins (signal transducers and activators of transcription) and the phosphorylated JAKs bind various STAT proteins. STAT proteins, or STATs, are DNA binding proteins activated by phosphorylation of tyrosine residues, and function both as signaling molecules and transcription factors and ultimately bind to specific DNA sequences present in the promoters of cytokine-responsive genes (Leonard et al., (2000), J. Allergy Clin. Immunol. 105:877-888).

JAK/STAT signaling has been implicated in the mediation of many abnormal immune responses such as allergies, asthma, autoimmune diseases such as transplant (allograft) rejection, rheumatoid arthritis, amyotrophic lateral sclerosis and multiple sclerosis, as well as in solid and hematologic malignancies such as leukemia and lymphomas.

Thus, the JAKs and STATs are components of multiple potentially intertwined signal-transduction pathways (*Oncogene* 19 (2000), pp. 5662-5679), which indicates the difficulty of specifically targeting one element of the JAK-STAT pathway without interfering with other signal transduction pathways.

The JAK kinases, including JAK3, are abundantly expressed in primary leukemic cells from children with acute lymphoblastic leukemia, the most common form of childhood cancer, and studies have correlated STAT activation in certain cells with signals regulating apoptosis (Demoulin et al., (1996), Mol. Cell. Biol. 16:4710-6; Jurlander et al., (1997), Blood. 89:4146-52; Kaneko et al., (1997), Clin. Exp. Immun. 109:185-193; and Nakamura et al., (1996), J. Biol. Chem. 271: 19483-8). They are also known to be important to lymphocyte differentiation, function and survival. JAK3 in particular plays an essential role in the function of lymphocytes, macrophages, and mast cells. Given the importance of this JAK kinase, compounds which modulate the JAK pathway, including those selective for JAK3, can be useful for treating diseases or conditions where the function of lymphocytes, macrophages, or mast cells is involved (Kudlacz et al., (2004) Am. J. Transplant 4:51-57; Changelian (2003) Science 302:875-878). Conditions in which targeting of the JAK pathway or modulation of the JAK kinases, particularly JAK3, are contemplated to be therapeutically useful include, leukemia, lymphoma, transplant rejection (e.g., pancreas islet transplant rejection, bone marrow transplant applications (e.g., graft-versus-host disease), autoimmune diseases (e.g., diabetes), and inflammation (e.g., asthma, allergic reactions). Conditions which can benefit for inhibition of JAK3 are discussed in greater detail below.

However, in contrast to the relatively ubiquitous expression of JAK1, JAK2 and Tyk2, JAK3 has a more restricted and regulated expression. Whereas some JAKs (JAK1, JAK2, Tyk2) are used by a variety of cytokine receptors, JAK3 is used only by cytokines that contain a γc in their receptor. JAK3, therefore, plays a role in cytokine signaling for cytokines which receptor was shown to date to use the common gamma chain; IL-2, IL-4, IL-7, IL-9, IL-15 and IL-21. JAK1 interacts with, among others, the receptors for cytokines IL-2, IL-4, IL-7, IL-9 and IL-21, while JAK2 interacts with, among others, the receptors for IL-9 and TNF-alpha. Upon the binding of certain cytokines to their receptors (e.g., IL-2, IL-4, IL-7, IL-9, IL-15 and IL-21), receptor oligomerization occurs, resulting in the cytoplasmic tails of associated JAK kinases being brought into proximity and facilitating the trans-phosphorylation of tyrosine residues on the JAK kinase. This trans-phosphorylation results in the activation of the JAK kinase.

Animal studies have suggested that JAK3 not only plays a critical role in B and T lymphocyte maturation, but that JAK3 is constitutively required to maintain T cell function. Modulation of immune activity through this novel mechanism can prove useful in the treatment of T cell proliferative disorders such as transplant rejection and autoimmune diseases.

In particular, JAK3 has been implicated in a variety of biological processes. For example, the proliferation and survival of murine mast cells induced by IL-4 and IL-9 have been shown to be dependent on JAK3- and gamma chain-signaling (Suzuki et al., (2000), Blood 96:2172-2180). JAK3 also plays a crucial role in IgE receptor-mediated mast cell degranulation responses (Malaviya et al., (1999), Biochem. Biophys. Res. Commun. 257:807-813), and inhibition of JAK3 kinase has been shown to prevent type I hypersensitivity reactions, including anaphylaxis (Malaviya et al., (1999), J. Biol. Chem. 274:27028-27038). JAK3 inhibition has also been shown to result in immune suppression for allograft rejection (Kirken, (2001), Transpl. Proc. 33:3268-3270). JAK3 kinases have also been implicated in the mechanism involved in early and late stages of rheumatoid arthritis (Muller-Ladner et al., (2000), J. Immunal. 164:3894-3901); familial amyotrophic lateral sclerosis (Trieu et al., (2000), Biochem Biophys. Res. Commun. 267:22-25); leukemia (Sudbeck et al., (1999), Clin. Cancer Res. 5:1569-1582); mycosis fungoides, a form of T-cell lymphoma (Nielsen et al., (1997), Prac. Natl. Acad.

Sci. USA 94:6764-6769); and abnormal cell growth (Yu et al., (1997), J. Immunol. 159:5206-5210; Catlett-Falcone et al., (1999), Immunity 10:105-115).

JAK3 inhibitors are useful therapy as immunosuppressive agents for organ transplants, xeno transplantation, lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, Alzheimer's disease, Leukemia and other indications where immunosuppression would be desirable.

Non-hematopoietic expression of JAK3 has also been reported, although the functional significance of this has yet to be clarified (J. Immunol. 168 (2002), pp. 2475-2482). Because bone marrow transplants for SCID are curative (Blood 103 (2004), pp. 2009-2018), it seems unlikely that JAK3 has essential non-redundant functions in other tissues or organs. Hence, in contrast with other targets of immunosuppressive drugs, the restricted distribution of JAK3 is appealing. Agents that act on molecular targets with expression limited to the immune system might lead to an optimal efficacy:toxicity ratio. Targeting JAK3 would, therefore, theoretically offer immune suppression where it is needed (i.e. on cells actively participating in immune responses) without resulting in any effects outside of these cell populations. Although defective immune responses have been described in various STAT$^{-/-}$ strains (J. Investig. Med. 44 (1996), pp. 304-311; Curr. Opin. Cell Biol. 9 (1997), pp. 233-239), the ubiquitous distribution of STATs and the fact that those molecules lack enzymatic activity that could be targeted with small-molecule inhibitors has contributed to their non-selection as key targets for immunosuppression.

SYK (Spleen Tyrosine Kinase) is a non-receptor tyrosine kinase that is essential for B-cell activation through BCR signaling. SYK become activated upon binding to phosphoryated BCR and thus initiates the early signaling events following BCR activation. Mice deficient in SYK exhibit an early block in B-cell development (Cheng et al. Nature 378: 303, 1995; Turner et al. Nature 378:298, 1995). Therefore inhibition of SYK enzymatic activity in cells is proposed as a treatment for autoimmune disease through its effects on autoantibody production.

In addition to the role of SYK in BCR signaling and B-cell activation, it also plays a key role in Fc RI mediated mast cell degranulation and eosinophil activation. Thus, SYK is implicated in allergic disorders including asthma (reviewed in Wong et al. Expert Opin Investig Drugs 13:743, 2004). SYK binds to the phosphorylated gamma chain of Fc RI via its SH2 domains and is essential for downstream signaling (Taylor et al. Mol. Cell. Biol. 15:4149, 1995). SYK deficient mast cells demonstrate defective degranulation, arachidonic acid and cytokine secretion (Costello et al. Oncogene 13:2595, 1996). This also has been shown for pharmacologic agents that inhibit SYK activity in mast cells (Yamamoto et al. J Pharmacol Exp Ther 306:1174, 2003). Treatment with SYK antisense oligonucleotides inhibits antigen-induced infiltration of eosinophils and neutrophils in an animal model of asthma (Stenton et al. J Immunol 169:1028, 2002). SYK deficient eosinophils also show impaired activation in response to Fc R stimulation (Lach-Trifilieffe et al. Blood 96:2506, 2000). Therefore, small molecule inhibitors of SYK will be useful for treatment of allergy-induced inflammatory diseases including asthma.

In view of the numerous conditions that are contemplated to benefit by treatment involving modulation of the JAK and/or SYK pathways it is immediately apparent that new compounds that modulate JAK and/or SYK pathways and methods of using these compounds should provide substantial therapeutic benefits to a wide variety of patients. Provided herein are novel pyrrolopyrazine derivatives for use in the treatment of conditions in which targeting of the JAK and/or SYK pathways or inhibition of JAK or SYK kinases, particularly JAK3, and are therapeutically useful for the treatment of auto-immune and inflammatory diseases.

SUMMARY OF THE INVENTION

The novel pyrrolopyrazine derivatives provided herein selectively inhibit JAK3 and are useful for the treatment of auto-immune and inflammatory diseases. The compounds of the invention modulate the JAK and/or SYK pathways and are useful novel pyrrolopyrazine derivatives for the treatment of auto-immune and inflammatory diseases, wherein preferred compounds selectively inhibit JAK3. For example, the compounds of the invention may inhibit JAK3 and SYK, wherein preferred compounds are selective for JAK3 of the JAK kinases and are useful novel pyrrolopyrazine derivatives for the treatment of auto-immune and inflammatory diseases. Furthermore, the compounds of the invention may inhibit JAK3 and JAK2, wherein preferred compounds are selective for JAK3 of the JAK kinases, and are useful novel pyrrolopyrazine derivatives for the treatment of auto-immune and inflammatory diseases. Similarly, the compounds of the invention may inhibit JAK3 and JAK1, wherein preferred compounds are selective for JAK3 of the JAK kinases, and are useful novel pyrrolopyrazine derivatives for the treatment of auto-immune and inflammatory diseases.

The application provides a compound of Formula I

wherein:
R is $R^1$, $R^2$, $R^3$, or $R^4$;
$R^1$ is lower alkyl, lower alkoxy, phenyl, benzyl, heteroaryl, cycloalkyl, heterocycloalkyl, or cycloalkyl alkylene, optionally substituted with one or more $R^{1a}$;
  $R^{1a}$ is $R^{1b}$ or $R^{1c}$;
    each $R^{1b}$ is independently halogen, oxo, hydroxy, or —CN;
    each $R^{1c}$ is independently —C(=O)O($R^{1f}$), —C(=O)($R^{1e}$), —C(=O)CH$_2$($R^{1e}$), —S($R^{1f}$), —S(=O)$_2$($R^{1f}$), —N($R^{1f}$)S(=O)$_2$($R^{1f}$), —S(=O)($R^{1f}$), lower alkyl, lower alkoxy, amino, amido, lower haloalkyl, phenyl, heteroaryl, cycloalkyl, heterocycloalkyl, cycloalkyloxy, or heterocycloalkyloxy optionally substituted with one or more $R^{1d}$;
      each $R^{1d}$ is independently halogen, hydroxy, lower alkyl, lower alkoxy, lower hydroxyalkyl, amino, amido, cyano, or lower haloalkyl;
      each $R^{1e}$ is independently H, lower alkyl, lower alkoxy, —CN, lower haloalkyl, phenyl, heteroaryl, cycloalkyl, or heterocycloalkyl;
      each $R^{1f}$ is independently H, lower alkyl, lower haloalkyl, lower alkenyl, phenyl, heteroaryl, cycloalkyl, or heterocycloalkyl;
$R^2$ is N($R^{2a}$)$_2$;
  each $R^{2a}$ is independently H or $R^{2b}$;

each $R^{2b}$ is independently lower alkyl, lower alkoxy, phenyl, heteroaryl, cycloalkyl, heterocycloalkyl, or heterocycloalkyl alkylene, optionally substituted with one or more $R^{2c}$;

$R^{2c}$ is $R^{2d}$ or $R^{2e}$;

each $R^{2d}$ is independently halogen, oxo, or hydroxy;

each $R^{2e}$ is independently —N($R^{2g}$)$_2$, —C(=O)($R^{2g}$), —C(=O)O($R^{2g}$), —C(=O)N($R^{2g}$)$_2$, —N($R^{2g}$)C(=O)($R^{2g}$), —S(=O)$_2$($R^{2g}$), —S(=O)$_2$N($R^{2g}$)$_2$, lower alkyl, lower alkoxy, lower haloalkyl, phenyl, heteroaryl, heteroaryloxy, cycloalkyl, or heterocycloalkyl, optionally substituted with one or more $R^{2f}$;

each $R^{2f}$ is independently H, halogen, lower alkyl, lower alkoxy, lower haloalkyl;

each $R^{2g}$ is independently H, lower alkyl, lower alkoxy, lower haloalkyl, or phenyl;

$R^3$ is —C(=O)$R^{3a}$;

$R^{1a}$ is lower alkyl, lower alkoxy, phenyl, or N($R^{3b}$)$_2$;

each $R^{4b}$ is independently H or lower alkyl;

$R^4$ is —O($R^{4a}$);

$R^{4a}$ is H or $R^{4b}$;

$R^{4b}$ is lower alkyl, phenyl, benzyl, lower haloalkyl, cycloalkyl, heterocycloalkyl, heteroaryl, optionally substituted with one or more $R^{4c}$;

each $R^{4c}$ is independently halogen, hydroxy, lower alkyl, lower haloalkyl, or lower alkoxy;

$Q^1$ is phenyl or indolyl, optionally substituted with one or more $Q^{1a}$;

each $Q^{1a}$ is independently $Q^{1b}$ or $Q^{1c}$;

each $Q^{1b}$ is independently halogen, hydroxy, —CN, —S($Q^{1e}$), —S(=O)$_2$($Q^{1e}$), or —S(=O)($Q^{1e}$);

each $Q^{1c}$ is independently $Q^{1d}$ or $Q^{1e}$;

each $Q^{1d}$ is independently —O($Q^{1e}$), —S(=O)$_2$($Q^{1e}$), —C(=O)N($Q^{1e}$)$_2$, —S(=O)($Q^{1e}$), —N($Q^{1e}$)S(=O)$_2$($Q^{1e}$), —C(=O)($Q^{1e}$), —C(=O)O($Q^{1e}$), —N($Q^{1e}$)$_2$, —N($Q^{1e}$)C(=O)($Q^{1e}$), N($Q^{1e}$)C(=O)O($Q^{1e}$), —Si($Q^{1e}$)$_3$, or —N($Q^{1e}$)C(=O)N($Q^{1e}$)$_2$;

each $Q^{1e}$ is independently H or $Q^{1e'}$;

each $Q^{1e'}$ is independently lower alkyl, amino, lower alkenyl, phenyl, benzyl, lower haloalkyl, lower thioalkyl, cycloalkyl, cycloalkenyl, heterocycloalkyl, heterocycloalkyl alkylene, or heteroaryl, optionally substituted with one or more $Q^{1f}$;

each $Q^{1f}$ is independently $Q^{1g}$ or $Q^{1h}$;

each $Q^{1g}$ is independently halogen, hydroxy, oxo, —(C($Q^{1h}$)$_2$)$_m$S(O)$_2$($Q^{1h}$), —(C($Q^{1h}$)$_2$)$_m$N($Q^{1h}$)(C($Q^{1h}$)$_2$)$_m$S(O)$_2$($Q^{1h}$); —(C($Q^{1h}$)$_2$)$_m$N($Q^{1h}$)$_2$, —(C($Q^{1h}$)$_2$)$_m$C(=O)($Q^{1h}$), or —N($Q^{1h}$)C(=O)($Q^{1h}$);

each m is independently 0, 1, or 2;

each $Q^{1h}$ is independently $Q^{1i}$ or $Q^{1j}$;

each $Q^{1i}$ is independently H or hydroxy;

each $Q^{1j}$ is independently lower alkyl, lower haloalkyl, lower alkoxy, lower thioalkyl, cyano, amino, phenyl, benzyl, cycloalkyl, heterocycloalkyl, or heteroaryl, optionally substituted with one or more $Q^{1k}$;

each $Q^{1k}$ is independently halogen, hydroxy, lower alkyl, lower haloalkyl, lower hydroxyalkyl, amino, lower thioalkyl, lower alkoxy, or cyano;

X is $X^1$ or $X^2$;

$X^1$ is H, halogen, or hydroxy;

$X^2$ is lower alkyl, lower alkoxy, lower haloalkyl, phenyl, cycloalkyl, heterocycloalkyl, or heteroaryl, optionally substituted with one or more $X^{2'}$;

each $X^{2'}$ is independently hydroxy, halogen, lower alkyl, lower alkoxy, lower haloalkyl, cycloalkyl, heterocycloalkyl, or heteroaryl;

or a pharmaceutically acceptable salt thereof.

In one variation of the above embodiment, X is H.

In one variation of the above embodiment, R is $R^1$.

In one variation of the above embodiment, $R^1$ is lower alkyl.

In one variation of the above embodiment, $R^1$ is tert-butyl.

In another variation of the above embodiment, $R^1$ is tert-butyl, $Q^{1a}$ is $Q^{1c}$, $Q^{1c}$ is $Q^{1e}$, $Q^{1e}$ is $Q^{1e'}$, and $Q^{1e'}$ is pyrrolidine.

In another variation of the above embodiment, $R^1$ is —CHC(CH$_3$)$_3$.

In another variation of the above embodiment, $R^1$ is isobutyl.

In another variation of the above embodiment, $R^1$ is isopropyl.

In one embodiment of the compound of Formula I, $R^1$ is cycloalkyl.

In one embodiment of the compound of Formula I, $R^1$ is heterocycloalkyl.

In one embodiment of the compound of Formula I, $R^1$ is benzyl.

In one embodiment of the compound of Formula I, $R^1$ is phenyl.

In one embodiment of the compound of Formula I, R is $R^2$.

In one embodiment of the compound of Formula I, R is $R^2$ and $R^2$ is NH($R^{2a}$).

In one variation of the above embodiment, $R^{2a}$ is $R^{2b}$.

In one variation of the above embodiment, $R^{2b}$ is lower alkyl.

In one variation of the above embodiment, $R^{2b}$ is isopropyl.

In one embodiment of the compound of Formula I, $R^{2b}$ is heterocycloalkyl.

In one embodiment of the compound of Formula I, $R^{2b}$ is cycloalkyl.

In one embodiment of the compound of Formula I, $R^{2b}$ is heterocycloalkyl alkylene.

In one variation of the above embodiment, $R^{2b}$ is pyrrolidine.

In one variation of the above embodiment, $R^{2b}$ is pyrrolidinyl methylene.

In one variation of the above embodiment, $Q^{1a}$ is $Q^{1c}$.

In another variation of the above embodiment, $Q^{1a}$ is $Q^{1c}$, $Q^{1c}$ is $Q^{1e}$, $Q^{1e}$ is $Q^{1e'}$, and $Q^{1e'}$ is heterocycloalkyl.

In yet another variation of the above embodiment, Q is $Q^1$, $Q^{1a}$ is $Q^{1c}$, $Q^{1c}$ is $Q^{1e}$, $Q^{1e}$ is $Q^{1e'}$, $Q^{1e'}$ is pyrrolidine.

In yet another variation of the above embodiment, Q is $Q^1$, $Q^{1a}$ is $Q^{1c}$, $Q^{1c}$ is $Q^{1d}$, $Q^{1d}$ is —O($Q^{1e}$), $Q^{1e}$ is $Q^{1e'}$, and $Q^{1e'}$ is lower alkyl.

In yet another variation of the above embodiment, Q is $Q^1$, $Q^{1a}$ is $Q^{1c}$, $Q^{1c}$ is $Q^{1d}$, $Q^{1d}$ is —O($Q^{1e}$), $Q^{1e}$ is $Q^{1e'}$, $Q^{1e'}$ is methyl.

In one embodiment of the compound of Formula I, $Q^{1a}$ is $Q^{1b}$.

In one variation of the above embodiment, $Q^{1b}$ is halogen.

In another variation of the above embodiment, $Q^{1b}$ is hydroxy.

In one embodiment of the compound of Formula I, $Q^{1a}$ is $Q^{1c}$.

In one variation of the above embodiment, $Q^{1c}$ is $Q^{1d}$, $Q^{1d}$ is —O($Q^{1e}$), $Q^{1e}$ is $Q^{1e'}$, and $Q^{1e'}$ is lower alkyl, optionally substituted with one or more $Q^{1f}$.

In one variation of the above embodiment, $Q^{1e'}$ is methyl optionally substituted with one or more $Q^{1f}$.

In another variation of the above embodiment, $Q^{1f}$ is $Q^{1h}$ and $Q^{1h}$ is heterocycloalkyl.

In one variation of the above embodiment, $Q^{1h}$ is morpholine.

In one embodiment of the compound of Formula I, $Q^{1a}$ is $Q^{1c}$, $Q^{1c}$ is $Q^{1e}$, $Q^{1e}$ is $Q^{1e'}$, and $Q^{1e'}$ is heterocycloalkyl, optionally substituted with one or more $Q^{1f}$.

In one variation of the above embodiment, $Q^{1e'}$ is pyrrolidine, optionally substituted with one or more $Q^{1f}$.

In another variation of the above embodiment, $Q^{1e'}$ is piperazine, optionally substituted with one or more $Q^{1f}$.

In yet another variation of the above embodiment, $Q^{1e'}$ is piperidine, optionally substituted with one or more $Q^{1f}$.

In yet another variation of the above embodiment, $Q^{1e'}$ is morpholine, optionally substituted with one or more $Q^{1f}$.

In yet another variation of the above embodiment, $Q^{1e'}$ is pyrrolidinone, optionally substituted with one or more $Q^{1f}$.

In one embodiment of the compound of Formula I, $Q^{1a}$ is $Q^{1c}$, $Q^{1c}$ is $Q^{1d}$, $Q^{1d}$ is —C(=O)($Q^{1e}$), $Q^{1e}$ is $Q^{1e'}$, and $Q^{1e'}$ is heterocycloalkyl, optionally substituted with one or more $Q^{1f}$.

In one aspect, the application provides a compound of Formula I selected from the group consisting of:

Phenyl-[2-(3,4,5-trimethoxy-phenyl)-5H-pyrrolo[2,3-b]pyrazin-7-yl]-methanone;
3-Methyl-1-[2-(3,4,5-trimethoxy-phenyl)-5H-pyrrolo[2,3-b]pyrazin-7-yl]-butan-1-one;
1-[2-(3,4,5-Trimethoxy-phenyl)-5H-pyrrolo[2,3-b]pyrazin-7-yl]-ethanone;
1-[2-(3,4-Dimethoxy-phenyl)-5H-pyrrolo[2,3-b]pyrazin-7-yl]-3-methyl-butan-1-one;
1-[2-(5-Fluoro-2-methoxy-phenyl)-5H-pyrrolo[2,3-b]pyrazin-7-yl]-3-methyl-butan-1-one;
3-Methyl-1-[2-(3-pyrrolidin-1-yl-phenyl)-5H-pyrrolo[2,3-b]pyrazin-7-yl]-butan-1-one;
4-[7-(3-Methyl-butyryl)-5H-pyrrolo[2,3-b]pyrazin-2-yl]-benzamide;
3-[7-(3-Methyl-butyryl)-5H-pyrrolo[2,3-b]pyrazin-2-yl]-benzamide;
N-Methyl-3-[7-(3-methyl-butyryl)-5H-pyrrolo[2,3-b]pyrazin-2-yl]-benzamide;
2-(3,4,5-Trimethoxy-phenyl)-5H-pyrrolo[2,3-b]pyrazine-7-carboxylic acid isopropylamide;
1-[2-(3,4-Dimethoxy-phenyl)-5H-pyrrolo[2,3-b]pyrazin-7-yl]-4-methyl-pentan-1-one;
2,2-Dimethyl-1-[2-(3,4,5-trimethoxy-phenyl)-5H-pyrrolo[2,3-b]pyrazin-7-yl]-propan-1-one;
N,N-Dimethyl-3-[7-(3-methyl-butyryl)-5H-pyrrolo[2,3-b]pyrazin-2-yl]-benzamide;
3-Methyl-1-(2-phenyl-5H-pyrrolo[2,3-b]pyrazin-7-yl)-butan-1-one;
2-(3,4,5-Trimethoxy-phenyl)-5H-pyrrolo[2,3-b]pyrazine-7-carboxylic acid (2-methoxy-1-methyl-ethyl)-amide;
2-Methyl-1-[2-(3,4,5-trimethoxy-phenyl)-5H-pyrrolo[2,3-b]pyrazin-7-yl]-propan-1-one;
2-(3,4-Dimethoxy-phenyl)-5H-pyrrolo[2,3-b]pyrazine-7-carboxylic acid isopropylamide;
2-(3,4,5-Trimethoxy-phenyl)-5H-pyrrolo[2,3-b]pyrazine-7-carboxylic acid (tetrahydro-pyran-4-yl)-amide;
2-(3,4-Dimethoxy-phenyl)-5H-pyrrolo[2,3-b]pyrazine-7-carboxylic acid pyrrolidin-3-ylamide;
2-(3,4-Dimethoxy-phenyl)-5H-pyrrolo[2,3-b]pyrazine-7-carboxylic acid cyclobutylamide;
2-(3,4-Dimethoxy-phenyl)-5H-pyrrolo[2,3-b]pyrazine-7-carboxylic acid (2-methoxy-1-methoxymethyl-ethyl)-amide;
2-(3,4-Dimethoxy-phenyl)-5H-pyrrolo[2,3-b]pyrazine-7-carboxylic acid isopropyl-methyl-amide;
2-(3,4-Dimethoxy-phenyl)-5H-pyrrolo[2,3-b]pyrazine-7-carboxylic acid tert-butylamide;
2-(3,4-Dimethoxy-phenyl)-5H-pyrrolo[2,3-b]pyrazine-7-carboxylic acid (2-methoxy-1-methyl-ethyl)-amide;
1-[2-(3,4-Dimethoxy-phenyl)-5H-pyrrolo[2,3-b]pyrazin-7-yl]-3,3-dimethyl-butan-1-one;
2-(3,4-Dimethoxy-phenyl)-5H-pyrrolo[2,3-b]pyrazine-7-carboxylic acid (2-hydroxy-1-hydroxymethyl-ethyl)-amide;
(2-{[2-(3,4-Dimethoxy-phenyl)-5H-pyrrolo[2,3-b]pyrazine-7-carbonyl]-amino}-2-methyl-propyl)-carbamic acid tert-butyl ester;
2-(3,4-Dimethoxy-phenyl)-5H-pyrrolo[2,3-b]pyrazine-7-carboxylic acid (2-hydroxy-1-methyl-ethyl)-amide;
2-(3,4-Dimethoxy-phenyl)-5H-pyrrolo[2,3-b]pyrazine-7-carboxylic acid (2-amino-1,1-dimethyl-ethyl)-amide;
2-(3-Pyrrolidin-1-yl-phenyl)-5H-pyrrolo[2,3-b]pyrazine-7-carboxylic acid tert-butylamide;
2-(3,4-Dimethoxy-phenyl)-5H-pyrrolo[2,3-b]pyrazine-7-carboxylic acid ((1S,2R)-2-carbamoyl-cyclopentyl)-amide;
2-(3,4-Dimethoxy-phenyl)-5H-pyrrolo[2,3-b]pyrazine-7-carboxylic acid (tetrahydro-pyran-4-yl)-amide;
2-(3,4-Dimethoxy-phenyl)-5H-pyrrolo[2,3-b]pyrazine-7-carboxylic acid piperidin-4-ylamide;
6-Methyl-2-(3,4,5-trimethoxy-phenyl)-5H-pyrrolo[2,3-b]pyrazine-7-carboxylic acid tert-butylamide;
1-[2-(3,4-Dimethoxy-phenyl)-5H-pyrrolo[2,3-b]pyrazin-7-yl]-2,2-dimethyl-propan-1-one;
2-Cyclohexyl-1-[2-(3,4,5-trimethoxy-phenyl)-5H-pyrrolo[2,3-b]pyrazin-7-yl]-ethanone;
2-(3-Methanesulfonyl-phenyl)-5H-pyrrolo[2,3-b]pyrazine-7-carboxylic acid isopropylamide;
2-(2-Methoxy-phenyl)-5H-pyrrolo[2,3-b]pyrazine-7-carboxylic acid isopropylamide;
1-Phenyl-2-[2-(3,4,5-trimethoxy-phenyl)-5H-pyrrolo[2,3-b]pyrazin-7-yl]-ethane-1,2-dione;
2,2-Dimethyl-1-{2-[4-(2-morpholin-4-yl-ethoxy)-phenyl]-5H-pyrrolo[2,3-b]pyrazin-7-yl}-propan-1-one;
2,2-Dimethyl-1-{2-[3-(2-morpholin-4-yl-ethoxy)-phenyl]-5H-pyrrolo[2,3-b]pyrazin-7-yl}-propan-1-one;
4-{4-[7-(2,2-Dimethyl-propionyl)-5H-pyrrolo[2,3-b]pyrazin-2-yl]-phenyl}-piperazine-1-carboxylic acid tert-butyl ester;
Pyrrolidin-3-yl-[2-(3,4,5-trimethoxy-phenyl)-5H-pyrrolo[2,3-b]pyrazin-7-yl]-methanone; compound with trifluoroacetic acid;
4-{3-[7-(2,2-Dimethyl-propionyl)-5H-pyrrolo[2,3-b]pyrazin-2-yl]-phenyl}-piperazine-1-carboxylic acid tert-butyl ester;
2,2-Dimethyl-1-[2-(4-piperazin-1-yl-phenyl)-5H-pyrrolo[2,3-b]pyrazin-7-yl]-propan-1-one;
2,2-Dimethyl-1-[2-(3-piperazin-1-yl-phenyl)-5H-pyrrolo[2,3-b]pyrazin-7-yl]-propan-1-one;
2-(3-Methylcarbamoyl-phenyl)-5H-pyrrolo[2,3-b]pyrazine-7-carboxylic acid isopropylamide;
2-[3-(1-Hydroxy-1-methyl-ethyl)-phenyl]-5H-pyrrolo[2,3-b]pyrazine-7-carboxylic acid isopropylamide;
2-Phenyl-1-[2-(3,4,5-trimethoxy-phenyl)-5H-pyrrolo[2,3-b]pyrazin-7-yl]-ethanone;
(1-Methyl-cyclopropyl)-[2-(3,4,5-trimethoxy-phenyl)-5H-pyrrolo[2,3-b]pyrazin-7-yl]-methanone;
2-(3,4,5-Trimethoxy-phenyl)-5H-pyrrolo[2,3-b]pyrazine-7-carboxylic acid (3-hydroxy-2,2-dimethyl-propyl)-amide;

(3-Methyl-oxetan-3-yl)-[2-(3,4,5-trimethoxy-phenyl)-5H-pyrrolo[2,3-b]pyrazin-7-yl]-methanone;
(4-Methyl-tetrahydro-pyran-4-yl)-[2-(3,4,5-trimethoxy-phenyl)-5H-pyrrolo[2,3-b]pyrazin-7-yl]-methanone;
[2-(3,4,5-Trimethoxy-phenyl)-5H-pyrrolo[2,3-b]pyrazin-7-yl]-(2,2,5-trimethyl-[1,3]dioxan-5-yl)-methanone;
3-Hydroxy-2-hydroxymethyl-2-methyl-1-[2-(3,4,5-trimethoxy-phenyl)-5H-pyrrolo[2,3-b]pyrazin-7-yl]-propan-1-one;
2,2-Diethoxy-1-[2-(3,4,5-trimethoxy-phenyl)-5H-pyrrolo[2,3-b]pyrazin-7-yl]-propan-1-one;
2-(3-Methoxy-phenyl)-5H-pyrrolo[2,3-b]pyrazine-7-carboxylic acid isopropylamide;
2-(5-Chloro-2-methoxy-phenyl)-5H-pyrrolo[2,3-b]pyrazine-7-carboxylic acid isopropylamide;
3,3-Dimethyl-1-[2-(3-morpholin-4-yl-phenyl)-5H-pyrrolo[2,3-b]pyrazin-7-yl]-butan-1-one;
3,3-Dimethyl-1-[2-(3-pyrrolidin-1-yl-phenyl)-5H-pyrrolo[2,3-b]pyrazin-7-yl]-butan-1-one;
2-[3-(Pyrrolidine-1-carbonyl)-phenyl]-5H-pyrrolo[2,3-b]pyrazine-7-carboxylic acid isopropylamide;
2-(2-Chloro-phenyl)-5H-pyrrolo[2,3-b]pyrazine-7-carboxylic acid isopropylamide;
1-[2-(3,4,5-Trimethoxy-phenyl)-5H-pyrrolo[2,3-b]pyrazin-7-yl]-propane-1,2-dione;
2,2-Dimethyl-1-[2-(3-pyrrolidin-1-yl-phenyl)-5H-pyrrolo[2,3-b]pyrazin-7-yl]-propan-1-one;
3-Methyl-3-[2-(3,4,5-trimethoxy-phenyl)-5H-pyrrolo[2,3-b]pyrazine-7-carbonyl]-piperidine-1-carboxylic acid tert-butyl ester;
2-(2-Trifluoromethoxy-phenyl)-5H-pyrrolo[2,3-b]pyrazine-7-carboxylic acid isopropylamide;
(3-Methyl-piperidin-3-yl)-[2-(3,4,5-trimethoxy-phenyl)-5H-pyrrolo[2,3-b]pyrazin-7-yl]-methanone;
2-(3,4,5-Trimethoxy-phenyl)-5H-pyrrolo[2,3-b]pyrazine-7-carboxylic acid phenylamide;
3-[7-(2,2-Dimethyl-propionyl)-5H-pyrrolo[2,3-b]pyrazin-2-yl]-benzoic acid tert-butyl ester;
3-(7-Isopropylcarbamoyl-5H-pyrrolo[2,3-b]pyrazin-2-yl)-benzoic acid tert-butyl ester;
3-{3-Methyl-3-[2-(3,4,5-trimethoxy-phenyl)-5H-pyrrolo[2,3-b]pyrazine-7-carbonyl]-piperidin-1-yl}-3-oxo-propionitrile;
2-(3,4-Dimethoxy-phenyl)-5H-pyrrolo[2,3-b]pyrazine-7-carboxylic acid amide;
2-(3,4,5-Trimethoxy-phenyl)-5H-pyrrolo[2,3-b]pyrazine-7-carboxylic acid (2-hydroxy-propyl)-amide;
2-(2,5-Dimethoxy-phenyl)-5H-pyrrolo[2,3-b]pyrazine-7-carboxylic acid isopropylamide;
3,3-Dimethyl-1-[2-(3-morpholin-4-ylmethyl-phenyl)-5H-pyrrolo[2,3-b]pyrazin-7-yl]-butan-1-one;
2-(3-Methylcarbamoyl-phenyl)-5H-pyrrolo[2,3-b]pyrazine-7-carboxylic acid (2-methoxy-1-methyl-ethyl)-amide;
2-(3-Methylcarbamoyl-phenyl)-5H-pyrrolo[2,3-b]pyrazine-7-carboxylic acid ((S)-2-methoxy-1-methyl-ethyl)-amide;
(4-Methyl-tetrahydro-thiopyran-4-yl)-[2-(3,4,5-trimethoxy-phenyl)-5H-pyrrolo[2,3-b]pyrazin-7-yl]-methanone;
2-(2,4-Dimethoxy-phenyl)-5H-pyrrolo[2,3-b]pyrazine-7-carboxylic acid isopropylamide;
(4-Methyl-1,1-dioxo-hexahydro-1$\lambda^6$-thiopyran-4-yl)-[2-(3,4,5-trimethoxy-phenyl)-5H-pyrrolo[2,3-b]pyrazin-7-yl]-methanone;
2-(3,4-Dimethoxy-phenyl)-5H-pyrrolo[2,3-b]pyrazine-7-carboxylic acid (1-acetyl-pyrrolidin-3-yl)-amide;
2-(3,4,5-Trimethoxy-phenyl)-5H-pyrrolo[2,3-b]pyrazine-7-carboxylic acid (2-methoxy-propyl)-amide;
2-({[2-(3,4,5-Trimethoxy-phenyl)-5H-pyrrolo[2,3-b]pyrazine-7-carbonyl]-amino}-methyl)-pyrrolidine-1-carboxylic acid tert-butyl ester;
2-(3,4-Dimethoxy-phenyl)-5H-pyrrolo[2,3-b]pyrazine-7-carboxylic acid (1-acetyl-piperidin-4-yl)-amide;
2-(3,4-Dimethoxy-phenyl)-5H-pyrrolo[2,3-b]pyrazine-7-carboxylic acid (1-methyl-pyrrolidin-3-yl)-amide;
2-[3-(3-Methoxy-pyrrolidin-1-yl)-phenyl]-5H-pyrrolo[2,3-b]pyrazine-7-carboxylic acid tert-butylamide;
2-[3-(3-Methoxy-pyrrolidin-1-yl)-phenyl]-5H-pyrrolo[2,3-b]pyrazine-7-carboxylic acid ((S)-2-methoxy-1-methyl-ethyl)-amide;
2-(3,4,5-Trimethoxy-phenyl)-5H-pyrrolo[2,3-b]pyrazine-7-carboxylic acid (tetrahydro-pyran-3-yl)-amide;
2-Methyl-2-[2-(3,4,5-trimethoxy-phenyl)-5H-pyrrolo[2,3-b]pyrazine-7-carbonyl]-pyrrolidine-1-carboxylic acid tert-butyl ester;
(2-Methyl-pyrrolidin-2-yl)-[2-(3,4,5-trimethoxy-phenyl)-5H-pyrrolo[2,3-b]pyrazin-7-yl]-methanone;
2-Phenyl-1-[2-(3,4,5-trimethoxy-phenyl)-5H-pyrrolo[2,3-b]pyrazin-7-yl]-propan-1-one;
2-(3,4,5-Trimethoxy-phenyl)-5H-pyrrolo[2,3-b]pyrazine-7-carboxylic acid (4-hydroxy-cyclohexyl)-amide;
2-(3,4,5-Trimethoxy-phenyl)-5H-pyrrolo[2,3-b]pyrazine-7-carboxylic acid (1,1-dioxo-tetrahydro-1$\lambda^6$-thiophen-3-yl)-amide;
2-(3,4,5-Trimethoxy-phenyl)-5H-pyrrolo[2,3-b]pyrazine-7-carboxylic acid (pyrrolidin-2-ylmethyl)-amide;
2-(3,4,5-Trimethoxy-phenyl)-5H-pyrrolo[2,3-b]pyrazine-7-carboxylic acid (1-acetyl-pyrrolidin-2-ylmethyl)-amide;
3-({[2-(3,4,5-Trimethoxy-phenyl)-5H-pyrrolo[2,3-b]pyrazine-7-carbonyl]-amino}-methyl)-pyrrolidine-1-carboxylic acid tert-butyl ester;
2-(3,4,5-Trimethoxy-phenyl)-5H-pyrrolo[2,3-b]pyrazine-7-carboxylic acid (pyrrolidin-3-ylmethyl)-amide;
2-(3,4,5-Trimethoxy-phenyl)-5H-pyrrolo[2,3-b]pyrazine-7-carboxylic acid (1-acetyl-pyrrolidin-3-ylmethyl)-amide;
1-{2-[4-(4-Acetyl-piperazin-1-yl)-phenyl]-5H-pyrrolo[2,3-b]pyrazin-7-yl}-2,2-dimethyl-propan-1-one;
1-{2-[3-(4-Acetyl-piperazin-1-yl)-phenyl]-5H-pyrrolo[2,3-b]pyrazin-7-yl}-2,2-dimethyl-propan-1-one;
2-(3-Dimethylamino-phenyl)-5H-pyrrolo[2,3-b]pyrazine-7-carboxylic acid isopropylamide;
2-Methyl-2-(tetrahydro-pyran-2-yloxy)-1-[2-(3,4,5-trimethoxy-phenyl)-5H-pyrrolo[2,3-b]pyrazin-7-yl]-propan-1-one;
3,3-Dimethyl-1-[2-(3,4,5-trimethoxy-phenyl)-5H-pyrrolo[2,3-b]pyrazin-7-yl]-butan-1-one;
2-[3-(2-oxo-pyrrolidin-1-yl)-phenyl]-5H-pyrrolo[2,3-b]pyrazine-7-carboxylic acid tert-butylamide;
2-(3,4,5-Trimethoxy-phenyl)-5H-pyrrolo[2,3-b]pyrazine-7-carboxylic acid (1-ethylcarbamoyl-pyrrolidin-3-ylmethyl)-amide;
2-(3,4,5-Trimethoxy-phenyl)-5H-pyrrolo[2,3-b]pyrazine-7-carboxylic acid (piperidin-4-ylmethyl)-amide;
2-(3,4,5-Trimethoxy-phenyl)-5H-pyrrolo[2,3-b]pyrazine-7-carboxylic acid (1-acetyl-piperidin-4-ylmethyl)-amide;
2-(3,4,5-Trimethoxy-phenyl)-5H-pyrrolo[2,3-b]pyrazine-7-carboxylic acid isobutyl-amide;
2-(3,4,5-Trimethoxy-phenyl)-5H-pyrrolo[2,3-b]pyrazine-7-carboxylic acid (2-methanesulfonyl-ethyl)-amide;
2-(3,4,5-Trimethoxy-phenyl)-5H-pyrrolo[2,3-b]pyrazine-7-carboxylic acid (2-sulfamoyl-ethyl)-amide
2-(3,4,5-Trimethoxy-phenyl)-5H-pyrrolo[2,3-b]pyrazine-7-carboxylic acid (2,3-dihydroxy-propyl)-amide
2-(3,4,5-Trimethoxy-phenyl)-5H-pyrrolo[2,3-b]pyrazine-7-carboxylic acid (tetrahydro-furan-3-yl)-amide;

1-{2-Methyl-2-[2-(3,4,5-trimethoxy-phenyl)-5H-pyrrolo[2,3-b]pyrazine-7-carbonyl]-pyrrolidin-1-yl}-ethanone;
2,2-Dimethyl-1-[2-(3,4,5-trimethoxy-phenyl)-5H-pyrrolo[2,3-b]pyrazin-7-yl]-butan-1-one;
2,2-Dimethyl-1-[2-(3-pyrazol-1-yl-phenyl)-5H-pyrrolo[2,3-b]pyrazin-7-yl]-propan-1-one;
2-(3-Chloro-5-fluoro-phenyl)-5H-pyrrolo[2,3-b]pyrazine-7-carboxylic acid isopropylamide;
(1-Methyl-cyclohexyl)-[2-(3,4,5-trimethoxy-phenyl)-5H-pyrrolo[2,3-b]pyrazin-7-yl]-methanone;
3,3,3-Trifluoro-2-methyl-2-trifluoromethyl-1-[2-(3,4,5-trimethoxy-phenyl)-5H-pyrrolo[2,3-b]pyrazin-7-yl]-propan-1-one;
1-[2-(3-Fluoro-phenyl)-5H-pyrrolo[2,3-b]pyrazin-7-yl]-2,2-dimethyl-propan-1-one;
2-(3,4,5-Trimethoxy-phenyl)-5H-pyrrolo[2,3-b]pyrazine-7-carboxylic acid (2-methoxy-ethyl)-amide;
2,2-Dimethyl-1-{2-[3-(5-methyl-[1,3,4]oxadiazol-2-yl)-phenyl]-5H-pyrrolo[2,3-b]pyrazin-7-yl}-propan-1-one;
2-(3,4,5-Trimethoxy-phenyl)-5H-pyrrolo[2,3-b]pyrazine-7-carboxylic acid (2,2-dimethyl-propyl)-amide;
2-(3,4,5-Trimethoxy-phenyl)-5H-pyrrolo[2,3-b]pyrazine-7-carboxylic acid (2-methoxy-2-methyl-propyl)-amide;
2,2-Dimethyl-1-[2-(4-pyrrolidin-1-yl-phenyl)-5H-pyrrolo[2,3-b]pyrazin-7-yl]-propan-1-one;
1-[2-(3-Dimethylamino-phenyl)-5H-pyrrolo[2,3-b]pyrazin-7-yl]-2,2-dimethyl-propan-1-one;
2,2-Dimethyl-1-{2-[3-(2H-pyrazol-3-yl)-phenyl]-5H-pyrrolo[2,3-b]pyrazin-7-yl}-propan-1-one;
2-(3,4,5-Trimethoxy-phenyl)-5H-pyrrolo[2,3-b]pyrazine-7-carboxylic acid (3-methoxy-propyl)-amide;
1-[2-(4-Methoxy-phenyl)-5H-pyrrolo[2,3-b]pyrazin-7-yl]-2,2-dimethyl-propan-1-one;
3-[7-(2,2-Dimethyl-propionyl)-5H-pyrrolo[2,3-b]pyrazin-2-yl]-N-methyl-benzamide;
1-[2-(3-Methoxymethyl-phenyl)-5H-pyrrolo[2,3-b]pyrazin-7-yl]-2,2-dimethyl-propan-1-one;
(1-Methyl-cyclohexyl)-[2-(3-pyrrolidin-1-yl-phenyl)-5H-pyrrolo[2,3-b]pyrazin-7-yl]-methanone;
1-[2-(4-Methoxymethyl-phenyl)-5H-pyrrolo[2,3-b]pyrazin-7-yl]-2,2-dimethyl-propan-1-one;
1-[2-(2-Methoxy-phenyl)-5H-pyrrolo[2,3-b]pyrazin-7-yl]-2,2-dimethyl-propan-1-one;
1-[2-(3-Methoxy-phenyl)-5H-pyrrolo[2,3-b]pyrazin-7-yl]-2,2-dimethyl-propan-1-one;
2,2-Dimethyl-1-(2-phenyl-5H-pyrrolo[2,3-b]pyrazin-7-yl)-propan-1-one;
N-Cyclopentyl-3-[7-(2,2-dimethyl-propionyl)-5H-pyrrolo[2,3-b]pyrazin-2-yl]-benzamide;
2,2-Dimethyl-1-[2-(3-piperidin-1-yl-phenyl)-5H-pyrrolo[2,3-b]pyrazin-7-yl]-propan-1-one;
2,2-Dimethyl-1-[2-(3-morpholin-4-yl-phenyl)-5H-pyrrolo[2,3-b]pyrazin-7-yl]-propan-1-one;
3-[7-(2,2-Dimethyl-propionyl)-5H-pyrrolo[2,3-b]pyrazin-2-yl]-benzoic acid;
1-[2-(3-Isopropenyl-phenyl)-5H-pyrrolo[2,3-b]pyrazin-7-yl]-2,2-dimethyl-propan-1-one;
1-[2-(3-Hydroxy-phenyl)-5H-pyrrolo[2,3-b]pyrazin-7-yl]-2,2-dimethyl-propan-1-one;
(1-Methyl-cyclopentyl)-[2-(3-pyrrolidin-1-yl-phenyl)-5H-pyrrolo[2,3-b]pyrazin-7-yl]-methanone;
4-Methoxy-1-[2-(3,4,5-trimethoxy-phenyl)-5H-pyrrolo[2,3-b]pyrazin-7-yl]-pentan-1-one;
(1-Methyl-cycloheptyl)-[2-(3-pyrrolidin-1-yl-phenyl)-5H-pyrrolo[2,3-b]pyrazin-7-yl]-methanone;
1-[2-(3-Ethylamino-phenyl)-5H-pyrrolo[2,3-b]pyrazin-7-yl]-2,2-dimethyl-propan-1-one;
1-[2-(3-Diethylamino-phenyl)-5H-pyrrolo[2,3-b]pyrazin-7-yl]-2,2-dimethyl-propan-1-one;
1-[2-(3-Amino-phenyl)-5H-pyrrolo[2,3-b]pyrazin-7-yl]-2,2-dimethyl-propan-1-one;
1-[2-(3-Methoxy-5-thiomorpholin-4-yl-phenyl)-5H-pyrrolo[2,3-b]pyrazin-7-yl]-2,2-dimethyl-propan-1-one;
1-{2-[3-Methoxy-5-(1-oxo-1$\lambda^4$-thiomorpholin-4-yl)-phenyl]-5H-pyrrolo[2,3-b]pyrazin-7-yl}-2,2-dimethyl-propan-1-one;
1-{2-[3-(1,1-Dioxo-1$\lambda^6$-thiomorpholin-4-yl)-5-methoxy-phenyl]-5H-pyrrolo[2,3-b]pyrazin-7-yl}-2,2-dimethyl-propan-1-one;
1-[2-(3-Methoxymethoxy-5-pyrrolidin-1-yl-phenyl)-5H-pyrrolo[2,3-b]pyrazin-7-yl]-2,2-dimethyl-propan-1-one;
1-[2-(3-Isopropoxy-5-pyrrolidin-1-yl-phenyl)-5H-pyrrolo[2,3-b]pyrazin-7-yl]-2,2-dimethyl-propan-1-one;
1-[2-(3-Ethoxy-5-pyrrolidin-1-yl-phenyl)-5H-pyrrolo[2,3-b]pyrazin-7-yl]-2,2-dimethyl-propan-1-one;
1-[2-(3-Hydroxy-5-pyrrolidin-1-yl-phenyl)-5H-pyrrolo[2,3-b]pyrazin-7-yl]-2,2-dimethyl-propan-1-one;
[2-(3-Methoxy-5-thiomorpholin-4-yl-phenyl)-5H-pyrrolo[2,3-b]pyrazin-7-yl]-(1-methyl-cyclohexyl)-methanone;
{2-[3-(1,1-Dioxo-1$\lambda^6$-thiomorpholin-4-yl)-5-methoxy-phenyl]-5H-pyrrolo[2,3-b]pyrazin-7-yl}-(1-methyl-cyclohexyl)-methanone;
{2-[3-Methoxy-5-(1-oxo-1$\lambda^4$-thiomorpholin-4-yl)-phenyl]-5H-pyrrolo[2,3-b]pyrazin-7-yl}-(1-methyl-cyclohexyl)-methanone;
1-{2-[3-(2,3-Dihydroxy-propoxy)-5-(1,1-dioxo-1$\lambda^6$-thiomorpholin-4-yl)-phenyl]-5H-pyrrolo[2,3-b]pyrazin-7-yl}-2,2-dimethyl-propan-1-one;
1-{2-[3-(3-Methanesulfonyl-propoxy)-5-pyrrolidin-1-yl-phenyl]-5H-pyrrolo[2,3-b]pyrazin-7-yl}-2,2-dimethyl-propan-1-one;
1-{2-[3-(2-Dimethylamino-ethoxy)-5-(1,1-dioxo-1$\lambda^6$-thiomorpholin-4-yl)-phenyl]-5H-pyrrolo[2,3-b]pyrazin-7-yl}-2,2-dimethyl-propan-1-one;
1-{2-[3-(1,1-Dioxo-1$\lambda^6$-thiomorpholin-4-yl)-5-(2-hydroxy-1-methyl-ethoxy)-phenyl]-5H-pyrrolo[2,3-b]pyrazin-7-yl}-2,2-dimethyl-propan-1-one;
1-{2-[3-(2-Methanesulfonyl-ethoxy)-5-pyrrolidin-1-yl-phenyl]-5H-pyrrolo[2,3-b]pyrazin-7-yl}-2,2-dimethyl-propan-1-one;
1-{2-[3-(1,1-Dioxo-1$\lambda^6$-thiomorpholin-4-yl)-5-(1-methyl-pyrrolidin-3-yloxy)-phenyl]-5H-pyrrolo[2,3-b]pyrazin-7-yl}-2,2-dimethyl-propan-1-one;
1-{2-[3-(1,1-Dioxo-1$\lambda^6$-thiomorpholin-4-yl)-5-(1-methyl-piperidin-4-yloxy)-phenyl]-5H-pyrrolo[2,3-b]pyrazin-7-yl}-2,2-dimethyl-propan-1-one;
1-{2-[3-(1,1-Dioxo-1$\lambda^6$-thiomorpholin-4-yl)-5-(2-hydroxy-1-hydroxymethyl-ethoxy)-phenyl]-5H-pyrrolo[2,3-b]pyrazin-7-yl}-2,2-dimethyl-propan-1-one;
1-{2-[3-(2-Dimethylamino-ethoxy)-5-(3,3-dimethyl-pyrrolidin-1-yl)-phenyl]-5H-pyrrolo[2,3-b]pyrazin-7-yl}-2,2-dimethyl-propan-1-one;
1-{2-[3-(2,3-Dihydroxy-propoxy)-5-(3,3-dimethyl-pyrrolidin-1-yl)-phenyl]-5H-pyrrolo[2,3-b]pyrazin-7-yl}-2,2-dimethyl-propan-1-one;
2,2-Dimethyl-1-{2-[3-(2$\lambda^4$-thia-7-aza-spiro[4.4]non-7-yl)-phenyl]-5H-pyrrolo[2,3-b]pyrazin-7-yl}-propan-1-one;
1-{2-[3-(2,2-Dioxo-2$\lambda^6$-thia-7-aza-spiro[4.4]non-7-yl)-phenyl]-5H-pyrrolo[2,3-b]pyrazin-7-yl}-2,2-dimethyl-propan-1-one;
2,2-Dimethyl-1-{2-[3-(2-oxo-2$\lambda^4$-thia-7-aza-spiro[4.4]non-7-yl)-phenyl]-5H-pyrrolo[2,3-b]pyrazin-7-yl}-propan-1-one;

2,2-Dimethyl-1-{2-[3-(3-trifluoromethyl-5,6-dihydro-8H-[1,2,4]triazolo[4,3-a]pyrazin-7-ylmethyl)-phenyl]-5H-pyrrolo[2,3-b]pyrazin-7-yl}-propan-1-one;
1-{2-[3-(5,6-Dihydro-8H-[1,2,4]triazolo[4,3-a]pyrazin-7-ylmethyl)-phenyl]-5H-pyrrolo[2,3-b]pyrazin-7-yl}-2,2-dimethyl-propan-1-one;
2,2-Dimethyl-1-{2-[4-(3-trifluoromethyl-5,6-dihydro-8H-[1,2,4]triazolo[4,3-a]pyrazin-7-ylmethyl)-phenyl]-5H-pyrrolo[2,3-b]pyrazin-7-yl}-propan-1-one;
4-{3-[7-(2,2-Dimethyl-propionyl)-5H-pyrrolo[2,3-b]pyrazin-2-yl]-phenyl}-1,5-dimethyl-piperazin-2-one;
[2-(3-Cyclopentylamino-phenyl)-5H-pyrrolo[2,3-b]pyrazin-7-yl]-(1-methyl-cyclohexyl)-methanone;
{2-[3-(Cyclopentyl-methyl-amino)-phenyl]-5H-pyrrolo[2,3-b]pyrazin-7-yl}-(1-methyl-cyclohexyl)-methanone;
1-[2-(3-Cyclopentylamino-phenyl)-5H-pyrrolo[2,3-b]pyrazin-7-yl]-2,2-dimethyl-propan-1-one;
1-{2-[3-(2-Hydroxy-cyclopentylamino)-phenyl]-5H-pyrrolo[2,3-b]pyrazin-7-yl}-2,2-dimethyl-propan-1-one;
3-Methyl-4-{3-[7-(1-methyl-cyclohexanecarbonyl)-5H-pyrrolo[2,3-b]pyrazin-2-yl]-phenyl}-piperazin-2-one;
1-(2-{3-[4-(2-Hydroxy-acetyl)-piperazin-1-yl]-phenyl}-5H-pyrrolo[2,3-b]pyrazin-7-yl)-2,2-dimethyl-propan-1-one;
2,2-Dimethyl-1-{2-[3-(1-methyl-pyrrolidin-3-ylamino)-phenyl]-5H-pyrrolo[2,3-b]pyrazin-7-yl}-propan-1-one;
2,2-Dimethyl-1-{2-[3-(tetrahydro-furan-3-ylamino)-phenyl]-5H-pyrrolo[2,3-b]pyrazin-7-yl}-propan-1-one;
1-(2-{4-[4-(2-Hydroxy-acetyl)-piperazin-1-yl]-phenyl}-5H-pyrrolo[2,3-b]pyrazin-7-yl)-2,2-dimethyl-propan-1-one;
1-(2-{4-[4-(2-Hydroxy-ethyl)-piperazin-1-yl]-phenyl}-5H-pyrrolo[2,3-b]pyrazin-7-yl)-2,2-dimethyl-propan-1-one;
1-[2-(3-Isopropylamino-phenyl)-5H-pyrrolo[2,3-b]pyrazin-7-yl]-2,2-dimethyl-propan-1-one;
1-{2-[3-(4-Methanesulfonyl-piperazin-1-yl)-phenyl]-5H-pyrrolo[2,3-b]pyrazin-7-yl}-2,2-dimethyl-propan-1-one;
1-{2-[4-(4-Methanesulfonyl-piperazin-1-yl)-phenyl]-5H-pyrrolo[2,3-b]pyrazin-7-yl}-2,2-dimethyl-propan-1-one;
1-(2-{3-[4-(2-Hydroxy-ethyl)-piperazin-1-yl]-phenyl}-5H-pyrrolo[2,3-b]pyrazin-7-yl)-2,2-dimethyl-propan-1-one;
1-{2-[3-((1R,2S)-2-Hydroxy-cyclopentylamino)-phenyl]-5H-pyrrolo[2,3-b]pyrazin-7-yl}-2,2-dimethyl-propan-1-one;
1-{2-[3-(1-Methanesulfonyl-piperidin-4-ylamino)-phenyl]-5H-pyrrolo[2,3-b]pyrazin-7-yl}-2,2-dimethyl-propan-1-one;
3-(4-{3-[7-(2,2-Dimethyl-propionyl)-5H-pyrrolo[2,3-b]pyrazin-2-yl]-phenyl}-piperazin-1-yl)-3-oxo-propionitrile;
2,2-Dimethyl-3-oxo-3-[2-(3,4,5-trimethoxy-phenyl)-5H-pyrrolo[2,3-b]pyrazin-7-yl]-propionitrile;
2,2-Dimethyl-3-oxo-3-[2-(3-pyrrolidin-1-yl-phenyl)-5H-pyrrolo[2,3-b]pyrazin-7-yl]-propionitrile;
2,2-Dimethyl-3-phenyl-1-[2-(3-pyrrolidin-1-yl-phenyl)-5H-pyrrolo[2,3-b]pyrazin-7-yl]-propan-1-one;
1-[2-(3-Pyrrolidin-1-yl-phenyl)-5H-pyrrolo[2,3-b]pyrazine-7-carbonyl]-cyclohexanecarbonitrile;
2,2-Dimethyl-3-oxo-3-[2-(3-piperazin-1-yl-phenyl)-5H-pyrrolo[2,3-b]pyrazin-7-yl]-propionitrile;
1-{2-[3-(5,6-Dihydro-8H-[1,2,4]triazolo[4,3-a]pyrazin-7-yl)-phenyl]-5H-pyrrolo[2,3-b]pyrazin-7-yl}-2,2-dimethyl-propan-1-one;
2,2-Dimethyl-1-{2-[3-(3-trifluoromethyl-5,6-dihydro-8H-[1,2,4]triazolo[4,3-a]pyrazin-7-yl)-phenyl]-5H-pyrrolo[2,3-b]pyrazin-7-yl}-propan-1-one;
N-Allyl-N-{2,2-dimethyl-3-oxo-3-[2-(3-pyrrolidin-1-yl-phenyl)-5H-pyrrolo[2,3-b]pyrazin-7-yl]-propyl}-benzenesulfonamide;
2,2-Dimethyl-3-phenyl-1-[2-(3,4,5-trimethoxy-phenyl)-5H-pyrrolo[2,3-b]pyrazin-7-yl]-propan-1-one;
1-[6-Bromo-2-(3-pyrrolidin-1-yl-phenyl)-5H-pyrrolo[2,3-b]pyrazin-7-yl]-2,2-dimethyl-propan-1-one;
1-[2,6-Bis-(3-pyrrolidin-1-yl-phenyl)-5H-pyrrolo[2,3-b]pyrazin-7-yl]-2,2-dimethyl-propan-1-one;
1-[6-Chloro-2-(3-pyrrolidin-1-yl-phenyl)-5H-pyrrolo[2,3-b]pyrazin-7-yl]-2,2-dimethyl-propan-1-one;
2,2-Dimethyl-1-[2-(3,4,5-trimethoxy-phenyl)-5H-pyrrolo[2,3-b]pyrazin-7-yl]-pent-4-yn-1-one;
2,2-Dimethyl-1-[2-(3-piperazin-1-yl-phenyl)-5H-pyrrolo[2,3-b]pyrazin-7-yl]-propan-1-one;
2-{2-Benzenesulfonylamino-4-[7-(2,2-dimethyl-propionyl)-5H-pyrrolo[2,3-b]pyrazin-2-yl]-phenoxy}-2-methyl-propionic acid ethyl ester;
2-(3,4,5-Trimethoxy-phenyl)-5H-pyrrolo[2,3-b]pyrazine-7-carboxylic acid isobutyl-amide;
2-(3,4,5-Trimethoxy-phenyl)-5H-pyrrolo[2,3-b]pyrazine-7-carboxylic acid (2-methanesulfonyl-ethyl)-amide;
2-(3,4,5-Trimethoxy-phenyl)-5H-pyrrolo[2,3-b]pyrazine-7-carboxylic acid (2-sulfamoyl-ethyl)-amide;
2-(3,4,5-Trimethoxy-phenyl)-5H-pyrrolo[2,3-b]pyrazine-7-carboxylic acid (2,3-dihydroxy-propyl)-amide;
2-(3,4,5-Trimethoxy-phenyl)-5H-pyrrolo[2,3-b]pyrazine-7-carboxylic acid (tetrahydro-furan-3-yl)-amide;
2-(3,4,5-Trimethoxy-phenyl)-5H-pyrrolo[2,3-b]pyrazine-7-carboxylic acid (2-methoxy-ethyl)-amide;
2-(3,4,5-Trimethoxy-phenyl)-5H-pyrrolo[2,3-b]pyrazine-7-carboxylic acid (2,2-dimethyl-propyl)-amide;
2-(3,4,5-Trimethoxy-phenyl)-5H-pyrrolo[2,3-b]pyrazine-7-carboxylic acid (2-methoxy-2-methyl-propyl)-amide;
2-(3,4,5-Trimethoxy-phenyl)-5H-pyrrolo[2,3-b]pyrazine-7-carboxylic acid (3-methoxy-propyl)-amide;
1-[2-(4-Methoxy-phenyl)-5H-pyrrolo[2,3-b]pyrazin-7-yl]-2,2-dimethyl-propan-1-one;
1-[2-(2-Methoxy-phenyl)-5H-pyrrolo[2,3-b]pyrazin-7-yl]-2,2-dimethyl-propan-1-one;
1-[2-(3-Methoxy-phenyl)-5H-pyrrolo[2,3-b]pyrazin-7-yl]-2,2-dimethyl-propan-1-one;
1-[2-(4-Methoxy-3-pyrrolidin-1-yl-phenyl)-5H-pyrrolo[2,3-b]pyrazin-7-yl]-2,2-dimethyl-propan-1-one;
1-[2-(3-Methoxy-5-pyrrolidin-1-yl-phenyl)-5H-pyrrolo[2,3-b]pyrazin-7-yl]-2,2-dimethyl-propan-1-one;
2,2-Dimethyl-1-[2-(4-methylsulfanyl-3-pyrrolidin-1-yl-phenyl)-5H-pyrrolo[2,3-b]pyrazin-7-yl]-propan-1-one;
1-[2-(4-Methanesulfinyl-3-pyrrolidin-1-yl-phenyl)-5H-pyrrolo[2,3-b]pyrazin-7-yl]-2,2-dimethyl-propan-1-one;
1-{2-[3-(3-Methanesulfonyl-pyrrolidin-1-yl)-phenyl]-5H-pyrrolo[2,3-b]pyrazin-7-yl}-2,2-dimethyl-propan-1-one;
1-{2-[3-(3,3-Dimethyl-pyrrolidin-1-yl)-phenyl]-5H-pyrrolo[2,3-b]pyrazin-7-yl}-2,2-dimethyl-propan-1-one;
1-{2-[3-(3-Methoxy-azetidin-1-yl)-phenyl]-5H-pyrrolo[2,3-b]pyrazin-7-yl}-2,2-dimethyl-propan-1-one;
(4-Methyl-piperidin-4-yl)-[2-(3,4,5-trimethoxy-phenyl)-5H-pyrrolo[2,3-b]pyrazin-7-yl]-methanone;
2-(3-Chloro-5-fluoro-phenyl)-5H-pyrrolo[2,3-b]pyrazine-7-carboxylic acid isopropylamide;
2-[3-(4-Methoxy-benzyloxy)-phenyl]-5H-pyrrolo[2,3-b]pyrazine-7-carboxylic acid isopropylamide;
2-[3-(2-Methoxymethyl-pyrrolidin-1-yl)-phenyl]-5H-pyrrolo[2,3-b]pyrazine-7-carboxylic acid isopropylamide;
1-{2-[3-(3-Methoxy-pyrrolidin-1-yl)-phenyl]-5H-pyrrolo[2,3-b]pyrazin-7-yl}-2,2-dimethyl-propan-1-one;
1-{2-[3-(4-Methoxy-benzyloxy)-phenyl]-5H-pyrrolo[2,3-b]pyrazin-7-yl}-2,2-dimethyl-propan-1-one;
1-[2-(3-Iodo-phenyl)-5H-pyrrolo[2,3-b]pyrazin-7-yl]-2,2-dimethyl-propan-1-one;

1-{2-[3-(3-Ethylamino-pyrrolidin-1-yl)-phenyl]-5H-pyrrolo [2,3-b]pyrazin-7-yl}-2,2-dimethyl-propan-1-one;
((3aS,6aS)-1-Methyl-octahydro-pentalen-1-yl)-[2-(3-pyrrolidin-1-yl-phenyl)-5H-pyrrolo[2,3-b]pyrazin-7-yl]-methanone;
1-{3-[7-(2,2-Dimethyl-propionyl)-5H-pyrrolo[2,3-b] pyrazin-2-yl]-phenyl}-3-methyl-pyrrolidine-3-carboxylic acid methyl ester;
(1-{3-[7-(2,2-Dimethyl-propionyl)-5H-pyrrolo[2,3-b] pyrazin-2-yl]-phenyl}-3-methyl-pyrrolidin-3-yl)-carbamic acid benzyl ester;
1-{3-[7-(2,2-Dimethyl-propionyl)-5H-pyrrolo[2,3-b] pyrazin-2-yl]-phenyl}-3-methyl-pyrrolidine-3-carboxylic acid methylamide;
[2-(3-Iodo-phenyl)-5H-pyrrolo[2,3-b]pyrazin-7-yl]-(1-methyl-cyclohexyl)-methanone;
((1S,2S)-1,2-Dimethyl-cyclopentyl)-[2-(3,4,5-trimethoxy-phenyl)-5H-pyrrolo[2,3-b]pyrazin-7-yl]-methanone;
1-{2-[3-(3-Amino-3-methyl-pyrrolidin-1-yl)-phenyl]-5H-pyrrolo[2,3-b]pyrazin-7-yl}-2,2-dimethyl-propan-1-one;
(1-{3-[7-(2,2-Dimethyl-propionyl)-5H-pyrrolo[2,3-b] pyrazin-2-yl]-phenyl}-3-methyl-pyrrolidin-3-yl)-carbamic acid ethyl ester;
(1-{3-[7-(2,2-Dimethyl-propionyl)-5H-pyrrolo[2,3-b] pyrazin-2-yl]-phenyl}-4,4-dimethyl-pyrrolidin-3-yl)-carbamic acid ethyl ester;
3-Methyl-3-[2-(3,4,5-trimethoxy-phenyl)-5H-pyrrolo[2,3-b]pyrazine-7-carbonyl]-cyclopentanone;
1-{2-Methyl-2-[2-(3,4,5-trimethoxy-phenyl)-5H-pyrrolo[2,3-b]pyrazine-7-carbonyl]-pyrrolidin-1-yl}-ethanone;
(1-Methyl-cyclohexyl)-[2-(3,4,5-trimethoxy-phenyl)-5H-pyrrolo[2,3-b]pyrazin-7-yl]-methanone;
(1-Methyl-cyclohexyl)-[2-(3-pyrrolidin-1-yl-phenyl)-5H-pyrrolo[2,3-b]pyrazin-7-yl]-methanone;
3-[7-(2,2-Dimethyl-propionyl)-5H-pyrrolo[2,3-b]pyrazin-2-yl]-benzoic acid;
(1-Methyl-cyclopentyl)-[2-(3-pyrrolidin-1-yl-phenyl)-5H-pyrrolo[2,3-b]pyrazin-7-yl]-methanone;
4-Methoxy-1-[2-(3,4,5-trimethoxy-phenyl)-5H-pyrrolo[2,3-b]pyrazin-7-yl]-pentan-1-one;
(1-Methyl-cycloheptyl)-[2-(3-pyrrolidin-1-yl-phenyl)-5H-pyrrolo[2,3-b]pyrazin-7-yl]-methanone;
2-Methoxy-2-methyl-1-[2-(3,4,5-trimethoxy-phenyl)-5H-pyrrolo[2,3-b]pyrazin-7-yl]-propan-1-one;
2-Methoxy-1-[2-(3,4,5-trimethoxy-phenyl)-5H-pyrrolo[2,3-b]pyrazin-7-yl]-ethanone;
1-[2-(3-Benzyloxy-phenyl)-5H-pyrrolo[2,3-b]pyrazin-7-yl]-2,2-dimethyl-propan-1-one;
1-[2-(3-Ethoxy-phenyl)-5H-pyrrolo[2,3-b]pyrazin-7-yl]-2,2-dimethyl-propan-1-one;
1-[2-(3-Isobutoxy-phenyl)-5H-pyrrolo[2,3-b]pyrazin-7-yl]-2,2-dimethyl-propan-1-one;
1-[2-(3-Isopropoxy-phenyl)-5H-pyrrolo[2,3-b]pyrazin-7-yl]-2,2-dimethyl-propan-1-one;
2,2-Dimethyl-1-[2-(3-propoxy-phenyl)-5H-pyrrolo[2,3-b] pyrazin-7-yl]-propan-1-one;
Adamantan-1-yl-[2-(3,4,5-trimethoxy-phenyl)-5H-pyrrolo [2,3-b]pyrazin-7-yl]-methanone;
3-Methoxy-2,2-dimethyl-1-[2-(3,4,5-trimethoxy-phenyl)-5H-pyrrolo[2,3-b]pyrazin-7-yl]-propan-1-one;
1-[2-(3-Ethyl-phenyl)-5H-pyrrolo[2,3-b]pyrazin-7-yl]-2,2-dimethyl-propan-1-one;
1-[2-(3,5-Dimethoxy-phenyl)-5H-pyrrolo[2,3-b]pyrazin-7-yl]-2,2-dimethyl-propan-1-one;
1-{2-[3-(3-Hydroxy-propyl)-phenyl]-5H-pyrrolo[2,3-b] pyrazin-7-yl}-2,2-dimethyl-propan-1-one;
1-[2-(3-Aminomethyl-phenyl)-5H-pyrrolo[2,3-b]pyrazin-7-yl]-2,2-dimethyl-propan-1-one;
1-{2-[3-(2-Hydroxy-ethyl)-phenyl]-5H-pyrrolo[2,3-b] pyrazin-7-yl}-2,2-dimethyl-propan-1-one;
3-Hydroxy-2,2-dimethyl-1-[2-(3,4,5-trimethoxy-phenyl)-5H-pyrrolo[2,3-b]pyrazin-7-yl]-propan-1-one;
2,2-Dimethyl-1-[2-(3-piperidin-1-ylmethyl-phenyl)-5H-pyrrolo[2,3-b]pyrazin-7-yl]-propan-1-one;
4-[7-(2,2-Dimethyl-propionyl)-5H-pyrrolo[2,3-b]pyrazin-2-yl]-benzoic acid;
(1-Methyl-cyclopentyl)-[2-(3,4,5-trimethoxy-phenyl)-5H-pyrrolo[2,3-b]pyrazin-7-yl]-methanone;
(1-Methyl-cyclohexyl)-[2-(3-morpholin-4-yl-phenyl)-5H-pyrrolo[2,3-b]pyrazin-7-yl]-methanone;
4-{3-[7-(1-Methyl-cyclohexanecarbonyl)-5H-pyrrolo[2,3-b]pyrazin-2-yl]-phenyl}-piperazine-1-carboxylic acid tert-butyl ester;
(1-Methyl-cyclohexyl)-[2-(3-piperazin-1-yl-phenyl)-5H-pyrrolo[2,3-b]pyrazin-7-yl]-methanone;
(1-Methyl-cyclopentyl)-[2-(3-morpholin-4-yl-phenyl)-5H-pyrrolo[2,3-b]pyrazin-7-yl]-methanone;
1-[2-(2-Fluoro-phenyl)-5H-pyrrolo[2,3-b]pyrazin-7-yl]-2,2-dimethyl-propan-1-one;
1-(4-{3-[7-(1-Methyl-cyclohexanecarbonyl)-5H-pyrrolo[2,3-b]pyrazin-2-yl]-phenyl}-piperazin-1-yl)-ethanone;
(1-Methyl-cyclohexyl)-{2-[3-(5-methyl-[1,3,4]oxadiazol-2-yl)-phenyl]-5H-pyrrolo[2,3-b]pyrazin-7-yl}-methanone;
{2-[3-(3-Hydroxy-propyl)-phenyl]-5H-pyrrolo[2,3-b] pyrazin-7-yl}-(1-methyl-cyclohexyl)-methanone;
4-{4-[7-(1-Methyl-cyclohexanecarbonyl)-5H-pyrrolo[2,3-b]pyrazin-2-yl]-phenyl}-piperazine-1-carboxylic acid tert-butyl ester;
[2-(3-Methoxy-phenyl)-5H-pyrrolo[2,3-b]pyrazin-7-yl]-(1-methyl-cyclohexyl)-methanone;
(1-Methyl-cyclohexyl)-[2-(4-piperazin-1-yl-phenyl)-5H-pyrrolo[2,3-b]pyrazin-7-yl]-methanone;
1-(4-{4-[7-(1-Methyl-cyclohexanecarbonyl)-5H-pyrrolo[2,3-b]pyrazin-2-yl]-phenyl}-piperazin-1-yl)-ethanone;
1-[2-(2-Hydroxy-phenyl)-5H-pyrrolo[2,3-b]pyrazin-7-yl]-2,2-dimethyl-propan-1-one;
(4-Hydroxy-1-methyl-cyclohexyl)-[2-(3,4,5-trimethoxy-phenyl)-5H-pyrrolo[2,3-b]pyrazin-7-yl]-methanone;
[2-(4-Dimethylamino-phenyl)-5H-pyrrolo[2,3-b]pyrazin-7-yl]-(1-methyl-cyclohexyl)-methanone;
3-(4-{3-[7-(1-Methyl-cyclohexanecarbonyl)-5H-pyrrolo[2,3-b]pyrazin-2-yl]-phenyl}-piperazin-1-yl)-3-oxo-propionitrile;
4-(4-{3-[7-(1-Methyl-cyclohexanecarbonyl)-5H-pyrrolo[2,3-b]pyrazin-2-yl]-phenyl}-piperazine-1-carbonyl)-piperidine-1-carboxylic acid tert-butyl ester;
4-{3-[7-(1-Methyl-cyclohexanecarbonyl)-5H-pyrrolo[2,3-b]pyrazin-2-yl]-phenyl}-piperazine-1-sulfonyl carbamic acid tert-butyl ester
{2-[3-(4-Methanesulfonyl-piperazin-1-yl)-phenyl]-5H-pyrrolo[2,3-b]pyrazin-7-yl}-(1-methyl-cyclohexyl)-methanone;
4-{3-[7-(1-Methyl-cyclohexanecarbonyl)-5H-pyrrolo[2,3-b]pyrazin-2-yl]-phenyl}-piperazine-1-sulfonic acid amide;
(1-Methyl-cyclohexyl)-(2-{3-[4-(piperidine-4-carbonyl)-piperazin-1-yl]-phenyl}-5H-pyrrolo[2,3-b]pyrazin-7-yl)-methanone;
(1-Methyl-cyclohexyl)-[2-(4-piperidin-1-yl-phenyl)-5H-pyrrolo[2,3-b]pyrazin-7-yl]-methanone;
[2-(4-Diethylamino-phenyl)-5H-pyrrolo[2,3-b]pyrazin-7-yl]-(1-methyl-cyclohexyl)-methanone;

(1,3-Dimethyl-cyclohexyl)-[2-(3,4,5-trimethoxy-phenyl)-5H-pyrrolo[2,3-b]pyrazin-7-yl]-methanone;
(1-Methyl-cyclohexyl)-[2-(4-morpholin-4-yl-phenyl)-5H-pyrrolo[2,3-b]pyrazin-7-yl]-methanone;
(1-Methyl-cyclohexyl)-{2-[4-(4-methyl-piperazin-1-yl)-phenyl]-5H-pyrrolo[2,3-b]pyrazin-7-yl}-methanone;
[2-(4-Methylamino-phenyl)-5H-pyrrolo[2,3-b]pyrazin-7-yl]-(1-methyl-cyclohexyl)-methanone;
(4-Hydroxy-1-methyl-cyclohexyl)-[2-(3,4,5-trimethoxy-phenyl)-5H-pyrrolo[2,3-b]pyrazin-7-yl]-methanone;
4-[7-(2,2-Dimethyl-propionyl)-5H-pyrrolo[2,3-b]pyrazin-2-yl]-N-methyl-benzenesulfonamide;
4-[7-(2,2-Dimethyl-propionyl)-5H-pyrrolo[2,3-b]pyrazin-2-yl]-benzenesulfonamide;
3-[7-(2,2-Dimethyl-propionyl)-5H-pyrrolo[2,3-b]pyrazin-2-yl]-benzenesulfonamide;
3-[7-(2,2-Dimethyl-propionyl)-5H-pyrrolo[2,3-b]pyrazin-2-yl]-N-methyl-benzenesulfonamide;
1-{2-[3-(2,8-Diaza-spiro[4.5]dec-2-yl)-phenyl]-5H-pyrrolo[2,3-b]pyrazin-7-yl}-2,2-dimethyl-propan-1-one;
1-{2-[3-(2,7-Diaza-spiro[4.4]non-2-yl)-phenyl]-5H-pyrrolo[2,3-b]pyrazin-7-yl}-2,2-dimethyl-propan-1-one;
1-{2-[3-(3-Aminomethyl-pyrrolidin-1-yl)-phenyl]-5H-pyrrolo[2,3-b]pyrazin-7-yl}-2,2-dimethyl-propan-1-one;
1-{2-[3-(3,3-Dimethyl-piperazin-1-yl)-phenyl]-5H-pyrrolo[2,3-b]pyrazin-7-yl}-2,2-dimethyl-propan-1-one;
1-{2-[3-(2,7-Diaza-spiro[4.5]dec-2-yl)-phenyl]-5H-pyrrolo[2,3-b]pyrazin-7-yl}-2,2-dimethyl-propan-1-one;
1-{2-[3-(3-Dimethylamino-pyrrolidin-1-yl)-phenyl]-5H-pyrrolo[2,3-b]pyrazin-7-yl}-2,2-dimethyl-propan-1-one;
1-{2-[3-(2-Hydroxy-2-methyl-propylamino)-phenyl]-5H-pyrrolo[2,3-b]pyrazin-7-yl}-2,2-dimethyl-propan-1-one;
1-{2-[3-(4-Amino-piperidin-1-yl)-phenyl]-5H-pyrrolo[2,3-b]pyrazin-7-yl}-2,2-dimethyl-propan-1-one;
2,2-Dimethyl-1-{2-[3-(3-methyl-piperazin-1-yl)-phenyl]-5H-pyrrolo[2,3-b]pyrazin-7-yl}-propan-1-one;
1-{2-[3-(4-Acetyl-3,3-dimethyl-piperazin-1-yl)-phenyl]-5H-pyrrolo[2,3-b]pyrazin-7-yl}-2,2-dimethyl-propan-1-one;
1-{2-[3-(3-Amino-azetidin-1-yl)-phenyl]-5H-pyrrolo[2,3-b]pyrazin-7-yl}-2,2-dimethyl-propan-1-one;
1-{2-[3-(3-Chloro-2-hydroxy-propylamino)-phenyl]-5H-pyrrolo[2,3-b]pyrazin-7-yl}-2,2-dimethyl-propan-1-one;
1-{2-[3-(2,2-Dimethyl-propylamino)-phenyl]-5H-pyrrolo[2,3-b]pyrazin-7-yl}-2,2-dimethyl-propan-1-one;
2,2-Dimethyl-1-[2-(3-pyrrolidin-1-yl-phenyl)-5H-pyrrolo[2,3-b]pyrazin-7-yl]-propan-1-one;
(1-Methyl-cyclohexyl)-[2-(3,4,5-trimethoxy-phenyl)-5H-pyrrolo[2,3-b]pyrazin-7-yl]-methanone;
1-[2-(3-Fluoro-phenyl)-5H-pyrrolo[2,3-b]pyrazin-7-yl]-2,2-dimethyl-propan-1-one;
(1-Methyl-cyclohexyl)-[2-(3-pyrrolidin-1-yl-phenyl)-5H-pyrrolo[2,3-b]pyrazin-7-yl]-methanone;
2,2-Dimethyl-1-(2-phenyl-5H-pyrrolo[2,3-b]pyrazin-7-yl)-propan-1-one;
2,2-Dimethyl-1-[2-(3,4,5-trimethoxy-phenyl)-5H-pyrrolo[2,3-b]pyrazin-7-yl]-pent-4-en-1-one;
2,2-Dimethyl-1-[2-(3,4,5-trimethoxy-phenyl)-5H-pyrrolo[2,3-b]pyrazin-7-yl]-pentan-1-one;
2,2-Dimethyl-4-morpholin-4-yl-1-[2-(3,4,5-trimethoxy-phenyl)-5H-pyrrolo[2,3-b]pyrazin-7-yl]-butan-1-one;
4,4-Dimethyl-5-oxo-5-[2-(3,4,5-trimethoxy-phenyl)-5H-pyrrolo[2,3-b]pyrazin-7-yl]-pentanenitrile;
5,5-Dimethyl-6-oxo-6-[2-(3,4,5-trimethoxy-phenyl)-5H-pyrrolo[2,3-b]pyrazin-7-yl]-hexanenitrile;
2,2-Dimethyl-1-[2-(3-pyrazol-1-yl-phenyl)-5H-pyrrolo[2,3-b]pyrazin-7-yl]-propan-1-one;
2,2-Dimethyl-1-{2-[3-(5-methyl-[1,3,4]oxadiazol-2-yl)-phenyl]-5H-pyrrolo[2,3-b]pyrazin-7-yl}-propan-1-one;
2,2-Dimethyl-1-{2-[3-(2H-pyrazol-3-yl)-phenyl]-5H-pyrrolo[2,3-b]pyrazin-7-yl}-propan-1-one;
3-[7-(2,2-Dimethyl-propionyl)-5H-pyrrolo[2,3-b]pyrazin-2-yl]-N-methyl-benzamide;
1-[2-(3-Methoxymethyl-phenyl)-5H-pyrrolo[2,3-b]pyrazin-7-yl]-2,2-dimethyl-propan-1-one;
1-[2-(4-Methoxymethyl-phenyl)-5H-pyrrolo[2,3-b]pyrazin-7-yl]-2,2-dimethyl-propan-1-one;
N-Cyclopentyl-3-[7-(2,2-dimethyl-propionyl)-5H-pyrrolo[2,3-b]pyrazin-2-yl]-benzamide;
3-[7-(2,2-Dimethyl-propionyl)-5H-pyrrolo[2,3-b]pyrazin-2-yl]-benzoic acid;
1-[2-(3-Isopropenyl-phenyl)-5H-pyrrolo[2,3-b]pyrazin-7-yl]-2,2-dimethyl-propan-1-one;
1-[2-(3-Hydroxy-phenyl)-5H-pyrrolo[2,3-b]pyrazin-7-yl]-2,2-dimethyl-propan-1-one;
1-[2-(3-tert-Butyl-5-methyl-phenyl)-5H-pyrrolo[2,3-b]pyrazin-7-yl]-2,2-dimethyl-propan-1-one;
1-(2-Biphenyl-3-yl-5H-pyrrolo[2,3-b]pyrazin-7-yl)-2,2-dimethyl-propan-1-one;
1-[2-(3-tert-Butoxymethyl-phenyl)-5H-pyrrolo[2,3-b]pyrazin-7-yl]-2,2-dimethyl-propan-1-one;
1-[2-(3-Isopropyl-phenyl)-5H-pyrrolo[2,3-b]pyrazin-7-yl]-2,2-dimethyl-propan-1-one;
1-{2-[3-(3,5-Dimethyl-isoxazol-4-yl)-phenyl]-5H-pyrrolo[2,3-b]pyrazin-7-yl}-2,2-dimethyl-propan-1-one;
1-[2-(3-Bromo-phenyl)-5H-pyrrolo[2,3-b]pyrazin-7-yl]-2,2-dimethyl-propan-1-one;
2,2-Dimethyl-1-{2-[3-(2-methyl-2H-pyrazol-3-yl)-phenyl]-5H-pyrrolo[2,3-b]pyrazin-7-yl}-propan-1-one;
1-[2-(3-Chloro-4-fluoro-phenyl)-5H-pyrrolo[2,3-b]pyrazin-7-yl]-2,2-dimethyl-propan-1-one;
2,2-Dimethyl-1-[2-(2'-methyl-biphenyl-3-yl)-5H-pyrrolo[2,3-b]pyrazin-7-yl]-propan-1-one;
1-[2-(3-Hydroxymethyl-phenyl)-5H-pyrrolo[2,3-b]pyrazin-7-yl]-2,2-dimethyl-propan-1-one;
1-[2-(3-Cyclopent-1-enyl-phenyl)-5H-pyrrolo[2,3-b]pyrazin-7-yl]-2,2-dimethyl-propan-1-one;
1-[2-(3-Acetyl-4-hydroxy-phenyl)-5H-pyrrolo[2,3-b]pyrazin-7-yl]-2,2-dimethyl-propan-1-one;
1-{2-[3-(3H-Imidazol-4-yl)-phenyl]-5H-pyrrolo[2,3-b]pyrazin-7-yl}-2,2-dimethyl-propan-1-one;
2,2-Dimethyl-1-[2-(3-oxazol-5-yl-phenyl)-5H-pyrrolo[2,3-b]pyrazin-7-yl]-propan-1-one;
2,2-Dimethyl-1-[2-(3-trimethylsilanyl-phenyl)-5H-pyrrolo[2,3-b]pyrazin-7-yl]-propan-1-one;
3-{3-[7-(2,2-Dimethyl-propionyl)-5H-pyrrolo[2,3-b]pyrazin-2-yl]-phenyl}-3-oxo-propionitrile;
1-[2-(3-Iodo-phenyl)-5H-pyrrolo[2,3-b]pyrazin-7-yl]-2,2-dimethyl-propan-1-one;
2,2-Dimethyl-1-{2-[3-(5-trifluoromethyl-2H-pyrazol-3-yl)-phenyl]-5H-pyrrolo[2,3-b]pyrazin-7-yl}-propan-1-one;
1-[2-(3-Cyclohex-1-enyl-phenyl)-5H-pyrrolo[2,3-b]pyrazin-7-yl]-2,2-dimethyl-propan-1-one;
2,2-Dimethyl-1-[2-(3-thiophen-2-yl-phenyl)-5H-pyrrolo[2,3-b]pyrazin-7-yl]-propan-1-one;
1-[2-(3-Cyclopentyl-phenyl)-5H-pyrrolo[2,3-b]pyrazin-7-yl]-2,2-dimethyl-propan-1-one;
1-(2-Biphenyl-4-yl-5H-pyrrolo[2,3-b]pyrazin-7-yl)-2,2-dimethyl-propan-1-one;
1-[2-(3-Imidazol-1-yl-phenyl)-5H-pyrrolo[2,3-b]pyrazin-7-yl]-2,2-dimethyl-propan-1-one;
2,2-Dimethyl-1-{2-[4-(5-methyl-[1,3,4]oxadiazol-2-yl)-phenyl]-5H-pyrrolo[2,3-b]pyrazin-7-yl}-propan-1-one;

2,2-Dimethyl-1-[2-(4-trimethylsilanyl-phenyl)-5H-pyrrolo [2,3-b]pyrazin-7-yl]-propan-1-one;
1-[2-(4-Iodo-phenyl)-5H-pyrrolo[2,3-b]pyrazin-7-yl]-2,2-dimethyl-propan-1-one;
1-{2-[4-(3,5-Dimethyl-isoxazol-4-yl)-phenyl]-5H-pyrrolo [2,3-b]pyrazin-7-yl}-2,2-dimethyl-propan-1-one;
2,2-Dimethyl-1-{2-[4-(2-methyl-2H-pyrazol-3-yl)-phenyl]-5H-pyrrolo[2,3-b]pyrazin-7-yl}-propan-1-one;
1-{2-[4-(3H-Imidazol-4-yl)-phenyl]-5H-pyrrolo[2,3-b] pyrazin-7-yl}-2,2-dimethyl-propan-1-one;
2,2-Dimethyl-1-{2-[4-(2-piperidin-1-yl-ethoxy)-phenyl]-5H-pyrrolo[2,3-b]pyrazin-7-yl}-propan-1-one;
1-{2-[3-(3,3-Dimethyl-pyrrolidin-1-yl)-phenyl]-5H-pyrrolo [2,3-b]pyrazin-7-yl}-2,2-dimethyl-propan-1-one;
3-[7-(2,2-Dimethyl-propionyl)-5H-pyrrolo[2,3-b]pyrazin-2-yl]-N-ethyl-benzamide;
1-{2-[3-((R)-3-Hydroxymethyl-pyrrolidin-1-yl)-phenyl]-5H-pyrrolo[2,3-b]pyrazin-7-yl}-2,2-dimethyl-propan-1-one;
1-{2-[3-((S)-3-Hydroxymethyl-pyrrolidin-1-yl)-phenyl]-5H-pyrrolo[2,3-b]pyrazin-7-yl}-2,2-dimethyl-propan-1-one;
(1-Methyl-cyclohexyl)-{2-[4-(2-piperidin-1-yl-ethoxy)-phenyl]-5H-pyrrolo[2,3-b]pyrazin-7-yl}-methanone;
2,2-Dimethyl-1-{2-[3-(1H-pyrazol-4-yl)-phenyl]-5H-pyrrolo[2,3-b]pyrazin-7-yl}-propan-1-one;
1-{2-[3-(3,3-Difluoro-azetidin-1-yl)-phenyl]-5H-pyrrolo[2,3-b]pyrazin-7-yl}-2,2-dimethyl-propan-1-one;
2,2-Dimethyl-1-{2-[3-(2-oxa-6-aza-spiro[3.3]hept-6-yl)-phenyl]-5H-pyrrolo[2,3-b]pyrazin-7-yl}-propan-1-one;
1-{3-[7-(2,2-Dimethyl-propionyl)-5H-pyrrolo[2,3-b] pyrazin-2-yl]-phenyl}-pyrrolidin-2-one;
1-{3-[7-(1-Methyl-cyclohexanecarbonyl)-5H-pyrrolo[2,3-b]pyrazin-2-yl]-phenyl}-pyrrolidin-2-one;
(1-Methyl-cyclohexyl)-[2-(3-pyrrol-1-yl-phenyl)-5H-pyrrolo[2,3-b]pyrazin-7-yl]-methanone;
2-3-(3,3-Dimethyl-pyrrolidin-1-yl)-phenyl]-5H-pyrrolo[2,3-b]pyrazine-7-carboxylic acid isopropylamide;
1-{3-[7-(2,2-Dimethyl-propionyl)-5H-pyrrolo[2,3-b] pyrazin-2-yl]-phenyl}-pyrrolidine-3-carbonitrile;
1-{2-[3-(3-Dimethylamino-azetidin-1-yl)-phenyl]-5H-pyrrolo[2,3-b]pyrazin-7-yl}-2,2-dimethyl-propan-1-one;
2-[3-(3,3-Dimethyl-pyrrolidin-1-yl)-phenyl]-5H-pyrrolo[2,3-b]pyrazine-7-carboxylic acid (3-hydroxy-2,2-dimethyl-propyl)-amide;
1-{2-[3-(3,3-Dimethyl-azetidin-1-yl)-phenyl]-5H-pyrrolo [2,3-b]pyrazin-7-yl}-2,2-dimethyl-propan-1-one;
2-[3-(3,3-Dimethyl-pyrrolidin-1-yl)-phenyl]-5H-pyrrolo[2,3-b]pyrazine-7-carboxylic acid tert-butylamide;
2-[3-(3,3-Dimethyl-pyrrolidin-1-yl)-phenyl]-5H-pyrrolo[2,3-b]pyrazine-7-carboxylic acid (2-methoxy-propyl)-amide;
2-[3-(3,3-Dimethyl-pyrrolidin-1-yl)-phenyl]-5H-pyrrolo[2,3-b]pyrazine-7-carboxylic acid (tetrahydro-pyran-3-yl)-amide;
2-Methyl-2-phenyl-1-[2-(3,4,5-trimethoxy-phenyl)-5H-pyrrolo[2,3-b]pyrazin-7-yl]-propan-1-one;
1-[2-(3,5-Di-pyrrolidin-1-yl-phenyl)-5H-pyrrolo[2,3-b] pyrazin-7-yl]-2,2-dimethyl-propan-1-one;
3-[7-(2,2-Dimethyl-propionyl)-5H-pyrrolo[2,3-b]pyrazin-2-yl]-benzonitrile;
3-[7-(1-Methyl-cyclohexanecarbonyl)-5H-pyrrolo[2,3-b] pyrazin-2-yl]-benzaldehyde;
(1-Methyl-cyclohexyl)-[2-(3-pyrrolidin-1-ylmethyl-phenyl)-5H-pyrrolo[2,3-b]pyrazin-7-yl]-methanone;
1-{2-[3-(4,5-Dihydro-1H-imidazol-2-ylamino)-phenyl]-5H-pyrrolo[2,3-b]pyrazin-7-yl}-2,2-dimethyl-propan-1-one;

1-{2-[3-(4,5-Dihydro-1H-imidazol-2-yl)-phenyl]-5H-pyrrolo[2,3-b]pyrazin-7-yl}-2,2-dimethyl-propan-1-one;
2,2-Dimethyl-1-{2-[3-(1,4,5,6-tetrahydro-pyrimidin-2-yl)-phenyl]-5H-pyrrolo[2,3-b]pyrazin-7-yl}-propan-1-one;
1-{2-[3-(5,5-Dimethyl-1,4,5,6-tetrahydro-pyrimidin-2-yl)-phenyl]-5H-pyrrolo[2,3-b]pyrazin-7-yl}-2,2-dimethyl-propan-1-one;
1-{2-[3-(4,4-Dimethyl-4,5-dihydro-1H-imidazol-2-yl)-phenyl]-5H-pyrrolo[2,3-b]pyrazin-7-yl}-2,2-dimethyl-propan-1-one;
2,2-Dimethyl-1-{2-[3-(1-methyl-4,5-dihydro-1H-imidazol-2-yl)-phenyl]-5H-pyrrolo[2,3-b]pyrazin-7-yl}-propan-1-one; Pyrrolidin-1-yl-[2-(3,4,5-trimethoxy-phenyl)-5H-pyrrolo[2,3-b]pyrazin-7-yl]-methanone;
(3,3-Dimethyl-pyrrolidin-1-yl)-[2-(3,4,5-trimethoxy-phenyl)-5H-pyrrolo[2,3-b]pyrazin-7-yl]-methanone;
2,2-Dimethyl-1-[2-(3,4,5-trimethoxy-phenyl)-5H-pyrrolo [2,3-b]pyrazin-7-yl]-butan-1-one;
3,3,3-Trifluoro-2-methyl-2-trifluoromethyl-1-[2-(3,4,5-trimethoxy-phenyl)-5H-pyrrolo[2,3-b]pyrazin-7-yl]-propan-1-one;
1-[2-(3-Ethylamino-phenyl)-5H-pyrrolo[2,3-b]pyrazin-7-yl]-2,2-dimethyl-propan-1-one;
1-[2-(3-Diethylamino-phenyl)-5H-pyrrolo[2,3-b]pyrazin-7-yl]-2,2-dimethyl-propan-1-one;
1-[2-(3-Amino-phenyl)-5H-pyrrolo[2,3-b]pyrazin-7-yl]-2,2-dimethyl-propan-1-one;
N-{3-[7-(2,2-Dimethyl-propionyl)-5H-pyrrolo[2,3-b] pyrazin-2-yl]-phenyl}-acetamide;
1-{2-[3-(3-Hydroxy-pyrrolidin-1-yl)-phenyl]-5H-pyrrolo[2, 3-b]pyrazin-7-yl}-2,2-dimethyl-propan-1-one;
1-{2-[3-(1,1-Dioxo-1λ6-thiomorpholin-4-yl)-phenyl]-5H-pyrrolo[2,3-b]pyrazin-7-yl}-2,2-dimethyl-propan-1-one;
1-[2-(3-Azetidin-1-yl-phenyl)-5H-pyrrolo[2,3-b]pyrazin-7-yl]-2,2-dimethyl-propan-1-one;
2,2-Dimethyl-1-{2-[3-(1-oxo-1λ4-thiomorpholin-4-yl)-phenyl]-5H-pyrrolo[2,3-b]pyrazin-7-yl}-propan-1-one;
2,2-Dimethyl-1-[2-(3-pyrrol-1-yl-phenyl)-5H-pyrrolo[2,3-b]pyrazin-7-yl]-propan-1-one;
1-{2-[3-(2-Methanesulfonyl-ethylamino)-phenyl]-5H-pyrrolo[2,3-b]pyrazin-7-yl}-2,2-dimethyl-propan-1-one;
1-{2-[(3aS,6aR)-3-(Hexahydro-pyrrolo[3,4-c]pyrrol-2-yl)-phenyl]-5H-pyrrolo[2,3-b]pyrazin-7-yl}-2,2-dimethyl-propan-1-one;
1-{2-[3-((S)-2-Hydroxymethyl-pyrrolidin-1-yl)-phenyl]-5H-pyrrolo[2,3-b]pyrazin-7-yl}-2,2-dimethyl-propan-1-one;
1-{2-[3-((R)-2-Hydroxymethyl-pyrrolidin-1-yl)-phenyl]-5H-pyrrolo[2,3-b]pyrazin-7-yl}-2,2-dimethyl-propan-1-one;
N-{3-[7-(2,2-Dimethyl-propionyl)-5H-pyrrolo[2,3-b] pyrazin-2-yl]-phenyl}-methanesulfonamide;
N-(4-{3-[7-(2,2-Dimethyl-propionyl)-5H-pyrrolo[2,3-b] pyrazin-2-yl]-phenylsulfamoyl}-phenyl)-acetamide;
4-Amino-N-{3-[7-(2,2-dimethyl-propionyl)-5H-pyrrolo[2, 3-b]pyrazin-2-yl]-phenyl}-benzenesulfonamide;
N-{3-[7-(2,2-Dimethyl-propionyl)-5H-pyrrolo[2,3-b] pyrazin-2-yl]-phenyl}-benzenesulfonamide;
N-(4-{5-[7-(2,2-Dimethyl-propionyl)-5H-pyrrolo[2,3-b] pyrazin-2-yl]-2-methyl-phenylsulfamoyl}-phenyl)-acetamide;
4-Amino-N-{5-[7-(2,2-dimethyl-propionyl)-5H-pyrrolo[2, 3-b]pyrazin-2-yl]-2-methyl-phenyl}-benzenesulfonamide;
1-{2-[3-(3-Hydroxy-3-methyl-pyrrolidin-1-yl)-phenyl]-5H-pyrrolo[2,3-b]pyrazin-7-yl}-2,2-dimethyl-propan-1-one;

1-{2-[3-(3-Hydroxy-3-methyl-pyrrolidin-1-yl)-phenyl]-5H-pyrrolo[2,3-b]pyrazin-7-yl}-2,2-dimethyl-propan-1-one;

3-[7-(2,2-Dimethyl-propionyl)-5H-pyrrolo[2,3-b]pyrazin-2-yl]-benzaldehyde;

2,2-Dimethyl-1-[2-(3-pyrrolidin-1-ylmethyl-phenyl)-5H-pyrrolo[2,3-b]pyrazin-7-yl]-propan-1-one;

1-{2-[3-(4-Dimethylamino-piperidin-1-ylmethyl)-phenyl]-5H-pyrrolo[2,3-b]pyrazin-7-yl}-2,2-dimethyl-propan-1-one;

2,2-Dimethyl-1-{2-[3-(4-methyl-piperazin-1-ylmethyl)-phenyl]-5H-pyrrolo[2,3-b]pyrazin-7-yl}-propan-1-one;

1-[2-(4-Aminomethyl-phenyl)-5H-pyrrolo[2,3-b]pyrazin-7-yl]-2,2-dimethyl-propan-1-one;

2,2-Dimethyl-1-{2-[3-(4-methylsulfanyl-piperidin-1-ylmethyl)-phenyl]-5H-pyrrolo[2,3-b]pyrazin-7-yl}-propan-1-one;

1-{2-[3-(3-Hydroxy-pyrrolidin-1-ylmethyl)-phenyl]-5H-pyrrolo[2,3-b]pyrazin-7-yl}-2,2-dimethyl-propan-1-one;

1-{2-[3-((S)-2-Hydroxymethyl-pyrrolidin-1-ylmethyl)-phenyl]-5H-pyrrolo[2,3-b]pyrazin-7-yl}-2,2-dimethyl-propan-1-one;

1-{2-[3-((R)-2-Hydroxymethyl-pyrrolidin-1-ylmethyl)-phenyl]-5H-pyrrolo[2,3-b]pyrazin-7-yl}-2,2-dimethyl-propan-1-one;

(1-{3-[7-(2,2-Dimethyl-propionyl)-5H-pyrrolo[2,3-b]pyrazin-2-yl]-benzyl}-pyrrolidin-3-yl)-carbamic acid tert-butyl ester;

1-[2-(3-{[Bis-(2-hydroxy-ethyl)-amino]-methyl}-phenyl)-5H-pyrrolo[2,3-b]pyrazin-7-yl]-2,2-dimethyl-propan-1-one;

1-[2-(3-{[Ethyl-(4-hydroxy-butyl)-amino]-methyl}-phenyl)-5H-pyrrolo[2,3-b]pyrazin-7-yl]-2,2-dimethyl-propan-1-one;

(S)-1-{3-[7-(2,2-Dimethyl-propionyl)-5H-pyrrolo[2,3-b]pyrazin-2-yl]-benzyl}-pyrrolidine-2-carboxylic acid amide;

(R)-1-{3-[7-(2,2-Dimethyl-propionyl)-5H-pyrrolo[2,3-b]pyrazin-2-yl]-benzyl}-pyrrolidine-2-carboxylic acid amide;

1-{2-[3-(4-Hydroxymethyl-piperidin-1-ylmethyl)-phenyl]-5H-pyrrolo[2,3-b]pyrazin-7-yl}-2,2-dimethyl-propan-1-one;

1-{2-[3-(3-Hydroxymethyl-pyrrolidin-1-ylmethyl)-phenyl]-5H-pyrrolo[2,3-b]pyrazin-7-yl}-2,2-dimethyl-propan-1-one;

1-{2-[3-(3-Amino-pyrrolidin-1-ylmethyl)-phenyl]-5H-pyrrolo[2,3-b]pyrazin-7-yl}-2,2-dimethyl-propan-1-one;

2,2-Dimethyl-1-{2-[3-(3-methylamino-pyrrolidin-1-ylmethyl)-phenyl]-5H-pyrrolo[2,3-b]pyrazin-7-yl}-propan-1-one;

1-{2-[3-(1H-Imidazol-2-yl)-phenyl]-5H-pyrrolo[2,3-b]pyrazin-7-yl}-2,2-dimethyl-propan-1-one;

1-{2-[3-(3-Benzyl-pyrrolidin-1-ylmethyl)-phenyl]-5H-pyrrolo[2,3-b]pyrazin-7-yl}-2,2-dimethyl-propan-1-one;

N-(1-{3-[7-(2,2-Dimethyl-propionyl)-5H-pyrrolo[2,3-b]pyrazin-2-yl]-benzyl}-pyrrolidin-3-yl)-N-methyl-methanesulfonamide;

N-(1-{3-[7-(2,2-Dimethyl-propionyl)-5H-pyrrolo[2,3-b]pyrazin-2-yl]-benzyl}-pyrrolidin-3-yl)-methanesulfonamide;

4-[7-(2,2-Dimethyl-propionyl)-5H-pyrrolo[2,3-b]pyrazin-2-yl]-2-pyrrolidin-1-yl-benzonitrile;

2,2-Dimethyl-1-{2-[3-(3-methyl-pyrrolidin-1-yl)-phenyl]-5H-pyrrolo[2,3-b]pyrazin-7-yl}-propan-1-one;

1-{2-[3-(3-Methoxymethyl-3-methyl-pyrrolidin-1-yl)-phenyl]-5H-pyrrolo[2,3-b]pyrazin-7-yl}-2,2-dimethyl-propan-1-one;

1-{2-[(1S,5R)-3-(3-Aza-bicyclo[3.1.0]hex-3-yl)-phenyl]-5H-pyrrolo[2,3-b]pyrazin-7-yl}-2,2-dimethyl-propan-1-one;

2,2-Dimethyl-1-[2-(3-piperidin-1-yl-phenyl)-5H-pyrrolo[2,3-b]pyrazin-7-yl]-propan-1-one;

2,2-Dimethyl-1-[2-(3-morpholin-4-yl-phenyl)-5H-pyrrolo[2,3-b]pyrazin-7-yl]-propan-1-one;

1-{2-[3-(1S,5R,6R)-6-Methanesulfonylmethyl-3-aza-bicyclo[3.1.0]hex-3-yl)-phenyl]-5H-pyrrolo[2,3-b]pyrazin-7-yl}-2,2-dimethyl-propan-1-one;

3-[7-(2,2-Dimethyl-propionyl)-5H-pyrrolo[2,3-b]pyrazin-2-yl]-5-pyrrolidin-1-yl-benzonitrile;

3-[7-(2,2-Dimethyl-propionyl)-5H-pyrrolo[2,3-b]pyrazin-2-yl]-N-(2-methanesulfonyl-ethyl)-5-pyrrolidin-1-yl-benzamide;

3-[7-(2,2-Dimethyl-propionyl)-5H-pyrrolo[2,3-b]pyrazin-2-yl]-5-pyrrolidin-1-yl-benzamide;

3-[7-(2,2-Dimethyl-propionyl)-5H-pyrrolo[2,3-b]pyrazin-2-yl]-N-(2-hydroxy-ethyl)-5-pyrrolidin-1-yl-benzamide;

2,2-Dimethyl-1-{2-[3-(4-methyl-piperazine-1-carbonyl)-5-pyrrolidin-1-yl-phenyl]-5H-pyrrolo[2,3-b]pyrazin-7-yl}-propan-1-one;

1-{2-[(3aS,6aR)-3-(Hexahydro-cyclopenta[c]pyrrol-2-yl)-phenyl]-5H-pyrrolo[2,3-b]pyrazin-7-yl}-2,2-dimethyl-propan-1-one;

3-[7-(2,2-Dimethyl-propionyl)-5H-pyrrolo[2,3-b]pyrazin-2-yl]-5-pyrrolidin-1-yl-benzoic acid;

3-[7-(2,2-Dimethyl-propionyl)-5H-pyrrolo[2,3-b]pyrazin-2-yl]-5-(3,3-dimethyl-pyrrolidin-1-yl)-benzamide;

2,2-Dimethyl-1-{2-[3-((1S,5R)-1-phenyl-3-aza-bicyclo[3.1.0]hex-3-yl)-phenyl]-5H-pyrrolo[2,3-b]pyrazin-7-yl}-propan-1-one;

1-{2-[3-(3,3-Diethyl-pyrrolidin-1-yl)-phenyl]-5H-pyrrolo[2,3-b]pyrazin-7-yl}-2,2-dimethyl-propan-1-one;

2,2-Dimethyl-1-{2-[3-(4-methyl-piperazin-1-ylmethyl)-5-pyrrolidin-1-yl-phenyl]-5H-pyrrolo[2,3-b]pyrazin-7-yl}-propan-1-one;

1-{2-[3-(1S,5R,6R)-6-Hydroxymethyl-3-aza-bicyclo[3.1.0]hex-3-yl)-phenyl]-5H-pyrrolo[2,3-b]pyrazin-7-yl}-2,2-dimethyl-propan-1-one;

{2-[3-((1S,5R,6R)-6-Hydroxymethyl-3-aza-bicyclo[3.1.0]hex-3-yl)-phenyl]-5H-pyrrolo[2,3-b]pyrazin-7-yl}-(1-methyl-cyclohexyl)-methanone;

1-{2-[3-((1R,5S,6R)-6-Methoxymethyl-3-aza-bicyclo[3.1.0]hex-3-yl)-phenyl]-5H-pyrrolo[2,3-b]pyrazin-7-yl}-2,2-dimethyl-propan-1-one;

{2-[3-((1R,5S,6R)-6-Hydroxymethyl-3-aza-bicyclo[3.1.0]hex-3-yl)-phenyl]-5H-pyrrolo[2,3-b]pyrazin-7-yl}-(1-methyl-cyclopentyl)-methanone;

1-{2-[3-(4-Hydroxy-piperidin-1-yl)-phenyl]-5H-pyrrolo[2,3-b]pyrazin-7-yl}-2,2-dimethyl-propan-1-one;

1-{2-[3-(4-Hydroxyl-4-methyl-piperidin-1-yl)-phenyl]-5H-pyrrolo[2,3-b]pyrazin-7-yl}-2,2-dimethyl-propan-1-one;

1-{2-[3-(3-Hydroxymethyl-3-methyl-pyrrolidin-1-yl)-phenyl]-5H-pyrrolo[2,3-b]pyrazin-7-yl}-2,2-dimethyl-propan-1-one;

N-(1-{3-[7-(2,2-Dimethyl-propionyl)-5H-pyrrolo[2,3-b]pyrazin-2-yl]-phenyl}-3-methyl-pyrrolidin-3-ylmethyl)-acetamide;

N-(1-{3-[7-(2,2-Dimethyl-propionyl)-5H-pyrrolo[2,3-b]pyrazin-2-yl]-phenyl}-3-methyl-pyrrolidin-3-ylmethyl)-methanesulfonamide;

(1-{3-[7-(2,2-Dimethyl-propionyl)-5H-pyrrolo[2,3-b]pyrazin-2-yl]-phenyl}-3-methyl-pyrrolidin-3-ylmethyl)-carbamic acid methyl ester;

2,2-Dimethyl-1-[2-(4-pyrrolidin-1-yl-phenyl)-5H-pyrrolo[2,3-b]pyrazin-7-yl]-propan-1-one;

1-[2-(3-Dimethylamino-phenyl)-5H-pyrrolo[2,3-b]pyrazin-7-yl]-2,2-dimethyl-propan-1-one;
N-{3-[7-(2,2-Dimethyl-propionyl)-5H-pyrrolo[2,3-b]pyrazin-2-yl]-benzyl}-methanesulfonamide;
N-{3-[7-(2,2-Dimethyl-propionyl)-5H-pyrrolo[2,3-b]pyrazin-2-yl]-benzyl}-C-phenyl-methanesulfonamide;
Cyclopropanesulfonic acid 3-[7-(2,2-dimethyl-propionyl)-5H-pyrrolo[2,3-b]pyrazin-2-yl]-benzylamide;
N-{3-[7-(2,2-Dimethyl-propionyl)-5H-pyrrolo[2,3-b]pyrazin-2-yl]-benzyl}-benzenesulfonamide;
N-{4-[7-(2,2-Dimethyl-propionyl)-5H-pyrrolo[2,3-b]pyrazin-2-yl]-benzyl}-C-phenyl-methanesulfonamide;
Cyclopropanesulfonic acid 4-[7-(2,2-dimethyl-propionyl)-5H-pyrrolo[2,3-b]pyrazin-2-yl]-benzylamide;
Propane-1-sulfonic acid 3-[7-(2,2-dimethyl-propionyl)-5H-pyrrolo[2,3-b]pyrazin-2-yl]-benzylamide;
1-{2-[3-(2-tert-Butyl-pyrrolidin-1-ylmethyl)-phenyl]-5H-pyrrolo[2,3-b]pyrazin-7-yl}-2,2-dimethyl-propan-1-one;
1-(2-{3-[(Cyclohexyl-methyl-amino)-methyl]-phenyl}-5H-pyrrolo[2,3-b]pyrazin-7-yl)-2,2-dimethyl-propan-1-one;
1-{2-[3-(3-Dimethylamino-pyrrolidin-1-ylmethyl)-phenyl]-5H-pyrrolo[2,3-b]pyrazin-7-yl}-2,2-dimethyl-propan-1-one;
2,2-Dimethyl-1-{2-[3-((S)-2-methyl-pyrrolidin-1-ylmethyl)-phenyl]-5H-pyrrolo[2,3-b]pyrazin-7-yl}-propan-1-one;
1-{2-[3-(3-Methoxy-pyrrolidin-1-ylmethyl)-phenyl]-5H-pyrrolo[2,3-b]pyrazin-7-yl}-2,2-dimethyl-propan-1-one;
1-(2-{3-[(Cyclopropylmethyl-propyl-amino)-methyl]-phenyl}-5H-pyrrolo[2,3-b]pyrazin-7-yl)-2,2-dimethyl-propan-1-one;
1-{2-[3-((R)-2-Methoxymethyl-pyrrolidin-1-ylmethyl)-phenyl]-5H-pyrrolo[2,3-b]pyrazin-7-yl}-2,2-dimethyl-propan-1-one;
1-(2-{3-[(4,5-Dihydro-1H-imidazol-2-ylamino)-methyl]-phenyl}-5H-pyrrolo[2,3-b]pyrazin-7-yl)-2,2-dimethyl-propan-1-one;
1-{2-[3-(3,3-Dimethyl-pyrrolidin-1-ylmethyl)-phenyl]-5H-pyrrolo[2,3-b]pyrazin-7-yl}-2,2-dimethyl-propan-1-one;
3-(4-{3-[7-(2,2-Dimethyl-propionyl)-5H-pyrrolo[2,3-b]pyrazin-2-yl]-benzyl}-piperazin-1-yl)-3-oxo-propionitrile;
2-(3,4,5-Trimethoxy-phenyl)-5H-pyrrolo[2,3-b]pyrazine-7-carboxylic acid (2-methoxy-1-methyl-ethyl)-amide;
2-Phenyl-1-[2-(3,4,5-trimethoxy-phenyl)-5H-pyrrolo[2,3-b]pyrazin-7-yl]-propan-1-one;
2-(3,4,5-Trimethoxy-phenyl)-5H-pyrrolo[2,3-b]pyrazine-7-carboxylic acid;
2-(3,4,5-Trimethoxy-phenyl)-5H-pyrrolo[2,3-b]pyrazine-7-carboxylic acid (1-acetyl-pyrrolidin-3-ylmethyl)-amide;
2-(3,4,5-Trimethoxy-phenyl)-5H-pyrrolo[2,3-b]pyrazine-7-carboxylic acid (1-ethylcarbamoyl-pyrrolidin-3-ylmethyl)-amide;
2-(3,4,5-Trimethoxy-phenyl)-5H-pyrrolo[2,3-b]pyrazine-7-carboxylic acid (piperidin-4-ylmethyl)-amide;
2-(3,4,5-Trimethoxy-phenyl)-5H-pyrrolo[2,3-b]pyrazine-7-carboxylic acid (1-acetyl-piperidin-4-ylmethyl)-amide;
1-{2-[3-(3,3-Dimethyl-pyrrolidin-1-yl)-5-(1-methyl-piperidin-4-yloxy)-phenyl]-5H-pyrrolo[2,3-b]pyrazin-7-yl}-2,2-dimethyl-propan-1-one;
2,2-Dimethyl-1-{2-[(3aR,6aS)-3-(tetrahydro-thieno[3,4-c]pyrrol-5-yl)-phenyl]-5H-pyrrolo[2,3-b]pyrazin-7-yl}-propan-1-one;
1-{2-[3-((1S,2S)-2-Hydroxy-cyclopentylamino)-phenyl]-5H-pyrrolo[2,3-b]pyrazin-7-yl}-2,2-dimethyl-propan-1-one;
1-(2-{3-[(2-Methanesulfonyl-ethylamino)-methyl]-5-pyrrolidin-1-yl-phenyl}-5H-pyrrolo[2,3-b]pyrazin-7-yl)-2,2-dimethyl-propan-1-one;
1-{2-[3-(3,3-Dimethyl-azetidin-1-yl)-phenyl]-5H-pyrrolo[2,3-b]pyrazin-7-yl}-2,2-dimethyl-propan-1-one;
1-{2-[3-(3-Aminomethyl-3-methyl-pyrrolidin-1-yl)-phenyl]-5H-pyrrolo[2,3-b]pyrazin-7-yl}-2,2-dimethyl-propan-1-one;
1-{2-[3-((3aR,6aS)-2,2-Dioxo-hexahydro-2λ6-thieno[3,4-c]pyrrol-5-yl)-phenyl]-5H-pyrrolo[2,3-b]pyrazin-7-yl}-2,2-dimethyl-propan-1-one;
2,2-Dimethyl-1-{2-[3-((3aR,6aS)-2-oxo-hexahydro-2λ4-thieno[3,4-c]pyrrol-5-yl)-phenyl]-5H-pyrrolo[2,3-b]pyrazin-7-yl}-propan-1-one;
2-Oxo-2,3-dihydro-benzooxazole-6-sulfonic acid {6-[7-(2,2-dimethyl-propionyl)-5H-pyrrolo[2,3-b]pyrazin-2-yl]-1H-indol-4-yl}-amide;
2-Methyl-2-phenyl-1-[2-(3,4,5-trimethoxy-phenyl)-5H-pyrrolo[2,3-b]pyrazin-7-yl]-propan-1-one;
1-{2-[3-(2-Amino-1,1-dimethyl-ethylamino)-phenyl]-5H-pyrrolo[2,3-b]pyrazin-7-yl}-2,2-dimethyl-propan-1-one;
1H-Indazole-5-sulfonic acid {6-[7-(2,2-dimethyl-propionyl)-5H-pyrrolo[2,3-b]pyrazin-2-yl]-1H-indol-4-yl}-amide;
(4-{3-[7-(2,2-Dimethyl-propionyl)-5H-pyrrolo[2,3-b]pyrazin-2-yl]-phenyl}-piperazin-1-yl)-acetic acid;
4-Amino-3-chloro-N-{6-[7-(2,2-dimethyl-propionyl)-5H-pyrrolo[2,3-b]pyrazin-2-yl]-1H-indol-4-yl}-benzenesulfonamide;
1-{2-[3-(2-Methoxy-2-methyl-propylamino)-phenyl]-5H-pyrrolo[2,3-b]pyrazin-7-yl}-2,2-dimethyl-propan-1-one;
2-[3-(3,3-Dimethyl-pyrrolidin-1-yl)-phenyl]-5H-pyrrolo[2,3-b]pyrazine-7-carboxylic acid tert-butylamide;
3,3-Dimethyl-4-oxo-4-[2-(3,4,5-trimethoxy-phenyl)-5H-pyrrolo[2,3-b]pyrazin-7-yl]-butyronitrile;
1-{2-[3-(3-Hydroxy-azetidin-1-yl)-phenyl]-5H-pyrrolo[2,3-b]pyrazin-7-yl}-2,2-dimethyl-propan-1-one;
1-[2-(3-Methanesulfonylmethoxy-5-pyrrolidin-1-yl-phenyl)-5H-pyrrolo[2,3-b]pyrazin-7-yl]-2,2-dimethyl-propan-1-one;
N-{6-[7-(2,2-Dimethyl-propionyl)-5H-pyrrolo[2,3-b]pyrazin-2-yl]-1H-indol-4-yl}-3-methoxy-benzenesulfonamide;
2-[3-(3,3-Dimethyl-pyrrolidin-1-yl)-phenyl]-5H-pyrrolo[2,3-b]pyrazine-7-carboxylic acid (2-methoxy-propyl)-amide;
(1-{3-[7-(2,2-Dimethyl-propionyl)-5H-pyrrolo[2,3-b]pyrazin-2-yl]-phenyl}-4,4-dimethyl-pyrrolidin-3-yl)-carbamic acid ethyl ester;
3-Methyl-3-[2-(3,4,5-trimethoxy-phenyl)-5H-pyrrolo[2,3-b]pyrazine-7-carbonyl]-cyclopentanone;
2-[3-(3,3-Dimethyl-pyrrolidin-1-yl)-phenyl]-5H-pyrrolo[2,3-b]pyrazine-7-carboxylic acid (tetrahydro-pyran-3-yl)-amide;
4-(4-Hydroxy-piperidin-1-yl)-2,2-dimethyl-1-[2-(3,4,5-trimethoxy-phenyl)-5H-pyrrolo[2,3-b]pyrazin-7-yl]-butan-1-one;
4-[(2-Hydroxy-ethyl)-methyl-amino]-2,2-dimethyl-1-[2-(3,4,5-trimethoxy-phenyl)-5H-pyrrolo[2,3-b]pyrazin-7-yl]-butan-1-one;
2,2-Dimethyl-1-{2-[3-(tetrahydro-pyran-4-ylamino)-phenyl]-5H-pyrrolo[2,3-b]pyrazin-7-yl}-propan-1-one;
3-Amino-N-{6-[7-(2,2-dimethyl-propionyl)-5H-pyrrolo[2,3-b]pyrazin-2-yl]-1H-indol-4-yl}-benzenesulfonamide;
2-[3-(3,3-Dimethyl-pyrrolidin-1-yl)-phenyl]-5H-pyrrolo[2,3-b]pyrazine-7-carboxylic acid ((S)-2-hydroxy-1,2-dimethyl-propyl)-amide;

1-[2-(3-Fluoro-phenyl)-5H-pyrrolo[2,3-b]pyrazin-7-yl]-2,2-dimethyl-propan-1-one;
(3-Hydroxy-1-methyl-cyclopentyl)-[2-(3,4,5-trimethoxy-phenyl)-5H-pyrrolo[2,3-b]pyrazin-7-yl]-methanone;
4-Amino-N-{6-[7-(2,2-dimethyl-propionyl)-5H-pyrrolo[2,3-b]pyrazin-2-yl]-1H-indol-4-yl}-3-fluoro-benzenesulfonamide;
2-{4-Methyl-4-[2-(3,4,5-trimethoxy-phenyl)-5H-pyrrolo[2,3-b]pyrazine-7-carbonyl]-piperidin-1-yl}-acetamide;
1-{4-Methyl-4-[2-(3,4,5-trimethoxy-phenyl)-5H-pyrrolo[2,3-b]pyrazine-7-carbonyl]-piperidin-1-yl}-ethanone;
6-Oxo-1,6-dihydro-pyridine-3-sulfonic acid {6-[7-(2,2-dimethyl-propionyl)-5H-pyrrolo[2,3-b]pyrazin-2-yl]-1H-indol-4-yl}-amide;
4-Amino-N-{6-[7-(2,2-dimethyl-propionyl)-5H-pyrrolo[2,3-b]pyrazin-2-yl]-1H-indol-4-yl}-3-trifluoromethyl-benzenesulfonamide;
1-{2-[3-(3,3-Dimethyl-pyrrolidin-1-yl)-5-(3-methanesulfonyl-propoxy)-phenyl]-5H-pyrrolo[2,3-b]pyrazin-7-yl}-2,2-dimethyl-propan-1-one;
N-{6-[7-(2,2-Dimethyl-propionyl)-5H-pyrrolo[2,3-b]pyrazin-2-yl]-1H-indol-4-yl}-4-hydroxy-benzenesulfonamide;
((1S,3S)-3-Hydroxy-1-methyl-cyclopentyl)-[2-(3,4,5-trimethoxy-phenyl)-5H-pyrrolo[2,3-b]pyrazin-7-yl]-methanone;
1-{2-[3-(2-Aza-bicyclo[2.1.1]hex-2-yl)-phenyl]-5H-pyrrolo[2,3-b]pyrazin-7-yl}-2,2-dimethyl-propan-1-one;
((1S,2R)-1,2-Dimethyl-cyclopentyl)-[2-(3-pyrrolidin-1-yl-phenyl)-5H-pyrrolo[2,3-b]pyrazin-7-yl]-methanone;
1-{2-[3-(3,3-Dimethyl-pyrrolidin-1-yl)-5-(2-hydroxy-propoxy)-phenyl]-5H-pyrrolo[2,3-b]pyrazin-7-yl}-2,2-dimethyl-propan-1-one;
1-{2-[3-(4,5-Dihydro-1H-imidazol-2-ylamino)-5-(3,3-dimethyl-pyrrolidin-1-yl)-phenyl]-5H-pyrrolo[2,3-b]pyrazin-7-yl}-2,2-dimethyl-propan-1-one;
2-[3-(3,3-Dimethyl-pyrrolidin-1-yl)-phenyl]-5H-pyrrolo[2,3-b]pyrazine-7-carboxylic acid phenylamide;
2-[3-(3,3-Dimethyl-pyrrolidin-1-yl)-phenyl]-5H-pyrrolo[2,3-b]pyrazine-7-carboxylic acid (2-hydroxy-1,1-dimethyl-ethyl)-amide;
2,2-Dimethyl-1-[2-(3-methylsulfanyl-5-pyrrolidin-1-yl-phenyl)-5H-pyrrolo[2,3-b]pyrazin-7-yl]-propan-1-one;
1-[2-(3-Methanesulfinyl-5-pyrrolidin-1-yl-phenyl)-5H-pyrrolo[2,3-b]pyrazin-7-yl]-2,2-dimethyl-propan-1-one;
1-[2-(3-Methanesulfonyl-5-pyrrolidin-1-yl-phenyl)-5H-pyrrolo[2,3-b]pyrazin-7-yl]-2,2-dimethyl-propan-1-one;
2,2-Dimethyl-1-{2-[3-(3-pyridin-4-yl-pyrrolidin-1-yl)-phenyl]-5H-pyrrolo[2,3-b]pyrazin-7-yl}-propan-1-one;
2,2-Dimethyl-1-{2-[3-(3-pyridin-2-yl-pyrrolidin-1-yl)-phenyl]-5H-pyrrolo[2,3-b]pyrazin-7-yl}-propan-1-one;
1-{2-[3-(1,7-Diaza-spiro[4.4]non-7-yl)-phenyl]-5H-pyrrolo[2,3-b]pyrazin-7-yl}-2,2-dimethyl-propan-1-one;
2,2-Dimethyl-1-{2-[3-(3-pyridin-3-yl-pyrrolidin-1-yl)-phenyl]-5H-pyrrolo[2,3-b]pyrazin-7-yl}-propan-1-one;
{4-Methyl-4-[2-(3,4,5-trimethoxy-phenyl)-5H-pyrrolo[2,3-b]pyrazine-7-carbonyl]-piperidin-1-yl}-acetonitrile;
2,2-Dimethyl-3-methylsulfanyl-1-[2-(3,4,5-trimethoxy-phenyl)-5H-pyrrolo[2,3-b]pyrazin-7-yl]-propan-1-one;
3-Methanesulfinyl-2,2-dimethyl-1-[2-(3,4,5-trimethoxy-phenyl)-5H-pyrrolo[2,3-b]pyrazin-7-yl]-propan-1-one;
2-[3-(2-Dimethylamino-ethoxy)-5-(3,3-dimethyl-pyrrolidin-1-yl)-phenyl]-5H-pyrrolo[2,3-b]pyrazine-7-carboxylic acid (3-hydroxy-2,2-dimethyl-propyl)-amide;
1-[2-(3-tert-Butylamino-phenyl)-5H-pyrrolo[2,3-b]pyrazin-7-yl]-2,2-dimethyl-propan-1-one; and
1-(2-{3-[3-(2,3-Dihydroxy-propyl)-3-methyl-pyrrolidin-1-yl]-phenyl}-5H-pyrrolo[2,3-b]pyrazin-7-yl)-2,2-dimethyl-propan-1-one.

In one aspect, the application provides a method for treating an inflammatory and/or autoimmune condition comprising administering to a patient in need thereof a therapeutically effective amount of the compound of Formula I.

In one variation of the above method, the above method further comprises administering an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

In one aspect, the application provides a method for treating an inflammatory condition comprising administering to a patient in need thereof a therapeutically effective amount of the compound of Formula I, wherein R is $R^1$.

In one aspect, the application provides a method for inhibiting T-cell proliferative disorder comprising administering to a patient in need thereof a therapeutically effective amount of the compound of Formula I.

In one aspect, the application provides a method for inhibiting T-cell proliferative disorder comprising administering to a patient in need thereof a therapeutically effective amount of the compound of Formula I, wherein R is $R^2$.

In one variation of the above method, the proliferative disorder is cancer.

In one aspect, the application provides a method for treating a B-cell proliferative disorder comprising administering to a patient in need thereof a therapeutically effective amount of the compound of Formula I.

In one aspect, the application provides a method for treating an immune disorder including lupus, multiple sclerosis, rheumatoid arthritis, psoriasis, Type I diabetes, complications from organ transplants, xeno transplantation, diabetes, cancer, asthma, atopic dermatitis, autoimmune thyroid disorders, ulcerative colitis, Crohn's disease, Alzheimer's disease, and Leukemia, comprising administering to a patient in need thereof a therapeutically effective amount of the compound of Formula I.

In one aspect, the application provides a method for preventing or treating all forms of organ rejection, including acute allograft or xenograft rejection and chronic allograft or xenograft rejection, of vascularized or non-vascularized transplants, comprising administering to a patient in need thereof a therapeutically effective amount of the compound of Formula I.

In one aspect, the application provides a method for inhibiting JAK3 activity comprising administering the compound of Formula I, wherein the compound exhibits an $IC_{50}$ of 50 micromolar or less in an in vitro biochemical assay of JAK3 activity.

In one variation of the above method, the compound exhibits an $IC_{50}$ of 100 nanomolar or less in an in vitro biochemical assay of JAK3 activity.

In one variation of the above method, the compound exhibits an $IC_{50}$ of 10 nanomolar or less in an in vitro biochemical assay of JAK3 activity.

In one aspect, the application provides a method for inhibiting SYK activity comprising administering the compound of Formula I, wherein the compound exhibits an $IC_{50}$ of 50 micromolar or less in an in vitro biochemical assay of SYK activity.

In one variation of the above method, the compound exhibits an $IC_{50}$ of 100 nanomolar or less in an in vitro biochemical assay of SYK activity.

In one variation of the above method, the compound exhibits an $IC_{50}$ of 10 nanomolar or less in an in vitro biochemical assay of SYK activity.

In one aspect, the application provides a method for treating an inflammatory condition comprising co-administering to a patient in need thereof an anti-inflammatory compound in combination with a therapeutically effective amount of the compound of Formula I.

In one aspect, the application provides a method for treating an immune disorder comprising co-administering to a patient in need thereof an immunosuppressant compound in combination with a therapeutically effective amount of the compound of Formula I.

The application provides a pharmaceutical composition comprising the compound of Formula I, admixed with at least one pharmaceutically acceptable carrier, excipient or diluent.

In one variation, the above pharmaceutical composition further comprises an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, and an agent for treating immunodeficiency disorders.

In one aspect, the application provides a use of the compound of Formula I in the manufacture of a medicament for the treatment of an inflammatory disorder.

In one aspect, the application provides a use of the compound of Formula I in the manufacture of a medicament for the treatment of an autoimmune disorder.

DETAILED DESCRIPTION OF THE INVENTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., R, R', or Q) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "-----" drawn through a bond each refer to the point of attachment of a functional group or other chemical moiety to the rest of the molecule of which it is a part. Thus, for example:

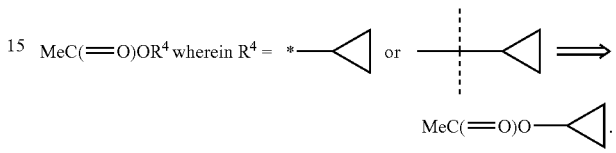

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The phrase "come together to form a bicyclic ring system" as used herein means join to form a bicyclic ring system, wherein each ring may be made up of either 4-7 carbon atoms or 4-7 carbon and heteroatoms, and may be saturated or unsaturated.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

The definitions described herein may be appended to form chemically-relevant combinations, such as "heteroalkylaryl," "haloalkylheteroaryl," "arylalkylheterocyclyl," "alkylcarbonyl," "alkoxyalkyl," "cycloalkylalkyl" and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

Compounds of formula I may exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10$^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl refers to a group —C(=O)R contain 6 carbon atoms. The term "arylcarbonyl" as used herein means a group of formula C(=O)R wherein R is an aryl group; the term "benzoyl" as used herein an "arylcarbonyl" group wherein R is phenyl.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"-, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl", "aryl alkyl", or "aralkyl" are interpreted similarly except R' is an aryl radical. The terms "heteroaryl alkyl" or "heteroarylalkyl" are interpreted similarly except R' is optionally an aryl or a heteroaryl radical.

The term "haloalkyl" as used herein denotes a unbranched or branched chain alkyl group as defined above wherein 1, 2, 3 or more hydrogen atoms are substituted by a halogen. The term "lower haloalkyl" denotes a straight or branched chain hydrocarbon residue containing 1 to 6 carbon atoms, wherein 1, 2, 3 or more hydrogen atoms are substituted by a halogen. Examples are 1-fluoromethyl, 1-chloromethyl, 1-bromomethyl, 1-iodomethyl, difluoromethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

The term "alkylene" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —CH$_2$CH(i-Pr)CH$_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The term "hydroxyalkyl" as used herein denotes an alkyl radical as herein defined wherein one to three hydrogen atoms on different carbon atoms is/are replaced by hydroxyl groups.

The term "cycloalkyl" as used herein refers to a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to an cycloalkyl composed of 3 to 7 carbons in the carbocyclic ring.

The term "halogen" or "halo" as used herein means fluorine, chlorine, bromine, or iodine.

The term "heteroaryl" or "heteroaromatic" as used herein means a monocyclic, bicyclic, or tricyclic radical of 5 to 18 ring atoms having at least one aromatic ring containing four to eight atoms per ring, incorporating one or more N, O, or S heteroatoms, the remaining ring atoms being carbon, with the understanding that the attachment point of the heteroaryl radical will be on an aromatic ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, pyrrolyl, pyrazolyl, imidazolyl, oxazol, isoxazole, thiazole, isothiazole, triazoline, thiadiazole and oxadiaxoline which can optionally be substituted with one or more, preferably one or two substituents selected from hydroxy, cyano, alkyl, alkoxy, thio, lower haloalkoxy, alkylthio, halo, haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole and benzisothiazole.

The term "heterocycloalkyl", "heterocyclyl" or "heterocycle" as used herein denotes a monovalent saturated cyclic radical, consisting of one or more rings, preferably one to two rings or three rings, of three to eight atoms per ring, incorporating one or more ring carbon atoms and one or more ring heteroatoms (chosen from N, O or S(=O)$_{0-2}$), wherein the point of attachment can be through either a carbon atom or a heteroatom, and which can optionally be independently substituted with one or more, preferably one or two or three substituents selected from hydroxy, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, unless otherwise indicated. Examples of heterocyclic radicals include, but are not limited to, azetidinyl, pyrrolidinyl, hexahydroazepinyl, oxetanyl, tetrahydrofuranyl, tetrahydrothiophenyl, oxazolidinyl, thiazolidinyl, isoxazolidinyl, morpholinyl, piperazinyl, piperidinyl, tetrahydropyranyl, thiomorpholinyl, quinuclidinyl and imidazolinyl.

The phrase "organ rejection" includes acute allograft or xenograft rejection and chronic allograft or xenograft rejection in the setting of vascularized and/or non-vascularized (e.g. bone marrow, pancreatic islet cells) transplants.

Commonly used abbreviations include: acetyl (Ac), azo-bis-isobutyrylnitrile (AIBN), atmospheres (Atm), 9-borabicyclo[3.3.1]nonane (9-BBN or BBN), tert-butoxycarbonyl (Boc), di-tert-butyl pyrocarbonate or boc anhydride (BOC$_2$O), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether (Et$_2$O), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), lithium hexamethyl disilazane (LiHMDS), methanol (MeOH), melting point (mp), MeSO$_2$— (mesyl or Ms), methyl (Me), acetonitrile (MeCN), m-chloroperbenzoic acid (MCPBA), mass spectrum (ms), methyl t-butyl ether (MTBE), N-bromosuccinimide (NBS), N-carboxyanhydride (NCA), N-chlorosuccinimide (NCS), N-methylmorpholine (NMM), N-methylpyrrolidone (NMP), pyridinium chlorochromate (PCC), pyridinium dichromate (PDC), phenyl (Ph), propyl (Pr), iso-propyl (i-Pr), pounds per square inch (psi), pyridine (pyr), room temperature (rt or RT), tert-butyldimethylsilyl or t-BuMe$_2$Si (TBDMS), triethylamine (TEA or Et$_3$N), 2,2,6,6-tetramethylpiperidine 1-oxyl (TEMPO), triflate or CF$_3$SO$_2$— (TO, trifluoroacetic acid (TFA), 1,1'-bis-2,2,6,6-tetramethyl-heptane-2,6-dione (TMHD), O-benzotriazol-1-yl-N,N,N', N'-tetramethyluronium tetrafluoroborate (TBTU), thin layer chromatography (TLC), tetrahydrofuran (THF), trimethylsilyl or Me$_3$Si (TMS), p-toluenesulfonic acid monohydrate (TsOH or pTsOH), 4-Me-C$_6$H$_4$SO$_2$— or tosyl (Ts), N-urethane-N-carboxyanhydride (UNCA). Conventional nomenclature including the prefixes normal (n), iso (i-), secondary (sec-), tertiary (tent-) and neo have their customary meaning when used with an alkyl moiety. (J. Rigaudy and D. P. Klesney, *Nomenclature in Organic Chemistry*, IUPAC 1979 Pergamon Press, Oxford.).

Compounds and Preparation

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I depicts exemplified compounds according to Formula I.

TABLE I

| | | |
|---|---|---|
| I-1 | Phenyl-[2-(3,4,5-trimethoxy-phenyl)-5H-pyrrolo[2,3-b]pyrazin-7-yl]-methanone | 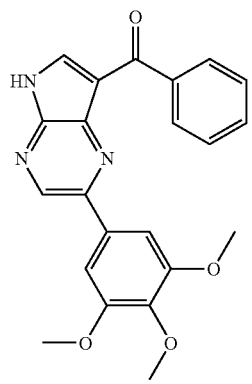 |

TABLE I-continued

| I-2 | 3-Methyl-1-[2-(3,4,5-trimethoxy-phenyl)-5H-pyrrolo[2,3-b]pyrazin-7-yl]-butan-1-one |
| I-3 | 1-[2-(3,4,5-Trimethoxy-phenyl)-5H-pyrrolo[2,3-b]pyrazin-7-yl]-ethanone |
| I-4 | 1-[2-(3,4-Dimethoxy-5H-pyrrolo[2,3-b]pyrazin-7-yl]-3-methyl-butan-1-one |
| I-5 | 1-[2-(5-Fluoro-2-methoxy-phenyl)-5H-pyrrolo[2,3-b]pyrazin-7-yl]-3-methyl-butan-1-one |

TABLE I-continued

| I-6 | 3-Methyl-1-[2-(3-pyrrolidin-1-yl-phenyl)-5H-pyrrolo[2,3-b]pyrazin-7-yl]-butan-1-one | |
| --- | --- | --- |
| I-7 | 4-[7-(3-Methyl-butyryl)-5H-pyrrolo[2,3-b]pyrazin-2-yl]-benzamide | |
| I-8 | 3-[7-(3-Methyl-butyryl)-5H-pyrrolo[2,3-b]pyrazin-2-yl]-benzamide | |
| I-9 | N-Methyl-3-[7-(3-methyl-butyryl)-5H-pyrrolo[2,3-b]pyrazin-2-yl]-benzamide | |

TABLE I-continued

| | | |
|---|---|---|
| I-10 | 2-(3,4,5-Trimethoxyphenyl)-5H-pyrrolo[2,3-b]pyrazine-7-carboxylic acid isopropylamide | |
| I-11 | 1-[2-(3,4-Dimethoxyphenyl)-5H-pyrrolo[2,3-b]pyrazin-7-yl]-4-methyl-pentan-1-one | |
| I-12 | 2,2-Dimethyl-1-[2-(3,4,5-trimethoxyphenyl)-5H-pyrrolo[2,3-b]pyrazin-7-yl]-propan-1-one | |
| I-13 | N,N-Dimethyl-3-[7-(3-methyl-butyryl)-5H-pyrrolo[2,3-b]pyrazin-2-yl]-benzamide | |

TABLE I-continued
| I-14 | 3-Methyl-1-(2-phenyl-5H-pyrrolo[2,3-b]pyrazin-7-yl)-butan-1-one | 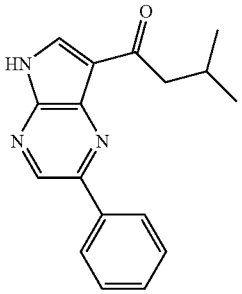 |
| I-15 | 2-(3,4,5-Trimethoxy-phenyl)-5H-pyrrolo[2,3-b]pyrazine-7-carboxylic acid (2-methoxy-1-methyl-ethyl)-amide | 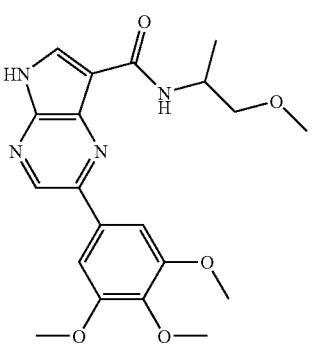 |
| I-16 | 2-Methyl-1-[2-(3,4,5-trimethoxy-phenyl)-5H-pyrrolo[2,3-b]pyrazin-7-yl]-propan-1-one | 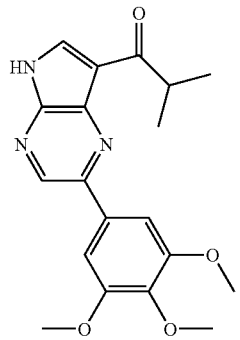 |
| I-17 | 2-(3,4-Dimethoxy-phenyl)-5H-pyrrolo[2,3-b]pyrazine-7-carboxylic acid isopropylamide | 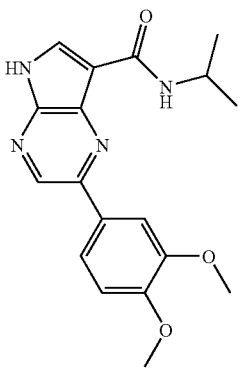 |

TABLE I-continued

| | | |
|---|---|---|
| I-18 | 2-(3,4,5-Trimethoxyphenyl)-5H-pyrrolo[2,3-b]pyrazine-7-carboxylic acid (tetrahydropyran-4-yl)-amide | |
| I-19 | 2-(3,4-Dimethoxyphenyl)-5H-pyrrolo[2,3-b]pyrazine-7-carboxylic acid pyrrolidin-3-ylamide; | |
| I-20 | 2-(3,4-Dimethoxyphenyl)-5H-pyrrolo[2,3-b]pyrazine-7-carboxylic acid cyclobutylamide | |
| I-21 | 2-(3,4-Dimethoxyphenyl)-5H-pyrrolo[2,3-b]pyrazine-7-carboxylic acid (2-methoxy-1-methoxymethyl-ethyl)-amide | |

TABLE I-continued

| | | |
|---|---|---|
| I-22 | 2-(3,4-Dimethoxyphenyl)-5H-pyrrolo[2,3-b]pyrazine-7-carboxylic acid isopropyl-methyl-amide | |
| I-23 | 2-(3,4-Dimethoxyphenyl)-5H-pyrrolo[2,3-b]pyrazine-7-carboxylic acid tert-butylamide | |
| I-24 | 2-(3,4-Dimethoxyphenyl)-5H-pyrrolo[2,3-b]pyrazine-7-carboxylic acid (2-methoxy-1-methyl-ethyl)-amide | |
| I-25 | 1-[2-(3,4-Dimethoxyphenyl)-5H-pyrrolo[2,3-b]pyrazin-7-yl]-3,3-dimethyl-butan-1-one | |

TABLE I-continued

| I-26 | 2-(3,4-Dimethoxy-phenyl)-5H-pyrrolo[2,3-b]pyrazine-7-carboxylic acid (2-hydroxy-1-hydroxymethyl-ethyl)-amide | |
|---|---|---|
| I-27 | (2-{[2-(3,4-Dimethoxy-phenyl)-5H-pyrrolo[2,3-b]pyrazine-7-carbonyl]-amino}-2-methyl-propyl)-carbamic acid tert-butyl ester | |
| I-28 | 2-(3,4-Dimethoxy-phenyl)-5H-pyrrolo[2,3-b]pyrazine-7-carboxylic acid (2-hydroxy-1-methyl-ethyl)-amide | |
| I-29 | 2-(3,4-Dimethoxy-phenyl)-5H-pyrrolo[2,3-b]pyrazine-7-carboxylic acid (2-amino-1,1-dimethyl-ethyl)-amide; | |

TABLE I-continued

| | | |
|---|---|---|
| I-30 | 2-(3-Pyrrolidin-1-yl-phenyl)-5H-pyrrolo[2,3-b]pyrazine-7-carboxylic acid tert-butylamide | |
| I-31 | 2-(3,4-Dimethoxy-phenyl)-5H-pyrrolo[2,3-b]pyrazine-7-carboxylic acid ((1S,2R)-2-carbamoyl-cyclopentyl)-amide | |
| I-32 | 2-(3,4-Dimethoxy-phenyl)-5H-pyrrolo[2,3-b]pyrazine-7-carboxylic acid (tetrahydro-pyran-4-yl)-amide | |
| I-33 | 2-(3,4-Dimethoxy-phenyl)-5H-pyrrolo[2,3-b]pyrazine-7-carboxylic acid piperidin-4-ylamide | |

TABLE I-continued

| | | |
|---|---|---|
| I-34 | 6-Methyl-2-(3,4,5-trimethoxyphenyl)-5H-pyrrolo[2,3-b]pyrazine-7-carboxylic acid tert-butylamide | |
| I-35 | 1-[2-(3,4-Dimethoxyphenyl)-5H-pyrrolo[2,3-b]pyrazin-7-yl]-2,2-dimethyl-propan-1-one | |
| I-36 | 2-Cyclohexyl-1-[2-(3,4,5-trimethoxyphenyl)-5H-pyrrolo[2,3-b]pyrazin-7-yl]-ethanone | |
| I-37 | 2-(3-Methanesulfonyl-phenyl)-5H-pyrrolo[2,3-b]pyrazine-7-carboxylic acid isopropylamide | |

TABLE I-continued

| | | |
|---|---|---|
| I-38 | 2-(2-Methoxy-phenyl)-5H-pyrrolo[2,3-b]pyrazine-7-carboxylic acid isopropylamide | |
| I-39 | 1-Phenyl-2-[2-(3,4,5-trimethoxy-phenyl)-5H-pyrrolo[2,3-b]pyrazin-7-yl]-ethane-1,2-dione | |
| I-40 | 2,2-Dimethyl-1-{2-[4-(2-morpholin-4-yl-ethoxy)-phenyl]-5H-pyrrolo[2,3-b]pyrazin-7-yl}-propan-1-one | |
| I-41 | 2,2-Dimethyl-1-{2-[3-(2-morpholin-4-yl-ethoxy)-phenyl]-5H-pyrrolo[2,3-b]pyrazin-7-yl}-propan-1-one | |

TABLE I-continued
| I-42 | 4-{4-[7-(2,2-(Dimethyl-propionyl)-5H-pyrrolo[2,3-b]pyrazin-2-yl]-phenyl}-piperazine-1-carboxylic acid tert-butyl ester | 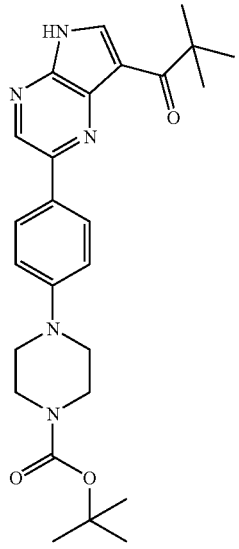 |
| --- | --- | --- |
| I-43 | Pyrrolidin-3-yl-[2-(3,4,5-trimethoxy-phenyl)-5H-pyrrolo[2,3-b]pyrazin-7-yl]-methanone; compound with trifluoro-acetic acid | 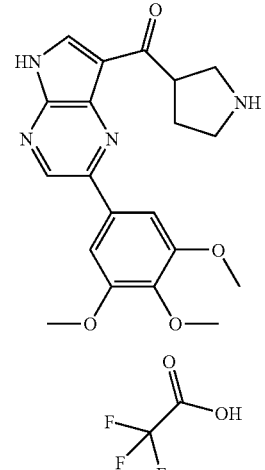 |
| I-44 | 4-{3-[7-(2,2-Dimethyl-propionyl)-5H-pyrrolo[2,3-b]pyrazin-2-yl]-phenyl}-piperazine-1-carboxylic acid tert-butyl ester | 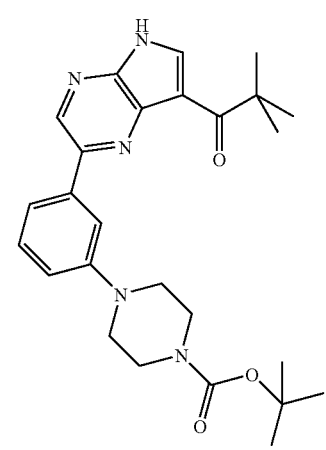 |

| | | |
|---|---|---|
| I-45 | 2,2-Dimethyl-1-[2-(4-piperazin-1-yl-phenyl)-5H-pyrrolo[2,3-b]pyrazin-7-yl]-propan-1-one | |
| I-46 | 2,2-Dimethyl-1-[2-(3-piperazin-1-yl-phenyl)-5H-pyrrolo[2,3-b]pyrazin-7-yl]-propan-1-one | |
| I-47 | 2-(3-Methylcarbamoyl-phenyl)-5H-pyrrolo[2,3-b]pyrazine-7-carboxylic acid isopropylamide | |
| I-48 | 2-[3-(1-Hydroxy-1-methyl-ethyl)-phenyl]-5H-pyrrolo[2,3-b]pyrazine-7-carboxylic acid isopropylamide | |

TABLE I-continued

| I-49 | 2-Phenyl-1-[2-(3,4,5-trimethoxy-phenyl)-5H-pyrrolo[2,3-b]pyrazin-7-yl]-ethanone | |
| --- | --- | --- |
| I-50 | (1-Methyl-cyclopropyl)-[2-(3,4,5-trimethoxy-phenyl)-5H-pyrrolo[2,3-b]pyrazin-7-yl]-methanone | |
| I-51 | 2-(3,4,5-Trimethoxy-phenyl)-5H-pyrrolo[2,3-b]pyrazine-7-carboxylic acid (3-hydroxy-2,2-dimethyl-propyl)-amide | |
| I-52 | (3-Methyl-oxetan-3-yl)-[2-(3,4,5-trimethoxy-phenyl)-5H-pyrrolo[2,3-b]pyrazin-7-yl]-methanone | |

TABLE I-continued

| I-53 | (4-Methyl-tetrahydro-pyran-4-yl)-[2-(3,4,5-trimethoxy-phenyl)-5H-pyrrolo[2,3-b]pyrazin-7-yl]-methanone | |
|---|---|---|
| I-54 | [2-(3,4,5-Trimethoxy-phenyl)-5H-pyrrolo[2,3-b]pyrazin-7-yl]-(2,2,5-trimethyl-[1,3]dioxan-5-yl)-methanone | |
| I-55 | 3-Hydroxy-2-hydroxymethyl-2-methyl-1-[2-(3,4,5-trimethoxy-phenyl)-5H-pyrrolo[2,3-b]pyrazin-7-yl]-propan-1-one | |
| I-56 | 2,2-Diethoxy-1-[2-(3,4,5-trimethoxy-phenyl)-5H-pyrrolo[2,3-b]pyrazin-7-yl]-propan-1-one | |

TABLE I-continued

| I-57 | 2-(3-Methoxy-phenyl)-5H-pyrrolo[2,3-b]pyrazine-7-carboxylic acid isopropylamide | |
| --- | --- | --- |
| I-58 | 2-(5-Chloro-2-methoxy-phenyl)-5H-pyrrolo[2,3-b]pyrazine-7-carboxylic acid isopropylamide | |
| I-59 | 3,3-Dimethyl-1-[2-(3-morpholin-4-yl-phenyl)-5H-pyrrolo[2,3-b]pyrazin-7-yl]-butan-1-one | |
| I-60 | 3,3-Dimethyl-1-[2-(3-pyrrolidin-1-yl-phenyl)-5H-pyrrolo[2,3-b]pyrazin-7-yl]-butan-1-one | |
| I-61 | 2-[3-(Pyrrolidine-1-carbonyl)-phenyl]-5H-pyrrolo[2,3-b]pyrazine-7-carboxylic acid isopropylamide | |

TABLE I-continued
| I-62 | 2-(2-Chloro-phenyl)-5H-pyrrolo[2,3-b]pyrazine-7-carboxylic acid isopropylamide | 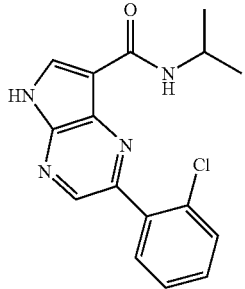 |
| --- | --- | --- |
| I-63 | 1-[2-(3,4,5-Trimethoxy-phenyl)-5H-pyrrolo[2,3-b]pyrazin-7-yl]-propane-1,2-dione | 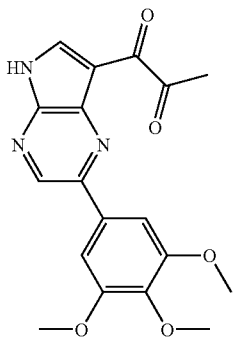 |
| I-64 | 2,2-Dimethyl-1-[2-(3-pyrrolidin-1-yl-phenyl)-5H-pyrrolo[2,3-b]pyrazin-7-yl]-propan-1-one | 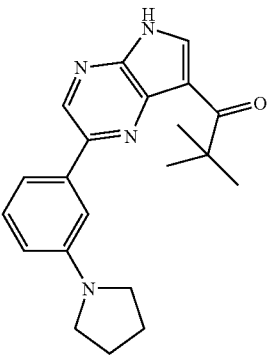 |
| I-65 | 3-Methyl-3-[2-(3,4,5-trimethoxy-phenyl)-5H-pyrrolo[2,3-b]pyrazine-7-carbonyl]-piperidine-1-carboxylic acid tert-butyl ester | 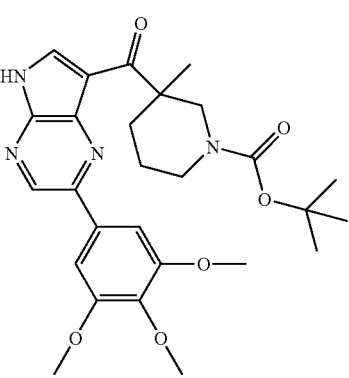 |

TABLE I-continued

| I-66 | 2-(2-Trifluoro-methoxy-phenyl)-5H-pyrrolo[2,3-b]pyrazine-7-carboxylic acid isopropylamide | |
|---|---|---|
| I-67 | (3-Methyl-piperidin-3-yl)-[2-(3,4,5-trimethoxy-phenyl)-5H-pyrrolo[2,3-b]pyrazin-7-yl]-methanone | |
| I-68 | 2-(3,4,5-Trimethoxy-phenyl)-5H-pyrrolo[2,3-b]pyrazine-7-carboxylic acid phenylamide | |
| I-69 | 3-[7-(2,2-Dimethyl-propionyl)-5H-pyrrolo[2,3-b]pyrazin-2-yl]-benzoic acid tert-butyl ester | |

TABLE I-continued

| | | |
|---|---|---|
| I-70 | 3-(7-Isopropyl-carbamoyl-5H-pyrrolo[2,3-b]pyrazin-2-yl)-benzoic acid tert-butyl ester | |
| I-71 | 3-{3-Methyl-3-[2-(3,4,5-trimethoxy-phenyl)-5H-pyrrolo[2,3-b]pyrazine-7-carbonyl]-piperidin-1-yl}-3-oxo-propionitrile | |
| I-72 | 2-(3,4-Dimethoxy-phenyl)-5H-pyrrolo[2,3-b]pyrazine-7-carboxylic acid amide | |
| I-73 | 2-(3,4,5-Trimethoxy-phenyl)-5H-pyrrolo[2,3-b]pyrazine-7-carboxylic acid (2-hydroxy-propyl)-amide | |

TABLE I-continued
| I-74 | 2-(2,5-Dimethoxyphenyl)-5H-pyrrolo[2,3-b]pyrazine-7-carboxylic acid isopropylamide | 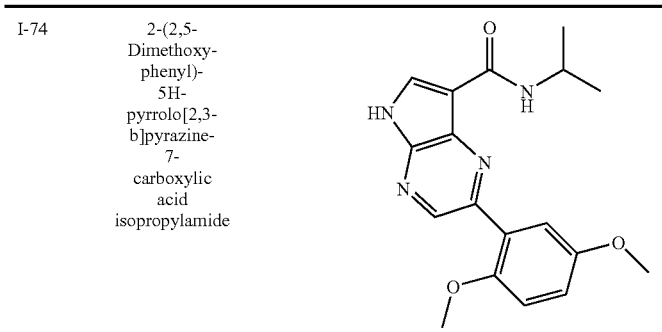 |
| I-75 | 3,3-Dimethyl-1-[2-(3-morpholin-4-ylmethylphenyl)-5H-pyrrolo[2,3-b]pyrazin-7-yl]-butan-1-one | 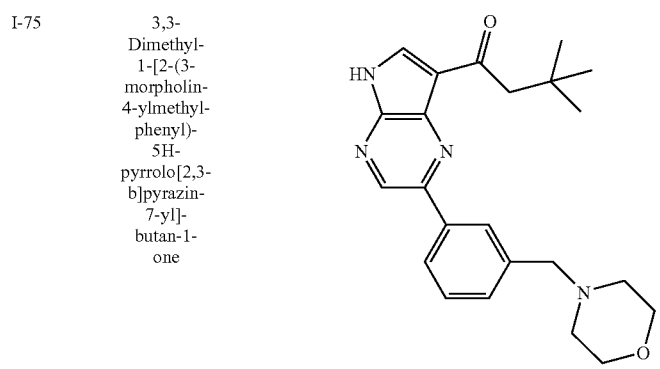 |
| I-76 | 2-(3-Methylcarbamoylphenyl)-5H-pyrrolo[2,3-b]pyrazine-7-carboxylic acid (2-methoxy-1-methyl-ethyl)-amide | 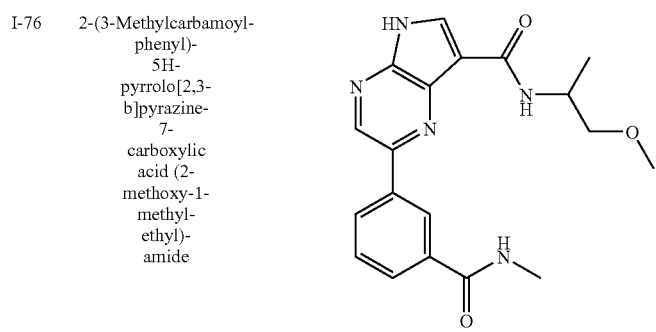 |
| I-77 | 2-(3-Methylcarbamoylphenyl)-5H-pyrrolo[2,3-b]pyrazine-7-carboxylic acid ((S)-2-methoxy-1-methyl-ethyl)-amide | 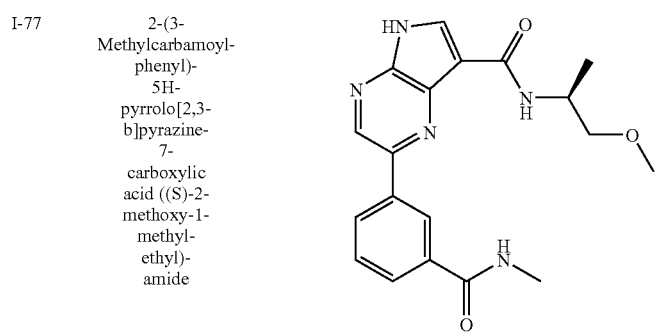 |

TABLE I-continued

| I-78 | (4-Methyl-tetrahydro-thiopyran-4-yl)-[2-(3,4,5-trimethoxy-phenyl)-5H-pyrrolo[2,3-b]pyrazin-7-yl]-methanone | |
| --- | --- | --- |
| I-79 | 2-(2,4-Dimethoxy-phenyl)-5H-pyrrolo[2,3-b]pyrazine-7-carboxylic acid isopropylamide | |
| I-80 | (4-Methyl-1,1-dioxo-hexahydro-1$\lambda^6$-thiopyran-4-yl)-[2-(3,4,5-trimethoxy-phenyl)-5H-pyrrolo[2,3-b]pyrazin-7-yl]-methanone | |
| I-81 | 2-(3,4-Dimethoxy-phenyl)-5H-pyrrolo[2,3-b]pyrazine-7-carboxylic acid (1-acetyl-pyrrolidin-3-yl)-amide | |

TABLE I-continued

| I-82 | 2-(3,4,5-Trimethoxy-phenyl)-5H-pyrrolo[2,3-b]pyrazine-7-carboxylic acid (2-methoxy-propyl)-amide | |
| --- | --- | --- |
| I-83 | 2-({[2-(3,4,5-Trimethoxy-phenyl)-5H-pyrrolo[2,3-b]pyrazine-7-carbonyl]-amino}-methyl)-pyrrolidine-1-carboxylic acid tert-butyl ester | |
| I-84 | 2-(3,4-Dimethoxy-phenyl)-5H-pyrrolo[2,3-b]pyrazine-7-carboxylic acid (1-acetyl-piperidin-4-yl)-amide | |
| I-85 | 2-(3,4-Dimethoxy-phenyl)-5H-pyrrolo[2,3-b]pyrazine-7-carboxylic acid (1-methyl-pyrrolidin-3-yl)-amide | |

TABLE I-continued

| | | |
|---|---|---|
| I-86 | 2-[3-(3-Methoxy-pyrrolidin-1-yl)-phenyl]-5H-pyrrolo[2,3-b]pyrazine-7-carboxylic acid tert-butylamide | |
| I-87 | 2-[3-(3-Methoxy-pyrrolidin-1-yl)-phenyl]-5H-pyrrolo[2,3-b]pyrazine-7-carboxylic acid ((S)-2-methoxy-1-methyl-ethyl)-amide | |
| I-88 | 2-(3,4,5-Trimethoxy-phenyl)-5H-pyrrolo[2,3-b]pyrazine-7-carboxylic acid (tetrahydro-pyran-3-yl)-amide | |
| I-89 | 2-Methyl-2-[2-(3,4,5-trimethoxy-phenyl)-5H-pyrrolo[2,3-b]pyrazine-7-carbonyl]-pyrrolidine-1-carboxylic acid tert-butyl ester | |

TABLE I-continued
| I-90 | (2-Methyl-pyrrolidin-2-yl)-[2-(3,4,5-trimethoxy-phenyl)-5H-pyrrolo[2,3-b]pyrazin-7-yl]-methanone | 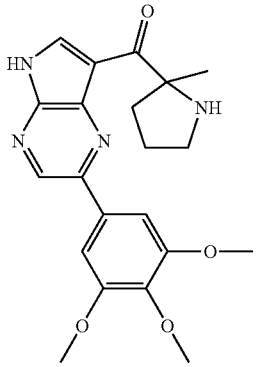 |
| --- | --- | --- |
| I-91 | 2-Phenyl-1-[2-(3,4,5-trimethoxy-phenyl)-5H-pyrrolo[2,3-b]pyrazin-7-yl]-propan-1-one | 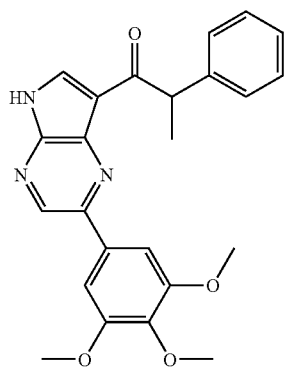 |
| I-92 | 2-(3,4,5-Trimethoxy-phenyl)-5H-pyrrolo[2,3-b]pyrazine-b]pyrazine-7-carboxylic acid (4-hydroxy-cyclohexyl)-amide | 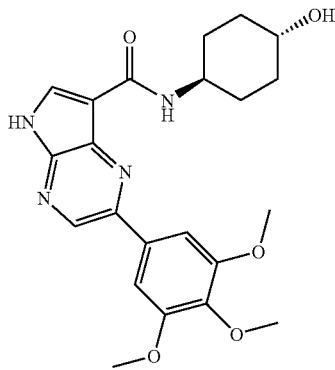 |
| I-93 | 2-(3,4,5-Trimethoxy-phenyl)-5H-pyrrolo[2,3-b]pyrazine-7-carboxylic acid (1,1-dioxo-tetrahydro-1$\lambda^6$-thiophen-3-yl)-amide | 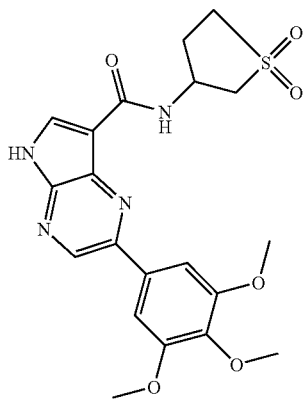 |

TABLE I-continued

| I-94 | 2-(3,4,5-Trimethoxy-phenyl)-5H-pyrrolo[2,3-b]pyrazine-7-carboxylic acid (pyrrolidin-2-ylmethyl)-amide | |
| --- | --- | --- |
| I-95 | 2-(3,4,5-Trimethoxy-phenyl)-5H-pyrrolo[2,3-b]pyrazine-7-carboxylic acid (1-acetyl-pyrrolidin-2-ylmethyl)-amide | |
| I-96 | 3-({[2-(3,4,5-Trimethoxy-phenyl)-5H-pyrrolo[2,3-b]pyrazine-7-carbonyl]-amino}-methyl)-pyrrolidine-1-carboxylic acid tert-butyl ester | |
| I-97 | 2-(3,4,5-Trimethoxy-phenyl)-5H-pyrrolo[2,3-b]pyrazine-7-carboxylic acid (pyrrolidin-3-ylmethyl)-amide | |

TABLE I-continued

| I-98 | 2-(3,4,5-Trimethoxy-phenyl)-5H-pyrrolo[2,3-b]pyrazine-carboxylic acid (1-acetyl-pyrrolidin-3-ylmethyl)-amide |
| --- | --- |
| I-99 | 1-{2-[4-(4-Acetyl-piperazin-1-yl)-phenyl]-5H-pyrrolo[2,3-b]pyrazin-7-yl}-2,2-dimethyl-propan-1-one |
| I-100 | 1-{2-[3-(4-Acetyl-piperazin-1-yl)-phenyl]-5H-pyrrolo[2,3-b]pyrazin-7-yl}-2,2-dimethyl-propan-1-one |
| I-101 | 2-(3-Dimethylamino-phenyl)-5H-pyrrolo[2,3-b]pyrazine-7-carboxylic acid isopropylamide |

TABLE I-continued

| | | |
|---|---|---|
| I-102 | 2-Methyl-2-(tetrahydro-pyran-2-yloxy)-1-[2-(3,4,5-trimethoxy-phenyl)-5H-pyrrolo[2,3-b]pyrazin-7-yl]-propan-1-one | |
| I-103 | 3,3-Dimethyl-1-[2-(3,4,5-trimethoxy-phenyl)-5H-pyrrolo[2,3-b]pyrazin-7-yl]-butan-1-one | |
| I-104 | 2-[3-(2-Oxo-pyrrolidin-1-yl)-phenyl]-5H-pyrrolo[2,3-b]pyrazine-7-carboxylic acid tert-butylamide | |
| I-105 | 2-(3,4,5-Trimethoxy-phenyl)-5H-pyrrolo[2,3-b]pyrazine-7-carboxylic acid(1-ethylcarbamoyl-pyrrolidin-3-ylmethyl)-amide | |

TABLE I-continued

| | | |
|---|---|---|
| I-106 | 2-(3,4,5-Trimethoxyphenyl)-5H-pyrrolo[2,3-b]pyrazine-7-carboxylic acid (piperidin-4-ylmethyl)-amide | |
| I-107 | 2-(3,4,5-Trimethoxyphenyl)-5H-pyrrolo[2,3-b]pyrazine-7-carboxylic acid(1-acetyl-piperidin-4-ylmethyl)-amide | |
| I-108 | 2-(3,4,5-Trimethoxyphenyl)-5H-pyrrolo[2,3-b]pyrazine-7-carboxylic acid isobutyl-amide | |
| I-109 | 2-(3,4,5-Trimethoxyphenyl)-5H-pyrrolo[2,3-b]pyrazine-7-carboxylic acid (2-methanesulfonyl-ethyl)-amide | |

TABLE I-continued

| I-110 | 2-(3,4,5-Trimethoxyphenyl)-5H-pyrrolo[2,3-b]pyrazine-7-carboxylic acid(2-sulfamoylethyl)-amide |
| --- | --- |
| I-111 | 2-(3,4,5-Trimethoxyphenyl)-5H-pyrrolo[2,3-b]pyrazine-7-carboxylic acid (2,3-dihydroxypropyl)-amide |
| I-112 | 2-(3,4,5-Trimethoxyphenyl)-5H-pyrrolo[2,3-b]pyrazine-7-carboxylic acid (tetrahydrofuran-3-yl)-amide |
| I-113 | 1-{2-Methyl-2-[2-(3,4,5-trimethoxyphenyl)-5H-pyrrolo[2,3-b]pyrazine-7-carbonyl]-pyrrolidin-1-yl}-ethanone |

TABLE I-continued

| I-114 | 2,2-Dimethyl-1-[2-(3,4,5-trimethoxy-phenyl)-5H-pyrrolo[2,3-b]pyrazin-7-yl]-butan-1-one | |
| --- | --- | --- |
| I-115 | 2,2-Dimethyl-1-[2-(3-pyrazol-1-yl-phenyl)-5H-pyrrolo[2,3-b]pyrazin-7-yl]-propan-1-one | |
| I-116 | 2-(3-Chloro-5-fluoro-phenyl)-5H-pyrrolo[2,3-b]pyrazine-7-carboxylic acid isopropylamide | |
| I-117 | (1-Methyl-cyclohexyl)-[2-(3,4,5-trimethoxy-phenyl)-5H-pyrrolo[2,3-b]pyrazin-7-yl]-methanone | |

TABLE I-continued

| | | |
|---|---|---|
| I-118 | 3,3,3-Trifluoro-2-methyl-2-trifluoromethyl-1-[2-(3,4,5-trimethoxy-phenyl)-5H-pyrrolo[2,3-b]pyrazin-7-yl]-propan-1-one | |
| I-119 | 1-[2-(3-Fluoro-phenyl)-5H-pyrrolo[2,3-b]pyrazin-7-yl]-2,2-dimethyl-propan-1-one | |
| I-120 | 2-(3,4,5-Trimethoxy-phenyl)-5H-pyrrolo[2,3-b]pyrazine-7-carboxylic acid (2-methoxy-ethyl)-amide | |
| I-121 | 2,2-Dimethyl-1-{2-[3-(5-methyl-[1,3,4]oxadiazol-2-yl-phenyl]-5H-pyrrolo[2,3-b]pyrazin-7-yl}-propan-1-one | |
| I-122 | 2-(3,4,5-Trimethoxy-phenyl)-5H-pyrrolo[2,3-b]pyrazine-7-carboxylic acid (2,2-dimethyl-propyl)-amide | |

TABLE I-continued
| | | |
|---|---|---|
| I-123 | 2-(3,4,5-Trimethoxy-phenyl)-5H-pyrrolo[2,3-b]pyrazine-7-carboxylic acid (2-methoxy-2-methyl-propyl)-amide | 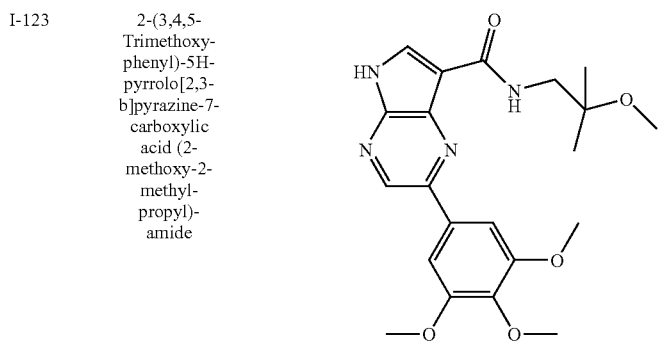 |
| I-124 | 2,2-Dimethyl-1-[2-(4-pyrrolidin-1-yl-phenyl)-5H-pyrrolo[2,3-b]pyrazin-7-yl]-propan-1-one | 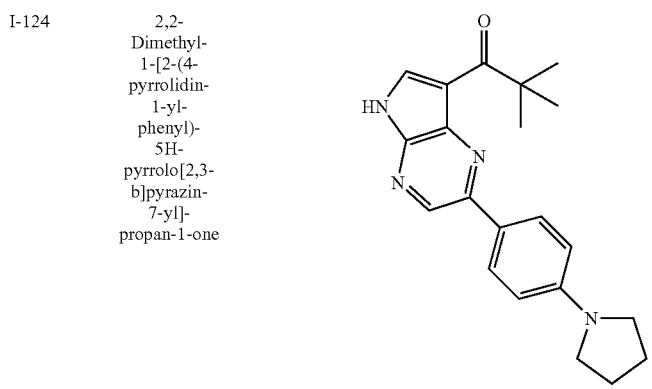 |
| I-125 | 1-[2-(3-Dimethylamino-phenyl)-5H-pyrrolo[2,3-b]pyrazin-7-yl]-2,2-dimethyl-propan-1-one | 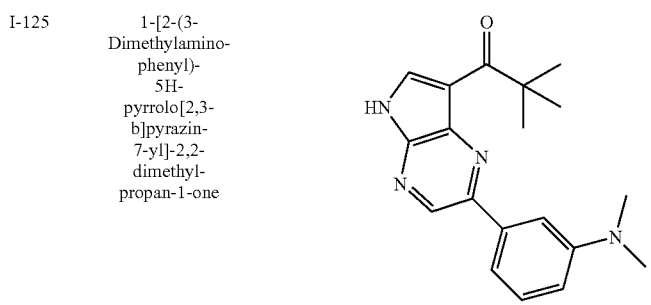 |
| I-126 | 2,2-Dimethyl-1-{2-[3-(2H-pyrazol-3-yl)-phenyl]-5H-pyrrolo[2,3-b]pyrazin-7-yl}-propan-1-one | 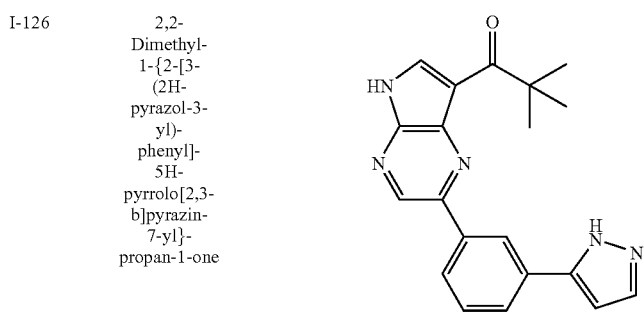 |

TABLE I-continued

| | | |
|---|---|---|
| I-127 | 2-(3,4,5-Trimethoxy-phenyl)-5H-pyrrolo[2,3-b]pyrazine-7-carboxylic acid (3-methoxy-propyl)-amide | |
| I-128 | 1-[2-(4-Methoxy-phenyl)-5H-pyrrolo[2,3-b]pyrazin-7-yl]-2,2-dimethyl-propan-1-one | |
| I-129 | 3-[7-(2,2-Dimethyl-propionyl)-5H-pyrrolo[2,3-b]pyrazin-2-yl]-N-methyl-benzamide | |
| I-130 | 1-[2-(3-Methoxymethyl-phenyl)-5H-pyrrolo[2,3-b]pyrazin-7-yl]-2,2-dimethyl-propan-1-one | |
| I-131 | (1-Methyl-cyclohexyl)-[2-(3-pyrrolidin-1-yl-phenyl)-5H-pyrrolo[2,3-b]pyrazin-7-yl]-methanone | |

TABLE I-continued
| I-132 | 1-[2-(4-Methoxymethyl-phenyl)-5H-pyrrolo[2,3-b]pyrazin-7-yl]-2,2-dimethyl-propan-1-one | 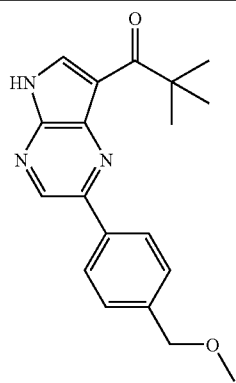 |
| --- | --- | --- |
| I-133 | 1-[2-(2-Methoxy-phenyl)-5H-pyrrolo[2,3-b]pyrazin-7-yl]-2,2-dimethyl-propan-1-one | 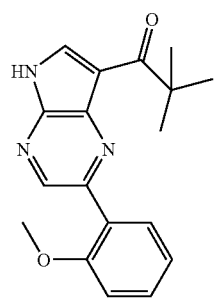 |
| I-134 | 1-[2-(3-Methoxy-phenyl)-5H-pyrrolo[2,3-b]pyrazin-7-yl]-2,2-dimethyl-propan-1-one | 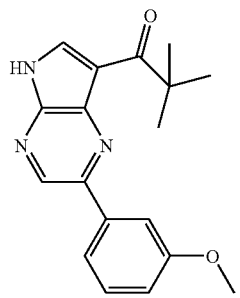 |
| I-135 | 2,2-Dimethyl-1-(2-phenyl-5H-pyrrolo[2,3-b]pyrazin-7-yl)-propan-1-one | 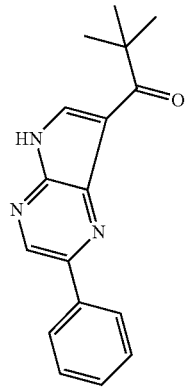 |

| | | |
|---|---|---|
| I-136 | N-Cyclopentyl-3-[7-(2,2-dimethyl-propionyl)-5H-pyrrolo[2,3-b]pyrazin-2-yl]-benzamide | |
| I-137 | 2,2-Dimethyl-1-[2-(3-piperidin-1-yl-phenyl)-5H-pyrrolo[2,3-b]pyrazin-7-yl]-propan-1-one | |
| I-138 | 2,2-Dimethyl-1-[2-(3-morpholin-4-yl-phenyl)-5H-pyrrolo[2,3-b]pyrazin-7-yl]-propan-1-one | |
| I-139 | 3-[7-(2,2-Dimethyl-propionyl)-5H-pyrrolo[2,3-b]pyrazin-2-yl]-benzoic acid | |
| I-140 | 1-[2-(3-Isopropenyl-phenyl)-5H-pyrrolo[2,3-b]pyrazin-7-yl]-2,2-dimethyl-propan-1-one | |

TABLE I-continued

| | | |
|---|---|---|
| I-141 | 1-[2-(3-Hydroxy-phenyl)-5H-pyrrolo[2,3-b]pyrazin-7-yl]-2,2-dimethyl-propan-1-one | |
| I-142 | (1-Methyl-cyclopentyl)-[2-(3-pyrrolidin-1-yl-phenyl)-5H-pyrrolo[2,3-b]pyrazin-7-yl]-methanone | |
| I-143 | 4-Methoxy-1-[2-(3,4,5-trimethoxy-phenyl)-5H-pyrrolo[2,3-b]pyrazin-7-yl]-pentan-1-one | |
| I-144 | (1-Methyl-cycloheptyl)-[2-(3-pyrrolidin-1-yl-phenyl)-5H-pyrrolo[2,3-b]pyrazin-7-yl]-methanone | |
| I-145 | 1-[2-(3-Ethylamino-phenyl)-5H-pyrrolo[2,3-b]pyrazin-7-yl]-2,2-dimethyl-propan-1-one | |

TABLE I-continued
| I-146 | 1-[2-(3-Diethylamino-phenyl)-5H-pyrrolo[2,3-b]pyrazin-7-yl]-2,2-dimethyl-propan-1-one | 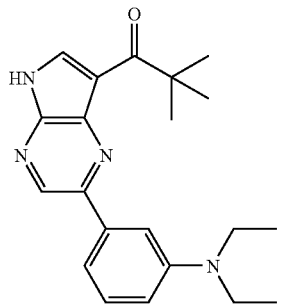 |
| --- | --- | --- |
| I-147 | 1-[2-(3-Amino-phenyl)-5H-pyrrolo[2,3-b]pyrazin-7-yl]-2,2-dimethyl-propan-1-one | 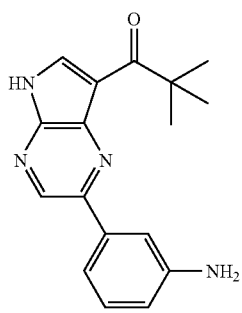 |
| I-148 | 1-[2-(3-Methoxy-5-thiomorpholin-4-yl-phenyl)-5H-pyrrolo[2,3-b]pyrazin-7-yl]-2,2-dimethyl-propan-1-one | 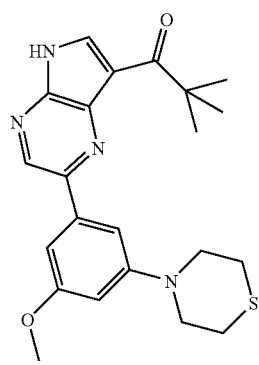 |
| I-149 | 1-{2-[3-Methoxy-5-(1-oxo-1$\lambda^4$-thiomorpholin-4-yl)-phenyl]-5H-pyrrolo[2,3-b]pyrazin-7-yl}-2,2-dimethyl-propan-1-one | 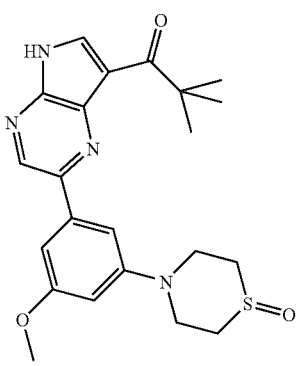 |

TABLE I-continued

| I-150 | 1-{2-[3-(1,1-Dioxo-1λ⁶-thiomorpholin-4-yl)-5-methoxy-phenyl]-5H-pyrrolo[2,3-b]pyrazin-7-yl}-2,2-dimethyl-propan-1-one | |
|---|---|---|
| I-151 | 1-[2-(3-Methoxymethoxy-5-pyrrolidin-1-yl-phenyl)-5H-pyrrolo[2,3-b]pyrazin-7-yl]-2,2-dimethyl-propan-1-one | |
| I-152 | 1-[2-(3-Isopropoxy-5-pyrrolidin-1-yl-phenyl)-5H-pyrrolo[2,3-b]pyrazin-7-yl]-2,2-dimethyl-propan-1-one | |
| I-153 | 1-[2-(3-Ethoxy-5-pyrrolidin-1-yl-phenyl)-5H-pyrrolo[2,3-b]pyrazin-7-yl]-2,2-dimethyl-propan-1-one | |

TABLE I-continued

| | | |
|---|---|---|
| I-154 | 1-[2-(3-Hydroxy-5-pyrrolidin-1-yl-phenyl)-5H-pyrrolo[2,3-b]pyrazin-7-yl]-2,2-dimethyl-propan-1-one | |
| I-155 | [2-(3-Methoxy-5-thiomorpholin-4-yl-phenyl)-5H-pyrrolo[2,3-b]pyrazin-7-yl]-(1-methyl-cyclohexyl)-methanone | |
| I-156 | {2-[3-(1,1-Dioxo-1λ$^6$-thiomorpholin-4-yl)-5-methoxy-phenyl]-5H-pyrrolo[2,3-b]pyrazin-7-yl}-(1-methyl-cyclohexyl)-methanone | |
| I-157 | {2-[3-Methoxy-5-(1-oxo-1λ$^4$-thiomorpholin-4-yl)-phenyl]-5H-pyrrolo[2,3-b]pyrazin-7-yl}-(1-methyl-cyclohexyl)-methanone | |

TABLE I-continued
| I-158 | 1-{2-[3-(2,3-Dihydroxy-propoxy)-5-(1,1-dioxo-1λ⁶-thiomorpholin-4-yl)-phenyl]-5H-pyrrolo[2,3-b]pyrazin-7-yl}-2,2-dimethyl-propan-1-one | 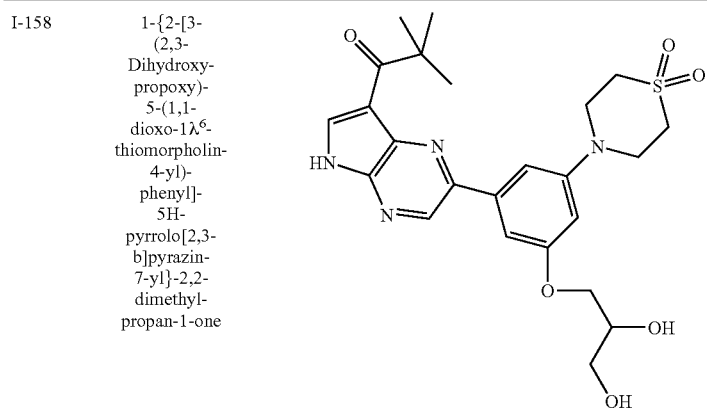 |
| --- | --- | --- |
| I-159 | 1-{2-[3-(3-Methanesulfonyl-propoxy)-pyrrolidin-1-yl-phenyl]-5H-pyrrolo[2,3-b]pyrazin-7-yl}-2,2-dimethyl-propan-1-one | 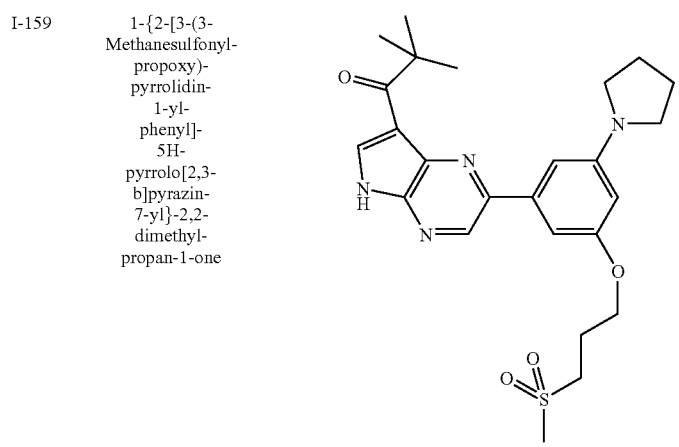 |
| I-160 | 1-{2-[3-(2-Dimethylamino-ethoxy)-5-(1,1-dioxo-1λ⁶-thiomorpholin-4-yl)-phenyl]-5H-pyrrolo[2,3-b]pyrazin-7-yl}-2,2-dimethyl-propan-1-one | 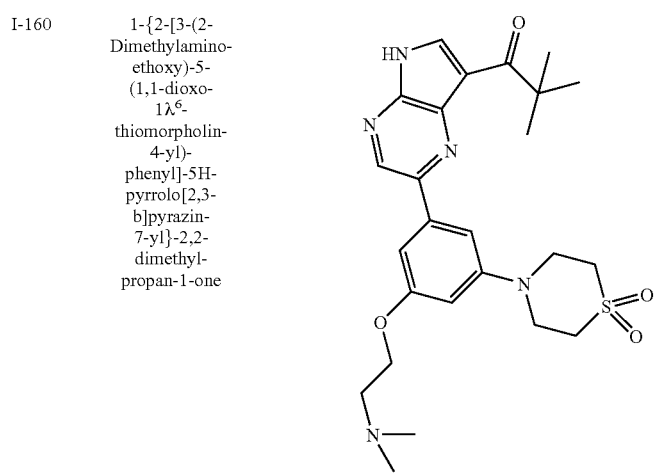 |

TABLE I-continued
| | | |
|---|---|---|
| I-161 | 1-{2-[3-(1,1-Dioxo-1λ⁶-thiomorpholin-4-yl)-5-(2-hydroxy-1-methyl-ethoxy)-phenyl]-5H-pyrrolo[2,3-b]pyrazin-7-yl}-2,2-dimethyl-propan-1-one | 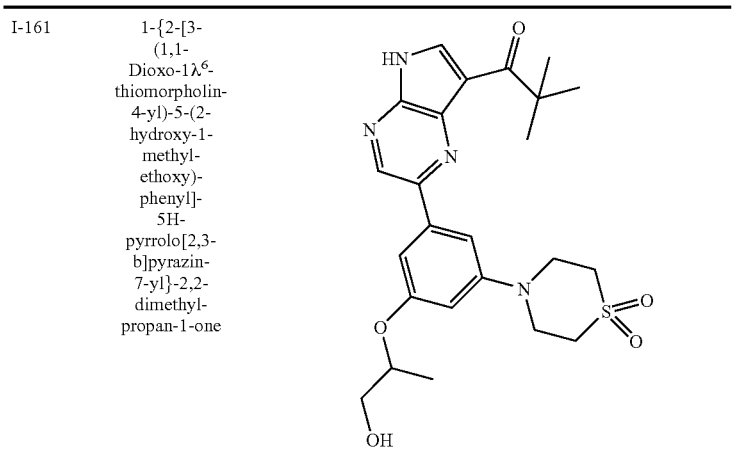 |
| I-162 | 1-{2-[3-(2-Methanesulfonyl-ethoxy)-5-pyrrolidin-1-yl-phenyl]-5H-pyrrolo[2,3-b]pyrazin-7-yl}-2,2-dimethyl-propan-1-one | 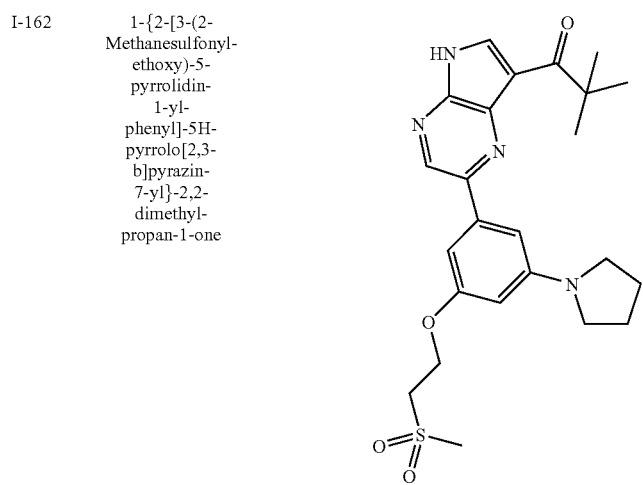 |
| I-163 | 1-{2-[3-(1,1-Dioxo-1λ⁶-thiomorpholin-4-yl)-5-(1-methyl-pyrrolidin-3-yloxy)-phenyl]-5H-pyrrolo[2,3-b]pyrazin-7-yl}-2,2-dimethyl-propan-1-one | 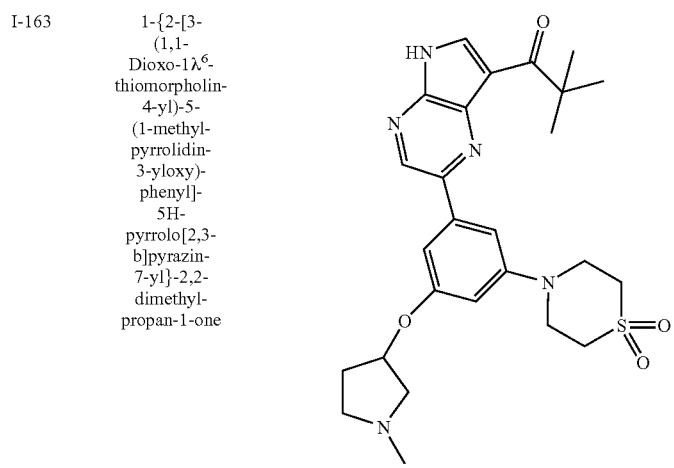 |

| | | |
|---|---|---|
| I-164 | 1-{2-[3-(1,1-Dioxo-1λ⁶-thiomorpholin-4-yl)-5-(1-methyl-piperidin-4-yloxy)-phenyl]-5H-pyrrolo[2,3-b]pyrazin-7-yl}-2,2-dimethyl-propan-1-one | 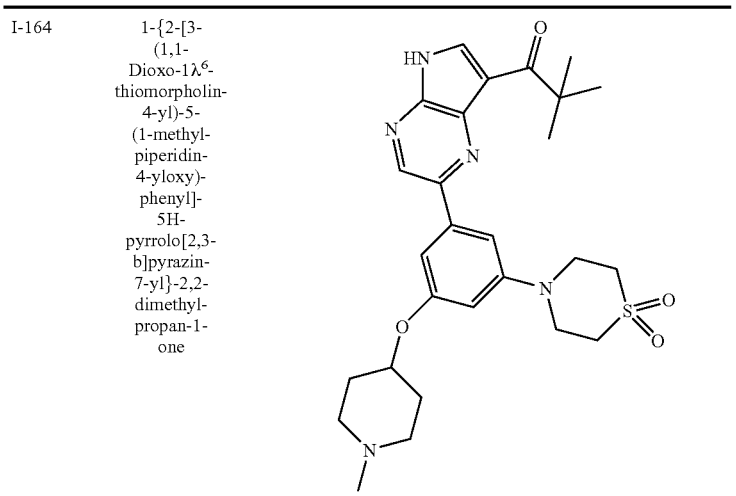 |
| I-165 | 1-{2-[3-(1,1-Dioxo-1λ⁶-thiomorpholin-4-yl)-5-(2-hydroxy-1-hydroxymethyl-ethoxy)-phenyl]-5H-pyrrolo[2,3-b]pyrazin-7-yl}-2,2-dimethyl-propan-1-one | 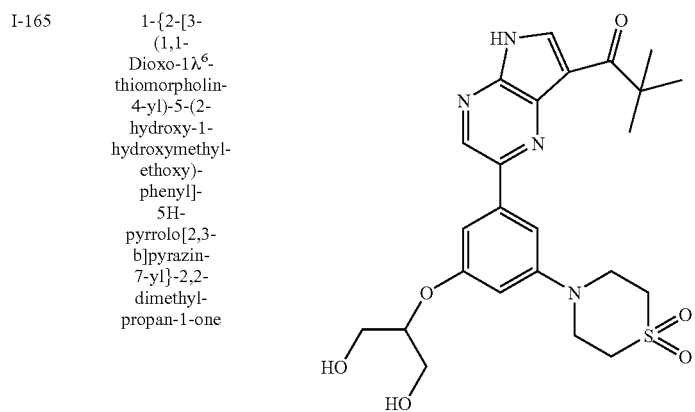 |
| I-166 | 1-{2-[3-(2-Dimethylamino-ethoxy)-5-(3,3-dimethyl-pyrrolidin-1-yl)-phenyl]-5H-pyrrolo[2,3-b]pyrazin-7-yl}-2,2-dimethyl-propan-1-one | 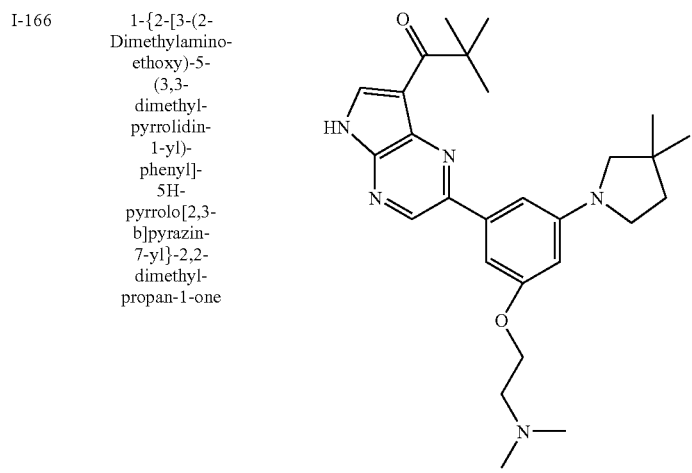 |

TABLE I-continued

| | | |
|---|---|---|
| I-167 | 1-{2-[3-(2,3-Dihydroxy-propoxy)-5-(3,3-dimethyl-pyrrolidin-1-yl)-phenyl]-5H-pyrrolo[2,3-b]pyrazin-7-yl}-2,2-dimethyl-propan-1-one | |
| I-168 | 2,2-Dimethyl-1-{2-[3-(2-thia-7-aza-spiro[4.4]non-7-yl)-phenyl]-5H-pyrrolo[2,3-b]pyrazin-7-yl}-propan-1-one | |
| I-169 | 1-{2-[3-(2,2-Dioxo-2$\lambda^6$-thia-7-aza-spiro[4.4]non-7-yl)-phenyl]-5H-pyrrolo[2,3-b]pyrazin-7-yl}-2,2-dimethyl-propan-1-one | |
| I-170 | 2,2-Dimethyl-1-{2-[3-(2-oxo-2$\lambda^4$-thia-7-aza-spiro[4.4]non-7-yl)-phenyl]-5H-pyrrolo[2,3-b]pyrazin-7-yl}-propan-1-one | |

TABLE I-continued

| I-171 | 2,2-Dimethyl-1-{2-[3-(3-trifluoromethyl-5,6-dihydro-8H-[1,2,4]triazolo[4,3-a]pyrazin-7-ylmethyl)-phenyl]-5H-pyrrolo[2,3-b]pyrazin-7-yl}-propan-1-one | |
|---|---|---|
| I-172 | 1-{2-[3-(5,6-Dihydro-8H-[1,2,4]triazolo[4,3-a]pyrazin-7-ylmethyl)-phenyl]-5H-pyrrolo[2,3-b]pyrazin-7-yl}-2,2-dimethyl-propan-1-one | |
| I-173 | 2,2-Dimethyl-1-{2-[4-(3-trifluoromethyl-5,6-dihydro-8H-[1,2,4]triazolo[4,3-a]pyrazin-7-ylmethyl)-phenyl]-5H-pyrrolo[2,3-b]pyrazin-7-yl}-propan-1-one compound with formic acid | |

TABLE I-continued
| I-174 | 4-{3-[7-(2,2-Dimethyl-propionyl)-5H-pyrrolo[2,3-b]pyrazin-2-yl]-phenyl}-1,5-dimethyl-piperazin-2-one | 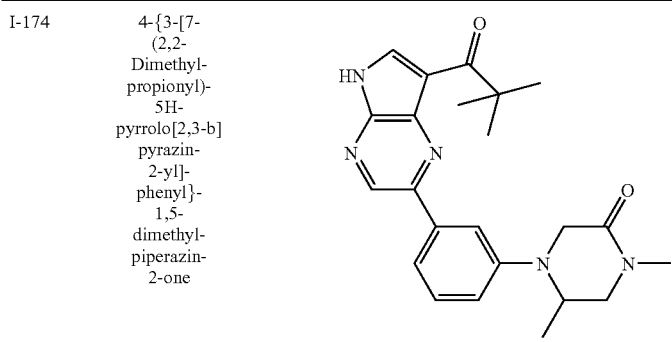 |
| --- | --- | --- |
| I-175 | [2-(3-Cyclopentylamino-phenyl)-5H-pyrrolo[2,3-b]pyrazin-7-yl]-(1-methyl-cyclohexyl)-methanone | 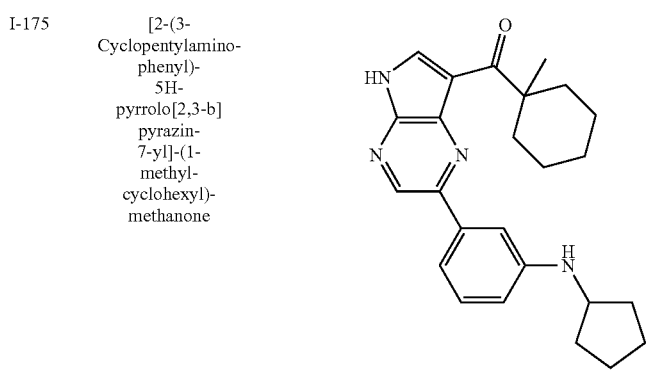 |
| I-176 | {2-[3-(Cyclopentyl-methyl-amino)-phenyl]-5H-pyrrolo[2,3-b]pyrazin-7-yl}-(1-methyl-cyclohexyl)-methanone | 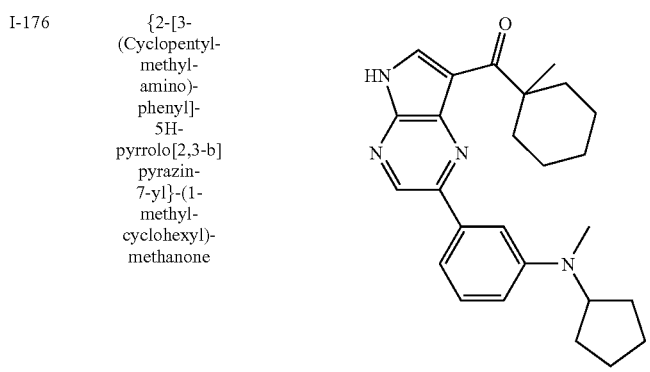 |
| I-177 | 1-[2-(3-Cyclopentylamino-phenyl)-5H-pyrrolo[2,3-b]pyrazin-7-yl]-2,2-dimethyl-propan-1-one | 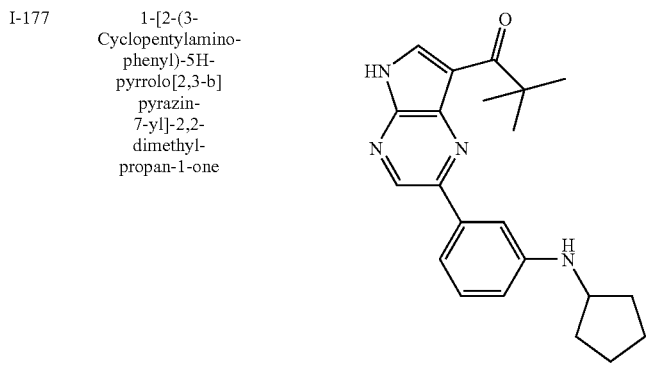 |

TABLE I-continued

| I-178 | 1-{2-[3-(2-Hydroxy-cyclopentylamino)-phenyl]-5H-pyrrolo[2,3-b]pyrazin-7-yl}-2,2-dimethyl-propan-1-one |
| I-179 | 3-Methyl-4-{3-[7-(1-methyl-cyclohexanecarbonyl)-5H-pyrrolo[2,3-b]pyrazin-2-yl]-phenyl}-piperazin-2-one |
| I-180 | 1-(2-{3-[4-(2-Hydroxy-acetyl)-piperazin-1-yl]-phenyl}-5H-pyrrolo[2,3-b]pyrazin-7-yl)-2,2-dimethyl-propan-1-one |
| I-181 | 2,2-Dimethyl-1-{2-[3-(1-methyl-pyrrolidin-3-ylamino)-phenyl]-5H-pyrrolo[2,3-b]pyrazin-7-yl}-propan-1-one |

TABLE I-continued
| I-182 | 2,2-Dimethyl-1-{2-[3-(tetrahydro-furan-3-ylamino)-phenyl]-5H-pyrrolo[2,3-b]pyrazin-7-yl}-propan-1-one | 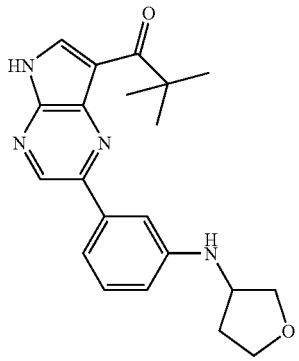 |
| --- | --- | --- |
| I-183 | 1-(2-{4-[4-(2-Hydroxy-acetyl)-piperazin-1-yl]-phenyl}-5H-pyrrolo[2,3-b]pyrazin-7-yl)-2,2-dimethyl-propan-1-one | 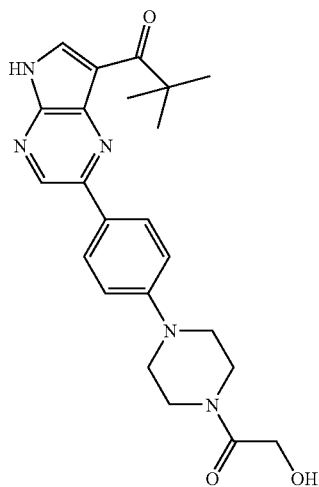 |
| I-184 | 1-(2-{4-[4-(2-Hydroxy-ethyl)-piperazin-1-yl]-phenyl}-5H-pyrrolo[2,3-b]pyrazin-7-yl)-2,2-dimethyl-propan-1-one | 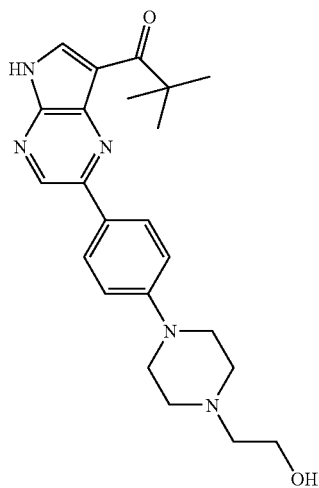 |

TABLE I-continued
| I-185 | 1-[2-(3-Isopropylamino-phenyl)-5H-pyrrolo[2,3-b]pyrazin-7-yl]-2,2-dimethyl-propan-1-one | 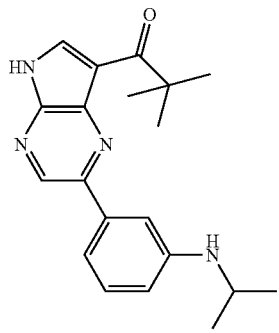 |
|---|---|---|
| I-186 | 1-{2-[3-(4-Methanesulfonyl-piperazin-1-yl)-phenyl]-5H-pyrrolo[2,3-b]pyrazin-7-yl}-2,2-dimethyl-propan-1-one | 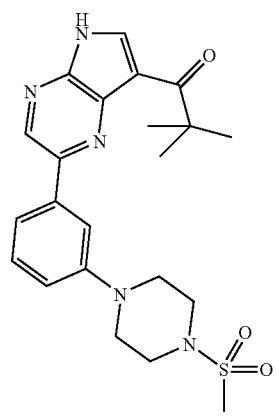 |
| I-187 | 1-{2-[4-(4-Methanesulfonyl-piperazin-1-yl)-phenyl]-5H-pyrrolo[2,3-b]pyrazin-7-yl}-2,2-dimethyl-propan-1-one | 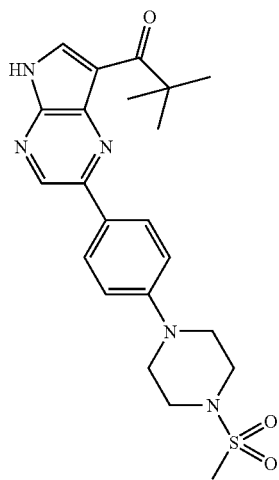 |

| | | |
|---|---|---|
| I-188 | 1-(2-{3-[4-(2-Hydroxy-ethyl)-piperazin-1-yl]-phenyl}-5H-pyrrolo[2,3-b]pyrazin-7-yl)-2,2-dimethyl-propan-1-one | 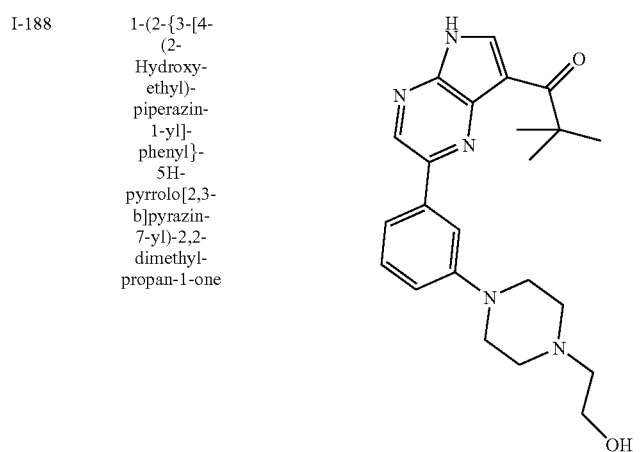 |
| I-189 | 1-{2-[3-((1R,2S)-2-Hydroxy-cyclopentylamino)-phenyl]-5H-pyrrolo[2,3-b]pyrazin-7-yl}-2,2-dimethyl-propan-1-one | 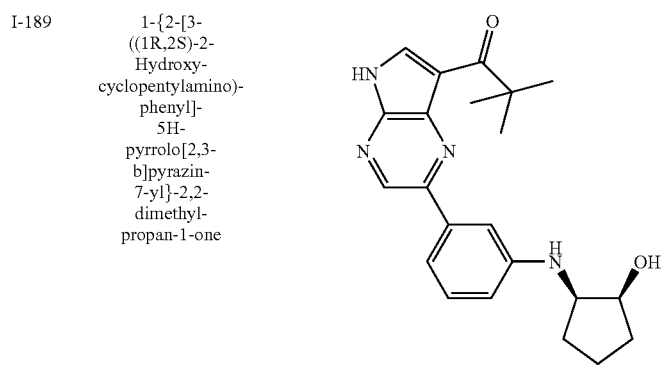 |
| I-190 | 1-{2-[3-(1-Methanesulfonyl-piperidin-4-ylamino)-phenyl]-5H-pyrrolo[2,3-b]pyrazin-7-yl}-2,2-dimethyl-propan-1-one | 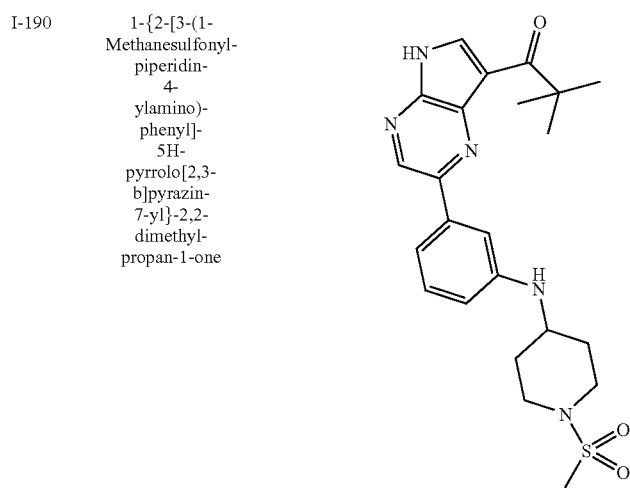 |

TABLE I-continued

| | | |
|---|---|---|
| I-191 | 3-(4-{3-[7-(2,2-Dimethyl-propionyl)-5H-pyrrolo[2,3-b]pyrazin-2-yl]-phenyl}-piperazin-1-yl)-3-oxo-propionitrile | |
| I-192 | 2,2-Dimethyl-3-oxo-3-[2-(3,4,5-trimethoxy-phenyl)-5H-pyrrolo[2,3-b]pyrazin-7-yl]-propionitrile | |
| I-193 | 2,2-Dimethyl-3-oxo-3-[2-(3-pyrrolidin-1-yl-phenyl)-5H-pyrrolo[2,3-b]pyrazin-7-yl]-propionitrile | |
| I-194 | 2,2-Dimethyl-3-phenyl-1-[2-(3-pyrrolidin-1-yl-phenyl)-5H-pyrrolo[2,3-b]pyrazin-7-yl]-propane-1-one | |

| | | |
|---|---|---|
| I-195 | 1-[2-(3-Pyrrolidin-1-yl-phenyl)-5H-pyrrolo[2,3-b]pyrazine-7-carbonyl]-cyclohexanecarbonitrile | |
| I-196 | 2,2-Dimethyl-3-oxo-3-[2-(3-piperazin-1-yl-phenyl)-5H-pyrrolo[2,3-b]pyrazin-7-yl]-propionitrile | |
| I-197 | 1-{2-[3-(5,6-Dihydro-8H-[1,2,4]triazolo[4,3-a]pyrazin-7-yl)-phenyl]-5H-pyrrolo[2,3-b]pyrazin-7-yl}-2,2-dimethyl-propan-1-one | |
| I-198 | 2,2-Dimethyl-1-{2-[3-(3-trifluoromethyl-5,6-dihydro-8H-[1,2,4]triazolo[4,3-a]pyrazin-7-yl)-phenyl]-5H-pyrrolo[2,3-b]pyrazin-7-yl}-propan-1-one | |

TABLE I-continued

| | | |
|---|---|---|
| I-199 | N-Allyl-N-{2,2-dimethyl-3-oxo-3-[2-(3-pyrrolidin-1-yl-phenyl)-5H-pyrrolo[2,3-b]pyrazin-7-yl]-propyl}-benzenesulfonamide | |
| I-200 | 2,2-Dimethyl-3-phenyl-1-[2-(3,4,5-trimethoxy-phenyl)-5H-pyrrolo[2,3-b]pyrazin-7-yl]-propan-1-one | |
| I-201 | 1-[6-Bromo-2-(3-pyrrolidin-1-yl-phenyl)-5H-pyrrolo[2,3-b]pyrazin-7-yl]-2,2-dimethyl-propan-1-one | |
| I-202 | 1-[2,6-Bis-(3-pyrrolidin-1-yl-phenyl)-5H-pyrrolo[2,3-b]pyrazin-7-yl]-2,2-dimethyl-propan-1-one | |

TABLE I-continued
| I-203 | 1-[6-Chloro-2-(3-pyrrolidin-1-yl-phenyl)-5H-pyrrolo[2,3-b]pyrazin-7-yl]-2,2-dimethyl-propan-1-one | 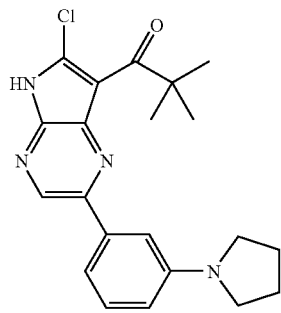 |
| --- | --- | --- |
| I-204 | 2,2-Dimethyl-1-[2-(3,4,5-trimethoxy-phenyl)-5H-pyrrolo[2,3-b]pyrazin-7-yl]-pent-4-yn-1-one | 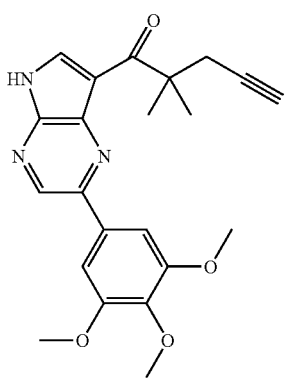 |
| I-205 | 2,2-Dimethyl-1-[2-(3-piperazin-1-yl-phenyl)-5H-pyrrolo[2,3-b]pyrazin-7-yl]-propan-1-one | 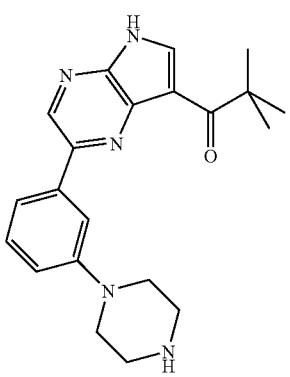 |
| I-206 | 2,2-Dimethyl-1-[2-(3-pyrrolidin-1-yl-phenyl)-5H-pyrrolo[2,3-b]pyrazin-7-yl]-propan-1-one | 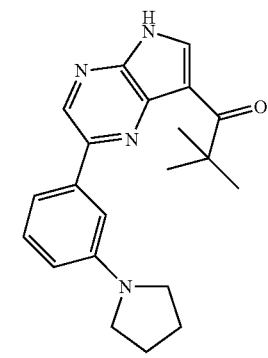 |

TABLE I-continued

| I-207 | 2-{2-Benzenesulfonylamino-4-[7-(2,2-dimethyl-propionyl)-5H-pyrrolo[2,3-b]pyrazin-2-yl]-phenoxy}-2-methyl-propionic acid ethyl ester | 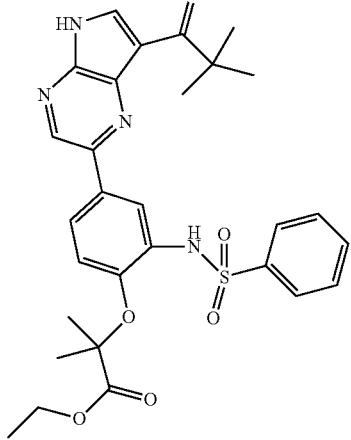 |
| --- | --- | --- |
| I-208 | 2-(3,4,5-Trimethoxy-phenyl)-5H-pyrrolo[2,3-b]pyrazine-7-carboxylic acid isobutyl-amide | 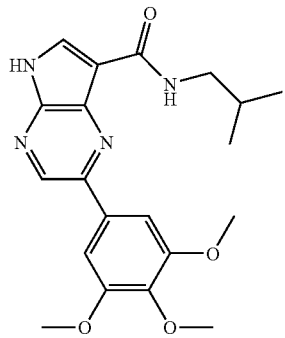 |
| I-209 | 2-(3,4,5-Trimethoxy-phenyl)-5H-pyrrolo[2,3-b]pyrazine-7-carboxylic acid (2-methanesulfonyl-ethyl)-amide | 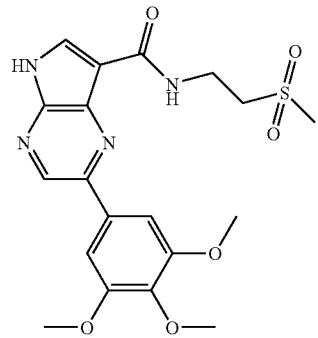 |
| I-210 | 2-(3,4,5-Trimethoxy-phenyl)-5H-pyrrolo[2,3-b]pyrazine-7-carboxylic acid (2-sulfamoyl-ethyl)-amide | 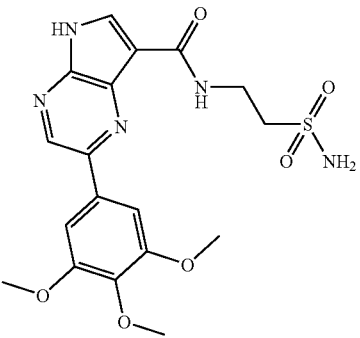 |

TABLE I-continued

| | | |
|---|---|---|
| I-211 | 2-(3,4,5-Trimethoxy-phenyl)-5H-pyrrolo[2,3-b]pyrazine-7-carboxylic acid (2,3-dihydroxy-propyl)-amide | |
| I-212 | 2-(3,4,5-Trimethoxy-phenyl)-5H-pyrrolo[2,3-b]pyrazine-7-carboxylic acid (tetrahydro-furan-3-yl)-amide | |
| I-213 | 2-(3,4,5-Trimethoxy-phenyl)-5H-pyrrolo[2,3-b]pyrazine-7-carboxylic acid (2-methoxy-ethyl)-amide | |
| I-214 | 2-(3,4,5-Trimethoxy-phenyl)-5H-pyrrolo[2,3-b]pyrazine-7-carboxylic acid (2,2-dimethyl-propyl)-amide | |

TABLE I-continued

| I-215 | 2-(3,4,5-Trimethoxy-phenyl)-5H-pyrrolo[2,3-b]pyrazine-7-carboxylic acid (2-methoxy-2-methyl-propyl)-amide |
| I-216 | 2-(3,4,5-Trimethoxy-phenyl)-5H-pyrrolo[2,3-b]pyrazine-7-carboxylic acid (3-methoxy-propyl)-amide |
| I-217 | 1-[2-(4-Methoxy-phenyl)-5H-pyrrolo[2,3-b]pyrazin-7-yl]-2,2-dimethyl-propan-1-one |
| I-218 | 1-[2-(2-Methoxy-phenyl)-5H-pyrrolo[2,3-b]pyrazin-7-yl]-2,2-dimethyl-propan-1-one |
| I-219 | 1-[2-(3-Methoxy-phenyl)-5H-pyrrolo[2,3-b]pyrazin-7-yl]-2,2-dimethyl-propan-1-one |

TABLE I-continued

| I-220 | 1-[2-(4-Methoxy-3-pyrrolidin-1-yl-phenyl)-5H-pyrrolo[2,3-b]pyrazin-7-yl]-2,2-dimethyl-propan-1-one |
| --- | --- |
| I-221 | 1-[2-(3-Methoxy-5-pyrrolidin-1-yl-phenyl)-5H-pyrrolo[2,3-b]pyrazin-7-yl]-2,2-dimethyl-propan-1-one |
| I-222 | 2,2-Dimethyl-1-[2-(4-methylsulfanyl-3-pyrrolidin-1-yl-phenyl)-5H-pyrrolo[2,3-b]pyrazin-7-yl]-propan-1-one |
| I-223 | 1-[2-(4-Methanesulfinyl-3-pyrrolidin-1-yl-phenyl)-5H-pyrrolo[2,3-b]pyrazin-7-yl]-2,2-dimethyl-propan-1-one |

TABLE I-continued

| | | |
|---|---|---|
| I-224 | 1-{2-[3-(3-Methanesulfonyl-1-yl)-pyrrolidin-1-yl)-phenyl]-5H-pyrrolo[2,3-b]pyrazin-7-yl}-2,2-dimethyl-propan-1-one | |
| I-225 | 1-{2-[3-(3,3-Dimethyl-pyrrolidin-1-yl)-phenyl]-5H-pyrrolo[2,3-b]pyrazin-7-yl}-2,2-dimethyl-propan-1-one | |
| I-226 | 1-{2-[3-(3-Methoxy-azetidin-1-yl)-phenyl]-5H-pyrrolo[2,3-b]pyrazin-7-yl}-2,2-dimethyl-propan-1-one | |
| I-227 | (4-Methyl-piperidin-4-yl)-[2-(3,4,5-trimethoxy-phenyl)-5H-pyrrolo[2,3-b]pyrazin-7-yl]-methanone | |
| I-228 | 2-(3-Chloro-5-fluoro-phenyl)-5H-pyrrolo[2,3-b]pyrazine-7-yl-carboxylic acid isopropylamide | |

TABLE I-continued
| | | |
|---|---|---|
| I-229 | 2-[3-(4-Methoxy-benzyloxy)-phenyl]-5H-pyrrolo[2,3-b]pyrazine-7-carboxylic acid isopropylamide | |
| I-230 | 2-[3-(2-Methoxymethyl-pyrrolidin-1-yl)-phenyl]-5H-pyrrolo[2,3-b]pyrazine-7-carboxylic acid isopropylamide | |
| I-231 | 1-{2-[3-(3-Methoxy-pyrrolidin-1-yl)-phenyl]-5H-pyrrolo[2,3-b]pyrazin-7-yl}-2,2-dimethyl-propan-1-one | |
| I-232 | 1-{2-[3-(4-Methoxy-benzyloxy)-phenyl]-5H-pyrrolo[2,3-b]pyrazin-7-yl}-2,2-dimethyl-propan-1-one | |
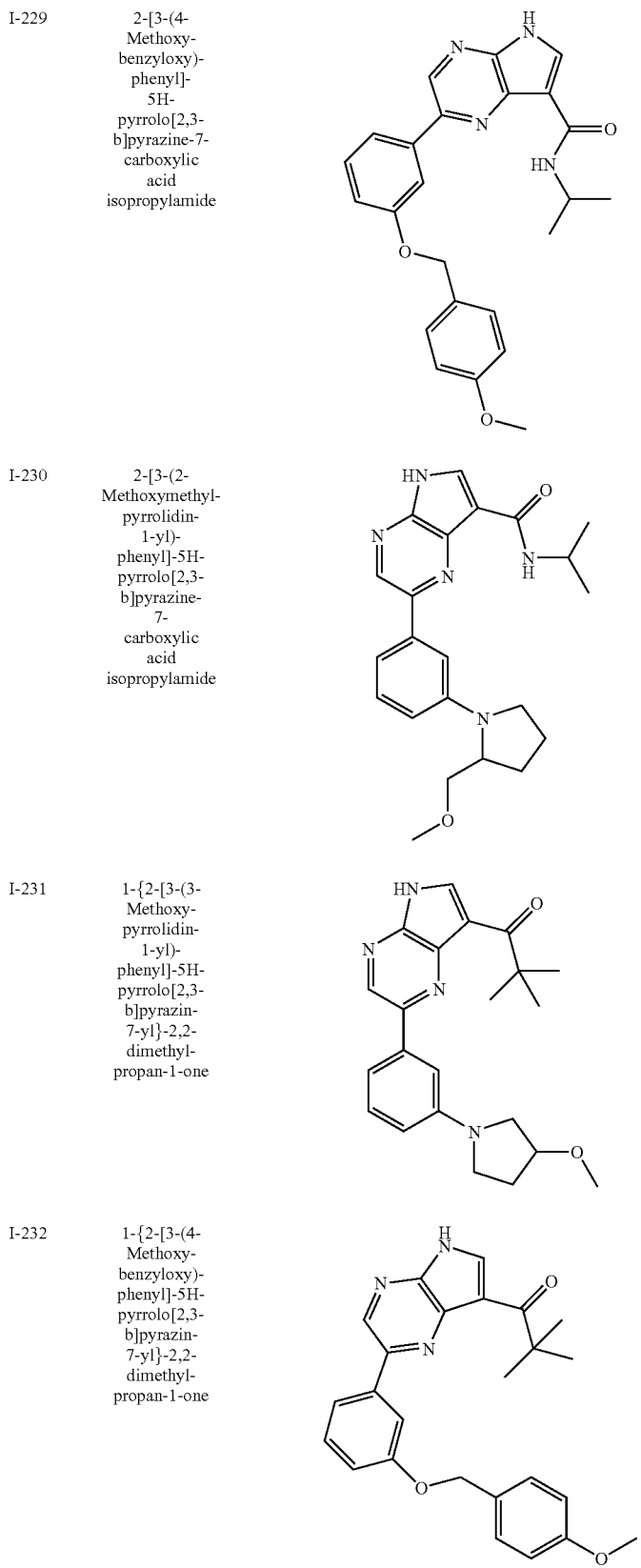

TABLE I-continued
| | | |
|---|---|---|
| I-233 | 1-[2-(3-Iodo-phenyl)-5H-pyrrolo[2,3-b]pyrazin-7-yl]-2,2-dimethyl-propan-1-one | 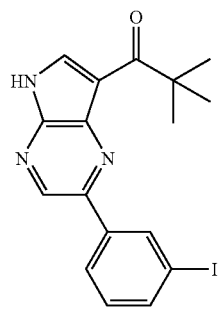 |
| I-234 | 1-{2-[3-(3-Ethylamino-pyrrolidin-1-yl)-phenyl]-5H-pyrrolo[2,3-b]pyrazin-7-yl}-2,2-dimethyl-propan-1-one | 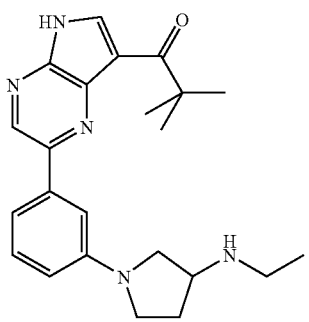 |
| I-235 | ((3aS,6aS)-1-Methyl-octahydro-pentalen-1-yl)-[2-(3-pyrrolidin-1-yl-phenyl)-5H-pyrrolo[2,3-b]pyrazin-7-yl]-methanone | 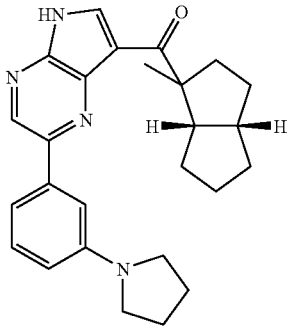 |
| I-236 | 1-{3-[7-(2,2-Dimethyl-propionyl)-5H-pyrrolo[2,3-b]pyrazin-2-yl]-phenyl}-3-methyl-pyrrolidine-3-carboxylic acid methyl ester | 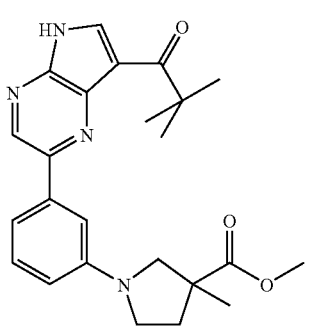 |

TABLE I-continued

| I-237 | (1-{3-[7-(2,2-Dimethyl-propionyl)-5H-pyrrolo[2,3-b]pyrazin-2-yl]-phenyl}-3-methyl-pyrrolidin-3-yl)-carbamic acid benzyl ester | 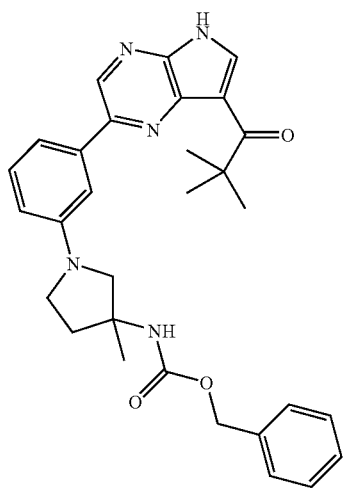 |
| --- | --- | --- |
| I-238 | 1-{3-[7-(2,2-Dimethyl-propionyl)-5H-pyrrolo[2,3-b]pyrazin-2-yl]-phenyl}-3-methyl-pyrrolidine-3-carboxylic acid methylamide | 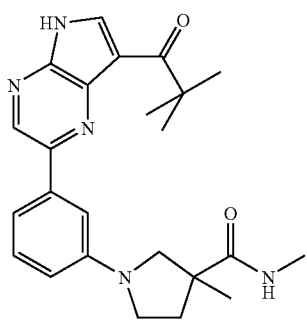 |
| I-239 | [2-(3-Iodo-phenyl)-5H-pyrrolo[2,3-b]pyrazin-7-yl]-(1-methyl-cyclohexyl)-methanone | 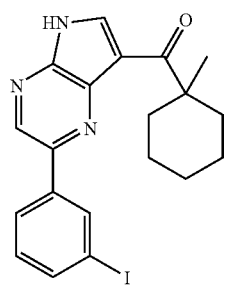 |
| I-240 | ((1S,2S)-1,2-Dimethyl-cyclopentyl)-[2-(3,4,5-trimethoxy-phenyl)-5H-pyrrolo[2,3-b]pyrazin-7-yl]-methanone | 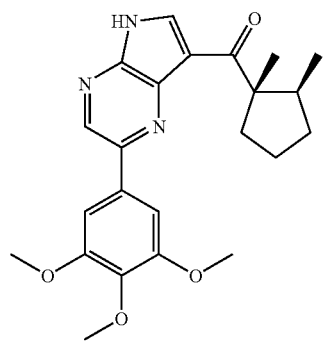 |

TABLE I-continued

| | | |
|---|---|---|
| I-241 | 1-{2-[3-(3-Amino-3-methyl-pyrrolidin-1-yl)-phenyl]-5H-pyrrolo[2,3-b]pyrazin-7-yl}-2,2-dimethyl-propan-1-one | |
| I-242 | (1-{3-[7-(2,2-Dimethyl-propionyl)-5H-pyrrolo[2,3-b]pyrazin-2-yl]-phenyl}-3-methyl-pyrrolidin-3-yl)-carbamic acid ethyl ester | |
| I-243 | (1-{3-[7-(2,2-Dimethyl-propionyl)-5H-pyrrolo[2,3-b]pyrazin-2-yl]-phenyl}-4,4-dimethyl-pyrrolidin-3-yl)-carbamic acid ethyl ester | |
| I-244 | 3-Methyl-3-[2-(3,4,5-trimethoxy-phenyl)-5H-pyrrolo[2,3-b]pyrazine-7-carbonyl]-cyclopentanone | |

TABLE I-continued
| I-245 | 1-{2-Methyl-2-[2-(3,4,5-trimethoxyphenyl)-5H-pyrrolo[2,3-b]pyrazine-7-carbonyl]-pyrrolidin-1-yl}-ethanone | 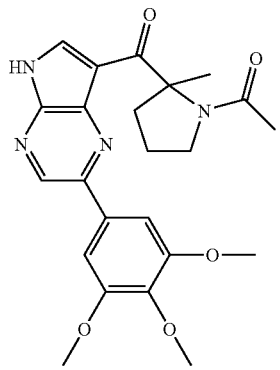 |
| --- | --- | --- |
| I-246 | (1-Methyl-cyclohexyl)-[2-(3,4,5-trimethoxyphenyl)-5H-pyrrolo[2,3-b]pyrazin-7-yl]-methanone | 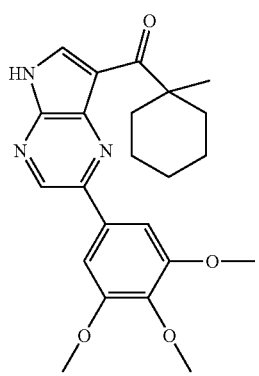 |
| I-247 | (1-Methyl-cyclohexyl)-[2-(3-pyrrolidin-1-yl-phenyl)-5H-pyrrolo[2,3-b]pyrazin-7-yl]-methanone | 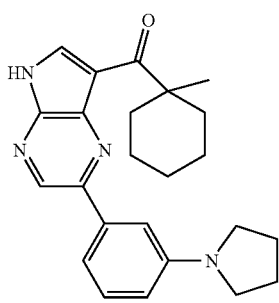 |
| I-248 | 3-[7-(2,2-Dimethyl-propionyl)-5H-pyrrolo[2,3-b]pyrazin-2-yl]-benzoic acid | 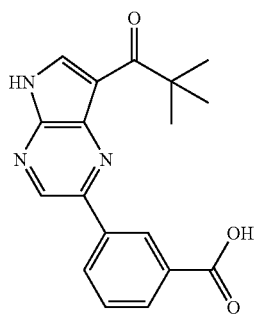 |

| | | |
|---|---|---|
| I-249 | (1-Methyl-cyclopentyl)-[2-(3-pyrrolidin-1-yl-phenyl)-5H-pyrrolo[2,3-b]pyrazin-7-yl]-methanone | 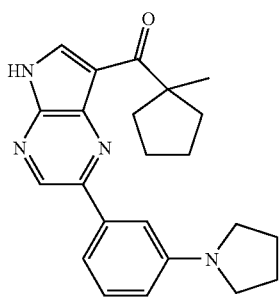 |
| I-250 | 4-Methoxy-1-[2-(3,4,5-trimethoxy-phenyl)-5H-pyrrolo[2,3-b]pyrazin-7-yl]-pentan-1-one | 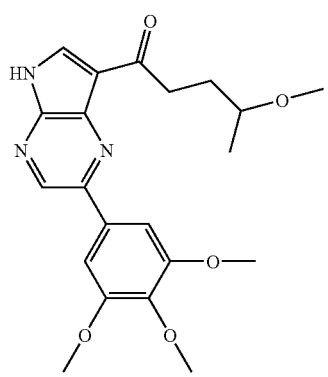 |
| I-251 | (1-Methyl-cycloheptyl)-[2-(3-pyrrolidin-1-yl-phenyl)-5H-pyrrolo[2,3-b]pyrazin-7-yl]-methanone | 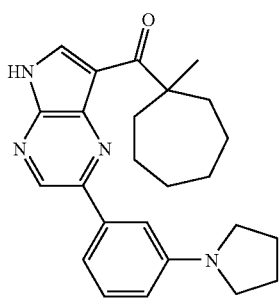 |
| I-252 | 2-Methoxy-2-methyl-1-[2-(3,4,5-trimethoxy-phenyl)-5H-pyrrolo[2,3-b]pyrazin-7-yl]-propan-1-one | 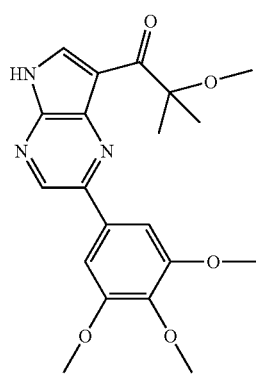 |

TABLE I-continued

| | | |
|---|---|---|
| I-253 | 2-Methoxy-1-[2-(3,4,5-trimethoxy-phenyl)-5H-pyrrolo[2,3-b]pyrazin-7-yl]-ethanone | |
| I-254 | 1-[2-(3-Benzyloxy-phenyl)-5H-pyrrolo[2,3-b]pyrazin-7-yl]-2,2-dimethyl-propan-1-one | |
| I-255 | 1-[2-(3-Ethoxy-phenyl)-5H-pyrrolo[2,3-b]pyrazin-7-yl]-2,2-dimethyl-propan-1-one | |
| I-256 | 1-[2-(3-Isobutoxy-phenyl)-5H-pyrrolo[2,3-b]pyrazin-7-yl]-2,2-dimethyl-propan-1-one | |
| I-257 | 1-[2-(3-Isopropoxy-phenyl)-5H-pyrrolo[2,3-b]pyrazin-7-yl]-2,2-dimethyl-propan-1-one | |

TABLE I-continued
| I-258 | 2,2-Dimethyl-1-[2-(3-propoxyphenyl)-5H-pyrrolo[2,3-b]pyrazin-7-yl]-propan-1-one | 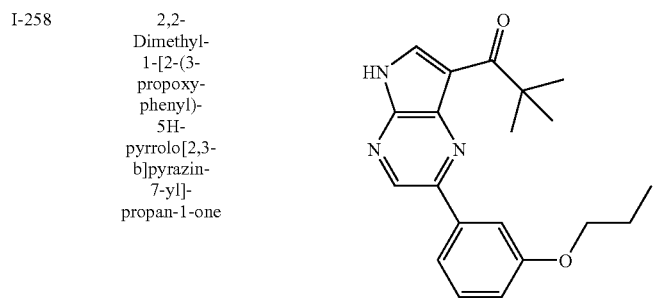 |
| --- | --- | --- |
| I-259 | Adamantan-1-yl-[2-(3,4,5-trimethoxyphenyl)-5H-pyrrolo[2,3-b]pyrazin-7-yl]-methanone | 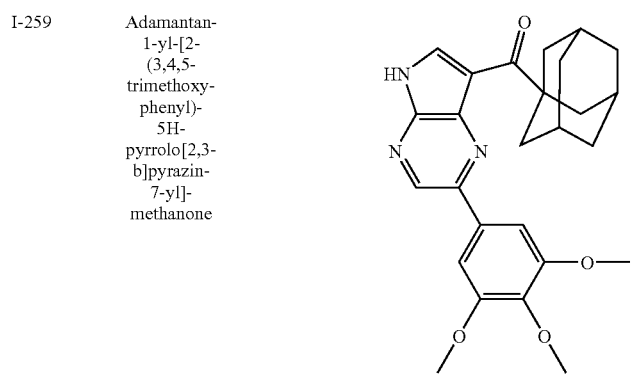 |
| I-260 | 3-Methoxy-2,2-dimethyl-1-[2-(3,4,5-trimethoxyphenyl)-5H-pyrrolo[2,3-b]pyrazin-7-yl]-propan-1-one | 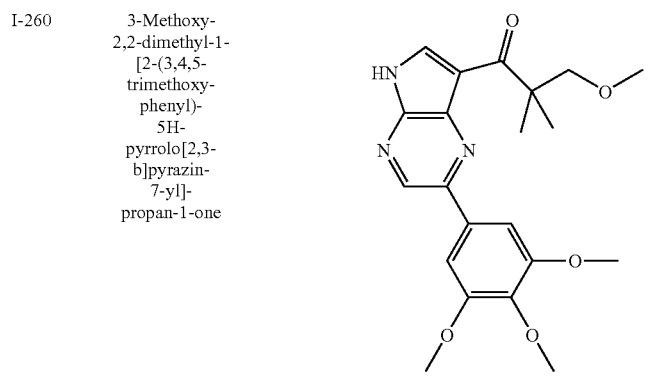 |
| I-261 | 1-[2-(3-Ethylphenyl)-5H-pyrrolo[2,3-b]pyrazin-7-yl]-2,2-dimethyl-propan-1-one | 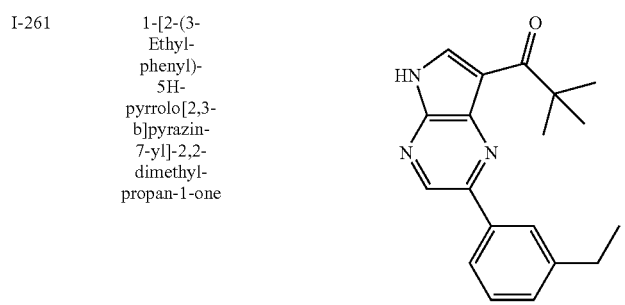 |

TABLE I-continued
| | | |
|---|---|---|
| I-262 | 1-[2-(3,5-Dimethoxy-phenyl)-5H-pyrrolo[2,3-b]pyrazin-7-yl]-2,2-dimethyl-propan-1-one | 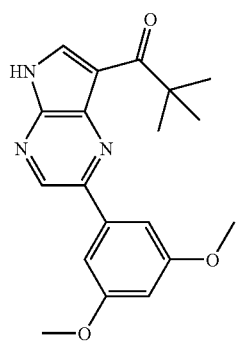 |
| I-263 | 1-{2-[3-(3-Hydroxy-propyl)-phenyl]-5H-pyrrolo[2,3-b]pyrazin-7-yl}-2,2-dimethyl-propan-1-one | 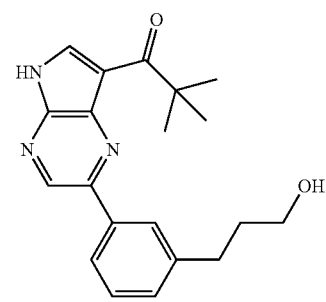 |
| I-264 | 1-[2-(3-Aminomethyl-phenyl)-pyrrolo[2,3-b]pyrazin-7-yl]-2,2-dimethyl-propan-1-one | 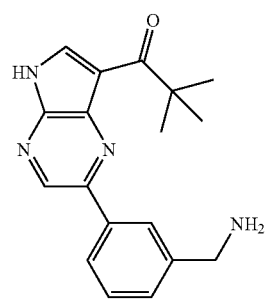 |
| I-265 | 1-{2-[3-(2-Hydroxy-ethyl)-phenyl]-5H-pyrrolo[2,3-b]pyrazin-7-yl}-2,2-dimethyl-propan-1-one | 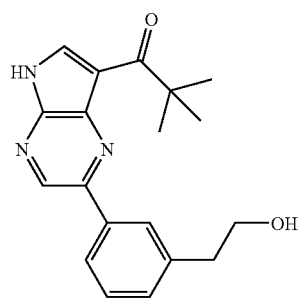 |
| I-266 | 3-Hydroxy-2,2-dimethyl-1-[2-(3,4,5-trimethoxy-phenyl)-5H-pyrrolo[2,3-b]pyrazin-7-yl]-propan-1-one | 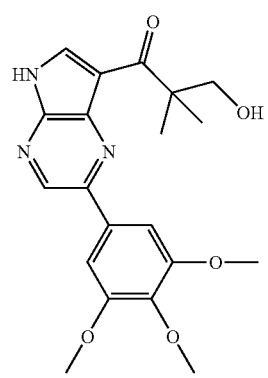 |

| | | |
|---|---|---|
| I-267 | 2,2-Dimethyl-1-[2-(3-piperidin-1-ylmethyl-phenyl)-5H-pyrrolo[2,3-b]pyrazin-7-yl]-propan-1-one | 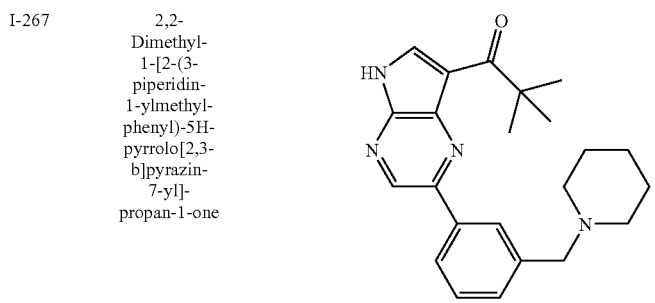 |
| I-268 | 4-[7-(2,2-Dimethyl-propionyl)-5H-pyrrolo[2,3-b]pyrazin-2-yl]-benzoic acid | 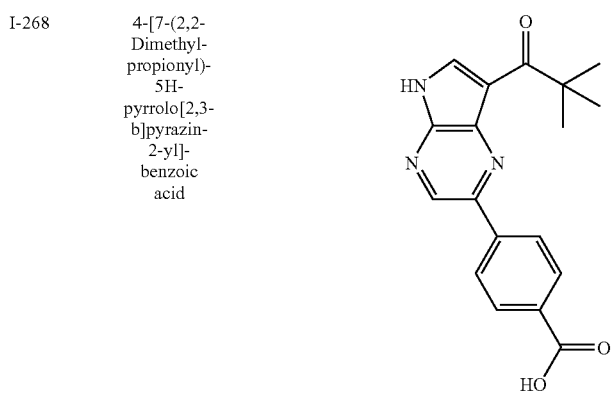 |
| I-269 | (1-Methyl-cyclopentyl)-[2-(3,4,5-trimethoxy-phenyl)-5H-pyrrolo[2,3-b]pyrazin-7-yl]-methanone | 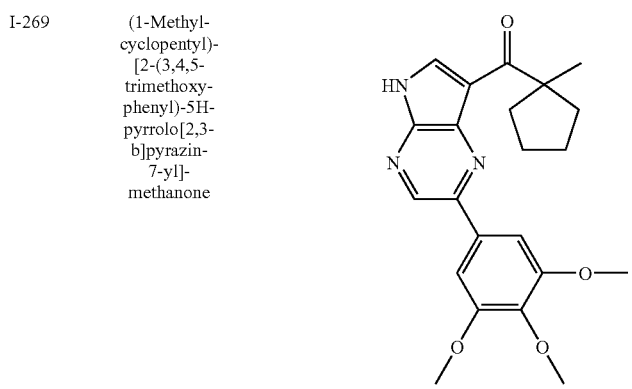 |
| I-270 | (1-Methyl-cyclohexyl)-[2-(3-morpholin-4-yl-phenyl)-5H-pyrrolo[2,3-b]pyrazin-7-yl]-methanone | 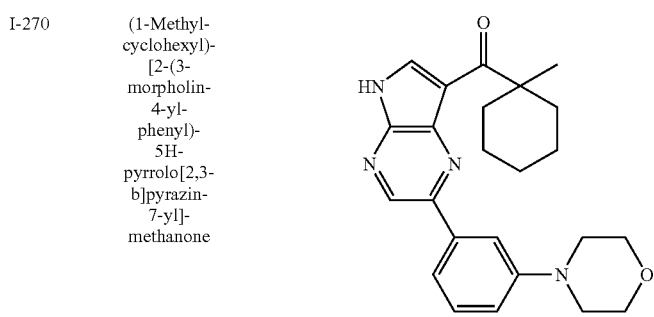 |

TABLE I-continued
| | | |
|---|---|---|
| I-271 | 4-{3-[7-(1-Methyl-cyclohexanecarbonyl)-5H-pyrrolo[2,3-b]pyrazin-2-yl]-phenyl}-piperazine-1-carboxylic acid tert-butyl ester | 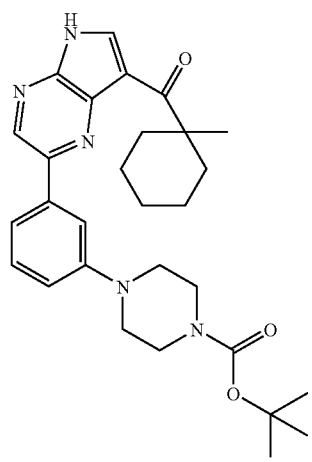 |
| I-272 | (1-Methyl-cyclohexyl)-[2-(3-piperazin-1-yl-phenyl)-5H-pyrrolo[2,3-b]pyrazin-7-yl]-methanone | 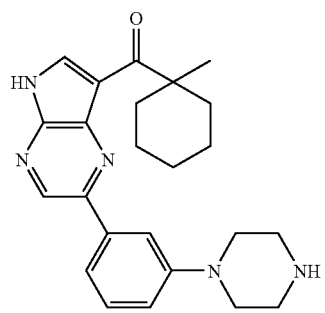 |
| I-273 | (1-Methyl-cyclopentyl)-[2-(3-morpholin-4-yl-phenyl)-5H-pyrrolo[2,3-b]pyrazin-7-yl]-methanone | 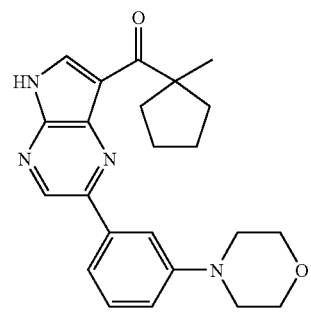 |
| I-274 | 1-[2-(2-Fluoro-phenyl)-5H-pyrrolo[2,3-b]pyrazin-7-yl]-2,2-dimethyl-propan-1-one | 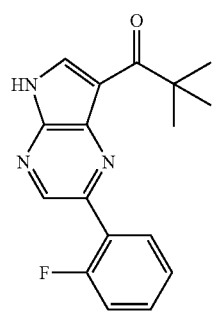 |

TABLE I-continued

| | | |
|---|---|---|
| I-275 | 1-(4-{3-[7-(1-Methyl-cyclohexanecarbonyl)-5H-pyrrolo[2,3-b]pyrazin-2-yl]-phenyl}-piperazin-1-yl)-ethanone | |
| I-276 | (1-Methyl-cyclohexyl)-{2-[3-(5-methyl-[1,3,4]oxadiazol-2-yl)-phenyl]-5H-pyrrolo[2,3-b]pyrazin-7-yl}-methanone | |
| I-277 | {2-[3-(3-Hydroxy-propyl)-phenyl]-5H-pyrrolo[2,3-b]pyrazin-7-yl}-(1-methyl-cyclohexyl)-methanone | |
| I-278 | 4-{4-[7-(1-Methyl-cyclohexanecarbonyl)-5H-pyrrolo[2,3-b]pyrazin-2-yl]-phenyl}-piperazine-1-carboxylic acid tert-butyl ester | |

TABLE I-continued
| I-279 | [2-(3-Methoxy-phenyl)-5H-pyrrolo[2,3-b]pyrazin-7-yl]-(1-methyl-cyclohexyl)-methanone | 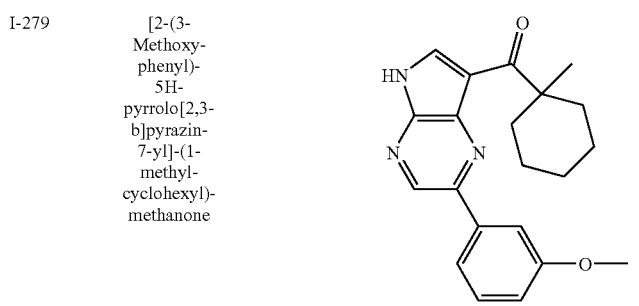 |
| I-280 | (1-Methyl-cyclohexyl)-[2-(4-piperazin-1-yl-phenyl)-5H-pyrrolo[2,3-b]pyrazin-7-yl]-methanone | 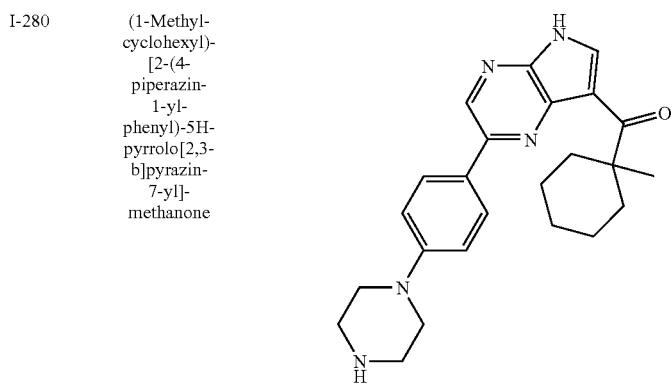 |
| I-281 | 1-(4-{4-[7-(1-Methyl-cyclohexane-carbonyl)-5H-pyrrolo[2,3-b]pyrazin-2-yl]-phenyl}-piperazin-1-yl)-ethanone | 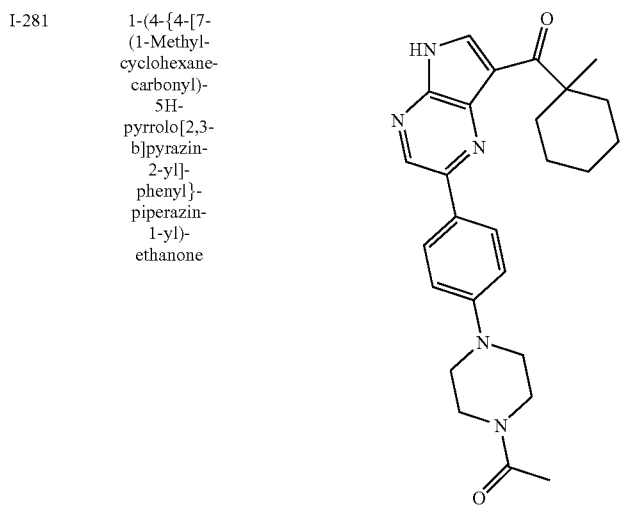 |
| I-282 | 1-[2-(2-Hydroxy-phenyl)-5H-pyrrolo[2,3-b]pyrazin-7-yl]-2,2-dimethyl-propan-1-one | 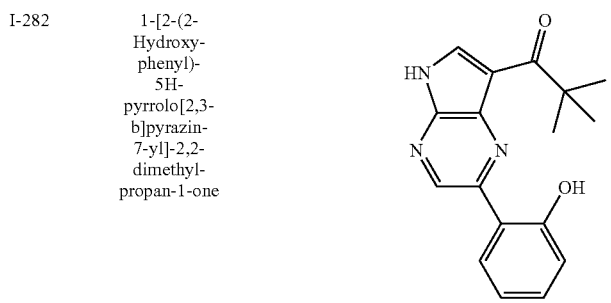 |

TABLE I-continued
| I-283 | (4-Hydroxy-1-methyl-cyclohexyl)-[2-(3,4,5-trimethoxy-phenyl)-5H-pyrrolo[2,3-b]pyrazin-7-yl]-methanone | 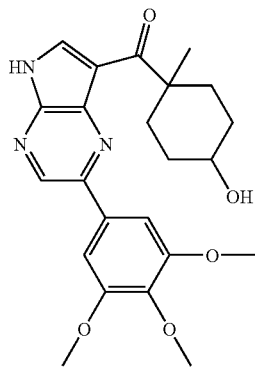 |
| I-284 | [2-(4-Dimethylamino-phenyl)-5H-pyrrolo[2,3-b]pyrazin-7-yl]-(1-methyl-cyclohexyl)-methanone | 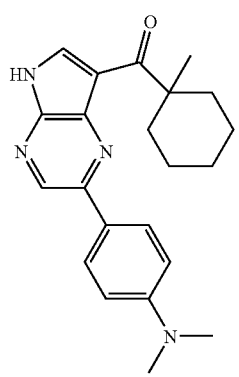 |
| I-285 | 3-(4-{3-[7-(1-Methyl-cyclohexanecarbonyl)-5H-pyrrolo[2,3-b]pyrazin-2-yl]-phenyl}-piperazin-1-yl)-3-oxo-propionitrile | 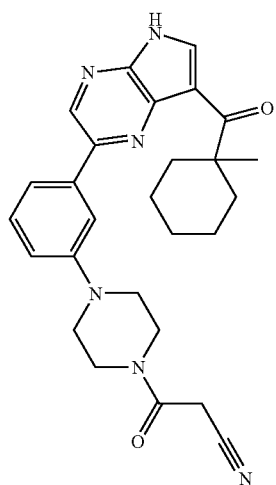 |

| | | |
|---|---|---|
| I-286 | 4-(4-{3-[7-(1-Methyl-cyclohexanecarbonyl)-5H-pyrrolo[2,3-b]pyrazin-2-yl]-phenyl}-piperazine-1-carbonyl)-piperidine-1-carboxylic acid tert butyl ester | 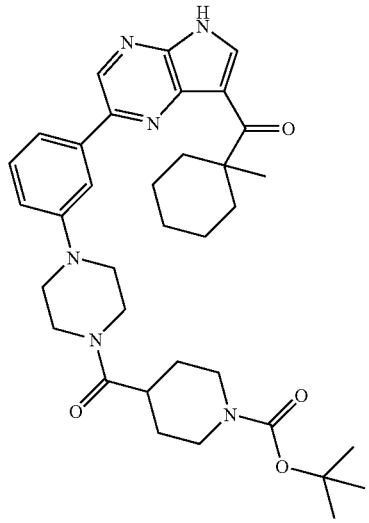 |
| I-287 | 4-{3-[7-(1-Methyl-cyclohexanecarbonyl)-5H-pyrrolo[2,3-b]pyrazin-2-yl]-phenyl}-piperazine-1-sulfonyl carbamic acid tert-butyl ester | 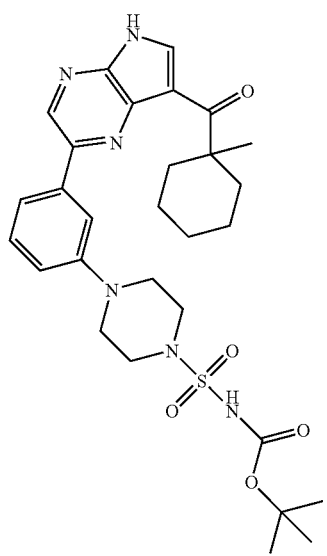 |
| I-288 | {2-[3-(4-Methanesulfonyl-piperazin-1-yl)-phenyl]-5H-pyrrolo[2,3-b]pyrazin-7-yl}-(1-methyl-cyclohexyl)-methanone | 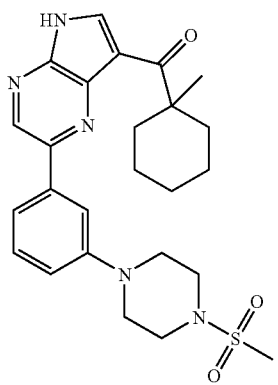 |

TABLE I-continued

| | | |
|---|---|---|
| I-289 | 4-{3-[7-(1-Methyl-cyclohexanecarbonyl)-5H-pyrrolo[2,3-b]pyrazin-2-yl]-phenyl}-piperazine-1-sulfonic acid amide | |
| I-290 | (1-Methyl-cyclohexyl)-(2-{3-4[4-(piperidine-4-carbonyl)-piperazin-1-yl]-phenyl}-5H-pyrrolo[2,3-b]pyrazin-7-yl)-methanone | |
| I-291 | (1-Methyl-cyclohexyl)-[2-(4-piperidin-1-yl-phenyl)-5H-pyrrolo[2,3-b]pyrazin-7-yl]-methanone | |

TABLE I-continued

| | | |
|---|---|---|
| I-292 | [2-(4-Diethylamino-phenyl)-5H-pyrrolo[2,3-b]pyrazin-7-yl]-(1-methyl-cyclohexyl)-methanone | |
| I-293 | (1,3-Dimethyl-cyclohexyl)-[2-(3,4,5-trimethoxy-phenyl)-5H-pyrrolo[2,3-b]pyrazin-7-yl]-methanone | |
| I-294 | (1-Methyl-cyclohexyl)-[2-(4-morpholin-4-yl-phenyl)-5H-pyrrolo[2,3-b]pyrazin-7-yl]-methanone | |
| I-295 | (1-Methyl-cyclohexyl)-{2-[4-(4-methyl-piperazin-1-yl)-phenyl]-5H-pyrrolo[2,3-b]pyrazin-7-yl}-methanone | |

TABLE I-continued
| | | |
|---|---|---|
| I-296 | [2-(4-Methylamino-phenyl)-5H-pyrrolo[2,3-b]pyrazin-7-yl]-(1-methyl-cyclohexyl)-methanone | 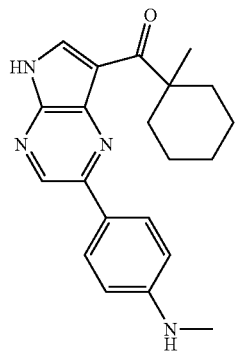 |
| I-297 | (4-Hydroxy-1-methyl-cyclohexyl)-[2-(3,4,5-trimethoxy-phenyl)-5H-pyrrolo[2,3-b]pyrazin-7-yl]-methanone | 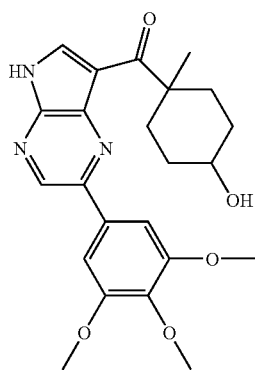 |
| I-298 | 4-[7-(2,2-Dimethyl-propionyl)-5H-pyrrolo[2,3-b]pyrazin-2-yl]-N-methyl-benzenesulfonamide | 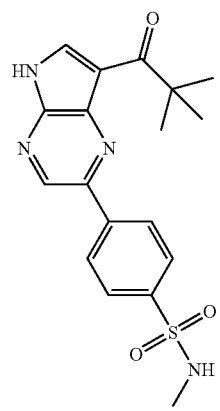 |
| I-299 | 4-[7-(2,2-Dimethyl-propionyl)-5H-pyrrolo[2,3-b]pyrazin-2-yl]-benzenesulfonamide | 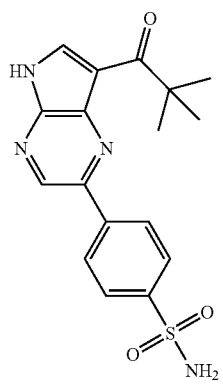 |

TABLE I-continued
| I-300 | 3-[7-(2,2-Dimethyl-propionyl)-5H-pyrrolo[2,3-b]pyrazin-2-yl]-benzenesulfonamide | 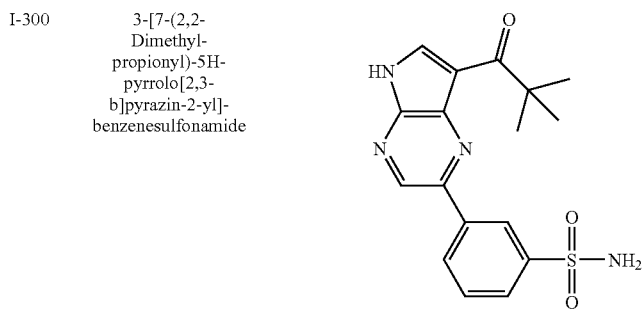 |
| --- | --- | --- |
| I-301 | 3-[7-(2,2-Dimethyl-propionyl)-5H-pyrrolo[2,3-b]pyrazin-2-yl]-N-methyl-benzenesulfonamide | 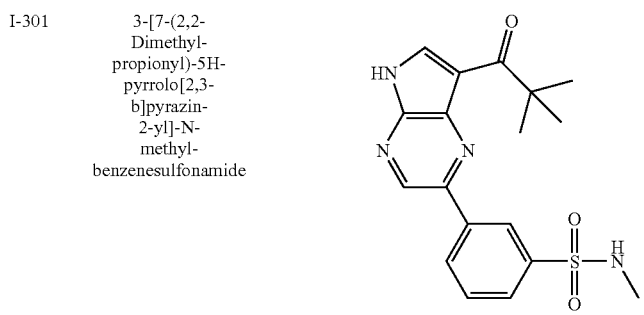 |
| I-302 | 1{2-[3-(2,8-Diaza-spiro[4.5]dec-2-yl)-phenyl]-5H-pyrrolo[2,3-b]pyrazin-7-yl}-2,2-dimethyl-propan-1-one | 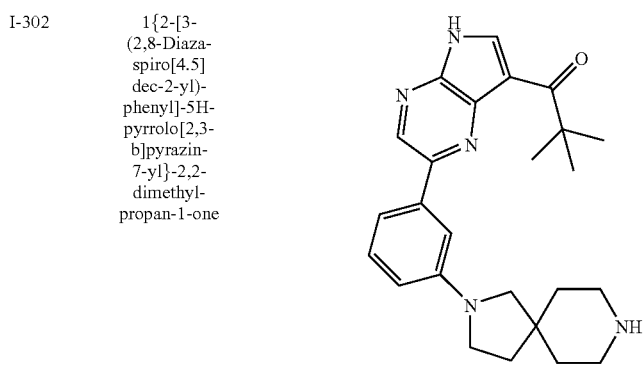 |
| I-303 | 1-{2-[3-(2,7-Diaza-spiro[4.4]non-2-yl)-phenyl]-5H-pyrrolo[2,3-b]pyrazin-7-yl}-2,2-dimethyl-propan-1-one | 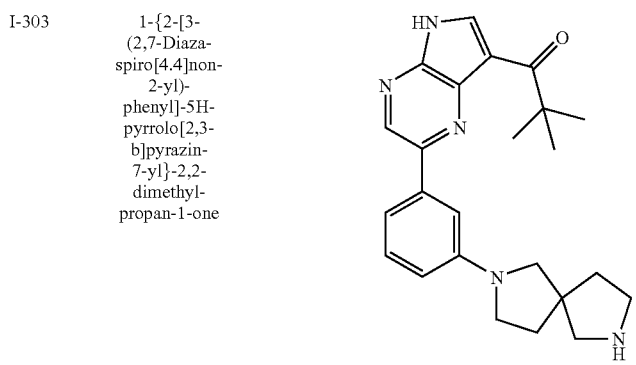 |

TABLE I-continued

| I-304 | 1-{2-[3-(3-Aminomethyl-pyrrolidin-1-yl)-phenyl]-5H-pyrrolo[2,3-b]pyrazin-7-yl}-2,2-dimethyl-propan-1-one | |
|---|---|---|
| I-305 | 1-{2-[3-(3,3-Dimethyl-piperazin-1-yl)-phenyl]-5H-pyrrolo[2,3-b]pyrazin-7-yl}-2,2-dimethyl-propan-1-one | |
| I-306 | 1-{2-[3-(2,7-Diaza-spiro[4.5]dec-2-yl)-phenyl]-5H-pyrrolo[2,3-b]pyrazin-7-yl}-2,2-dimethyl-propan-1-one | |
| I-307 | 1-{2-[3-(3-Dimethylamino-pyrrolidin-1-yl)-phenyl]-5H-pyrrolo[2,3-b]pyrazin-7-yl}-2,2-dimethyl-propan-1-one | |

TABLE I-continued

| | | |
|---|---|---|
| I-308 | 1-{2-[3-(2-Hydroxy-2-methyl-propylamino)-phenyl]-5H-pyrrolo[2,3-b]pyrazin-7-yl}2,2-dimethyl-propan-1-one | |
| I-309 | 1-{2-[3-(4-Amino-piperidin-1-yl)-phenyl]-5H-pyrrolo[2,3-7-yl}-2,2-dimethyl-propan-1-one | |
| I-310 | 2,2-Dimethyl-1-{2-[3-(3-methyl-piperazin-1-yl)-phenyl]-5H-pyrrolo[2,3-b]pyrazin-7-yl}-propan-1-one | |
| I-311 | 1-{2-[3-(4-Acetyl-3,3-dimethyl-piperazin-1-yl)-phenyl]-5H-pyrrolo[2,3-b]pyrazin-7-yl}-2,2-dimethyl-propan-1-one | |

TABLE I-continued

| | | |
|---|---|---|
| I-312 | 1-{2-[3-(3-Amino-azetidin-1-yl)-phenyl]-5H-pyrrolo[2,3-b]pyrazin-7-yl}-2,2-dimethyl-propan-1-one | |
| I-313 | 1-{2-[3-(3-Chloro-2-hydroxy-propylamino)-phenyl]-5H-pyrrolo[2,3-b]pyrazin-7-yl}-2,2-dimethyl-propan-1-one | |
| I-314 | 1-{2-[3-(2,2-Dimethyl-propylamino)-phenyl]-5H-pyrrolo[2,3-b]pyrazin-7-yl}-2,2-dimethyl-propan-1-one | |
| I-315 | (1-Methyl-cyclohexyl)-[2-(3,4,5-trimethoxy-phenyl)-5H-pyrrolo[2,3-b]pyrazin-7-yl]-methanone | |

| | | |
|---|---|---|
| I-316 | 1-[2-(3-Fluoro-phenyl)-5H-pyrrolo[2,3-b]pyrazin-7-yl]-2,2-dimethyl-propan-1-one | 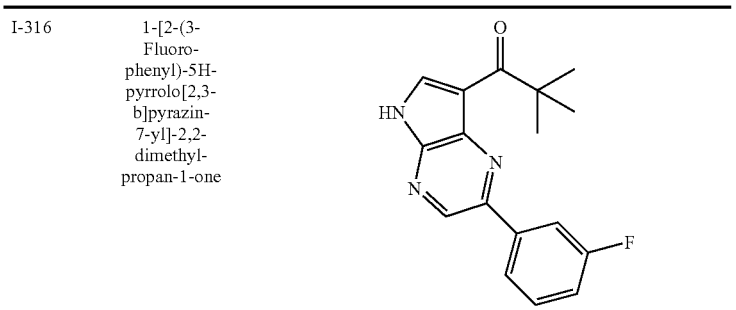 |
| I-317 | (1-Methyl-cyclohexyl)-[2-(3-pyrrolidin-1-yl-phenyl)-5H-pyrrolo[2,3-b]pyrazin-7-yl]-methanone | 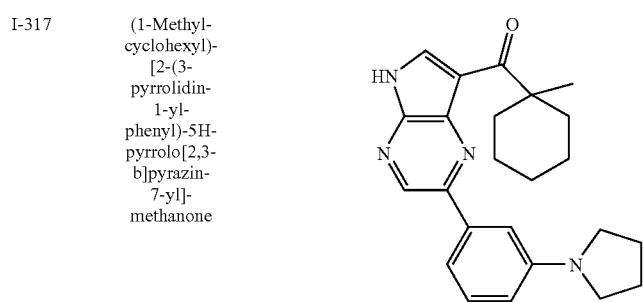 |
| I-318 | 2,2-Dimethyl-1-(2-phenyl-5H-pyrrolo[2,3-b]pyrazin-7-yl)-propan-1-one | 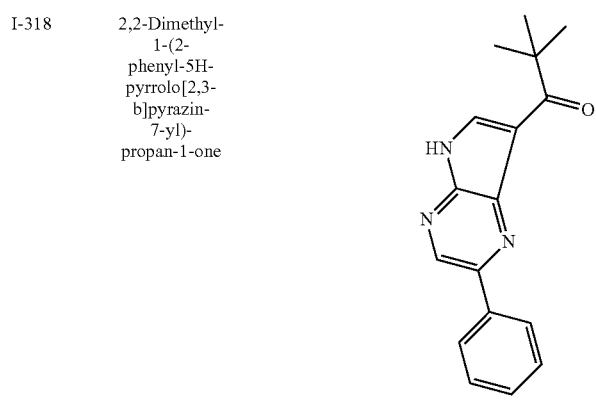 |
| I-319 | 2,2-Dimethyl-1-[2-(3,4,5-trimethoxy-phenyl)-5H-pyrrolo[2,3-b]pyrazin-7-yl]-pent-4-en-1-one | 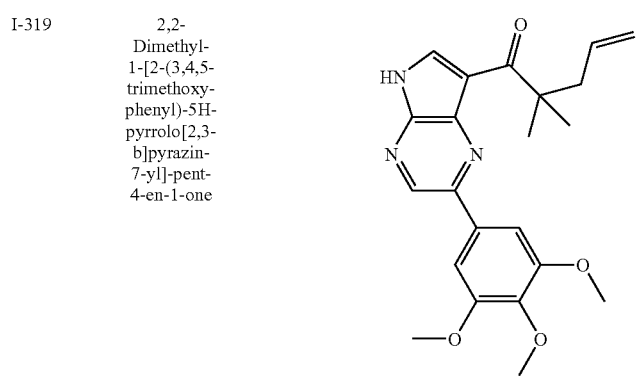 |

TABLE I-continued

| | | |
|---|---|---|
| I-320 | 2,2-Dimethyl-1-[2-(3,4,5-trimethoxyphenyl)-5H-pyrrolo[2,3-b]pyrazin-7-yl]-pentan-1-one | |
| I-321 | 2,2-Dimethyl-4-morpholin-4-yl-1-[2-(3,4,5-trimethoxyphenyl)-5H-pyrrolo[2,3-b]pyrazin-7-yl]-butan-1-one | |
| I-322 | 4,4-Dimethyl-5-oxo-5-[2-(3,4,5-trimethoxyphenyl)-5H-pyrrolo[2,3-b]pyrazin-7-yl]-pentanenitrile | |
| I-323 | 5,5-Dimethyl-6-oxo-6-[2-(3,4,5-trimethoxyphenyl)-5H-pyrrolo[2,3-b]pyrazin-7-yl]-hexanenitrile | |

TABLE I-continued

| | | |
|---|---|---|
| I-324 | 2,2-Dimethyl-1-[2-(3-pyrazol-1-yl-phenyl)-5H-pyrrolo[2,3-b]pyrazin-7-yl]-propan-1-one | |
| I-325 | 2,2-Dimethyl-1-{2-[3-(5-methyl-[1,3,4]oxadiazol-2-yl)-phenyl]-5H-pyrrolo[2,3-b]pyrazin-7-yl}-propan-1-one | |
| I-326 | 2,2-Dimethyl-1-{2-[3-(2H-pyrazol-3-yl)-phenyl]-5H-pyrrolo[2,3-b]pyrazin-7-yl}-propan-1-one | |
| I-327 | 3-[7-(2,2-Dimethyl-propionyl)-5H-pyrrolo[2,3-b]pyrazin-2-yl]-N-methyl-benzamide | |
| I-328 | 1-[2-(3-Methoxymethyl-phenyl)-5H-pyrrolo[2,3-b]pyrazin-7-yl]-2,2-dimethyl-propan-1-one | |

TABLE I-continued

| I-329 | 1-[2-(4-Methoxymethyl-phenyl)-5H-pyrrolo[2,3-b]pyrazin-7-yl]-2,2-dimethyl-propan-1-one | |
| --- | --- | --- |
| I-330 | N-Cyclopentyl-3-[7-(2,2-dimethyl-propionyl)-5H-pyrrolo[2,3-b]pyrazin-2-yl]-benzamide | |
| I-331 | 3-[7-(2,2-Dimethyl-propionyl)-5H-pyrrolo[2,3-b]pyrazin-2-yl]-benzoic acid | |
| I-332 | 1-[2-(3-Isopropenyl-phenyl)-5H-pyrrolo[2,3-b]pyrazin-7-yl]-2,2-dimethyl-propan-1-one | |
| I-333 | 1-[2-(3-Hydroxy-phenyl)-5H-pyrrolo[2,3-b]pyrazin-7-yl]-2,2-dimethyl-propan-1-one | |

TABLE I-continued
| I-334 | 1-[2-(3-tert-Butyl-5-methyl-phenyl)-5H-pyrrolo[2,3-b]pyrazin-7-yl]-2,2-dimethyl-propan-1-one | 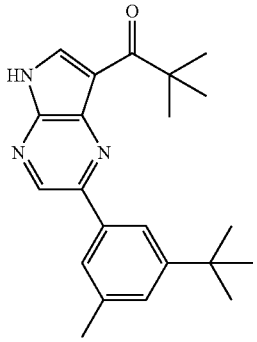 |
| I-335 | 1-(2-Biphenyl-3-yl-5H-pyrrolo[2,3-b]pyrazin-7-yl)-2,2-dimethyl-propan-1-one | 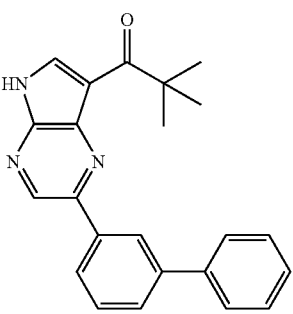 |
| I-336 | 1-[2-(3-tert-Butoxymethyl-phenyl)-5H-pyrrolo[2,3-b]pyrazin-7-yl]-2,2-dimethyl-propan-1-one | 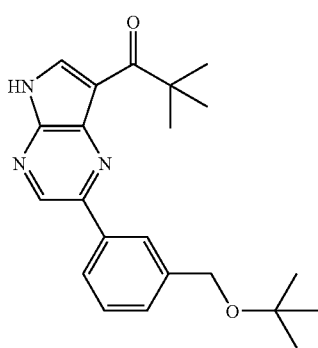 |
| I-337 | 1-[2-(3-Isopropyl-phenyl)-5H-pyrrolo[2,3-b]pyrazin-7-yl]-2,2-dimethyl-propan-1-one | 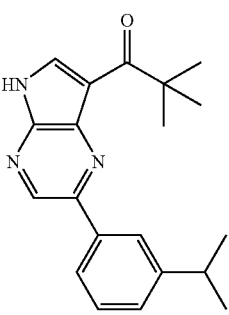 |

| | | |
|---|---|---|
| I-338 | 1-{2-[3-(3,5-Dimethyl-isoxazol-4-yl)-phenyl]-5H-pyrrolo[2,3-b]pyrazin-7-yl}-2,2-dimethyl-propan-1-one | |
| I-339 | 1-{2-(3-Bromo-phenyl)-5H-pyrrolo[2,3-b]pyrazin-7-yl]-2,2-dimethyl-propan-1-one | |
| I-340 | 2,2-Dimethyl-1-{2-[3-(2-methyl-2H-pyrazol-3-yl)-phenyl]-5H-pyrrolo[2,3-b]pyrazin-7-yl}-propan-1-one | |
| I-341 | 1-[2-(3-Chloro-4-fluoro-phenyl)-5H-pyrrolo[2,3-b]pyrazin-7-yl]-2,2-dimethyl-propan-1-one | |

TABLE I-continued

| | | |
|---|---|---|
| I-342 | 2,2-Dimethyl-1-[2-(2'-methyl-biphenyl-3-yl)-5H-pyrrolo[2,3-b]pyrazin-7-yl]-propan-1-one | |
| I-343 | 1-[2-(3-Hydroxymethyl)-phenyl)-5H-pyrrolo[2,3-b]pyrazin-7-yl]-2,2-dimethyl-propan-1-one | |
| I-344 | 1-[2-(3-Cyclopent-1-enyl-phenyl)-5H-pyrrolo[2,3-b]pyrazin-7-yl]-2,2-dimethyl-propan-1-one | |
| I-345 | 1-[2-(3-Acetyl-4-hydroxy-phenyl)-5H-pyrrolo[2,3-b]pyrazin-7-yl]-2,2-dimethyl-propan-1-one | |
| I-346 | 1-{2-[3-(3H-Imidazol-4-yl)-phenyl]-5H-pyrrolo[2,3-b]pyrazin-7-yl}-2,2-dimethyl-propan-1-one | |

TABLE I-continued

| I-347 | 2,2-Dimethyl-1-[2-(3-oxazol-5-yl-phenyl)-5H-pyrrolo[2,3-b]pyrazin-7-yl]-propan-1-one | |
|---|---|---|
| I-348 | 2,2-Dimethyl-trimethylsilanyl-phenyl)-5H-pyrrolo[2,3-b]pyrazin-7-yl]-propan-1-one | |
| I-349 | 3-{3-[7-(2,2-Dimethyl-propionyl)-5H-pyrrolo[2,3-b]pyrazin-2-yl]-phenyl}-3-oxo-propionitrile | |
| I-350 | 1-[2-(3-Iodo-phenyl)-5H-pyrrolo[2,3-b]pyrazin-7-yl]-2,2-dimethyl-propan-1-one | |
| I-351 | 2,2-Dimethyl-1-{2-[3-(5-trifluoromethyl-2H-pyrazol-3-yl)-phenyl]-5H-pyrrolo[2,3-b]pyrazin-7-yl}-propan-1-one | |

TABLE I-continued

| I-352 | 1-[2-(3-Cyclohex-1-enyl-phenyl)-5H-pyrrolo[2,3-b]pyrazin-7-yl]-2,2-dimethyl-propan-1-one | |
| --- | --- | --- |
| I-353 | 2,2-Dimethyl-1-[2-(3-thiophen-2-yl-phenyl)-5H-pyrrolo[2,3-b]pyrazin-propan-1-one | |
| I-354 | 1-[2-(3-Cyclopentyl-phenyl)-5H-pyrrolo[2,3-b]pyrazin-7-yl]-2,2-dimethyl-propan-1-one | |
| I-355 | 1-(2-Biphenyl-4-yl-5H-pyrrolo[2,3-b]pyrazin-7-yl)-2,2-dimethyl-propan-1-one | |

TABLE I-continued

| | | |
|---|---|---|
| I-356 | 1-[2-(3-Imidazol-1-yl-phenyl)-5H-pyrrolo[2,3-b]pyrazin-7-yl]-2,2-dimethyyl-propan-1-one | |
| I-357 | 2,2-Dimethyl-1-{2-[4-(5-methyl-[1,3,4]oxadiazol-2-yl)-phenyl]-5H-pyrrolo[2,3-b]pyrazin-7-yl}-propan-1-one | |
| I-358 | 2,2-Dimethyl-1-[2-(4-trimethylsilanyl-phenyl)-5H-pyrrolo[2,3-b]pyrazin-7-yl]-propan-1-one | |
| I-359 | 1-[2-(4-Iodo-phenyl)-5H-pyrrolo[2,3-b]pyrazin-7-yl]-2,2-dimethyl-propan-1-one | |

TABLE I-continued
| I-360 | 1-{2-[4-(3,5-Dimethyl-isoxazol-4-yl)-phenyl]-5H-pyrrolo[2,3-b]pyrazin-7-yl}-2,2-dimethyl-propan-1-one | 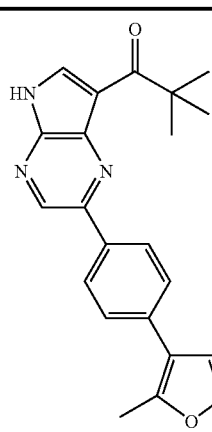 |
| --- | --- | --- |
| I-361 | 2,2-Dimethyl-1-{2-[4-(2-methyl-2H-pyrazol-3-yl)-phenyl]-5H-pyrrolo[2,3-b]pyrazin-7-yl}-propan-1-one | 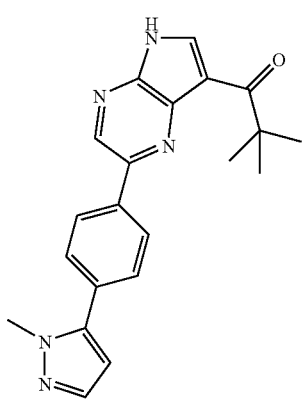 |
| I-362 | 1-{2-[4-(3H-Imidazol-4-yl)-phenyl]-5H-pyrrolo[2,3-b]pyrazin-7-yl}-2,2-dimethyl-propan-1-one | 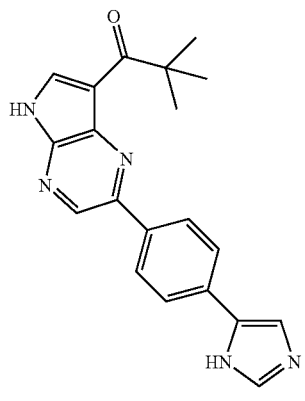 |
| I-363 | 2,2-Dimethyl-1-{2-[4-(2-piperidin-1-yl-ethoxy)-phenyl]-5H-pyrrolo[2,3-b]pyrazin-7-yl}-propan-1-one | 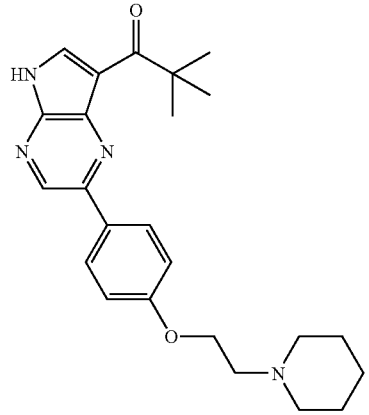 |

TABLE I-continued
| I-364 | 1-{2-[3-(3,3-Dimethyl-pyrrolidin-1-yl)-phenyl]-5H-pyrrolo[2,3-b]pyrazin-7-yl}-2,2-dimethyl-propan-1-one | 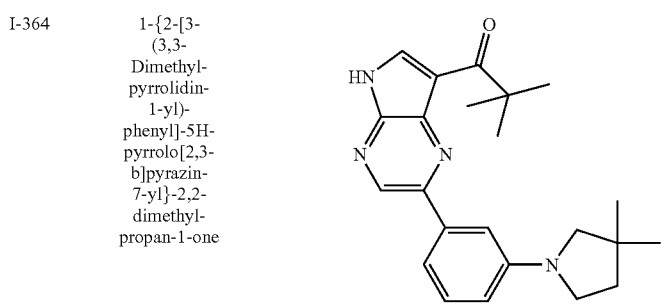 |
| --- | --- | --- |
| I-365 | 3-[7-(2,2-Dimethyl-propionyl)-5H-pyrrolo[2,3-b]pyrazin-2-yl]-N-ethyl-benzamide | 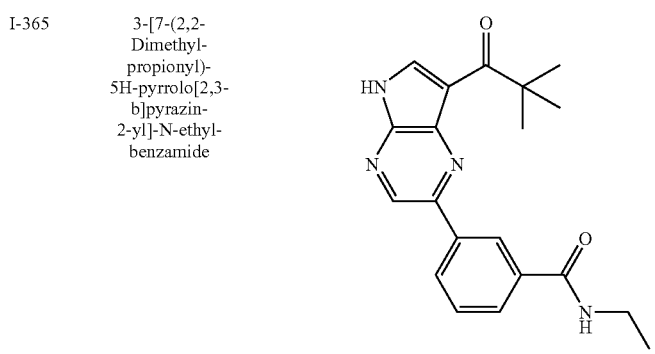 |
| I-366 | 1-{2-[3-((R)-3-Hydroxymethyl-pyrrolidin-1-yl)-phenyl]-5H-pyrrolo[2,3-b]pyrazin-7-yl}-2,2-dimethyl-propan-1-one | 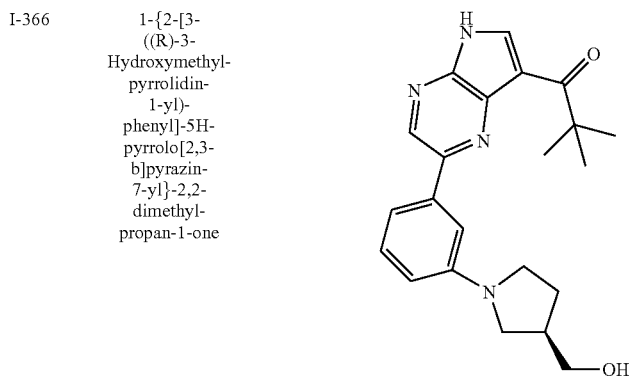 |
| I-367 | 1-{2-[3-((S)-3-Hydroxymethyl-pyrrolidin-1-yl)-phenyl]-5H-pyrrolo[2,3-b]pyrazin-7-yl}-2,2-dimethyl-propan-1-one | 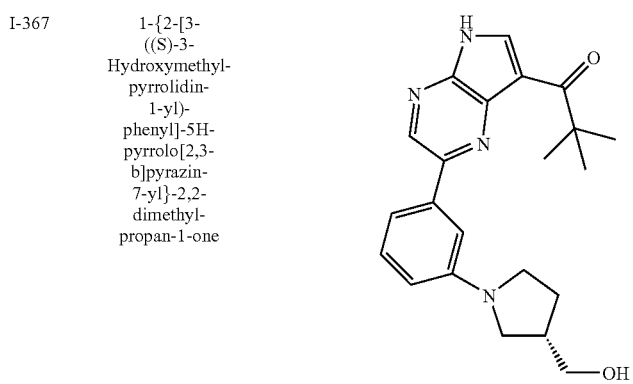 |

TABLE I-continued

| | | |
|---|---|---|
| I-368 | (1-Methyl-cyclohexyl)-{2-[4-(2-piperidin-1-yl-ethoxy)-phenyl]-5H-pyrrolo[2,3-b]pyrazin-7-yl}-methanone | |
| I-369 | 2,2-Dimethyl-1-{2-[3-(1H-pyrazol-4-yl)-phenyl]-5H-pyrrolo[2,3-b]pyrazin-7-yl}-propan-1-one | |
| I-370 | 1-{2-[3-(3,3-Difluoro-azetidin-1-yl)-phenyl]-5H-pyrrolo[2,3-b]pyrazin-7-yl}-2,2-dimethyl-propan-1-one | |
| I-371 | 2,2-Dimethyl-1-{2-[3-(2-oxa-6-aza-spiro[3.3]hept-6-yl)-phenyl]-5H-pyrrolo[2,3-b]pyrazin-7-yl}-propan-1-one | |

TABLE I-continued

| | | |
|---|---|---|
| I-372 | 1-{3-[7-(2,2-Dimethyl-propionyl)-5H-pyrrolo[2,3-b]pyrazin-2-yl]-phenyl}-pyrolidin-2-one | |
| I-373 | 1-{3-[7-(1-Methyl-cyclohexanecarbonyl)-5H-pyrrolo[2,3-b]pyrazin-2-yl]-phenyl}-pyrrolidin-2-one | |
| I-374 | (1-Methyl-cyclohexyl)-[2-(3-pyrrol-1-yl-phenyl)-5H-pyrrolo[2,3-b]pyrazin-7-yl]-methanone | |
| I-375 | 2-[3-(3,3-Dimethyl-pyrrolidin-1-yl)-phenyl]-5H-pyrrolo[2,3-b]pyrazine-7-carboxylic acid isopropylamide | |
| I-376 | 1-{3-[7-(2,2-Dimethyl-propionyl)-5H-pyrrolo[2,3-b]pyrazin-2-yl]-phenyl}-pyrrolidine-3-carbonitrile | |

TABLE I-continued

| | | |
|---|---|---|
| I-377 | 1-{2-[3-(3-Dimethylamino-azetidin-1-yl)-phenyl]-5H-pyrrolo[2,3-b]pyrazin-7-yl}-2,2-dimethyl-propan-1-one | |
| I-378 | 2-[3-(3,3-Dimethyl-pyrrolidin-1-yl)-phenyl]-5H-pyrrolo[2,3-b]pyrazine-7-carboxylic acid (3-hydroxy-2,2-dimethyl-propyl)-amide | |
| I-379 | 1-{2-[3-(3,3-Dimethyl-azetidin-1-yl)-phenyl]-5H-pyrrolo[2,3-b]pyrazin-7-yl}-2,2-dimethyl-propan-1-one | |
| I-380 | 2-[3-(3,3-Dimethyl-pyrrolidin-1-yl)-phenyl]-5H-pyrrolo[2,3-b]pyrazine-7-carboxylic acid tert-butylamide | |
| I-381 | 2-[3-(3,3-Dimethyl-pyrrolidin-1-yl)-phenyl]-5H-pyrrolo[2,3-b]pyrazine-7-carboxylic acid (2-methoxy-propyl)-amide | |

TABLE I-continued

| I-382 | 2-[3-(3,3-Dimethyl-pyrrolidin-1-yl)-phenyl]-5H-pyrrolo[2,3-b]pyrazine-7-carboxylic acid (tetrahydro-pyran-3-yl)-amide | |
|---|---|---|
| I-383 | 2-Methyl-2-phenyl-1-[2-(3,4,5-trimethoxy-phenyl)-5H-pyrrolo[2,3-b]pyrazin-7-yl]-propan-1-one | |
| I-384 | 1-[2-(3,5-Di-pyrrolidin-1-yl-phenyl)-5H-pyrrolo[2,3-b]pyrazin-7-yl]-2,2-dimethyl-propan-1-one | |
| I-385 | 3-[7-(2,2-Dimethyl-propionyl)-5H-pyrrolo[2,3-b]pyrazin-2-yl]-benzonitrile | |

TABLE I-continued

| | | |
|---|---|---|
| I-386 | 3-[7-(1-Methyl-cyclohexane-carbonyl)-5H-pyrrolo[2,3-b]pyrazin-2-yl]-benzaldehyde | |
| I387 | (1-Methyl-cyclohexyl)-[2-(3-pyrrolidin-1-ylmethyl-phenyl)-5H-pyrrolo[2,3-b]pyrazin-7-yl]-methanone | |
| I-388 | 1-{2-[3-(4,5-Dihydro-1H-imidazol-2-ylamino)-phenyl]-5H-pyrrolo[2,3-b]pyrazin-7-yl}-2,2-dimethyl-propan-1-one | |
| I-389 | 1-{2-[3-(4,5-Dihydro-1H-imidazol-2-yl)-phenyl]-5H-pyrrolo[2,3-b]pyrazin-7-yl}-2,2-dimethyl-propan-1-one | |
| I-390 | 2,2-Dimethyl-1-{2-[3-(1,4,5,6-tetrahydro-pyrimidin-2-yl)-phenyl]-5H-pyrrolo[2,3-b]pyrazin-7-yl}-propan-1-one | |

TABLE I-continued
I-391 1-{2-[3-(5,5-Dimethyl-1,4,5,6-tetrahydro-pyrimidin-2-yl)-phenyl]-5H-pyrrolo[2,3-b]pyrazin-7-yl}-2,2-dimethyl-propan-1-one
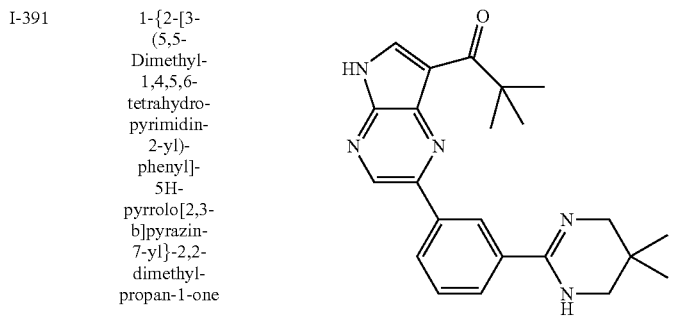
I-392 1-{2-[3-(4,4-Dimethyl-4,5-dihydro-1H-imidazol-2-yl)-phenyl]-5H-pyrrolo[2,3-b]pyrazin-7-yl}-2,2-dimethyl-propan-1-one
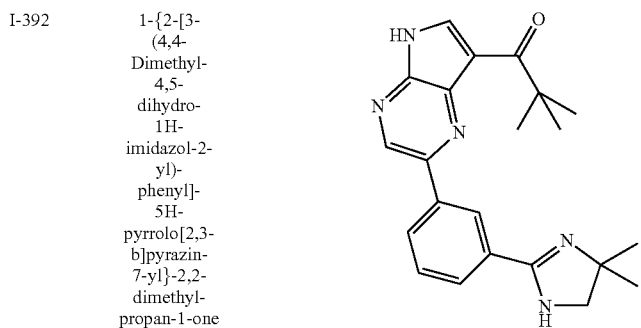
I-393 2,2-Dimethyl-1-{2-[3-(1-methyl-4,5-dihydro-1H-imidazol-2-yl)-phenyl]-5H-pyrrolo[2,3-b]pyrazin-7-yl}-propan-1-one
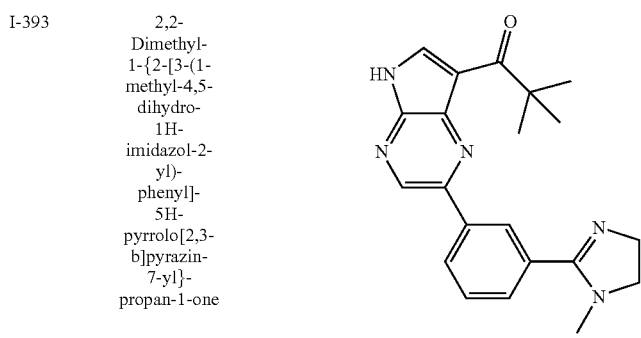
I-394 Pyrrolidin-1-yl-[2-(3,4,5-trimethoxy-phenyl)-5H-pyrrolo[2,3-b]pyrazin-7-yl]-methanone
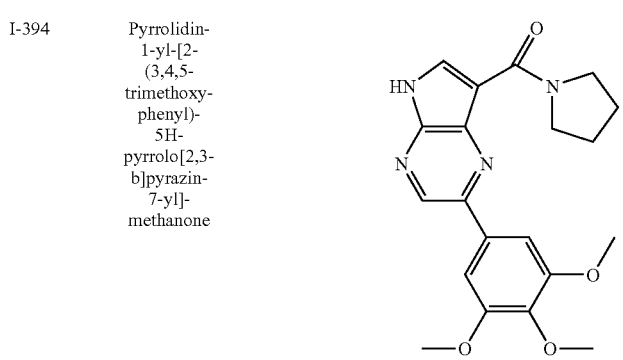

TABLE I-continued
| I-395 | (3,3-Dimethyl-pyrrolidin-1-yl)-[2-(3,4,5-trimethoxy-phenyl)-5H-pyrrolo[2,3-b]pyrazin-7-yl]-methanone | 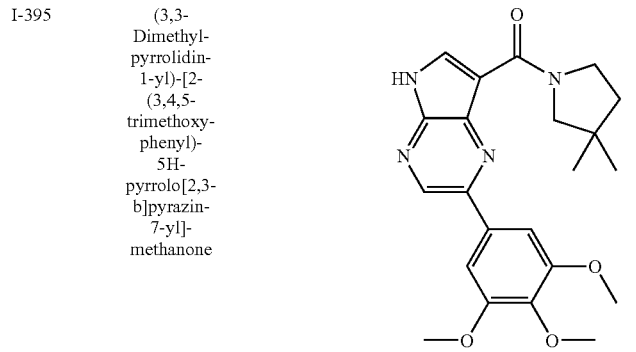 |
| --- | --- | --- |
| I-396 | 2,2-Dimethyl-1-[2-(3,4,5-trimethoxy-phenyl)-5H-pyrrolo[2,3-b]pyrazin-7-yl]-butan-1-one | 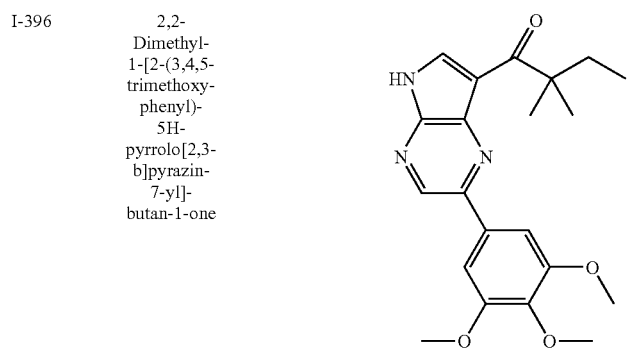 |
| I-397 | 3,3,3-Trifluoro-2-methyl-2-trifluoromethyl-1-[2-thyl-1-[2-(3,4,5-trimethoxy-phenyl)-5H-pyrrolo[2,3-b]pyrazin-7-yl]-propan-1-one | 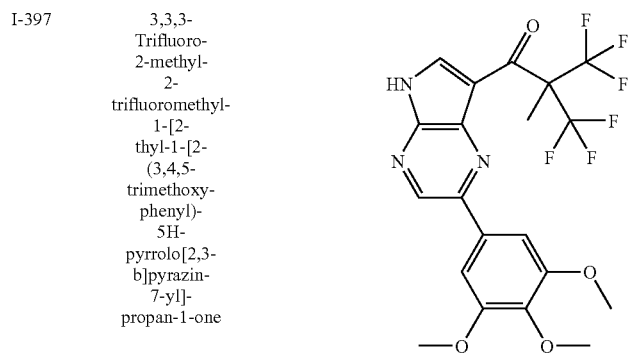 |
| I-398 | 1-[2-(3-Ethylamino-phenyl)-5H-pyrrolo[2,3-b]pyrazin-7-yl]-2,2-dimethyl-propan-1-one | 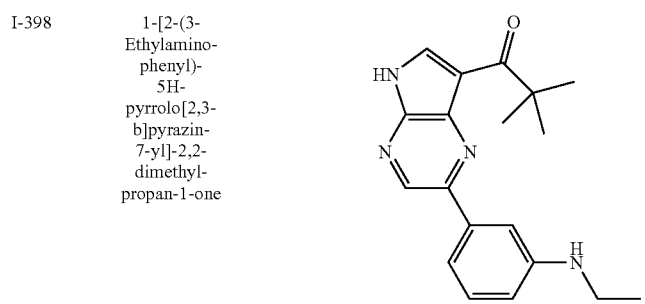 |

TABLE I-continued

| I-399 | 1-[2-(3-Diethylamino-phenyl)-5H-pyrrolo[2,3-b]pyrazin-7-yl]-2,2-dimethyl-propan-1-one | |
| I-400 | 1-[2-(3-Amino-phenyl)-5H-pyrrolo[2,3-b]pyrazin-7-yl]-2,2-dimethyl-propan-1-one | |
| I-401 | N-{3-[7-(2,2-Dimethyl-propionyl)-5H-pyrrolo[2,3-b]pyrazin-2-yl]-phenyl}-acetamide | |
| I-402 | 1-{2-[3-(3-Hydroxy-pyrrolidin-1-yl)-phenyl]-5H-pyrrolo[2,3-b]pyrazin-7-yl}-2,2-dimethyl-propan-1-one | |
| I-403 | 1-{2-[3-(1,1-Dioxo-1λ6-thiomorpholin-4-yl)-phenyl]-5H-pyrrolo[2,3-b]pyrazin-7-yl}-2,2-dimethyl-propan-1-one | |

TABLE I-continued

| I-404 | 1-[2-(3-Azetidin-1-yl-phenyl)-5H-pyrrolo[2,3-b]pyrazin-7-yl]-2,2-dimethyl-propan-1-one |
| --- | --- |
| I-405 | 2,2-Dimethyl-1-{2-[3-(1-oxo-1λ4-thiomorpholin-4-yl)-phenyl]-5H-pyrrolo[2,3-b]pyrazin-7-yl}-propan-1-one |
| I-406 | 2,2-Dimethyl-1-[2-(3-pyrrol-1-yl-phenyl)-5H-pyrrolo[2,3-b]pyrazin-7-yl]-propan-1-one |
| I-407 | 1-{2-[3-(2-Methanesulfonyl-ethylamino)-phenyl]-5H-pyrrolo[2,3-b]pyrazin-7-yl}-2,2-dimethyl-propan-1-one |

TABLE I-continued

| | | |
|---|---|---|
| I-408 | 1-{2-[(3aS,6aR)-3-(Hexahydro-pyrrolo[3,4-c]pyrrol-2-yl)-phenyl]-5H-pyrrolo[2,3-b]pyrazin-7-yl}-2,2-dimethyl-propan-1-one | |
| I-409 | 1-{2-[3-((S)-2-Hydroxymethyl-pyrrolidin-1-yl)-phenyl]-5H-pyrrolo[2,3-b]pyrazin-7-yl}-2,2-dimethyl-propan-1-one | |
| I-410 | 1-{2-[3-((R)-2-Hydroxymethyl-pyrrolidin-1-yl)-phenyl]-5H-pyrrolo[2,3-b]pyrazin-7-yl}-2,2-dimethyl-propan-1-one | |
| I-411 | N-{3-[7-2,2-Dimethyl-propionyl)-5H-pyrrolo[2,3-b]pyrazin-2-yl]-phenyl}-methanesulfonamide | |

TABLE I-continued
| | | |
|---|---|---|
| I-412 | N-(4-{3-[7-(2,2-Dimethyl-propionyl)-5H-pyrrolo[2,3-b]pyrazin-2-yl]-phenylsulfamoyl}-phenyl)-acetamide | 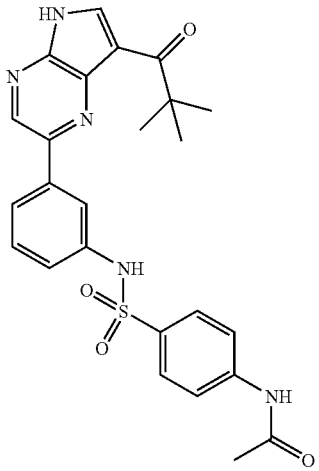 |
| I-413 | 4-Amino-N-{3-[7-(2,2-dimethyl-propionyl)-5H-pyrrolo[2,3-b]pyrazin-2-yl]-phenyl}-benzenesulfonamide | 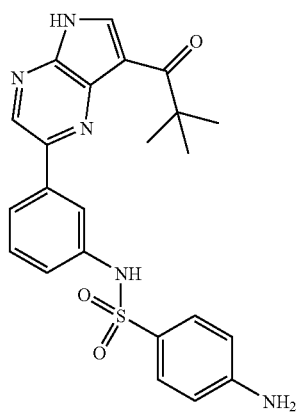 |
| I-414 | N-{3-[7-(2,2-Dimethyl-propionyl)-5H-pyrrolo[2,3-b]pyrazin-2-yl]-phenyl}-benzenesulfonamide | 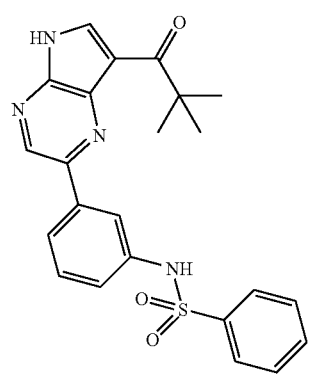 |

TABLE I-continued

| | | |
|---|---|---|
| I-415 | N-(4-{5-[7-(2,2-Dimethyl-propionyl)-5H-pyrrolo[2,3-b]pyrazin-2-yl]-2-methyl-phenylsulfamoyl}-phenyl)-acetamide | |
| I-416 | 4-Amino-N-{5-[7-(2,2-dimethyl-propionyl)-5H-pyrrolo[2,3-b]pyrazin-2-yl]-2-methyl-phenyl}-benzenesulfonamide | |
| I-417 | 1-{2-[3-(3-Hydroxy-3-methyl-pyrrolidin-1-yl)-phenyl]-5H-pyrrolo[2,3-b]pyrazin-7-yl}-2,2-dimethyl-propan-1-one | |
| I-418 | 1-{2-[3-(3-Hydroxy-3-methyl-pyrrolidin-1-yl)-phenyl]-5H-pyrrolo[2,3-b]pyrazin-7-yl}-2,2-dimethyl-propan-1-one | |

TABLE I-continued
| | | |
|---|---|---|
| I-419 | 3-[7-(2,2-Dimethyl-propionyl)-5H-pyrrolo[2,3-b]pyrazin-2-yl]-benzaldehyde | 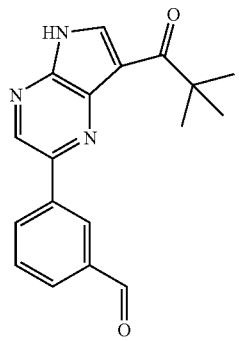 |
| I-420 | 2,2-Dimethyl-1-[2-(3-pyrrolidin-1-ylmethyl-phenyl)-5H-pyrrolo[2,3-b]pyrazin-7-yl]-propan-1-one | 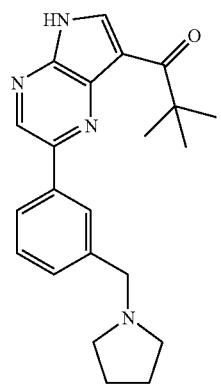 |
| I-421 | 1-{2-[3-(4-Dimethylamino-piperidin-1-ylmethyl)-phenyl]-5H-pyrrolo[2,3-b]pyrazin-7-yl}-2,2-dimethyl-propan-1-one | 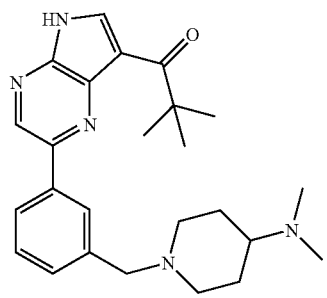 |
| I-422 | 2,2-Dimethyl-1-{2-[3-(4-methyl-piperazin-1-ylmethyl)-phenyl]-5H-pyrrolo[2,3-b]pyrazin-7-yl}-propan-1-one | 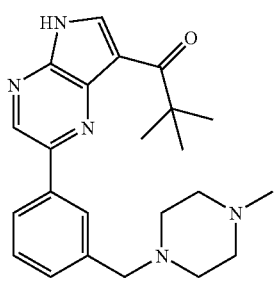 |

TABLE I-continued

| | | |
|---|---|---|
| I-423 | 1-[2-(4-Aminomethyl-phenyl)-5H-pyrrolo[2,3-b]pyrazin-7-yl]-2,2-dimethyl-propan-1-one | |
| I-424 | 2,2-Dimethyl-1-{2-[3-(4-methylsulfanyl-piperidin-1-ylmethyl)-phenyl]-5H-pyrrolo[2,3-b]pyrazin-7-yl}-propan-1-one | |
| I-425 | 1-{2-[3-(3-Hydroxy-pyrrolidin-1-ylmethyl)-phenyl]-5H-pyrrolo[2,3-b]pyrazin-7-yl}-2,2-dimethyl-propan-1-one | |
| I-426 | 1-{2-[3-((S)-2-Hydroxymethyl-pyrrolidin-1-ylmethyl)-phenyl]-5H-pyrrolo[2,3-b]pyrazin-7-yl}-2,2-dimethyl-propan-1-one | |

TABLE I-continued
| | | |
|---|---|---|
| I-427 | 1-{2-[3-((R)-2-Hydroxymethyl-pyrrolidin-1-ylmethyl)-phenyl]-5H-pyrrolo[2,3-b]pyrazin-7-yl}-2,2-dimethyl-propan-1-one | 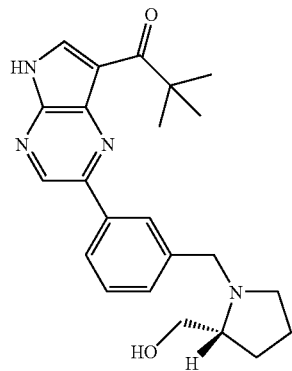 |
| I-428 | (1-{3-[7-(2,2-Dimethyl-propionyl)-5H-pyrrolo[2,3-b]pyrazin-2-yl]-benzyl}-pyrrolidin-3-yl)-carbamic acid tert-butyl ester | 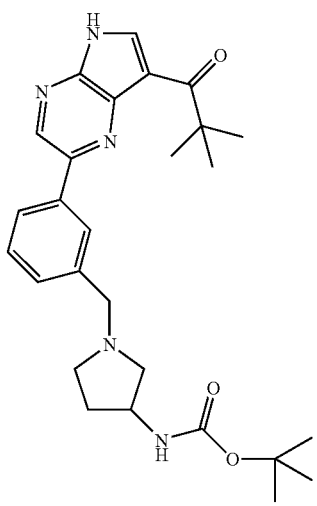 |
| I-429 | 1-[2-(3-{[Bis-(2-hydroxy-ethyl)-amino]-methyl}-phenyl)-5H-pyrrolo[2,3-b]pyrazin-7-yl]2,2-dimethyl-propan-1-one | 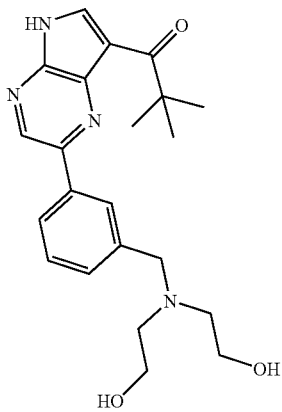 |

TABLE I-continued
| I-430 | 1-[2-(3-{[Ethyl-(4-hydroxybutyl)-amino]-methyl}-phenyl)-5H-pyrrolo[2,3-b]pyrazin-7-yl]2,2-dimethyl-propan-1-one | 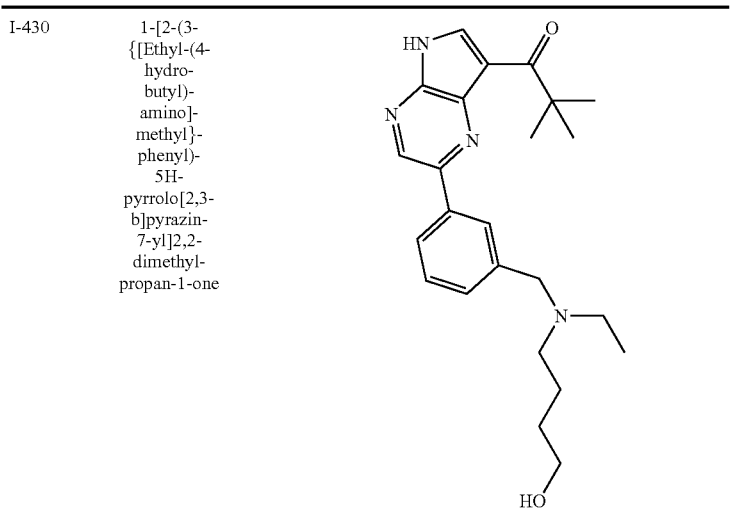 |
| --- | --- | --- |
| I-431 | (S)-1-{3-[7-(2,2-Dimethyl-propionyl)-5H-pyrrolo[2,3-b]pyrazin-2-yl]-benzyl}-pyrrolidine-2-carboxylic acid amide | 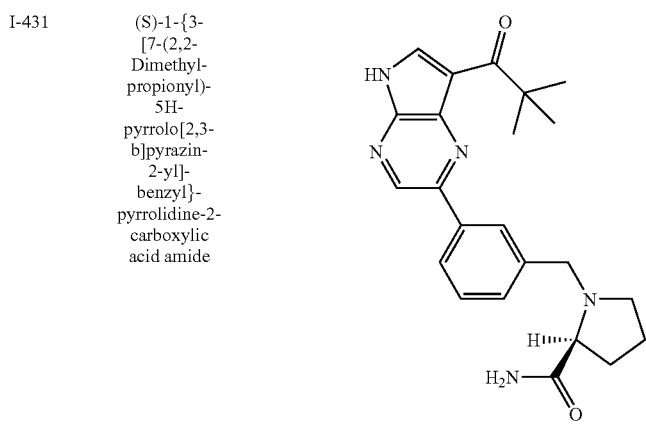 |
| I-432 | (R)-1-{3-[7-(2,2-Dimethyl-propionyl)-5H-pyrrolo[2,3-b]pyrazin-2-yl]-benzyl}-pyrrolidine-2-carboxylic acid amide | 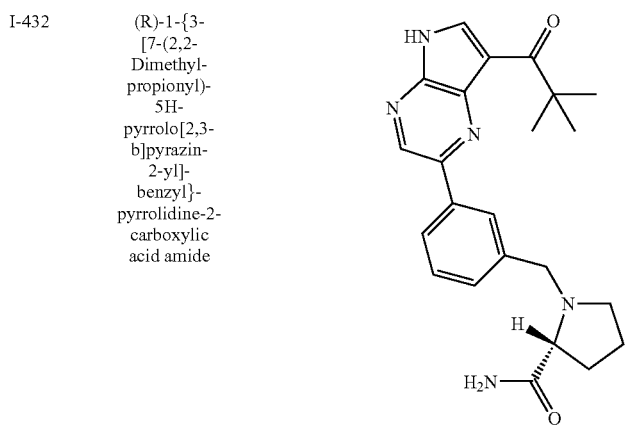 |

TABLE I-continued

| I-433 | 1-{2-[3-(4-Hydroxymethyl-piperidin-1-ylmethyl)-phenyl]-5H-pyrrolo[2,3-b]pyrazin-7-yl}-2,2-dimethyl-propan-1-one | |
|---|---|---|
| I-434 | 1-{2-[3-(3-Hydroxymethyl-pyrrolidin-1-ylmethyl)-phenyl]-5H-pyrrolo[2,3-b]pyrazin-7-yl}-2,2-dimethyl-propan-1-one | |
| I-435 | 1-{2-[3-(3-Amino-pyrrolidin-1-ylmethyl)-phenyl]-5H-pyrrolo[2,3-b]pyrazin-7-yl}-2,2-dimethyl-propan-1-one | |
| I-436 | 2,2-Dimethyl-1-{2-[3-(3-methylamino-pyrrolidin-1-ylmethyl)-phenyl]-5H-pyrrolo[2,3-b]pyrazin-7-yl}-propan-1-one | |

TABLE I-continued

| | | |
|---|---|---|
| I-437 | 1-{2-[3-(1H-Imidazol-2-yl)-phenyl]-5H-pyrrolo[2,3-b]pyrazin-7-yl}-2,2-dimethyl-propan-1-one | |
| I-438 | 1-{2-[3-(3-Benzyl-pyrrolidin-1-ylmethyl)-phenyl]-5H-pyrrolo[2,3-b]pyrazin-7-yl}-2,2-dimethyl-propan-1-one | |
| I-439 | N-(1-{3-[7-(2,2-Dimethyl-propionyl)-5H-pyrrolo[2,3-b]pyrazin-2-yl]-benzyl}-pyrrolidin-3-yl)-N-methyl-methanesulfonamide | |
| I-440 | N-(1-{3-[7-(2,2-Dimethyl-propionyl)-5H-pyrrolo[2,3-b]pyrazin-2-yl]-benzyl}-pyrrolidin-3-yl)-methanesulfonamide | |

TABLE I-continued

| | | |
|---|---|---|
| I-441 | 4-[7-(2,2-Dimethyl-propionyl)-5H-pyrrolo[2,3-b]pyrazin-2-yl]-2-pyrrolidin-1-yl-benzonitrile | |
| I-442 | 2,2-Dimethyl-1-{2-[3-(3-methyl-pyrrolidin-1-yl)-phenyl]-5H-pyrrolo[2,3-b]pyrazin-7-yl}-propan-1-one | |
| I-443 | 1-{2-[3-(3-Methoxymethyl-3-methyl-pyrrolidin-1-yl)-phenyl]-5H-pyrrolo[2,3-b]pyrazin-7-yl}-2,2-dimethyl-propan-1-one | |
| I-444 | 1-{2-[(1S,5R)-3-(3-Aza-bicyclo[3.1.0]hex-3-yl)-phenyl]-5H-pyrrolo[2,3-b]pyrazin-7-yl}-2,2-dimethyl-propan-1-one | |
| I-445 | 2,2-Dimethyl-1-[2-(3-piperidin-1-yl-phenyl)-5H-pyrrolo[2,3-b]pyrazin-7-yl]-propan-1-one | |

TABLE I-continued
| | | |
|---|---|---|
| I-446 | 2,2-Dimethyl-1-[2-(3-morpholin-4-yl-phenyl)-5H-pyrrolo[2,3-b]pyrazin-7-yl]-propan-1-one | |
| I-447 | 1-{2-[3-((1S,5R,6R)-6-Methanesulfonylmethyl-3-aza-bicyclo[3.1.0]hex-3-yl)-phenyl]-5H-pyrrolo[2,3-b]pyrazin-7-yl}-2,2-dimethyl-propan-1-one | |
| I-448 | 3-[7-(2,2-Dimethyl-propionyl)-5H-pyrrolo[2,3-b]pyrazin-2-yl]-5-pyrrolidin-1-yl-benzonitrile | |
| I-449 | 3-[7-(2,2-Dimethyl-propionyl)-5H-pyrrolo[2,3-b]pyrazin-2-yl]-N-(2-methanesulfonyl-ethyl)-5-pyrrolidin-1-yl-benzamide | |
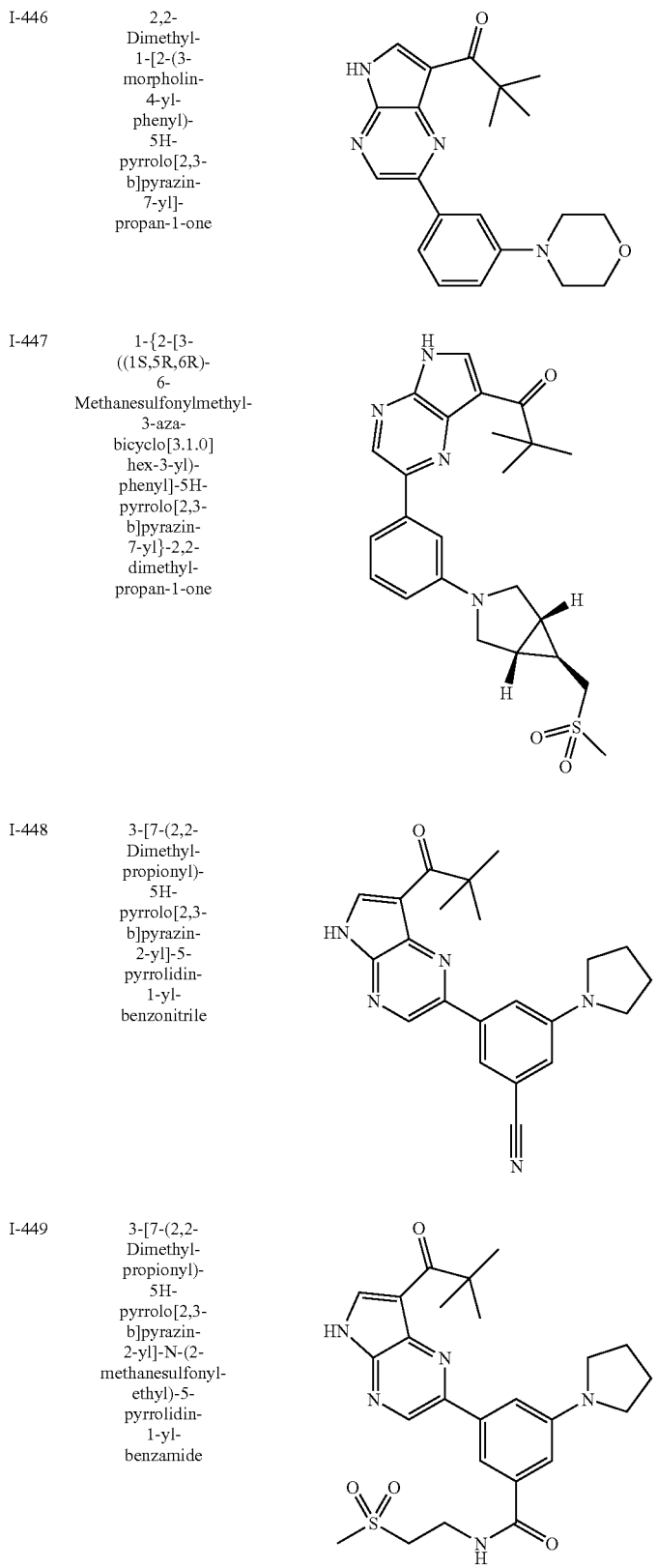

| | | |
|---|---|---|
| I-450 | 3-[7-(2,2-Dimethyl-propionyl)-5H-pyrrolo[2,3-b]pyrazin-2-yl]-5-pyrrolidin-1-yl-benzamide | |
| I-451 | 3-[7-(2,2-Dimethyl-propionyl)-5H-pyrrolo[2,3-b]pyrazin-2-yl]-N-(2-hydroxy-ethyl)-5-pyrrolidin-1-yl-benzamide | |
| I-452 | 2,2-Dimethyl-1-{2-[3-(4-methyl-piperazine-1-carbonyl)-5-pyrrolidin-1-yl-phenyl]-5H-pyrrolo[2,3-b]pyrazin-7-yl}-propan-1-one | |
| I-453 | 1-{2-[(3aS,6aR)-3-(Hexahydro-cyclopenta[c]pyrrol-2-yl)-phenyl]-5H-pyrrolo[2,3-b]pyrazin-7-yl}-2,2-dimethyl-propan-1-one | |

TABLE I-continued

| | | |
|---|---|---|
| I-454 | 3-[7-(2,2-Dimethyl-propionyl)-5H-pyrrolo[2,3-b]pyrazin-2-yl]-5-pyrrolidin-1-yl-benzoic acid | |
| I-455 | 3-[7-(2,2-Dimethyl-propionyl)-5H-pyrrolo[2,3-b]pyrazin-2-yl]-5-(3,3-dimethyl-pyrrolidin-1-yl)-benzamide | |
| I-456 | 2,2-Dimethyl-1-{2-[3-((1S,5R)-1-phenyl-3-aza-bicyclo[3.1.0]hex-3-yl)-phenyl]-5H-pyrrolo[2,3-b]pyrazin-7-yl}-propan-1-one | |
| I-457 | 1-{2-[3-(3,3-Diethyl-pyrrolidin-1-yl)-phenyl]-5H-pyrrolo[2,3-b]pyrazin-7-yl}-2,2-dimethyl-propan-1-one | |

| | | |
|---|---|---|
| I-458 | 2,2-Dimethyl-1-{2-[3-(4-methyl-piperazin-1-ylmethyl)-5-pyrrolidin-1-yl-phenyl]-5H-pyrrolo[2,3-b]pyrazin-7-yl}-propan-1-one | |
| I-459 | 1-{2-[3-((1S,5R,6R)-6-Hydroxymethyl-3-aza-bicyclo[3.1.0]hex-3-yl)-phenyl]-5H-pyrrolo[2,3-b]pyrazin-7-yl}-2,2-dimethyl-propan-1-one | |
| I-460 | {2-[3-((1S,5R,6R)-6-Hydroxymethyl-3-aza-bicyclo[3.1.0]hex-3-yl)-phenyl]-5H-pyrrolo[2,3-b]pyrazin-7-yl}-(1-methyl-cyclohexyl)-methanone | |
| I-461 | 1-{2-[3-((1R,5S,6R)-6-Methoxymethyl-3-aza-bicyclo[3.1.0]hex-3-yl)-phenyl]-5H-pyrrolo[2,3-b]pyrazin-7-yl}-2,2-dimethyl-propan-1-one | |

TABLE I-continued
| I-462 | {2-[3-((1R,5S,6R)-6-Hydroxymethyl-3-aza-bicyclo[3.1.0]hex-3-yl)-phenyl]-5H-pyrrolo[2,3-b]pyrazin-7-yl}-(1-methyl-cyclopentyl)-methanone | 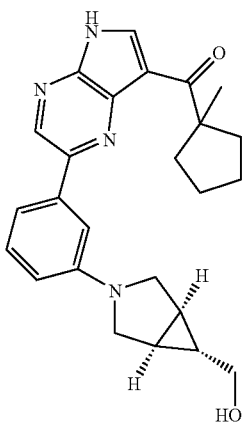 |
| --- | --- | --- |
| I-463 | 1-{2-[3-(4-Hydroxy-piperidin-1-yl)-phenyl]-5H-pyrrolo[2,3-b]pyrazin-7-yl}-2,2-dimethyl-propan-1-one | 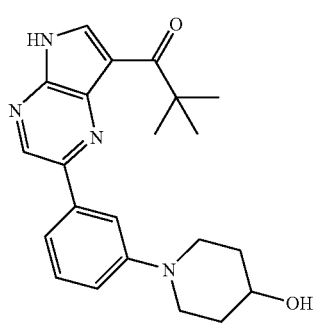 |
| I-464 | 1-{2-[3-(4-Hydroxy-4-methyl-piperidin-1-yl)-phenyl]-5H-pyrrolo[2,3-b]pyrazin-7-yl}-2,2-dimethyl-propan-1-one | 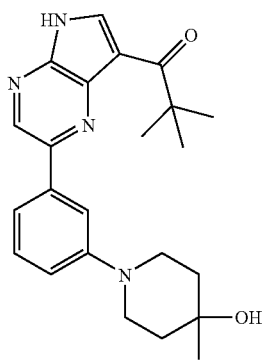 |
| I-465 | 1-{2-[3-(3-Hydroxymethyl-3-methyl-pyrrolidin-1-yl)-phenyl]-5H-pyrrolo[2,3-b]pyrazin-7-yl}-2,2-dimethyl-propan-1-one | 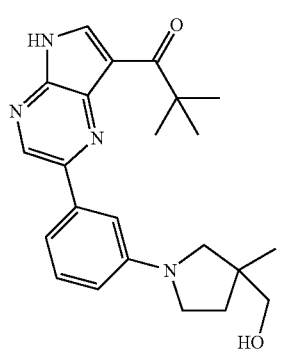 |

TABLE I-continued

| | | |
|---|---|---|
| I-466 | N-(1-{3-[7-(2,2-Dimethyl-propionyl)-5H-pyrrolo[2,3-b]pyrazin-2-yl]-phenyl}-3-methyl-pyrrolidin-3-ylmethyl)-acetamide | |
| I-467 | N-(1-{3-[7-(2,2-Dimethyl-propionyl)-5H-pyrrolo[2,3-b]pyrazin-2-yl]-phenyl}-3-methyl-pyrrolidin-3-ylmethyl)-methanesulfonamide | |
| I-468 | (1-{3-[7-(2,2-Dimethyl-propionyl)-5H-pyrrolo[2,3-b]pyrazin-2-yl]-phenyl}-3-methyl-pyrrolidin-3-ylmethyl)-carbamic acid methyl ester | |
| I-469 | 2,2-Dimethyl-1-[2-(4-pyrrolidin-1-yl-phenyl)-5H-pyrrolo[2,3-b]pyrazin-7-yl]-propan-1-one | |

TABLE I-continued
| I-470 | 1-[2-(3-Dimethylamino-phenyl)-5H-pyrrolo[2,3-b]pyrazin-7-yl]-2,2-dimethyl-propan-1-one | 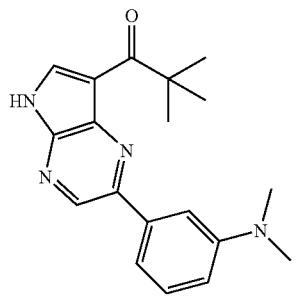 |
| I-471 | N-{3-[7-(2,2-Dimethyl-propionyl)-5H-pyrrolo[2,3-b]pyrazin-2-yl]-benzyl}-methanesulfonamide | 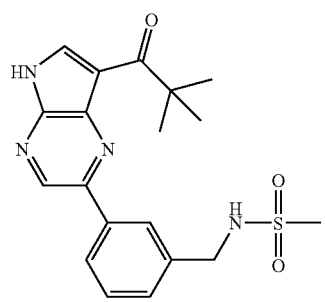 |
| I-472 | N-{3-[7-(2,2-Dimethyl-propionyl)-5H-pyrrolo[2,3-b]pyrazin-2-yl]-benzyl}-C-phenyl-methanesulfonamide | 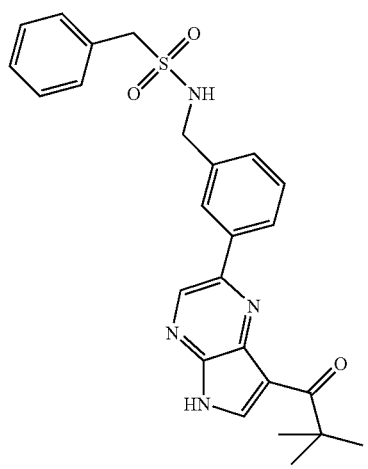 |
| I-473 | Cyclopropanesulfonic acid 3-[7-(2,2-dimethyl-propionyl)-5H-pyrrolo[2,3-b]pyrazin-2-yl]-benzylamide | 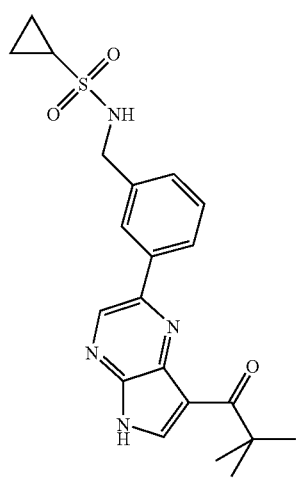 |

TABLE I-continued
| | | |
|---|---|---|
| I-474 | N-{3-[7-(2,2-Dimethyl-propionyl)-5H-pyrrolo[2,3-b]pyrazin-2-yl]-benzyl}-benzenesulfonamide | 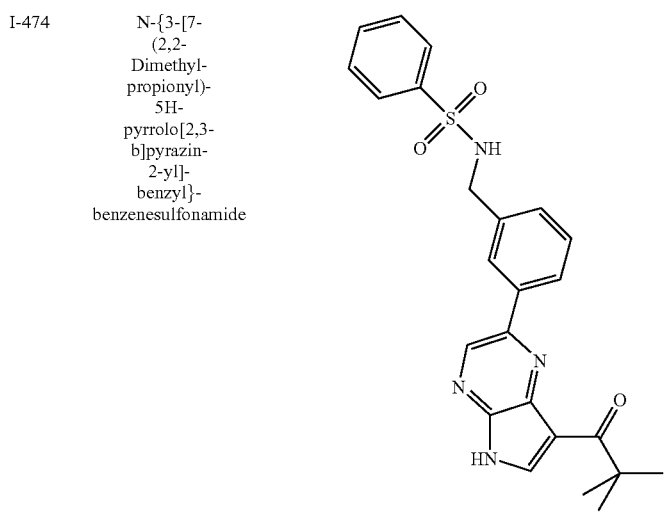 |
| I-475 | N-{4-[7-(2,2-Dimethyl-propionyl)-5H-pyrrolo[2,3-b]pyrazin-2-yl]-benzyl}-C-phenyl-methanesulfonamide | 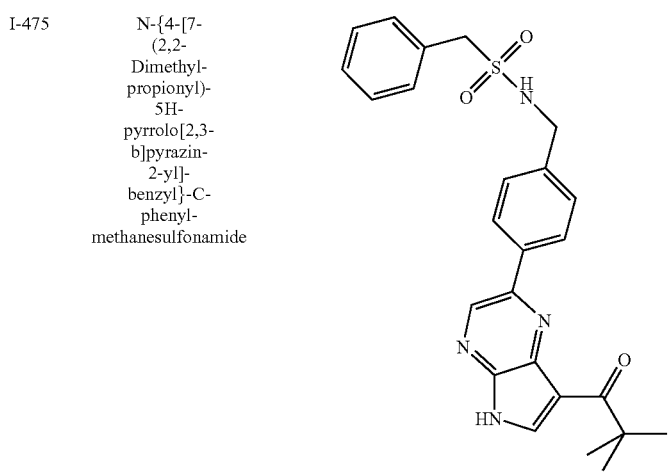 |
| I-476 | Cyclopropanesulfonic acid 4-[7-(2,2-dimethyl-propionyl)-5H-pyrrolo[2,3-b]pyrazin-2-yl]-benzylamide | 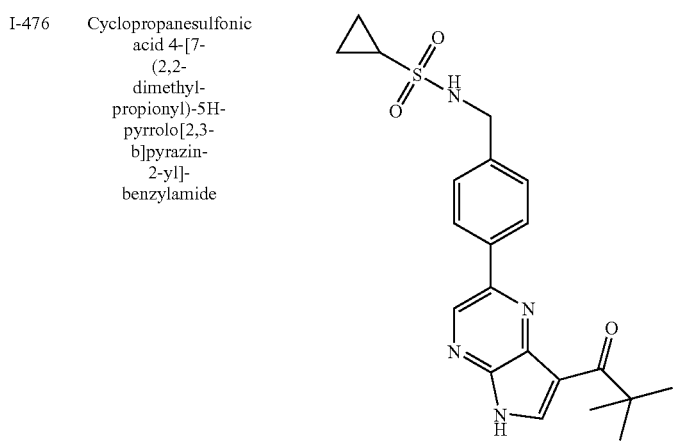 |

TABLE I-continued
| I-477 | Propane-1-sulfonic acid 3-[7-(2,2-dimethyl-propionyl)-5H-pyrrolo[2,3-b]pyrazin-2-yl]-benzylamide | 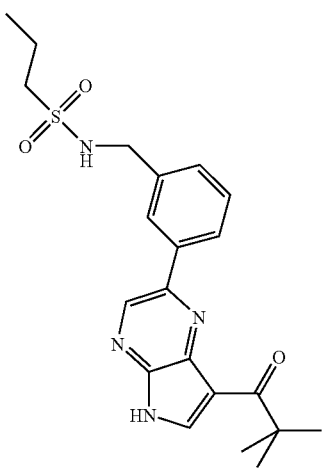 |
| I-478 | 1-{2-[3-(2-tert-Butyl-pyrrolidin-1-ylmethyl)-phenyl]-5H-pyrrolo[2,3-b]pyrazin-7-yl}-2,2-dimethyl-propan-1-one | 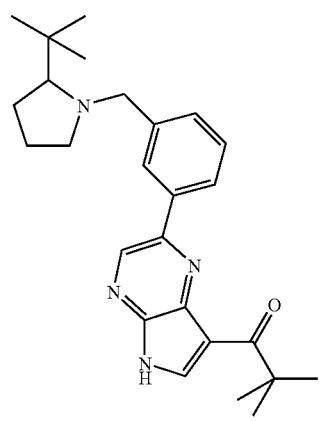 |
| I-479 | 1-(2-{3-[(Cyclohexyl-methyl-amino)-methyl]-phenyl}-5H-pyrrolo[2,3-b]pyrazin-7-yl)-2,2-dimethyl-propan-1-one | 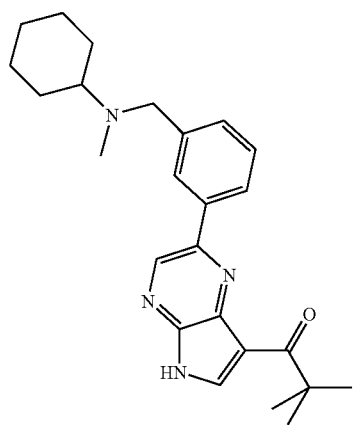 |

TABLE I-continued

| I-480 | 1-{2-[3-(3-Dimethylamino-pyrrolidin-1-ylmethyl)-phenyl]-5H-pyrrolo[2,3-b]pyrazin-7-yl}-2,2-dimethyl-propan-1-one | |
| --- | --- | --- |
| I-481 | 2,2-Dimethyl-1-{2-[3-((S)-2-methyl-pyrrolidin-1-ylmethyl)-phenyl]-5H-pyrrolo[2,3-b]pyrazin-7-yl}-propan-1-one | |
| I-482 | 1-{2-[3-(3-Methoxy-pyrrolidin-1-ylmethyl)-phenyl]-5H-pyrrolo[2,3-b]pyrazin-7-yl}-2,2-dimethyl-propan-1-one | |
| I-483 | 1-(2-{3-[(Cyclopropylmethyl-propyl-amino)-methyl]-phenyl}-5H-pyrrolo[2,3-b]pyrazin-7-yl)-2,2-dimethyl-propan-1-one | |

TABLE I-continued
| I-484 | 1-{2-[3-((R)-2-Methoxymethyl-pyrrolidin-1-ylmethyl)-phenyl]-5H-pyrrolo[2,3-b]pyrazin-7-yl}-2,2-dimethyl-propan-1-one | 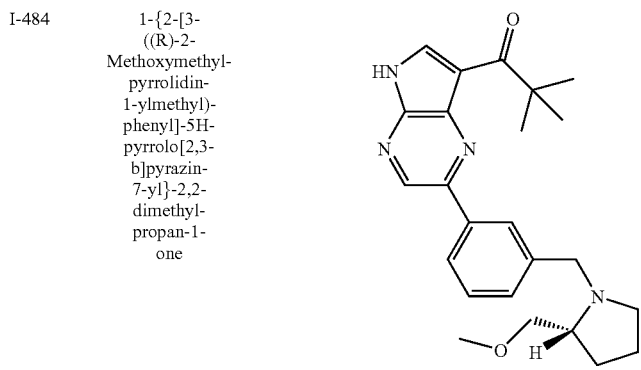 |
| --- | --- | --- |
| I-485 | 1-(2-{3-[(4,5-Dihydro-1H-imidazol-2-ylamino)-methyl]-phenyl}-5H-pyrrolo[2,3-b]pyrazin-7-yl)-2,2-dimethyl-propan-1-one | 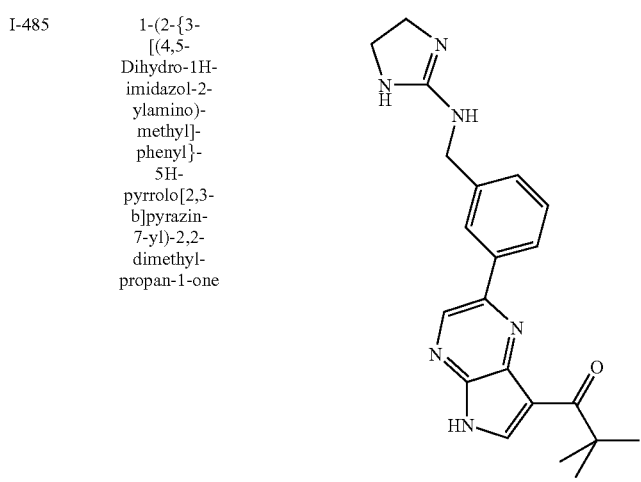 |
| I-486 | 1-{2-[3-(3,3-Dimethyl-pyrrolidin-1-ylmethyl)-phenyl]-5H-pyrrolo[2,3-b]pyrazin-7-yl}-2,2-dimethyl-propan-1-one | 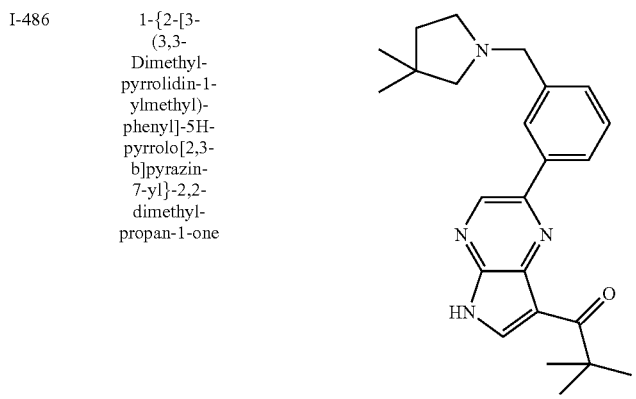 |

| | | |
|---|---|---|
| I-487 | 3-(4-{3-[7-(2,2-Dimethyl-propionyl)-5H-pyrrolo[2,3-b]pyrazin-2-yl]-benzyl}-piperazin-1-yl)-3-oxo-propionitrile | 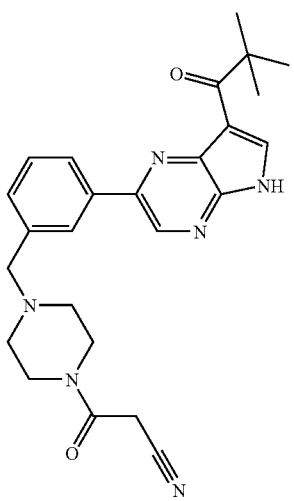 |
| I-488 | 2-(3,4,5-Trimethoxy-phenyl)-5H-pyrrolo[2,3-b]pyrazine-7-carboxylic acid (2-methoxy-1-methyl-ethyl)-amide | 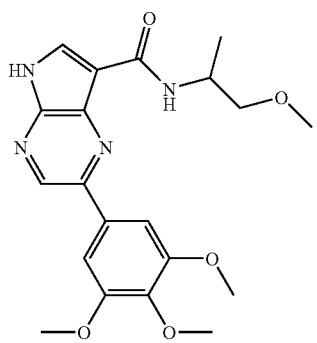 |
| I-489 | 2-Phenyl-1-[2-(3,4,5-trimethoxy-phenyl)-5H-pyrrolo[2,3-b]pyrazin-7-yl]-propan-1-one | 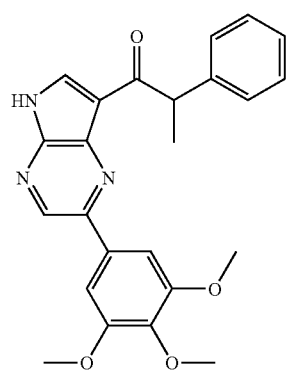 |
| I-490 | 2-(3,4,5-Trimethoxy-phenyl)-5H-pyrrolo[2,3-b]pyrazine-7-carboxylic acid | 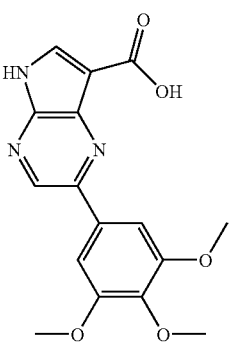 |

TABLE I-continued

| I-491 | 2-(3,4,5-Trimethoxy-phenyl)-5H-pyrrolo[2,3-b]pyrazine-7-carboxylic acid (1-acetyl-pyrrolidin-3-ylmethyl)-amide |
| I-492 | 2-(3,4,5-Trimethoxy-phenyl)-5H-pyrrolo[2,3-b]pyrazine-7-carboxylic acid (1-ethylcarbamoyl-pyrrolidin-3-ylmethyl)-amide |
| I-493 | 2-(3,4,5-Trimethoxy-phenyl)-5H-pyrrolo[2,3-b]pyrazine-7-carboxylic acid (piperidin-4-ylmethyl)-amide |
| I-494 | 2-(3,4,5-Trimethoxy-phenyl)-5H-pyrrolo[2,3-b]pyrazine-7-carboxylic acid (1-acetyl-piperidin-4-ylmethyl)-amide |

TABLE I-continued

| I-495 | 1-{2-[3-(3,3-Dimethyl-pyrrolidin-1-yl)-5-(1-methyl-piperidin-4-yloxy)-phenyl]-5H-pyrrolo[2,3-b]pyrazin-7-yl}-2,2-dimethyl-propan-1-one | |
|---|---|---|
| I-496 | 2,2-Dimethyl-1-{2-[(3aR,6aS)-3-(tetrahydro-thieno[3,4-c]pyrrol-5-yl)-phenyl]-5H-pyrrolo[2,3-b]pyrazin-7-yl}-propan-1-one | |
| I-497 | 1-{2-[3-((1S,2S)-2-Hydroxy-cyclopentylamino)-phenyl]-5H-pyrrolo[2,3-b]pyrazin-7-y}-2,2-dimethyl-propan-1-one | |
| I-498 | 1-(2-{3-[(2-Methanesulfonyl-ethylamino)-methyl]-5-pyrrolidin-1-yl-phenyl}-5H-pyrrolo[2,3-b]pyrazin-7-yl)-2,2-dimethyl-propan-1-one | |

TABLE I-continued

| I-499 | 1-{2-[3-(3,3-Dimethyl-azetidin-1-yl)-phenyl]-5H-pyrrolo[2,3-b]pyrazin-7-yl}-2,2-dimethyl-propan-1-one | |
| --- | --- | --- |
| I-500 | 1-{2-[3-(3-Aminomethyl-3-methyl-pyrrolidin-1-yl)-phenyl]-5H-pyrrolo[2,3-b]pyrazin-7-yl}-2,2-dimethyl-propan-1-one | |
| I-501 | 1-{2-[3-((3aR,6aS)-2,2-Dioxo-hexahydro-2λ6-thieno[3,4-c]pyrrol-5-yl)-phenyl]-5H-pyrrolo[2,3-b]pyrazin-7-yl}-2,2-dimethyl-propan-1-one | |
| I-502 | 2,2-Dimethyl-1-{2-[3-((3aR,6aS)-2-oxo-hexahydro-2λ4-thieno[3,4-c]pyrrol-5-yl)-phenyl]-5H-pyrrolo[2,3-b]pyrazin-7-yl}-propan-1-one | |

| | | |
|---|---|---|
| I-503 | 2-Oxo-2,3-dihydro-benzooxazole-6-sulfonic acid {6-[7-(2,2-dimethyl-propionyl)-5H-pyrrolo[2,3-b]pyrazin-2-yl]-1H-indol-4-yl}-amide | 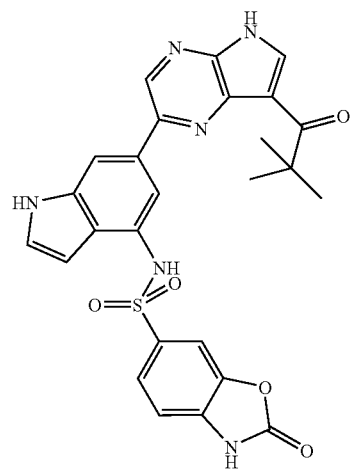 |
| I-504 | 2-Methyl-2-phenyl-1-[2-(3,4,5-trimethoxy-phenyl)-5H-pyrrolo[2,3-b]pyrazin-7-yl]-propan-1-one | 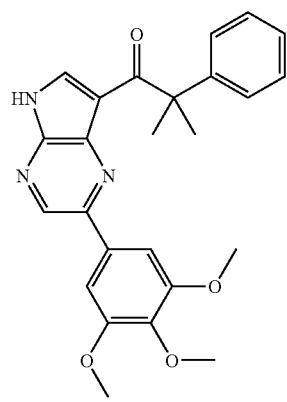 |
| I-505 | 1-{2-[3-(2-Amino-1,1-dimethyl-ethylamino)-phenyl]-5H-pyrrolo[2,3-b]pyrazin-7-yl}-2,2-dimethyl-propan-1-one | 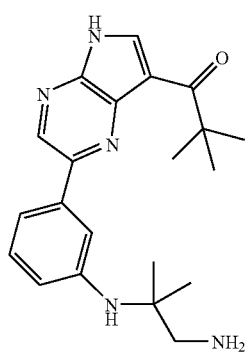 |

| | | |
|---|---|---|
| I-506 | 1H-Indazole-5-sulfonic acid {6-[7-(2,2-dimethyl-propionyl)-5H-pyrrolo[2,3-b]pyrazin-2-yl]-1H-indol-4-yl}-amide | 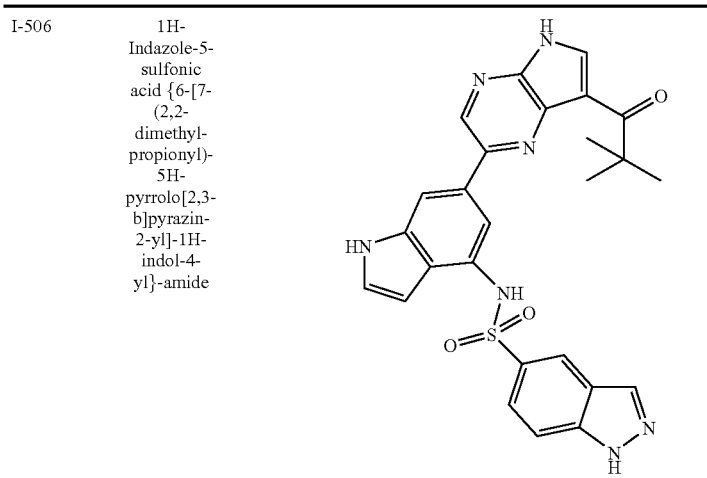 |
| I-507 | (4-{3-[7-(2,2-Dimethyl-propionyl)-5H-pyrrolo[2,3-b]pyrazin-2-yl]-phenyl}-piperazin-1-yl)-acetic acid | 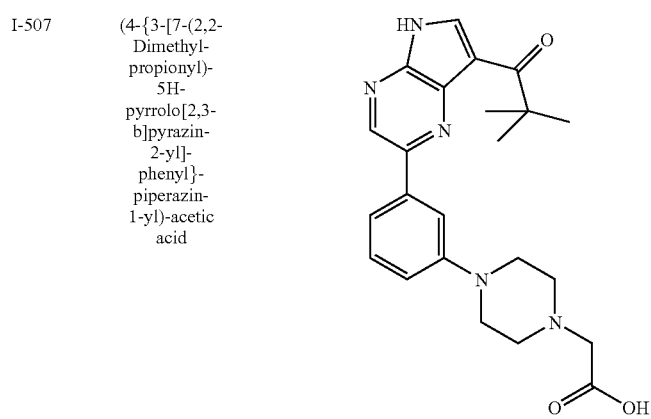 |
| I-508 | 4-Amino-3-chloro-N-{6-[7-(2,2-dimethyl-propionyl)-5H-pyrrolo[2,3-b]pyrazin-2-yl]-1H-indol-4-yl}-benzenesulfonamide | 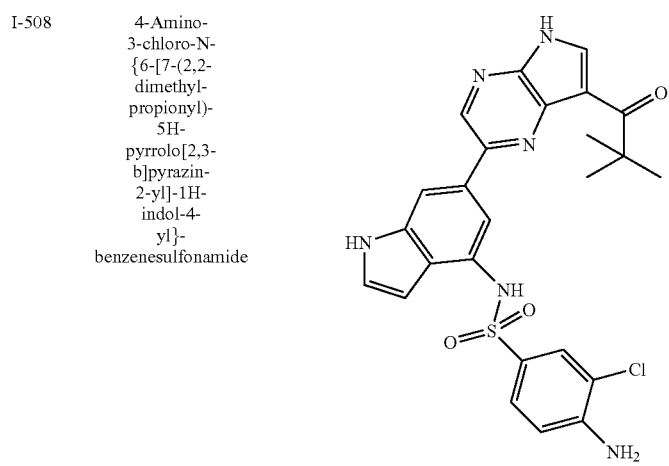 |

TABLE I-continued
| I-509 | 1-{2-[3-(2-Methoxy-2-methyl-propylamino)-phenyl]-5H-pyrrolo[2,3-b]pyrazin-7-yl}-2,2-dimethyl-propane-1-one | 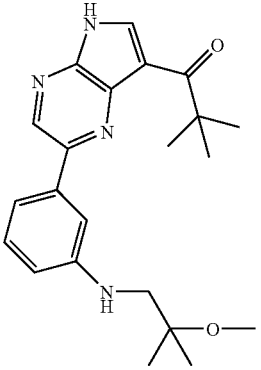 |
| --- | --- | --- |
| I-510 | 2-[3-(3,3-Dimethyl-pyrrolidin-1-yl)-phenyl]-5H-pyrrolo[2,3-b]pyrazine-7-carboxylic acid tert-butylamide | 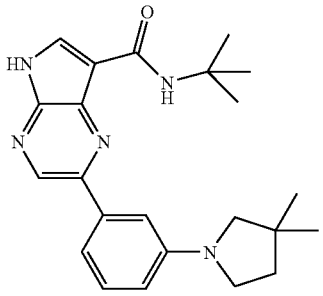 |
| I-511 | 3,3-Dimethyl-4-oxo-4-[2-(3,4,5-trimethoxy-phenyl)-5H-pyrrolo[2,3-b]pyrazin-7-yl]-butyronitrile | 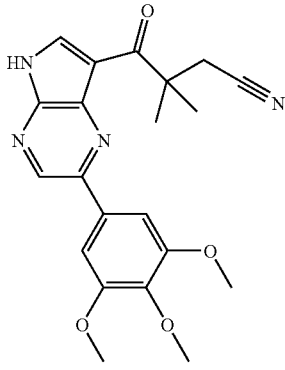 |
| I-512 | 1-{2-[3-(3-Hydroxy-azetidin-1-yl)-phenyl]-5H-pyrrolo[2,3-b]pyrazin-7-yl}-2,2-dimethyl-propan-1-one | 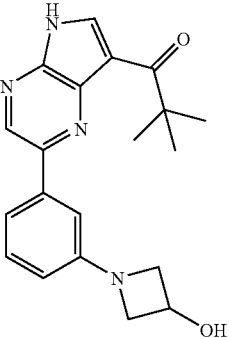 |

TABLE I-continued

| I-513 | 1-[2-(3-Methanesulfonyl-methoxy-5-pyrrolidin-1-yl-phenyl)-5H-pyrrolo[2,3-b]pyrazin-7-yl]-2,2-dimethyl-propan-1-one |
| --- | --- |
| I-514 | N-{6-[7-(2,2-Dimethyl-propionyl)-5H-pyrrolo[2,3-b]pyrazin-2-yl]-1H-indol-4-yl}-3-methoxy-benzenesulfonamide |
| I-515 | 2-[3-(3,3-Dimethyl-pyrrolidin-1-yl)-phenyl]-5H-pyrrolo[2,3-b]pyrazine-7-carboxylic acid (2-methoxy-propyl)-amide |
| I-516 | (1-{3-[7-(2,2-Dimethyl-propionyl)-5H-pyrrolo[2,3-b]pyrazin-2-yl]-phenyl}-4,4-dimethyl-pyrrolidin-3-yl)-carbamic acid ethyl ester |

TABLE I-continued
| I-517 | 3-Methyl-3-[2-(3,4,5-trimethoxyphenyl)-5H-pyrrolo[2,3-b]pyrazine-7-carbonyl]-cyclopentanone | 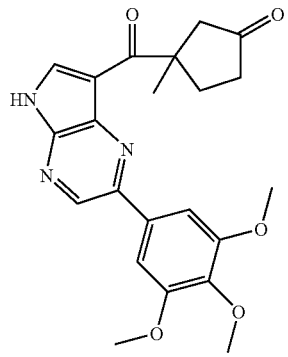 |
| --- | --- | --- |
| I-518 | 2-[3-(3,3-Dimethyl-pyrrolidin-1-yl)-phenyl]-5H-pyrrolo[2,3-b]pyrazine-7-carboxylic acid | 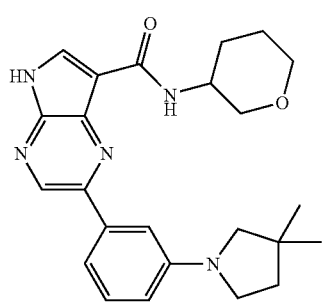 |
| I-519 | 4-(4-Hydroxy-piperidin-1-yl)-2,2-dimethyl-1-[2-(3,4,5-trimethoxyphenyl)-5H-pyrrolo[2,3-b]pyrazin-7-yl]-butan-1-one | 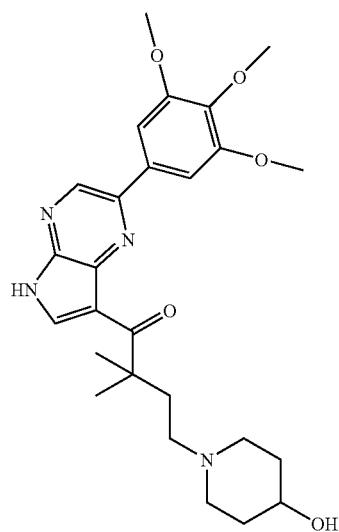 |

TABLE I-continued

| I-520 | 4-[(2-Hydroxy-ethyl)-methyl-amino]-2,2-dimethyl-1-[2-(3,4,5-trimethoxy-phenyl)-5H-pyrrolo[2,3-b]pyrazin-7-yl]-butan-1-one |
| --- | --- |
| I-521 | 2,2-Dimethyl-1-{2-[3-(tetrahydro-pyran-4-ylamino)-phenyl]-5H-pyrrolo[2,3-b]pyrazin-7-yl}-propan-1-one |
| I-522 | 3-Amino-N-{6-[7-(2,2-dimethyl-propionyl)-5H-pyrrolo[2,3-b]pyrazin-2-yl]-1H-indol-4-yl}-benzenesulfonamide |
| I-523 | 2-[3-(3,3-Dimethyl-pyrrolidin-1-yl)-phenyl]-5H-pyrrolo[2,3-b]pyrazine-7-carboxylic acid ((S)-2-hydroxy-1,2-dimethyl-propyl)-amide |

TABLE I-continued

| I-524 | 1-[2-(3-Fluorophenyl)-5H-pyrrolo[2,3-b]pyrazin-7-yl]-2,2-dimethyl-propan-1-one |
| --- | --- |
| I-525 | (3-Hydroxy-1-methyl-cyclopentyl)-[2-(3,4,5-trimethoxy-phenyl)-5H-pyrrolo[2,3-b]pyrazin-7-yl]-methanone |
| I-526 | 4-Amino-N-{6-[7-(2,2-dimethyl-propionyl)-5H-pyrrolo[2,3-b]pyrazin-2-yl]-1H-indol-4-yl}-3-fluoro-benzenesulfonamide |
| I-527 | 2-{4-Methyl-4-[2-(3,4,5-trimethoxy-phenyl)-5H-pyrrolo[2,3-b]pyrazine-7-carbonyl]-piperidin-1-yl}-acetamide |

TABLE I-continued
| I-528 | 1-{4-Methyl-4-[2-(3,4,5-trimethoxyphenyl)-5H-pyrrolo[2,3-b]pyrazine-7-carbonyl]-piperidin-1-yl}-ethanone | 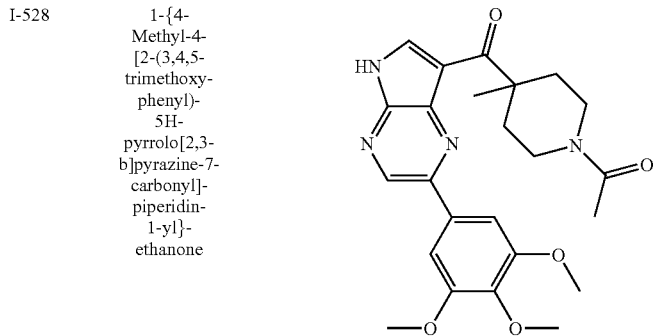 |
| I-529 | 6-Oxo-1,6-dihydropyridine-3-sulfonic acid {6-[7-(2,2-dimethylpropionyl)-5H-pyrrolo[2,3-b]pyrazin-2-yl]-1H-indol-4-yl}-amide | 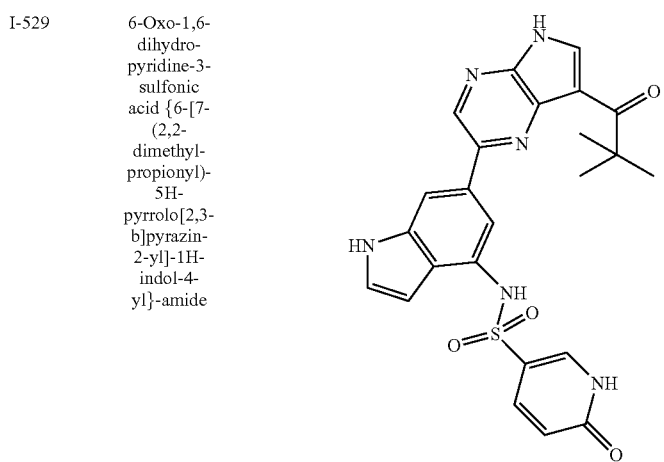 |
| I-530 | 4-Amino-N-{6-[7-(2,2-dimethylpropionyl)-5H-pyrrolo[2,3-b]pyrazin-2-yl]-1H-indol-4-yl}-3-trifluoromethyl-benzenesulfonamide | 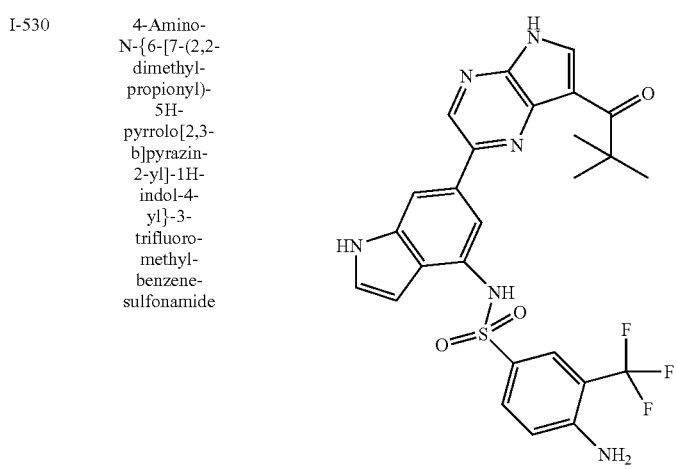 |

TABLE I-continued

| I-531 | 1-{2-[3-(3,3-Dimethyl-pyrrolidin-1-yl)-5-(3-methanesulfonyl-propoxy)-phenyl]-5H-pyrrolo[2,3-b]pyrazin-7-yl}-2,2-dimethyl-propan-1-one | |
|---|---|---|
| I-532 | N-{6-[7-(2,2-Dimethyl-propionyl)-5H-pyrrolo[2,3-b]pyrazin-2-yl]-1H-indol-4-yl}-4-hydroxy-benzene-sulfonamide | |
| I-533 | ((1S,3S)-3-Hydroxy-1-methyl-cyclopentyl)-[2-(3,4,5-trimethoxy-phenyl)-5H-pyrrolo[2,3-b]pyrazin-7-yl]-methanone | |
| I-534 | 1-{2-[3-(2-Aza-bicyclo[2.1.1]hex-2-yl)-phenyl]-5H-pyrrolo[2,3-b]pyrazin-7-yl}-2,2-dimethyl-propan-1-one | |

| | | |
|---|---|---|
| I-535 | ((1S,2R)-1,2-Dimethyl-cyclopentyl)-[2-(3-pyrrolidin-1-yl-phenyl)-5H-pyrrolo[2,3-b]pyrazin-7-yl]-methanone | |
| I-536 | 1-{2-[3-(3,3-Dimethyl-pyrrolidin-1-yl)-5-(2-hydroxy-propoxy)-phenyl]-5H-pyrrolo[2,3-b]pyrazin-7-yl}-2,2-dimethyl-propan-1-one | |
| I-537 | 1-{2-[3-(4,5-Dihydro-1H-imidazol-2-ylamino)-5-(3,3-dimethyl-pyrrolidin-1-yl)-phenyl]-5H-pyrrolo[2,3-b]pyrazin-7-yl}-2,2-dimethyl-propan-1-one | |
| I-538 | 2-[3-(3,3-Dimethyl-pyrrolidin-1-yl)-phenyl]-5H-pyrrolo[2,3-b]pyrazine-7-carboxylic acid phenylamide | |

TABLE I-continued

| I-539 | 2-[3-(3,3-Dimethyl-pyrrolidin-1-yl)-phenyl]-5H-pyrrolo[2,3-b]pyrazine-7-carboxylic acid (2-hydroxy-1,1-dimethyl-ethyl)-amide | |
| --- | --- | --- |
| I-540 | 2,2-Dimethyl-1-[2-(3-methylsulfanyl-5-pyrrolidin-1-yl-phenyl)-5H-pyrrolo[2,3-b]pyrazin-7-yl]-propan-1-one | |
| I-541 | 1-[2-(3-Methanesulfinyl-5-pyrrolidin-1-yl-phenyl)-5H-pyrrolo[2,3-b]pyrazin-7-yl]-2,2-dimethyl-propan-1-one | |
| I-542 | 1-[2-(3-Methanesulfonyl-5-pyrrolidin-1-yl-phenyl)-5H-pyrrolo[2,3-b]pyrazin-7-yl]-2,2-dimethyl-propan-1-one | |

TABLE I-continued

| I-543 | 2,2-Dimethyl-1-{2-[3-(3-pyridin-4-yl-pyrrolidin-1-yl)-phenyl]-5H-pyrrolo[2,3-b]pyrazin-7-yl}-propan-1-one | |
| --- | --- | --- |
| I-544 | 2,2-Dimethyl-1-{2-[3-(3-pyridin-2-yl-pyrrolidin-1-yl)-phenyl]-5H-pyrrolo[2,3-b]pyrazin-7-yl}-propan-1-one | |
| I-545 | 1-{2-[3-(1,7-Diaza-spiro[4.4]non-7-yl)-phenyl]-5H-pyrrolo[2,3-b]pyrazin-7-yl}-2,2-dimethyl-propan-1-one | |
| I-546 | 2,2-Dimethyl-1-{2-[3-(3-pyridin-3-yl-pyrrolidin-1-yl)-phenyl]-5H-pyrrolo[2,3-b]pyrazin-7-yl}-propan-1-one | |

TABLE I-continued

| I-547 | {4-Methyl-4-[2-(3,4,5-trimethoxyphenyl)-5H-pyrrolo[2,3-b]pyrazine-7-carbonyl]-piperidin-1-yl}-acetonitrile |
| --- | --- |
| I-548 | 2,2-Dimethyl-3-methylsulfanyl-1-[2-(3,4,5-trimethoxyphenyl)-5H-pyrrolo[2,3-b]pyrazin-7-yl]-propan-1-one |
| I-549 | 3-Methanesulfinyl-2,2-dimethyl-1-[2-(3,4,5-trimethoxyphenyl)-5H-pyrrolo[2,3-b]pyrazin-7-yl]-propan-1-one |
| I-550 | 3-Methanesulfonyl-2,2-dimethyl-1-[2-(3,4,5-trimethoxyphenyl)-5H-pyrrolo[2,3-b]pyrazin-7-yl]-propan-1-one |

TABLE I-continued

| I-551 | 2-[3-(2-Dimethylamino-ethoxy)-5-(3,3-dimethyl-pyrrolidin-1-yl)-phenyl]-5H-pyrrolo[2,3-b]pyrazine-7-carboxylic acid (3-hydroxy-2,2-dimethyl-propyl)-amide | |
|---|---|---|
| I-552 | 1-[2-(3-tert-Butylamino-phenyl)-5H-pyrrolo[2,3-b]pyrazin-7-yl]-2,2-dimethyl-propan-1-one | |
| I-553 | 1-(2-{3-[3-(2,3-Dihydroxy-propyl)-3-methyl-pyrrolidin-1-yl]-phenyl}-5H-pyrrolo[2,3-b]pyrazin-7-yl)-2,2-dimethyl-propan-1-one | |

Dosage and Administration

The compounds of the present invention may be formulated in a wide variety of oral administration dosage forms and carriers. Oral administration can be in the form of tablets, coated tablets, dragés, hard and soft gelatine capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof.

EXAMPLES

Example 1

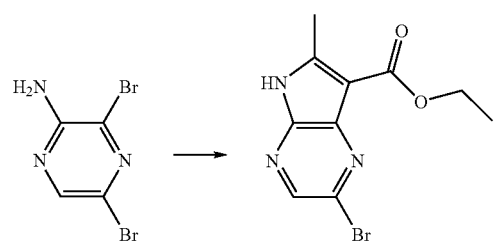

2-Bromo-6-methyl-5H-pyrrolo[2,3-b]pyrazine-7-carboxylic acid ethyl ester

To a flask charged with 20 mL of anhydrous N-meythlpyrrolidine at 0° C. was added 60% NaH (840 mg, 21 mmol).

After stirring 15 min, ethyl acetoacetate (2.73 g, 10.8 mmol) was added slowly. After stirring an additional 20 min 3,5-Dibromo-pyrazin-2-ylamine (5.04 g, 20 mmol). The reaction vessel was then removed from the ice bath and heated to 140° C. for 3 days. The dark mixture was cooled to rt and diluted with diethyl ether and water. The mixture was filtered and then partitioned. The organic layer was washed with water and then brine, dried over $Na_2SO_4$, filtered, and concentrated to afford a dark red oil. This was purified by silica gel chromatography (4:1 Hexanes:EtOAc) to afford 290 mg of 2-Bromo-6-methyl-5H-pyrrolo[2,3-b]pyrazine-7-carboxylic acid ethyl ester.

Example 2

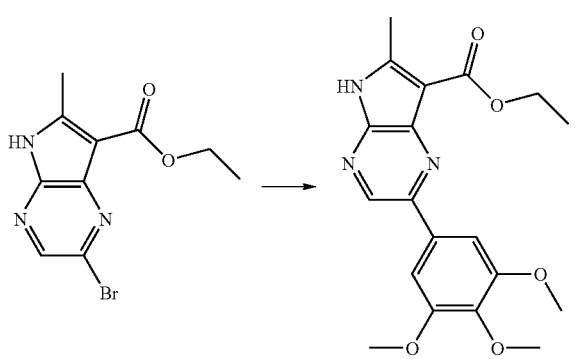

6-Methyl-2-(3,4,5-trimethoxy-phenyl)-5H-pyrrolo[2,3-b]pyrazine-7-carboxylic acid ethyl ester To a flask charged with 2-Bromo-6-methyl-5H-pyrrolo[2,3-b]pyrazine-7-carboxylic acid ethyl ester (360 mg, 1.26 mmol), 3,4,5-trimethoxyphenylboronic acid (320 mg, 1.51 mMol), Pd(dppf)Cl$_2$ (31 mg, 0.038 mmol) was added $K_2CO_3$ (520 mg, 3.75 mmol). The mixture was heated to 100° C. overnight. The reaction mixture was cooled, diluted with EtOAc and filtered over celite. The solution was washed with water and brine, dried over $Na_2SO_4$, filtered, and concentrated. Flash chromatography afforded 105 mg of 6-Methyl-2-(3,4,5-trimethoxy-phenyl)-5H-pyrrolo[2,3-b]pyrazine-7-carboxylic acid ethyl ester.

Example 3

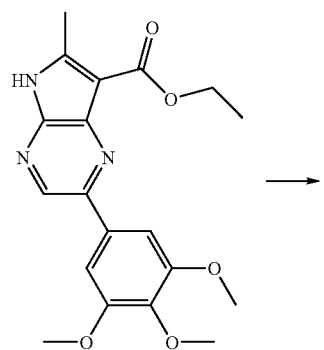

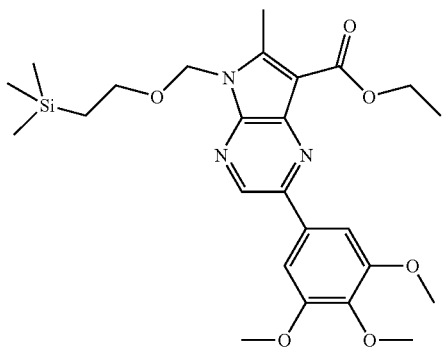

6-Methyl-2-(3,4,5-trimethoxy-phenyl)-5-(2-trimethylsilanyl-ethoxymethyl)-5H-pyrrolo[2,3-b]pyrazine-7-carboxylic acid ethyl ester To a solution of 6-Methyl-2-(3,4,5-trimethoxy-phenyl)-5H-pyrrolo[2,3-b]pyrazine-7-carboxylic acid ethyl ester (108 mg) in 3 ml of DMF was added 60% NaH. After stirring 15 minutes, (2-Chloromethoxy-ethyl)-trimethyl-silane (108 mg) was added and the mixture stirred at rt for 14 h. The mixture was partitioned between water and diethylether. The organic phase was concentrated and purified by flash chromatography (9:1 Hexanes:Ethyl acetate). Obtain 110 mg of 6-Methyl-2-(3,4,5-trimethoxy-phenyl)-5-(2-trimethylsilanyl-ethoxymethyl)-5H-pyrrolo[2,3-b]pyrazine-7-carboxylic acid ethyl ester.

Example 4

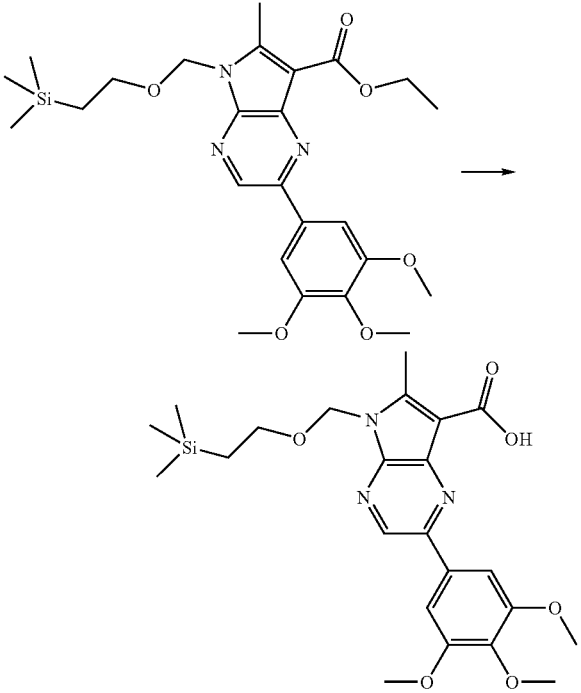

6-Methyl-2-(3,4,5-trimethoxy-phenyl)-5-(2-trimethylsilanyl-ethoxymethyl)-5H-pyrrolo[2,3-b]pyrazine-7-carboxylic acid To a solution of 6-Methyl-2-(3,4,5-trimethoxy-phenyl)-5-(2-trimethylsilanyl-ethoxymethyl)-5H-pyrrolo[2,3-b]pyrazine-7-carboxylic acid ethyl ester (110 mg, 0.22 mmol) in 1.0 mL of THF was added a 500 uL of 5.0 M aqueous NaOH. Heated to 60° C. for 3 days. Diluted with THF, made acidic with 1.0 M HCl and partitioned into methylene chloride. Dried the organic phase over Na₂SO₄, filtered, and concentrated. Collect 107 mg of 6-Methyl-2-(3,4,5-trimethoxy-phenyl)-5-(2-trimethylsilanyl-ethoxymethyl)-5H-pyrrolo[2,3-b]pyrazine-7-carboxylic acid sufficiently pure for the next step.

Example 5

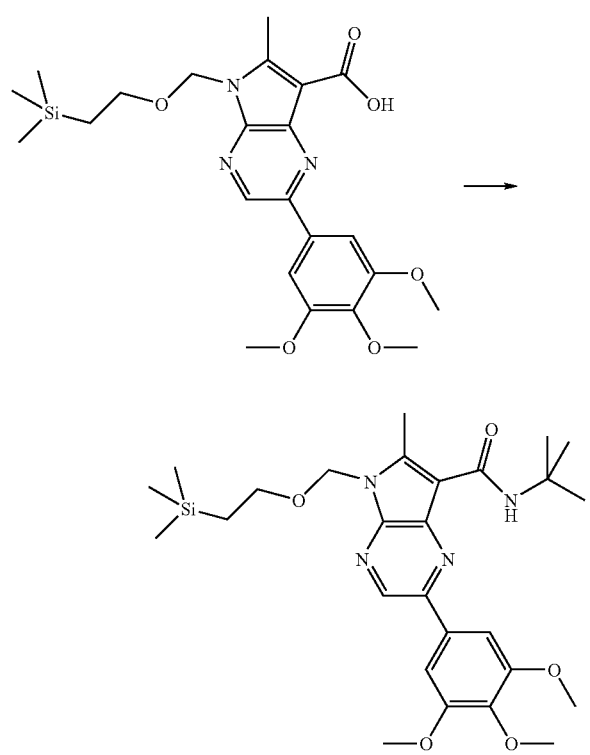

6-Methyl-2-(3,4,5-trimethoxy-phenyl)-5-(2-trimethylsilanyl-ethoxymethyl)-5H-pyrrolo[2,3-b]pyrazine-7-carboxylic acid tert-butylamide To a solution of 6-Methyl-2-(3,4,5-trimethoxy-phenyl)-5-(2-trimethylsilanyl-ethoxymethyl)-5H-pyrrolo[2,3-b]pyrazine-7-carboxylic acid (95 mg) in 1.5 mL of DMF was added PyBOP (128 mg) followed by tert-Butyl amine (70 mg). After stirring for 2 h, the mixture was partitioned between water and diethylether. The organic phase was washed with brine, dried over Na₂SO₄, filtered, and concentrated. Flash chromatography (4:1 Hexanes:ethylacetate) afforded 70 mg of 6-Methyl-2-(3,4,5-trimethoxy-phenyl)-5-(2-trimethylsilanyl-ethoxymethyl)-5H-pyrrolo[2,3-b]pyrazine-7-carboxylic acid tert-butylamide.

Example 6

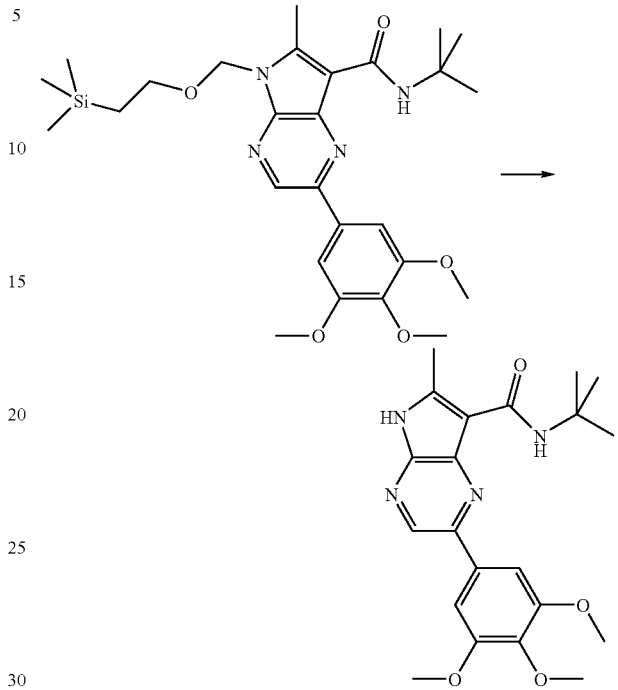

6-Methyl-2-(3,4,5-trimethoxy-phenyl)-5H-pyrrolo[2,3-b]pyrazine-7-carboxylic acid tert-butylamide To a solution of 6-Methyl-2-(3,4,5-trimethoxy-phenyl)-5-(2-trimethylsilanyl-ethoxymethyl)-5H-pyrrolo[2,3-b]pyrazine-7-carboxylic acid tert-butylamide (64 mg) in 0.5 mL of THF was added 400 uL of 1.0 M TBAF in THF. Heated the mixture to 60° C. for 14 h. Diluted with diethyl ether and water and partitioned. The organic phase was washed with brine, dried over Na₂SO₄, filtered, and concentrated. Flash purification (95:5 methylene chloride:Methanol) afforded 12 mg of 6-Methyl-2-(3,4,5-trimethoxy-phenyl)-5H-pyrrolo[2,3-b]pyrazine-7-carboxylic acid tert-butylamide as a yellow solid.

Example 7

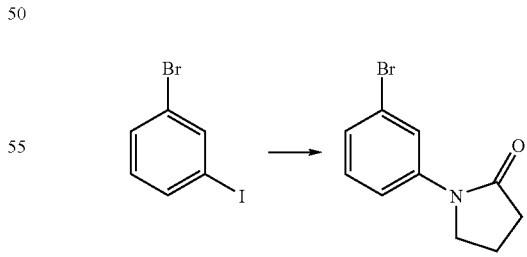

1-(3-Bromo-phenyl)-pyrrolidin-2-one

To a flask charged with Cs₂CO₃ (4.74 g), Copper(I) bromide (99 mg), and ethyl-2-cyclohexanone-carboxylate (248 mg) was added 3 mL of DMSO under an argon atmosphere. 1-bromo-3-iodobenzene (2.0 g) was added followed by a solution of 2-pyrrolidinone (715 mg) in 3 mL of DMSO. The reaction mixture was stirred at rt for 16 h and then heated to 90° C. for 24 h. The mixture was filtered over celite, concentrated and purified by flash chromatography (65:35 hexanes: ethyl acetate) to afford 983 mg of 1-(3-Bromo-phenyl)-pyrrolidin-2-one as a brown solid.

Example 8

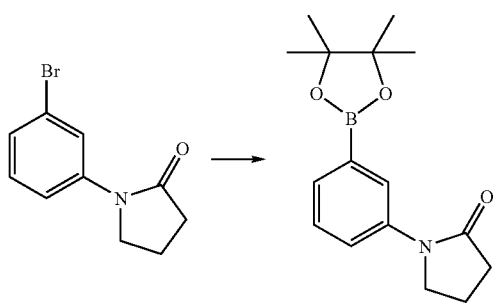

1-[3-(4,4,5,5-Tetramethyl-[1,3,2]dioxaborolan-2-yl)-phenyl]-pyrrolidin-2-one

To a flask charged with 1-(3-Bromo-phenyl)-pyrrolidin-2-one (713 mg), bis(pinacolato)diboron (1.51 g), [1,1'-bis(diphenylphosphino)ferrocene]dichloropalladium(II) complex (121 mg) and potassium acetate (874 mg) was added 10 mL of DMSO and the resulting mixture stirred at 90° C. for 16 h. The reaction mixture was cooled and filtered over celite. The mixture was then partitioned between water and dichloromethane and the organic phase was dried over $Na_2SO_4$, filtered and concentrated. Purification by silica gel chromatography (0-100% ethyl acetate in hexanes) afforded a 286 mg of 1-[3-(4,4,5,5-Tetramethyl-[1,3,2]dioxaborolan-2-yl)-phenyl]-pyrrolidin-2-one. Subsequent steps involved the standard Suzuki coupling, iodination, and aminocarbonylation.

3,3-Dimethyl-1-[3-(4,4,5,5-tetramethyl-[1,3,2]dioxaborolan-2-yl)-phenyl]-pyrrolidine was prepared following general procedures described in these Examples.

Example 9

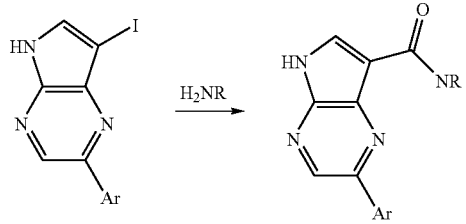

A flask was charged with aryliodide (1.0 equiv), palladium acetate 0.1 equiv, potassium carbonate (2.0 equiv) and 4,5-bis(diphenylphosphino)-9,9-dimethyxanthene (0.1 equiv) and toluene added (concentration=0.2 M). The mixture was heated to 70° C. and then carbon monoxide was bubbled slowly through the mixture for 2-3 minutes. Then the amine (4.0 equiv) was added slowly in a dropwise manner, maintaining an atmosphere of carbon monoxide. After 2 h at 70° C., the mixture was filtered over celite, and concentrated. Chromatography (methylene chloride: MeOH) affords the desired amides.

2-(3-Chloro-5-fluoro-phenyl)-5H-pyrrolo[2,3-b]pyrazine-7-carboxylic acid isopropylamide was prepared according to the by replacing aryl iodide with 2-(3-chloro-5-fluoro-phenyl)-7-iodo-5H-pyrrolo[2,3-b]pyrazine and amine with isopropyl amine: foam; MS m/z 333 ($M^{+H}$).

Example 10

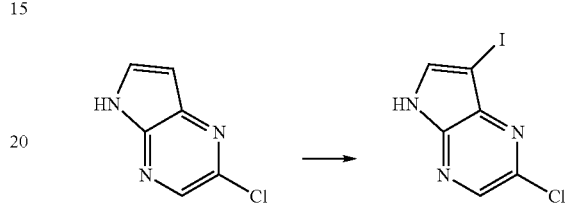

A solution of 2-Chloro-5H-pyrrolo[2,3-b]pyrazine (0.62 g, 4 mmol) in 20 mL dimethylformamide at 0° C. under argon atmosphere was treated with potassium hydroxide (0.47 g, 8.4 mmol, crushed) and iodine was added in portions (1.03 g, 4 mmol). The mixture was warmed to ambient temperature and stirred at that temperature for 10 m. The mixture was then diluted with ethyl acetate and washed with saturated aqueous sodium bisulfite. The aqueous layer was washed with ethyl acetate four times, then the combined organic layers were dried over magnesium sulfate, filtered, and concentrated to carry on to the next example.

Example 11

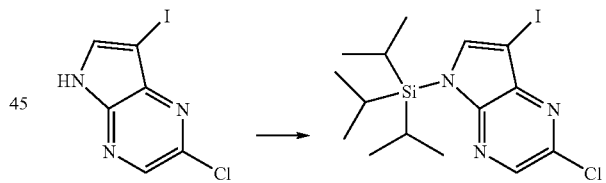

2-Chloro-7-iodo-5-triisopropylsilanyl-5H-pyrrolo[2,3-b]pyrazine

A solution of the 2-Chloro-7-iodo-5H-pyrrolo[2,3-b]pyrazine from the previous step in 30 mL of tetrahydrofuran stirring at 0° C. under argon atmosphere was treated with lithium hexamethyldisilylazide (6 mL, 1 M in hexanes, 6 mmol), followed by triisopropylsilyl chloride (1.1 mL, 5.2 mmol). After 30 m at 0° C., the solution was warmed to ambient temperature and diluted with 20% ethyl acetate in hexanes, then washed twice with water and once with brine. After drying the organic layer over magnesium sulfate, filtration was followed by solvent removal and flash chromatography of the resultant residue using 2.5% ethyl acetate in hexanes, to furnish 2-Chloro-7-iodo-5-triisopropylsilanyl-5H-pyrrolo[2,3-b]pyrazine (1.68 g, 95% over two steps).

Example 12

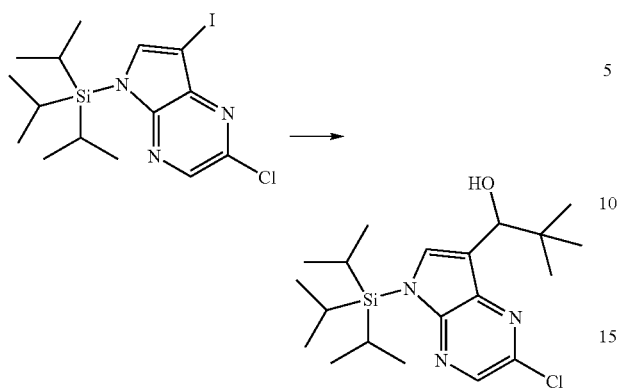

1-(2-Chloro-5-triisopropylsilanyl-5H-pyrrolo[2,3-b]pyrazin-7-yl)-2,2-dimethyl-propan-1-ol 2-Chloro-7-iodo-5-triisopropylsilanyl-5H-pyrrolo[2,3-b]pyrazine (0.56 g, 1.28 mmol) was dissolved in 10 mL of dry tetrahydrofuran and stirred under argon with cooling to −78° C. A solution of isopropylmagnesium chloride with lithium chloride (3 mL, 1M, 3 mmol) was added via syringe. After 10 m, neat pivaldehyde (0.325 mL, 3 mmol, distilled) was added all at once. After 1 h at −78° C., the reaction was quenched by the addition of saturated aqueous ammonium chloride, then diluted with ethyl acetate and allowed to warm to ambient temperature. The organic layer was then washed successively with saturated aqueous sodium bicarbonate and brine. After drying over magnesium sulfate, the solution was filtered and solvent removed, and carried directly into the next step.

Example 13

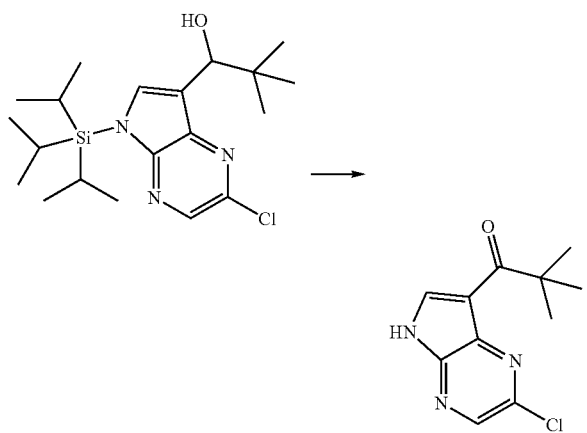

1-(2-Chloro-5H-pyrrolo[2,3-b]pyrazin-7-yl)-2,2-dimethyl-propan-1-one

The residue from the previous example was dissolved in 30 mL methylene chloride and treated with the Dess-Martin periodinane (0.76 g). After 10 m, the reaction was diluted with ethyl acetate and washed successively with saturated aqueous sodium bisulfite, saturated aqueous sodium bicarbonate and brine. After drying over magnesium sulfate, filtration, and solvent removal, the residue was taken up in 30 mL of tetrahydrofuran and treated with 10 drops each of 1 M sodium hydroxide and saturated aqueous sodium bicarbonate. The mixture was stirred for 2 h, then diluted with ethyl acetate and washed two times with saturated aqueous sodium bicarbonate and once with brine. The organic layer was dried over magnesium sulfate, filtered, and concentrated under reduced pressure. Flash chromatography using 20% ethyl acetate in hexanes then furnished the desired 1-(2-Chloro-5H-pyrrolo[2,3-b]pyrazin-7-yl)-2,2-dimethyl-propan-1-one (0.18 g, 59% for the sequence). The material was a solid, m.p. 209-210° C.

Example 14

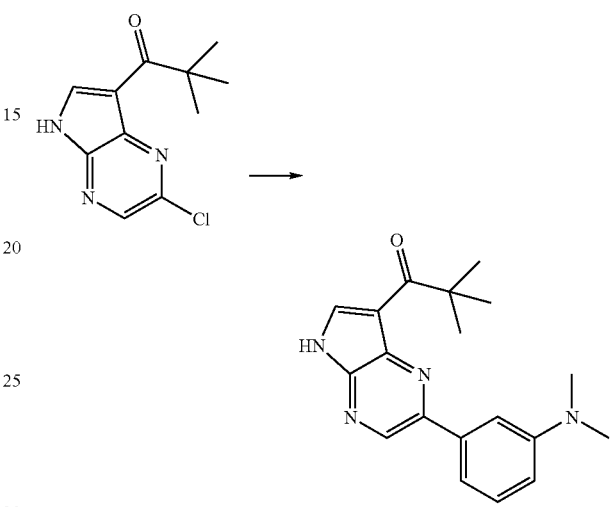

1-[2-(3-Dimethylamino-phenyl)-5H-pyrrolo[2,3-b]pyrazin-7-yl]-2,2-dimethyl-propan-1-one Into a microwave vial containing a stir bar was placed 3-pivaloyl-5-chloropyrrolopyrazine (69 mg), 3-dimethylaminophenylboronic acid (73 mg), potassium carbonate (164 mg) and 1,1'-Bis(diphenylphosphino)ferrocene]palladium(II) dichloride dichloromethane complex (1:1) (20 mg). To the solids were then added dioxane (4 mL) and water (1 mL). Argon was briefly bubbled through the stirred solution and the microwave vial was securely capped. The entire contents were then heated in the microwave at 150° C. for 40 m. Upon completion, the reaction was diluted with ethyl acetate and washed with saturated sodium bicarbonate and brine. After drying and solvent removal, the residue was chromatographed using a gradient from 10% ethyl acetate in hexanes to 30% ethyl acetate in hexanes. After recrystallization of the product containing fractions using hot dichloromethane and hexanes 36 mg of the product was obtained (m.p. 223.2-228.4° C.).

Example 15

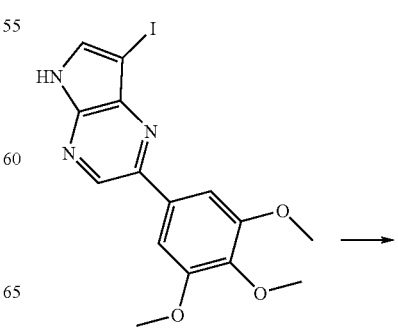

-continued

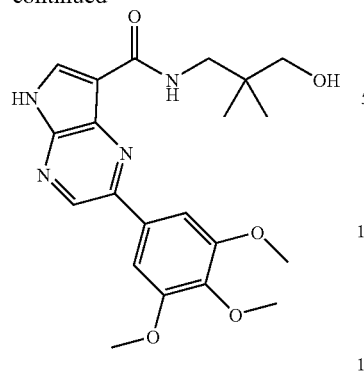

2-(3,4,5-Trimethoxy-phenyl)-5H-pyrrolo[2,3-b]pyrazine-7-carboxylic acid (3-hydroxy-2,2-dimethylpropyl)-amide A mixture of 7-iodo-2-(3,4,5-trimethoxy-phenyl)-5H-pyrrolo[2,3-b]pyrazine (100 mg, 0.24 mmol), 4,5-bis(diphenylphosphino)-9,9-dimethylxanthene (Xantphos) (14 mg, 0.02 mmol), Pd(OAc)$_2$ (5.5 mg, 0.02 mmol), and K$_2$CO$_3$ (88 mg, 0.64 mmol) in DMF (1 mL) was heated to 60° C. as CO was bubbled through the reaction mixture. In a separate reaction flask, a mixture of 7-iodo-2-(3,4,5-trimethoxy-phenyl)-5H-pyrrolo[2,3-b]pyrazine (100 mg, 0.24 mmol) and Pd(OAc)$_2$ (5.5 mg, 0.02 mmol) in DMF (1 mL) was heated to 60° C. as CO was bubbled through the reaction mixture. For each reaction flask, a solution of 3-amino-2,2-dimethyl-propan-1-ol (50 mg, 0.49 mmol) in DMF (1 mL) was added slowly to the resultant solution which was then stirred under a CO atmosphere at 60° C. for 2 h. For each reaction flask, an additional solution of 3-amino-2,2-dimethyl-propan-1-ol (75 mg, 0.74 mmol) in DMF (0.5 mL) was added to the reaction mixture which was then stirred under a CO atmosphere at 60° C. for 1.5 h, 75° C. for 3 h, and room temperature for 3 d. Both reaction mixtures were combined and partitioned between saturated NH$_4$Cl and CH$_2$Cl$_2$. The aqueous layer was extracted with CH$_2$Cl$_2$ and the combined organic phases were washed with water, dried (Na$_2$SO$_4$) and concentrated to give 400 mg of a brown oil. The crude product was purified by flash chromatography using a 0-10% of MeOH, basified with 5% of concentrated aqueous NH$_4$OH, in CH$_2$Cl$_2$ as eluant to afford 160 mg of crude product which was further purified by preparative thin layer chromatography using 85:14.25:0.75 CH$_2$Cl$_2$:MeOH:concentrated aqueous NH$_4$OH as eluant to provide 30 mg of an oily solid. Treatment of this residue with MeOH and CH$_2$Cl$_2$ and collection of the resultant solids which were then washed with Et$_2$O gave 26 mg (13%) of 2-(3,4,5-trimethoxy-phenyl)-5H-pyrrolo[2,3-b]pyrazine-7-carboxylic acid (3-hydroxy-2,2-dimethyl-propyl)-amide as a pale yellow solid. MP 224-225° C., M+H 415.

Example 16

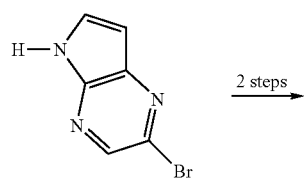

-continued

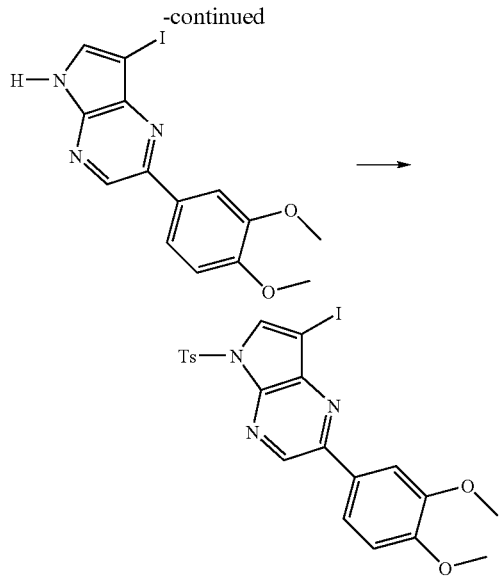

2-(3,4-Dimethoxy-phenyl)-7-iodo-5H-pyrrolo[2,3-b]pyrazine was prepared starting from 2-bromo-5H-pyrrolo[2,3-b]pyrazine and 3,4-dimethoxyphenylboronic acid. To a 0° C. solution of 2-(3,4-dimethoxy-phenyl)-7-iodo-5H-pyrrolo[2,3-b]pyrazine (821 mg, 2.1 mmol) in THF (20 mL) was added NaH (55% dispersion in mineral oil, 168 mg, 3.85 mmol) portionwise and the resultant mixture was stirred for 15 min, treated with TsCl (736 mg, 3.85 mmol), stirred overnight at room temperature, and poured into water and EtOAc. A yellow solid precipitated and the heterogeneous biphasic mixture was filtered to afford 680 mg (39%) of 2-(3,4-dimethoxy-phenyl)-7-iodo-5-(toluene-4-sulfonyl)-5H-pyrrolo[2,3-b]pyrazine as a yellow solid.

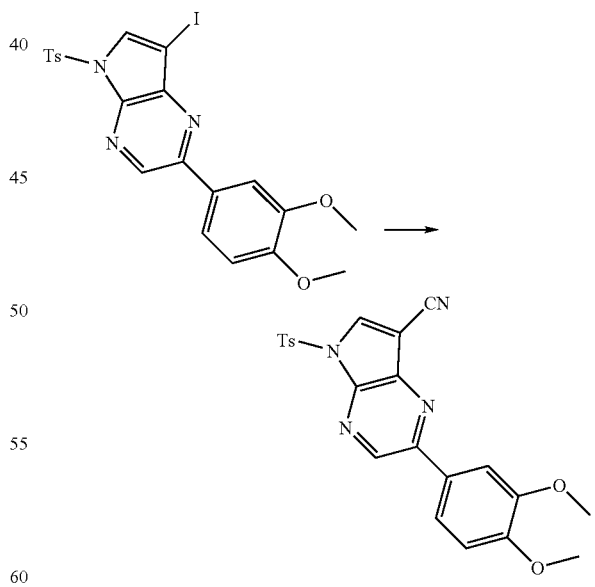

2-(3,4-Dimethoxy-phenyl)-5-(toluene-4-sulfonyl)-5H-pyrrolo[2,3-b]pyrazine-7-carbonitrile A mixture of 2-(3,4-dimethoxy-phenyl)-7-iodo-5-(toluene-4-sulfonyl)-5H-pyrrolo[2,3-b]pyrazine (380 mg, 0.71 mmol), CuCN (256, 2.8 mmol), bis(dibenzylideneacetone)palladium(0) [Pd$_2$(dba)$_3$] (26 mg, 0.03 mmol), and 1,1'-bis(diphenylphosphino)ferrocene (63 mg, 0.11 mmol) in dioxane (7 mL) was stirred at 90° C. overnight. Additional CuCN (50, 0.56 mmol), Pd$_2$(dba)$_3$ (6 mg, 0.01 mmol), and 1,1'-bis(diphenylphosphino)ferrocene (15 mg, 0.03 mmol) was added to the reaction mixture which was then stirred at 90° C. for 4 h and partitioned between water and EtOAc. The aqueous layer was extracted with EtOAc and the combined organic phases were concentrated. The residue was purified by flash chromatography using 40 g of silica gel and 0-70% EtOAc in hexanes as eluant to afford 60 mg (20%) of 2-(3,4-dimethoxy-phenyl)-5-(toluene-4-sulfonyl)-5H-pyrrolo[2,3-b]pyrazine-7-carbonitrile as a white solid and 50 mg (16%) as a yellow solid. MP 233-234° C., M+H 435.

Example 17

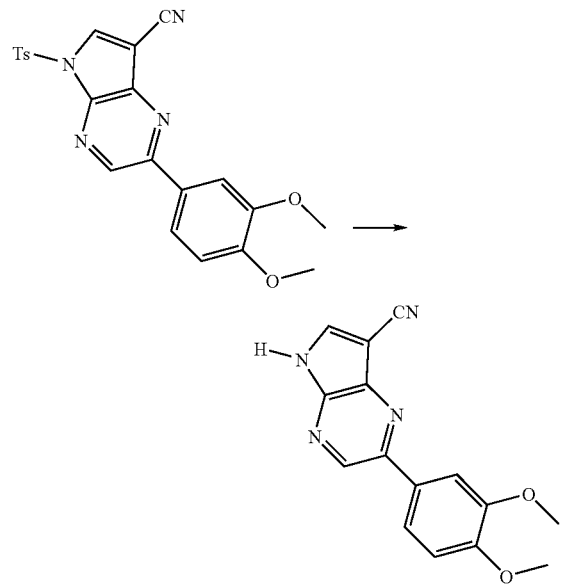

2-(3,4-Dimethoxy-phenyl)-5H-pyrrolo[2,3-b]pyrazine-7-carbonitrile

A solution of 2-(3,4-dimethoxy-phenyl)-5-(toluene-4-sulfonyl)-5H-pyrrolo[2,3-b]pyrazine-7-carbonitrile (90 mg, 0.2 mmol) and 3 M NaOH (0.2 mL, 0.6 mmol) in MeOH (2 mL) was stirred at 50° C. for 30 min, allowed to cool to room temperature, and partitioned between 1 N HCl and EtOAc. The aqueous layer was extracted with EtOAc and the combined organic phases were dried (Na$_2$SO$_4$) and concentrated to give 90 mg of a pale yellow solid. The crude product was purified by flash chromatography using 4 g of silica gel and a gradient of MeOH, basified with 5% of concentrated aqueous NH$_4$OH, in CH$_2$Cl$_2$ as eluant to afford 40 mg of a tan solid which was washed with MeOH followed by a mixture of CH$_2$Cl$_2$ and Et$_2$O to provide 2-(3,4-dimethoxy-phenyl)-5H-pyrrolo[2,3-b]pyrazine-7-carbonitrile as a light tan solid. MP 284-285° C., M+H 281.

Example 18

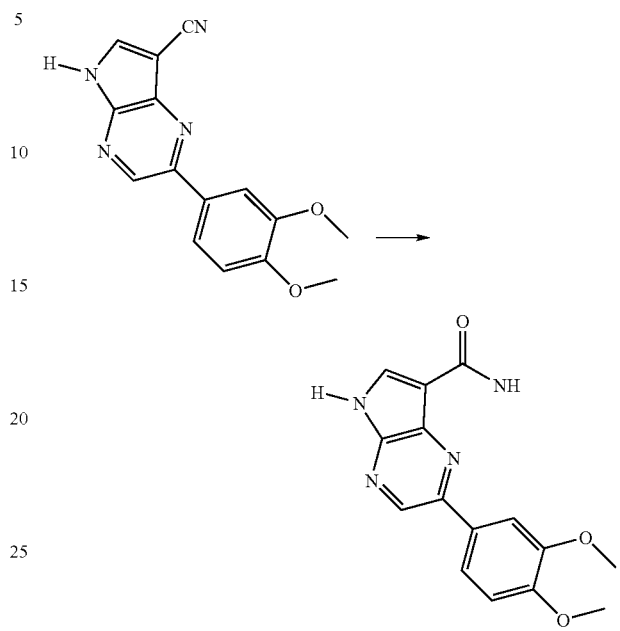

2-(3,4-Dimethoxy-phenyl)-5H-pyrrolo[2,3-b]pyrazine-7-carboxylic acid amide

A 0.2 M solution of NaOMe was prepared from Na (80 mg) in MeOH (18 mL). A mixture of 2-(3,4-dimethoxy-phenyl)-5H-pyrrolo[2,3-b]pyrazine-7-carbonitrile (40 mg, 0.14 mmol), NaOMe (0.2 M in MeOH, 0.5 mL, 0.1 mmol), and 3 M NaOH (0.3 mL, 1 mmol) was microwaved at 150° C. for 30 min, treated with NaOH (90 mg, 2.3 mmol, microwaved at 150° C. for an additional 45 min, and partitioned between saturated NH$_4$Cl and EtOAc. The aqueous layer was extracted with EtOAc and the combined organic phases were dried (Na$_2$SO$_4$) and concentrated to give 36 mg of a pale yellow solid. The crude product was washed with CH$_2$Cl$_2$ and Et$_2$O to afford 25 mg (60%) 2-(3,4-dimethoxy-phenyl)-5H-pyrrolo[2,3-b]pyrazine-7-carboxylic acid amide as a pale yellow solid. MP 290-292.4° C., M+H 299.

Example 19

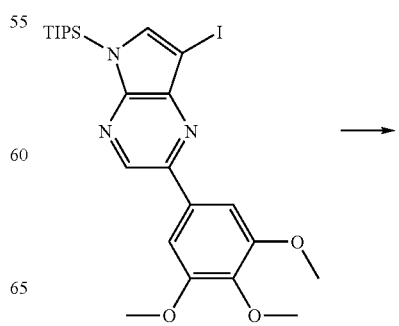

2-(3,4,5-Trimethoxy-phenyl)-5H-pyrrolo[2,3-b]pyrazine-7-carboxylic acid

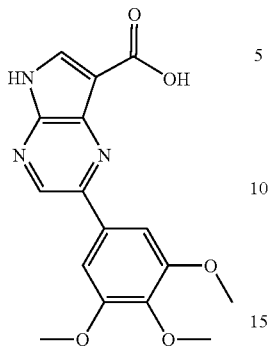

To a −78° C. solution of 7-iodo-5-triisopropylsilanyl-2-(3,4,5-trimethoxy-phenyl)-5H-pyrrolo[2,3-b]pyrazine (1.28 g, 2.25 mmol) in THF (5.6 mL) was dropwise added iPrMgCl—LiCl (1 M in THF, 5.6 mL, 5.6 mmol). The solution was stirred for 10 min and $CO_2$ was bubbled into the solution for 5 min. The solution was allowed to slowly warm to ~10° C. over 4 h and treated with 10% aqueous citric acid, resulting in the precipitation of solids and gelatinous material. The heterogeneous mixture was partitioned between saturated 10% aqueous citric acid and EtOAc. The aqueous layer was extracted with EtOAc. Most of the gelatinous material dissipated during the extractions but much of the solids were still present in the combined organic phases. Filtration of the combined organic phases provided 750 mg (105%) of 2-(3,4,5-trimethoxy-phenyl)-5H-pyrrolo[2,3-b]pyrazine-7-carboxylic acid as a yellow powder. MP 237.8-238.4° C., M+H 330.

2-[3-(3,3-Dimethyl-pyrrolidin-1-yl)-phenyl]-5-H-pyrrolo[2,3-b]pyrazine-7-carboxylic acid was prepared following general procedures described in these Examples.

Example 20

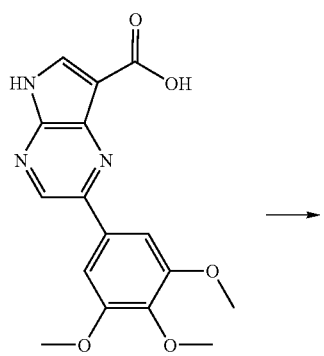

2-(3,4,5-Trimethoxy-phenyl)-5H-pyrrolo[2,3-b]pyrazine-7-carboxylic acid isobutyl-amide

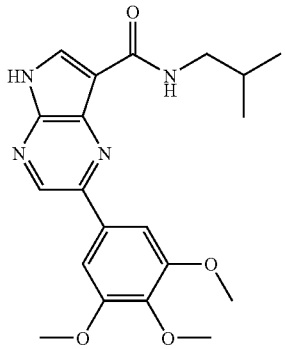

A mixture of 2-(3,4,5-trimethoxy-phenyl)-5H-pyrrolo[2,3-b]pyrazine-7-carboxylic acid (70 mg, 0.2 mmol), isobutylamine (44 μL, 0.42 mmol), 1-hydroxybenzotriazole hydrate (56 mg, 0.41 mmol), and N-(3-dimethylaminopropyl)-N'-ethylcarbodiimide hydrochloride (84 mg, 0.44 mmol) in DMF and $CH_2Cl_2$ was stirred at 70° C. overnight and partitioned between saturated $NH_4Cl$ and $CH_2Cl_2$. The aqueous layer was extracted with $CH_2Cl_2$ and the combined organic phases were washed with water, dried ($Na_2SO_4$), and concentrated. The residue was purified by preparative thin layer chromatography using 90:9.5:0.5 $CH_2Cl_2$:MeOH:concentrated aqueous $NH_4OH$ as eluant to afford 42 mg (50%) of 2-(3,4,5-trimethoxy-phenyl)-5H-pyrrolo[2,3-b]pyrazine-7-carboxylic acid isobutyl-amide as a pale yellow powder. M+H 403.

2-[3-(3,3-Dimethyl-pyrrolidin-1-yl)-phenyl]-5-H-pyrrolo[2,3-b]pyrazine-7-carboxylic acid (3-hydroxy-2,2-dimethyl-propyl)-amide, $(M+H)^+=422$, was prepared following general procedures described in these Examples, with the addition of 2 equivalents of triethyl amine.

Other Compounds Prepared Using this General Procedure (prepared starting from 2-(3,4,5-trimethoxy-phenyl)-5H-pyrrolo[2,3-b]pyrazine-7-carboxylic acid and the appropriate amine):
2-(3,4,5-Trimethoxy-phenyl)-5H-pyrrolo[2,3-b]pyrazine-7-carboxylic acid (2,3-dihydroxy-propyl)-amide;
2-(3,4,5-Trimethoxy-phenyl)-5H-pyrrolo[2,3-b]pyrazine-7-carboxylic acid (tetrahydro-furan-3-yl)-amide;
2-(3,4,5-Trimethoxy-phenyl)-5H-pyrrolo[2,3-b]pyrazine-7-carboxylic acid (2-methoxy-ethyl)-amide;
2-(3,4,5-Trimethoxy-phenyl)-5H-pyrrolo[2,3-b]pyrazine-7-carboxylic acid (2,2-dimethyl-propyl)-amide;
2-(3,4,5-Trimethoxy-phenyl)-5H-pyrrolo[2,3-b]pyrazine-7-carboxylic acid (3-methoxy-propyl)-amide

Example 21

Other Compounds Prepared Using this General Procedure (prepared starting from 2-(3,4,5-trimethoxy-phenyl)-5H-pyrrolo[2,3-b]pyrazine-7-carboxylic acid and the appropriate amine following general procedures as described in these Examples, but with triethylamine added):
2-(3,4,5-Trimethoxy-phenyl)-5H-pyrrolo[2,3-b]pyrazine-7-carboxylic acid (1,1-dioxo-tetrahydro-1λ6-thiophen-3-yl)-amide;
2-(3,4,5-Trimethoxy-phenyl)-5H-pyrrolo[2,3-b]pyrazine-7-carboxylic acid (2-methanesulfonyl-ethyl)-amide;
2-(3,4,5-Trimethoxy-phenyl)-5H-pyrrolo[2,3-b]pyrazine-7-carboxylic acid (2-sulfamoyl-ethyl)-amide;

2-(3,4,5-Trimethoxy-phenyl)-5H-pyrrolo[2,3-b]pyrazine-7-carboxylic acid (2-methoxy-2-methyl-propyl)-amide.

Example 22

2-(3,4,5-Trimethoxy-phenyl)-5H-pyrrolo[2,3-b]pyrazine-7-carboxylic acid (2-hydroxy-propyl)-amide was prepared starting from 2-(3,4,5-trimethoxy-phenyl)-5H-pyrrolo[2,3-b]pyrazine-7-carboxylic acid and 1-amino-propan-2-ol following the general procedures described in these Examples but with DMF as solvent. MP 201.9-202.6° C., M+H 387.

Example 23

2-(3,4,5-Trimethoxy-phenyl)-5H-pyrrolo[2,3-b]pyrazine-7-carboxylic acid (tetrahydro-pyran-3-yl)-amide was prepared starting from 2-(3,4,5-trimethoxy-phenyl)-5H-pyrrolo[2,3-b]pyrazine-7-carboxylic acid and tetrahydro-pyran-3-ylamine hydrochloride following the general procedures described in these Examples but with triethylamine and DMAP added. MP 191-192° C., M+H 413.

Example 24

2-(3,4,5-Trimethoxy-phenyl)-5H-pyrrolo[2,3-b]pyrazine-7-carboxylic acid (2-methoxy-propyl)-amide was prepared starting from 2-(3,4,5-trimethoxy-phenyl)-5H-pyrrolo[2,3-b]pyrazine-7-carboxylic acid and 2-methoxy-propylamine hydrochloride following the general procedures described in these Examples but with 1-[3-(dimethylamino)propyl]-3-ethylcarbodiimide methiodide instead of N-(3-dimethylaminopropyl)-N'-ethylcarbodiimide hydrochloride and with triethylamine. MP 199-200° C., M+H 401.

Example 25

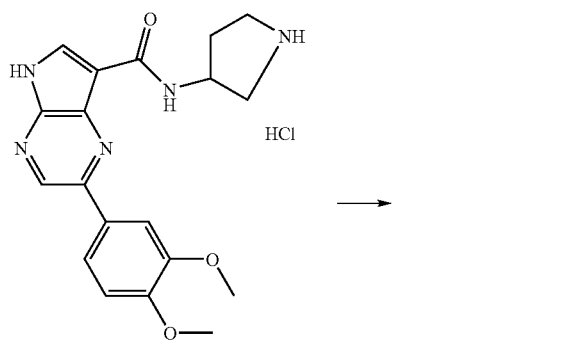

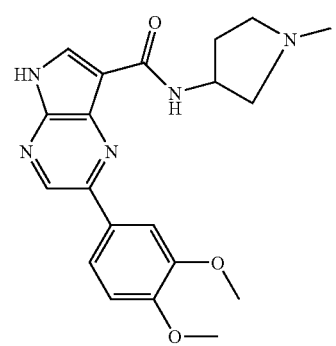

2-(3,4-Dimethoxy-phenyl)-5H-pyrrolo[2,3-b]pyrazine-7-carboxylic acid (1-methyl-pyrrolidin-3-yl)-amide To a mixture of 2-(3,4-dimethoxy-phenyl)-5H-pyrrolo[2,3-b]pyrazine-7-carboxylic acid pyrrolidin-3-ylamide hydrochloride (12 mg, 0.03 mmol) in MeOH (0.5 mL) was added NaBH$_3$CN (15 mg, 0.23 mmol). A solution of HOAc (1 drop) in MeOH (1 mL) was prepared and 2 drops of this solution was added to the reaction mixture so that the pH ~4. Aqueous CH$_2$O (37%, 25 µL, 0.34 mmol) was added to the reaction mixture which was then stirred at room temperature for 2 h, partitioned between saturated Na$_2$CO$_3$ and CH$_2$Cl$_2$. The aqueous layer was extracted with CH$_2$Cl$_2$ and the combined organic phases were dried (Na$_2$SO$_4$) and concentrated to give a pale yellow solid. The crude product was washed with Et$_2$O to afford 11 mg (100%) of 2-(3,4-dimethoxy-phenyl)-5H-pyrrolo[2,3-b]pyrazine-7-carboxylic acid (1-methyl-pyrrolidin-3-yl)-amide as a yellow powder. MP 193-194° C., M+H 382.

Example 26

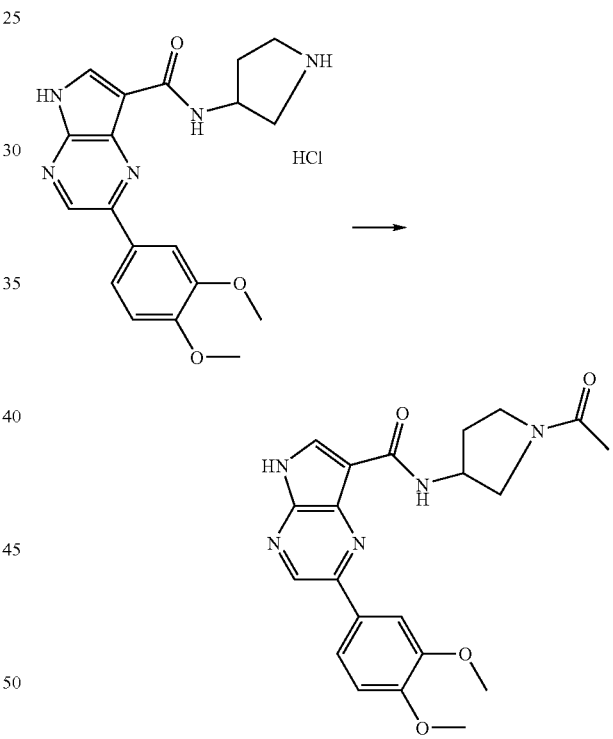

2-(3,4-Dimethoxy-phenyl)-5H-pyrrolo[2,3-b]pyrazine-7-carboxylic acid (1-acetyl-pyrrolidin-3-yl)-amide To a mixture of 2-(3,4-dimethoxy-phenyl)-5H-pyrrolo[2,3-b]pyrazine-7-carboxylic acid pyrrolidin-3-ylamide hydrochloride (8 mg, 0.02 mmol) in DMF (0.1 mL) and CH$_2$Cl$_2$ (0.1 mL) was sequentially added triethylamine (3.2 µL, 0.02 mmol) and acetic anhydride (1.5 µL, 0.02 mmol). The reaction mixture was stirred, treated with additional triethylamine (10 µL, 0.07 mmol) and acetic anhydride (1.5 µL, 0.02 mmol), and partitioned between saturated NH$_4$Cl and CH$_2$Cl$_2$. The aqueous layer was extracted with CH$_2$Cl$_2$ and the combined organic phases were washed with saturated NaHCO₃, dried (Na₂SO₄), and concentrated. The residue was treated with a 1:1 solution of MeOH: saturated Na₂CO₃ overnight. The reaction was partitioned between saturated NH₄Cl and CH₂Cl₂. The aqueous layer was extracted with CH₂Cl₂ and the combined organic phases were washed with saturated NaHCO₃, dried (Na₂SO₄), and concentrated to give 8 mg of an oil which precipitates upon treatment with MeOH. The solids were collected and washed with CH₂Cl₂ and Et₂O to afford 6 mg (75%) of 2-(3,4-dimethoxy-phenyl)-5H-pyrrolo[2,3-b]pyrazine-7-carboxylic acid (1-acetyl-pyrrolidin-3-yl)-amide as a cream colored solid. MP 211-212° C., M+H 410.

Example 27

(3,4-Dimethoxy-phenyl)-5H-pyrrolo[2,3-b]pyrazine-7-carboxylic acid (1-acetyl-piperidin-4-yl)-amide was prepared starting from 2-(3,4-dimethoxy-phenyl)-5H-pyrrolo[2,3-b]pyrazine-7-carboxylic acid piperidin-4-ylamide using a procedure similar to previous Example. M+H 424.

Example 28

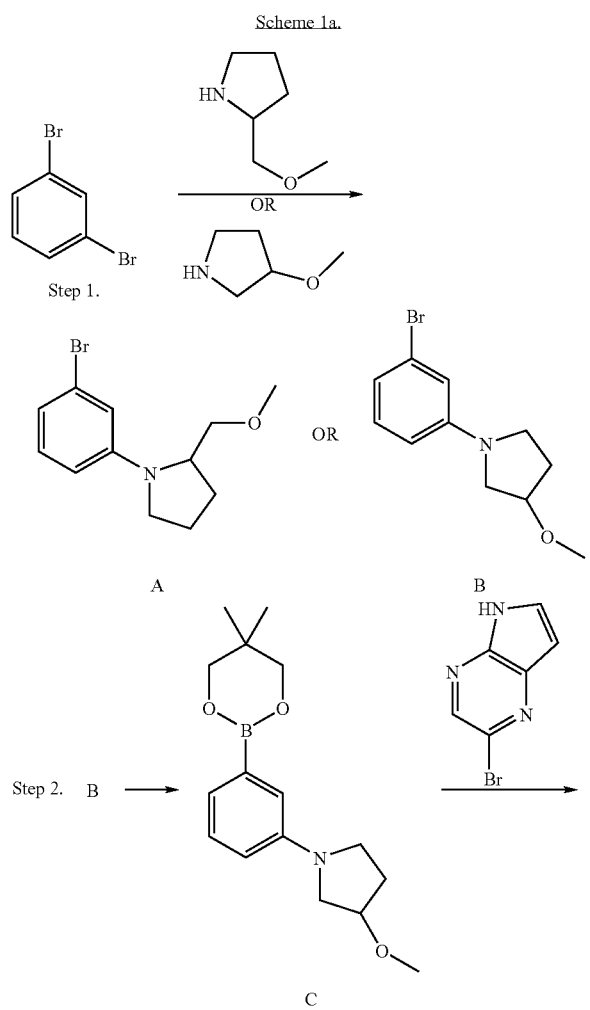

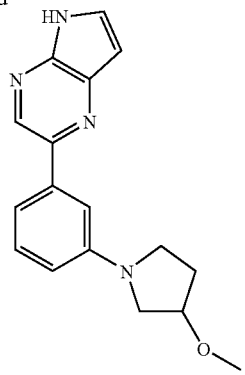

D

2-[3-(3-Methoxy-pyrrolidin-1-yl)-phenyl]-5H-pyrrolo[2,3-b]pyrazine-7-carboxylic acid tert-butylamide and 2-[3-(3-Methoxy-pyrrolidin-1-yl)-phenyl]-5H-pyrrolo[2,3-b]pyrazine-7-carboxylic acid ((S)-2-methoxy-1-methyl-ethyl)-amide Step 1. Potassium fluoride on Alumina (40%, 25.5 g, Sigma-Aldrich Co.), Pd₂(dba)₃ (297 mg, 0.3 mmol), and rac-BINAP (405 mg, 0.65 mmol) were combined and treated according to SynLett 2005, 1275-1278. While the mixture was still warm, it was treated with rac-2-methyloxymethylpyrrolidine (1.86 g, 16.2 mmol) and 1,3-dibromobenzene (4.0 mL, 32.2 mmol) and the resulted mixture was heated to 85 Celsius for 3 hours. Upon cooling, it was subjected to silica gel chromatography (SGC) with the desired material eluted with 5 to 20% ethyl acetate in hexanes. The desired material (A, 2.93 g) displayed spectroscopic properties consistent with the proposed structure.

3-Methoxypyrrolidine hydrochloride (500 mg, 3.6 mmol, Matrix Co.), N,N-dimethylacetamide (4 mL), K₂CO₃ (1.26 g, 9.1 mmol), 1,3-dibromobenzene (1.1 mL, 9.1 mmol) and Cu(I) Br dimethyl sulfide (148 mg, 0.72 mmol) were combined and treated according to *Bioorg. Med. Chem.* 2006, 14, 6807. The mixture was heated to 120 Celsius for 5 hours. Upon cooling, it was poured into water and extracted with 1:1 mixture of hexane: Et₂O. Upon storage over anhydrous sodium sulfate, it was subjected to silica gel chromatography (SGC) with the desired material eluted with 10 to 20% ethyl acetate in hexanes. The oily material (B, 340 mg) displayed spectroscopic properties consistent with the proposed structure.

Step 2. Bromide (B, 450 mg, 1.8 mmol), KOAc (620 mg, 6.3 mmol), and bis(neopentylglycolato)diboron (425 mg, 1.9 mmol) were combined in 1,4-dioxane (10 mL) under Argon. The mixture was immediately treated with palladium(dppf) chloride (74 mg, 0.09 mmol) and heated to reflux. The dark solution was cooled after 3 hours and treated with 5-bromopyrrolopyrazine (C, 360 mg, 1.8 mmol), cesium carbonate (880 mg, 2.7 mmol), water (1 mL), and [Ph₃P]₄Pd(0) (105 mg, 0.09 mmol) and returned to reflux. After 44 hours, the mixture was partitioned between water and ethyl acetate. The volatiles were removed and the residue subjected to SGC. The desired material (D, 350 mg) eluted with 40 to 90% ethyl acetate in hexanes and displayed spectroscopic properties consistent with the proposed structure.

Scheme 1b.

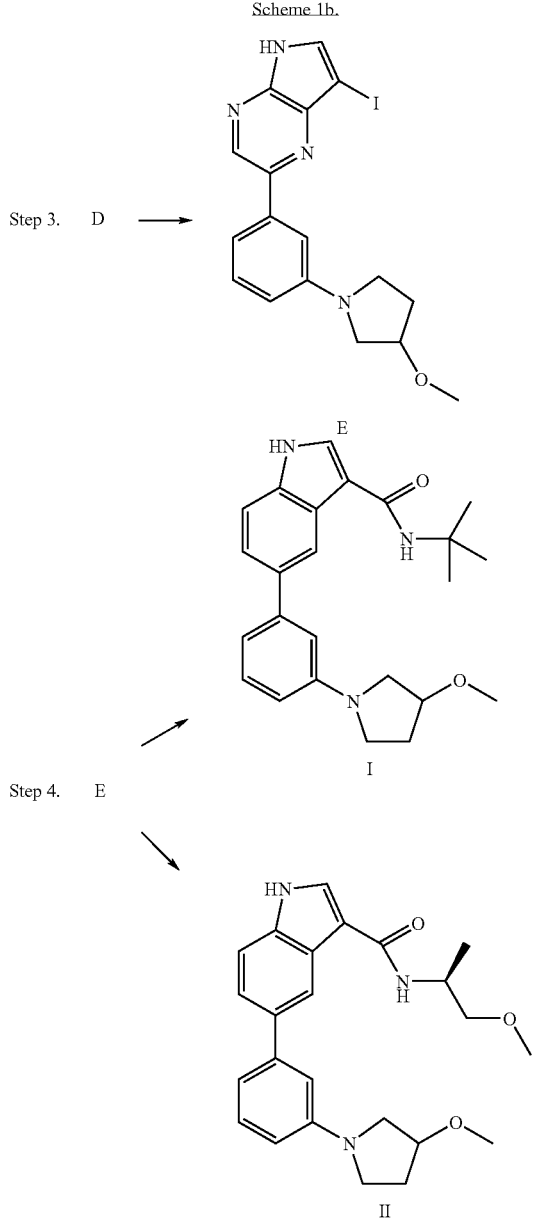

Step 3. Pyrrolopyrazine D (350 mg, 1.2 mmol) was dissolved in N,N-dimethylformamide (5 mL) and cooled to 0 Celsius. Powdered potassium hydroxide (170 mg, 3 mmol) and iodine (320 mg, 1.25 mmol) were added in sequence which gave a tan solution after 30 minutes at 0 Celsius. The solution was treated with water, decolorized with 10% sodium thiosulfate$_{(aq)}$ and the resulting precipitate was filtered. The filter cake was washed with fresh water and stored in vacuo at 50 Celsius overnight. The tan powder (E, 240 mg) displayed spectroscopic properties consistent with the proposed structure.

Step 4. 3-Iodo substrate (E, 95 mg, 0.23 mmol) was treated with XantPhos (13 mg, 0.023 mmol, Strem Co.) and tert-butylamine (0.04 mL, 0.4 mmol) in toluene (5 mL) and carbon monoxide was bubbled through the suspension for 60 to 90 seconds. Palladium acetate (5.1 mg, 0.023 mmol) was added and the mixture was heated to 65 Celsius under 1 atm of CO. After 21 hours, the mixture was cooled and subjected to SGC. The desired amide I (11 mg) was eluted with 0 to 5% ethanol in ethyl acetate and obtained as a foam: ESMS m/z 394 (M$^{+1}$) for MW of 393.

The desired amide II was prepared according to step 4 with E (130 mg, 0.31 mmol) by replacing the amine with S-1-methoxy-2-propylamine (0.05 mL, 0.54 mmol). It was obtained as a foam (55 mg): ESMS m/z 410 (M$^{+1}$) for MW of 409.

2-[3-(4-Methoxy-benzyloxy)-phenyl]-5H-pyrrolo[2,3-b]pyrazine-7-carboxylic acid isopropylamide was prepared following general procedures described in these Examples and was obtained by providing 2-[3-(4-methoxy-benzyloxy)-phenyl]-4,4,5,5-tetramethyl-[1,3,2]dioxaborolane in step 2 and replacing tert-butylamine with 2-propylamine in step 4: m.p. 215-216° C.; MS m/z 417 (M$^{+1}$).

2-[3-(2-Methoxymethyl-pyrrolidin-1-yl)-phenyl]-5H-pyrrolo[2,3-b]pyrazine-7-carboxylic acid isopropylamide was prepared following general procedures described in these Examples and was obtained by providing 2-methoxymethyl-1-[3-(4,4,5,5-tetramethyl-[1,3,2]dioxaborolan-2-yl)-phenyl]-pyrrolidine in step 2 and replacing tert-butylamine with 2-propylamine in step 4: m.p. 187-190° C.; MS m/z 394 (M$^{+1}$).

Example 29

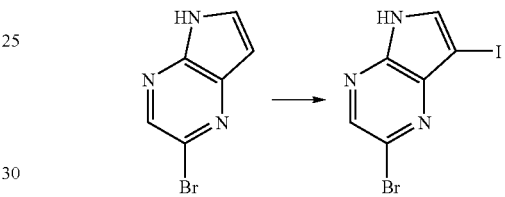

2-bromo-7-iodo-5H-pyrrolo[2,3-b]pyrazine. 1.5 g of 2-bromo-5H-pyrrolo[2,3-b]pyrazine (7.57 mmol, 1 eq) was dissolved in 20 ml of N,N-dimethylformamide. 1.27 g of crushed potassium hydroxide pellets (22.7 mmol, 3 eq) were then added and the mixture was stirred for 10 min. The reaction flask was cooled in an ice bath and 1.92 g of iodine (7.57 mmol, 1 eq) was added in several portions over 1 hr. After 30 min. more the reaction was complete and about 10 ml 1M sodium thiosulfate solution, water and ethyl acetate were added. The layers were separated and the aqueous layer was extracted with ethyl acetate two times more. The combined ethyl acetate layers were washed with water and saturated sodium chloride solution, and then dried over sodium sulfate. After filtration and evaporation of solvent 2.4 g of solid (97%) was obtained and used directly in the next reaction.

Example 30

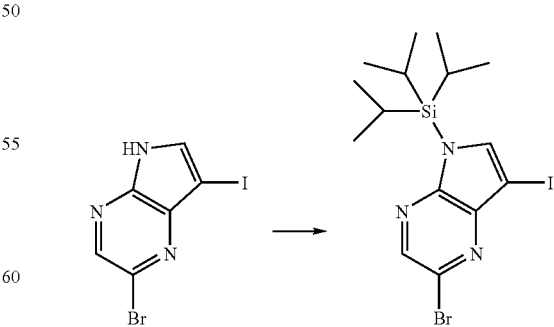

2-bromo-7-iodo-5-triisopropylsilanyl-5H-pyrrolo[2,3-b]pyrazine. 2.4 g of 2-bromo-7-iodo-5H-pyrrolo[2,3-b]pyrazine (7.4 mmol, 1 eq) was dissolved in 74 ml of tetrahydrofuran. The reaction flask was cooled in an ice bath and 8 ml lithium bis(trimethylsilyl)amide (1M hexanes solution, 8 mmol, 1.08 eq) was added dropwise. The reaction solution was stirred at room temperature for 20 min. The reaction was cooled in an ice bath and 1.7 ml triisopropylsilyl chloride (7.94 mmol, 1.07 eq) was then added slowly. After 1 hr. at room temperature, more lithium bis(trimethylsilyl)amide (0.4 ml, 0.4 mmol, 0.05 eq) and triisopropylsilyl chloride (0.2 ml, 0.9 mmol, 0.12 eq) were added. After 1 hr. more the reaction was complete. The reaction flask was cooled in an ice bath and ethyl acetate, water and sodium bicarbonate solution were added. The layers were separated and the aqueous layer was extracted once more with ethyl acetate. The ethyl acetate layers were washed with saturated sodium chloride solution, dried over sodium sulfate, filtered and evaporated. The crude residue was purified by silica gel chromatography (ethyl acetate/hexanes) to give 2.3 g (64%) of product and 0.84 g of starting material (35%).

Example 31

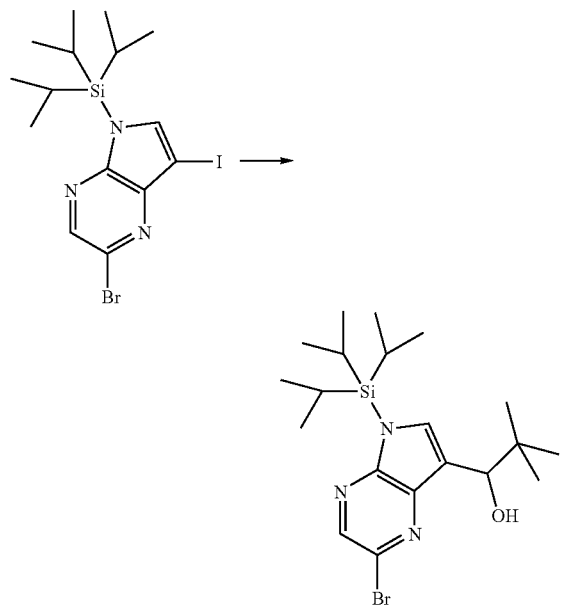

1-(2-bromo-5-triisopropylsilanyl-5H-pyrrolo[2,3-b]pyrazin-7-yl)-2,2-dimethyl-propan-1-ol. 2.05 g of 2-bromo-7-iodo-5-triisopropylsilanyl-5H-pyrrolo[2,3-b]pyrazine (4.28 mmol, 1 eq) was dissolved in 60 ml of dry tetrahydrofuran. The solution was cooled in a dry ice/acetone bath under argon. 1.91 ml of butyl lithium (2.13M hexanes solution, 4.07 mmol, 0.95 eq) was added. After 30 sec., 1.16 ml of trimethylacetaldehyde (distilled, 10.71 mmol, 2.5 eq) was quickly added. The mixture was stirred for 30 min. at −78 C, then quenched by addition of ammonium chloride solution, and then stirred to room temperature. Ethyl acetate and water were added to the reaction mixture and the layers separated. The aqueous layer was extracted once more with ethyl acetate, and the ethyl acetate layers were washed with saturated sodium chloride solution, dried over sodium sulfate, filtered and evaporated. The crude residue was purified by silica gel chromatography (ethyl acetate/hexanes) to give 0.39 g (20%) of product and 0.64 g of the product acetal (27%). Both compounds are carried into the next reaction.

Example 32

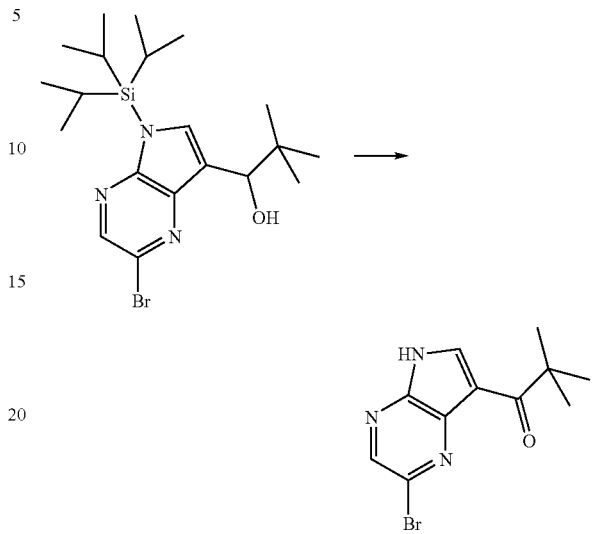

1-(2-bromo-5H-pyrrolo[2,3-b]pyrazin-7-yl)-2,2-dimethyl-propan-1-one. 0.4 g of 1-(2-bromo-5-triisopropylsilanyl-5H-pyrrolo[2,3-b]pyrazin-7-yl)-2,2-dimethyl-propan-1-ol (0.9 mmol, 1 eq) was dissolved in 9 ml of tetrahydrofuran. 1.8 ml of tetrabutylammonium fluoride (1M THF solution, 1.8 mmol, 2 eq) was added and the reaction was stirred at room temperature. After two hours, the reaction was complete and water, sodium bicarbonate solution and ethyl acetate were added. The layers were separated and the aqueous layer was extracted twice more with ethyl acetate. The ethyl acetate layers were washed with saturated sodium chloride solution, dried over sodium sulfate and evaporated to a residue.

The residue from the deprotection of 2.2 mmol of starting compound was dissolved in 22 ml of dichloromethane. 1.02 g Dess-Martin periodinane (2.4 mmol, 1.1 eq) was added and the mixture stirred at room temperature. After one hour the reaction was worked up by addition of water, sodium bicarbonate solution and ethyl acetate. The layers were separated and the aqueous layer was extracted with ethyl acetate once more. The ethyl acetate layers were washed with saturated sodium chloride solution, dried over sodium sulfate, filtered and evaporated. The crude residue was purified by silica gel chromatography (ethyl acetate/hexanes) to give 0.53 g (85%) of product.

Example 33

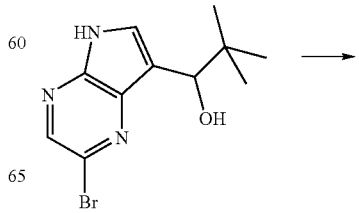

-continued

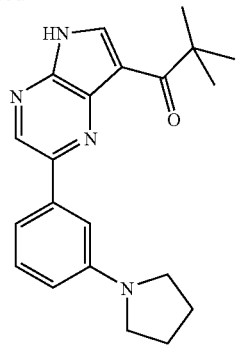

2,2-dimethyl-1-[2-(3-pyrrolidin-1-yl-phenyl)-5H-pyrrolo[2,3-b]pyrazin-7-yl]-propan-1-one. 90 mg of 1-(2-bromo-5H-pyrrolo[2,3-b]pyrazin-7-yl)-2,2-dimethyl-propan-1-one (0.32 mmol, 1 eq) was dissolved in 3.2 ml of 4:1 1,4-dioxane:water in a microwave reaction vial. The solution was purged with a stream of argon gas. 84 mg of 3-(1-pyrrolidino)phenyl boronic acid (0.335 mmol, 1.05 eq), 21 mg of 1,1'-bis(diphenylphosphino)-ferrocene) palladium dichloride (1:1 dichloromethane complex, 0.025 mmol, 0.08 eq) and then 110 mg of potassium carbonate (0.78 mmol, 2.5 eq) were added. The vial was sealed, placed in a microwave reactor and run at 15° C. for 30 min. The reaction was worked up by addition of water, ethyl acetate and sodium bicarbonate solution. The layers were separated and the aqueous layer was extracted once more with ethyl acetate. The ethyl acetate layers were washed with sodium bicarbonate solution and then dried over sodium sulfate. After filtration and evaporation, the crude residue was purified by silica gel chromatography (methanol/dichloromethane) and then recrystallized from dichloromethane/methanol/hexanes. 46 mg (55%) of product was obtained. (mp 262-264.2 C; MS: (M+H)$^+$=349.

The above general procedure was followed for synthesis the following compounds:

4-Amino-N-{6-[7-(2,2-dimethyl-propionyl)-5H-pyrrolo[2,3-b]pyrazin-2-yl]-1-methyl-1H-indol-4-yl}-N-methyl-benzenesulfonamide: (M+H)$^+$=517; MP=281-282° C.;

4-Amino-N-{6-[7-(2,2-dimethyl-propionyl)-5H-pyrrolo[2,3-b]pyrazin-2-yl]-1H-indol-4-yl}-N-methyl-benzenesulfonamide: (M+H)$^+$=503; MP=272-274° C.;

2,2-Dimethyl-1-[2-(3-methyl-1H-indazol-5-yl)-5H-pyrrolo[2,3-b]pyrazin-7-yl]-propan-1-one: (M+H)$^+$=334; $^1$H NMR (DMSO): δ 9.07 (s), 8.51 (s), 2.58 (s) ppm; only using the Sem-protected starting material as prepared in Ex 35, followed by deprotection as described below.

[2-(1H-Indol-5-yl)-5H-pyrrolo[2,3-b]pyrazin-7-yl]-(1-methyl-cyclohexyl)-methanone; (M+H)$^+$=359; $^1$H NMR (DMSO): δ 8.95 (s), 8.47 (s), 1.62 (s) ppm; only using the Sem-protected starting material as prepared following the general procedures described in these Examples and followed by deprotection as described below.

1-(2-Furan-3-yl-5H-pyrrolo[2,3-b]pyrazin-7-yl)-2,2-dimethyl-propan-1-one was prepared according to the above general procedure and was obtained by replacing 3-(1-pyrrolidino)phenyl boronic acid with 3-furan boronic acid: m.p. 256-258° C.; MS m/z 270 (M$^{+H}$).

The above general procedure was followed for the synthesis of the following compounds:

1-[2-(3-tert-Butyl-5-methyl-phenyl)-5H-pyrrolo[2,3-b]pyrazin-7-yl]-2,2-dimethyl-propan-1-one (M+H)$^+$=350; MP=234.9-236.1° C.

1-(2-Biphenyl-3-yl-5H-pyrrolo[2,3-b]pyrazin-7-yl)-2,2-dimethyl-propan-1-one (M+H)$^+$=356; MP=219.9-221.1° C.

1-[2-(3-tert-Butoxymethyl-phenyl)-5H-pyrrolo[2,3-b]pyrazin-7-yl]-2,2-dimethyl-propan-1-one (M+H)$^+$=366; MP=202.0-203.0° C.

1-[2-(3-Isopropyl-phenyl)-5H-pyrrolo[2,3-b]pyrazin-7-yl]-2,2-dimethyl-propan-1-one (M+H)$^+$=322; MP=197.0-198.0° C.

1-{2-[3-(3,5-Dimethyl-isoxazol-4-yl)-phenyl]-5H-pyrrolo[2,3-b]pyrazin-7-yl}-2,2-dimethyl-propan-1-one (M+H)$^+$=375;

2,2-Dimethyl-1-(2-quinolin-5-yl-5H-pyrrolo[2,3-b]pyrazin-7-yl)-propan-1-one (M+H)$^+$=331; MP=251.0-252.0° C.

1-[2-(3-Bromo-phenyl)-5H-pyrrolo[2,3-b]pyrazin-7-yl]-2,2-dimethyl-propan-1-one (M+H)$^+$=358;

1-(2-Cyclopent-1-enyl-5H-pyrrolo[2,3-b]pyrazin-7-yl)-2,2-dimethyl-propan-1-one (M+H)$^+$=270; MP=252.0-253.0° C.

2,2-Dimethyl-1-{2-[3-(2-methyl-2H-pyrazol-3-yl)-phenyl]-5H-pyrrolo[2,3-b]pyrazin-7-yl}-propan-1-one (M+H)$^+$=360;

1-[2-(3-Chloro-4-fluoro-phenyl)-5H-pyrrolo[2,3-b]pyrazin-7-yl]-2,2-dimethyl-propan-1-one (M+H)$^+$=332; MP=233.0-234.0° C.

1-[2-(1H-Indazol-4-yl)-5H-pyrrolo[2,3-b]pyrazin-7-yl]-2,2-dimethyl-propan-1-one (M+H)$^+$=320; MP>300° C.

2,2-Dimethyl-1-[2-(2'-methyl-biphenyl-3-yl)-5H-pyrrolo[2,3-b]pyrazin-7-yl]propan-1-one (M+H)$^+$=370

1-[2-(3-Hydroxymethyl-phenyl)-5H-pyrrolo[2,3-b]pyrazin-7-yl]-2,2-dimethyl-propan-1-one (M+H)$^+$=310; MP=208.0-210.0° C.

1-[2-(1H-Indazol-5-yl)-5H-pyrrolo[2,3-b]pyrazin-7-yl]-2,2-dimethyl-propan-1-one (M+H)$^+$=320; MP=286.0-287.0° C.

1-[2-(3-Acetyl-4-hydroxy-phenyl)-5H-pyrrolo[2,3-b]pyrazin-7-yl]-2,2-dimethyl-propan-1-one (In this case the product was formed by removal of a carbon from the chromen-4-one boronate by water during the course of the Suzuki reaction.)

(M+H)⁺=338; MP=237.9-242.1° C.

2,2-Dimethyl-1-(2-quinolin-6-yl-5H-pyrrolo[2,3-b]
pyrazin-7-yl)-propan-1-one (M+H)⁺=331

2,2-Dimethyl-1-[2-(3-trimethylsilanyl-phenyl)-5H-
pyrrolo[2,3-b]pyrazin-7-yl]-propan-1-one (M+H)⁺=352

1-(2-Biphenyl-4-yl-5H-pyrrolo[2,3-b]pyrazin-7-yl)-
2,2-dimethyl-propan-1-one (M+H)⁺=356; MP=275.0-277.0° C.

2,2-Dimethyl-1-{2-[4-(5-methyl-[1,3,4]oxadiazol-2-
yl)-phenyl]-5H-pyrrolo[2,3-b]pyrazin-7-yl}-propan-
1-one (M+H)⁺=362; MP>300° C.

2,2-Dimethyl-1-[2-(4-trimethylsilanyl-phenyl)-5H-
pyrrolo[2,3-b]pyrazin-7-yl]propan-1-one (M+H)⁺=352; MP=233.0-235.0° C.

2,2-Dimethyl-1-{2-[4-(2-piperidin-1-yl-ethoxy)-
phenyl]-5H-pyrrolo[2,3-b]pyrazin-7-yl}-propan-1-
one (M+H)⁺=407; MP=207.0-208.0° C.

3-[7-(2,2-Dimethyl-propionyl)-5H-pyrrolo[2,3-b]
pyrazin-2-yl]-N-ethyl-benzamide (M+H)⁺=351; MP=232.0-233.0° C.

2,2-Dimethyl-1-[2-(1-methyl-1H-indazol-4-yl)-5H-
pyrrolo[2,3-b]pyrazin-7-yl]propan-1-one (M+H)⁺=334; MP=255.0-256.0° C.

After synthesis of boronates from the corresponding bromo compounds following the general procedure described in these Examples, the following compounds were prepared:

1-{2-[3-(3H-Imidazol-4-yl)-phenyl]-5H-pyrrolo[2,3-
b]pyrazin-7-yl}-2,2-dimethyl-propan-1-one (M+H)⁺=346; MP=287.0-288.0° C.

2,2-Dimethyl-1-[2-(3-oxazol-5-yl-phenyl)-5H-pyr-
rolo[2,3-b]pyrazin-7-yl]propan-1-one (M+H)⁺=347; MP=259.0-260.0° C.

3-{3-[7-(2,2-Dimethyl-propionyl)-5H-pyrrolo[2,3-b]
pyrazin-2-yl]phenyl}-3-oxo-propionitrile In this case the isoxazole ring of 5-(3-bromo-phenyl)-isoxazole opened during formation of the boronate. (M+H)⁺=347.

1-{2-[4-(1H-Imidazol-4-yl)-phenyl]-5H-pyrrolo[2,3-
b]pyrazin-7-yl}-2,2-dimethyl-propan-1-one (M+H)⁺=346; MP>300° C.

1-{3-[7-(2,2-Dimethyl-propionyl)-5H-pyrrolo[2,3-b]
pyrazin-2-yl]-phenyl}-pyrrolidin-2-one (M+H)⁺=363; MP=260.0-262.0° C.

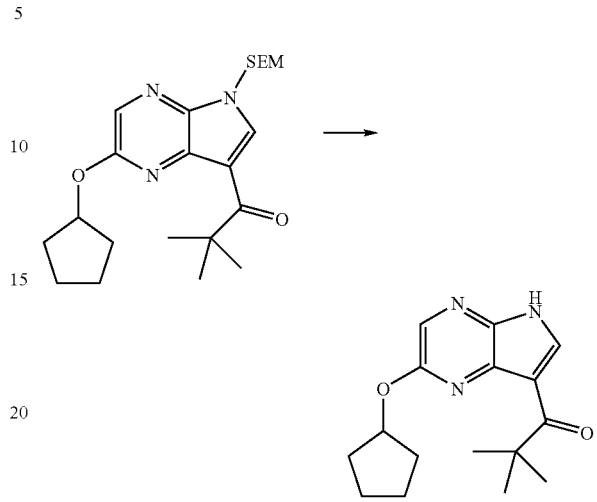

1-(2-cyclopentyloxy-5H-pyrrolo[2,3-b]pyrazin-7-yl)-
2,2-dimethyl-propan-1-one

A solution of 1-[2-cyclopentyloxy-5-(2-trimethylsilanyl-ethoxymethyl)-5H-pyrrolo[2,3-b]pyrazin-7-yl]-2,2-dimethyl-propan-1-one (0.017 g, 0.041 mmol) in 1 mL of dichloromethane and 1 mL of trifluoroacetic acid was stirred for 5 h then concentrated to a yellow oil. Silica gel chromatography (0→40% EtOAc/hexanes) afforded 0.012 g of a white solid. ¹H NMR spectroscopy indicated that this intermediate was the formaldehyde adduct of the desired product. The solid was dissolved in 1 mL of ethanol and the solution was treated with sodium acetate trihydrate (0.064 g, 0.47 mmol). The colorless mixture was stirred for 5 h then concentrated. The residue was partitioned between 5 mL of ethyl acetate and 5 mL of water. The organic layer was sequentially washed with 5 mL of water and 5 mL of a sat. aq. NaCl solution, dried over MgSO₄, filtered and concentrated to 0.007 g (57%) of 1-(2-cyclopentyloxy-5H-pyrrolo[2,3-b]pyrazin-7-yl)-2,2-dimethyl-propan-1-one as a slightly impure white solid.

Example 34

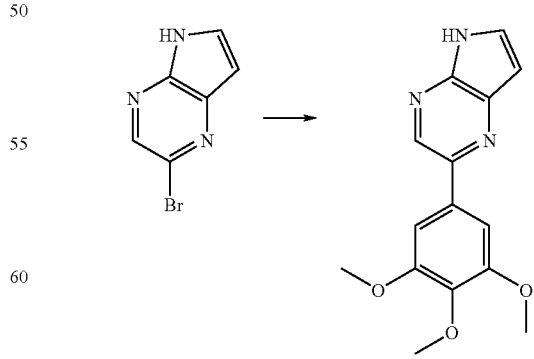

2-(3,4,5-trimethoxy-phenyl)-5H-pyrrolo[2,3-b]pyrazine.
1.5 g of 2-bromo-5H-pyrrolo[2,3-b]pyrazine (7.57 mmol, 1 eq) and 1.76 g of 3,4,5-trimethoxyphenyl boronic acid (8.32 mmol, 1.1 eq) were partly dissolved in 47 ml of 4:1 1,4-dioxane:water. The mixture was purged with argon gas. 0.49 g of 1,1'-bis(diphenylphosphino)-ferrocene) palladium dichloride (1:1 dichloromethane complex, 0.6 mmol, 0.08 eq) and then 2.6 g of potassium carbonate (18.9 mmol, 2.5 eq) were added. The reaction mixture was stirred at 80 C for 18 hr. The reaction was worked up by addition of ethyl acetate, filtration through Celite and then addition to the filtrate of water and sodium bicarbonate solution. The layers were separated and the aqueous layer was extracted twice more with ethyl acetate. The ethyl acetate layers were washed with sodium bicarbonate solution and saturated sodium chloride solution and dried over sodium sulfate. After filtration and evaporation the crude residue was purified by silica gel chromatography (ethyl acetate/hexanes) and then recrystallized from hot ethyl acetate/hexanes. 1.75 g (81%) of product was obtained.

The general procedures described in these Examples were followed for synthesis the following compounds:

1-[2-(1-Benzenesulfonyl-1H-indol-3-yl)-5H-pyrrolo[2,3-b]pyrazin-7-yl]-2,2-dimethyl-propan-1-one, MP=267.0-268.0, (M+H)+=459;

2,2-Dimethyl-1-{2-[4-(2-morpholin-4-yl-ethoxy)-phenyl]-5H-pyrrolo[2,3-b]pyrazin-7-yl}-propan-1-one, MP=198.4-202.7, (M+H)+=409;

2,2-Dimethyl-1-{2-[3-(2-morpholin-4-yl-ethoxy)-phenyl]-5H-pyrrolo[2,3-b]pyrazin-7-yl}-propan-1-one, MP=152.9-154.7, (M+H)+=409, (the boronic ester was prepared by Mitsunobu reaction of 3-hydroxyphenyl boronic acid, pinacol ester, and N-(2-hydroxyethyl)-morpholine);

4-{-4-[7-(2,2-Dimethyl-propionyl)-5H-pyrrolo[2,3-b]pyrazin-2-yl]-phenyl}-piperazine-1-carboxylic acid tert-butyl ester, MP=241-247, (M+H)+=464;

4-{3-[7-(2,2-Dimethyl-propionyl)-5H-pyrrolo[2,3-b]pyrazin-2-yl]-phenyl}-piperazine-1-carboxylic acid tert-butyl ester, MP=215.2-215.8, (M+H)+=464;

1-[2-(1H-Indol-3-yl)-5H-pyrrolo[2,3-b]pyrazin-7-yl]-2,2-dimethyl-propan-1-one, (M+H)+=319, (prepared from 1-[2-(1-benzenesulfonyl-1H-indol-3-yl)-5H-pyrrolo[2,3-b]pyrazin-7-yl]-2,2-dimethyl-propan-1-one by treatment with aqueous sodium hydroxide);

2,2-Dimethyl-1-[2-(4-piperazin-1-yl-phenyl)-5H-pyrrolo[2,3-b]pyrazin-7-yl]-propan-1-one, MP=234-246, (M+H)+=364, (prepared, respectively, from 4-{-4-[7-(2,2-Dimethyl-propionyl)-5H-pyrrolo[2,3-b]pyrazin-2-yl]-phenyl}-piperazine-1-carboxylic acid tert-butyl ester or 4-{3-[7-(2,2-Dimethyl-propionyl)-5H-pyrrolo[2,3-b]pyrazin-2-yl]-phenyl}-piperazine-1-carboxylic acid tert-butyl ester by treatment with HCl/dioxane);

2,2-Dimethyl-1-[2-(3-piperazin-1-yl-phenyl)-5H-pyrrolo[2,3-b]pyrazin-7-yl]-propan-1-one, MP=216-222, (M+H)+=364, (prepared, respectively, from 4-{-4-[7-(2,2-Dimethyl-propionyl)-5H-pyrrolo[2,3-b]pyrazin-2-yl]-phenyl}-piperazine-1-carboxylic acid tert-butyl ester or 4-{3-[7-(2,2-Dimethyl-propionyl)-5H-pyrrolo[2,3-b]pyrazin-2-yl]-phenyl}-piperazine-1-carboxylic acid tert-butyl ester by treatment with HCl/dioxane);

2,2-Dimethyl-1-[2-(4-methyl-3,4-dihydro-2H-benzo[1,4]oxazin-7-yl)-5H-pyrrolo[2,3-b]pyrazin-7-yl]-propan-1-one, MP=233.0-234.0, (M+H)+=351, 1-{2-[2-(4-Acetyl-piperazin-1-yl)-pyridin-4-yl]-5H-pyrrolo[2,3-b]pyrazin-7-yl}-2,2-dimethyl-propan-1-one, MP=257.0-260.0, (M+H)+=407;

1-{2-[4-(4-Acetyl-piperazin-1-yl)-phenyl]-5H-pyrrolo[2,3-b]pyrazin-7-yl}-2,2-dimethyl-propan-1-one, MP=266.0-267.0, (M+H)+=406, (prepared, respectively, from 4-{-4-[7-(2,2-Dimethyl-propionyl)-5H-pyrrolo[2,3-b]pyrazin-2-yl]-phenyl}-piperazine-1-carboxylic acid tert-butyl ester or 4-{3-[7-(2,2-Dimethyl-propionyl)-5H-pyrrolo[2,3-b]pyrazin-2-yl]-phenyl}-piperazine-1-carboxylic acid tert-butyl ester by reaction with acetic anhydride/DMF at 0° C.);

1-{2-[3-(4-Acetyl-piperazin-1-yl)-phenyl]-5H-pyrrolo[2,3-b]pyrazin-7-yl}-2,2-dimethyl-propan-1-one, MP=238.0-239.0, (M+H)+=406, (prepared, respectively, from 4-{-4-[7-(2,2-Dimethyl-propionyl)-5H-pyrrolo[2,3-b]pyrazin-2-yl]-phenyl}-piperazine-1-carboxylic acid tert-butyl ester or 4-{3-[7-(2,2-Dimethyl-propionyl)-5H-pyrrolo[2,3-b]pyrazin-2-yl]-phenyl}-piperazine-1-carboxylic acid tert-butyl ester by reaction with acetic anhydride/DMF at 0° C.); and 1-[7-(2,2-Dimethyl-propionyl)-5H-pyrrolo[2,3-b]pyrazin-2-yl]-2,2-dimethyl-propan-1-one, MP=188-198, (M+H)+=288, (isolated from 1-(2-bromo-5-triisopropylsilanyl-5H-pyrrolo[2,3-b]pyrazin-7-yl)-2,2-dimethyl-propan-1-ol.

Example 35

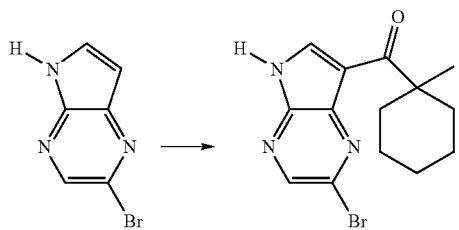

(2-Bromo-5H-pyrrolo[2,3-b]pyrazin-7-yl)-(1-methyl-cyclohexyl)-methanone

A suspension of 2-bromo-5H-pyrrolo[2,3-b]pyrazine (104 mg, 0.53 mmol) in anhydrous dichloromethane (3 ml) was cooled to 0° C. under $N_2$. Diethyl aluminum chloride (1M in hexanes, 1.57 ml, 1.57 mmol) was added quickly, and the reaction mixture was stirred for 30 minutes. 1-Methyl-cyclohexanecarbonyl chloride (844 mg, 5.3 mmol) was added dropwise, and the reaction mixture was refluxed overnight. The reaction mixture was cooled to 0° C. and quenched with saturated aqueous $NaHCO_3$. The biphasic solution was concentrated, and the remaining aqueous solution was extracted with ethyl acetate (3×). The organic layers were collected, dried over $MgSO_4$, filtered, and concentrated giving a greenish oil. The residue was purified by silica gel chromatography using 20-50% EtOAc in hexanes as eluant to provide 144 mg (85%) of (2-bromo-5H-pyrrolo[2,3-b]pyrazin-7-yl)-(1-methyl-cyclohexyl)-methanone as a light yellow solid. MP 198-199° C., M+H=322.

Example 36

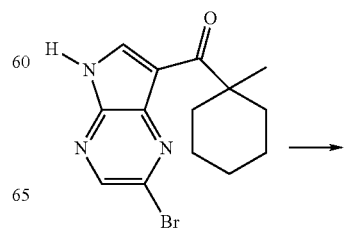

-continued

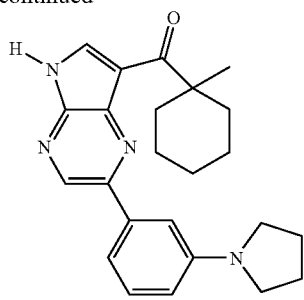

(1-Methyl-cyclohexyl)-[2-(3-pyrrolidin-1-yl-phenyl)-5H-pyrrolo[2,3-b]pyrazin-7-yl]-methanone A microwave tube was charged with (2-bromo-5H-pyrrolo[2,3-b]pyrazin-7-yl)-(1-methyl-cyclohexyl)-methanone (95 mg, 0.29 mmol), 3-pyrrolidino phenylboronic acid (62 mg, 0.32 mmol), [1,1'-bis(diphenylphosphino)ferrocene]dichloro-palladium(ll) (19 mg, 0.02 mmol), and freshly grounded K$_2$CO$_3$ (102 mg, 0.74 mmol). Dioxane (3 ml) and water (0.7 ml) were added, and the reaction mixture was microwaved at 150° C. for 30 minutes. The reaction mixture was partitioned between EtOAc/water. The organic layers were collected, dried over MgSO$_4$, filtered, and concentrated giving a dark brown solid. The residue was purified by silica gel chromatography using 10-50% EtOAc in hexanes as eluant to provide 70 mg (61%) of (1-methyl-cyclohexyl)-[2-(3-pyrrolidin-1-yl-phenyl)-5H-pyrrolo[2,3-b]pyrazin-7-yl]-methanone as a yellow solid. MP 243-245.4° C., M+H=389.

The above general procedure was followed for the synthesis of the following compound:
(1-Methyl-cyclohexyl)-{2-[4-(2-piperidin-1-yl-ethoxy)-phenyl]-5H-pyrrolo[2,3-b]pyrazin-7-yl}-methanone (M+H)$^+$=447; MP=180.0-182.0° C.

The following compounds were prepared analogously:
1-[2-(3-Amino-phenyl)-5-(2-trimethylsilanyl-ethoxymethyl)-5H-pyrrolo[2,3-b]pyrazin-7-yl]-2,2-dimethyl-propan-1-one M+1 425 (Prepared using 1-[2-Bromo-5-(2-trimethylsilanyl-ethoxymethyl)-5H-pyrrolo[2,3-b]pyrazin-7-yl]-2,2-dimethyl-propan-1-one in place of 1-(2-Bromo-5H-pyrrolo[2,3-b]pyrazin-7-yl)-2,2-dimethyl-propan-1-one and heating for 10 minutes at 110° C.)

2,2-Dimethyl-1-(2-thiophen-2-yl-5H-pyrrolo[2,3-b]pyrazin-7-yl)-propan-1-one M+1 286, M.P. 282-283° C. (Heated for 10 minutes at 110° C.)

2-[7-(2,2-Dimethyl-propionyl)-5H-pyrrolo[2,3-b]pyrazin-2-yl]-pyrrole-1-carboxylic acid tert-butyl ester M+1 369, M.P. 198-199° C. (Heated for 10 minutes at 110° C.) Using the procedures described herein this compound was converted into 2,2-Dimethyl-1-[2-(1H-pyrrol-2-yl)-5H-pyrrolo[2,3-b]pyrazin-7-yl]-propan-1-one M+1 269, M.P. 269-271° C.

2,2-Dimethyl-1-(2-thiophen-3-yl-5H-pyrrolo[2,3-b]pyrazin-7-yl)-propan-1-one M+1 286, M.P. 268.8-272.9° C. (Heated for 10 minutes at 110° C.)

2,2-Dimethyl-1-(2-oxazol-5-yl-5H-pyrrolo[2,3-b]pyrazin-7-yl)-propan-1-one M+1 271, (used 4 equivalences of 5-(4,4,5,5-Tetramethyl-[1,3,2]dioxaborolan-2-yl)-oxazole and heated 30 minutes at 130° C.)

2-[7-(2,2-Dimethyl-propionyl)-5H-pyrrolo[2,3-b]pyrazin-2-yl]-pyrrole-1-carboxylic acid tert-butyl ester M+1 370 and 2,2-Dimethyl-1-[2-(1H-pyrrol-2-yl)-5H-pyrrolo[2,3-b]pyrazin-7-yl]-propan-1-one M+1 270, M.P.>300° C. were both isolated from the reaction with 4-(4,4,5,5-Tetramethyl-[1,3,2]dioxaborolan-2-yl)-pyrazole-1-carboxylic acid tert-butyl ester and heating for 10 minutes at 110° C.

1-[2-(3-Hydroxy-phenyl)-5-(2-trimethylsilanyl-ethoxymethyl)-5H-pyrrolo[2,3-b]pyrazin-7-yl]-2,2-dimethyl-propan-1-one M+1 426 (Heated for 10 minutes at 110° C.)

2,2-Dimethyl-1-[2-(2H-pyrazol-3-yl)-5H-pyrrolo[2,3-b]pyrazin-7-yl]-propan-1-one M+1 270, M.P. 290-291° C.

[1-[2-(3-Amino-4-methyl-phenyl)-5H-pyrrolo[2,3-b]pyrazin-7-yl]-2,2-dimethyl-propan-1-one M+1 309 (Heated for 40 minutes at 120° C.)

[2,2-Dimethyl-1-[2-(1H-pyrrol-3-yl)-5H-pyrrolo[2,3-b]pyrazin-7-yl]-propan-1-one (Heated for 10 minutes at 110° C., additional 3 equivalences tips protected boronic acid and 3.5 equivalences potassium carbonate added and heated 120° C. for 20 minutes, TIPS protecting group removed at room temperature using general procedures as described in these Examples) M+1 269, m.p. 286-287° C.

Example 37

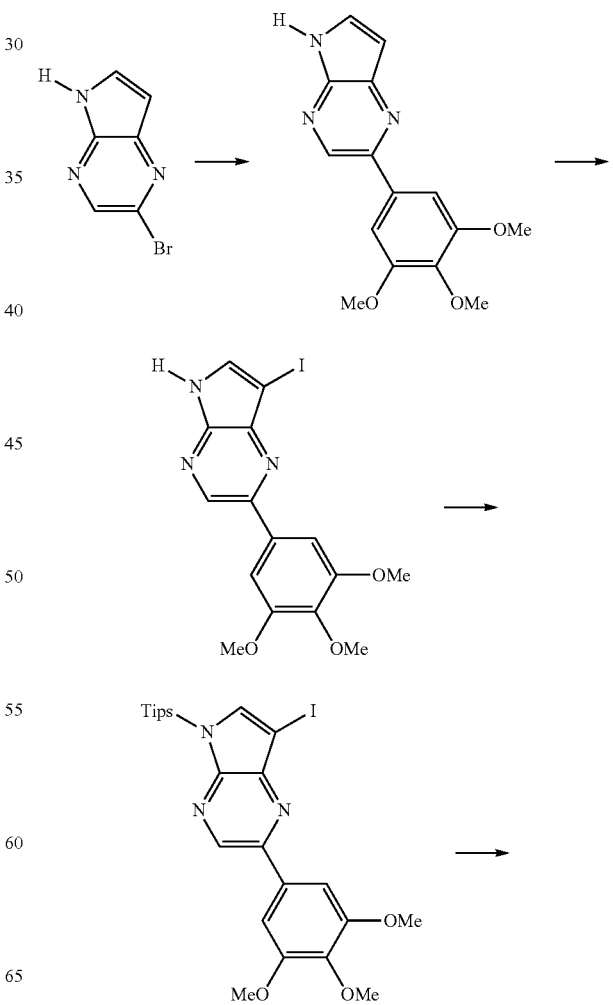

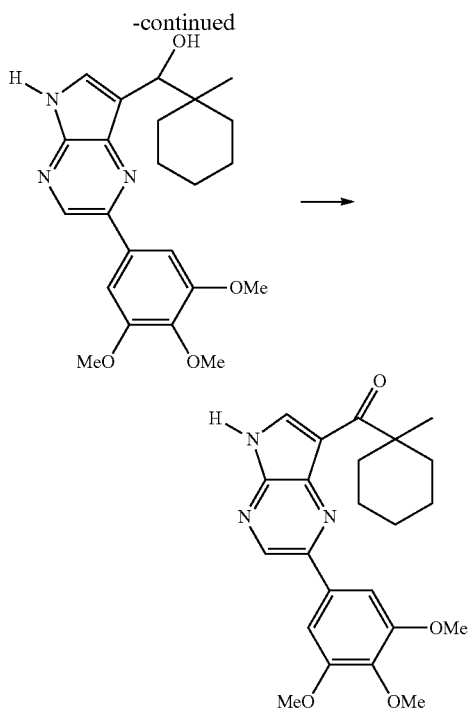

2-(3,4,5-Trimethoxy-phenyl)-5H-pyrrolo[2,3-b]pyrazine. A flask was charged with 2-bromo-5H-pyrrolo[2,3-b]pyrazine (9.5 g, 48 mmol), 3,4,5-trimethoxyphenylboronic acid (13.22, 62 mmol), and $K_2CO_3$ (19.9, 144 mmol). Dioxane (213 ml) and water (71 ml) were added, and the solution was vacuum degassed under argon. [1,1'-bis(Diphenylphosphino)ferrocene]dichloro-palladium(ll) (3.92 g, 4.8 mmol) was added, and the reaction mixture was refluxed (110° C.) overnight. The reaction mixture was filtered through a plug of celite using dichloromethane, and the filtrate was concentrated giving a black oil. The oil was purified by silica gel chromatography using 5%-60% EtOAc in hexanes as eluant to provide 12.12 g (89%) of 2-(3,4,5-trimethoxy-phenyl)-5H-pyrrolo[2,3-b]pyrazine.

Example 38

7-Iodo-2-(3,4,5-trimethoxy-phenyl)-5H-pyrrolo[2,3-b]pyrazine

To a 0° C. mixture of 2-(3,4,5-trimethoxy-phenyl)-5H-pyrrolo[2,3-b]pyrazine (2.4 g, 8.4 mmol) in dimethylformamide (30 ml) was added KOH (2 g, 36 mmol). After 20 min, iodine (3.2 g, 13 mmol) was added portionwise over 10 min and the reaction mixture was stirred for 4 h and poured into 0° C. saturated aqueous sodium thiosulfate (~300 mL). Ice cold water (~100 mL) was added and the resultant precipitate was collected, washed with water and dried in vacuo at 60° C. to afford 3.1 g (89%) of 7-iodo-2-(3,4,5-trimethoxy-phenyl)-5H-pyrrolo[2,3-b]pyrazine as a brown solid. MP 230-232° C., M+H=412.

Example 39

7-Iodo-5-triisopropylsilanyl-2-(3,4,5-trimethoxy-phenyl)-5H-pyrrolo[2,3-b]pyrazine A solution of 7-iodo-2-(3,4,5-trimethoxy-phenyl)-5H-pyrrolo[2,3-b]pyrazine (6.7 g, 16.29 mmol) in anhydrous tetrahydrofuran (150 ml) was cooled to 0° C. and treated with potassium bis(trimethylsilyl)amide (0.5M in toluene, 35.85 ml, 17.9 mmol) dropwise. After complete addition, the reaction mixture was stirred at room temperature for 1 hour, treated dropwise with chloro-triisopropyl-silane (3.9 ml, 18.4 mmol), and allowed to stir at room temperature for 16 hours. Chloro-triisopropyl-silane (1.0 ml, 4.7 mmol) was added, and the reaction mixture was stirred at room temperature for 16 hours, and then at 60° C. for 16 hours. The reaction mixture was partitioned between EtOAc/saturated aqueous $NH_4Cl$. The organic layers were collected, dried over $MgSO_4$, filtered, and concentrated giving a dark solid. The residue was purified by silica gel chromatography using 3-100% EtOAc in hexanes as eluant to provide 7.4 g (80%) of 7-iodo-5-triisopropylsilanyl-2-(3,4,5-trimethoxy-phenyl)-5H-pyrrolo[2,3-b]pyrazine as a white solid. MP 156.5-157.2, M+H=568.

Example 40

(1-Methyl-cyclohexyl)-[2-(3,4,5-trimethoxy-phenyl)-5H-pyrrolo[2,3-b]pyrazin-7-yl]-methanol A solution of 7-iodo-5-triisopropylsilanyl-2-(3,4,5-trimethoxy-phenyl)-5H-pyrrolo[2,3-b]pyrazine (247 mg, 0.435 mmol) in anhydrous tetrahydrofuran (5 ml) was cooled to −78° C. and treated with iPrMgCl—LiCl (1M in tetrahydrofuran, 0.87 ml, 0.87 mmol) dropwise. The reaction mixture was allowed to stir for 20 minutes, and then 1-methyl-cyclohexanecarbaldehyde (219 mg, 1.74 mmol) was added rapidly. The reaction mixture was allowed to stir at −78° C. for 1 hour and then room temperature for 1 hour. The reaction mixture was partitioned between EtOAc/saturated aqueous. $NH_4Cl$. The organic layers were collected, dried over $MgSO_4$, filtered, and concentrated. The residue was purified by silica gel chromatography using 15-100% EtOAc in hexanes as eluant to provide 81 mg (45%) of (1-methyl-cyclohexyl)-[2-(3,4,5-trimethoxy-phenyl)-5H-pyrrolo[2,3-b]pyrazin-7-yl]-methanol as a pale yellow solid. M+H=412.

Example 41

(1-methyl-cyclohexyl)-[2-(3,4,5-trimethoxy-phenyl)-5H-pyrrolo[2,3-b]pyrazin-7-yl]-methanone (1-Methyl-cyclohexyl)-[2-(3,4,5-trimethoxy-phenyl)-5H-pyrrolo[2,3-b]pyrazin-7-yl]-methanone. To a solution of (1-methyl-cyclohexyl)-[2-(3,4,5-trimethoxy-phenyl)-5H-pyrrolo[2,3-b]pyrazin-7-yl]-methanol (81 mg, 0.196 mmol) in dichloromethane (6 ml) was added Dess-Martin periodinane (125 mg, 0.295 mmol). The reaction mixture was allowed to stir at room temperature for 2 hours. The reaction mixture was partitioned between dichloromethane and 2:1 saturated aqueous $NaHCO_3$:10% aqueous $Na_2S_2O_3$. The organic layers were collected, dried over $Na_2SO_4$, filtered, and concentrated. The residue was purified by silica gel chromatography using 20-50% EtOAc in hexanes as eluant to provide 18 mg (22%) of (1-methyl-cyclohexyl)-[2-(3,4,5-trimethoxy-phenyl)-5H-pyrrolo[2,3-b]pyrazin-7-yl]-methanone as an off white solid. MP 246-247° C., M+H=439.

The general procedures described in these Examples were followed for synthesis the following compounds:

2-Methyl-2-phenyl-1-[2-(3,4,5-trimethoxy-phenyl)-5H-pyrrolo[2,3-b]pyrazin-7-yl]-propan-1-one: $(M+H)^+=5432$; MP=252-254° C.;

Example 42

4-Methyl-tetrahydro-thiopyran-4-carbonitrile

4-Methyl-tetrahydro-thiopyran-4-carbonitrile. A solution of tetrahydro-thiopyran-4-carbonitrile (3.05 g, 24 mmol) in anhydrous tetrahydrofuran (60 ml) was cooled to −78° C. and treated with lithium bis(trimethylsilyl)amide (1M in tetrahydrofuran, 26.4 ml, 26.4 mmol) dropwise. After 30 minutes of stirring, iodomethane (1.8 ml, 29 mmol) was added dropwise. The cooling bath was removed, and the reaction mixture was allowed to slowly rise to room temperature and stir overnight. The reaction mixture was quenched with saturated aqueous NH$_4$Cl and extracted with EtOAc. The organic layers were collected, dried over MgSO$_4$, filtered, and concentrated giving an orange oil. The oil was purified by silica gel chromatography using 5-50% EtOAc in hexanes as eluant to provide 1.81 g (53%) of 4-methyl-tetrahydro-thiopyran-4-carbonitrile as a colorless oil.

Example 43

4-Methyl-tetrahydro-thiopyran-4-carbaldehyde

A solution of 4-methyl-tetrahydro-thiopyran-4-carbonitrile (893 mg, 6.3 mmol) in anhydrous dichloromethane (44 ml) was cooled to −40° C. and treated with diisobutylaluminum hydride (2.25 ml, 12.6 mmol) dropwise. The reaction mixture was allowed to stir at −40° C. for 2 hours and then placed in the freezer overnight. The reaction mixture was partitioned between dichloromethane/1N HCl. The organic layers were collected, dried over Na$_2$SO$_4$, filtered, and concentrated giving a colorless oil. The oil was purified by silica gel chromatography using 10-50% EtOAc in hexanes as eluant to provide 610 mg (67%) of 4-methyl-tetrahydro-thiopyran-4-carbaldehyde as a colorless oil.

Example 44

(4-Methyl-tetrahydro-thiopyran-4-yl)-[2-(3,4,5-trimethoxy-phenyl)-5H-pyrrolo[2,3-b]pyrazin-7-yl]-methanol A solution of 7-iodo-5-triisopropylsilanyl-2-(3,4,5-trimethoxy-phenyl)-5H-pyrrolo[2,3-b]pyrazine (400 mg, 0.7 mmol) in anhydrous tetrahydrofuran (5 ml) was cooled to −78° C. and treated with nBuLi (2.23M in hexanes, 0.42 ml, 0.94 mmol) dropwise. The reaction mixture was stirred for 30 seconds and then treated with a solution of 4-methyl-tetrahydro-thiopyran-4-carbaldehyde (0.305 mg, 2.1 mmol) in anhydrous tetrahydrofuran (2 ml), dropwise. The reaction mixture was allowed to stir at −78° C. for 30 minutes. The reaction mixture was partitioned between EtOAc/saturated aqueous NH$_4$Cl. The organic layers were collected, dried over MgSO$_4$, filtered, and concentrated giving a yellowish oil. The oil was purified by silica gel chromatography using 3-100% EtOAc in hexanes as eluant to provide 97 mg (32%) of (4-methyl-tetrahydro-thiopyran-4-yl)-[2-(3,4,5-trimethoxy-phenyl)-5H-pyrrolo[2,3-b]pyrazin-7-yl]-methanol as a pale yellow solid. M+H=430.

Example 45

(4-Methyl-tetrahydro-thiopyran-4-yl)-[2-(3,4,5-trimethoxy-phenyl)-5H-pyrrolo[2,3-b]pyrazin-7-yl]-methanone (4-methyl-tetrahydro-thiopyran-4-yl)-[2-(3,4,5-trimethoxy-phenyl)-5H-pyrrolo[2,3-b]pyrazin-7-yl]-methanone was prepared starting from (4-methyl-tetrahydro-thiopyran-4-yl)-[2-(3,4,5-trimethoxy-phenyl)-5H-pyrrolo[2,3-b]pyrazin-7-yl]-methanol, following the same general procedures from Examples 37-41. M+H=428.

Example 46

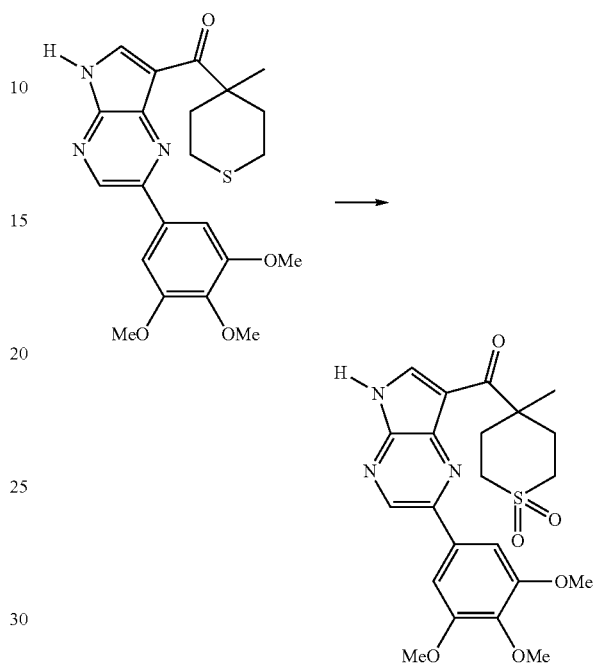

(4-Methyl-1,1-dioxo-hexahydro-1lambda*6*-thiopyran-4-yl)-[2-(3,4,5-trimethoxy-phenyl)-5H-pyrrolo[2,3-b]pyrazin-7-yl]-methanone A suspension of (4-methyl-tetrahydro-thiopyran-4-yl)-[2-(3,4,5-trimethoxy-phenyl)-5H-pyrrolo[2,3-b]pyrazin-7-yl]-methanone (9 mg, 0.02 mmol) in acetonitrile (0.4 ml), MeOH (0.4 ml), and water (0.2 ml) was treated with Oxone (26 mg, 0.04 mmol) and stirred overnight at room temperature. The reaction mixture was partitioned between EtOAc/water. The organic layers were collected, dried over Na$_2$SO$_4$, filtered, and concentrated. The residue was purified by preparative thin layer chromatography using 30% EtOAc in hexanes as eluant to provide 6 mg (62%) of (4-methyl-1,1-dioxo-hexahydro-1lambda*6*-thiopyran-4-yl)-[2-(3,4,5-trimethoxy-phenyl)-5H-pyrrolo[2,3-b]pyrazin-7-yl]-methanone as an off white solid. M+H=460.

Example 47

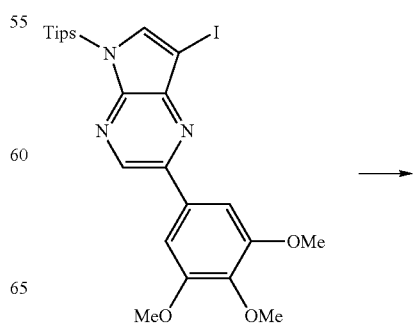

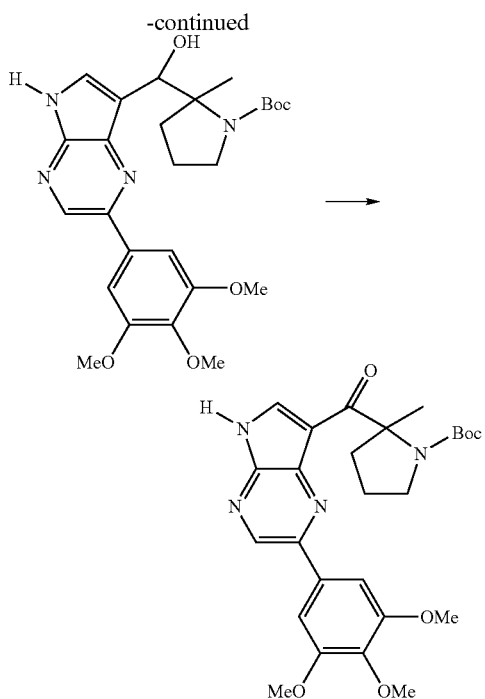

2-{Hydroxy-[2-(3,4,5-trimethoxy-phenyl)-5H-pyrrolo[2,3-b]pyrazin-7-yl]-methyl}-2-methyl-pyrrolidine-1-carboxylic acid tert-butyl ester 2-{Hydroxy-[2-(3,4,5-trimethoxy-phenyl)-5H-pyrrolo[2,3-b]pyrazin-7-yl]-methyl}-2-methyl-pyrrolidine-1-carboxylic acid tert-butyl ester was prepared starting from 7-iodo-5-triisopropylsilanyl-2-(3,4,5-trimethoxy-phenyl)-5H-pyrrolo[2,3-b]pyrazine and 2-formyl-2-methyl-pyrrolidine-1-carboxylic acid tert-butyl ester (*J. Org. Chem.* 72 (15), 5608-5617, 2007) following the general procedures described in these Examples.

Example 48

2-Methyl-2-[2-(3,4,5-trimethoxy-phenyl)-5H-pyrrolo[2,3-b]pyrazine-7-carbonyl]-pyrrolidine-1-carboxylic acid tert-butyl ester 2-Methyl-2-[2-(3,4,5-trimethoxy-phenyl)-5H-pyrrolo[2,3-b]pyrazine-7-carbonyl]-pyrrolidine-1-carboxylic acid tert-butyl ester was prepared starting from 2-{hydroxy-[2-(3,4,5-trimethoxy-phenyl)-5H-pyrrolo[2,3-b]pyrazin-7-yl]-methyl}-2-methyl-pyrrolidine-1-carboxylic acid tert-butyl ester following the same general procedures from Examples 37-41. M+H=497.

Example 49

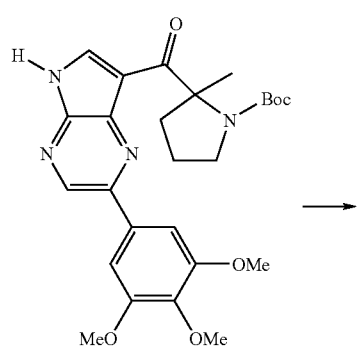

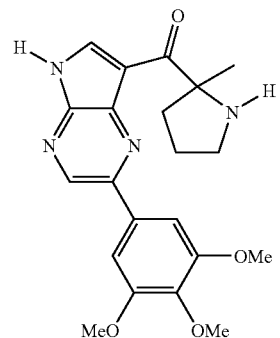

(2-Methyl-pyrrolidin-2-yl)-[2-(3,4,5-trimethoxy-phenyl)-5H-pyrrolo[2,3-b]pyrazin-7-yl]-methanone To a solution of 2-methyl-2-[2-(3,4,5-trimethoxy-phenyl)-5H-pyrrolo[2,3-b]pyrazine-7-carbonyl]-pyrrolidine-1-carboxylic acid tert-butyl ester (18 mg, 0.04 mmol) in anhydrous dichloromethane (3.0 ml) was added trifluoroacetic acid (1.0 ml, 13.5 mmol) dropwise. The reaction mixture was stirred for two days. The reaction mixture was partitioned between EtOAc/saturated aqueous Na₂CO₃. The organic layers were collected, dried over MgSO₄, filtered, and concentrated. The residue was purified by preparative thin layer chromatography using 0.5:9.5:90 concentrated aqueous NH₄OH: MeOH: dichloromethane as eluant to provide 10 mg (70%) of (2-methyl-pyrrolidin-2-yl)-[2-(3,4,5-trimethoxy-phenyl)-5H-pyrrolo[2,3-b]pyrazin-7-yl]-methanone as a light yellow solid. M+H=397.

Example 50

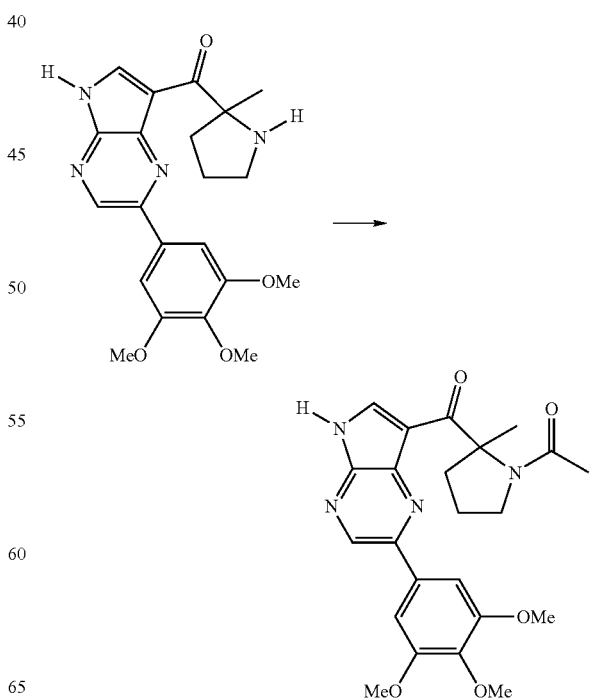

351

1-{2-Methyl-2-[2-(3,4,5-trimethoxy-phenyl)-5H-pyrrolo[2,3-b]pyrazine-7-carbonyl]-pyrrolidin-1-yl}-ethanone A solution of (2-methyl-pyrrolidin-2-yl)-[2-(3,4,5-trimethoxy-phenyl)-5H-pyrrolo[2,3-b]pyrazin-7-yl]-methanone (8 mg, 0.02 mmol) in anhydrous dichloromethane (0.3 ml) was cooled to 0° C. and treated with acetic anhydride (2 mg, 0.02 mmol). The reaction mixture was stirred for 1 hour and then allowed to warm to room temperature and stir for 3 hours. The reaction mixture was partitioned between EtOAc/saturated aqueous NaHCO$_3$. The organic layers were collected, dried over MgSO$_4$, filtered, and concentrated giving a brownish oil. The residue was purified by preparative thin layer chromatography using 50% EtOAc in hexanes as eluant to provide 2 mg (17%) of 1-{2-methyl-2-[2-(3,4,5-trimethoxy-phenyl)-5H-pyrrolo[2,3-b]pyrazine-7-carbonyl]-pyrrolidin-1-yl}-ethanone as a light yellow solid. M+H=439.

Example 51

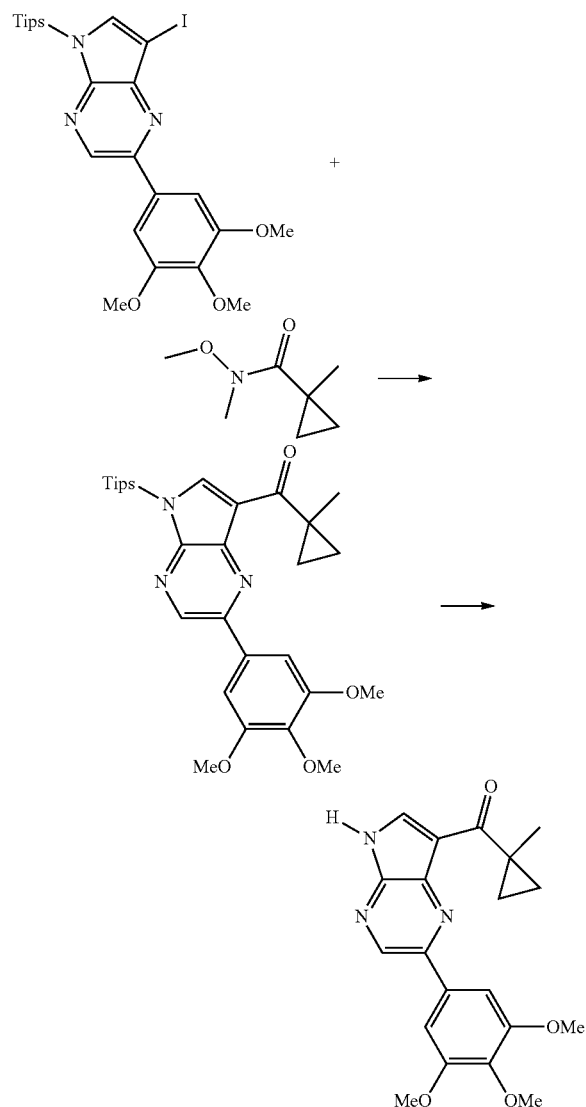

352

(1-Methyl-cyclopropyl)-[5-triisopropylsilanyl-2-(3,4,5-trimethoxy-phenyl)-5H-pyrrolo[2,3-b]pyrazin-7-yl]-methanone A solution of 7-iodo-5-triisopropylsilanyl-2-(3,4,5-trimethoxy-phenyl)-5H-pyrrolo[2,3-b]pyrazine (116 mg, 0.2 mmol) in anhydrous tetrahydrofuran (3 ml) was cooled to −78° C. and treated with nBuLi (2.13M in hexanes, 0.13 ml, 0.27 mmol) dropwise. The solution was stirred for 30 seconds and 1-methyl-cyclopropanecarboxylic acid methoxy-methyl-amide (88 mg, 0.61 mmol) was added in one portion. The reaction mixture was stirred at −78° C. for 30 minutes. The reaction mixture was quenched with saturated aqueous NaHSO$_4$ and then partitioned between EtOAc/brine. The organic layers were collected, dried over MgSO$_4$, filtered, and concentrated giving a yellow oil. The oil was purified by silica gel chromatography using 2-30% EtOAc in hexanes as eluant to provide 20 mg (19%) of (1-methyl-cyclopropyl)-[5-triisopropylsilanyl-2-(3,4,5-trimethoxy-phenyl)-5H-pyrrolo[2,3-b]pyrazin-7-yl]-methanone.

Example 52

(1-Methyl-cyclopropyl)-[2-(3,4,5-trimethoxy-phenyl)-5H-pyrrolo[2,3-b]pyrazin-7-yl]-methanone A solution of (1-methyl-cyclopropyl)-[5-triisopropylsilanyl-2-(3,4,5-trimethoxy-phenyl)-5H-pyrrolo[2,3-b]pyrazin-7-yl]-methanone (20 mg, 0.4 mmol) in anhydrous tetrahydrofuran (2 ml) was treated with tetrabutyl ammonium fluoride (1M in tetrahydrofuran, 0.1 ml, 0.1 mmol) dropwise. The reaction mixture was allowed to stir at room temperature for 10 minutes, and then partitioned between EtOAc/water. The organic layers were collected, dried over MgSO$_4$, filtered, and concentrated giving a yellow solid. The residue was purified by preparative thin layer chromatography using 70% EtOAc in hexanes as eluant to provide 10 mg (71%) of (1-methyl-cyclopropyl)-[2-(3,4,5-trimethoxy-phenyl)-5H-pyrrolo[2,3-b]pyrazin-7-yl]-methanone as a white solid. M+H=368.

Example 53

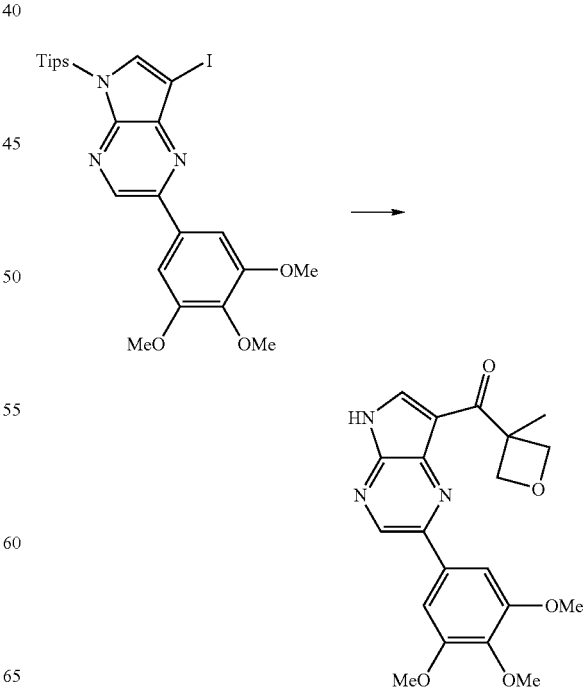

(3-Methyl-oxetan-3-yl)-[2-(3,4,5-trimethoxy-phenyl)-5H-pyrrolo[2,3-b]pyrazin-7-yl]-methanone A solution of 7-iodo-5-triisopropylsilanyl-2-(3,4,5-trimethoxy-phenyl)-5H-pyrrolo[2,3-b]pyrazine (200 mg, 0.35 mmol) in anhydrous tetrahydrofuran (3 ml) was cooled to −78° C. and treated with nBuLi (2.13M in hexanes, 0.19 ml, 0.39 mmol) dropwise. The solution was stirred for 30 seconds and 3-methyl-oxetane-3-carbaldehyde (106 mg, 1.1 mmol) was added in one portion. After stirring at −78° C. for 30 minutes, the reaction mixture was quenched with saturated aqueous NH₄Cl and partitioned between EtOAc/water. The organic layers were collected, dried over MgSO₄, filtered, and concentrated giving a yellow oil.

A solution of the crude oil in anhydrous tetrahydrofuran (5 ml), was treated with tetrabutyl ammonium fluoride (1M in tetrahydrofuran, 0.7 ml, 0.7 mmol) and allowed to stir at room temperature for 15 minutes. The reaction mixture was partitioned between EtOAc/water and the organic layers were collected, dried over MgSO₄, filtered, and concentrated.

The crude product was dissolved in dichloromethane (10 ml), treated with Dess-Martin periodinane (300 mg, 0.7 mmol), and stirred for 2 hours. The reaction mixture was filtered through a filter funnel, and the filtrate was collected and concentrated giving a solid. The residue was purified by preparative thin layer chromatography using 70% EtOAc in hexanes as eluant to provide 7 mg (5%) of (3-methyl-oxetan-3-yl)-[2-(3,4,5-trimethoxy-phenyl)-5H-pyrrolo[2,3-b]pyrazin-7-yl]-methanone as an off white solid. M+H=384.

Example 54

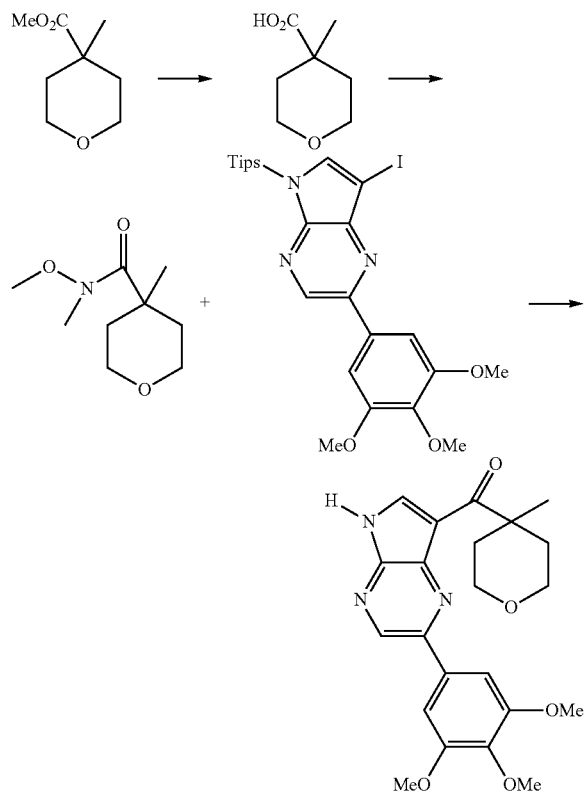

4-Methyl-tetrahydro-pyran-4-carboxylic acid

A solution of 4-methyl-tetrahydro-pyran-4-carboxylic acid methyl ester (3.64 g, 23 mmol) in tetrahydrofuran (136 ml) was treated with a solution of lithium hydroxide (4.83 g, 115 mmol) in deionized water (27 ml). The reaction mixture was heated to 50° C. for overnight and then partitioned between EtOAc/water. The aqueous phase was collected and then partitioned between EtOAc/ice cold 1N HCl. The organic layers were dried over MgSO₄, filtered, and concentrated providing 3 grams (90%) of 4-methyl-tetrahydro-pyran-4-carboxylic acid.

Example 55

4-Methyl-tetrahydro-pyran-4-carboxylic acid methoxy-methyl-amide

A solution of 4-methyl-tetrahydro-pyran-4-carboxylic acid in dichloromethane (30 ml) and dimethylformamide (0.5 ml) was cooled to 0° C. and treated with oxalyl chloride (0.97 ml, 11 mmol) dropwise. After stirring for 2 hours, the reaction mixture was concentrated in vaccuo giving a yellow semisolid.

The yellow semisolid was suspended in anhydrous tetrahydrofuran, cooled to 0° C., and treated with O,N-dimethylhydroxylamine hydrogen chloride (1.45 g, 15 mmol) in one portion followed by dropwise addition of triethylamine (3.1 ml, 22 mmol). The reaction mixture was stirred at room temperature overnight and then partitioned between EtOAc/water. The organic layers were collected, brined, dried over MgSO₄, filtered, and concentrated giving an oil. The oil was purified by silica gel chromatography using 40-100% EtOAc in hexanes as eluant to provide 900 mg (65%) of 4-methyl-tetrahydro-pyran-4-carboxylic acid methoxy-methyl-amide.

Example 56

(4-Methyl-tetrahydro-pyran-4-yl)-[2-(3,4,5-trimethoxy-phenyl)-5H-pyrrolo[2,3-b]pyrazin-7-yl]-methanone (4-Methyl-tetrahydro-pyran-4-yl)-[2-(3,4,5-trimethoxy-phenyl)-5H-pyrrolo[2,3-b]pyrazin-7-yl]-methanone was prepared starting from 7-iodo-5-triisopropylsilanyl-2-(3,4,5-trimethoxy-phenyl)-5H-pyrrolo[2,3-b]pyrazine and 4-methyl-tetrahydro-pyran-4-carboxylic acid methoxy-methyl-amide following general procedures as described in these Examples. 66, to afford a pale yellow solid. M+H=412.

The Following Compound was Prepared Analogously:
2,2-Dimethyl-1-[2-(1H-pyrrol-2-yl)-5H-pyrrolo[2,3-b]pyrazin-7-yl]-propan-1-one (purified by simple recrystallization from acetonitrile instead of the pardoning and chromatography) M+1 269 m.p. 269-271° C.

Example 57

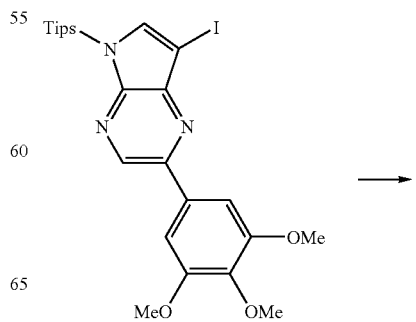

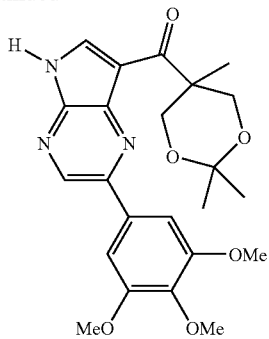

[2-(3,4,5-Trimethoxy-phenyl)-5H-pyrrolo[2,3-b]pyrazin-7-yl]-(2,2,5-trimethyl-[1,3]dioxan-5-yl)-methanone

[2-(3,4,5-Trimethoxy-phenyl)-5H-pyrrolo[2,3-b]pyrazin-7-yl]-(2,2,5-trimethyl-[1,3]dioxan-5-yl)-methanone was prepared starting from 7-iodo-5-triisopropylsilanyl-2-(3,4,5-trimethoxy-phenyl)-5H-pyrrolo[2,3-b]pyrazine following general procedures as described in these Examples, but the Dess-Martin oxidation was done before the tetrabutyl ammonium fluoride deprotection. M+H=442.

Example 58

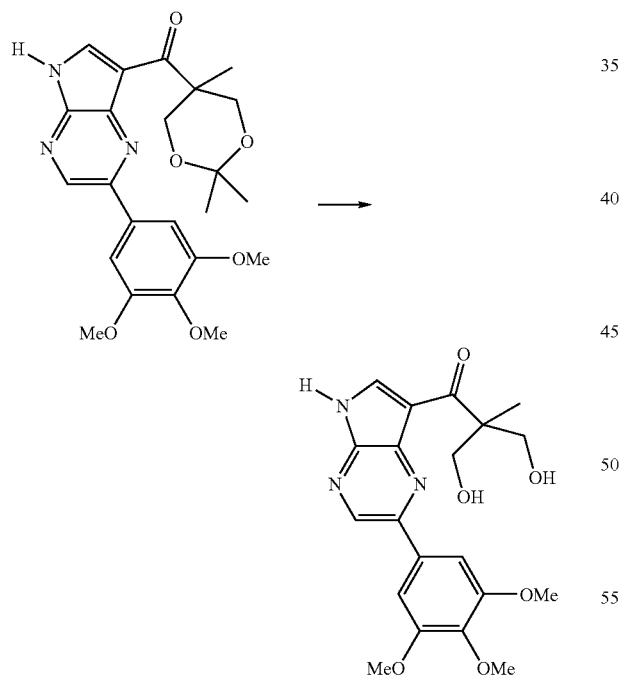

3-Hydroxy-2-hydroxymethyl-2-methyl-1-[2-(3,4,5-trimethoxy-phenyl)-5H-pyrrolo[2,3-b]pyrazin-7-yl]-propan-1-one A suspension of [2-(3,4,5-trimethoxy-phenyl)-5H-pyrrolo[2,3-b]pyrazin-7-yl]-(2,2,5-trimethyl-[1,3]dioxan-5-yl)-methanone (30 mg, 0.7 mmol) in tetrahydrofuran (5 ml) and MeOH (4 ml) was heated using a heat gun until homogeneity was achieved. The reaction mixture was treated with 1M HCl (1.0 ml, 1.0 mmol) and stirred for 1 hour. The reaction mixture was concentrated to 3 ml of solvent and then partitioned between EtOAc/saturated aqueous NaHCO₃. The organic layers were collected, dried over MgSO₄, filtered, and concentrated affording 20 mg (73%) of 3-hydroxy-2-hydroxymethyl-2-methyl-1-[2-(3,4,5-trimethoxy-phenyl)-5H-pyrrolo[2,3-b]pyrazin-7-yl]-propan-1-one as a pale yellow solid. MP 222-223° C., M+H=402.

Example 59

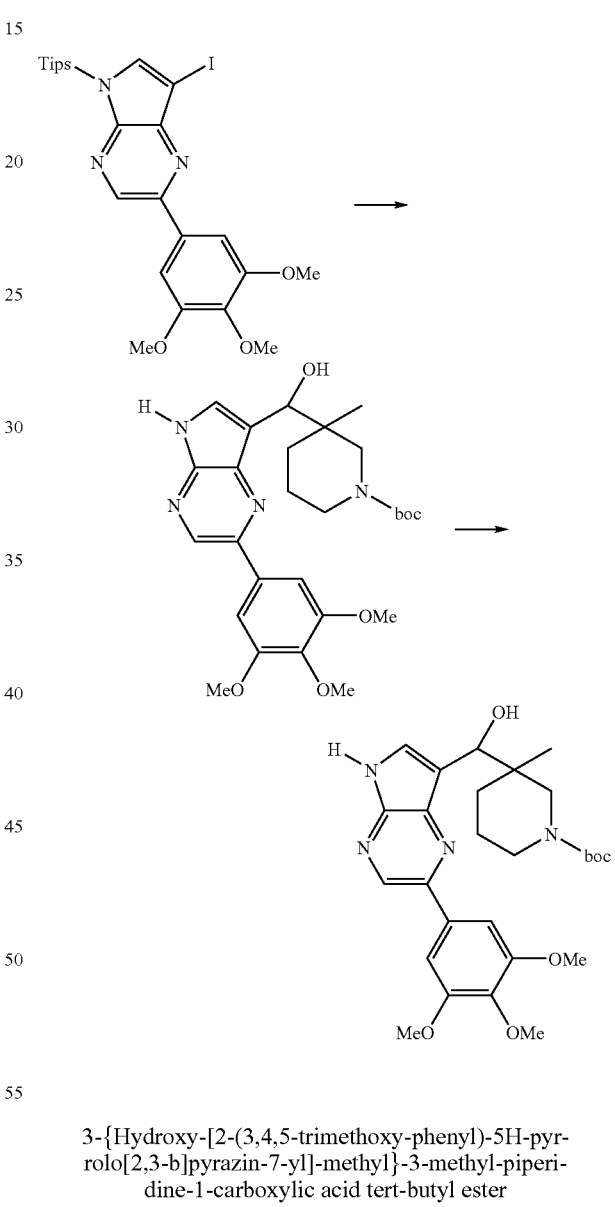

3-{Hydroxy-[2-(3,4,5-trimethoxy-phenyl)-5H-pyrrolo[2,3-b]pyrazin-7-yl]-methyl}-3-methyl-piperidine-1-carboxylic acid tert-butyl ester 3-{Hydroxy-[2-(3,4,5-trimethoxy-phenyl)-5H-pyrrolo[2,3-b]pyrazin-7-yl]-methyl}-3-methyl-piperidine-1-carboxylic acid tert-butyl ester was prepared starting from 7-iodo-5-triisopropylsilanyl-2-(3,4,5-trimethoxy-phenyl)-5H-pyrrolo[2,3-b]pyrazine and 3-formyl-3-methyl-piperidine-1-carboxylic acid tert-butyl ester (WO 2002024679) following general procedures as described in these Examples.

Example 60

3-Methyl-3-[2-(3,4,5-trimethoxy-phenyl)-5H-pyrrolo[2,3-b]pyrazine-7-carbonyl]-piperidine-1-carboxylic acid tert-butyl ester 3-methyl-3-[2-(3,4,5-trimethoxy-phenyl)-5H-pyrrolo[2,3-b]pyrazine-7-carbonyl]-piperidine-1-carboxylic acid tert-butyl ester was prepared starting from 3-{hydroxy-[2-(3,4,5-trimethoxy-phenyl)-5H-pyrrolo[2,3-b]pyrazin-7-yl]-methyl}-3-methyl-piperidine-1-carboxylic acid tert-butyl ester following the same general procedures from Examples 37-41. M+H 511.

Example 61

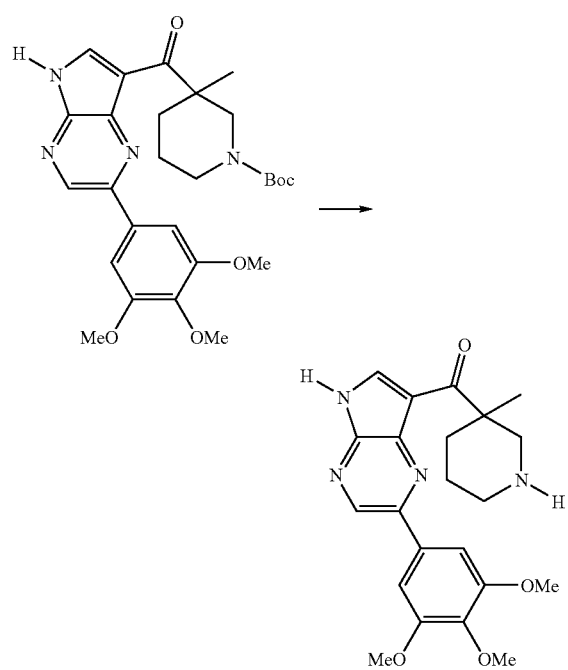

(3-Methyl-piperidin-3-yl)-[2-(3,4,5-trimethoxy-phenyl)-5H-pyrrolo[2,3-b]pyrazin-7-yl]-methanone (3-Methyl-piperidin-3-yl)-[2-(3,4,5-trimethoxy-phenyl)-5H-pyrrolo[2,3-b]pyrazin-7-yl]-methanone was prepared starting from 3-methyl-3-[2-(3,4,5-trimethoxy-phenyl)-5H-pyrrolo[2,3-b]pyrazine-7-carbonyl]-piperidine-1-carboxylic acid tert-butyl ester following general procedures as described in these Examples. M+H=411.

Example 62

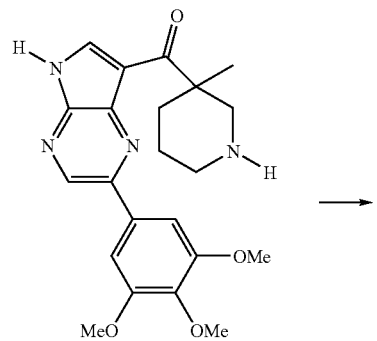

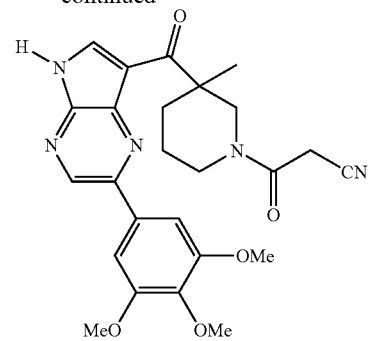

3-{3-Methyl-3-[2-(3,4,5-trimethoxy-phenyl)-5H-pyrrolo[2,3-b]pyrazine-7-carbonyl]-piperidin-1-yl}-3-oxo-propionitrile A solution of (3-methyl-piperidin-3-yl)-[2-(3,4,5-trimethoxy-phenyl)-5H-pyrrolo[2,3-b]pyrazin-7-yl]-methanone (11 mg, 0.27 mmol), benzotriazol-1-ol (4.0 mg, 0.03 mmol), 2-cyanoacetic acid (3 mg, 0.04 mmol), and (3-dimethylamino-propyl)-ethyl-carbodiimide hydrogen chloride (6.0 mg, 0.03 mmol) in anhydrous dichloromethane was treated with triethylamine (0.01 ml, 0.08 mmol) and allowed to stir at room temperature overnight. The reaction mixture was partitioned between dichloromethane/water and the organic layers were collected, dried over MgSO$_4$, filtered, and concentrated. The residue was purified by preparative thin layer chromatography using 0.25:4.75:95 concentrated aqueous NH$_4$OH: MeOH: dichloromethane as eluant to provide 5 mg (42%) of 3-{3-methyl-3-[2-(3,4,5-trimethoxy-phenyl)-5H-pyrrolo[2,3-b]pyrazine-7-carbonyl]-piperidin-1-yl}-3-oxo-propionitrile as a light yellow solid. M+H 578.

Example 63

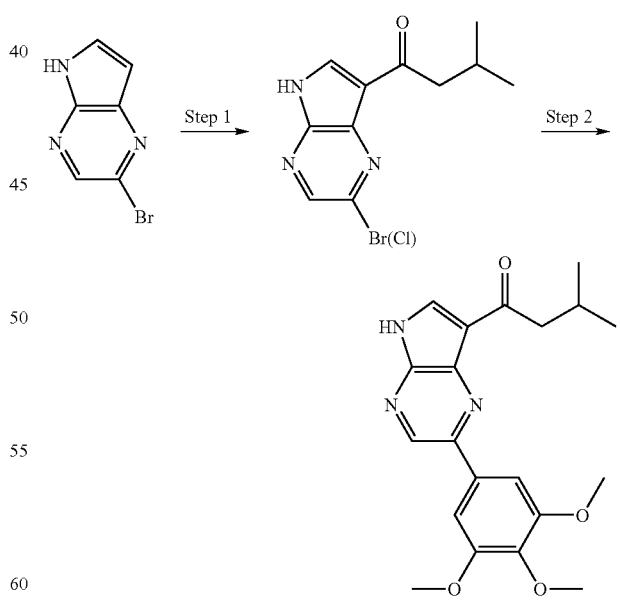

3-methyl-1-[2-(3,4,5-trimethoxy-phenyl)-5H-pyrrolo[2,3-b]pyrazin-7-yl]-butan-1-one Step 1

Aluminum chloride (333 mg, 2.5 mmol) was suspended in 7.5 ml of dichloroethane in a 20 ml microwave vial. 2-Bromo- 5H-pyrrolo[2,3-b]pyrazine (100 mg, 0.5 mmol) was dissolved in 12.5 ml of dichloroethane with the aid of heat and sonication and added to the aluminum chloride suspension. The vial was capped and placed under nitrogen and the mixture was stirred at room temperature for one hour. 3-Methylbutyryl chloride (302 mg, 2.5 mmol) was added dropwise. The vial was heated in a microwave reactor at 120° C. for 1.5 hours, and then at 150° C. for an additional 1.5 hours. Methanol (2.5 ml) was added dropwise and the solvents were evaporated using a rotary evaporator. The crude residue was purified by preparative thin layer chromatography to yield 57 mg of a mixture of 1-(2-bromo-5H-pyrrolo[2,3-b]pyrazin-7-yl)-3-methyl-butan-1-one and 1-(2-chloro-5H-pyrrolo[2,3-b]pyrazin-7-yl)-3-methyl-butan-1-one. MS: $(M-H)^-=280$ and $(M-H)^-=236$.

Step 2

A mixture of 1-(2-bromo-5H-pyrrolo[2,3-b]pyrazin-7-yl)-3-methyl-butan-1-one and 1-(2-chloro-5H-pyrrolo[2,3-b]pyrazin-7-yl)-3-methyl-butan-1-one (55 mg), potassium carbonate (95 mg, 0.69 mmol), 3,4,5-trimethoxyphenylboronic acid (47 mg, 0.22 mmol) and Pd(dppf)Cl$_2$-DCM (16 mg, 0.02 mmol) was placed in a 5 ml microwave vial. The vial was capped and purged with nitrogen. Solvent was added (2 ml of 20% aqueous dioxane) and the vial was purged again with nitrogen. The reaction mixture was heated in a microwave reactor at 150° C. for 30 min. The solvents were evaporated and the crude product was purified by flash chromatography using a gradient of 20% ethyl acetate in hexanes up to 50% to yield 30 mg of 3-methyl-1-[2-(3,4,5-trimethoxy-phenyl)-5H-pyrrolo[2,3-b]pyrazin-7-yl]-butan-1-one. MS: $(M+H)^+=370$, MP=210.0-211.4° C.

Other Compounds Prepared Using this General Procedure:

Phenyl-[2-(3,4,5-trimethoxy-phenyl)-5H-pyrrolo[2,3-b]pyrazin-7-yl]-methanone, $(M+H)^+=390$;

1-[2-(3,4,5-Trimethoxy-phenyl)-5H-pyrrolo[2,3-b]pyrazin-7-yl]-ethanone, $(M+H)^+=328$;

1-[2-(3,4-Dimethoxy-phenyl)-5H-pyrrolo[2,3-b]pyrazin-7-yl]-3-methyl-butan-1-one $(M+H)^+=340$, MP=212.0-213.0;

1-(5-Benzo[b]thiophen-2-yl-1H-pyrrolo[2,3-b]pyridin-3-yl)-3-methyl-butan-1-one, $(M+H)^+=335$;

1-[2-(5-Fluoro-2-methoxy-phenyl)-5H-pyrrolo[2,3-b]pyrazin-7-yl]-3-methyl-butan-1-one, $(M+H)^+=328$ MP=186.0-187.0;

3-Methyl-1-[2-(3-pyrrolidin-1-yl-phenyl)-5H-pyrrolo[2,3-b]pyrazin-7-yl]-butan-1-one, $(M+H)^+=349$ MP=260.0-261.0;

4-[7-(3-Methyl-butyryl)-5H-pyrrolo[2,3-b]pyrazin-2-yl]-benzamide, $(M+H)^+=323$; 3-[7-(3-Methyl-butyryl)-5H-pyrrolo[2,3-b]pyrazin-2-yl]-benzamide, $(M+H)^+=323$;

N-Methyl-3-[7-(3-methyl-butyryl)-5H-pyrrolo[2,3-b]pyrazin-2-yl]-benzamide, $(M+H)^+=337$ MP=243.0-244.0;

1-[2-(3,4-Dimethoxy-phenyl)-5H-pyrrolo[2,3-b]pyrazin-7-yl]-4-methyl-pentan-1-one, $(M+H)^+=354$; N,N-Dimethyl-3-[7-(3-methyl-butyryl)-5H-pyrrolo[2,3-b]pyrazin-2-yl]-benzamide, $(M+H)^+=351$;

3-Methyl-1-(2-phenyl-5H-pyrrolo[2,3-b]pyrazin-7-yl)-butan-1-one, $(M+H)^+=280$; 1-[2-(2,3-Dihydro-benzo[1,4]dioxin-6-yl)-5H-pyrrolo[2,3-b]pyrazin-7-yl]-3-methyl-butan-1-one, $(M+H)^+=338$;

1-(2-Benzo[1,3]dioxol-5-yl-5H-pyrrolo[2,3-b]pyrazin-7-yl)-3-methyl-butan-1-one, $(M+H)^+=324$.

Example 64

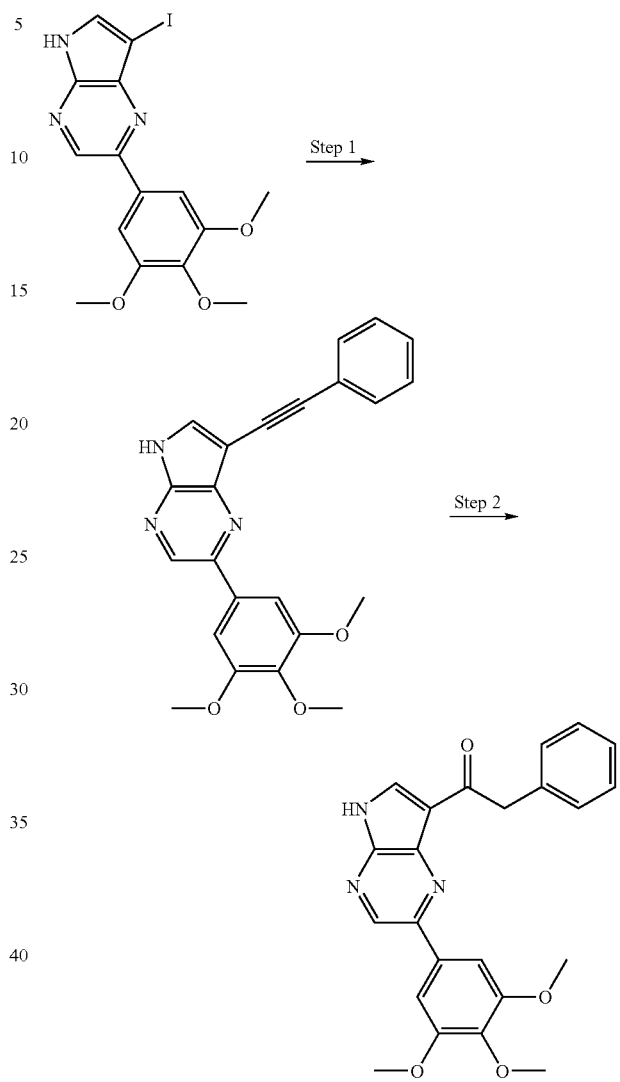

2-phenyl-1-[2-(3,4,5-trimethoxy-phenyl]-5H-pyrrolo[2,3-b]pyrazin-7-yl]-ethanone

Step 1

7-Iodo-2-(3,4,5-trimethoxy-phenyl)-5H-pyrrolo[2,3-b]pyrazine (500 mg, 1.22 mmol), PdCl$_2$(PPh$_3$)$_2$ (43 mg, 0.061 mmol), and cuprous iodide (6 mg, 0.031 mmol) were added to a 20 ml microwave vial. The vial was capped and purged with nitrogen. Ethynyl benzene (0.4 ml, 3.6 mmol), triethylamine (5 ml) and N,N-dimethylformamide (5 ml) were added through the septum and the vial was purged again with nitrogen. The mixture was heated in a microwave reactor at 70° C. for 30 minutes. The crude mixture was diluted with ethyl acetate and washed with dilute hydrochloric acid and water/brine. The organic layer was filtered through celite and concentrated. The residue was triturated with a mixture of ethyl acetate and hexanes and filtered, washed with hexanes, and dried to give 427 mg of 7-phenylethynyl-2-(3,4,5-trimethoxy-phenyl)-5H-pyrrolo[2,3-b]pyrazine. MS: $(M+H)^+=386$.

Step 2

7-Phenylethynyl-2-(3,4,5-trimethoxy-phenyl)-5H-pyrrolo[2,3-b]pyrazine (405 mg, 1.05 mmol) and p-toluenesulfonic acid monohydrate (40 mg, 0.21 mmol) were placed in a 20 ml microwave vial with 14 ml of a 2:1 mixture of methanol and acetone. The reaction was heated in a microwave reactor at 100° C. for 1.5 hours. The reaction was diluted with ethyl acetate, washed two times with saturated sodium bicarbonate and water, dried and concentrated. The residue was triturated with ethyl acetate and hexanes, filtered, and dried to yield 175 mg of 2-phenyl-1-[2-(3,4,5-trimethoxy-phenyl]-5H-pyrrolo[2,3-b]pyrazin-7-yl]-ethanone. MS: (M+H)$^+$=404. MP=226.0-227.0° C.

Other Compounds Prepared Using this General Procedure:

3,3-Dimethyl-1-[2-(3-morpholin-4-yl-phenyl)-5H-pyrrolo[2,3-b]pyrazin-7-yl]-butan-1-one, (M+H)$^+$=379;

3,3-Dimethyl-1-[2-(3-pyrrolidin-1-yl-phenyl)-5H-pyrrolo[2,3-b]pyrazin-7-yl]-butan-1-one, (M+H)$^+$=363;

3,3-Dimethyl-1-[2-(3-morpholin-4-ylmethyl-phenyl)-5H-pyrrolo[2,3-b]pyrazin-7-yl]-butan-1-one, (M+H)$^+$=393;

3,3-Dimethyl-1-[2-(3,4,5-trimethoxy-phenyl)-5H-pyrrolo[2,3-b]pyrazin-7-yl]-butan-1-one, (M+H)$^+$=384

Example 65

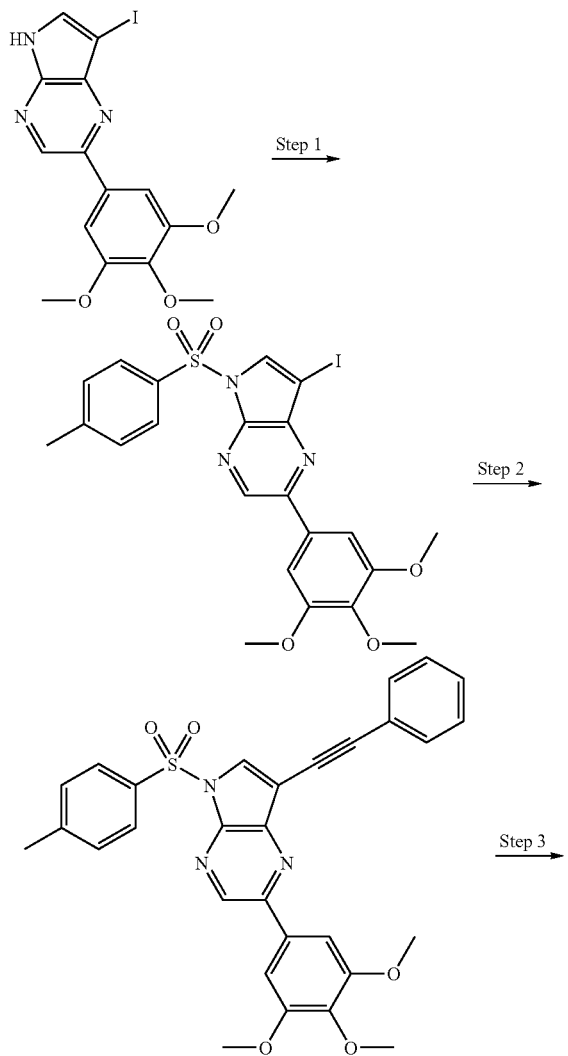

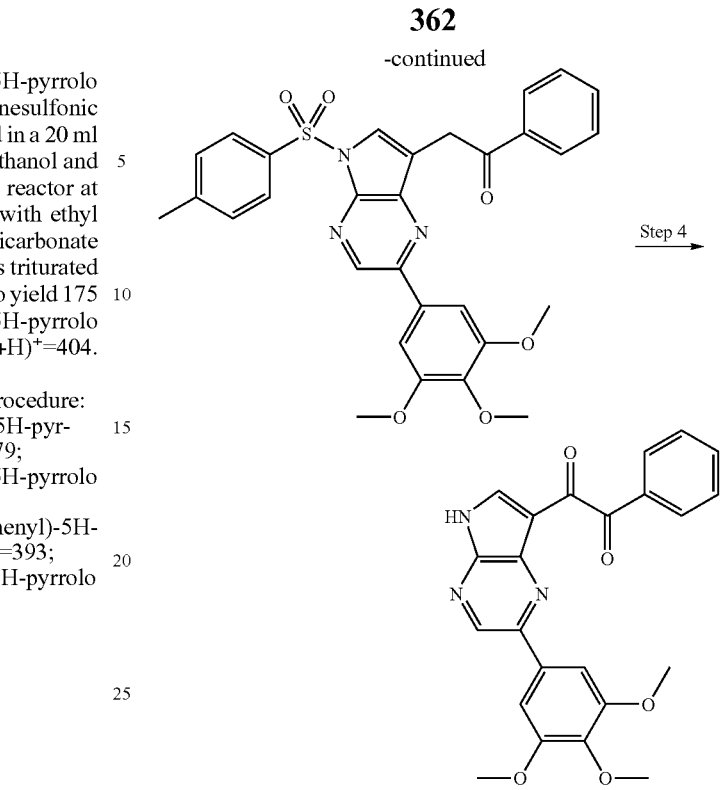

1-phenyl-2-[2-(3,4,5-trimethoxy-phenyl)-5H-pyrrolo[2,3-b]pyrazin-7-yl]-ethane-1,2-dione

Step 1

7-Iodo-2-(3,4,5-trimethoxy-phenyl)-5H-pyrrolo[2,3-b]pyrazine (371 mg, 0.9 mmol) was suspended in 5 ml of THF and cooled to 0° C. in an ice bath. Sodium hydride, 60% dispersion in mineral oil (43 mg, 1.08 mmol) was added and the suspension was stirred for 20 minutes. 4-Methyl-benzenesulfonyl chloride (189 mg, 0.99 mmol) was added, the ice bath was removed, and the reaction was stirred at room temperature for 3 hours. The solvent was evaporated on a rotary evaporator. The residue was triturated with 1M potassium hydroxide. The solid was filtered, washed with water, and dried to yield 480 mg of 7-iodo-5-(toluene-4-sulfonyl)-2-(3,4,5-trimethoxy-phenyl)-5H-pyrrolo[2,3-b]pyrazine which was used without further purification.

Step 2

7-Iodo-5-(toluene-4-sulfonyl)-2-(3,4,5-trimethoxy-phenyl)-5H-pyrrolo[2,3-b]pyrazine (275 mg, 0.49 mmol), PdCl$_2$(PPh$_3$)$_2$ (17 mg, 0.02 mmol), and cuprous iodide (5 mg, 0.02 mmol) were placed in a 5 ml microwave vial. The vial was capped and purged with nitrogen. Triethylamine (0.35 ml, 2.45 mmol) and 2.5 ml of DMF were added through the septum and the flask was purged again with nitrogen three times. Ethynyl-benzene (0.19 ml, 1.75 mmol) was added and the reaction was heated in a microwave reactor at 100° C. for 30 minutes. The crude reaction mixture was diluted with ethyl acetate, washed with water two times, dried and concentrated. The mixture was purified by flash chromatography using a gradient of 0% ethyl acetate in hexanes up to 30% to yield 195 mg of 7-phenylethynyl-5-(toluene-4-sulfonyl)-2-(3,4,5-trimethoxy-phenyl)-5H-pyrrolo[2,3-b]pyrazine. MS: (M+H)$^+$=540.

Step 3

7-Phenylethynyl-5-(toluene-4-sulfonyl)-2-(3,4,5-trimethoxy-phenyl)-5H-pyrrolo[2,3-b]pyrazine (154 mg, 0.29 mmol), mercury(II) sulfate (127 mg, 0.43 mmol), concentrated sulfuric acid (0.031 ml, 0.58 mmol) and 3 ml of a 3:1 mixture of acetone and water were added to a 5 ml microwave vial. The reaction was heated in a microwave reactor at 110° C. for one hour. The solvent was evaporated and ethyl acetate and aqueous sodium carbonate were added to the residue. The aqueous layer was removed using a reparatory funnel, the organic layer was washed with water twice, then dried and concentrated. The residue was purified by flash chromatography using a gradient of 0% ethyl acetate in hexanes up to 30% to give 100 mg of 1-phenyl-2-[5-(toluene-4-sulfonyl)-2-(3,4,5-trimethoxy-phenyl)-5H-pyrrolo[2,3-b]pyrazin-7-yl]-ethanone as the major product. MS: $(M+H)^+=558$.

Step 4

1-Phenyl-2-[5-(toluene-4-sulfonyl)-2-(3,4,5-trimethoxy-phenyl)-5H-pyrrolo[2,3-b]pyrazin-7-yl]-ethanone (100 mg, 0.18 mmol) was suspended in 4 ml of a 1:1 mixture of THF and methanol and 5N potassium hydroxide (0.180 ml, 0.9 mmol) was added dropwise. The reaction was heated at 40° C. for 2 hours. The solvents were evaporated using a rotary evaporator. Ethyl acetate and 1M hydrochloric acid were added to the residue and the layers were separated. The organic layer was washed with water, dried and concentrated. The crude reaction mixture was purified by preparative thin layer chromatography (50% ethyl acetate in hexanes) and flash chromatography to yield 4 mg of 1-phenyl-2-[2-(3,4,5-trimethoxy-phenyl)-5H-pyrrolo[2,3-b]pyrazin-7-yl]-ethane-1,2-dione. MS: $(M+H)^+=418$.

Another Compound Prepared Using this General Procedure:

2-cyclohexyl-1-[2-(3,4,5-trimethoxy-phenyl)-5H-pyrrolo[2,3-b]pyrazin-7-yl]-ethanone Example 66

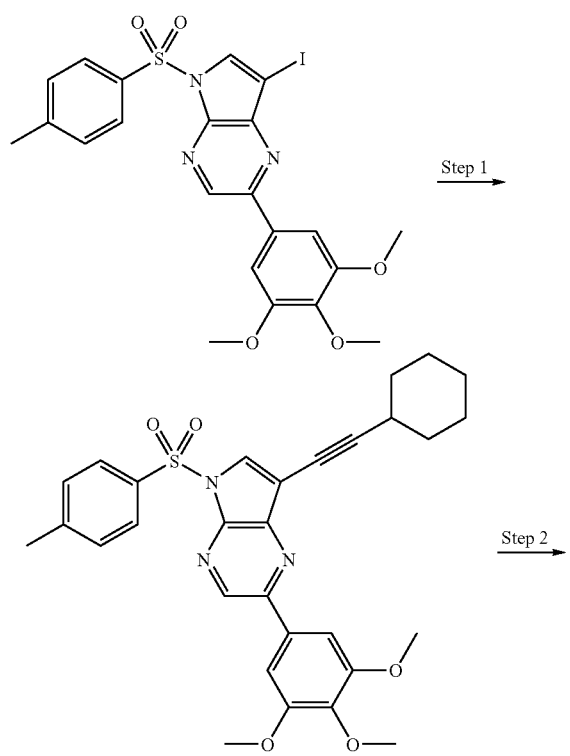

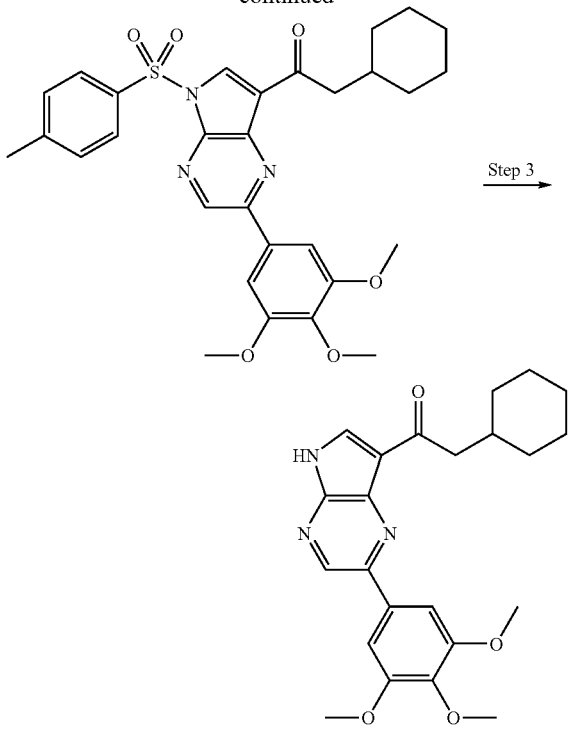

2-cyclohexyl-1-[2-(3,4,5-trimethoxy-phenyl)-5H-pyrrolo[2,3-b]pyrazin-7-yl]-ethanone Step 1

7-Cyclohexylethynyl-5-(toluene-4-sulfonyl)-2-(3,4,5-trimethoxy-phenyl)-5H-pyrrolo[2,3-b]pyrazine was prepared as in Example 65, Step 2, using ethynyl-cyclohexane in place of ethynyl-benzene.

Step 2

2-Cyclohexyl-1-[5-(toluene-4-sulfonyl)-2-(3,4,5-trimethoxy-phenyl)-5H-pyrrolo[2,3-b]pyrazin-7-yl]-ethanone was prepared as in Example 65, Step 3.

Step 3

2-Cyclohexyl-1-[2-(3,4,5-trimethoxy-phenyl)-5H-pyrrolo[2,3-b]pyrazin-7-yl]-ethanone was prepared as in Example 65, Step 4. MS: $(M+H)^+=410$.

Compounds prepared using the iPr-MgCl/LiCl Grignard route described herein, followed by the standard Suzuki coupling approach:

2,2-Dimethyl-1-[2-(3-pyrazol-1-yl-phenyl)-5H-pyrrolo[2,3-b]pyrazin-7-yl]-propan-1-one, $(M+H)^+=346$ MP=219.3-221.1° C.;

2,2-Dimethyl-1-{2-[3-(5-methyl-[1,3,4]oxadiazol-2-yl)-phenyl]-5H-pyrrolo[2,3-b]pyrazin-7-yl}-propan-1-one, $(M+H)^+=362$ MP=260.9-264.4° C.;

2,2-Dimethyl-1-{2-[3-(2H-pyrazol-3-yl)-phenyl]-5H-pyrrolo[2,3-b]pyrazin-7-yl}-propan-1-one, $(M+H)^+=346$ MP=277.0-278.0° C.;

1-[2-(3-Isopropenyl-phenyl)-5H-pyrrolo[2,3-b]pyrazin-7-yl]-2,2-dimethyl-propan-1-one, $(M+H)^+=320$.

Compounds prepared using the diethylaluminum chloride Friedel Crafts route described herein, using the 1-(2-bromo-5H-pyrrolo[2,3-b]pyrazin-7-yl)-2,2-dimethyl-propan-1-one intermediate, followed by the standard Suzuki coupling approach):

3-[7-(2,2-Dimethyl-propionyl)-5H-pyrrolo[2,3-b]pyrazin-2-yl]-N-methyl-benzamide, $(M+H)^+=336$ MP=257.0-258.0° C.;

1-[2-(3-Methoxymethyl-phenyl)-5H-pyrrolo[2,3-b]pyrazin-7-yl]-2,2-dimethyl-propan-1-one, (M+H)+=324 MP=143.0-144.0° C.;
1-[2-(4-Methoxymethyl-phenyl)-5H-pyrrolo[2,3-b]pyrazin-7-yl]-2,2-dimethyl-propan-1-one, (M+H)+=324 MP=191.0-192.0° C.;
N-Cyclopentyl-3-[7-(2,2-dimethyl-propionyl)-5H-pyrrolo[2,3-b]pyrazin-2-yl]-benzamide, (M+H)+=391 MP=227.0-228.5° C.;
3-[7-(2,2-Dimethyl-propionyl)-5H-pyrrolo[2,3-b]pyrazin-2-yl]-benzoic acid, (M+H)+=324; 1-[2-(3-Hydroxy-phenyl)-5H-pyrrolo[2,3-b]pyrazin-7-yl]-2,2-dimethyl-propan-1-one, (M+H)+=296 MP=267.0-268.0° C.

Example 67

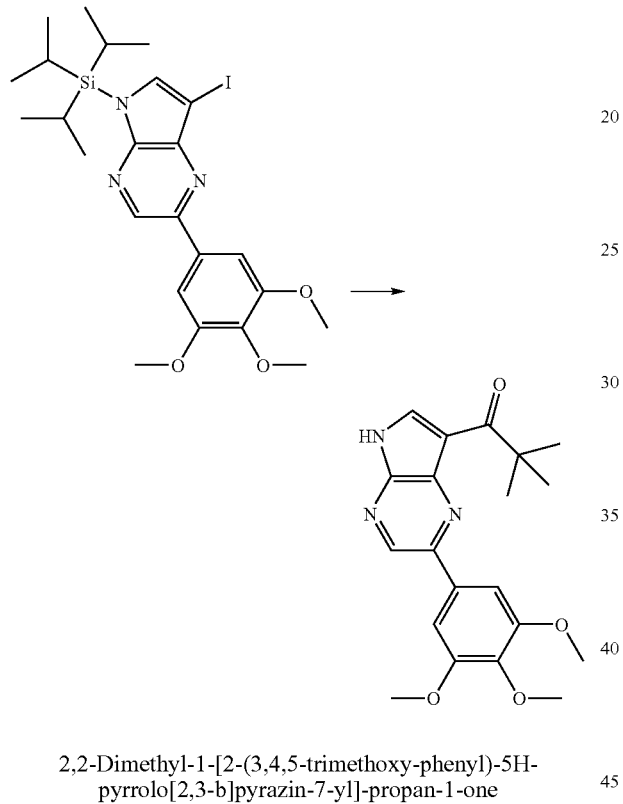

2,2-Dimethyl-1-[2-(3,4,5-trimethoxy-phenyl)-5H-pyrrolo[2,3-b]pyrazin-7-yl]-propan-1-one The general procedures from Examples 40 and 41 were used, wherein 2,2-Dimethyl-propionaldehyde instead of 1-Methyl-cyclohexanecarbaldehyde was used. MS: 370 M+1, M.P. 240-241° C.

Example 68

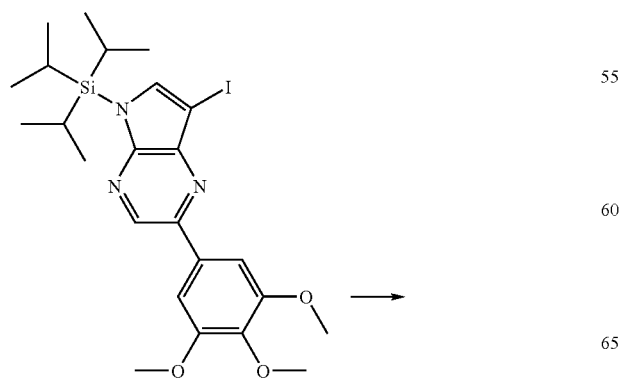

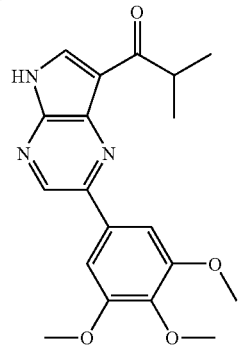

2-Methyl-1-[2-(3,4,5-trimethoxy-phenyl)-5H-pyrrolo[2,3-b]pyrazin-7-yl]-propan-1-one The general procedures from Examples 40 and 41 were used, wherein 2-Methyl-propionaldehyde instead of 1-Methyl-cyclohexanecarbaldehyde was used. (M+H)+=356, M.P. 189-190° C.

Example 69

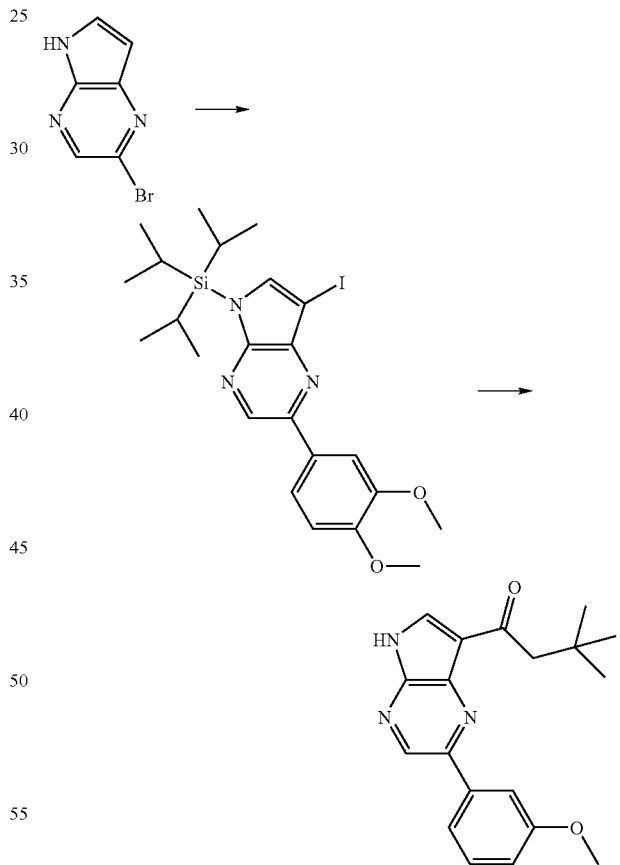

1-[2-(3,4-Dimethoxy-phenyl)-5H-pyrrolo[2,3-b]pyrazin-7-yl]-3,3-dimethyl-butan-1-one The general procedures from Examples 37-41 were used, wherein 3,4-Dimethoxyphenylboronic acid instead of 3,4,5-Trimethoxyphenylboronic acid and with 3,3-Dimethyl-butyraldehyde instead of 1-Methyl-cyclohexanecarbaldehyde was used. (M+H)+=354.

Example 70

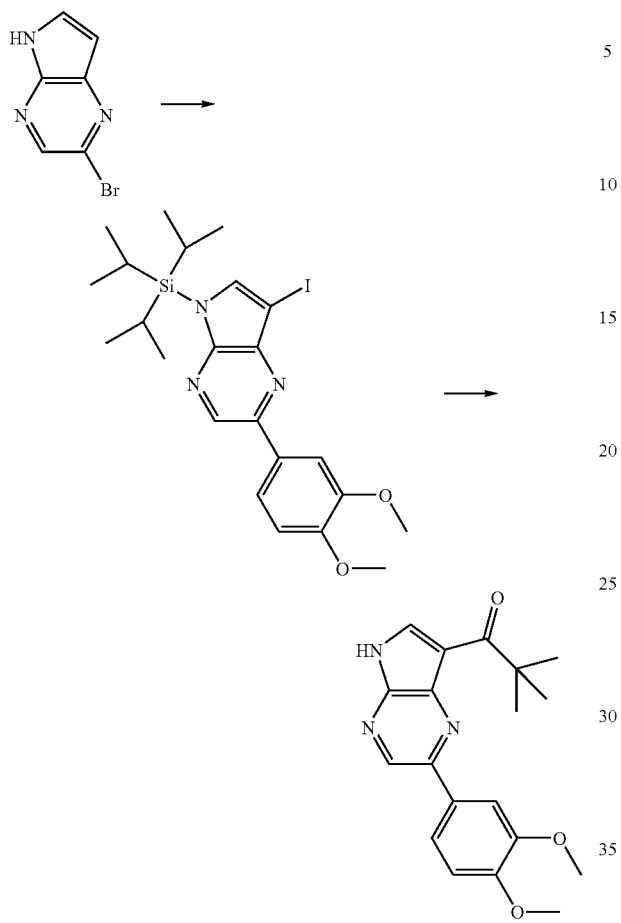

1-[2-(3,4-Dimethoxy-phenyl)-5H-pyrrolo[2,3-b]
pyrazin-7-yl]-2,2-dimethyl-propan-1-one The general procedures from Examples 37-41 were used, wherein 3,4-Dimethoxyphenylboronic acid instead of 3,4,5-Trimethoxyphenylboronic acid and 2,2-Dimethyl-propionaldehyde instead of 1-Methyl-cyclohexanecarbaldehyde was used. (M+H)+=340.

Example 71

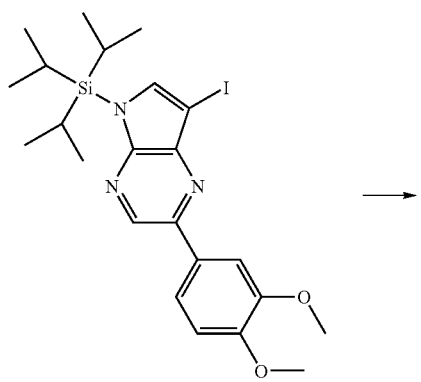

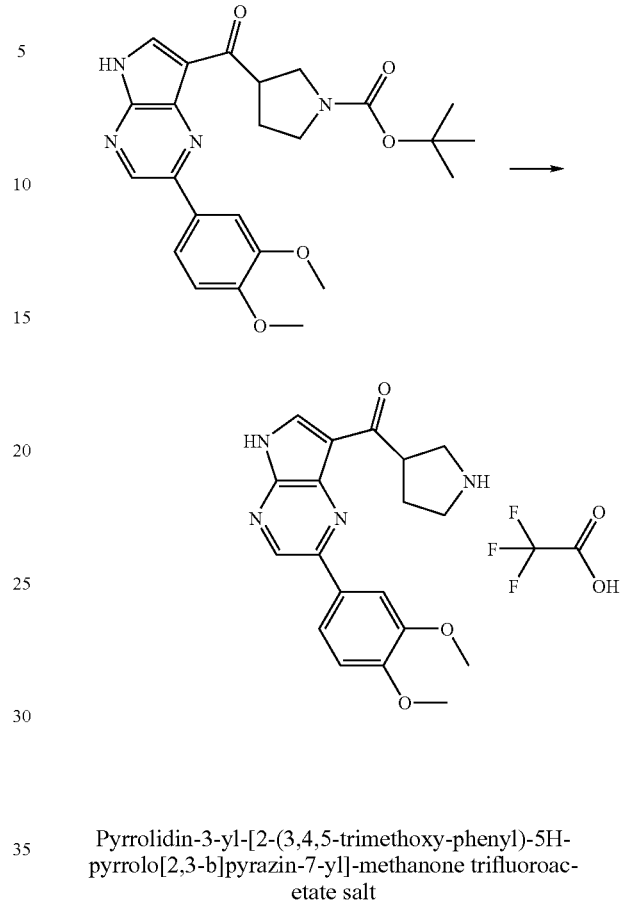

Pyrrolidin-3-yl-[2-(3,4,5-trimethoxy-phenyl)-5H-pyrrolo[2,3-b]pyrazin-7-yl]-methanone trifluoroacetate salt 7-Iodo-5-triisopropylsilanyl-2-(3,4,5-trimethoxy-phenyl)-5H-pyrrolo[2,3-b]pyrazine 0.057 gm, 0.1 mM was placed in an oven dried flask and 1 ml anhydrous THF was added. The flask was chilled in an Acetone-dry ice slurry and evacuated and refilled 3 times with nitrogen. Via syringe 0.061 ml of 2.13M BuLi in hexane solution (0.13 mM, 1.3 eq) was added and the now yellow mixture was stirred for 30 seconds then 3-(Methoxy-methyl-carbamoyl)-pyrrolidine-1-carboxylic acid tert-butyl ester, 0.052 gm, 0.2 mM, 2 eq.) in a minimal amount of THF was added by syringe. The mixture was stirred for 30 minutes, removed from the dry ice-acetone bath and immediately quenched with a saturated aqueous ammonium chloride solution. The mixture was extracted two times with ethyl acetate and the organic extracts dried over magnesium sulfate. After filtering and concentrating, the oil was redissolved in THF and 0.2 ml of 1M Tetrabutylammonium Fluoride in THF added. After 5 minutes the mixture was concentrated and purified on a preparative thin-layer chromatography plate (Ethylacetate/hexane) to give 3-[2-(3,4,5-Trimethoxy-phenyl)-5H-pyrrolo[2,3-b]pyrazine-7-carbonyl]-pyrrolidine-1-carboxylic acid tert-butyl ester. The 3-[2-(3,4,5-Trimethoxy-phenyl)-5H-pyrrolo[2,3-b]pyrazine-7-carbonyl]-pyrrolidine-1-carboxylic acid tert-butyl ester was dissolved in 3 ml of dichloromethane and 0.4 ml trifluoroacetic acid was added and stirred overnight. The solution was concentrated and the solid dried overnight at 2 torr in a 60° C. vacuum oven to give 0.012 gm of Pyrrolidin-3-yl-[2-(3,4,5-trimethoxy-phenyl)-5H-pyrrolo[2,3-b]pyrazin-7-yl]-methanone trifluoroacetate salt. (M+H)+=383.

Example 72

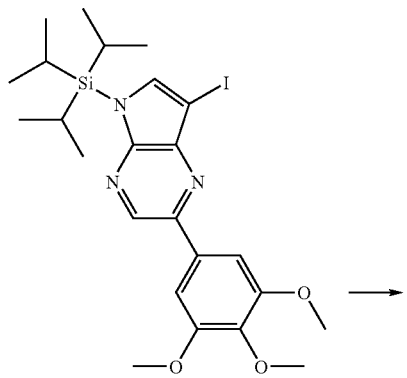

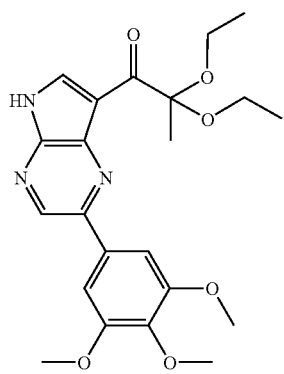

2,2-Diethoxy-1-[2-(3,4,5-trimethoxy-phenyl)-5H-pyrrolo[2,3-b]pyrazin-7-yl]-propan-1-one The general procedures from Examples 40 and 41 were used, wherein 2,2-Diethoxy-propionaldehyde (JACS 126(9) 2660 (2004)) instead of 1-Methyl-cyclohexanecarbaldehyde was used. (M+H)+=430, M.P. 198.2-201° C.

Example 73

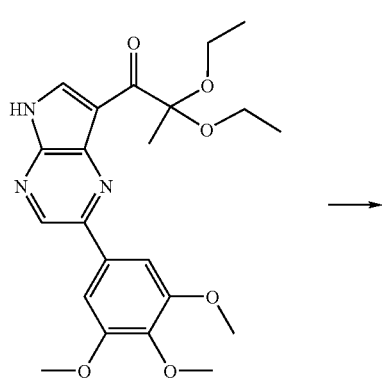

1-[2-(3,4,5-Trimethoxy-phenyl)-5H-pyrrolo[2,3-b]pyrazin-7-yl]-propane-1,2-dione 2,2-Diethoxy-1-[2-(3,4,5-trimethoxy-phenyl)-5H-pyrrolo[2,3-b]pyrazin-7-yl]-propan-1-one (0.027 mg, 0.06 mM) was dissolved in 3 ml dichloromethane and 0.3 gm silica gel was added followed by 0.03 ml 10% aqueous citric acid solution. After stirring overnight 0.03 ml trifluoroacetic acid was added and stirred again overnight. To the orange mixture was added aqueous sodium bicarbonate, the mixture filtered and the silica gel rinsed with a methanol/dichloromethane mixture (20/80). The rinses were concentrate and the oil purified on a preparative thin layer chromatography plate eluting with methanol/dichloromethane (4/96). The product was dissolved in acetonitrile to induce crystallization, stripped and dried overnight at 2 torr in a vacuum oven at 60° C. to give 1-[2-(3,4,5-Trimethoxy-phenyl)-5H-pyrrolo[2,3-b]pyrazin-7-yl]-propane-1,2-dione. (M+H)+=356.

Example 74

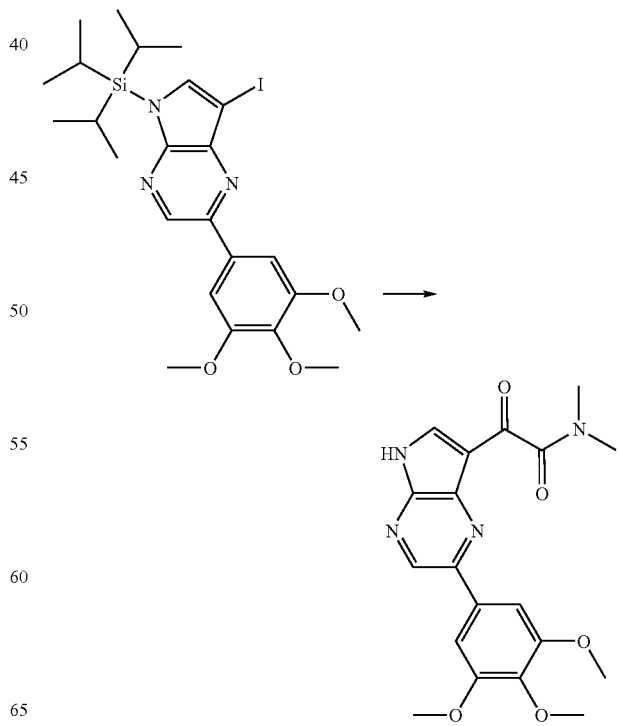

N,N-Dimethyl-2-oxo-2-[2-(3,4,5-trimethoxy-phenyl)-5H-pyrrolo[2,3-b]pyrazin-7-yl]-acetamide The general procedures from Examples 37-41 were used, wherein N,N-Dimethyl-2-oxo-acetamide (WO 9005721) instead of 1-Methyl-cyclohexanecarbaldehyde was used. (M+H)+=385, M.P. 227-228° C.

Example 75

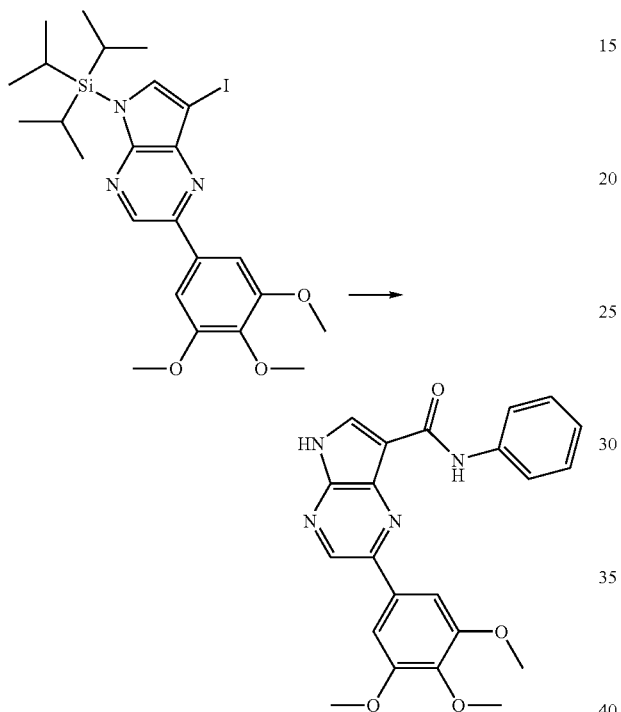

2-(3,4,5-Trimethoxy-phenyl)-5H-pyrrolo[2,3-b]pyrazine-7-carboxylic acid phenylamide 7-Iodo-5-triisopropylsilanyl-2-(3,4,5-trimethoxy-phenyl)-5H-pyrrolo[2,3-b]pyrazine 0.057 gm, 0.1 mM was placed in an oven dried flask and 1 ml anhydrous THF was added. The flask was chilled in an Acetone-dry ice slurry and evacuated and refilled 3 times with nitrogen. Via syringe 0.065 ml of 2.13M BuLi in hexane solution (0.14 mM, 1.4 eq) was added and the now yellow mixture was stirred for 30 seconds then phenylisocyanate, 0.027 ml, 0.25 mM, 2.5 eq.) was added. The mixture was stirred for 30 minutes, removed from the dry ice-acetone bath and immediately quenched with saturated aqueous ammonium chloride. Ethyl acetate was added and insoluble material removed by filtration and discarded. The mixture was separated and the aqueous layer was extracted two times with ethyl acetate. The organic layers were rinsed three times with 0.1M HCl and dried over magnesium sulfate. The solution was concentrated and purified on a silica gel column (ethyl acetate/hexane gradient). The product was recrystallized from acetonitrile and dried at 2 torr in a 60° C. vacuum oven overnight to give 2-(3,4,5-Trimethoxy-phenyl)-5H-pyrrolo[2,3-b]pyrazine-7-carboxylic acid phenylamide. (M+H)+=405.

Example 76

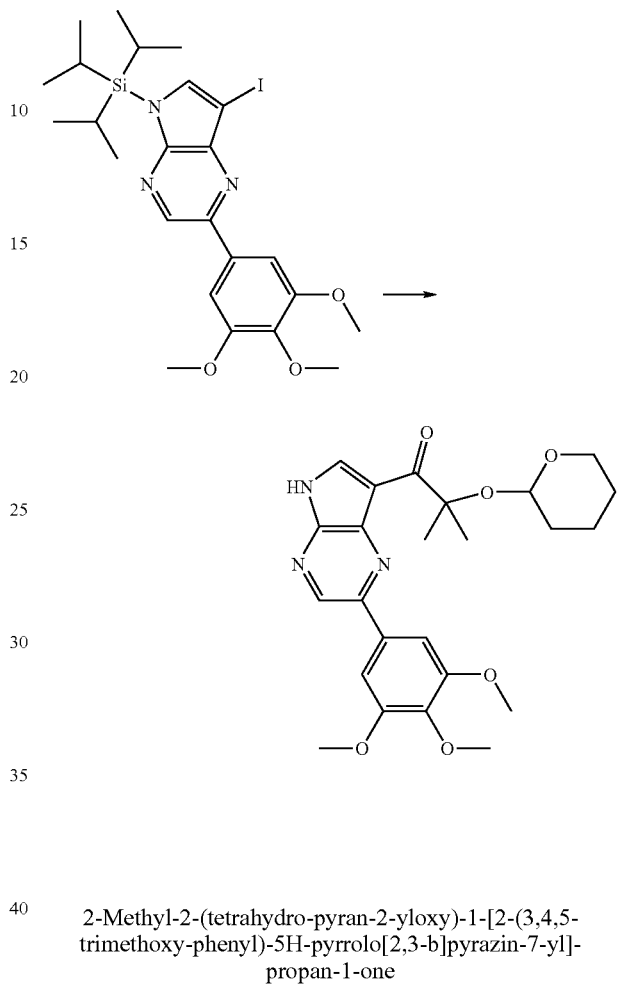

2-Methyl-2-(tetrahydro-pyran-2-yloxy)-1-[2-(3,4,5-trimethoxy-phenyl)-5H-pyrrolo[2,3-b]pyrazin-7-yl]-propan-1-one The general procedures from Examples 37-41 were used, wherein 2-Methyl-2-(tetrahydro-pyran-2-yloxy)-propionaldehyde (JOC 42(24) 3846 (1977)) instead of 1-Methyl-cyclohexanecarbaldehyde was used. (M+H)+=456.

Example 77

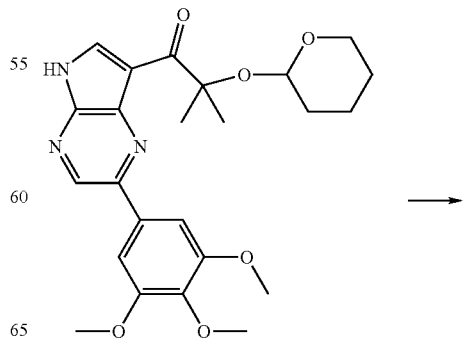

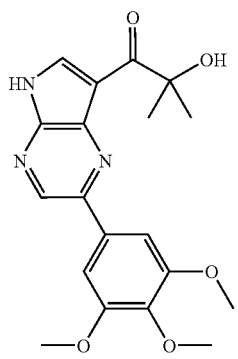

2-Hydroxy-2-methyl-1-[2-(3,4,5-trimethoxy-phenyl)-5H-pyrrolo[2,3-b]pyrazin-7-yl]-propan-1-one 2-Methyl-2-(tetrahydro-pyran-2-yloxy)-1-[2-(3,4,5-trimethoxy-phenyl)-5H-pyrrolo[2,3-b]pyrazin-7-yl]-propan-1-one, 0.012 gm, was mixed with 0.8 ml acetic acid, 0.4 ml THF and 0.2 ml water and heated for 90 minutes in a 50° C. oil bath. The mixture was concentrated, saturated aqueous sodium bicarbonate was added and the mixture extracted twice with ethyl acetate, dried over magnesium sulfate, filtered and stripped and the solid dried overnight at 2 torr in an 80° C. vacuum oven to give 2-Hydroxy-2-methyl-1-[2-(3,4,5-trimethoxy-phenyl)-5H-pyrrolo[2,3-b]pyrazin-7-yl]-propan-1-one. (M+H)+=372.

Example 78

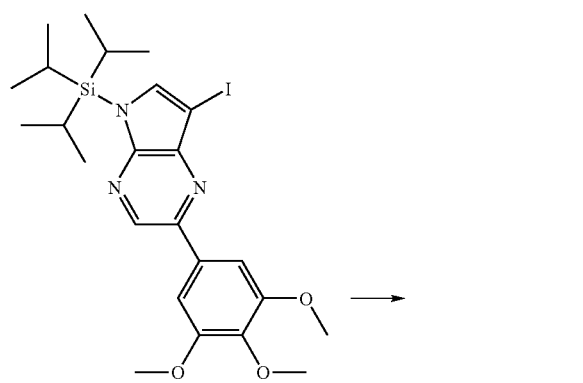

2,2-Dimethyl-1-[2-(3,4,5-trimethoxy-phenyl)-5H-pyrrolo[2,3-b]pyrazin-7-yl]-butan-1-one The general procedures from Examples 37-41 were used, wherein 2,2-Dimethyl-butyraldehyde instead of 1-Methyl-cyclohexanecarbaldehyde was used. (M+H)+=384.

Example 79

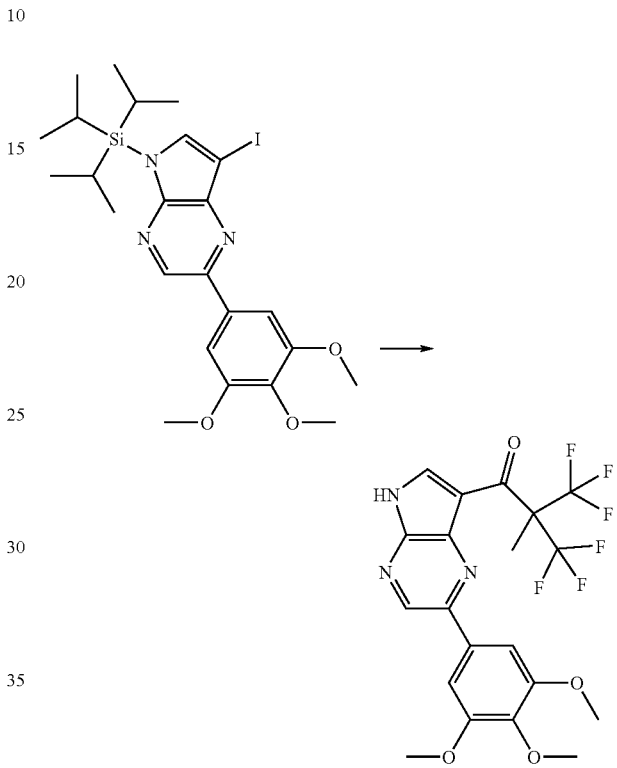

3,3,3-Trifluoro-2-methyl-2-trifluoromethyl-1-[2-(3,4,5-trimethoxy-phenyl)-5H-pyrrolo[2,3-b]pyrazin-7-yl]-propan-1-one 7-Iodo-5-triisopropylsilanyl-2-(3,4,5-trimethoxy-phenyl)-5H-pyrrolo[2,3-b]pyrazine 0.057 gm, 0.1 mM was placed in an oven dried flask and 1 ml anhydrous THF was added. The flask was chilled in an Acetone-dry ice slurry and evacuated and refilled 3 times with nitrogen. Isopropylmagnesium Chloride lithium chloride complex, 1.3M, 0.23 ml, 0.3 mM, 3 eq, was added via syringe and the mixture stirred for 30 minutes. 3,3,3-Trifluoro-2-methyl-2-trifluoromethyl-propionaldehyde, 0.1 gm, 0.52 ml, 5.2 eq, added and the mixture stirred for another 30 minutes in the dry ice-acetone bath then 30 minutes in an ice bath. Saturated aqueous ammonium chloride was added and the mixture extracted three times with ethyl acetate which was dried over magnesium sulfate and stripped to an oil, 0.077 gm.

The oil was added to 2 ml dichloromethane along with Dess-Martin Periodinane, 0.085 gm, 0.2 mM and stirred overnight at room temperature. The mixture was concentrated, 2 ml methanol, 2 ml THF and 1 ml water was added and heated to 60° C. for twenty minutes. The solution was concentrated and the residue purified by chromatography (ethyl acetate/hexane) and the product dried overnight at 2 torr in a 75° C. vacuum oven to give 3,3,3-Trifluoro-2-methyl-2-trifluoromethyl-1-[2-(3,4,5-trimethoxy-phenyl)-5H-pyrrolo[2,3-b]pyrazin-7-yl]-propan-1-one. (M+H)+=478.

Example 80

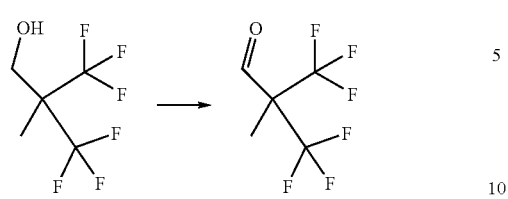

3,3,3-Trifluoro-2-methyl-2-trifluoromethyl-propionaldehyde 3,3,3-Trifluoro-2-methyl-2-trifluoromethyl-propan-1-ol, 1 gm, 5.1 mM, and Dess-Martin Periodinane, 4.3 gm, 10.2 mM, 2 eq. was added to ten ml of 1,1,1,3 tetrachloroethane and the mixture stirred for several hours. A short path distillation head was added and the receiver flask was cooled in dry ice-acetone bath. The mixture was heated to 100° C. and the pressure lowered to 180 Ton. The desired product 3,3,3-Trifluoro-2-methyl-2-trifluoromethyl-propionaldehyde condensed in the receiver flask and was used without further purification in the above reaction.

Scheme A

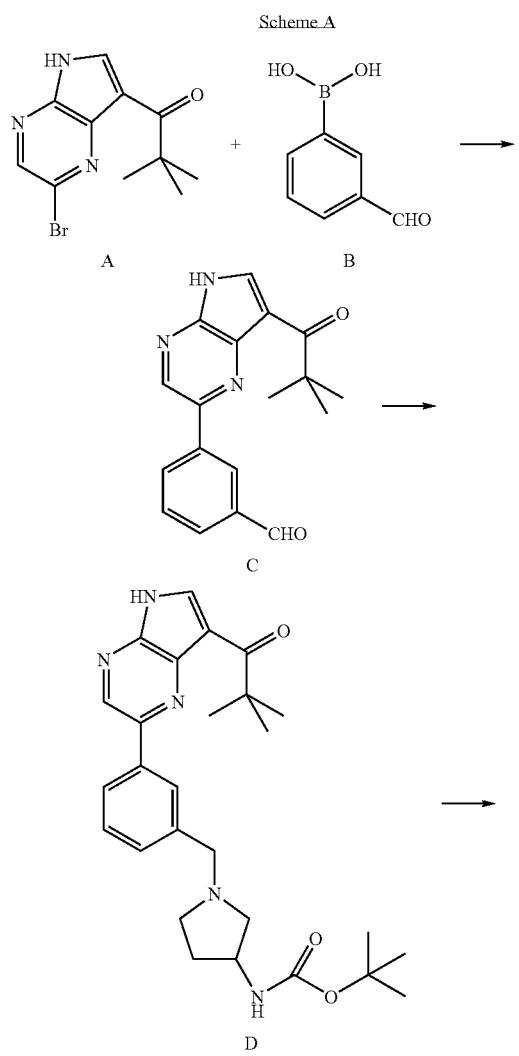

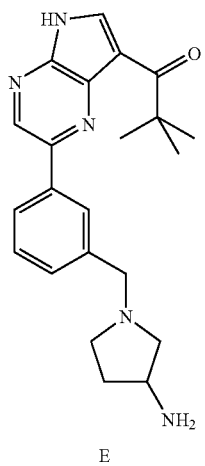

Example 81

Preparation of C:

Reaction mixture containing 0.563 g (2 mM) of bromopyrazine A, 0.45 g (3 mM) of boronic acid B, 3 ml (6 mM) of 2 M sodium carbonate aq. Solution, and 0.141 g (0.2 mM) of bis triphenylphosphine palladium dichloride in 10 ml of degassed THF was heated at 150° C. in a microwave reactor for 30 min. The reaction mixture was cooled and diluted with EtOAc and washed with water and brine. The EtOAc extract dried over sodium sulfate and solvent removed under reduced pressure. Trituration of the with EtOAc-Hexanes (1:3) gave desired product C as a light orange color solid (0.429 g, 70%) mp 219-220° C.

General Procedure for the of Preparation of D:

(Example Using 3-Amino-boc-pyrrolidine)

To a reaction mixture containing 0.461 g (1.5 mM) of aldehyde C, 0.419 g (2.25 mM) of N-Methylpiperazine, approximately 300 mg of freshly activated 4 A molecular sieves, one drop of Acetic acid in 6 ml of chloroform, 0.508 mg (1.8 mM) of tetrabutylammoniumcyanoborohydride was added and the resulting mixture stirred at room temperature for ca 12 hr. The reaction mixture diluted with chloroform and washed sequentially with 5% sodium carbonate solution, water and brine. The organic layer separated, dried over sodium sulfate and the solvent removed under reduced pressure. The residue was chromatographed on silica gel (10-50% 60:10:1 $CH_2Cl_2$:MeOH:$NH_4OH$—$CH_2Cl_2$) to give 0.357 g (50%) of desired amine D, mp 179-180° C.

General procedure for the of Preparation of E:

(Example Using 3-Amino-boc-pyrrolidine Product D)

A solution of 0.293 g (0.613 mM) in 10 ml of hexafluoroisopropanol was heated in a microwave reactor at 150° C. for 2 hr. The reaction mixture was concentrated under reduced pressure and the residue was chromatographed on silica gel column (20-60% 60:10:1 $CH_2Cl_2$:MeOH:$NH_4OH$—$CH_2Cl_2$). Crystallization from EtOAc-Hexanes gave E as a white solid (0.129 g, 56%), mp 135-138° C.

Following compounds were synthesized using above procedure.

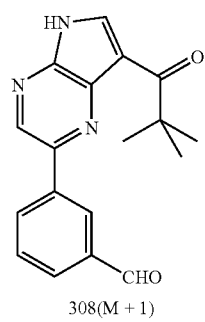
308(M + 1)
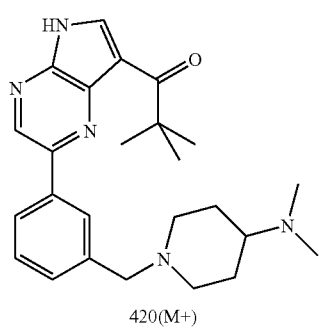
420(M+)
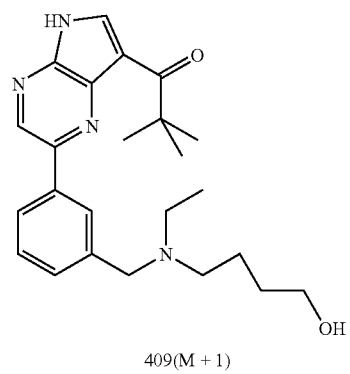
409(M + 1)
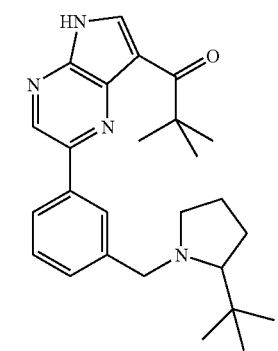
419(M + 1)
-continued
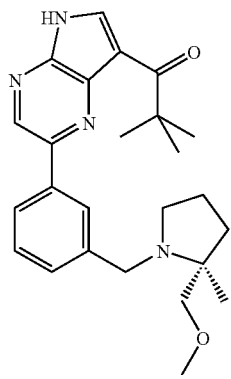
407(M + 1)
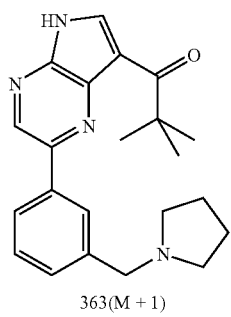
363(M + 1)
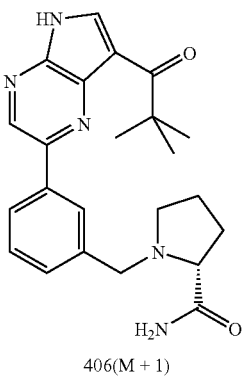
406(M + 1)
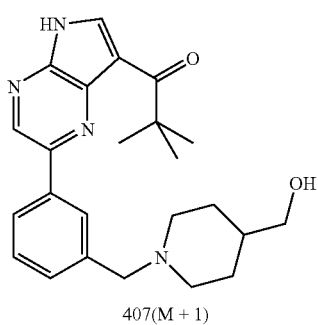
407(M + 1)

| 379 | 380 |
|---|---|
| -continued | -continued |
| 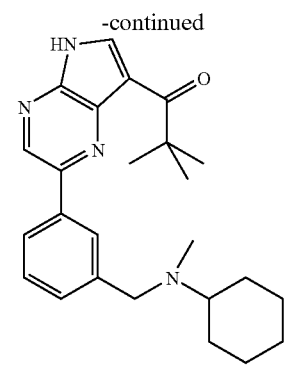 405(M + 1) | 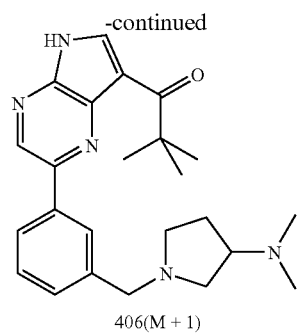 406(M + 1) |
| 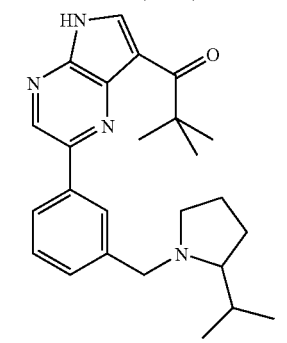 391(M + 1) | 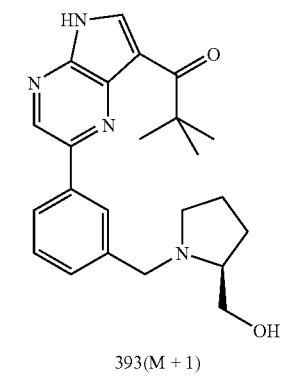 393(M + 1) |
| 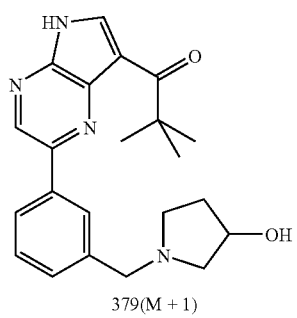 379(M + 1) | 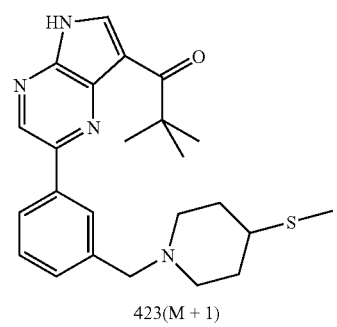 423(M + 1) |
| 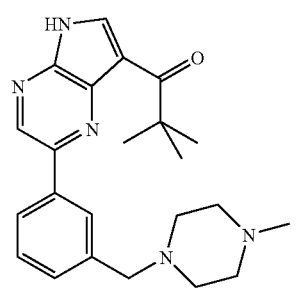 392(M + 1) | 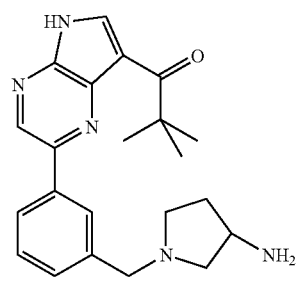 378(M + 1) |
| 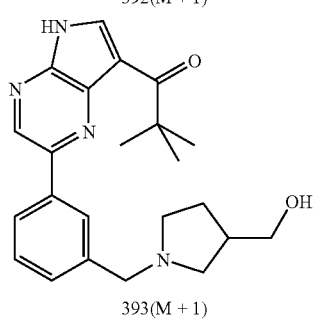 393(M + 1) | 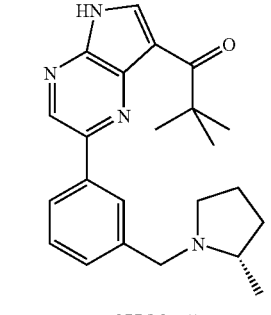 377(M + 1) |

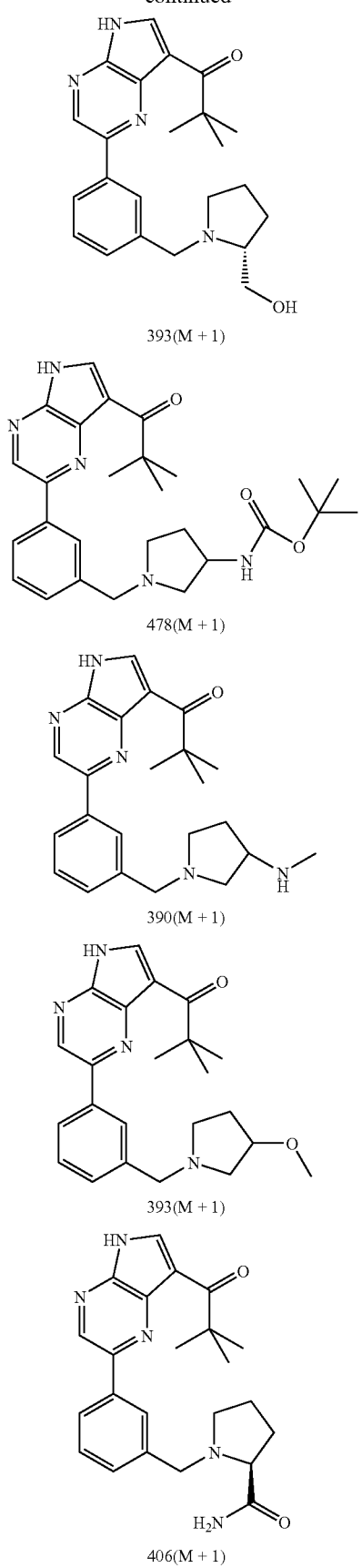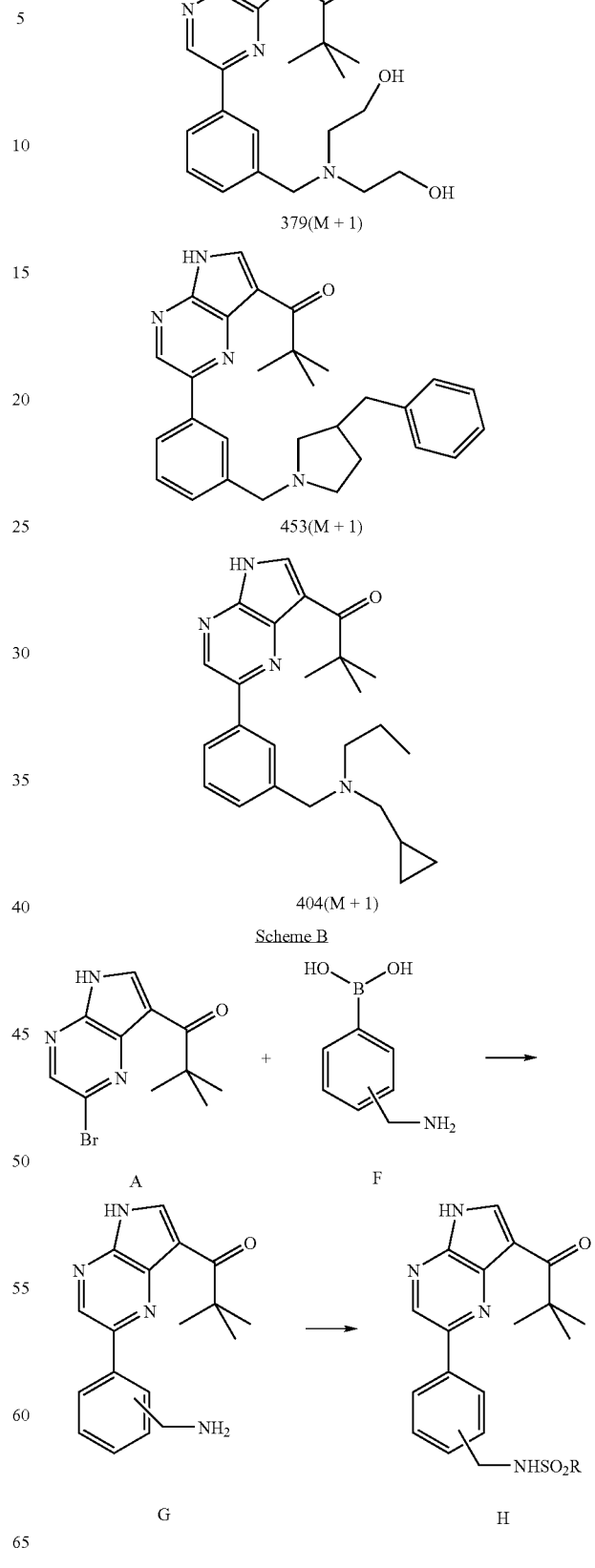

Example 82

General Preparation of F:
(Example Using 3-methylamino-benzeneboronic acid)

Reaction mixture containing 0.563 g (2 mM) of bromopyrazine A, 0.45 g (2.4 mM) of 3-methylaminon-benzeneboronic acid HCl salt F, 0.697 g (6 mM) of $K_2CO_3$, and 0.163 g (0.2 mM) of $Pd(dppf)_2Cl_2 \cdot CH_2Cl_2$ in 15 ml of degassed dioxane and 3 ml of water, was heated at 150° C. in a microwave reactor for 30 min. The reaction mixture was cooled and diluted with EtOAc and washed with water and brine. The EtOAc extract dried over sodium sulfate and solvent removed under reduced pressure and the dark brown residue was chromatographed on silica gel column (2-10% MeOH—$CH_2Cl_2$). The product on trituration with toluene gave brown powder (0.310 g, 50%). This compound used in the next step.

General Preparation of H:
(Example Using Methanesulfonyl Chloride

A mixture containing 100 mg (0.32 mM) of aminopyrazine G and 0.17 ml (1.2 mM) triethylamine in 5 ml dichloromethane was stirred in an ice bath. To this was added 0.025 ml (0.32 mM) methanesulfonyl chloride drop wise and stirred cold for three hours followed by the addition of water. The reaction mixture was diluted with water and extracted into dichloromethane, then the organics were washed with brine. The organic layer dried and the solvent removed under reduced pressure and the crude product was purified by silica gel chromatography (0-50% 60:10:1 $CH_2Cl_2$:MeOH:$NH_4OH$—$CH_2Cl_2$) to yield H as a white solid (71 mg, 57%).

Following compounds were prepared using the above procedures:

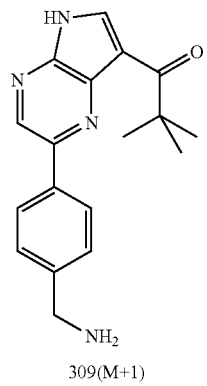

309(M+1)

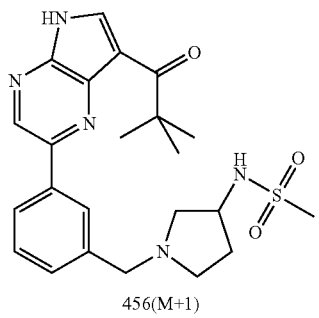

456(M+1)

-continued

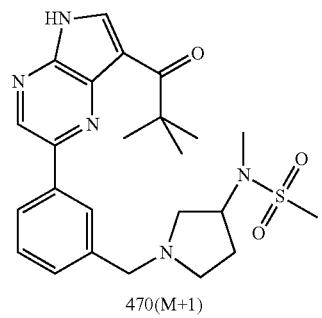

470(M+1)

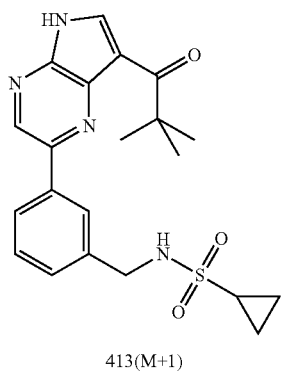

413(M+1)

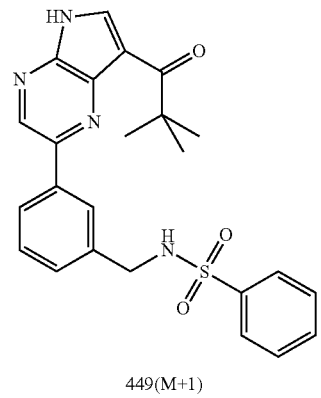

449(M+1)

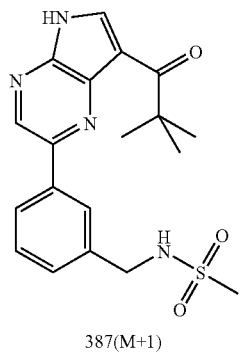

387(M+1)

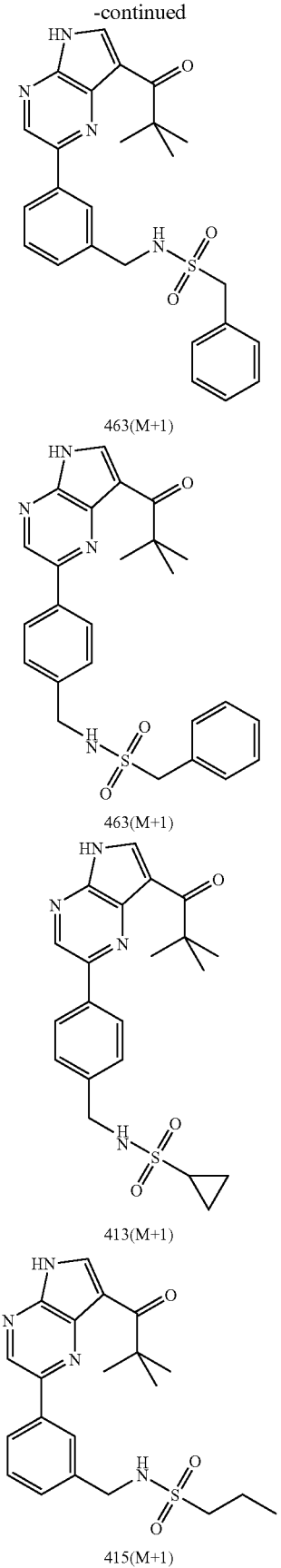

463(M+1)

463(M+1)

413(M+1)

415(M+1)

Scheme C

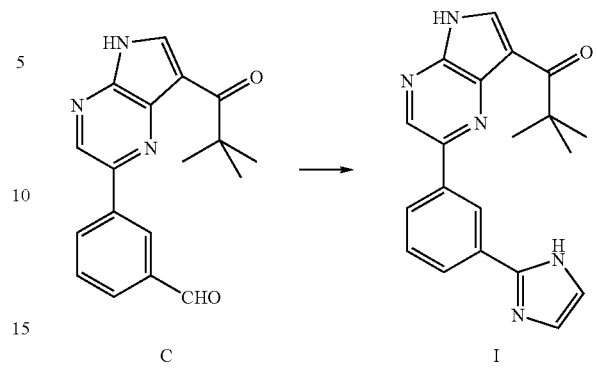

Example 83

Preparation of I:

A mixture containing 0.307 g (1 mM) of aldehyde C, 0.158 g (2 mM) of ammonium bicarbonate, 0.145 g (1 mM) of 40% aqueous glyoxal solution in 4 ml of THF and 1 ml of MeOH was stirred at room temperature over night. LCMS indicated only 12% conversion to the desired product. Additional 0.158 g of ammonium bicarbonate and 0.145 g of glyoxal solution added and stirring continued for an additional 24 hrs. The reaction mixture was diluted with EtOAc and washed with water and brine. The organic layer dried and the solvent removed under reduced pressure and the crude product was purified by silica gel chromatography (0-50% 60:10:1 $CH_2Cl_2$:MeOH:$NH_4$OH—$CH_2Cl_2$) to yield 53 mg of I as a light yellow solid. Mp 287-290° C., 346 (M+1).

Scheme D

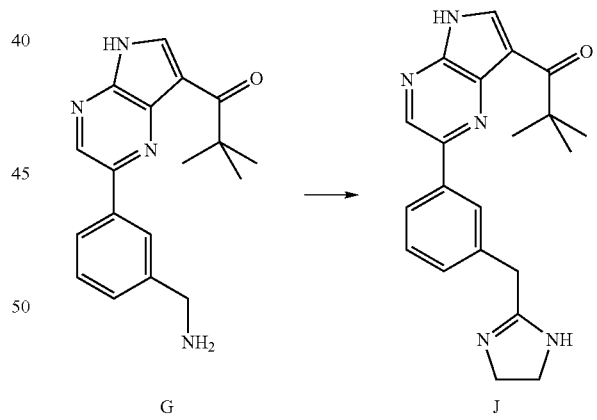

Example 84

Preparation of J:

Reaction mixture containing 100 mg (0.32 mM) of aminopyrazine G and 40 mg (0.38 mM) of 2-chloro-2-imidazoline in 2 ml isopropanol was stirred at room temperature under argon for 24 hours. An additional 40 mg (0.38 mM) of 2-chloro-2-imidazoline in 1 ml isopropanol added and the reaction mixture was stirred for additional three days, then temperature raised to 800° C. and continued stirring for 24 hours. The reaction was allowed to cool, and solvent removed under reduced pressure. The residue was chromatographed on silica gel (10-50% 60:10:1 CH$_2$Cl$_2$:MeOH:NH$_4$OH—CH$_2$Cl$_2$) to give 55 mg (46%) of desired amine J as a light brown solid.

The following compound was synthesized using the above procedure:

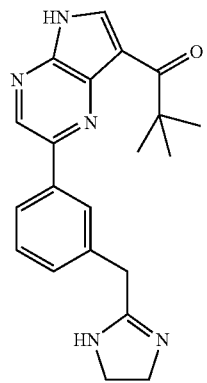

MS: 377(M + 1)

Scheme E

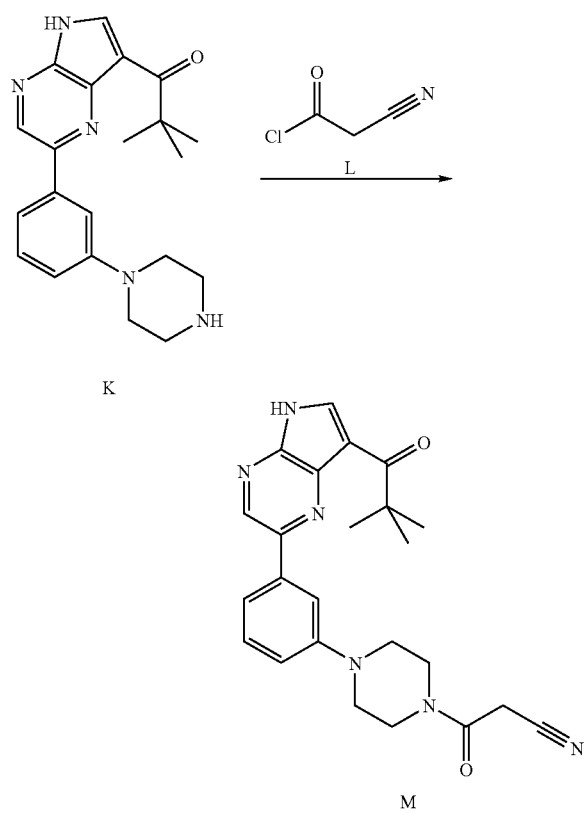

Example 85

A reaction mixture of 335 mg (0.89 mM) piperazine K, (prepared as in Scheme I), and 0.37 ml (2.7 mM) triethylamine in 10 ml dichloromethane was stirred in an ice bath and then treated with 4.6 ml (1.1 mM) of a 0.24M solution of L in dichloromethane, (prepared by treating cyano acetic acid with oxalyl chloride. The above reaction mixture was stirred in an ice bath for three hours, then diluted with water. The reaction mixture was extracted with dichloromethane and the organic extract washed with brine. The dichloromethane extract dried over sodium sulfate and solvent removed under reduced pressure then chromatographed on silica gel column (0-50% 60:10:1 CH$_2$Cl$_2$:MeOH:NH$_4$OH—CH$_2$Cl$_2$). Gave M as a white solid (210 mg, 53%).

The following compound was synthesized using the above procedure:

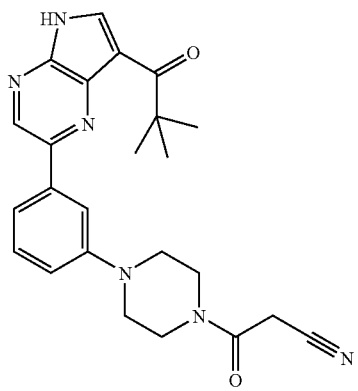

MS: 445(M + 1)

Example 86

TBAF Deprotection

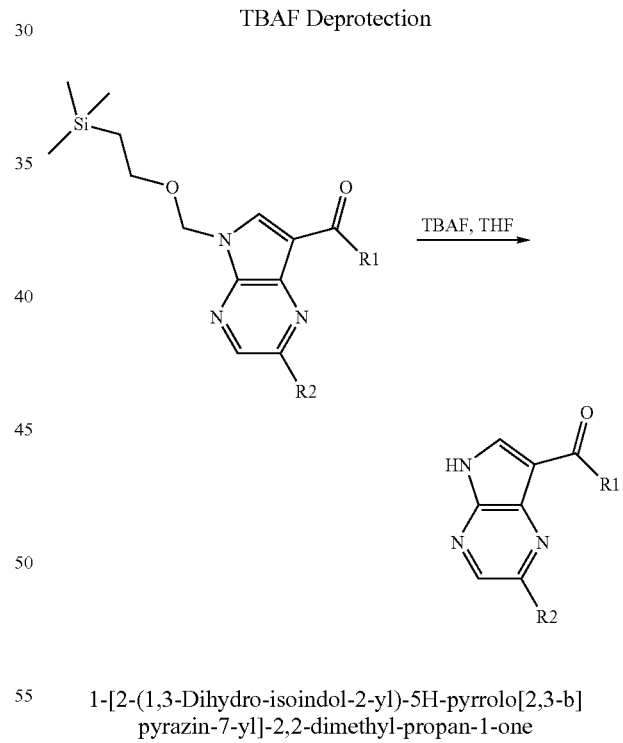

1-[2-(1,3-Dihydro-isoindol-2-yl)-5H-pyrrolo[2,3-b]pyrazin-7-yl]-2,2-dimethyl-propan-1-one To a solution of 1-[2-(1,3-Dihydro-isoindol-2-yl)-5-(2-trimethylsilanyl-ethoxymethyl)-5H-pyrrolo[2,3-b]pyrazin-7-yl]-2,2-dimethyl-propan-1-one (270 mg, 0.599 mmol) in 7 mL of THF was added 5.99 mL (5.99 mmol) of 1.0 M TBAF in THF. Heated the mixture to 85° C. for 2 h. The reaction was quenched with 5 mL acetone and 15 mL of saturated aqueous NaHCO$_3$ then diluted with ethyl acetate and water and partitioned. The organic phase was washed with brine, dried over MgSO$_4$, filtered, and concentrated. Recrystallization from dichloromethane afforded 153.3 mg (80% yield) of 1-[2-(1, 3-Dihydro-isoindol-2-yl)-5H-pyrrolo[2,3-b]pyrazin-7-yl]-2,2-dimethyl-propan-1-one as a white solid.

Example 87

TFA/NaOAc Deprotection

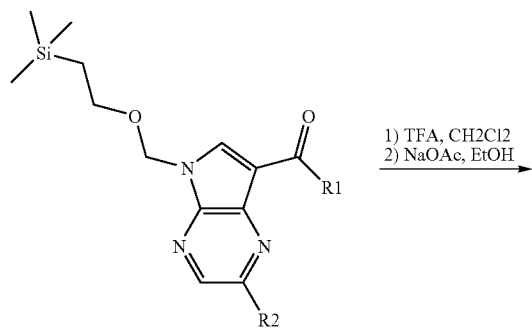

1-[7-(2,2-Dimethyl-propionyl)-5H-pyrrolo[2,3-b]pyrazin-2-yl]-3,4-dihydro-1H-quinolin-2-one A solution of 1-[7-(2,2-Dimethyl-propionyl)-5-(2-trimethylsilanyl-ethoxymethyl)-5H-pyrrolo[2,3-b]pyrazin-2-yl]-3,4-dihydro-1H-quinolin-2-one (0.2562 g, 0.535 mmol) in 2 mL of dichloromethane and 2 mL of trifluoroacetic acid was stirred for 5 h then concentrated to a yellow oil. The oil was dissolved in 2 mL of ethanol and the solution was treated with sodium acetate trihydrate (01.3 g, 9.55 mmol). Silica gel chromatography (0→50% 60:10:1 CH$_2$Cl$_2$:MeOH:NH$_4$OH/dichloromethane) afforded 0.1626 g (87% yield) of 1-[7-(2,2-Dimethyl-propionyl)-5H-pyrrolo[2,3-b]pyrazin-2-yl]-3,4-dihydro-1H-quinolin-2-one as a yellow solid.

Example 88

TFA/KOH Deprotection

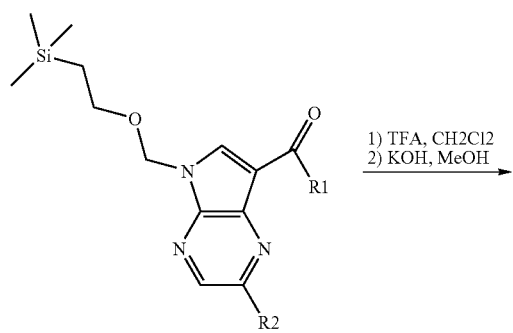

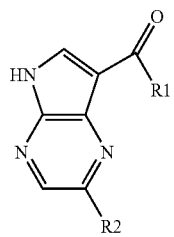

1-[2-(3-Cyclopentylamino-phenyl)-5H-pyrrolo[2,3-b]pyrazin-7-yl]-2,2-dimethyl-propan-1-one A solution of 1-[2-(3-Cyclopentylamino-phenyl)-5-(2-trimethylsilanyl-ethoxymethyl)-5H-pyrrolo[2,3-b]pyrazin-7-yl]-2,2-dimethyl-propan-1-one (0.1781 g, 0.361 mmol) in 1 mL of dichloromethane and 1 mL of trifluoroacetic acid was stirred for 3 h then concentrated to a yellow oil. The oil was dissolved in 1 mL of methanol and the solution was treated with potassium hydroxide (0.24 g, 4.34 mmol). Preparative thin layer chromatography (50% 60:10:1 CH$_2$Cl$_2$:MeOH:NH$_4$OH/dichloromethane) afforded 0.070 g (53% yield) of 1-[2-(3-Cyclopentylamino-phenyl)-5H-pyrrolo[2,3-b]pyrazin-7-yl]-2,2-dimethyl-propan-1-one as a yellow solid.

Example 89

CuI/Proline Coupling

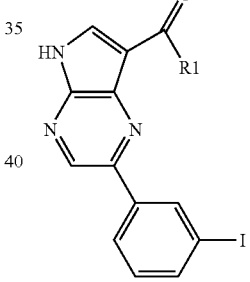

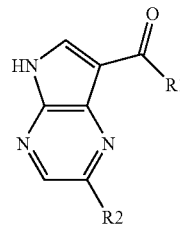

1-[2-(3-Isopropylamino-phenyl)-5H-pyrrolo[2,3-b]pyrazin-7-yl]-2,2-dimethyl-propan-1-one DMSO (1.5 mL) was added to a mixture of copper iodide (10.6 mg; 0.056 mmol), d,l-proline (12.8 mg; 0.11 mmol), potassium carbonate (113 mg; 0.81 mmol), and 1-[2-(3-Iodo-phenyl)-5H-pyrrolo[2,3-b]pyrazin-7-yl]-2,2-dimethyl-propan-1-one (150 mg; 0.37 mmol). Isopropyl amine (0.315 mL;

0.219 g, 3.7 mmol) was added and the resulting mixture was stirred at 110° C. (oil bath) for 24 hrs. The reaction mixture was quenched with water and extracted 3 times with EtOAc. The organic layers were combined, washed with brine, dried over MgSO$_4$, and concentrated to give a yellow oil. Preparative HPLC afforded 6.1 mg (5% yield) of 1-[2-(3-Isopropylamino-phenyl)-5H-pyrrolo[2,3-b]pyrazin-7-yl]-2,2-dimethyl-propan-1-one as a yellow solid Example 90

EDCI/HOBT Coupling

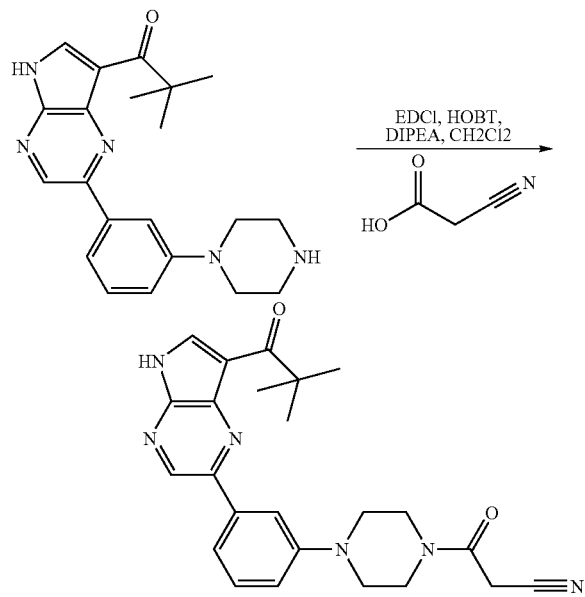

3-(4-{3-[7-(2,2-Dimethyl-propionyl)-5H-pyrrolo[2,3-b]pyrazin-2-yl]-phenyl}-piperazin-1-yl)-3-oxo-propionitrile Dichloromethane (1 mL) was added to a mixture of EDCI (0.181 g, 0.945 mmol), HOBT monohydrate (0.128 g, 0.945 mmol), cyanoacetic acid (0.060 g, 0.71 mmol), and 2,2-Dimethyl-1-[2-(3-piperazin-1-yl-phenyl)-5H-pyrrolo[2,3-b]pyrazin-7-yl]-propan-1-one (0.1718 g, 0.473 mmol) under argon. Diisopropylethylamine (DIPEA, 0.41 mL; 0.304 g, 2.36 mmol) was subsequently added and the reaction was stirred overnight at ambient temperature. The reaction was quenched with saturated aqueous NaHCO$_3$ and extracted 3 times with dichloromethane. The combined organic layers were dried over MgSO$_4$, filtered and concentrated in vacuo. Preparative thin layer chromatography afforded 0.0402 g (20% yield) of 3-(4-{3-[7-(2,2-Dimethyl-propionyl)-5H-pyrrolo[2,3-b]pyrazin-2-yl]-phenyl}-piperazin-1-yl)-3-oxo-propionitrile as an off-white solid.
Characterization Data for Final Compounds
1-[2-(1,3-Dihydro-isoindol-2-yl)-5H-pyrrolo[2,3-b]pyrazin-7-yl]-2,2-dimethyl-propan-1-one 2,2-Dimethyl-1-{2-[3-(3-trifluoromethyl-5,6-dihydro-8H-[1,2,4]triazolo[4,3-a]pyrazin-7-ylmethyl)-phenyl]-5H-pyrrolo[2,3-b]pyrazin-7-yl}-propan-1-one
Product isolated as a white solid, 0.0204 g, 57% yield.
1H-NMR (CDCl3, 400 MHz): 10.95 (s, 1H), 8.67 (s, 1H), 8.39 (d, 1H, J=3.1 Hz), 8.06 (s, 1H), 7.98 (d, 1H, J=7.8 Hz), 7.45 (t, 1H, J=7.6 Hz), 7.36 (d, 1H, J=7.6 Hz), 4.11 (t, 2H, J=5.4 Hz), 3.93 (s, 2H), 3.83 (s, 2H), 2.97 (t, 2H, J=5.6 Hz), 1.46 ppm (s, 9H). MS (E/I): 484 (M+H)

1-{2-[3-(5,6-Dihydro-8H-[1,2,4]triazolo[4,3-a]pyrazin-7-ylmethyl)-phenyl]-5H-pyrrolo[2,3-b]pyrazin-7-yl}-2,2-dimethyl-propan-1-one Product isolated as a white solid, 0.0245 g, 43% yield.
1H-NMR (CDCl3, 400 MHz): 8.69 (s, 1H), 8.45 (s, 1H), 8.06 (s, 1H), 8.16 (s, 1H), 8.11 (s, 1H), 8.04 (d, 1H, J=7.7 Hz), 7.50 (t, 1H, J=7.6 Hz), 7.43 (d, 1H, J=7.5 Hz), 4.12 (t, 2H, J=5.5 Hz), 3.96 (s, 2H), 3.88 (s, 2H), 2.99 (t, 2H, J=5.4 Hz), 1.56 ppm (s, 9H). MS (E/I): 416 (M+H)

2,2-Dimethyl-1-{2-[4-(3-trifluoromethyl-5,6-dihydro-8H-[1,2,4]triazolo[4,3-a]pyrazin-7-ylmethyl)-phenyl]-5H-pyrrolo[2,3-b]pyrazin-7-yl}-4-propan-1-one Product isolated as an off-white solid, 0.0141 g, 31% yield.
1H-NMR (CDCl3, 400 MHz): 9.86 (s, 1H), 8.77 (s, 1H), 8.43 (d, 1H, J=3.2 Hz), 8.13 (d, 1H, J=8.3 Hz), 4.18 (t, 2H, J=5.5 Hz), 3.98 (s, 2H), 3.87 (s, 2H), 3.02 (t, 2H, J=5.3 Hz), 1.57 ppm (s, 9H). MS (E/I): 484 (M+H)

4-{3-[7-(2,2-Dimethyl-propionyl)-5H-pyrrolo[2,3-b]pyrazin-2-yl]-phenyl}-1,5-dimethyl-piperazin-2-one Product isolated as a White solid, 0.0096 g, 33% yield.
1H-NMR (CDCl3, 400 MHz): 8.77 (s, 1H), 8.46 (s, 1H), 7.73 (d, 1H, J=8.7 Hz), 7.56 (t, 1H, J=8.0 Hz), 7.42 (t, 1H, J=8.0 Hz), 6.92 (t, 1H, J=8.8 Hz), 4.15 (m, 1H), 3.87 (m, 2H), 3.06 (s, 2H), 1.57 (s, 9H), 1.43 (d, 2H, 6.3 Hz), 1.26 ppm (d, 3H, 6.2 Hz). MS (E/I): 406 (M+H)

[2-(3-Cyclopentylamino-phenyl)-5H-pyrrolo[2,3-b]pyrazin-7-yl]-(1-methyl-cyclohexyl)-methanone Product isolated as a yellow solid, 0.0275 g, 80% yield.
1H-NMR (CDCl3, 400 MHz): 10.21 (s, 1H), 8.77 (s, 1H), 8.41 (s, 1H), 7.47 (m, 1H), 7.30 (t, 1H, J=7.9 Hz), 6.69 (m, 1H), 3.92 (quintet, 1H, J=6.3 Hz), 2.56 (m, 2H), 2.10 (m, 2H), 1.8-1.2 (m, 14H), 1.57 (s, 3H). 13C-NMR (CDCl3, 76 MHz): 203.3, 149.7, 149.4, 141.7, 139.5, 138.0, 136.3, 135.7, 130.8, 118.4, 116.5, 115.6, 112.1, 55.9, 48.8, 35.9, 34.7, 27.3, 25.1, 24.4, 24.3 ppm. MS (E/I): 403 (M+H). MP=190-192° C.

{2-[3-(Cyclopentyl-methyl-amino)-phenyl]-5H-pyrrolo[2,3-b]pyrazin-7-yl}-(1-methyl-cyclohexyl)-methanone Product isolated as a yellow solid, 0.0097 g, 84% yield.
1H-NMR (CDCl3, 400 MHz): 9.74 (s, 1H), 8.80 (s, 1H), 8.41 (s, 1H), 7.77 (s, 1H), 7.38 (m, 2H), 6.93 (m, 1H), 4.34 (quintet, 1H, J=8 Hz), 2.91 (s, 3H), 2.56 (m, 2H), 1.96 (m, 2H), 1.8-1.2 (m, 13H), 1.57 (s, 3H). MS (E/I): 417 (M+H).

1-[2-(3-Cyclopentylamino-phenyl)-5H-pyrrolo[2,3-b]pyrazin-7-yl]-2,2-dimethyl-propan-1-one Product isolated as a yellow solid, 0.070 g, 53% yield.
1H-NMR (CDCl3, 400 MHz): 8.79 (s, 1H), 8.47 (s, 1H), 7.50 (m, 1H), 7.38 (m, 1H), 7.27 (t, 1H, J=7.7 Hz), 6.69 (m, 1H), 3.88 (m, 1H), 2.11 (m, 2H), 1.9-1.4 (m, 6H), 1.59 (s, 9H). MS (E/I): 363 (M+H). MP=207-209° C.

1-{2-[3-(2-Hydroxy-cyclopentylamino)-phenyl]-5H-pyrrolo[2,3-b]pyrazin-7-yl}-2,2-dimethyl-propan-1-one Product isolated as a yellow solid and mixture of diastereomers, 0.0232 g, 37% yield. 1H-NMR (CDCl3, 400 MHz): 8.70 (s, 1H), 8.40 (s, 1H), 7.45 (s, 1H), 7.37 (m, 1H), 7.26 (m, 1H), 6.71 (m, 1H), 4.17 (m, 1H), 3.75 (m, 1H), 2.34 (m, 1H), 2.06 (m, 1H), 1.95-1.4 (m, 6H), 1.54 ppm (s, 9H). IR (KBr): 3412, 2961, 2871, 1636, 1606, 1384, 1089 cm-1. MS (E/I): 379 (M+H). MP=178-180° C.

3-Methyl-4-{3-[7-(1-methyl-cyclohexanecarbonyl)-5H-pyrrolo[2,3-b]pyrazin-2-yl]-phenyl}-piperazin-2-one Product isolated as a light yellow solid, 0.018 g, 85% yield. 1H-NMR (MeOD, 400 MHz): 8.62 (s, 2H), 7.86 (s, 1H), 7.55 (d, 1H, J=7.9 Hz), 7.37 (t, 1H, J=7.89 Hz), 6.99 (dd, 1H, J=8.13, 2.46 Hz), 4.45 (q, 1H, J=6.9 Hz), 3.8-3.35 (m, 4H), 2.61 (m, 2H), 1.8-1.2 (m, 8H), 1.57 (s, 3H), 1.43 ppm (d, 3H, J=7.0 Hz). MS (E/I): 432 (M+H).

1-(2-{3-[4-(2-Hydroxy-acetyl)-piperazin-1-yl]-phenyl}-5H-pyrrolo[2,3-b]pyrazin-7-yl)-2,2-dimethyl-propan-1-one Product isolated as a White solid, 0.0056 g, 20% yield. 1H-NMR (CD3OD, 400 MHz): 8.82 (s, 1H), 8.47 (d, 1H, J=4.5 Hz), 7.89 (s, 1H), 7.63 (m, 1H), 7.40 (m, 1H), 7.10 (m, 1H), 4.30 (s, 2H), 3.81 (m, 2H), 3.65 (m, 2H), 3.26 (m, 2H), 3.02 (m, 2H), 1.56 (s, 9H). MS (E/I): 422 (M+H)

2,2-Dimethyl-1-{2-[3-(1-methyl-pyrrolidin-3-ylamino)-phenyl]-5H-pyrrolo[2,3-b]pyrazin-7-yl}-propan-1-one Product isolated as a white solid, 0.0562 g, 61% yield. 1H-NMR (CDCl3, 400 MHz): 8.85 (s, 1H), 8.37 (s, 1H), 7.49 (d, 1H, J=7.7 Hz), 7.40 (s, 1H), 7.32 (t, 1H, J=7.9 Hz), 6.62 (d, 1H, J=7.4 Hz), 4.33 (s, 1H), 3.34 (m, 2H), 2.77 (m, 1H), 2.63 (m, 3H), 2.6-2.5 (m, 2H), 2.02 (m, 1H), 1.55 ppm (s, 9H). MS (E/I): 378 (M+H). MP=223-225° C.

2,2-Dimethyl-1-{2-[3-(tetrahydro-furan-3-ylamino)-phenyl]-5H-pyrrolo[2,3-b]pyrazin-7-yl}-propan-1-one Product isolated as a yellow solid, 0.054 g, 83% yield. 1H-NMR (CDCl3, 400 MHz): 8.84 (s, 1H), 8.50 (s, 1H), 7.49 (m, 1H), 7.36 (m, 1H), 6.73 (m, 1H), 4.50 (m, 1H), 4.29 (m, 1H), 4.12 (m, 1H), 3.98 (m, 1H), 2.41 (m, 1H), 2.07 (m, 1H), 1.62 ppm (s, 1H). MS (E/I): 365 (M+H). MP=212-214° C.

1-(2-{-4-[4-(2-Hydroxy-acetyl)-piperazin-1-yl]-phenyl}-5H-pyrrolo[2,3-b]pyrazin-7-yl)-2,2-dimethyl-propan-1-one Product isolated as a yellow solid, 0.017 g, 20% yield. 1H-NMR (CDCl3, 400 MHz): 9.72 (br s, 1H), 8.74 (s, 1H), 8.40 (s, 1H), 8.09 (d, 2H, J=8.8 Hz), 7.05 (d, 2H, J=8.9 Hz), 4.25 (d, 2H, J=4.4 Hz), 3.89 (t, 2H, J=4.9 Hz), 3.49 (t, 2H, J=4.6 Hz), 3.32 (m, 4H), 2.82 (br s, 1H), 1.57 ppm (s, 9H). IR (KBr): 3432, 1653, 1559, 1521, 1457, 1385, 1229, 1086, 528, 518, 507, 495, 485, 474, 462, 409 cm-1. MS (E/I): 422 (M+H).

1-(2-{4-[4-(2-Hydroxy-ethyl)-piperazin-1-yl]-phenyl}-5H-pyrrolo[2,3-b]pyrazin-7-yl)-2,2-dimethyl-propan-1-one Product isolated as a yellow solid, 0.0137 g, 30% yield. 1H-NMR (CDCl3, 400 MHz): 8.73 (s, 1H), 8.39 (s, 1H), 8.06 (d, 2H, J=8.9 Hz), 7.05 (d, 2H, J=9.0 Hz), 3.70 (t, 2H, J=5.4 Hz), 3.34 (t, 2H, J=5.1 Hz), 2.72 (t, 2H, J=4.9 Hz), 2.65 (t, 2H, J=5.2 Hz), 1.58 ppm (s, 9H). IR (KBr): 3431, 2926, 1653, 1636, 1540, 1521, 1457, 1385, 1228, 1087, 467, 426, 415 cm-1. MS (E/I): 408 (M+H). MP=211-213° C.

1-[2-(3-Isopropylamino-phenyl)-5H-pyrrolo[2,3-b]pyrazin-7-yl]-2,2-dimethyl-propan-1-one Product isolated as a yellow solid, 0.0061 g, 5% yield. 1H-NMR (CDCl3, 400 MHz): 8.79 (s, 1H), 8.42 (s, 1H), 7.49 (m, 1H), 7.38 (m, 1H), 7.30 (m, 1H), 6.69 (m, 1H), 3.76 (m, 1H), 1.59 (s, 9H), 1.29 ppm (d, 6H, J=6.1 Hz). MS (E/I): 337 (M+H).

1-{2-[3-(4-Methanesulfonyl-piperazin-1-yl)-phenyl]-5H-pyrrolo[2,3-b]pyrazin-7-yl}-2,2-dimethyl-propan-1-one Product isolated as a yellow solid, 0.0186 g, 26% yield. 1H-NMR (CDCl3, 400 MHz): 8.80 (s, 1H), 8.42 (s, 1H), 7.86 (m, 1H), 7.64 (d, 1H, J=7.8 Hz), 7.45 (t, 1H, J=8.0 Hz), 7.04 (m, 1H), 3.44 (m, 8H), 2.86 (s, 3H), 1.58 ppm (s, 9H). MS (E/I): 442 (M+H). MP=243-245° C.

1-{2-[4-(4-M ethanesulfonyl-piperazin-1-yl)-phenyl]-5H-pyrrolo[2,3-b]pyrazin-7-yl}-2,2-dimethyl-propan-1-one Product isolated as a yellow solid, 0.0186 g, 24% yield. 1H-NMR (CDCl3, 400 MHz): 8.73 (s, 1H), 8.36 (s, 1H), 8.08 (d, 2H, J=8.6 Hz), 7.07 (d, 2H, J=8.7 Hz), 3.49 (m, 8H), 2.85 (s, 3H), 1.56 ppm (s, 9H). IR (KBr): 3427, 2868, 1644, 1609, 1521, 1455, 1417, 1397, 1385, 1324, 1233, 1159, 1120, 957, 779, 517 cm-1. MS (E/I): 442 (M+H). MP=288-290° C.

1-(2-{3-[4-(2-Hydroxy-ethyl)-piperazin-1-yl]-phenyl}-5H-pyrrolo[2,3-b]pyrazin-7-yl)-2,2-dimethyl-propan-1-one Product isolated as a yellow solid, 0.0234 g, 48% yield. 1H-NMR (CDCl3, 400 MHz): 8.78 (s, 1H), 8.46 (s, 1H), 7.82 (m, 1H), 7.54 (m, 1H), 7.39 (m, 1H), 7.02 (m, 1H), 3.73 (t, 2H, J=5.3 Hz), 3.34 (m, 4H), 2.75 (m, 4H), 2.66 (t, 2H, J=4.6 Hz), 1.58 ppm (s, 9H). MS (E/I): 408 (M+H). MP=103-105° C.

1-{2-[3-((cis)-2-Hydroxy-cyclopentylamino)-phenyl]-5H-pyrrolo[2,3-b]pyrazin-7-yl}-2,2-dimethyl-propan-1-one Product isolated as a yellow solid, 0.0158 g, 32% yield. 1H-NMR (CDCl3, 400 MHz): 8.76 (s, 1H), 8.42 (s, 1H), 7.55 (s, 1H), 7.43 (d, 1H, J=7.3 Hz), 7.31 (t, 1H, J=7.8 Hz), 6.77 (m, 1H), 4.41 (m, 1H), 4.27 (m, 1H), 3.74 (br s, 1H), 2.2-1.6 (m, 6H), 1.57 ppm (s, 9H). MS (E/I): 379 (M+H). MP=115-117° C.

1-{2-[3-(1-Methanesulfonyl-piperidin-4-ylamino)-phenyl]-5H-pyrrolo[2,3-b]pyrazin-7-yl}-2,2-dimethyl-propan-1-one Product isolated as a yellow solid, 0.0087 g, 26% yield. 1H-NMR (CDCl3, 400 MHz): 8.77 (s, 1H), 8.39 (s, 1H), 7.5-7.4 (m, 2H), 7.33 (t, 1H, J=7.7 Hz), 6.70 (d, 1H, J=8.0 Hz), 3.81 (m, 2H), 3.73 (m, 1H), 3.43 (s, 1H), 2.97 (m, 2H), 2.84 (s, 3H), 2.26 (m, 2H), 1.66 (m, 2H), 1.57 ppm (s, 9H). MS (E/I): 456 (M+H). MP=264-266° C.

3-(4-{3-[7-(2,2-Dimethyl-propionyl)-5H-pyrrolo[2,3-b]pyrazin-2-yl]-phenyl}-piperazin-1-yl)-3-oxo-propionitrile Product isolated as an off-white solid, 0.0402 g, 20% yield. 1H-NMR (d-DMSO, 300 MHz): 8.99 (s, 1H), 8.52 (s, 1H), 7.82 (m, 1H), 7.66 (d, 1H, J=8.0 Hz), 7.41 (t, 1H, J=8.0 Hz), 7.08 (m, 1H), 4.12 (s, 2H), 3.7-3.2 (m, 8H), 1.50 ppm (s, 9H). MS (E/I): 431 (M+H). MP=240-242° C.

1-{2-[3-((trans)-2-Hydroxy-cyclopentylamino)-phenyl]-5H-pyrrolo[2,3-b]pyrazin-7-yl}-2,2-dimethyl-propan-1-one Product isolated as a yellow solid, 0.0236 g, 47% yield. 1H-NMR (CDCl3, 400 MHz): 8.70 (s, 1H), 8.40 (s, 1H), 7.44 (m, 1H), 7.37 (m, 1H), 7.25 (m, 1H), 6.70 (m, 1H), 4.19 (m, 1H), 3.88 (br s, 1H), 3.75 (s, 1H), 2.37 (m, 1H), 2.07 (m, 1H), 1.95-1.65 (m, 4H), 1.54 ppm (s, 9H). MS (E/I): 379 (M+H). MP=103-105° C.

(4-{3-[7-(2,2-Dimethyl-propionyl)-5H-pyrrolo[2,3-b]pyrazin-2-yl]-phenyl}-piperazin-1-yl)-acetic acid Product isolated as an off-white solid, 0.082 g, 75% yield. 1H-NMR (CD3OD, 400 MHz): 8.83 (s, 1H), 8.35 (s, 1H), 7.71 (s, 1H), 7.51 (m, 1H), 7.27 (m, 1H), 6.99 (m, 1H), 3.65 (s, 2H), 3.55-3.4 (m, 8H), 1.43 ppm (s, 9H). MS (E/I): 422 (M+H). MP=188-190° C.

Example 91

Preparation of Benzyl Triazolopyrazines

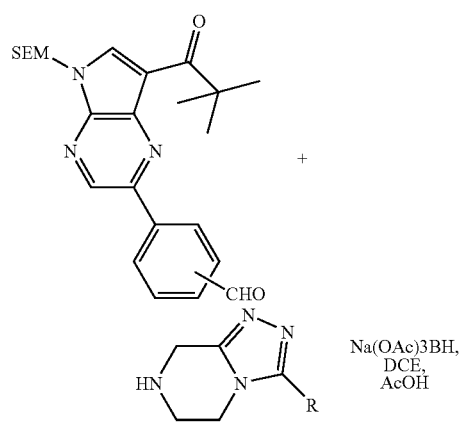

1-[2-[3-(5,6-Dihydro-8H-[1,2,4]triazolo[4,3-a]pyrazin-7-ylmethyl)-phenyl]-5-(2-trimethylsilanyl-ethoxymethyl)-5H-pyrrolo[2,3-b]pyrazin-7-yl]-2,2-dimethyl-propan-1-one

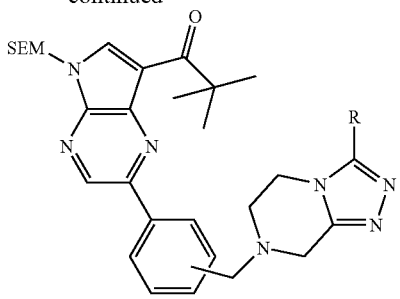

To a solution of 3-[7-(2,2-Dimethyl-propionyl)-5-(2-trimethylsilanyl-ethoxymethyl)-5H-pyrrolo[2,3-b]pyrazin-2-yl]-benzaldehyde (0.150 g, 0.3428 mmol) and 5,6,7,8-Tetrahydro-[1,2,4]triazolo[4,3-a]pyrazine (0.064 g, 0.514 mmol) in 1.2 mL of dichloroethane was added 1.2 mL acetic acid and 0.109 g of sodium triacetoxyborohydride (0.514 mmol). The reaction was stirred overnight at room temperature before quenching with saturated aqueous Na2CO3. The reaction mixture was extracted 3 times with ethyl acetate, combined organics dried over MgSO4, filtered and concentrated in vacuo. Silica gel chromatography (0→100% EtOAc/hexanes over 30 minutes, followed by a flush with 100% methanol) afforded 0.0744 g (40% yield) of 1-[2-[3-(5,6-Dihydro-8H-[1,2,4]triazolo[4,3-a]pyrazin-7-ylmethyl)-phenyl]-5-(2-trimethylsilanyl-ethoxymethyl)-5H-pyrrolo[2,3-b]pyrazin-7-yl]-2,2-dimethyl-propan-1-one as a white solid. MS (E/I): 546 (M+H)

2,2-Dimethyl-1-[2-[3-(3-trifluoromethyl-5,6-dihydro-8H-[1,2,4]triazolo[4,3-a]pyrazin-7-ylmethyl)-phenyl]-5-(2-trimethylsilanyl-ethoxymethyl)-5H-pyrrolo[2,3-b]pyrazin-7-yl]-propan-1-one. MS (E/I): 614 (M+H)

2,2-Dimethyl-1-[2-[4-(3-trifluoromethyl-5,6-dihydro-8H-[1,2,4]triazolo[4,3-a]pyrazin-7-ylmethyl)-phenyl]-5-(2-trimethylsilanyl-ethoxymethyl)-5H-pyrrolo[2,3-b]pyrazin-7-yl]-propan-1-one. MS (E/I): 614 (M+H)

Example 92

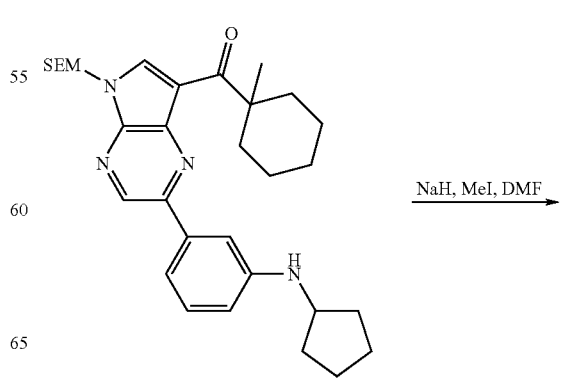

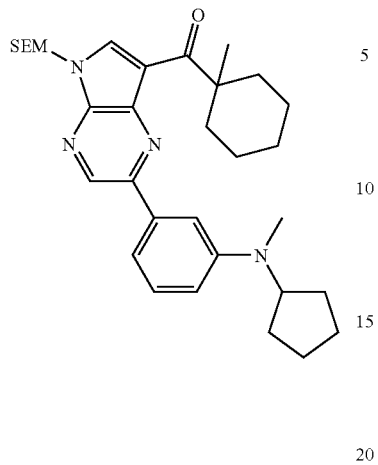

Preparation of [2-[3-(Cyclopentyl-methyl-amino)-phenyl]-5-(2-trimethylsilanyl-ethoxymethyl)-5H-pyrrolo[2,3-b]pyrazin-7-yl]-(1-methyl-cyclohexyl)-methanone To a solution of [2-(3-Cyclopentylamino-phenyl)-5-(2-trimethylsilanyl-ethoxymethyl)-5H-pyrrolo[2,3-b]pyrazin-7-yl]-(1-methyl-cyclohexyl)-methanone in dimethyl formamide was added sodium hydride (60% dispersion in mineral oil, 9 mg, 0.218 mmol) under argon. The reaction mixture was stirred at room temperature for 15 minutes before the addition of methyl iodide via syringe. The reaction was stirred for 14 h before quenching with water and extracting 3 times with dichloromethane. The combined organics were washed with water, dried over MgSO4, filtered and concentrated in vacuo. Preparative thin layer chromatography (25% EtOAc/hexanes) afforded 0.0152 g (15% yield) of [2-[3-(Cyclopentyl-methyl-amino)-phenyl]-5-(2-trimethylsilanyl-ethoxymethyl)-5H-pyrrolo[2,3-b]pyrazin-7-yl]-(1-methyl-cyclohexyl)-methanone as a yellow oil. MS (E/I): 547 (M+H)

Example 93

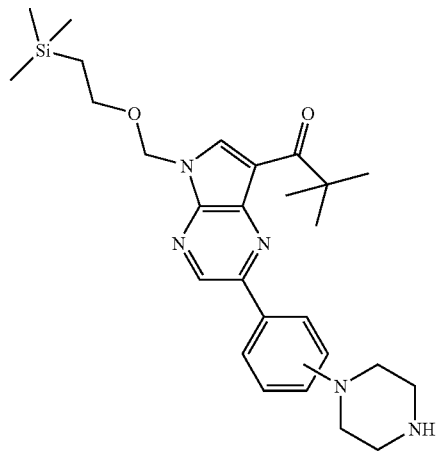

2,2-Dimethyl-1-[2-(3-piperazin-1-yl-phenyl)-5-(2-trimethylsilanyl-ethoxymethyl)-5H-pyrrolo[2,3-b]pyrazin-7-yl]-propan-1-one. Procedure for selective BOC deprotection A solution of 4-{3-[7-(2,2-Dimethyl-propionyl)-5-(2-trimethylsilanyl-ethoxymethyl)-5H-pyrrolo[2,3-b]pyrazin-2-yl]-phenyl}-piperazine-1-carboxylic acid tert-butyl ester (0.1226 g, 0.206 mmol) in 4 mL of hexafluoroisopropanol was stirred at 150° C. for 1 h under microwave irradiation. The reaction mixture was concentrated in vacuo. Silica gel chromatography (0→40% 60:10:1 CH$_2$Cl$_2$:MeOH:NH$_4$OH/dichloromethane over 20 minutes) afforded 0.0704 g (69% yield) of 2,2-Dimethyl-1-[2-(3-piperazin-1-yl-phenyl)-5-(2-trimethylsilanyl-ethoxymethyl)-5H-pyrrolo[2,3-b]pyrazin-7-yl]-propan-1-one as an off-white solid. MS (E/I): 494 (M+H)

2,2-Dimethyl-1-[2-(4-piperazin-1-yl-phenyl)-5-(2-trimethylsilanyl-ethoxymethyl)-5H-pyrrolo[2,3-b]pyrazin-7-yl]-propan-1-one. MS (E/I): 494 (M+H)

Example 94

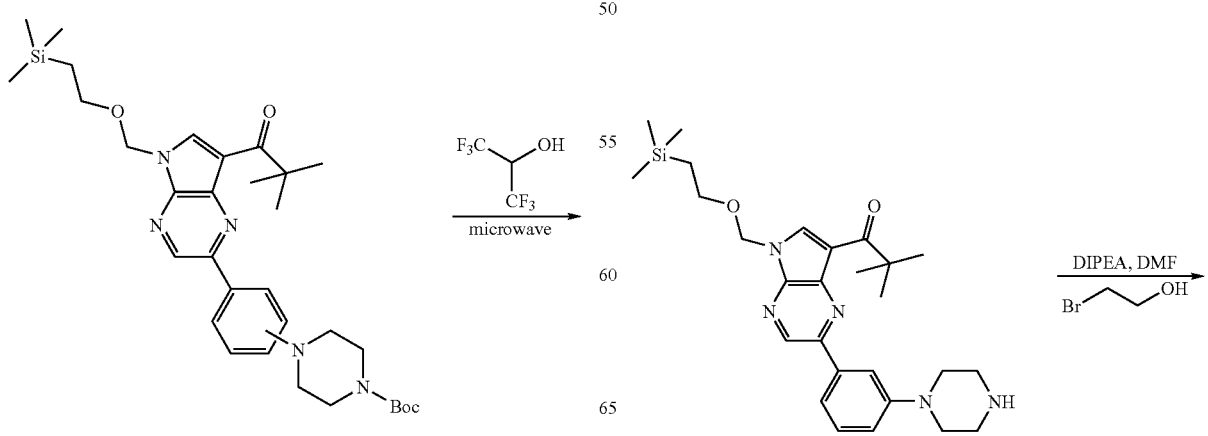

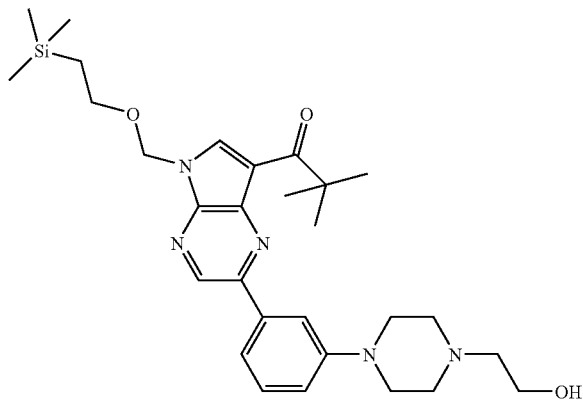

Preparation of (2-hydroxyethyl)-piperazines. 1-[2-{3-[4-(2-Hydroxy-ethyl)-piperazin-1-yl]-phenyl}-5-(2-trimethylsilanyl-ethoxymethyl)-5H-pyrrolo[2,3-b]pyrazin-7-yl]-2,2-dimethyl-propan-1-one To a solution of 2,2-Dimethyl-1-[2-(3-piperazin-1-yl-phenyl)-5-(2-trimethylsilanyl-ethoxymethyl)-5H-pyrrolo[2,3-b]pyrazin-7-yl]-propan-1-one (0.10 g, 0.203 mmol) in 2 mL dimethyl formamide under argon was added 0.088 mL of diisopropylethylamine (0.066 g, 0.508 mmol) and 0.036 mL of 2-bromoethanol (0.0635 g, 0.508 mmol). The reaction was stirred overnight at room temperature before quenching with water and extracting with dichloromethane. The combined organics were washed with water, dried over MgSO4, filtered and concentrated in vacuo. Silica gel chromatography (0→40% 60:10:1 CH$_2$Cl$_2$:MeOH:NH$_4$OH/dichloromethane over 30 minutes) afforded 0.0648 g (59% yield) of 1-[2-{3-[4-(2-Hydroxy-ethyl)-piperazin-1-yl]-phenyl}-5-(2-trimethylsilanyl-ethoxymethyl)-5H-pyrrolo[2,3-b]pyrazin-7-yl]-2,2-dimethyl-propan-1-one as a yellow oil. MS (E/I): 538 (M+H)

1-[2-{4-[4-(2-Hydroxy-ethyl)-piperazin-1-yl]-phenyl}-5-(2-trimethylsilanyl-ethoxymethyl)-5H-pyrrolo[2,3-b]pyrazin-7-yl]-2,2-dimethyl-propan-1-one. MS (E/I): 538 (M+H)

Example 95

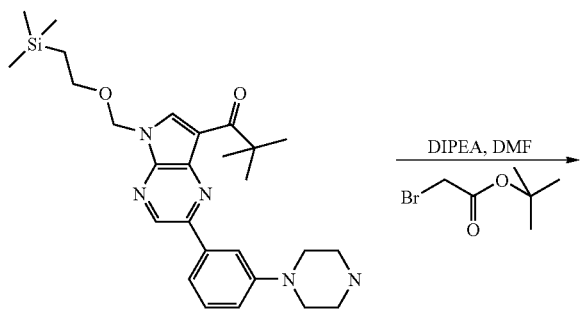

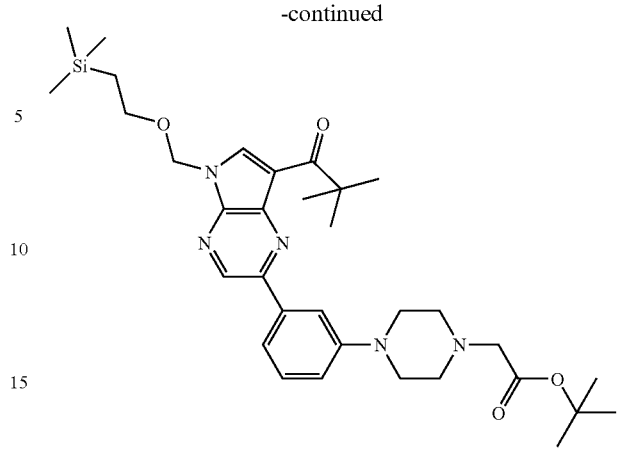

(4-{3-[7-(2,2-Dimethyl-propionyl)-5-(2-trimethylsilanyl-ethoxymethyl)-5H-pyrrolo[2,3-b]pyrazin-2-yl]-phenyl}-piperazin-1-yl)-acetic acid tert-butyl ester To a solution of 2,2-Dimethyl-1-[2-(3-piperazin-1-yl-phenyl)-5-(2-trimethylsilanyl-ethoxymethyl)-5H-pyrrolo[2,3-b]pyrazin-7-yl]-propan-1-one (0.233 g, 0.473 mmol) in 2 mL of dimethyl formamide was added 0.074 mL of diisopropylethylamine (0.055 g, 0.425 mmol) and 0.629 mL of tert-butyl bromoacetate (0.083 g, 0.425 mmol). The reaction was stirred at room temperature overnight before quenching with water and extracting with dichloromethane. The combined organics were washed with water, dried over MgSO4, filtered and concentrated in vacuo. Silica gel chromatography (10→60% EtOAc/hexanes over 30 minutes) afforded 0.1582 g (61% yield) of (4-{3-[7-(2,2-Dimethyl-propionyl)-5-(2-trimethylsilanyl-ethoxymethyl)-5H-pyrrolo[2,3-b]pyrazin-2-yl]-phenyl}-piperazin-1-yl)-acetic acid tert-butyl ester as a yellow oil. MS (E/I): 608 (M+H).

Preparation of 1-[2-{3-[4-(2-Hydroxy-acetyl)-piperazin-1-yl]-phenyl}-5-(2-trimethylsilanyl-ethoxymethyl)-5H-pyrrolo[2,3-b]pyrazin-7-yl]-2,2-dimethyl-propan-1-one and 1-[2-{4-[4-(2-Hydroxy-acetyl)-piperazin-1-yl]-phenyl}-5-(2-trimethylsilanyl-ethoxymethyl)-5H-pyrrolo[2,3-b]pyrazin-7-yl]-2,2-dimethyl-propan-1-one. See Procedure E (EDCI/HOBT Coupling)

1-[2-{3-[4-(2-Hydroxy-acetyl)-piperazin-1-yl]-phenyl}-5-(2-trimethylsilanyl-ethoxymethyl)-5H-pyrrolo[2,3-b]pyrazin-7-yl]-2,2-dimethyl-propan-1-one. MS (E/I): 552 (M+H).

1-[2-{4-[4-(2-Hydroxy-acetyl)-piperazin-1-yl]-phenyl}-5-(2-trimethylsilanyl-ethoxymethyl)-5H-pyrrolo[2,3-b]pyrazin-7-yl]-2,2-dimethyl-propan-1-one. MS (E/I): 552 (M+H).

Example 96

1-[2-[4-(4-Methanesulfonyl-piperazin-1-yl)-phenyl]-5-(2-trimethylsilanyl-ethoxymethyl)-5H-pyrrolo[2,3-b]pyrazin-7-yl]-2,2-dimethyl-propan-1-one To a solution of 2,2-Dimethyl-1-[2-(4-piperazin-1-yl-phenyl)-5-(2-trimethylsilanyl-ethoxymethyl)-5H-pyrrolo[2,3-b]pyrazin-7-yl]-propan-1-one (0.10 g, 0.203 mmol) in dichloromethane was added 0.042 mL of diisopropylethylamine (0.031 g, 0.244 mmol) and the reaction mixture was subsequently cooled to 0° C. Methane sulfonyl chloride (0.019 mL;

0.028 g, 0.244 mmol) was added via syringe and the reaction was slowly warmed to room temperature and stirred overnight. The reaction was quenched with water and extracted 3 times with dichloromethane. Combined organics were dried over MgSO4, filtered and conc in vacuo. Silica gel chromatography (15→65% EtOAc/hexanes over 30 minutes) afforded 0.1014 g (87% yield) of 1-[2-[4-(4-Methanesulfonyl-piperazin-1-yl)-phenyl]-5-(2-trimethylsilanyl-ethoxymethyl)-5H-pyrrolo[2,3-b]pyrazin-7-yl]-2,2-dimethyl-propan-1-one as a yellow oil. MS (E/I): 572 (M+H).

1-[2-[3-(4-Methanesulfonyl-piperazin-1-yl)-phenyl]-5-(2-trimethylsilanyl-ethoxymethyl)-5H-pyrrolo[2,3-b]pyrazin-7-yl]-2,2-dimethyl-propan-1-one MS (E/I): 572 (M+H).

Prepared According to General Procedures Described in these Examples:

1-[2-(1H-Indol-4-yl)-5H-pyrrolo[2,3-b]pyrazin-7-yl]-2,2-dimethyl-propan-1-one. Substituting indole 4-boronic acid for 3-(1-pyrrolidino)phenyl boronic acid. MP=257-258 C, (M+H)$^+$=319. 1-[2-(1H-Indol-6-yl)-5H-pyrrolo[2,3-b]pyrazin-7-yl]-2,2-dimethyl-propan-1-one. Substituting indole 6-boronic acid for 3-(1-pyrrolidino)phenyl boronic acid. MP=>300 C, (M+H)$^+$=319. 1-[2-(1H-Indol-5-yl)-5H-pyrrolo[2,3-b]pyrazin-7-yl]-2,2-dimethyl-propan-1-one. Substituting 5-indoleboronic acid for 3-(1-pyrrolidino)phenyl boronic acid. MP=296-297 C, (M+H)=319.

Example 97

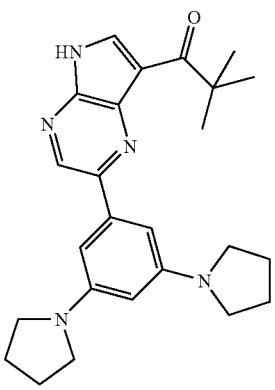

1-[2-(3,5-Di-pyrrolidin-1-yl-phenyl)-5H-pyrrolo[2,3-b]pyrazin-7-yl]-2,2-dimethyl-propan-1-one 1-(3-chloro-5-pyrrolidinophenyl)-pyrrolidine (0.15 g, 0.6 mmol, prepared from 5-chloro-m-phenylenediamine by the method found in Synthesis, 1999(1), 74) was dissolved in 2.5 ml 1,4-dioxane. The solution was purged with argon and bis(pinacolato)diboron (0.17 g, 0.66 mmol) was added, followed by tris(benzylidenediacetone) dipalladium (11 mg, 0.012 mmol), dicyclohexyl-(2',6'-dimethoxy-biphenyl-2-yl)-phosphane (25 mg, 0.06 mmol) and potassium acetate (118 mg, 1.2 mmol). The reaction was sealed and run on a microwave reactor at 15° C. for 2 hr. The reaction mixture was then poured into ethyl acetate and water and the layers were separated. The aqueous layer was extracted once more with ethyl acetate, and the combined ethyl acetate layers were washed with saturated sodium chloride solution and dried over sodium sulfate. After filtration and evaporation, 290 mg of solid product was obtained and used in place of 3-(1-pyrrolidino)phenyl boronic acid using general procedures described in these Examples, a 39% yield of product was obtained. MP=291-303 C, (M+H)$^+$=418.

Example 98

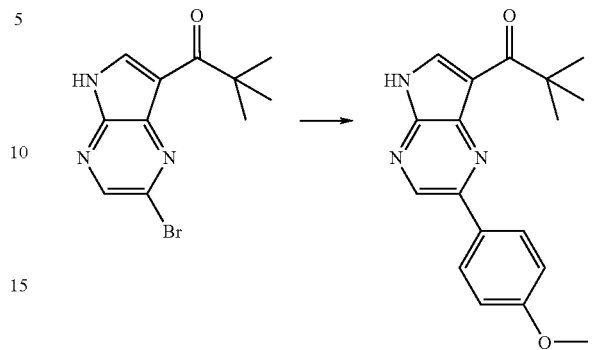

1-[2-(4-Methoxy-phenyl)-5H-pyrrolo[2,3-b]pyrazin-7-yl]-2,2-dimethyl-propan-1-one A mixture of 1-(2-bromo-5H-pyrrolo[2,3-b]pyrazin-7-yl)-2,2-dimethyl-propan-1-one (60 mg, 0.21 mmol), 4-methoxyphenyl boronic acid (33 mg, 0.22 mmol), potassium carbonate (69 mg, 0.5 mmol), Pd(dppf)Cl$_2$CH$_2$Cl$_2$ (13 mg, 0.016 mmol), 1.7 mL dioxane and 0.4 mL water was stirred at 150° C. in a microwave for 30 min. The resulting mixture was partitioned between ethyl acetate and water. The combined organic layers were dried over Na$_2$SO$_4$ and concentrated to give a dark brown solid. The crude product was purified by preparative thin layer chromatography using 90:9.5:0.5 CH$_2$Cl$_2$:MeOH:conc NH$_4$OH as eluant. The resultant brown solid was washed with ethyl ether to provide 31 mg (50%) of 1-[2-(4-methoxy-phenyl)-5H-pyrrolo[2,3-b]pyrazin-7-yl]-2,2-dimethyl-propan-1-one as a brown solid. MP 207-208° C., M+H 310.

Other Compounds Prepared Using this General Procedure (prepared starting from 1-(2-bromo-5H-pyrrolo[2,3-b]pyrazin-7-yl)-2,2-dimethyl-propan-1-one and the appropriate boronic acid, but washing the final product with a combination of CH$_2$Cl$_2$, Et$_2$O, and hexanes):

1-[2-(2-Methoxy-phenyl)-5H-pyrrolo[2,3-b]pyrazin-7-yl]-2,2-dimethyl-propan-1-one, MP 199.5-200.7° C., M+H 310;

1-[2-(3-Methoxy-phenyl)-5H-pyrrolo[2,3-b]pyrazin-7-yl]-2,2-dimethyl-propan-1-one, MP 197.4-198.8° C., M+H 310.

Example 99

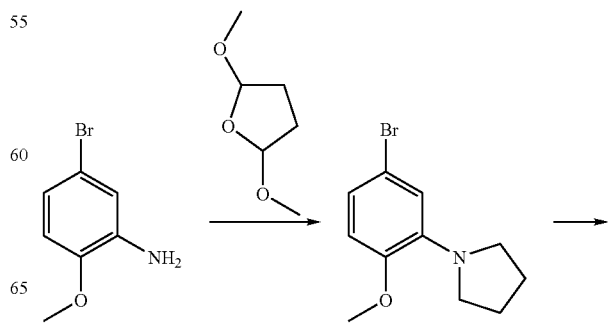

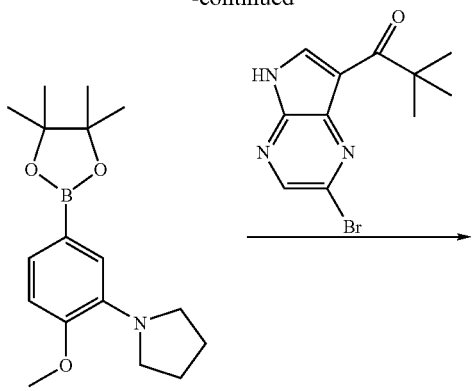

1-(5-Bromo-2-methoxy-phenyl)-pyrrolidine

To a 10° C. solution of 5-bromo-2-methoxy-phenylamine (3.6 g, 17.8 mmol.) in THF (20 mL) and MeOH (20 mL) was slowly added a solution of 2,5-dimethoxy-tetrahydro-furan (3 mL, 23 mmol) and 2.5 M $H_2SO_4$ (17.8 mL, 44.5 mmol) in THF (25 mL) via addition funnel over 15 min. The reaction was cooled to 0° C. and $NaBH_4$ (2.7 g, 71 mmol) was added portionwise over 30 min. The reaction mixture was allowed to slowly warm to room temperature, stirred at room temperature overnight, diluted with water (30 mL), basified with NaOH (~5 g) until pH~10 while cooling with an ice bath, and extracted with $Et_2O$. The combined organic extracts were extracted with 6 N HCl (40 mL). The aqueous phase was washed with $Et_2O$, basified with NaOH (~10 g) until pH~10, and extracted with $Et_2O$. The organic extract was washed with brine, dried with $Na_2SO_4$ and concentrated to give 2.8 g of a brown oil. The crude product was purified by flash chromatography using 40 g of silica gel and 0-80% EtOAc in hexanes as eluant to afford 2 g of 1-(5-bromo-2-methoxy-phenyl)-pyrrolidine. MP 47-48° C., M+H 256/258.

Example 100

1-[2-Methoxy-5-(4,4,5,5-tetramethyl-[1,3,2]dioxaborolan-2-yl)-phenyl]-pyrrolidine To a −78° C. solution of 1-(5-bromo-2-methoxy-phenyl)-pyrrolidine (270 mg, 1.1 mmol) in THF (17 mL) was added dropwise a solution of t-BuLi (1.3 mL, 1.7 M solution in pentane, 2.2 mmol). The resultant yellow solution was stirred for 30 min, treated with additional t-BuLi (1.3 mL, 1.7 M solution in pentane, 2.2 mmol), stirred for 45 min, and treated dropwise with 2-isopropoxy-4,4,5,5-tetramethyl-[1,3,2]dioxaborolane (0.8 mL, 4.4 mmol). The reaction was allowed to slowly warm to room temperature, stirred at room temperature overnight, and partitioned between saturated $NH_4Cl$ and EtOAc. The combined organic phases were dried with $Na_2SO_4$ and concentrated to give a tan oil. The crude product was purified by flash chromatography using 25 g of silica gel and 0-50% EtOAc in hexanes as eluant to afford 120 mg (35%) of 1-[2-methoxy-5-(4,4,5,5-tetramethyl-[1,3,2]dioxaborolan-2-yl)-phenyl]-pyrrolidine as a white solid. M+H 304.

Example 101

1-[2-(4-Methoxy-3-pyrrolidin-1-yl-phenyl)-5H-pyrrolo[2,3-b]pyrazin-7-yl]-2,2-dimethyl-propan-1-one A mixture of 1-(2-bromo-5H-pyrrolo[2,3-b]pyrazin-7-yl)-2,2-dimethyl-propan-1-one (50 mg, 0.18 mmol), 1-[2-methoxy-5-(4,4,5,5-tetramethyl-[1,3,2]dioxaborolan-2-yl)-phenyl]-pyrrolidine (60 mg, 0.2 mmol), potassium carbonate (63 mg, 0.46 mmol), Pd(dppf)$Cl_2$.$CH_2Cl_2$ (11 mg, 0.013 mmol), 1.4 mL dioxane and 0.3 mL water was stirred at 150° C. in a microwave for 30 min. The resulting mixture was treated with additional Pd(dppf)$Cl_2$.$CH_2Cl_2$ (2 mg, 0.002 mmol), stirred at 160° C. in a microwave for 10 min, and partitioned between ethyl acetate and water. The combined organic layers were dried over $Na_2SO_4$ and concentrated to give a dark brown residue. The crude product was purified by preparative thin layer chromatography using 140:9.5:0.5 $CH_2Cl_2$:MeOH:conc $NH_4OH$ as eluant. The resultant brown solid was washed with $CH_2Cl_2$ and ethyl ether to provide 20 mg (29%) of 1-[2-(4-methoxy-3-pyrrolidin-1-yl-phenyl)-5H-pyrrolo[2,3-b]pyrazin-7-yl]-2,2-dimethyl-propan-1-one as a yellow solid. MP 211-213° C., M+H 379.

Example 102

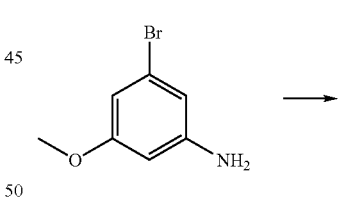

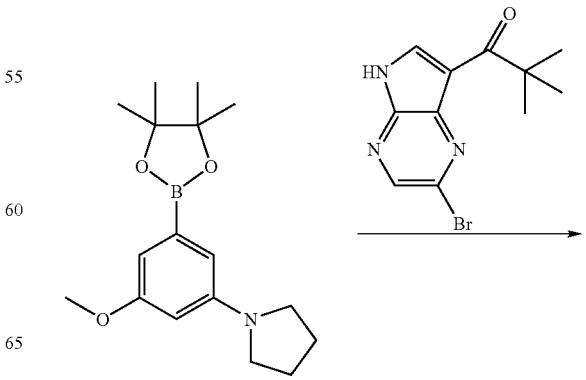

-continued

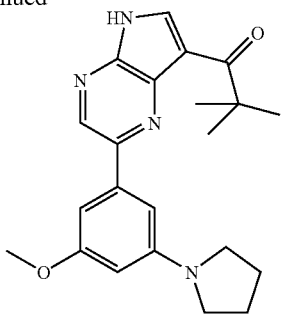

1-[3-Methoxy-5-(4,4,5,5-tetramethyl-[1,3,2]dioxaborolan-2-yl)-phenyl]-pyrrolidine To a −78° C. solution of pyrrolidine (4 mL, 48 mmol) in THF (15 mL) was slowly added a solution of n-BuLi (21 mL, 2.3 M solution in hexane, 48 mmol). The reaction was stirred at −78° C. for 15 min and allowed to slowly warm to 0° C. To a −78° C. solution of 1,3-dibromo-5-methoxy-benzene (6.5 g, 24 mmol.) and LiBr (1.74 g, 20 mmol) in THF (30 mL) was slowly added via syringe the solution of lithium pyrrolidinylamide. The reaction was allowed to slowly warm to room temperature, stirred at room temperature overnight, and quenched with saturated $NH_4Cl$. The aqueous layer was acidified with 1 N HCl until pH ~5 and extracted with EtOAc. The combined organic phases were dried with $Na_2SO_4$ and concentrated to give a brown oil. The oil was treated with hexanes and $Et_2O$ to precipitate an impurity. After decanting the solvent, the brown solid was washed with $Et_2O$ and the solvent decanted. The organic washes were combined and more resultant precipitate was separated by filtration. The mother liquor was concentrated to provide 4.5 g of a medium brown oil. The crude product was purified by flash chromatography using 90 g of silica gel and 0-80% EtOAc in hexanes as eluant to afford 3.25 g (53%) of a 3:1 mixture of 1-(3-bromo-5-methoxy-phenyl)-pyrrolidine:1-(3-methoxy-phenyl)-pyrrolidine as a colorless oil. M+H 256/258, 178.

To a −10° C. solution of the impure 1-(3-bromo-5-methoxy-phenyl)-pyrrolidine (0.5 g) from above in THF (30 mL) was added dropwise a solution of t-BuLi (3.5 mL, 1.7 M solution in pentane, 6 mmol). The resultant yellow solution was stirred for 30 min and treated dropwise with 2-isopropoxy-4,4,5,5-tetramethyl-[1,3,2]dioxaborolane (1.2 mL, 6.6 mmol). The reaction was allowed to slowly warm to room temperature, stirred at room temperature overnight, heated to reflux for 6 h, allowed to cool to room temperature, and partitioned between saturated $NH_4Cl$ and EtOAc. The combined organic phases were dried with $Na_2SO_4$ and concentrated to give 1.5 g of a brown oil. The crude product was purified by flash chromatography using 40 g of silica gel and 0-50% EtOAc in hexanes as eluant to afford 135 mg of 1-[3-methoxy-5-(4,4,5,5-tetramethyl-[1,3,2]dioxaborolan-2-yl)-phenyl]-pyrrolidine as an oil which became a white solid. M+H 304.

Example 103

1-[2-(3-Methoxy-5-pyrrolidin-1-yl-phenyl)-5H-pyrrolo[2,3-b]pyrazin-7-yl]-2,2-dimethyl-propan-1-one A mixture of 1-(2-bromo-5H-pyrrolo[2,3-b]pyrazin-7-yl)-2,2-dimethyl-propan-1-one (55 mg, 0.2 mmol), 1-[3-methoxy-5-(4,4,5,5-tetramethyl-[1,3,2]dioxaborolan-2-yl)-phenyl]-pyrrolidine (67 mg, 0.22 mmol), potassium carbonate (70 mg, 0.51 mmol), Pd(dppf)Cl$_2$.CH$_2$Cl$_2$ (12 mg, 0.015 mmol), 1.5 mL dioxane and 0.3 mL water was stirred at 160° C. in a microwave for 30 min. The resulting mixture was partitioned between ethyl acetate and water. The combined organic layers were dried over $Na_2SO_4$ and concentrated to give a dark brown residue. The crude product was purified by preparative thin layer chromatography using 140:9.5:0.5 $CH_2Cl_2$:MeOH:conc $NH_4OH$ as eluant. The resultant brown solid was washed with ethyl ether to provide 18 mg (24%) of 1-[2-(3-methoxy-3-pyrrolidin-1-yl-phenyl)-5H-pyrrolo[2,3-b]pyrazin-7-yl]-2,2-dimethyl-propan-1-one as a yellow solid. MP 245-256° C., M+H 379.

Example 104

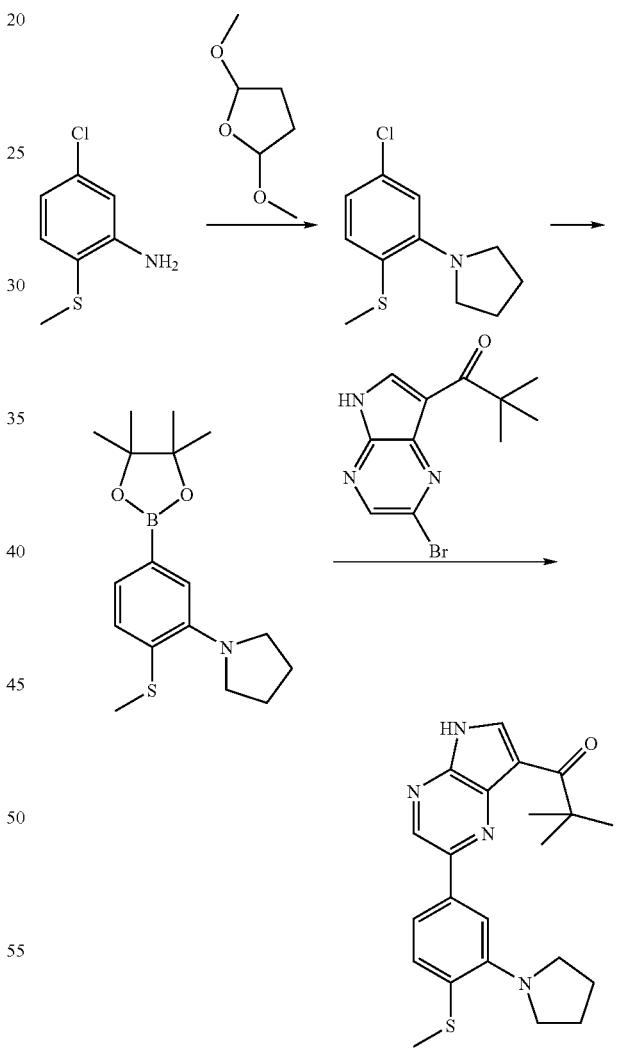

1-(5-Chloro-2-methylsulfanyl-phenyl)-pyrrolidine

To a tan solution of 5-chloro-2-methylsulfanyl-phenylamine (5.4 g, 31 mmol.) in THF (35 mL) and MeOH (35 mL)

was added dropwise a solution of 2,5-dimethoxy-tetrahydrofuran (5.3 mL, 40 mmol) and 2.5 M H₂SO₄ (31 mL, 78 mmol) in THF (45 mL) via addition funnel over 1 h. The reaction was cooled to 0° C. and NaBH₄ (4.7 g, 124 mmol) was added portionwise over 1 h with vigorous stirring. The reaction mixture was allowed to slowly warm to room temperature, stirred at room temperature overnight, diluted with water (60 mL), stirred at room temperature overnight, slowly basified with NaOH (~7 g) until pH~10 while cooling with an ice bath, and extracted with Et₂O. The combined organic extracts were extracted with 6 N HCl (100 mL). The aqueous phase was basified with NaOH (~30 g, 0.75 mmol) until pH~10, and extracted with Et₂O. The organic extract was dried with Na₂SO₄ and concentrated to give 2 g of the crude product. The crude product was purified by flash chromatography using 40 g of silica gel and 5-50% EtOAc in hexanes as eluant to afford 0.55 g of 1-(5-chloro-2-methylsulfanyl-phenyl)-pyrrolidine. M+H 228.

Example 105

1-[2-Methylsulfanyl-5-(4,4,5,5-tetramethyl-[1,3,2]dioxaborolan-2-yl)-phenyl]-pyrrolidine A mixture of 1-(5-chloro-2-methylsulfanyl-phenyl)-pyrrolidine (192 mg, 0.84 mmol), Pd₂(dba)₃ (17 mg, 0.02 mmol), bis(pinacolato)diboron (208 mg, 0.82 mmol), KOAc (166 mg, 1.7 mmol), and dicyclohexyl-(2',6'-dimethoxy-biphenyl-2-yl)-phosphane (33 mg, 0.08 mmol) in dioxane (3.3 mL) was stirred at 150° C. in a microwave for 2 h. The resulting mixture was partitioned between ethyl acetate and water. The combined organic layers were dried over Na₂SO₄ and concentrated to give a brown oil. The crude product was purified by flash chromatography using 12 g of silica gel and 0-40% EtOAc in hexanes as eluant to afford 0.14 g (50%) of 1-[2-methylsulfanyl-5-(4,4,5,5-tetramethyl-[1,3,2]dioxaborolan-2-yl)-phenyl]-pyrrolidine as a tan oil. M+H 320.

Example 106

2,2-Dimethyl-1-[2-(4-methylsulfanyl-3-pyrrolidin-1-yl-phenyl)-5H-pyrrolo[2,3-b]pyrazin-7-yl]-propan-1-one A mixture of 1-(2-bromo-5H-pyrrolo[2,3-b]pyrazin-7-yl)-2,2-dimethyl-propan-1-one (125 mg, 0.44 mmol), 1-[2-methylsulfanyl-5-(4,4,5,5-tetramethyl-[1,3,2]dioxaborolan-2-yl)-phenyl]-pyrrolidine (140 mg, 0.4 mmol), potassium carbonate (138 mg, 1 mmol), and Pd(dppf)Cl₂.CH₂Cl₂ (28 mg, 0.03 mmol) in dioxane (3.4 mL) and water (0.8 mL) was stirred at 160° C. in a microwave for 30 min. The resulting mixture was partitioned between ethyl acetate and water. The combined organic layers were dried over Na₂SO₄ and concentrated to give 280 mg of a dark brown oily solid. The crude product was purified by flash chromatography using 12 g of silica gel and 9.5:0.5 MeOH:conc NH₄OH in CH₂Cl₂ as eluant to afford 0.22 g of impure product. Purification by preparative thin layer chromatography using 95:4.75:0.25 CH₂Cl₂:MeOH:conc NH₄OH as eluant provided 60 mg (30%) of 2,2-dimethyl-1-[2-(4-methylsulfanyl-3-pyrrolidin-1-yl-phenyl)-5H-pyrrolo[2,3-b]pyrazin-7-yl]-propan-1-one as a brown oil. M+H 395.

Example 107

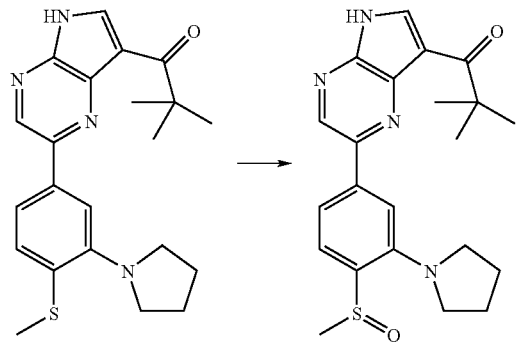

1-[2-(4-Methanesulfinyl-3-pyrrolidin-1-yl-phenyl)-5H-pyrrolo[2,3-b]pyrazin-7-yl]-2,2-dimethyl-propan-1-one To a brown solution of 2,2-dimethyl-1-[2-(4-methylsulfanyl-3-pyrrolidin-1-yl-phenyl)-5H-pyrrolo[2,3-b]pyrazin-7-yl]-propan-1-one (54 mg, 0.14 mmol) in CH₂Cl₂ (1 mL) was added mCPBA (30 mg, 0.13 mmol). After the reaction was complete as determined by TLC using 95:4.75:0.25 CH₂Cl₂:MeOH:conc NH₄OH as eluant, it was partitioned between saturated NaHCO₃ and CH₂Cl₂. The combined organic layers were dried over Na₂SO₄ and concentrated to give 80 mg of a brown oil. The crude product was purified by preparative thin layer chromatography using 93:6.65:0.35 CH₂Cl₂:MeOH:conc NH₄OH as eluant to afford 31 mg (60%) of 1-[2-(4-methanesulfinyl-3-pyrrolidin-1-yl-phenyl)-5H-pyrrolo[2,3-b]pyrazin-7-yl]-2,2-dimethyl-propan-1-one as a yellow glass. MP 150-152° C., M+H 411.

Example 108

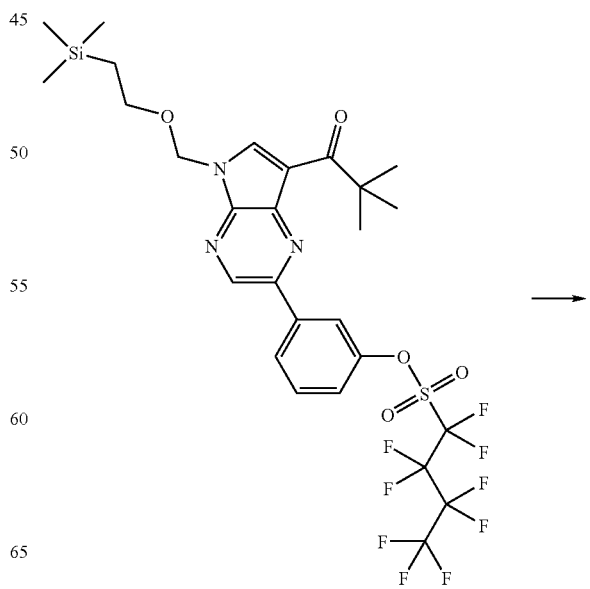

-continued

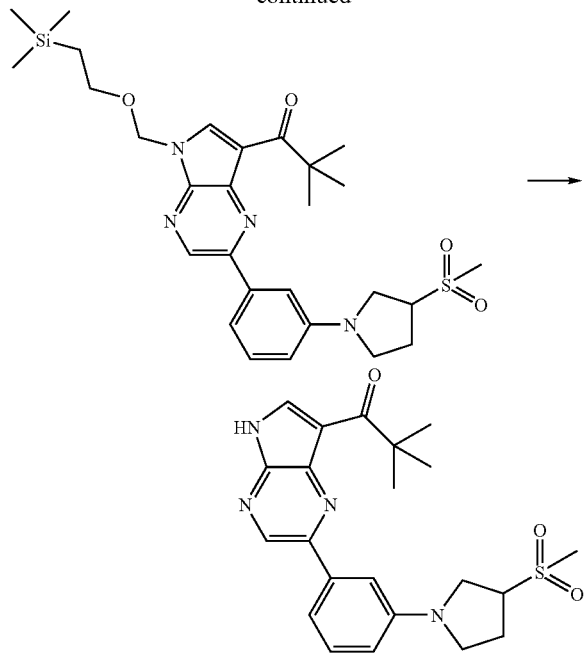

1-[2-[3-(3-Methanesulfonyl-pyrrolidin-1-yl)-phenyl]-5-(2-trimethylsilanyl-ethoxymethyl)-5H-pyrrolo[2,3-b]pyrazin-7-yl]-2,2-dimethyl-propan-1-one A mixture of 1,1,2,2,3,3,4,4,4-nonafluoro-butane-1-sulfonic acid 3-[7-(2,2-dimethyl-propionyl)-5-(2-trimethylsilanyl-ethoxymethyl)-5H-pyrrolo[2,3-b]pyrazin-2-yl]-phenyl ester (120 mg, 0.17 mmol), 3-methanesulfonyl-pyrrolidine (~40 mg, 0.26 mmol), $Pd_2(dba)_3$ (8 mg, 0.009 mmol), Xantphos (11 mg, 0.02 mmol), and $K_3PO_4$ (72 mg, 0.34 mmol) in toluene (1.5 mL) was stirred in a sealed tube under argon at 115° C. overnight. The resulting mixture was partitioned between ethyl acetate and water. The combined organic layers were dried over $Na_2SO_4$ and concentrated. The crude product was purified by flash chromatography using 4 g of silica gel and 20-100% EtOAc in hexanes as eluant to afford 0.08 g of impure 1-[2-[3-(3-methanesulfonyl-pyrrolidin-1-yl)-phenyl]-5-(2-trimethylsilanyl-ethoxymethyl)-5H-pyrrolo[2,3-b]pyrazin-7-yl]-2,2-dimethyl-propan-1-one. M+Na 579.

Example 109

1-{2-[3-(3-Methanesulfonyl-pyrrolidin-1-yl)-phenyl]-5H-pyrrolo[2,3-b]pyrazin-7-yl}-2,2-dimethyl-propan-1-one Following the general procedures described in these Examples, 1-[2-[3-(3-methanesulfonyl-pyrrolidin-1-yl)-phenyl]-5-(2-trimethylsilanyl-ethoxymethyl)-5H-pyrrolo[2,3-b]pyrazin-7-yl]-2,2-dimethyl-propan-1-one from above was deprotected. The crude product was purified by preparative thin layer chromatography using 150:9.5:0.5 $CH_2Cl_2$:MeOH:conc $NH_4OH$ as eluant to provide a pale yellow solid. The yellow solid was washed with $Et_2O$ to afford 9 mg (12% over 2 steps) of 1-{2-[3-(3-methanesulfonyl-pyrrolidin-1-yl)-phenyl]-5H-pyrrolo[2,3-b]pyrazin-7-yl}-2,2-dimethyl-propan-1-one as a cream-colored solid. MP 223-225° C., M+H 427.

Example 110

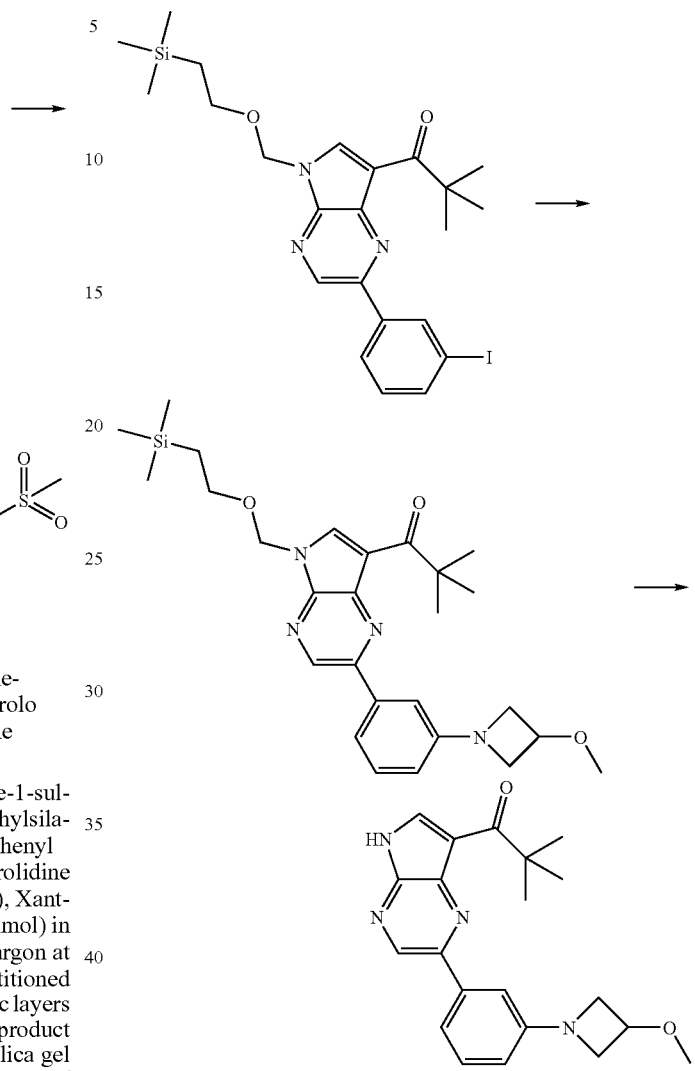

1-[2-[3-(3-Methoxy-azetidin-1-yl)-phenyl]-5-(2-trimethylsilanyl-ethoxymethyl)-5H-pyrrolo[2,3-b]pyrazin-7-yl]-2,2-dimethyl-propan-1-one A mixture of 1-[2-(3-iodo-phenyl)-5-(2-trimethylsilanyl-ethoxymethyl)-5H-pyrrolo[2,3-b]pyrazin-7-yl]-2,2-dimethyl-propan-1-one (107 mg, 0.2 mmol), 3-methoxy-azetidine (175 mg, 2 mmol), potassium carbonate (61 mg, 0.44 mmol), CuI (6 mg, 0.03 mmol), and racemic proline (7 mg, 0.06 mmol) in DMSO (1.5 mL) was stirred under argon at 95° C. in a sealed tube overnight. The resulting mixture was treated with additional 3-methoxy-azetidine (130 mg, 1.5 mmol) in DMSO (0.5 mL), potassium carbonate (60 mg, 0.44 mmol), CuI (4 mg, 0.02 mmol), and racemic proline (5 mg, 0.04 mmol) and stirred at 100° C. in a sealed tube overnight. The resulting mixture was allowed to cool to room temperature and partitioned between ethyl acetate and water. The combined organic layers were washed with water, dried over $Na_2SO_4$, and concentrated to give 100 mg of a brown oil. The crude product was purified by flash chromatography using 4 g of silica gel and 0-50% of 9.5:0.5 MeOH:conc $NH_4OH$ in

411

CH$_2$Cl$_2$ as eluant to afford 0.08 g (80%) of 1-[2-[3-(3-methoxy-azetidin-1-yl)-phenyl]-5-(2-trimethylsilanyl-ethoxymethyl)-5H-pyrrolo[2,3-b]pyrazin-7-yl]-2,2-dimethyl-propan-1-one as a yellow oil that solidifies. M+H 495.

Example 111

1-{2-[3-(3-Methoxy-azetidin-1-yl)-phenyl]-5H-pyrrolo[2,3-b]pyrazin-7-yl}-2,2-dimethyl-propan-1-one Following the general procedures described in these Examples, 1-[2-[3-(3-methoxy-azetidin-1-yl)-phenyl]-5-(2-trimethylsilanyl-ethoxymethyl)-5H-pyrrolo[2,3-b]pyrazin-7-yl]-2,2-dimethyl-propan-1-one from above was deprotected. The crude product was purified by preparative thin layer chromatography using 95:4.75:0.25 CH$_2$Cl$_2$:MeOH:conc NH$_4$OH as eluant to provide 42 mg of a pale yellow solid. The yellow solid was washed with CH$_2$Cl$_2$ and Et$_2$O to afford 18 mg (25% over 2 steps) of 1-{2-[3-(3-methoxy-azetidin-1-yl)-phenyl]-5H-pyrrolo[2,3-b]pyrazin-7-yl}-2,2-dimethyl-propan-1-one as a solid. MP 196-198° C., M+H 365.

Example 112

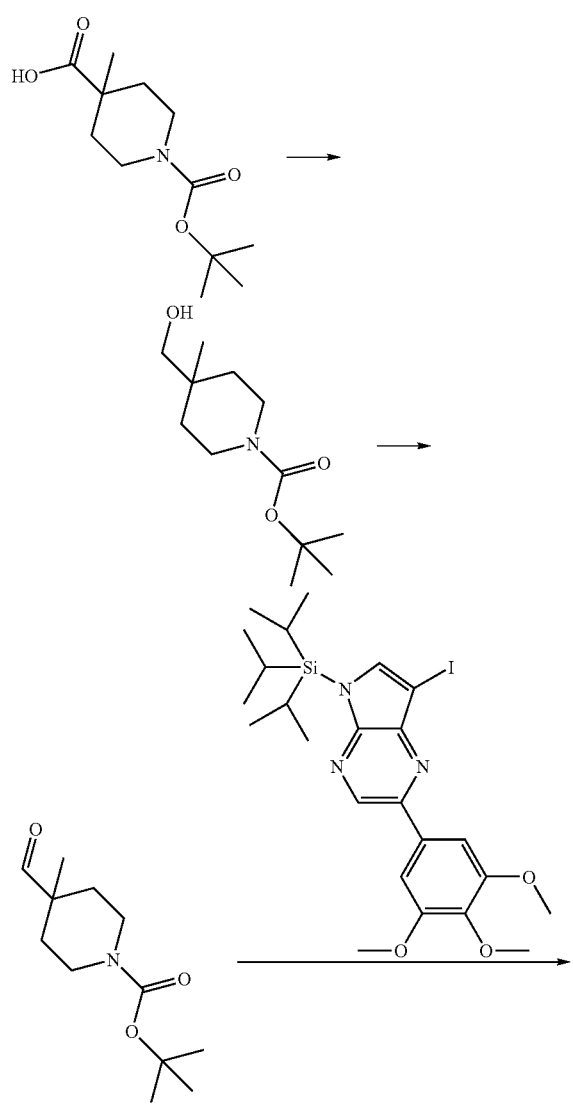

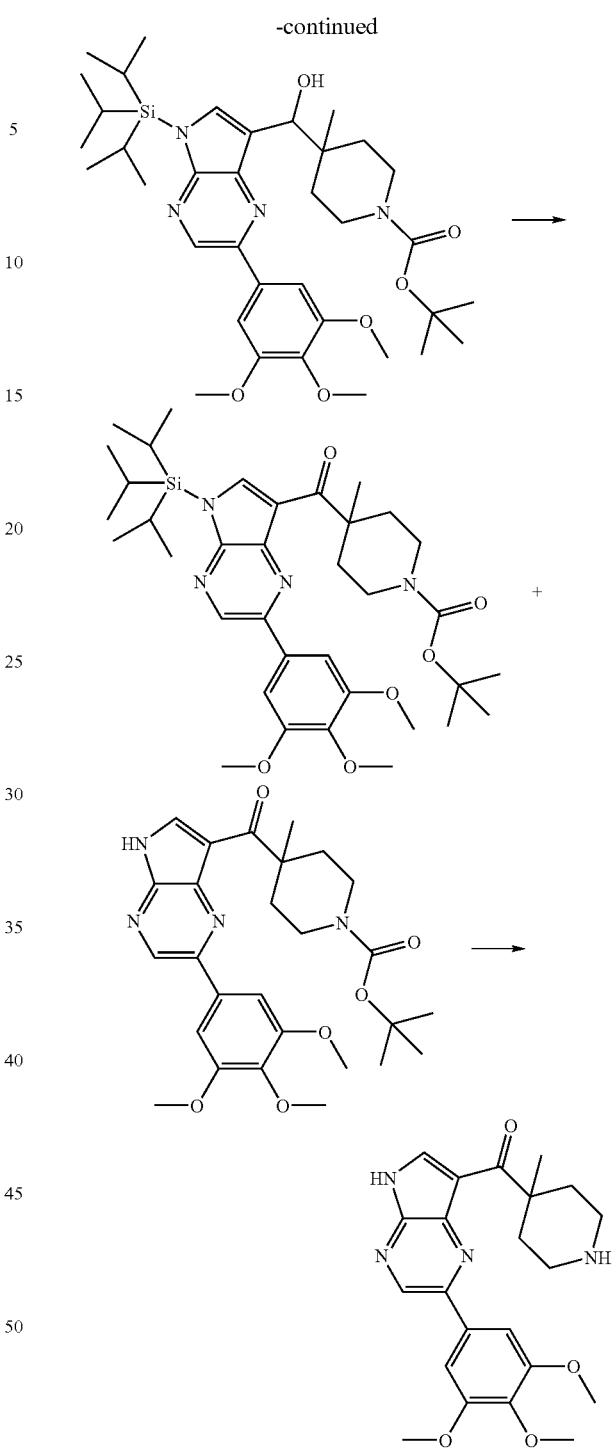

4-Formyl-4-methyl-piperidine-1-carboxylic acid tert-butyl ester

To a 0° C. solution of 4-methyl-piperidine-1,4-dicarboxylic acid mono-tert-butyl ester (5 g, 20.6 mmol) in THF (70 mL) was added dropwise over 20 min BH$_3$.THF (31 mL, 1 M solution in THF, 31 mmol). The resultant reaction was allowed to warm slowly to room temperature, stirred at room temperature overnight, stirred at reflux for 4.5 h, allowed to cool to room temperature, treated with additional BH$_3$.THF (30 mL, 1 M solution in THF, 30 mmol), and stirred at room temperature overnight. The reaction was divided into two batches and each was quenched with saturated NaHCO₃ and extracted with EtOAc and the organic phase was dried over Na₂SO₄ and concentrated. The crude product from one batch was purified by flash chromatography using 110 g of silica gel and 0-50% of 9.5:0.5 MeOH:conc NH₄OH in CH₂Cl₂ as eluant to afford 2.4 g of 4-hydroxymethyl-4-methyl-piperidine-1-carboxylic acid tert-butyl ester as a colorless oil.

To a −78° C. solution of (COCl)₂ (1 mL, 11.5 mmol) in CH₂Cl₂ (36 mL) was added dropwise over 20 min DMSO (1.4 mL, 19.7 mmol). The reaction was stirred for 20 min at −78° C. and 4-hydroxymethyl-4-methyl-piperidine-1-carboxylic acid tert-butyl ester from above (2.4 g, 10 mmol) in CH₂Cl₂ (22 mL) was added slowly. The reaction was stirred for 30 min at −78° C., treated with triethylamine (4.2 mL, 30 mmol), stirred for an additional 20 min at −78° C., and allowed to slowly warm to room temperature. The resultant cloudy mixture was partitioned between saturated NaHCO₃ and CH₂Cl₂ and the aqueous phase was extracted with CH₂Cl₂. The combined organic phases were dried over Na₂SO₄ and concentrated to give 2.44 g of a yellow oil. The crude product was purified by flash chromatography using 80 g of silica gel and 0-30% of 9.5:0.5 MeOH:conc NH₄OH in CH₂Cl₂ as eluant to afford 0.83 g (36%) of desired 4-formyl-4-methyl-piperidine-1-carboxylic acid tert-butyl ester as a colorless oil and 1.5 g (68%) of a 2:1 mixture of desired 4-formyl-4-methyl-piperidine-1-carboxylic acid tert-butyl ester:starting 4-hydroxymethyl-4-methyl-piperidine-1-carboxylic acid tert-butyl ester as a viscous oil.

Example 113

4-{Hydroxy-[5-triisopropylsilanyl-2-(3,4,5-trimethoxy-phenyl)-5H-pyrrolo[2,3-b]pyrazin-7-yl]-methyl}-4-methyl-piperidine-1-carboxylic acid tert-butyl ester To a −78° C. solution of 7-iodo-5-triisopropylsilanyl-2-(3,4,5-trimethoxy-phenyl)-5H-pyrrolo[2,3-b]pyrazine (680 mg, 1.2 mmol) in THF (4 mL) was added iPrMgCl.LiCl (2.7 mL, 1.3 M in THF, 3.5 mmol) dropwise along the side of the flask. The reaction was stirred for 10 min at −78° C. and a solution of 4-formyl-4-methyl-piperidine-1-carboxylic acid tert-butyl ester (700 mg, 3.1 mmol) in THF (4 mL) was added slowly along the side of the flask. The reaction was allowed to slowly warm to room temperature, stirred overnight, and partitioned between saturated NH₄Cl and EtOAc. The aqueous phase was extracted with EtOAc and the combined organic phases were dried over Na₂SO₄ and concentrated to give a yellow oil. The crude product was purified by flash chromatography using 40 g of silica gel and 0-50% of 9.5:0.5 MeOH:conc NH₄OH in CH₂Cl₂ as eluant to afford 950 mg of impure 4-{hydroxy-[5-triisopropylsilanyl-2-(3,4,5-trimethoxy-phenyl)-5H-pyrrolo[2,3-b]pyrazin-7-yl]-methyl}-4-methyl-piperidine-1-carboxylic acid tert-butyl ester. M+Na 691.

Example 114

4-Methyl-4-[5-triisopropylsilanyl-2-(3,4,5-trimethoxy-phenyl)-5H-pyrrolo[2,3-b]pyrazine-7-carbonyl]-piperidine-1-carboxylic acid tert-butyl ester and 4-Methyl-4-[2-(3,4,5-trimethoxy-phenyl)-5H-pyrrolo[2,3-b]pyrazine-7-carbonyl]-piperidine-1-carboxylic acid tert-butyl ester To a solution of 4-{hydroxy-[5-triisopropylsilanyl-2-(3,4,5-trimethoxy-phenyl)-5H-pyrrolo[2,3-b]pyrazin-7-yl]-methyl}-4-methyl-piperidine-1-carboxylic acid tert-butyl ester from above (950 mg, ~1.4 mmol) in CH₂Cl₂ (5 mL) was added Dess-Martin periodinane (900 mg, 2.1 mmol) portionwise. The resultant orange suspension was allowed to stir for 1 h and partitioned between 1:1 saturated Na₂S₂O₃:saturated NaHCO₃ and CH₂Cl₂. The aqueous phase was extracted with CH₂Cl₂ and the combined organic phases were dried over Na₂SO₄ and concentrated to give a tan solid. The crude product was purified by flash chromatography using 25 g of silica gel and 0-30% of 9.5:0.5 MeOH:conc NH₄OH in CH₂Cl₂ as eluant to afford 150 mg of impure 4-methyl-4-[2-(3,4,5-trimethoxy-phenyl)-5H-pyrrolo[2,3-b]pyrazine-7-carbonyl]-piperidine-1-carboxylic acid tert-butyl ester, M+Na 533, and 0.24 g of impure 4-methyl-4-[5-triisopropylsilanyl-2-(3,4,5-trimethoxy-phenyl)-5H-pyrrolo[2,3-b]pyrazine-7-carbonyl]-piperidine-1-carboxylic acid tert-butyl ester, M+Na 689.

Example 115

(4-Methyl-piperidin-4-yl)-[2-(3,4,5-trimethoxy-phenyl)-5H-pyrrolo[2,3-b]pyrazin-7-yl]-methanone To a solution of impure 4-methyl-4-[2-(3,4,5-trimethoxy-phenyl)-5H-pyrrolo[2,3-b]pyrazine-7-carbonyl]-piperidine-1-carboxylic acid tert-butyl ester from above (150 mg) in MeOH (1 mL) was added AcCl (42 uL) portionwise and MeOH (3 mL) over 5 d, with heating at 40° C. on days 2 and 3. The reaction was concentrated and partitioned between saturated NaHCO₃ and CH₂Cl₂. The aqueous phase was extracted with CH₂Cl₂ and the combined organic phases were dried over Na₂SO₄ and concentrated to give 70 mg of crude product as a yellow oil.

To a solution of impure 4-methyl-4-[5-triisopropylsilanyl-2-(3,4,5-trimethoxy-phenyl)-5H-pyrrolo[2,3-b]pyrazine-7-carbonyl]-piperidine-1-carboxylic acid tert-butyl ester from above (240 mg) in MeOH (3 mL) was added AcCl (30 uM). The resultant yellow suspension was stirred at 40° C. for 1 h, treated with additional AcCl (30 uL) and stirred at 40° C. overnight. The reaction was concentrated and partitioned between saturated Na₂CO₃ and CH₂Cl₂. The aqueous phase was extracted with CH₂Cl₂ and the combined organic phases were dried over Na₂SO₄ and concentrated to give 100 mg of crude product.

The combined batches of crude product were purified by reverse phase chromatography using 10 g of C-18 and 10-90% of MeOH with 0.1% TFA in water with 0.1% TFA as eluant followed by flash chromatography using a 14 g Thomson Instrument Amine Column and 0-50% of 9.5:0.5 MeOH:conc NH₄OH in CH₂Cl₂ as eluant to afford 60 mg of (4-methyl-piperidin-4-yl)-[2-(3,4,5-trimethoxy-phenyl)-5H-pyrrolo[2,3-b]pyrazin-7-yl]-methanone. M+H 411.

Example 116

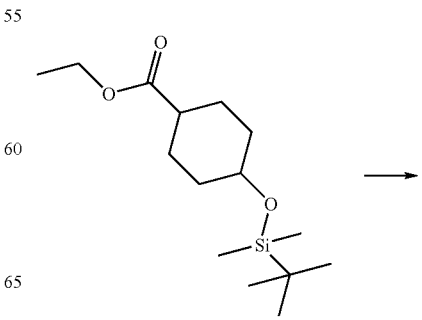

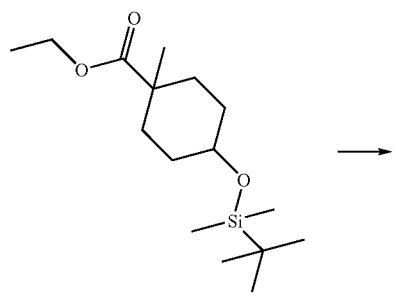

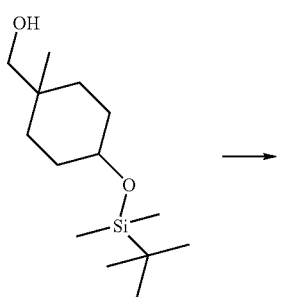

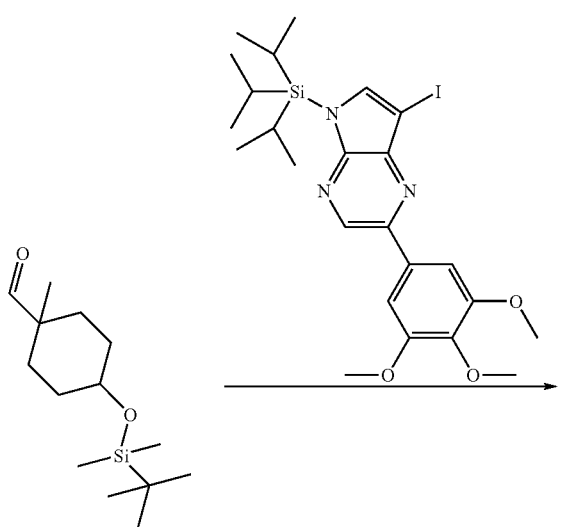

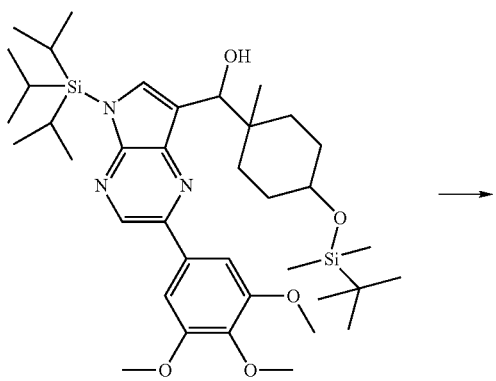

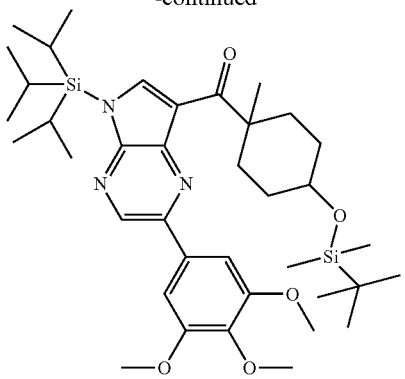

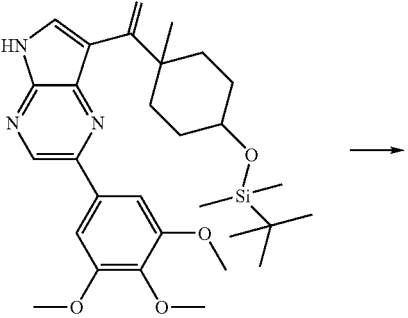

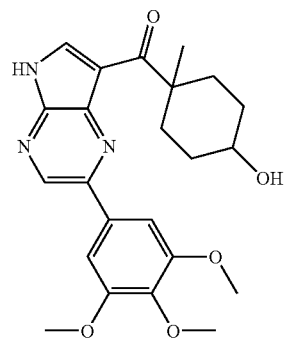

Cis- and trans-(4-Hydroxy-1-methyl-cyclohexyl)-[2-(3,4,5-trimethoxy-phenyl)-5H-pyrrolo[2,3-b]pyrazin-7-yl]-methanone A solution of 4-(tert-butyl-dimethyl-silanyloxy)-cyclohexanecarboxylic acid ethyl ester (14.7 g, 51.3 mmol) (Breitenbucher, J. Guy; Lee-Dutra, Alice; Neff, Danielle K., US 2006004039) in anhydrous THF (155 ml), at −78° C., was treated with LDA (2M in hexane/THF/ethylbenzene, 38.5 ml, 77 mmol) dropwise. The reaction mixture was stirred for 1.5 hours at which time MeI (6.42 ml, 102.6 mmol) was added dropwise. After stirring at room temperature for approximately 2 hours, the reaction mixture was partitioned between EtOAc/sat. NH$_4$Cl. The organic layers were collected, dried over MgSO$_4$, filtered, and concentrated. The crude product was purified by silica gel chromatography using 10-60% DCM in hexanes as eluant providing 5.71 g (37%) of a 2:1 mixture of major:minor diastereomers of 4-(tert-butyl-dimethyl-silanyloxy)-1-methyl-cyclohexanecarboxylic acid ethyl ester as a colorless oil and 3.0 g (19%) of the major diastereomer as a colorless oil.

To a 0° C. solution of a 2:1 mixture of major:minor diastereomers of 4-(tert-butyl-dimethyl-silanyloxy)-1-methyl-cyclohexanecarboxylic acid ethyl ester from above (2.9 g, 10 mmol) in Et₂O (100 mL) was added LiAlH₄ (380 mg, 10 mmol) portionwise over 5 min. The resultant mixture was stirred at 0° C. for 1 h, treated slowly with water (0.38 mL), 15% NaOH (1.14 mL), and then water (0.38 mL) while stirring vigorously, allowed to warm to room temperature, and stirred vigorously for 40 min. The resultant white granular solids were filtered away and the mother liquor concentrated to afford 2.7 g of a colorless oil. The crude product was purified by flash chromatography using 80 g of silica gel and 0-50% of EtOAc in hexanes as eluant to afford 700 mg of a 9:1 mixture of major:minor diastereomers of [4-(tert-butyl-dimethyl-silanyloxy)-1-methyl-cyclohexyl]-methanol, 1.43 g of an impure 3:1 mixture of major:minor diastereomers of [4-(tert-butyl-dimethyl-silanyloxy)-1-methyl-cyclohexyl]-methanol, and 600 mg of an impure 1:2 mixture of major:minor diastereomers of [4-(tert-butyl-dimethyl-silanyloxy)-1-methyl-cyclohexyl]-methanol (94% total yield).

To a −78° C. solution of (COCl)₂ (0.9 mL, 10.4 mmol) in CH₂Cl₂ (30 mL) was added slowly DMSO (1.5 mL, 21 mmol). The reaction was stirred for 15 min at −78° C. and an impure 3:1 mixture of major:minor diastereomers of [4-(tert-butyl-dimethyl-silanyloxy)-1-methyl-cyclohexyl]-methanol from above (1.43 g, 5.54 mmol) in CH₂Cl₂ (24 mL) was added slowly over 15 min. The reaction was stirred for 1 h at −78° C., treated with triethylamine (5.8 mL, 41 mmol), and allowed to slowly warm to room temperature. The reaction was partitioned between saturated NaHCO₃ and CH₂Cl₂ and the aqueous phase was extracted with CH₂Cl₂. The combined organic phases were dried over Na₂SO₄ and concentrated. The crude product was purified by flash chromatography using 40 g of silica gel and 0-20% of EtOAc in hexanes as eluant to afford 0.8 g (56%) of an impure 4:1 mixture of diastereomers of 4-(tert-butyl-dimethyl-silanyloxy)-1-methyl-cyclohexanecarbaldehyde.

To a −78° C. solution of 7-iodo-5-triisopropylsilanyl-2-(3,4,5-trimethoxy-phenyl)-5H-pyrrolo[2,3-b]pyrazine (640 mg, 1.1 mmol) in THF (3.2 mL) was added iPrMgCl.LiCl (2.4 mL, 1.3 M in THF, 3.1 mmol) dropwise along the side of the flask. The reaction was stirred for 10 min at −78° C. and a solution of an impure 4:1 mixture of diastereomers of 4-(tert-butyl-dimethyl-silanyloxy)-1-methyl-cyclohexanecarbaldehyde (800 mg, 3.1 mmol) in THF (3 mL) was added slowly along the side of the flask. The reaction was allowed to slowly warm to room temperature, stirred overnight, and partitioned between saturated NH₄Cl and EtOAc. The aqueous phase was extracted with EtOAc and the combined organic phases were dried over Na₂SO₄ and concentrated to give 1.4 g of a crude mixture of diastereomers of [4-(tert-butyl-dimethyl-silanyloxy)-1-methyl-cyclohexyl]-[5-triisopropylsilanyl-2-(3,4,5-trimethoxy-phenyl)-5H-pyrrolo[2,3-b]pyrazin-7-yl]-methanol as a yellow oil which was taken onto the next step. M+H 698.

To a solution of a crude mixture of diastereomers of [4-(tert-butyl-dimethyl-silanyloxy)-1-methyl-cyclohexyl]-[5-triisopropylsilanyl-2-(3,4,5-trimethoxy-phenyl)-5H-pyrrolo[2,3-b]pyrazin-7-yl]-methanol from above (1.4 g) in CH₂Cl₂ (3 mL) was added Dess-Martin periodinane (300 mg, 0.7 mmol) portionwise. The resultant suspension was allowed to stir for 3 d and partitioned between 1:1 saturated Na₂S₂O₃:saturated NaHCO₃ and CH₂Cl₂. The aqueous phase was extracted with CH₂Cl₂ and the combined organic phases were dried over Na₂SO₄ and concentrated. The crude product was purified by flash chromatography using 40 g of silica gel and 0-50% of 9.5:0.5 MeOH:conc NH₄OH in CH₂Cl₂ as eluant to afford 600 mg of an impure mixture of diastereomers of [4-(tert-butyl-dimethyl-silanyloxy)-1-methyl-cyclohexyl]-[5-triisopropylsilanyl-2-(3,4,5-trimethoxy-phenyl)-5H-pyrrolo[2,3-b]pyrazin-7-yl]-methanone, M+H 696, and [4-(tert-butyl-dimethyl-silanyloxy)-1-methyl-cyclohexyl]-[2-(3,4,5-trimethoxy-phenyl)-5H-pyrrolo[2,3-b]pyrazin-7-yl]-methanone, M−H 538, as a yellow oil with solids and 324 mg of an impure 5:2 mixture of diastereomers of [4-(tert-butyl-dimethyl-silanyloxy)-1-methyl-cyclohexyl]-[2-(3,4,5-trimethoxy-phenyl)-5H-pyrrolo[2,3-b]pyrazin-7-yl]-methanone as a tan glassy foam, M+H 540.

To a suspension of an impure 5:2 mixture of diastereomers of [4-(tert-butyl-dimethyl-silanyloxy)-1-methyl-cyclohexyl]-[2-(3,4,5-trimethoxy-phenyl)-5H-pyrrolo[2,3-b]pyrazin-7-yl]-methanone from above (320 mg) in MeOH (2 mL) was added AcCl (7.5 uL). The suspension was stirred for 2 d, concentrated and partitioned between saturated NaHCO₃ and CH₂Cl₂. The aqueous phase was extracted with CH₂Cl₂ and the combined organic phases were dried over Na₂SO₄ and concentrated to give 200 mg of crude product as a yellow solid. The crude product was purified by preparative thin layer chromatography using 90:9.5:0.5 CH₂Cl₂:MeOH:conc NH₄OH as eluant to afford 52 mg of 1 diastereomer of (4-hydroxy-1-methyl-cyclohexyl)-[2-(3,4,5-trimethoxy-phenyl)-5H-pyrrolo[2,3-b]pyrazin-7-yl]-methanone, M+H 426, and 70 mg of the other diastereomer of (4-hydroxy-1-methyl-cyclohexyl)-[2-(3,4,5-trimethoxy-phenyl)-5H-pyrrolo[2,3-b]pyrazin-7-yl]-methanone, M+H 426.

Example 117

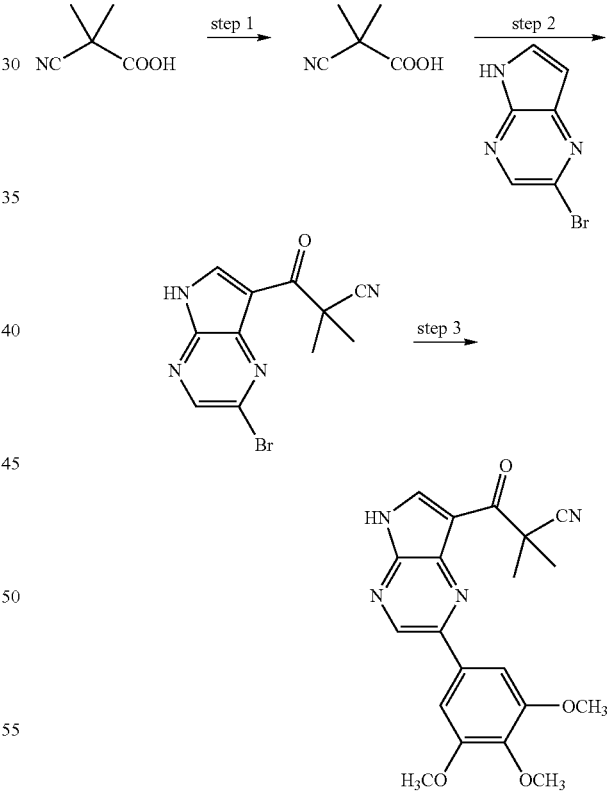

2,2-Dimethyl-3-oxo-3-[2-(3,4,5-trimethoxy-phenyl)-5H-pyrrolo[2,3-b]pyrazin-7-yl]-propionitrile Step 1: To a solution of cyano-dimethyl-acetic acid (3.89 g, 34.4 mmol) and two small drops of DMF in anhydrous DCM (20 mL) at 0° C. was added oxalyl chloride (3.62 mL, 41.3 mmol). Ice bath for cooling was removed. The reaction mixture was stirred at room temperature for 1.5 h and concentrated under reduced pressure. The residue was diluted with anhydrous DCM and reconcentrated. This procedure was repeated one more time to give an oil which was used in the next step without further purification.

Step 2: General procedures described in these Examples were followed except no silica gel chromatography was carried out. The crude product was used in the next step without further purification. MS [M+H]+: 293.

Step 3: General procedures described in these Examples were followed except replacing 3-pyrrolidino phenylboronic acid with 3,4,5-trimethoxyphenylboronic acid. The product was first purified by flash column chromatography on silica gel with a mixture of 28% aqueous ammonium hydroxide:methanol:DCM (1:10:60) in DCM (20% to 50% gradient over 30 min) followed by HPLC purification to give 2,2-Dimethyl-3-oxo-3-[2-(3,4,5-trimethoxy-phenyl)-5H-pyrrolo[2,3-b]pyrazin-7-yl]-propionitrile as a off-white powder. $^1$H NMR (DMSO-d$_6$): δ 9.09 (s, 1H), 8.88 (s, 1H), 7.64 (s, 2H), 3.92 (s, 6H), 3.74 (s, 3H), 1.86 (s, 6H); MS [M+H]+: 381.

Example 118

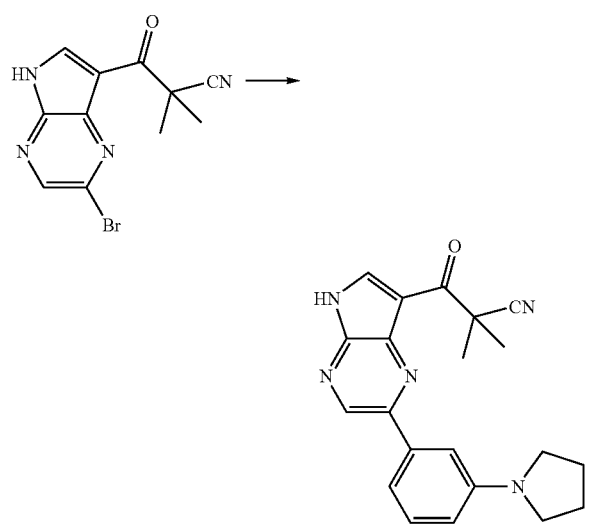

2,2-Dimethyl-3-oxo-3-[2-(3-pyrrolidin-1-yl-phenyl)-5H-pyrrolo[2,3-b]pyrazin-7-yl]-propionitrile General procedures described in these Examples were followed. $^1$H NMR (DMSO-d$_6$): δ 9.0 (s, 1H), 8.7 (s, 1H), 7.5 (s, 1H), 7.4 (d, J=8 Hz, 1H), 7.3 (t, J=8.0 Hz, 1H), 6.65 (dd, J=2.3, 8.1 Hz, 1H), 3.35 (m, 4H), 2.02-1.98 (m, 4H), 1.88 (s, 6H); MS [M+H]+: 360.

Example 119

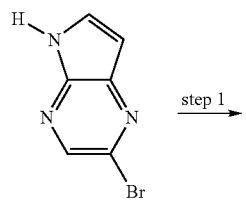

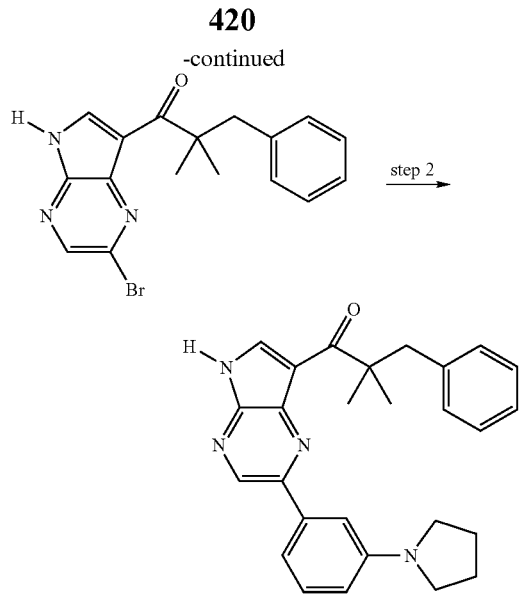

1-(2-Bromo-5H-pyrrolo[2,3-b]pyrazin-7-yl)-2,2-dimethyl-3-phenyl-propan-1-one 2,2-Dimethyl-3-phenyl-1-[2-(3-pyrrolidin-1-yl-phenyl)-5H-pyrrolo[2,3-b]pyrazin-7-yl]-propan-1-one General procedures described in these Examples were followed except replacing 1-methyl-cyclohexanecarbonyl chloride with 2,2-Dimethyl-3-phenyl-propionyl chloride in step 1. Characterization for intermediate: $^1$H NMR (CDCl$_3$, 400 MHz): δ 9.63 (s, 1H), 8.42 (s, 1H), 8.40 (d, J=3.3 Hz, 1H), 7.63-7.18 (m, 5H), 3.39 (s, 2H), 1.38 (s, 6H); MS [M+H]+: 358.

Characterization for product: $^1$H NMR (CDCl$_3$): δ 8.84 (s, 1H), 8.49 (d, J=3.2 Hz, 1H), 7.42 (s, 1H), 7.38-7.35 (m, 2H), 7.15-7.10 (m, 5H), 6.71-6.66 (m, 1H), 3.64 (s, 2H), 3.38-3.34 (m, 4H), 2.04-2.01 (m, 4H), 1.52 (s, 6H); MS [M+H]+: 425.

Example 120

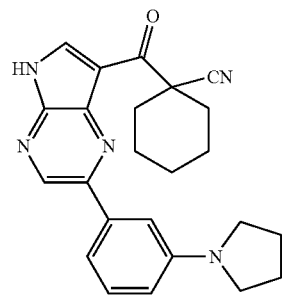

1-[2-(3-Pyrrolidin-1-yl-phenyl)-5H-pyrrolo[2,3-b]pyrazine-7-carbonyl]-cyclohexanecarbonitrile General procedures described in these Examples were followed except replacing cyano-dimethyl-acetic acid with 1-cyano-cyclohexanecarboxylic acid in step 1 and 3,4,5-trimethoxyphenylboronic acid with 3-pyrrolidino phenylboronic acid in step 3. $^1$H NMR (CDCl$_3$): δ 9.32 (m, 1H), 8.81

(s, 1H), 8.45 (s, 1H), 7.49 (s, 1H), 7.42-7.32 (m, 2H), 6.70-6.64 (m, 1H), 3.48-3.37 (m, 4H), 2.68 (br s, 2H), 2.08-1.76 (m, 12H); MS [M+H]+: 400.

Example 121

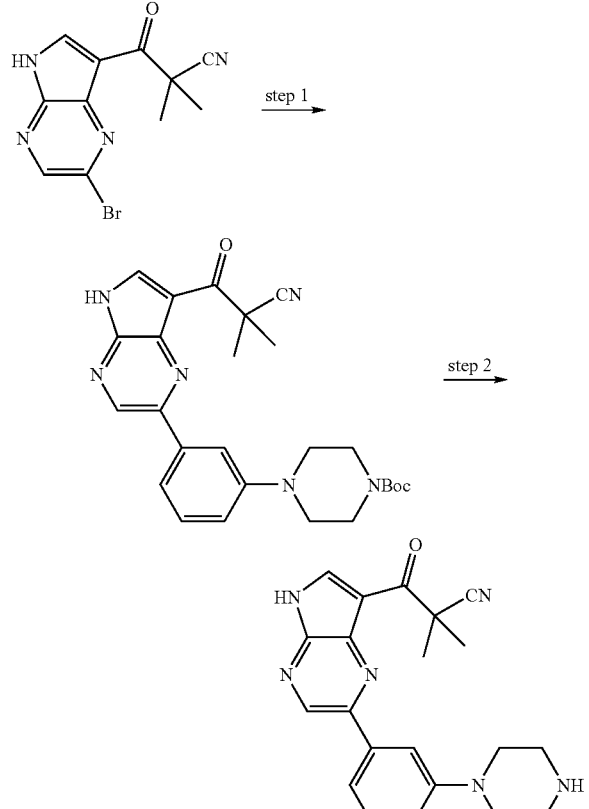

2,2-Dimethyl-3-oxo-3-[2-(3-piperazin-1-yl-phenyl)-5H-pyrrolo[2,3-b]pyrazin-7-yl]-propionitrile Step 1: General procedures described in these Examples were followed except replacing 3-pyrrolidino phenylboronic acid with 4-[3-(4,4,5,5-Tetramethyl-[1,3,2]dioxaborolan-2-yl)-phenyl]-piperazine-1-carboxylic acid tert-butyl ester. MS [M+H]+: 475.

Step 2: A solution of 4-{3-[7-(2-Cyano-2,2-dimethyl-acetyl)-5H-pyrrolo[2,3-b]pyrazin-2-yl]-phenyl}-piperazine-1-carboxylic acid tert-butyl ester from step 1 in hexafluor-oisopropanol was heated at 150° C. in a microwave oven for 45 min. The reaction mixture was cooled to room temperature and concentrated under reduced pressure. The residue was purified by flash column chromatography on silica gel with a mixture of 28% aqueous ammonium hydroxide:methanol:DCM (1:10:60) in DCM (20% to 80% gradient over 30 min) to give 39 mg of the desired product as a yellow powder. $^1$H NMR (CDCl$_3$, 400 MHz): δ 8.81 (s, 1H), 8.50 (s, 1H), 7.91 (s, 1H), 7.60-7.54 (m, 1H), 7.42 (t, J=7.9 Hz, 1H), 7.08-7.04 (m, 1H), 3.35 (t, J=4 Hz, 2H), 3.14 (t, J=4 Hz, 2H), 1.92 (s, 6H); MS [M+H]+: 375.

Example 122

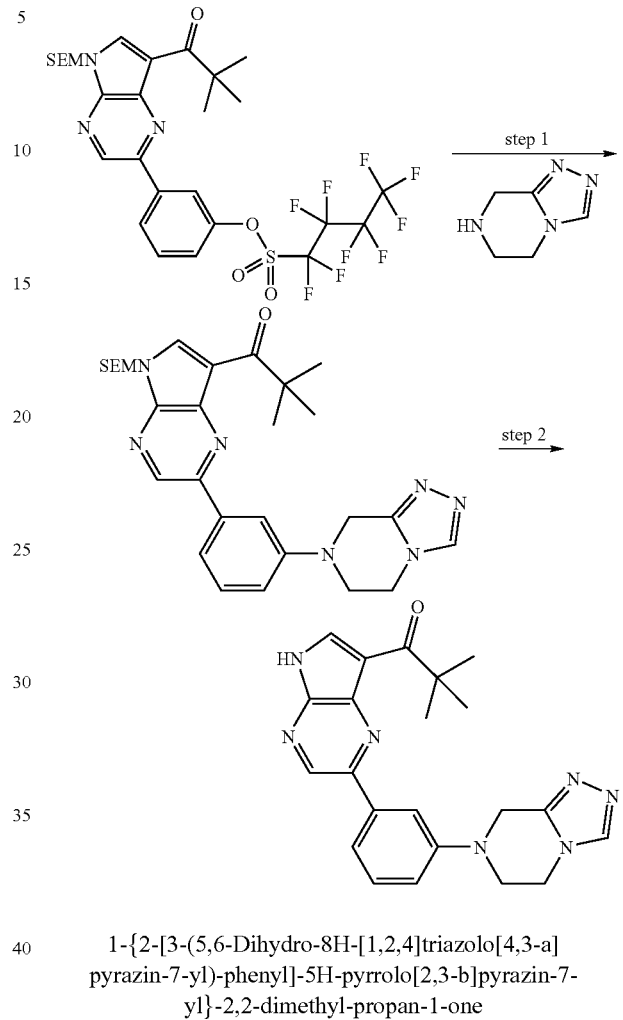

1-{2-[3-(5,6-Dihydro-8H-[1,2,4]triazolo[4,3-a]pyrazin-7-yl)-phenyl]-5H-pyrrolo[2,3-b]pyrazin-7-yl}-2,2-dimethyl-propan-1-one Step 1: A mixture of 1,1,2,2,3,3,4,4,4-nonafluoro-butane-1-sulfonic acid 3-[7-(2,2-dimethyl-propionyl)-5-(2-trimethylsilanyl-ethoxymethyl)-5H-pyrrolo[2,3-b]pyrazin-2-yl]-phenyl ester (0.175 g, 0.25 mmol, see the experimental below preparation of this compound), 5,6,7,8-Tetrahydro-[1,2,4]triazolo[4,3-a]pyrazine (0.061 g, 0.5 mmol), Pd$_2$(dba)$_3$ (0.041 g, 0.41 mmol), XANPHOS (0.046 g, 0.08 mmol) and K$_3$PO$_4$ in toluene (2 mL) were heated in a microwave oven under an argon atmosphere at 115° C. for 1 h. After cooling to room temperature, the reaction mixture was directly purified by flash column chromatography on silica gel with a mixture of 28% aqueous ammonium hydroxide:methanol:DCM (1:10:60) in DCM (20% to 80% gradient over 30 min) to give 20 mg of the desired product as a yellow foam. $^1$H NMR (CDCl$_3$, 400 MHz): δ 8.84 (s, 1H), 8.47 (s, 1H), 8.23 (s, 1H), 7.95 (s, 1H), 7.71 (d, J=7.7 Hz, 1H), 7.52 (t, J=8.0 Hz, 1H), 7.13 (d, J=8.2 Hz, 1H), 5.74 (s, 2H), 4.77 (s, 2H), 4.30 (t, J=5.3 Hz, 2H), 3.88 (t, J=5.4 Hz, 2H), 3.65 (t, J=8.2 Hz, 2H), 1.62 (s, 9H), 0 (s, 9H); MS [M+H]+: 532.

Step 2: Following the general procedures described in these Examples. $^1$H NMR (CDCl$_3$, 400 MHz): δ 9.71 (s, 1H), 8.80 (s, 1H), 8.43 (d, J=3.3 Hz, 1H), 8.21 (s, 1H), 7.91 (br s, 1H), 7.67 (d, J=8.0 Hz, 1H) 7.50 (t, J=7.6 Hz, 1H), 7.10 (dd, J=2.5, 8.1 Hz, 1H), 4.75 (s, 2H), 4.28 (t, J=5.3 Hz, 2H), 3.85 (t, J=5.5 Hz, 2H), 1.59 (s, 9H); MS [M+H]+: 402.

Example 123

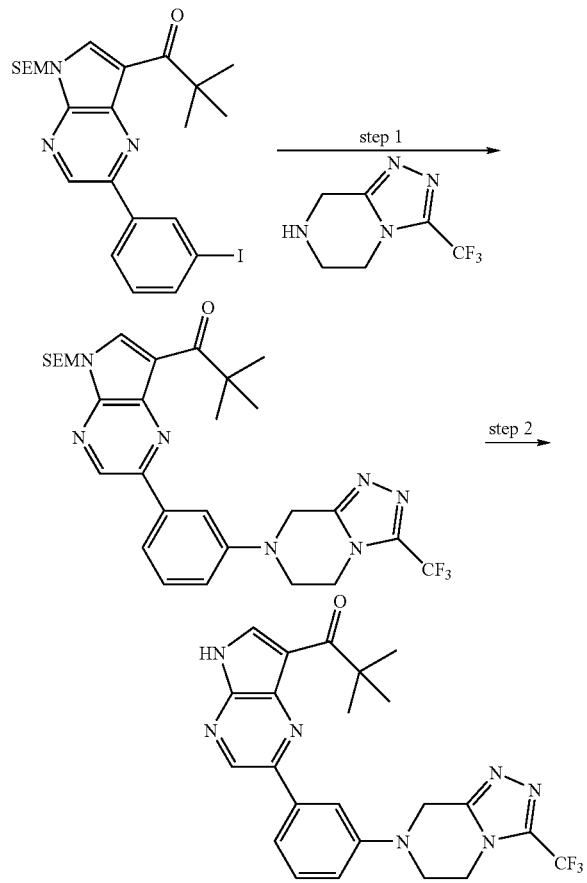

Example 124

2,2-Dimethyl-1-{2-[3-(3-trifluoromethyl-5,6-dihydro-8H-[1,2,4]triazolo[4,3-a]pyrazin-7-yl)-phenyl]-5H-pyrrolo[2,3-b]pyrazin-7-yl}-propan-1-one Step 1: A mixture of 1-[2-(3-iodo-phenyl)-5-(2-trimethyl-silanyl-ethoxymethyl)-5H-pyrrolo[2,3-b]pyrazin-7-yl]-2,2-dimethyl-propan-1-one (0.083 g, 0.16 mmol), 3-trifluoromethyl-5,6,7,8-tetrahydro-[1,2,4]triazolo[4,3-a]pyrazine hydrochloride (0.05 g, 0.24 mmol), Pd(PPh3)4 (0.023 g, 0.02 mmol) and sodium t-butoxide (0.046 g, 0.48 mmol) in toluene (2 mL) were heated under an argon atmosphere in a microwave oven at 90° C. for 1 h. After cooling to room temperature, the reaction mixture was directly purified by flash column chromatography on silica gel with a mixture of 28% aqueous ammonium hydroxide:methanol:DCM (1:10:60) in DCM (20% to 80% gradient over 30 min) to give 25 mg of the desired product as a yellow oil. 1H NMR (CDCl3, 400 MHz): δ 8.84 (s, 1H), 8.48 (s, 1H), 8.23 (s, 1H), 7.95 (br s, 1H), 7.74 (d, J=7.7 Hz, 1H), 7.54 (t, J=8.0 Hz, 1H), 7.14 (d, J=8.2 Hz, 1H), 5.74 (s, 2H), 4.80 (s, 2H), 4.37 (t, J=5.3 Hz, 2H), 3.91 (t, J=5.4 Hz, 2H), 3.66 (dd, J=8.2 Hz, 2H), 1.62 (s, 9H), 0 (s, 9H); MS [M+H]+: 600.

Step 2: Following the general procedures described in these Examples. 1H NMR (CDCl3, 400 MHz): δ 9.46 (s, 1H), 8.80 (s, 1H), 8.43 (d, J=3.3 Hz, 1H), 8.21 (s, 1H), 7.91 (t, J=2.2 Hz, 1H), 7.71 (d, J=8.0 Hz, 1H), 7.50 (t, J=8.0 Hz, 1H), 7.09 (dd, J=2.6, 8.2 Hz, 1H), 4.77 (s, 2H), 4.33 (t, J=5.3 Hz, 2H), 3.87 (t, J=5.6 Hz, 2H), 1.59 (s, 9H); MS [M+H]+: 455.

Example 124

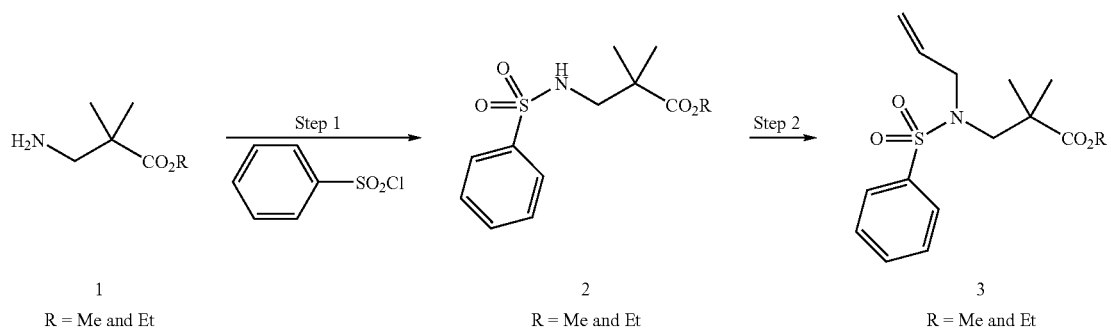

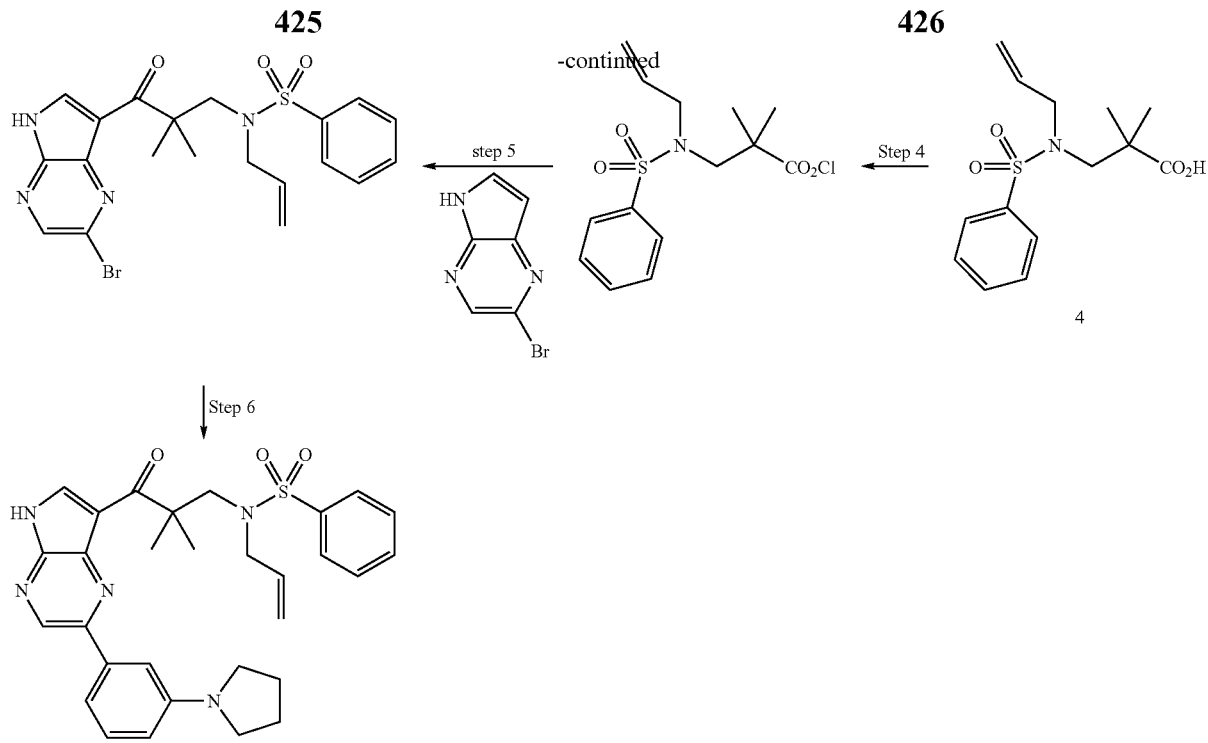

N-Allyl-N-{2,2-dimethyl-3-oxo-3-[2-(3-pyrrolidin-1-yl-phenyl)-5H-pyrrolo[2,3-b]pyrazin-7-yl]-propyl}-benzenesulfonamide Step 1: To a solution of 1 (5.4 g, prepared according to reference Maibaum, J. et al. Journal of Medicinal Chemistry (2007), 50(20), 4832-4844 as a 1:1 mixture of methyl and ethyl esters) in DCM (40 mL) at 0° C. was added triethylamine (10.4 mL, 75 mmol) followed by benzenesulfonyl chloride (4.77 mL, 37.2 mmol). The ice bath was removed and the reaction was stirred at room temperature for 2 h. The reaction mixture was poured into saturated aqueous NaHCO$_3$ and extracted with DCM (3×). The combined DCM extracts were dried (MgSO$_4$), filtered and concentrated to afford 2 (10.9 g) as an oil.

Step 2: To a solution of 2 (10.9 g) in DMF (30 mL) at 0° C. was added NaH (1.84 g, 60% in mineral oil, 46 mmol). The reaction was stirred at 0° C. for 1 h before allyl iodide (3.8 mL, 42 mmol) was added. The ice bath was removed. The reaction mixture was stirred at room temperature for 2 h, poured into 1:1 brine:H$_2$O and extracted with DCM (3×). The combined DCM layer was dried (MgSO$_4$), filtered and concentrated to give 3 (8.75 g) as an oil.

Step 3: To a solution of KOH (6 g, 108 mmol) in methanol (60 mL) was added a solution of 3 (8.75 g) in methanol (20 mL) at room temperature. The reaction mixture was stirred at room temperature overnight and then concentrated under reduced pressure. The residue was diluted with H$_2$O. After extracting with Et2O (2×), the aqueous layer was acidified with 6M HCl to PH 2 and extracted (4×) with Et2O. The combined Et2O layer was dried (MgSO$_4$), filtered concentrated to give acid 4 (7.7 g) as a clear oil. $^1$H NMR (CDCl$_3$, 400 MHz): δ 7.82-7.80 (m, 2H), 7.60-7.56 (m, 1H), 7.52-7.49 (m, 2H), 5.46-5.30 (m, 1H), 5.08-5.04 (m, 2H), 3.79 (d, J=6.5 Hz, 2H), 3.80 (s, 2H), 1.29 (s, 6H).

Step 4: General procedures described in these Examples were followed. The crude acid chloride was used in the next step without further purification.

Step 5: General procedures described in these Examples were followed except replacing 1-Methyl-cyclohexanecarbonyl chloride with 3-(allyl-benzenesulfonyl-amino)-2,2-dimethyl-propionyl chloride. 0.2 g product was obtained. MS [M+H]$^+$: 477.

Step 6: General procedures described in these Examples were followed. $^1$H NMR (CDCl$_3$, 400 MHz): δ 10.0 (s, 1H), 8.80 (s, 1H), 8.44 (d, J=12.1 Hz, 1H), 7.69 (dd, J=0.8 12.0 Hz, 2H), 7.44-7.23 (m, 6H), 6.72-6.69 (m, 2H), 5.35-5.25 (m, 1H), 4.80-4.74 (m, 2H), 4.25 (s, 2H), 3.78 (d, J=6.3 Hz, 2H), 3.39-3.36 (m, 4H), 2.09-2.05 (m, 4H), 1.61 (s, 6H); MS [M+H]$^+$: 544.

Example 125

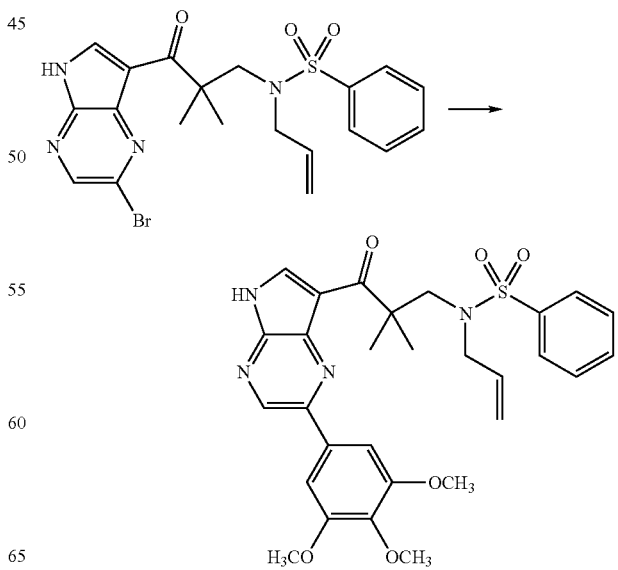

N-Allyl-N-{2,2-dimethyl-3-oxo-3-[2-(3,4,5-trimethoxy-phenyl)-5H-pyrrolo[2,3-b]pyrazin-7-yl]-propyl}-benzenesulfonamide General procedures described in these Examples were followed except replacing 3-pyrrolidino phenylboronic acid with 3,4,5-trimethoxyphenylboronic acid. $^1$H NMR (CDCl$_3$, 300 MHz): δ 9.39 (s, 1H), 8.79 (s, 1H), 8.41 (d, J=3.2 Hz, 1H), 7.48-7.43 (m, 1H), 7.31-7.26 (m, 2H), 5.38-5.27 (m, 1H), 4.87-4.80 (m, 2H), 4.18 (s, 2H), 3.97 (s, 6H), 3.96 (s, 3H), 3.80 (d, J=6.4 Hz, 2H), 1.58 (s, 6H); MS [M+H]$^+$: 565.

Example 126

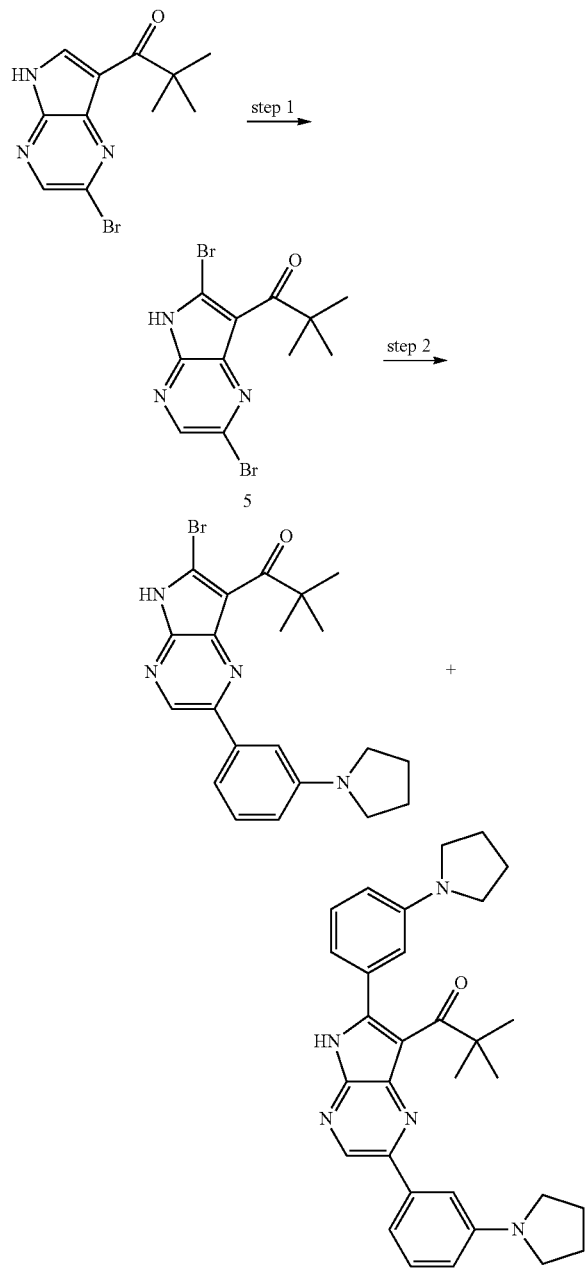

1-[6-Bromo-2-(3-pyrrolidin-1-yl-phenyl)-5H-pyrrolo[2,3-b]pyrazin-7-yl]-2,2-dimethyl-propan-1-one

1-[2,6-Bis-(3-pyrrolidin-1-yl-phenyl)-5H-pyrrolo[2,3-b]pyrazin-7-yl]-2,2-dimethyl-propan-1-one Step 1: A mixture of 1-(2-bromo-5H-pyrrolo[2,3-b]pyrazin-7-yl)-2,2-dimethyl-propan-1-one (1 g, 3.55 mmol) and N-bromosuccinimide (0.82 g, 4.6 mmol) in CCl$_4$ was heated at 140° C. for 14 h. After cooling to room temperature, the reaction mixture was purified by flash column chromatography with EtOAc in hexane (20% to 80% gradient over 30 min) to give the desired product 5 and starting material as an inseperable mixture (0.36 g). [M+H]$^+$: 358, 360, 362.

Step 2: General procedures described in these Examples were followed. Characterization for intermediate: $^1$H NMR (CDCl$_3$, 400 MHz): δ 10.2 (br s, 1H), 8.78 (s, 1H), 7.43 (s, 1H), 7.39-7.26 (m, 2H), 6.68 (d, J=5.7 Hz, 1H), 3.41-3.37 (m, 4H), 2.08-2.05 (m, 4H), 1.54 (s, 9H); [M+H]$^+$: 427, 429. Characterization for product: $^1$H NMR (CDCl$_3$, 400 MHz): δ 10.95 (s, 1H), 8.66 (s, 1H), 7.43 (s, 1H), 7.38-7.28 (m, 3H), 6.93 (d, J=7.6 Hz, 1H), 6.81 (s, 1H), 6.68-6.64 (m 2H), 3.41-3.37 (m, 4H), 3.34-3.31 (m, 4H), 2.07-2.03 (m, 4H), 2.01-1.98 (m, 4H), 1.45 (s, 9H); [M+H]$^+$: 494.

Example 127

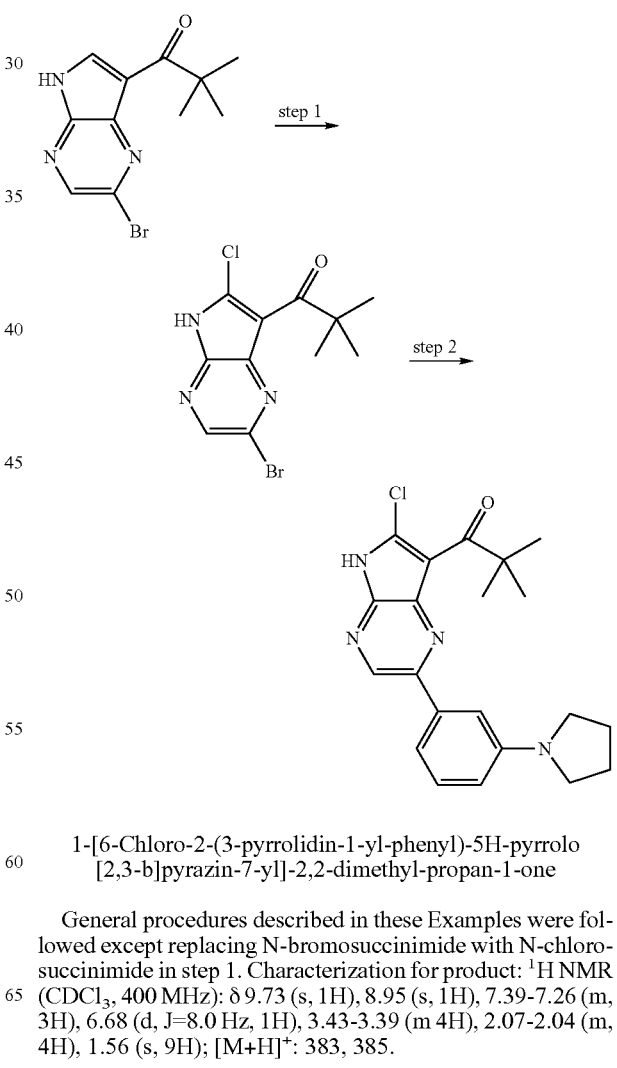

1-[6-Chloro-2-(3-pyrrolidin-1-yl-phenyl)-5H-pyrrolo[2,3-b]pyrazin-7-yl]-2,2-dimethyl-propan-1-one General procedures described in these Examples were followed except replacing N-bromosuccinimide with N-chlorosuccinimide in step 1. Characterization for product: $^1$H NMR (CDCl$_3$, 400 MHz): δ 9.73 (s, 1H), 8.95 (s, 1H), 7.39-7.26 (m, 3H), 6.68 (d, J=8.0 Hz, 1H), 3.43-3.39 (m 4H), 2.07-2.04 (m, 4H), 1.56 (s, 9H); [M+H]$^+$: 383, 385.

Example 128

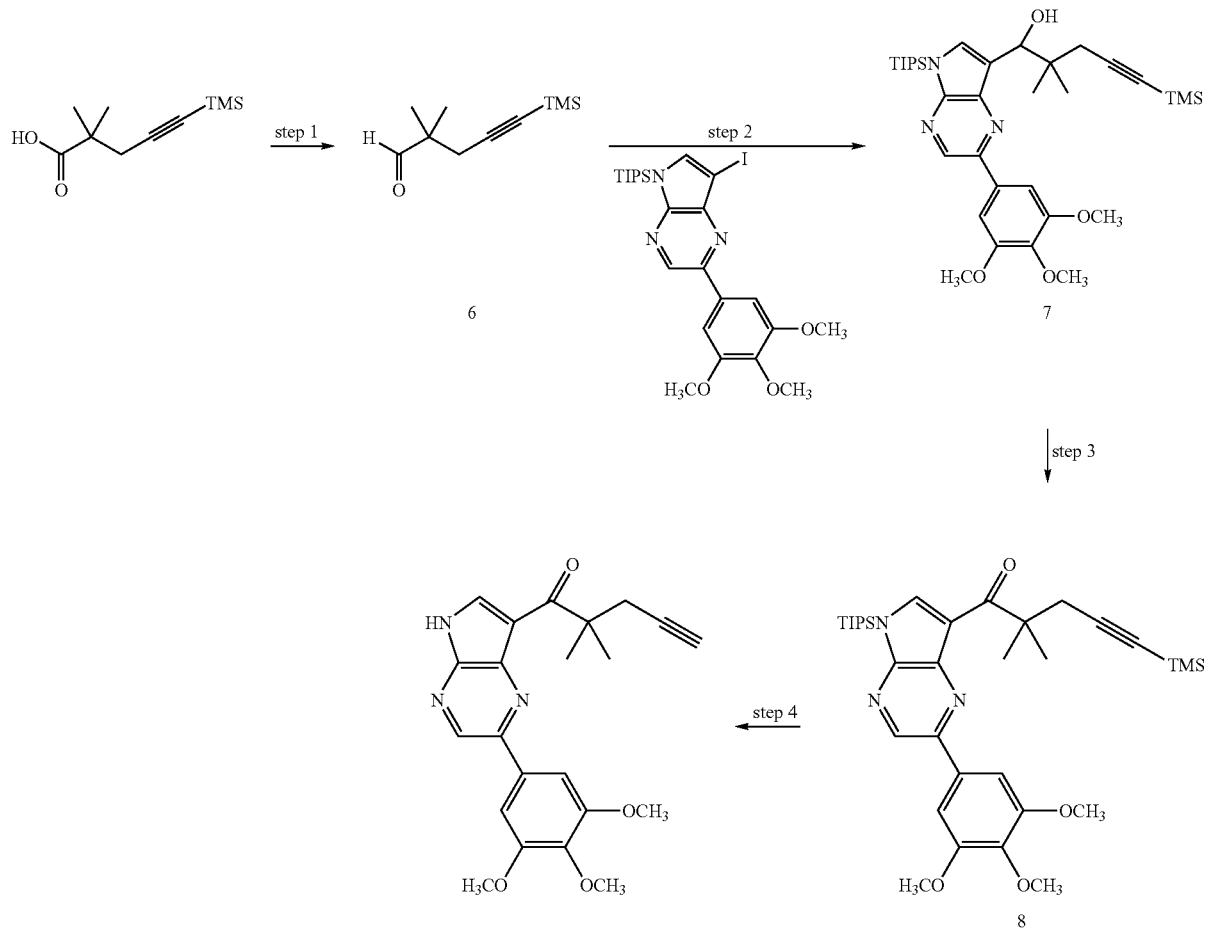

2,2-Dimethyl-1-[2-(3,4,5-trimethoxy-phenyl)-5H-pyrrolo[2,3-b]pyrazin-7-yl]-pent-4-yn-1-one Step 1: To a solution of 2,2-Dimethyl-5-trimethylsilanyl-pent-4-ynoic acid ethyl ester (5.6 g, 24.8 mmol, prepared according to reference Trost, B. M. et al. Journal of the American Chemical Society (2006), 128(20), 6745-6754) in DCM (50 mL) at −78° C. was added DIBAL-H (1 M in toluene, cooled to −78° C., 30 mL, 30 mmol) via a cannula. The reaction was stirred at −78° C. for 1 h and quenched with cold (~78° C.) MeOH via a cannula. After stirring for an additional 5 min at −78° C., saturated aqueous Rochelle salt (60 mL) was added. Dry ice-acetone bath was removed. The mixture was stirred for 3 h at room temperature and extracted with EtOAc (3×), the combined organic layer was dried (MgSO$_4$), filtered, and concentrated. The residue was purified by flash column chromatography on silica gel with EtOAc in hexane (1% to 10% gradient over 25 min) to afford aldehyde 6 (2.4 g) as a clear oil. $^1$H NMR (CDCl$_3$, 400 MHz): δ 9.40 (s, 1H), 2.22 (s, 2H), 1.01 (s, 6H), 0 (s, 9H).

Step 2: General procedures described in these Examples were followed except replacing 1-methyl-cyclohexanecarbaldehyde with 2,2-Dimethyl-5-trimethylsilanyl-pent-4-ynal 6. $^1$H NMR (CDCl$_3$, 400 MHz): δ 8.64 (s, 1H), 7.54 (s, 1H), 7.25 (s, 2H), 4.98 (d, J=8.7 Hz, 1H), 4.51 (d, J=8.7 Hz, 1H), 3.97 (s, 6H), 3.92 (s, 3H), 2.37 (d, J=16.8 Hz, 1H), 2.23 (d, J=16.8 Hz, 1H), 1.94-1.78 (m, 3H), 1.16 (s, 18H), 1.13 (s, 6H), 0.18 (s, 9H).

Step 3: To a suspension of compound 7 (0.63 g, 1 mmol) and NaHCO$_3$ (0.2 g, 2.4 mmol) in dichloromethane (20 ml) at 0° C. was added Dess-Martin periodinane (0.51 g, 1.2 mmol). The reaction mixture was allowed to stir at room temperature for 2 hours. The reaction mixture was partitioned between dichloromethane and 2:1 saturated aqueous NaHCO$_3$:10% aqueous Na$_2$S$_2$O$_3$. The organic layers were collected, dried over Na$_2$SO$_4$, filtered, and concentrated. The residue was purified by silica gel chromatography using 5%-10% EtOAc in hexanes as eluant to provide of ketone 8 (0.6 g, 95% yield) as a white foam.

Step 4: A suspension of ketone 8 (0.22 g, 0.35 mmol) and K$_2$CO$_3$ (0.29 g, 2.1 mmol) in MeOH (10 mL) was stirred at room temperature overnight. MeOH was removed under reduced pressure. The residue was diluted with H$_2$O and extracted with EtOAc (3×). The combined organic layer was dried (MgSO$_4$), filtered and concentrated to give RO5426752 (50 mg, 36% yield) as an off-white solid. $^1$H NMR (DMSO-d$_6$, 400 MHz): δ 13.02 (s, 1H), 9.07 (s, 1H), 8.54 (s, 1H), 7.54 (s, 2H), 3.91 (s, 6H), 3.73 (s, 3H), 3.09 (d, J=2.7 Hz, 2H), 2.73 (t, J=2.5 Hz, 1H), 1.52 (s, 6H); [M+H]$^+$: 394.

Example 129

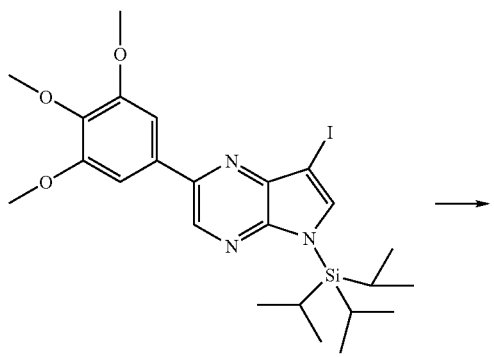

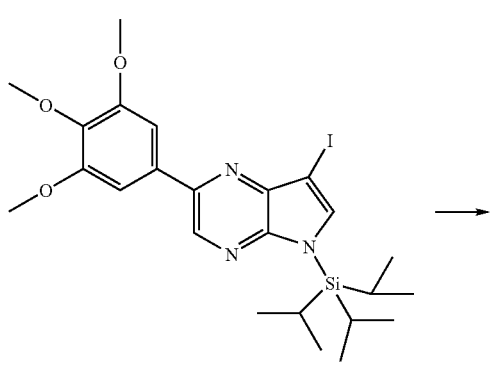

4-Methoxy-1-[2-(3,4,5-trimethoxy-phenyl)-5H-pyrrolo[2,3-b]pyrazin-7-yl]-pentan-1-one 4-Methoxy-1-[2-(3,4,5-trimethoxy-phenyl)-5H-pyrrolo[2,3-b]pyrazin-7-yl]-pentan-1-one was prepared starting from 7-iodo-5-triisopropylsilanyl-2-(3,4,5-trimethoxy-phenyl)-5H-pyrrolo[2,3-b]pyrazine and 4-methoxy-pentanal (Berichte der Deutschen Chemischen Gesellschaft [Abteilung] B: Abhandlungen (1919), 52B 1800-12) following general procedures as described in these Examples 66, to afford a brown solid. MP 150-151° C., M+H=400.

Example 130

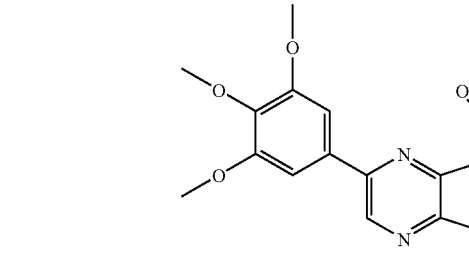

2,N-Dimethoxy-2,N-dimethyl-propionamide

A solution of 2-methoxy-2-methyl-propionic acid (1.0 g, 8.46 mmol) in anhydrous dichloromethane (10 ml) was slowly treated with DCC (1M in DCM, 10.16 ml, 10.16 mmol), O,N-Dimethyl-hydroxylamine (991 mg, 10.16 mmol), DMAP (103 mg, 0.843 mmol), and TEA (1.42 ml, 10.16 mmol). The reaction mixture was allowed to stir at room temperature for 16 hours. The reaction mixture was partitioned between DCM/1N HCl. The organic layers were collected, dried over MgSO$_4$, filtered, and concentrated. The crude product was purified by silica gel chromatography using 5-60% EtOAc in hexanes as eluant providing 200 mg (14.66%) of 2,N-dimethoxy-2,N-dimethyl-propionamide as a colorless oil.

Example 131

2-Methoxy-2-methyl-1-[2-(3,4,5-trimethoxy-phenyl)-5H-pyrrolo[2,3-b]pyrazin-7-yl]-propan-1-one A solution of 7-iodo-5-triisopropylsilanyl-2-(3,4,5-trimethoxy-phenyl)-5H-pyrrolo[2,3-b]pyrazine (233 mg, 0.410 mmol) in anhydrous tetrahydrofuran (3 ml) was cooled to −78° C. and treated with nBuLi (2.29M in hexanes, 0.25 ml, 0.57 mmol) dropwise. The solution was stirred for 30 seconds and then 2,N-dimethoxy-2,N-dimethyl-propionamide (198 mg, 1.23 mmol), dissolved in THF (5 ml), was added dropwise. The reaction mixture was stirred at −78° C. for 30 minutes and then at room temperature 30 minutes. The reaction mixture was quenched with saturated aqueous NaHSO$_4$ and then partitioned between EtOAc/water. The organic layers were collected, dried over MgSO$_4$, filtered, and concentrated giving a brown oil. The oil was purified by silica gel chromatography using 10-100% EtOAc in hexanes as eluant providing 14 mg (9%) of 2-methoxy-2-methyl-1-[2-(3,4,5-trimethoxy-phenyl)-5H-pyrrolo[2,3-b]pyrazin-7-yl]-propan-1-one as a yellow solid. MP 237.8-239.1° C., M+H=386.

Example 132

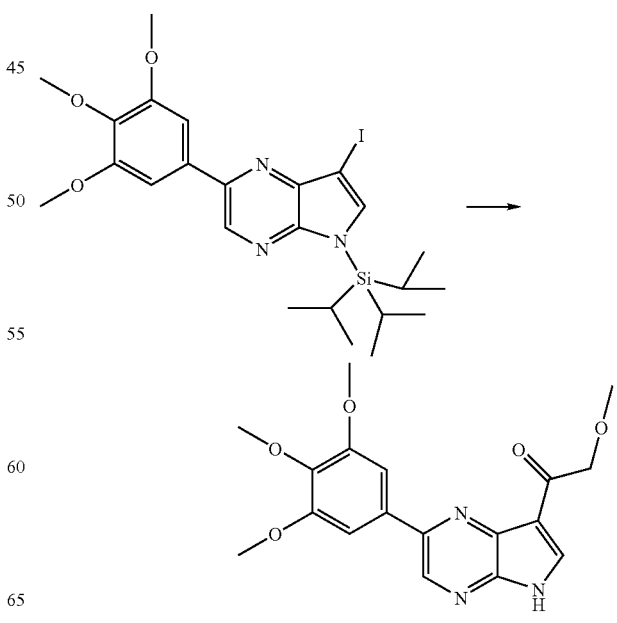

2-Methoxy-1-[2-(3,4,5-trimethoxy-phenyl)-5H-pyrrolo[2,3-b]pyrazin-7-yl]-ethanone 2-Methoxy-1-[2-(3,4,5-trimethoxy-phenyl)-5H-pyrrolo[2,3-b]pyrazin-7-yl]-ethanone was prepared starting from 7-iodo-5-triisopropylsilanyl-2-(3,4,5-trimethoxy-phenyl)-5H-pyrrolo[2,3-b]pyrazine and 2,N-dimethoxy-N-methyl-acetamide (Journal of Medicinal Chemistry, 47(10), 2405-2408; 2004) following general procedures as described in these Examples, to afford a pale yellow solid. MP 229-230° C., M+H=358.

Example 133

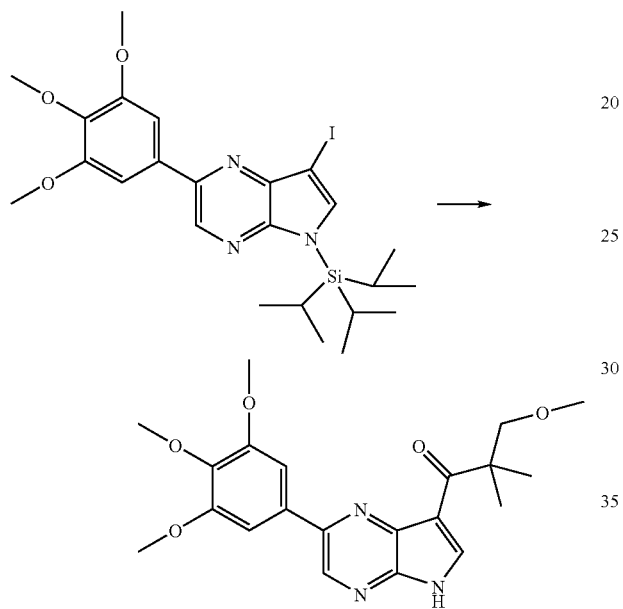

3,N-Dimethoxy-2,2,N-trimethyl-propionamide

A solution of 3-methoxy-2,2-dimethyl-propionic acid (1.0 g, 7.6 mmol) in thionyl chloride (5 ml) was heated to 50° C. for 16 hours. The reaction mixture was concentrated to a yellow residue and then dissolved in DCM (15 ml). O,N-Dimethyl-hydroxylamine-hydrogen chloride (886 mg, 9.1 mmol) and powdered $K_2CO_3$ (2.2 g, 16 mmol) were added, and the reaction mixture was stirred at room temperature for 16 hours. The reaction mixture was filtered through a filter funnel, and the filtrate was collected and concentrated giving a white semisolid. The crude product was purified by silica gel chromatography using 20-50% EtOAc in hexanes as eluant providing 260 mg (20%) of 3,N-dimethoxy-2,2,N-trimethyl-propionamide as a colorless oil.

Example 134

3-Methoxy-2,2-dimethyl-1-[2-(3,4,5-trimethoxy-phenyl)-5H-pyrrolo[2,3-b]pyrazin-7-yl]-propan-1-one 3-Methoxy-2,2-dimethyl-1-[2-(3,4,5-trimethoxy-phenyl)-5H-pyrrolo[2,3-b]pyrazin-7-yl]-propan-1-one was prepared starting from 7-iodo-5-triisopropylsilanyl-2-(3,4,5-trimethoxy-phenyl)-5H-pyrrolo[2,3-b]pyrazine and 3,N-dimethoxy-2,2,N-trimethyl-propionamide following general procedures as described in these Examples, to afford a pale yellow solid. M+H=400.

Example 135

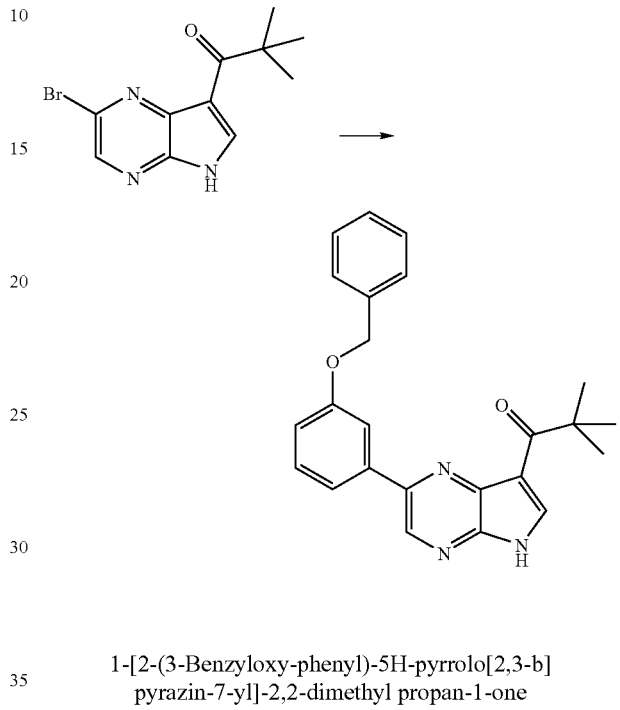

1-[2-(3-Benzyloxy-phenyl)-5H-pyrrolo[2,3-b]pyrazin-7-yl]-2,2-dimethyl propan-1-one A microwave tube was charged with 1-(2-bromo-5H-pyrrolo[2,3-b]pyrazin-7-yl)-2,2-dimethyl-propan-1-one (157 mg, 0.56 mmol), 3-[(phenylmethyl)oxy]phenyl]boronic acid (140 mg, 0.61 mmol), [1,1'-bis(diphenylphosphino)ferrocene]dichloro-palladium(II) (36 mg, 0.040 mmol), and $K_2CO_3$ (192 mg, 1.39 mmol). Dioxane (4 ml) and water (1 ml) were added, and the tube was microwaved at 130° C. and 150° C. each for 30 min. The reaction mixture was partitioned between EtOAc/water. The organic layers were collected, dried over $MgSO_4$, filtered, and concentrated giving a dark brown solid. The crude product was purified by silica gel chromatography using 20-100% EtOAc in hexanes as eluant to provide 50 mg (23%) of 1-[2-(3-benzyloxy-phenyl)-5H-pyrrolo[2,3-b]pyrazin-7-yl]-2,2-dimethyl propan-1-one as a yellow solid. MP 184-185° C., M+H=385.

Example 136

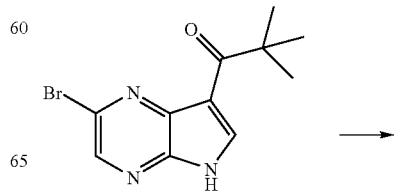

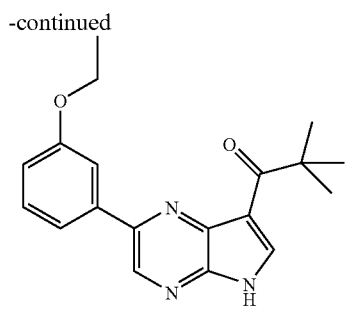

1-[2-(3-Ethoxy-phenyl)-5H-pyrrolo[2,3-b]pyrazin-7-yl]-2,2-dimethyl-propan-1-one

A microwave tube was charged with 1-(2-bromo-5H-pyrrolo[2,3-b]pyrazin-7-yl)-2,2-dimethyl-propan-1-one (146 mg, 0.52 mmol), 3-ethoxybenzeneboronic acid (94 mg, 0.57 mmol), [1,1'-bis(diphenylphosphino)ferrocene]dichloro-palladium(II) (34 mg, 0.041 mmol), and $K_2CO_3$ (179 mg, 1.30 mmol). Dioxane (4 ml) and water (1 ml) were added, and the tube was microwaved at 150° C. for 30 min. The reaction mixture was partitioned between EtOAc/water. The organic layers were collected, dried over $MgSO_4$, filtered, and concentrated giving a dark brown solid. The crude product was purified by preparative thin layer chromatography (70% EtOAc/Hexane) as eluant to provide 120 mg (72%) of 1-[2-(3-ethoxy-phenyl)-5H-pyrrolo[2,3-b]pyrazin-7-yl]-2,2-dimethyl-propan-1-one as a yellow solid. MP 195-196° C., M+H=324.

Example 137

1-[2-(3-Isobutoxy-phenyl)-5H-pyrrolo[2,3-b]pyrazin-7-yl]-2,2-dimethyl-propan-1-one 1-[2-(3-Isobutoxy-phenyl)-5H-pyrrolo[2,3-b]pyrazin-7-yl]-2,2-dimethyl-propan-1-one was prepared starting from 1-(2-bromo-5H-pyrrolo[2,3-b]pyrazin-7-yl)-2,2-dimethyl-propan-1-one and 3-Isobutoxyphenylboronic acid following general procedures as described in these Examples. Silica gel chromatography using 30-100% EtOAc in hexanes as eluant provided 170 mg (94%) of a pale yellow solid. MP 177-178° C., M+H=351.

Example 138

1-[2-(3-Isopropoxy-phenyl)-5H-pyrrolo[2,3-b]pyrazin-7-yl]-2,2-dimethyl-propan-1-one 1-[2-(3-Isopropoxy-phenyl)-5H-pyrrolo[2,3-b]pyrazin-7-yl]-2,2-dimethyl-propan-1-one was prepared starting from 1-(2-bromo-5H-pyrrolo[2,3-b]pyrazin-7-yl)-2,2-dimethyl-propan-1-one and 3-Isopropoxybenzeneboronic acid following general procedures as described in these Examples. Silica gel chromatography using 30-70% EtOAc in hexanes as eluant provided 140 mg (82%) of a yellow solid. MP 149-150° C., M+H=338

Example 139

2,2-Dimethyl-1-[2-(3-propoxy-phenyl)-5H-pyrrolo[2,3-b]pyrazin-7-yl]-propan-1-one 2,2-Dimethyl-1-[2-(3-propoxy-phenyl)-5H-pyrrolo[2,3-b]pyrazin-7-yl]-propan-1-one was prepared starting from 1-(2-bromo-5H-pyrrolo[2,3-b]pyrazin-7-yl)-2,2-dimethyl-propan-1-one and 3-propyloxybenzene boronic acid following general procedures as described in these Examples. Silica gel chromatography using 30-70% EtOAc in hexanes as eluant provided 56 mg (38%) of a yellow solid. MP 179-180° C., M+H=338.

Example 140

4-[7-(2,2-Dimethyl-propionyl)-5H-pyrrolo[2,3-b]pyrazin-2-yl]-benzenesulfonamide

4-[7-(2,2-Dimethyl-propionyl)-5H-pyrrolo[2,3-b]pyrazin-2-yl]-benzenesulfonamide was prepared starting from 1-(2-bromo-5H-pyrrolo[2,3-b]pyrazin-7-yl)-2,2-dimethyl-propan-1-one and 4-(aminosulphonyl)benzeneboronic acid following general procedures as described in these Examples. MP 277-278° C., M+H=359.

Example 141

3-[7-(2,2-Dimethyl-propionyl)-5H-pyrrolo[2,3-b]pyrazin-2-yl]-N-methyl-benzenesulfonamide 3-[7-(2,2-Dimethyl-propionyl)-5H-pyrrolo[2,3-b]pyrazin-2-yl]-N-methyl-benzenesulfonamide was prepared starting from 1-(2-bromo-5H-pyrrolo[2,3-b]pyrazin-7-yl)-2,2-dimethyl-propan-1-one and 3-methylsulfamoylphenylboronic acid following general procedures as described in these Examples. MP 245-247° C., M+H=373.

Example 142

4-[7-(2,2-Dimethyl-propionyl)-5H-pyrrolo[2,3-b]pyrazin-2-yl]-N-methyl-benzenesulfonamide 4-[7-(2,2-Dimethyl-propionyl)-5H-pyrrolo[2,3-b]pyrazin-2-yl]-N-methyl-benzenesulfonamide was prepared starting from 1-(2-bromo-5H-pyrrolo[2,3-b]pyrazin-7-yl)-2,2-dimethyl-propan-1-one and 4-methylsulfamoylphenylboronic acid following general procedures as described in these Examples. MP 278-280° C., M+H=373.

Example 143

1-{2-[3-(3-Hydroxy-propyl)-phenyl]-5H-pyrrolo[2,3-b]pyrazin-7-yl}-2,2-dimethyl-propan-1-one 1-{2-[3-(3-Hydroxy-propyl)-phenyl]-5H-pyrrolo[2,3-b]pyrazin-7-yl}-2,2-dimethyl-propan-1-one was prepared starting from 1-(2-bromo-5H-pyrrolo[2,3-b]pyrazin-7-yl)-2,2-dimethyl-propan-1-one and 3-(3-hydroxypropyl)benzeneboronic acid following general procedures as described in these Examples. Silica gel chromatography using 20-100% EtOAc in hexanes as eluant provided 80 mg (48%) of a yellow solid. MP 170-171° C., M+H=338.

Example 144

3-[7-(2,2-Dimethyl-propionyl)-5H-pyrrolo[2,3-b]pyrazin-2-yl]-benzene sulfonamide 3-[7-(2,2-Dimethyl-propionyl)-5H-pyrrolo[2,3-b]pyrazin-2-yl]-benzenesulfonamide was prepared starting from 1-(2-bromo-5H-pyrrolo[2,3-b]pyrazin-7-yl)-2,2-dimethyl-propan-1-one and (3-aminosulfonylphenyl)Boronic Acid following general procedures as described in these Examples. Silica gel chromatography using 20-100% EtOAc in hexanes as eluant provided 60 mg (37%) of a pale yellow solid. MP 275-277° C., M+H=359.

Example 145

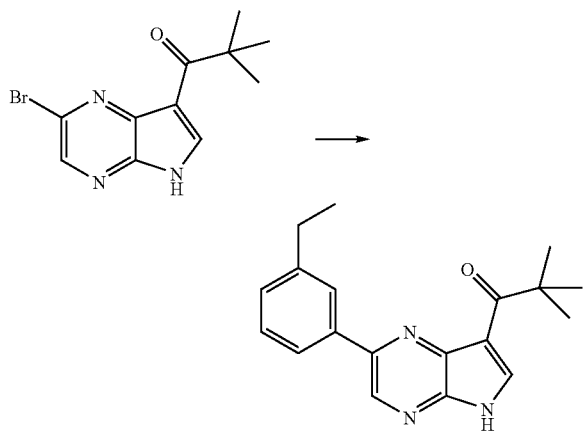

1-[2-(3-Ethyl-phenyl)-5H-pyrrolo[2,3-b]pyrazin-7-yl]-2,2-dimethyl-propan-1-one

A microwave tube was charged with 1-(2-bromo-5H-pyrrolo[2,3-b]pyrazin-7-yl)-2,2-dimethyl-propan-1-one (152 mg, 0.54 mmol), 3-ethylphenylboronic acid (89 mg, 0.59 mmol), [1,1'-bis(diphenylphosphino)ferrocene]dichloro-palladium(II) (35 mg, 0.042 mmol), and K$_2$CO$_3$ (186 mg, 1.34 mmol). Dioxane (4 ml) and water (1 ml) were added, and the tube was microwaved at 150° C. for 45 min. The reaction mixture was filtered through a plug of celite. The filtrate was collected and partitioned between EtOAc/water. The organic layers were collected, dried over MgSO$_4$, filtered, and concentrated giving a dark brown solid. The crude product was purified by silica gel chromatography using 20-50% EtOAc in hexanes as eluant provided 82 mg (50%) of 1-[2-(3-ethyl-phenyl)-5H-pyrrolo[2,3-b]pyrazin-7-yl]-2,2-dimethyl-propan-1-one as a yellow solid. MP 199-200.1° C., M+H=308.

Example 146

1-[2-(3,5-Dimethoxy-phenyl)-5H-pyrrolo[2,3-b]pyrazin-7-yl]-2,2-dimethyl-propan-1-one 1-[2-(3,5-Dimethoxy-phenyl)-5H-pyrrolo[2,3-b]pyrazin-7-yl]-2,2-dimethyl-propan-1-one was prepared starting from 1-(2-bromo-5H-pyrrolo[2,3-b]pyrazin-7-yl)-2,2-dimethyl-propan-1-one and (3,5-dimethoxyphenyl)boronic acid following general procedures as described in these Examples. Silica gel chromatography using 10-50% EtOAc in hexanes as eluant provided 90 mg (52%) of a yellow solid. MP 206.9-207.7° C., M+H=340.

Example 147

(1-Methyl-cyclopentyl)-[2-(3,4,5-trimethoxy-phenyl)-5H-pyrrolo[2,3-b]pyrazin-7-yl]-methanone (1-Methyl-cyclopentyl)-[2-(3,4,5-trimethoxy-phenyl)-5H-pyrrolo[2,3-b]pyrazin-7-yl]-methanone was prepared starting from (2-bromo-5H-pyrrolo[2,3-b]pyrazin-7-yl)-(1-methyl-cyclopentyl)-methanone and 3,4,5-trimethoxyphenylboronic acid following general procedures as described in these Examples. Silica gel chromatography using 2-50% EtOAc in hexanes as eluant gave a pale brown solid which was washed with 1:1 Et$_2$O/Hexanes provided 10 mg (7.7%) of an off white solid. MP 244-246° C., M+H=396.

Example 148

1-{2-[3-(2-Hydroxy-ethyl)-phenyl]-5H-pyrrolo[2,3-b]pyrazin-7-yl}-2,2-dimethyl-propan-1-one 1-{2-[3-(2-Hydroxy-ethyl)-phenyl]-5H-pyrrolo[2,3-b]pyrazin-7-yl}-2,2-dimethyl-propan-1-one was prepared starting from 1-(2-bromo-5H-pyrrolo[2,3-b]pyrazin-7-yl)-2,2-dimethyl-propan-1-one and 3-(2-hydroxyethyl)benzeneboronic acid following general procedures as described in these Examples. Silica gel chromatography using 20-100% EtOAc in hexanes as eluant provided 69 mg (41%) of a yellow solid. MP 202-203° C., M+H=324.

Example 149

1-[2-(3-Aminomethyl-phenyl)-5H-pyrrolo[2,3-b]pyrazin-7-yl]-2,2-dimethyl-propan-1-one 1-[2-(3-Aminomethyl-phenyl)-5H-pyrrolo[2,3-b]pyrazin-7-yl]-2,2-dimethyl-propan-1-one was prepared starting from 1-(2-bromo-5H-pyrrolo[2,3-b]pyrazin-7-yl)-2,2-dimethyl-propan-1-one and (3-aminomethylphenyl)boronic acid hydrochloride following general procedures as described in these Examples. Silica gel chromatography using 0-20% [5% NH$_4$OH:MeOH]/DCM as eluant gave a brown solid which was washed with 1:2 Et$_2$O/Hexanes to provide 75 mg (48%) of a pale brown solid. MP 176-178° C., M+H=309.

Example 150

2,2-Dimethyl-1-[2-(3-piperidin-1-ylmethyl-phenyl)-5H-pyrrolo[2,3-b]pyrazin-7-yl]-propan-1-one 2,2-Dimethyl-1-[2-(3-piperidin-1-ylmethyl-phenyl)-5H-pyrrolo[2,3-b]pyrazin-7-yl]-propan-1-one was prepared starting from 1-(2-bromo-5H-pyrrolo[2,3-b]pyrazin-7-yl)-2,2-dimethyl-propan-1-one and 3-(piperidin-1-ylmethyl)phenylboronic acid hydrochloride following general procedures as described in these Examples. Silica gel chromatography using 0-20% [5% NH$_4$OH:MeOH]/DCM as eluant gave a brown solid which was washed with 1:2 Et$_2$O/Hexanes to provide 70 mg (36%) of a pale brown solid. MP 176-177° C., M+H=377.

Example 151

1-[2-(2-Fluoro-phenyl)-5H-pyrrolo[2,3-b]pyrazin-7-yl]-2,2-dimethyl-propan-1-one

1-[2-(2-Fluoro-phenyl)-5H-pyrrolo[2,3-b]pyrazin-7-yl]-2,2-dimethyl-propan-1-one was prepared starting from 1-(2-bromo-5H-pyrrolo[2,3-b]pyrazin-7-yl)-2,2-dimethyl-propan-1-one and 3-fluorobenzeneboronic acid following general procedures as described in these Examples. Silica gel chromatography using 20-100% EtOAc in hexanes as eluant gave a brown solid which was washed with 1:1 Et$_2$O/Hexanes to provide 10 mg (12%) of a pale yellow solid. M+H=298.

Example 152

1-[2-(2-Hydroxy-phenyl)-5H-pyrrolo[2,3-b]pyrazin-7-yl]-2,2-dimethyl-propan-1-one 1-[2-(2-Hydroxy-phenyl)-5H-pyrrolo[2,3-b]pyrazin-7-yl]-2,2-dimethyl-propan-1-one was prepared starting from 1-(2-bromo-5H-pyrrolo[2,3-b]pyrazin-7-yl)-2,2-dimethyl-propan-1-one and 2-hydroxybenzeneboronic acid following general procedures as described in these Examples. Silica gel chromatography using 5-70% EtOAc in hexanes as eluant gave 53 mg (28%) of a yellow solid. MP 282-283° C., M+H=296.

Example 153

(1-Methyl-cyclohexyl)-[2-(3-morpholin-4-yl-phenyl)-5H-pyrrolo[2,3-b]pyrazin-7-yl]-methanone (1-Methyl-cyclohexyl)-[2-(3-morpholin-4-yl-phenyl)-5H-pyrrolo[2,3-b]pyrazin-7-yl]-methanone was prepared starting from (2-bromo-5H-pyrrolo[2,3-b]pyrazin-7-yl)-(1-methyl-cyclohexyl)-methanone and 4-[3-(4,4,5,5-tetramethyl-1,3,2-dioxaborolan-2-yl)phenyl]morpholine following general procedures as described in these Examples. MP 208-209° C., M+H=405.

Example 154

(1-Methyl-cyclopentyl)-[2-(3-morpholin-4-yl-phenyl)-5H-pyrrolo[2,3-b]pyrazin-7-yl]-methanone (1-Methyl-cyclopentyl)-[2-(3-morpholin-4-yl-phenyl)-5H-pyrrolo[2,3-b]pyrazin-7-yl]-methanone was prepared starting from (2-bromo-5H-pyrrolo[2,3-b]pyrazin-7-yl)-(1-methyl-cyclopentyl)-methanone and 4-[3-(4,4,5,5-tetramethyl-1,3,2-dioxaborolan-2-yl)phenyl]morpholine following general procedures as described in these Examples. M+H=391.

Example 155

(1-Methyl-cyclohexyl)-{2-[3-(5-methyl-[1,3,4]oxadiazol-2-yl)-phenyl]-5H-pyrrolo[2,3-b]pyrazin-7-yl}-methanone (1-Methyl-cyclohexyl)-{2-[3-(5-methyl-[1,3,4]oxadiazol-2-yl)-phenyl]-5H-pyrrolo[2,3-b]pyrazin-7-yl}-methanone was prepared starting from (2-bromo-5H-pyrrolo[2,3-b]pyrazin-7-yl)-(1-methyl-cyclohexyl)-methanone and 3-(5-Methyl-1,3,4-oxadiazol-2-yl)phenylboronic acid following general procedures as described in these Examples. MP 234-236° C., M+H=402.

Example 156

{2-[3-(3-Hydroxy-propyl)-phenyl]-5H-pyrrolo[2,3-b]pyrazin-7-yl}-(1-methyl-cyclohexyl)-methanone {2-[3-(3-Hydroxy-propyl)-phenyl]-5H-pyrrolo[2,3-b]pyrazin-7-yl}-(1-methyl-cyclohexyl)-methanone was prepared starting from (2-bromo-5H-pyrrolo[2,3-b]pyrazin-7-yl)-(1-methyl-cyclohexyl)-methanone and 3-(3-hydroxypropyl)phenylboronic acid following general procedures as described in these Examples. MP 80-83° C., M+H=378.

Example 157

[2-(3-Methoxy-phenyl)-5H-pyrrolo[2,3-b]pyrazin-7-yl]-(1-methyl-cyclohexyl)-methanone

[2-(3-Methoxy-phenyl)-5H-pyrrolo[2,3-b]pyrazin-7-yl]-(1-methyl-cyclohexyl)-methanone was prepared starting from (2-bromo-5H-pyrrolo[2,3-b]pyrazin-7-yl)-(1-methyl-cyclohexyl)-methanone and 3-methoxyphenyl boronic acid following general procedures as described in these Examples. MP 173-175° C., M+H=350.

Example 158

[2-(4-Dimethylamino-phenyl)-5H-pyrrolo[2,3-b]pyrazin-7-yl]-(1-methyl-cyclohexyl)-methanone

[2-(4-Dimethylamino-phenyl)-5H-pyrrolo[2,3-b]pyrazin-7-yl]-(1-methyl-cyclohexyl)-methanone was prepared starting from (2-bromo-5H-pyrrolo[2,3-b]pyrazin-7-yl)-(1-methyl-cyclohexyl)-methanone and 4-(dimethylamino)phenylboronic acid following general procedures as described in these Examples. MP 272-274° C., M+H=363.

Example 159

4-[7-(2,2-Dimethyl-propionyl)-5H-pyrrolo[2,3-b]pyrazin-2-yl]-benzoic acid

4-[7-(2,2-Dimethyl-propionyl)-5H-pyrrolo[2,3-b]pyrazin-2-yl]-benzoic acid was prepared starting from 1-(2-bromo-5H-pyrrolo[2,3-b]pyrazin-7-yl)-2,2-dimethyl-propan-1-one and 4-carboxyphenylboronic acid following general procedures as described in these Examples. Silica gel chromatography using 50-100% [5% AcOH:EtOAc]/Hexanes as eluant gave 10 mg (6%) of a pale brown solid. M+H=324.

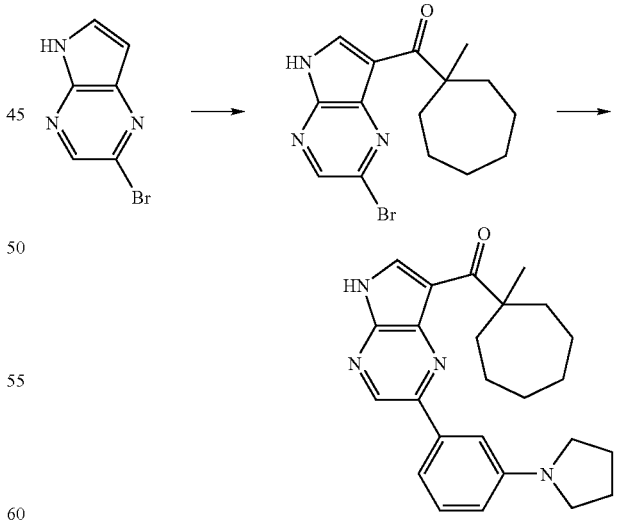

1-Methyl-cycloheptanecarbonyl chloride

A solution of 1-methyl-cycloheptanecarboxylic acid (156 mg, 0.998 mmol) (Journal of Organic Chemistry (1982), 47(17), 3242-7) in thionyl chloride (5 ml) was stirred at room temperature for 2 days and then concentrated on high vacuum giving 174 mg (99%) of 1-methyl-cycloheptanecarbonyl chloride as a yellow oil.

Example 160

(1-Methyl-cycloheptyl)-[2-(3-pyrrolidin-1-yl-phenyl)-5H-pyrrolo[2,3-b]pyrazin-7-yl]-methanone (1-Methyl-cycloheptyl)-[2-(3-pyrrolidin-1-yl-phenyl)-5H-pyrrolo[2,3-b]pyrazin-7-yl]-methanone was prepared starting from (2-bromo-5H-pyrrolo[2,3-b]pyrazin-7-yl)-(1-methyl-cycloheptyl)-methanone and 3-(1-pyrrolidinyl)phenylboronic acid following general procedures as described in these Examples. MP 192-193° C., M+H=403.

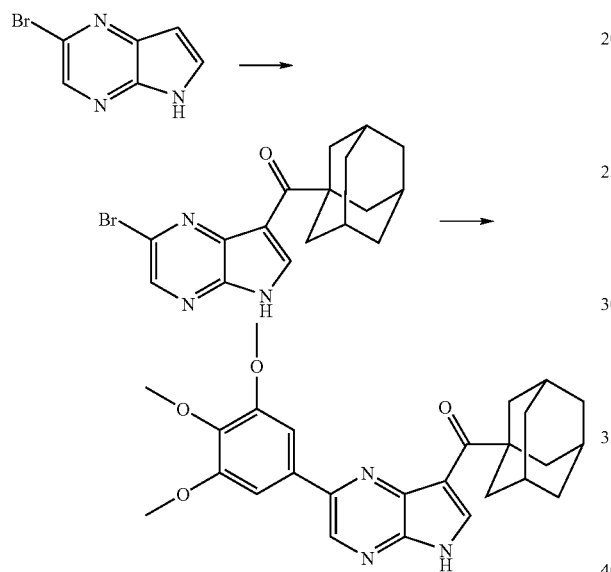

Example 161

Adamantan-1-yl-(2-bromo-5H-pyrrolo[2,3-b]pyrazin-7-yl)-methanone

Adamantan-1-yl-(2-bromo-5H-pyrrolo[2,3-b]pyrazin-7-yl)-methanone was prepared starting from 2-bromo-5H-pyrrolo[2,3-b]pyrazine and adamantane-1-carbonyl chloride following general procedures as described in these Examples. MP 279-280° C., M+H=360.

Example 162

Adamantan-1-yl-[2-(3,4,5-trimethoxy-phenyl)-5H-pyrrolo[2,3-b]pyrazin-7-yl]-methanone Adamantan-1-yl-[2-(3,4,5-trimethoxy-phenyl)-5H-pyrrolo[2,3-b]pyrazin-7-yl]-methanone was prepared starting from adamantan-1-yl-(2-bromo-5H-pyrrolo[2,3-b]pyrazin-7-yl)-methanone and 3,4,5-trimethoxyphenylboronic acid following general procedures as described in these Examples. MP 267-268° C., M+H=448.

Example 163

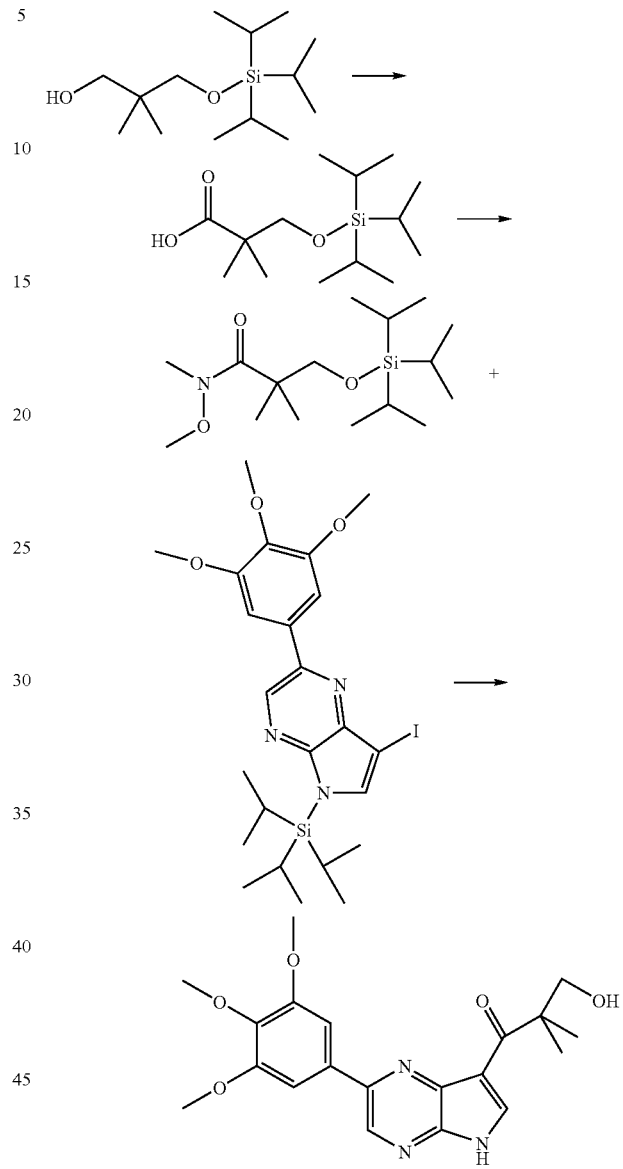

2,2-Dimethyl-3-triisopropylsilanyloxy-propionic acid

A solution of 2,2-Dimethyl-3-triisopropylsilanyloxy-propan-1-ol (1.39 g, 5.34 mmol) (Journal of the American Chemical Society, 123(39), 9687-9688; 2001) dissolved in ACN (14 ml), $CCl_4$ (14 ml), and water (22 ml) was treated with sodium periodate (4.57 g, 21.4 mmol) and then $RuCl_3$—$H_2O$ (33 mg, 0.16 mmol). After stirring at room temperature for approximately 2 hours, the reaction mixture was partitioned between DCM/water. The organic layers were collected, dried over $MgSO_4$, filtered, and concentrated giving a black oil. Silica gel chromatography using 0-30% EtOAc in hexanes as eluant provided 1.23 mg (84%) of 2,2-dimethyl-3-triisopropylsilanyloxy-propionic acid. M−H=569.

Example 164

N-Methoxy-2,2,N-trimethyl-3-triisopropylsilanyloxy-propionamide

A solution of 2,2-dimethyl-3-triisopropylsilanyloxy-propionic acid in anhydrous dichloromethane (13 ml) was slowly treated with EDCI (1.03 g, 5.38 mmol) followed by N,O-dimethylhydroxylamine hydrochloride (525 mg, 5.4 mmol), DMAP (55 mg, 0.045 mmol), and TEA (0.75 ml, 5.38 mmol). After stirring overnight at room temperature the reaction mixture was partitioned between DCM/water. The organic layers were collected, dried over MgSO$_4$, filtered, and concentrated giving a greenish oil. Silica gel chromatography using 10-60% EtOAc in hexanes as eluant provided 1.13 mg (79%) of N-methoxy-2,2,N-trimethyl-3-triisopropylsilanyloxy-propionamide as a colorless oil. M+H=318.

Example 165

2-Methoxy-2-methyl-1-[2-(3,4,5-trimethoxy-phenyl)-5H-pyrrolo[2,3-b]pyrazin-7-yl]-propan-1-one A solution of 7-iodo-5-triisopropylsilanyl-2-(3,4,5-trimethoxy-phenyl)-5H-pyrrolo[2,3-b]pyrazine (233 mg, 0.410 mmol) in anhydrous tetrahydrofuran (3 ml) was cooled to −78° C. and treated with nBuLi (2.29M in hexanes, 0.25 ml, 0.57 mmol) dropwise. The solution was stirred for 30 seconds and then 2,N-dimethoxy-2,N-dimethyl-propionamide (198 mg, 1.23 mmol), dissolved in THF (5 ml), was added dropwise. The reaction mixture was stirred at −78° C. for 30 minutes and then at room temperature 30 minutes. The reaction mixture was quenched with saturated aqueous NaHSO$_4$ and then partitioned between EtOAc/water. The organic layers were collected, dried over MgSO$_4$, filtered, and concentrated giving a brown oil. The oil was purified by silica gel chromatography using 10-50% EtOAc in hexanes as eluant providing a yellow solid. The yellow solid was dissolved in THF (5 ml) and treated with TBAF (1M in THF, 5.3 ml, 5.3 mmol) and refluxed for 6 hours. The reaction mixture was partitioned between EtOAc/1N HCl. The organic layers were collected, dried over MgSO$_4$, filtered, and concentrated giving a yellow solid. The crude product was purified by preparative thin layer chromatography using 10% [5% NH$_4$OH:MeOH]/DCM as eluant providing 30 mg (11%) of 3-hydroxy-2,2-dimethyl-1-[2-(3,4,5-trimethoxy-phenyl)-5H-pyrrolo[2,3-b]pyrazin-7-yl]-propan-1-one as a pale yellow solid. MP 227-229° C., M+H=386.

Example 166

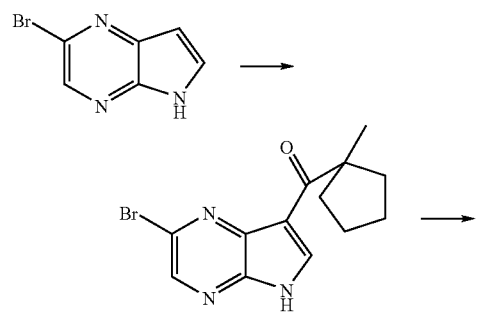

(2-Bromo-5H-pyrrolo[2,3-b]pyrazin-7-yl)-(1-methyl-cyclopentyl)-methanone

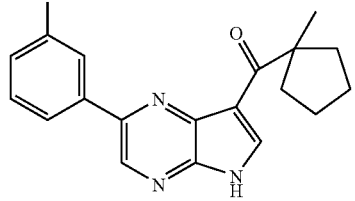

(2-Bromo-5H-pyrrolo[2,3-b]pyrazin-7-yl)-(1-methyl-cyclopentyl)-methanone was prepared starting from 2-bromo-5H-pyrrolo[2,3-b]pyrazine and 1-methyl-cyclopentanecarbonyl chloride following general procedures as described in these Examples. MP 206.9-207.9° C., M+H=308.

Example 167

Methyl-cyclopentyl)-[2-(3-pyrrolidin-1-yl-phenyl)-5H-pyrrolo[2,3-b]pyrazin-7-yl]-methanone (1-Methyl-cyclopentyl)-[2-(3-pyrrolidin-1-yl-phenyl)-5H-pyrrolo[2,3-b]pyrazin-7-yl]-methanone was prepared starting from (2-bromo-5H-pyrrolo[2,3-b]pyrazin-7-yl)-(1-methyl-cyclopentyl)-methanone and 3-(1-pyrrolidinyl)phenylboronic acid following general procedures as described in these Examples. MP 242-243° C., M+H=375.

Example 168

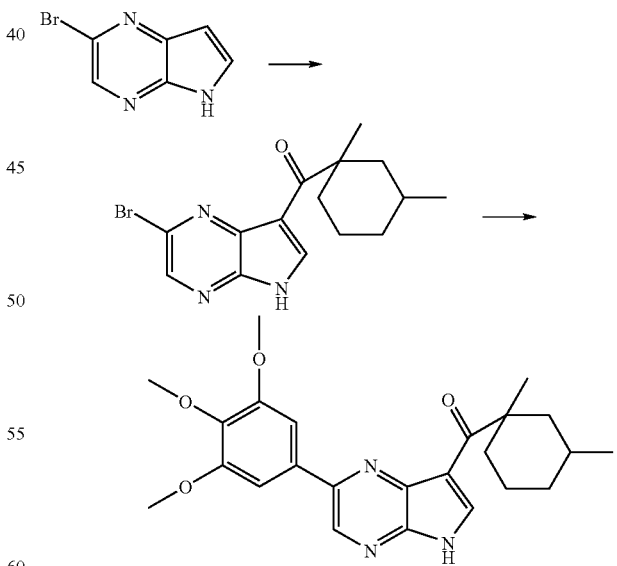

(2-Bromo-5H-pyrrolo[2,3-b]pyrazin-7-yl)-(1,3-dimethyl-cyclohexyl)-methanone (2-Bromo-5H-pyrrolo[2,3-b]pyrazin-7-yl)-(1,3-dimethyl-cyclohexyl)-methanone was prepared starting from 2-bromo- 5H-pyrrolo[2,3-b]pyrazine and 1,3-dimethyl cyclohexanecarbonyl chloride (Journal of Organic Chemistry (1951), 16 920-9) following general procedures as described in these Examples. M+H=336.

Example 169

(1,3-Dimethyl-cyclohexyl)-[2-(3,4,5-trimethoxy-phenyl)-5H-pyrrolo[2,3-b]pyrazin-7-yl]-methanone (1,3-Dimethyl-cyclohexyl)-[2-(3,4,5-trimethoxy-phenyl)-5H-pyrrolo[2,3-b]pyrazin-7-yl]-methanone was prepared starting from (2-bromo-5H-pyrrolo[2,3-b]pyrazin-7-yl)-(1,3-dimethyl-cyclohexyl)-methanone and 3,4,5-trimethoxy-benzeneboronic acid following general procedures as described in these Examples. MP 229-231° C., M+H=424.

Example 170

(1-Methyl-cyclohexyl)-{2-[4-(4-methyl-piperazin-1-yl)-phenyl]-5H-pyrrolo[2,3-b]pyrazin-7-yl}-methanone (1-Methyl-cyclohexyl)-{2-[4-(4-methyl-piperazin-1-yl)-phenyl]-5H-pyrrolo[2,3-b]pyrazin-7-yl}-methanone was prepared starting from (2-bromo-5H-pyrrolo[2,3-b]pyrazin-7-yl)-(1-methyl-cyclohexyl)-methanone and 1-methyl-4-[4-(4,4,5,5-tetramethyl-[1,3,2]dioxaborolan-2-yl)-phenyl]-piperazine following general procedures as described in these Examples. MP 225-226° C., M+H=418.

Example 171

[2-(4-Methylamino-phenyl)-5H-pyrrolo[2,3-b]pyrazin-7-yl]-(1-methyl-cyclohexyl)-methanone

[2-(4-Methylamino-phenyl)-5H-pyrrolo[2,3-b]pyrazin-7-yl]-(1-methyl-cyclohexyl)-methanone was prepared starting from (2-bromo-5H-pyrrolo[2,3-b]pyrazin-7-yl)-(1-methyl-cyclohexyl)-methanone and methyl-[4-(4,4,5,5-tetramethyl-[1,3,2]dioxaborolan-2-yl)-phenyl]-amine following general procedures as described in these Examples. MP 273-275° C., M+H=349.

Example 172

(1-Methyl-cyclohexyl)-[2-(4-morpholin-4-yl-phenyl)-5H-pyrrolo[2,3-b]pyrazin-7-yl]-methanone (1-Methyl-cyclohexyl)-[2-(4-morpholin-4-yl-phenyl)-5H-pyrrolo[2,3-b]pyrazin-7-yl]-methanone was prepared starting from (2-bromo-5H-pyrrolo[2,3-b]pyrazin-7-yl)-(1-methyl-cyclohexyl)-methanone and 4-morpholin-4-yl-phenylboronic acid following general procedures as described in these Examples. MP 233-235° C., M+H=405.

Example 173

[2-(4-Diethylamino-phenyl)-5H-pyrrolo[2,3-b]pyrazin-7-yl]-(1-methyl-cyclohexyl)-methanone

[2-(4-Diethylamino-phenyl)-5H-pyrrolo[2,3-b]pyrazin-7-yl]-(1-methyl-cyclohexyl)-methanone was prepared starting from (2-bromo-5H-pyrrolo[2,3-b]pyrazin-7-yl)-(1-methyl-cyclohexyl)-methanone and 4-(diethylamino)phenylboronic acid following general procedures as described in these Examples. MP 211-213° C., M+H=391.

Example 174

(1-Methyl-cyclohexyl)-[2-(4-piperidin-1-yl-phenyl)-5H-pyrrolo[2,3-b]pyrazin-7-yl]-methanone (1-Methyl-cyclohexyl)-[2-(4-piperidin-1-yl-phenyl)-5H-pyrrolo[2,3-b]pyrazin-7-yl]-methanone was prepared starting from (2-bromo-5H-pyrrolo[2,3-b]pyrazin-7-yl)-(1-methyl-cyclohexyl)-methanone and 1-[4-(4,4,5,5-tetramethyl-[1,3,2]dioxaborolan-2-yl)-phenyl]-piperidine following general procedures as described in these Examples. MP 234-236° C., M+H=403.

Example 175

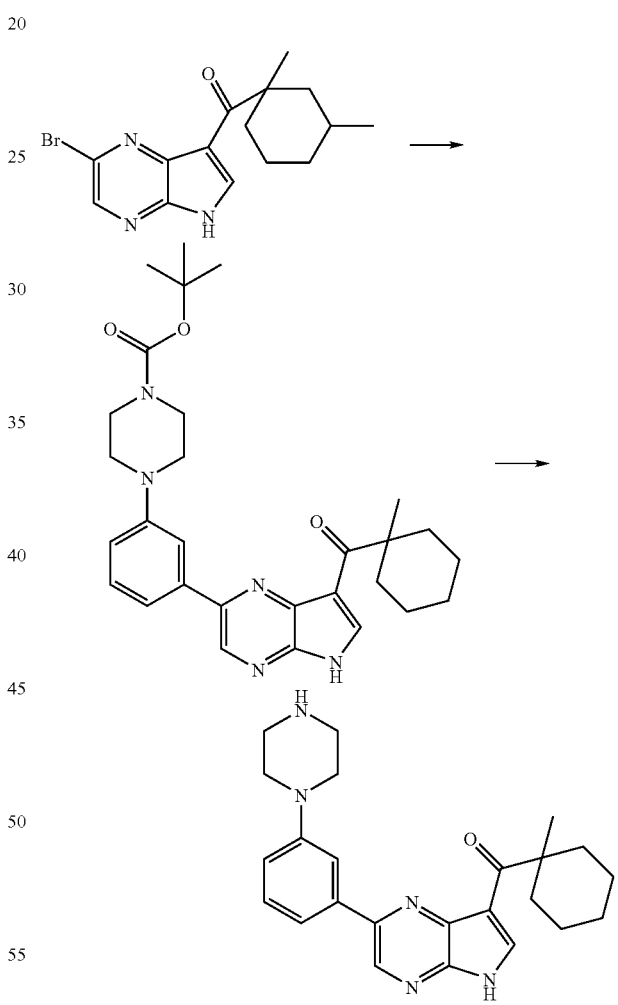

4-{3-[7-(1-Methyl-cyclohexanecarbonyl)-5H-pyrrolo[2,3-b]pyrazin-2-yl]-phenyl}-piperazine-1-carboxylic acid tert-butyl ester 4-{3-[7-(1-Methyl-cyclohexanecarbonyl)-5H-pyrrolo[2,3-b]pyrazin-2-yl]-phenyl}-piperazine-1-carboxylic acid tert-butyl ester was prepared starting from (2-bromo-5H-pyrrolo[2,3-b]pyrazin-7-yl)-(1-methyl-cyclohexyl)-methanone and 4-[3-(4,4,5,5-tetramethyl-[1,3,2]dioxaborolan-2-yl)-phenyl]-piperazine-1-carboxylic acid tert-butyl ester following general procedures as described in these Examples. MP 212-213° C., M+H=504.

Example 176

(1-Methyl-cyclohexyl)-[2-(3-piperazin-1-yl-phenyl)-5H-pyrrolo[2,3-b]pyrazin-7-yl]-methanone A solution of 4-{3-[7-(1-methyl-cyclohexanecarbonyl)-5H-pyrrolo[2,3-b]pyrazin-2-yl]-phenyl}-piperazine-1-carboxylic acid tert-butyl ester (134 mg, 0.266 mmol) in DCM (10 ml) was treated with TFA (1.0 ml, 13.4 mmol) and allowed to stir for 16 hours. The reaction mixture was concentrated to dryness, and the resulting residue was partitioned between sat. NaHCO₃ and EtOAc. The organic layers were collected, dried over MgSO₄, filtered, and concentrated giving a yellow solid. The yellow solid was filtered through a Buchner funnel and washed with 1:2 Et₂O/Hex to provide 66 mg (61%) of (1-methyl-cyclohexyl)-[2-(3-piperazin-1-yl-phenyl)-5H-pyrrolo[2,3-b]pyrazin-7-yl]-methanone as a pale yellow solid. M+H=404.

Example 177

1-(4-{3-[7-(1-Methyl-cyclohexanecarbonyl)-5H-pyrrolo[2,3-b]pyrazin-2-yl]-phenyl}-piperazin-1-yl)-ethanone A 0° C. solution of (1-methyl-cyclohexyl)-[2-(3-piperazin-1-yl-phenyl)-5H-pyrrolo[2,3-b]pyrazin-7-yl]-methanone (24 mg, 0.06 mmol) in DMF (1 ml) was treated with Acetic anhydride (0.01 ml, 0.06 mmol). The reaction mixture was removed from the ice bath and allowed to stir at room temperature for 16 hours. The reaction mixture was partitioned between EtOAc/sat. NaHCO₃. The organic layers were collected, dried over MgSO₄, filtered, and concentrated giving a white solid which was filtered through a Buchner funnel and washed with Et₂O and Hexanes to afford a yellow solid. The yellow solid was dissolved in THF (2 ml) and treated with 1N NaOH (0.05 ml, 0.05 mmol). After stirring at room temperature for 16 hours, the reaction mixture was partitioned between 1N HCl and EtOAc. The organic layers were collected, dried over MgSO₄, filtered, and concentrated giving a light brown oil. The oil was triturated with Et₂O providing 4 mg (15%) of 1-(4-{3-[7-(1-methyl-cyclohexanecarbonyl)-5H-pyrrolo[2,3-b]pyrazin-2-yl]-phenyl}-piperazin-1-yl)-ethanone as a pale brown solid. M+H=446.

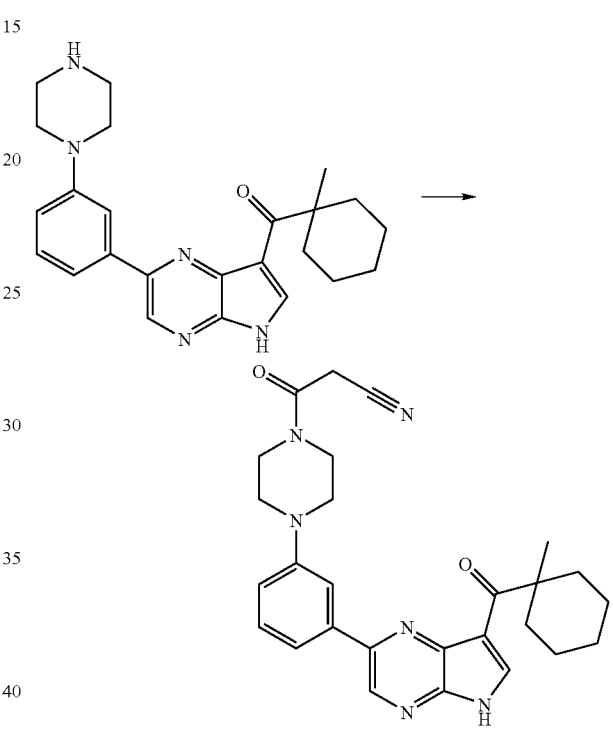

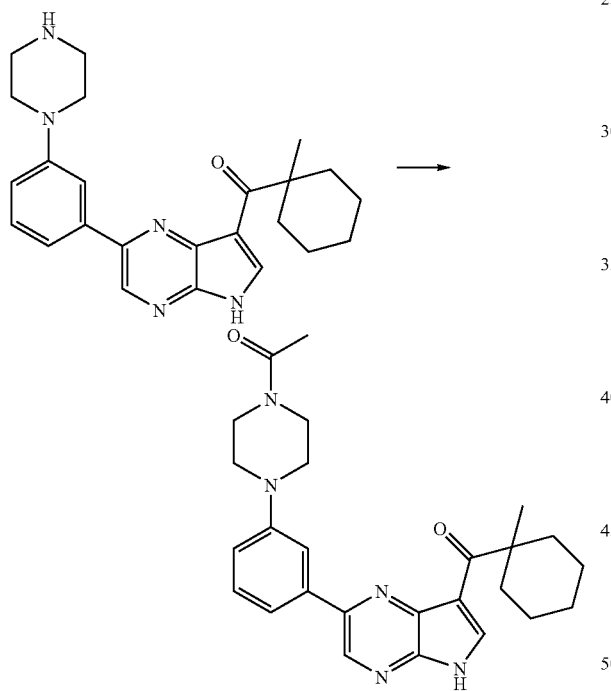

Example 178

3-(4-{3-[7-(1-Methyl-cyclohexanecarbonyl)-5H-pyrrolo[2,3-b]pyrazin-2-yl]-phenyl}-piperazin-1-yl)-3-oxo-propionitrile A solution of (1-methyl-cyclohexyl)-[2-(3-piperazin-1-yl-phenyl)-5H-pyrrolo[2,3-b]pyrazin-7-yl]-methanone (130 mg, 0.32 mmol), benzotriazol-1-ol (52 mg, 0.38 mmol), cyano-acetic acid (74 mg, 0.39 mmol), and 3-(3-dimethylaminopropyl)-1-ethylcarbodiimide hydrochloride (74 mg, 0.39 mmol), in DCM (35 ml), was treated with TEA (0.13 ml, 0.97 mmol). After stirring at room temperature for 16 hours, the reaction mixture was partitioned between DCM and water. The organic layers were collected, dried over MgSO₄, filtered, and concentrated. Trituration of the resulting solid with 1:1 Et₂O/Hex provided 85 mg (56%) of 3-(4-{3-[7-(1-methyl-cyclohexanecarbonyl)-5H-pyrrolo[2,3-b]pyrazin-2-yl]-phenyl}-piperazin-1-yl)-3-oxo-propionitrile as an off white solid. MP 214-216° C., M+H=471.

Example 179

4-(4-{3-[7-(1-Methyl-cyclohexanecarbonyl)-5H-pyrrolo[2,3-b]pyrazin-2-yl]-phenyl}-piperazine-1-carbonyl)-piperidine-1-carboxylic acid tert-butyl ester 4-(4-{3-[7-(1-Methyl-cyclohexanecarbonyl)-5H-pyrrolo[2,3-b]pyrazin-2-yl]-phenyl}-piperazine-1-carbonyl)-piperidine-1-carboxylic acid tert-butyl ester was prepared starting from (1-methyl-cyclohexyl)-[2-(3-piperazin-1-yl-phenyl)-5H-pyrrolo[2,3-b]pyrazin-7-yl]-methanone and piperidine-1,4-dicarboxylic acid mono-tert-butyl ester following general procedures as described in these Examples. M+H=615.

Example 180

(1-Methyl-cyclohexyl)-(2-{3-[4-(piperidine-4-carbonyl)-piperazin-1-yl]-phenyl}-5H-pyrrolo[2,3-b]pyrazin-7-yl)-methanone Methyl-cyclohexyl)-(2-{3-[4-(piperidine-4-carbonyl)-piperazin-1-yl]-phenyl}-5H-pyrrolo[2,3-b]pyrazin-7-yl)-methanone was prepared following general procedures as described in these Examples. MP>300° C., M+H=515.

Example 181

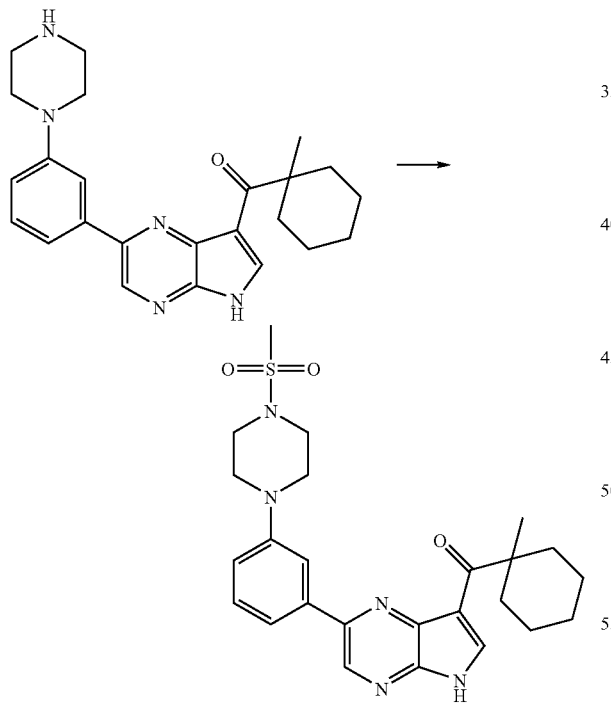

{2-[3-(4-Methanesulfonyl-piperazin-1-yl)-phenyl]-5H-pyrrolo[2,3-b]pyrazin-7-yl}-(1-methyl-cyclohexyl)-methanone A solution of (1-methyl-cyclohexyl)-[2-(3-piperazin-1-yl-phenyl)-5H-pyrrolo[2,3-b]pyrazin-7-yl]-methanone (135 mg, 0.33 mmol) in pyridine (3 ml), at 0° C., was treated with methane sulfonyl chloride (0.03 ml, 0.367 mmol). The reaction mixture was allowed to stir at 0° C. for 1.5 hours, and then room temperature for 16 hours. The reaction mixture was poured onto ice cold 1N HCl and extracted with DCM. The organic layers were collected, dried over MgSO$_4$, filtered and concentrated giving a yellow film. The crude product was purified by preparative thin layer chromatography using 3% [5% NH$_4$OH:MeOH]/DCM as eluant providing 36 mg (22%) of {2-[3-(4-methanesulfonyl-piperazin-1-yl)-phenyl]-5H-pyrrolo[2,3-b]pyrazin-7-yl}-(1-methyl-cyclohexyl)-methanone as an off white solid. MP 230-231° C., M+H=482.

Example 182

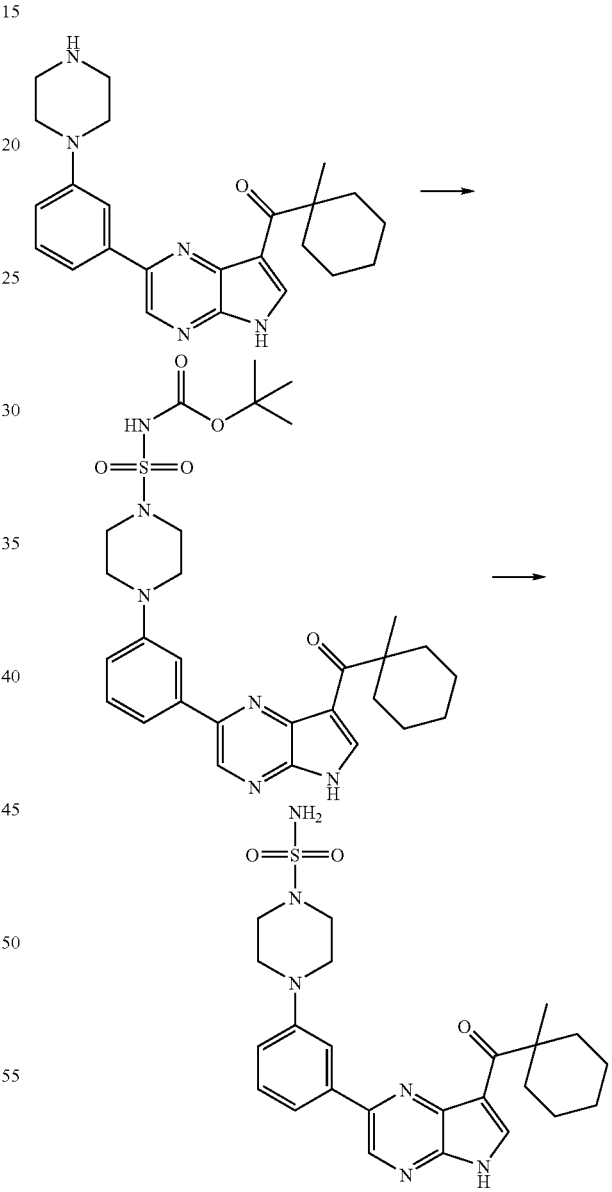

Carbamic acid, N-[4-{3-[7-(1-Methyl-cyclohexanecarbonyl)-5H-pyrrolo[2,3-b]pyrazin-2-yl]-phenyl}-piperazine-1-sulfonyl]-, 1,1-dimethylethyl ester A solution of chlorosulfonyl isocyanate (0.07 ml, 0.77 mmol) in DCM (5 ml), at 0° C., was treated dropwise with 2-methyl-propan-2-ol (0.07 ml, 0.77 mmol). After stirring for 30 minutes, TEA (0.36 ml, 2.58 mmol) was added, followed by a solution of (1-methyl-cyclohexyl)-[2-(3-piperazin-1-yl-phenyl)-5H-pyrrolo[2,3-b]pyrazin-7-yl]-methanone (260 mg, 0.644 mmol) in 1:1 DCM/DMF (5 ml). The reaction mixture was stirred for 16 hours and then partitioned between EtOAc/water. The organic layers were collected, dried over $MgSO_4$, filtered, and concentrated. The crude product was purified by silica gel chromatography using 20-100% EtOAc in hexanes as eluant providing 193 mg (51%) of carbamic acid, N-[4-{3-[7-(1-methyl-cyclohexanecarbonyl)-5H-pyrrolo[2,3-b]pyrazin-2-yl]-phenyl}-piperazine-1-sulfonyl]-, 1,1-dimethylethyl ester as a pale yellow solid. M+H=583.

Example 183

4-{3-[7-(1-Methyl-cyclohexanecarbonyl)-5H-pyrrolo[2,3-b]pyrazin-2-yl]-phenyl}-piperazine-1-sulfonic acid amide A solution of carbamic acid, N-[4-{3-[7-(1-methyl-cyclohexanecarbonyl)-5H-pyrrolo[2,3-b]pyrazin-2-yl]-phenyl}-piperazine-1-sulfonyl]-, 1,1-dimethylethyl ester (180 mg, 0.309 mmol) in DCM (5 ml), at 0° C., was treated with TFA (1.0 ml, 13.4 mmol). The reaction mixture was then allowed to stir at room temperature for 16 hours. The reaction mixture was partitioned between sat. $Na_2CO_3$ and DCM. The organic layers were collected, dried over $MgSO_4$, filtered, and concentrated giving a yellow solid. The yellow solid was filtered through a Buchner funnel and washed with 1:1 $Et_2O$/Hex providing 98 mg (66%) of 4-{3-[7-(1-methyl-cyclohexanecarbonyl)-5H-pyrrolo[2,3-b]pyrazin-2-yl]-phenyl}-piperazine-1-sulfonic acid amide as an off white solid. MP 233-235° C., M+H=483.

Example 184

Example 185

(1-Methyl-cyclohexyl)-[2-(4-piperazin-1-yl-phenyl)-5H-pyrrolo[2,3-b]pyrazin-7-yl]-methanone A solution of 4-{4-[7-(1-methyl-cyclohexanecarbonyl)-5H-pyrrolo[2,3-b]pyrazin-2-yl]-phenyl}-piperazine-1-carboxylic acid tert-butyl ester (35 mg, 0.069 mmol) in DCM (5 ml), at 0° C., was treated with TFA (0.15 ml, 2.01 mmol). The reaction mixture was stirred at room temperature for 16 hours, and then refluxed for 1.5 hours. The reaction mixture was concentrated to dryness, and the resulting residue was partitioned between sat. $NaHCO_3$ and EtOAc. The organic layers were collected, dried over $MgSO_4$, filtered, and concentrated providing 25 mg (89%) of (1-methyl-cyclohexyl)-[2-(4-piperazin-1-yl-phenyl)-5H-pyrrolo[2,3-b]pyrazin-7-yl]-methanone as a yellow solid. MP 214-216° C., M+H=404.

Example 186

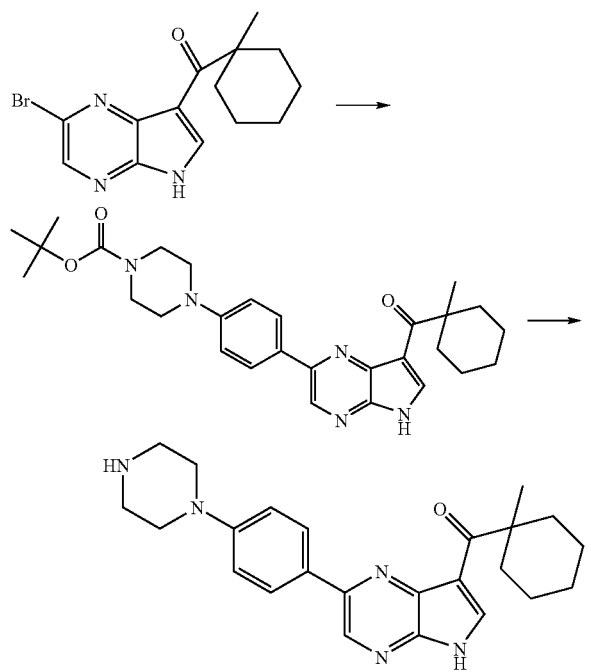

4-{4-[7-(1-Methyl-cyclohexanecarbonyl)-5H-pyrrolo[2,3-b]pyrazin-2-yl]-phenyl}-piperazine-1-carboxylic acid tert-butyl ester 4-{4-[7-(1-Methyl-cyclohexanecarbonyl)-5H-pyrrolo[2,3-b]pyrazin-2-yl]-phenyl}-piperazine-1-carboxylic acid tert-butyl ester was prepared starting from (2-bromo-5H-pyrrolo[2,3-b]pyrazin-7-yl)-(1-methyl-cyclohexyl)-methanone and 4-[4-(4,4,5,5-tetramethyl-[1,3,2]dioxaborolan-2-yl)-phenyl]-piperazine-1-carboxylic acid tert-butyl ester following general procedures as described in these Examples. M+H=504.

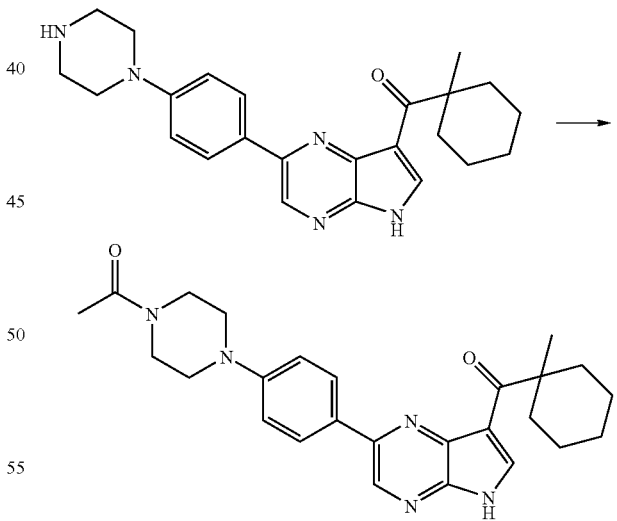

1-(4-{4-[7-(1-Methyl-cyclohexanecarbonyl)-5H-pyrrolo[2,3-b]pyrazin-2-yl]-phenyl}-piperazin-1-yl)-ethanone 1-(4-{4-[7-(1-Methyl-cyclohexanecarbonyl)-5H-pyrrolo[2,3-b]pyrazin-2-yl]-phenyl}-piperazin-1-yl)-ethanone was prepared following general procedures as described in these Examples. MP 278-284.9° C., M+H=446.

Example 187

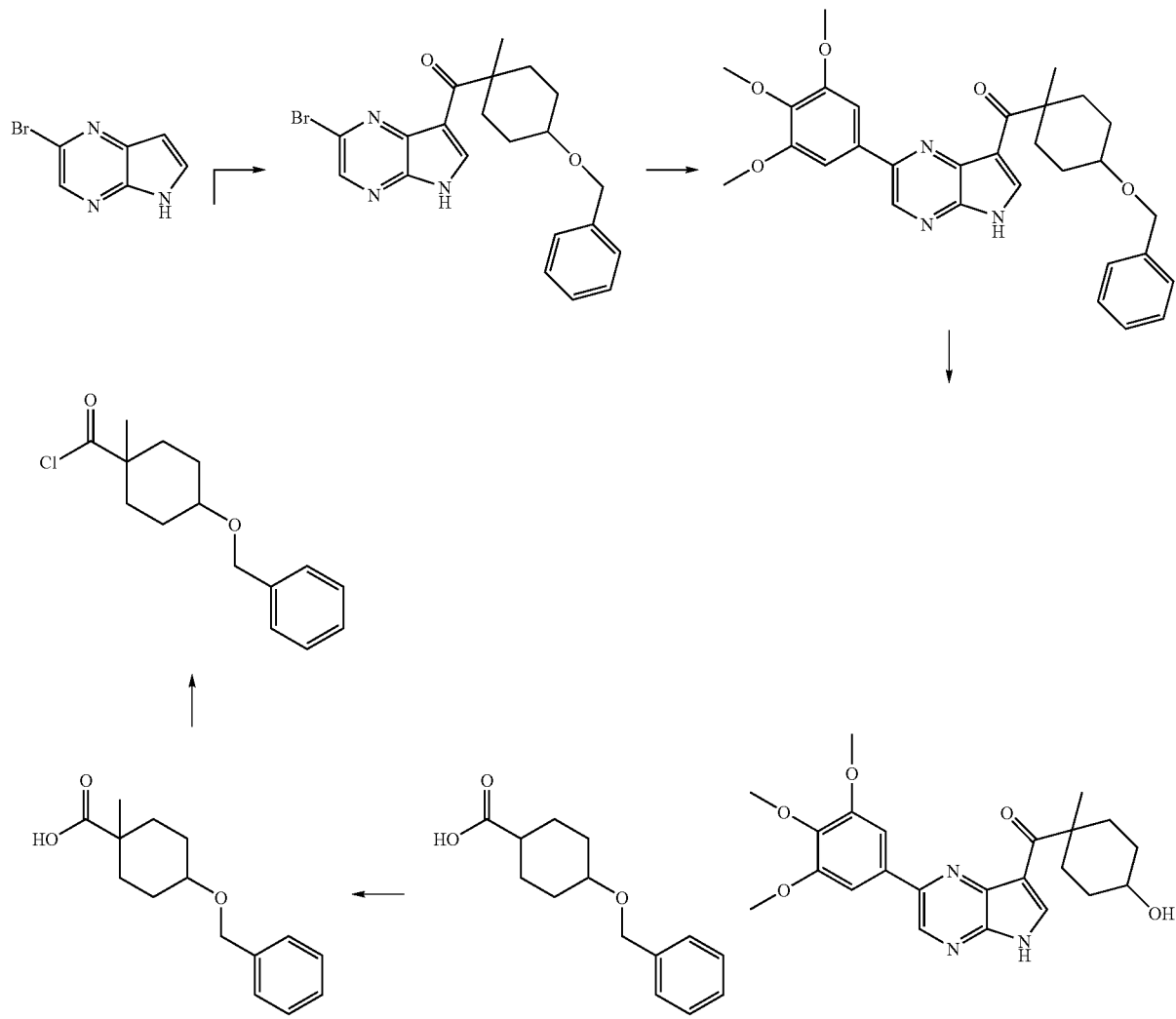

4-Benzyloxy-1-methyl-cyclohexanecarboxylic acid

To a solution of LDA (made by dropwise addition of nBuLi (2.38M, 13.45 ml, 32.01 mmol) to a −78° C. solution of diisopropyl amine (4.5 ml, 32.0 mmol), in THF (160 ml), in THF, at −78° C.), was added 4-benzyloxy-cyclohexanecarboxylic acid (3.75 g, 16.0 mmol) (Eur. Pat. Appl. (1984), 33 pp. EP 123238A2) dissolved in THF (24 ml). After complete addition, the reaction mixture was stirred at 50° C. for approximately 2 hours. The reaction mixture was cooled to room temperature and MeI (filtered through basic alumina) was added to the reaction mixture, dropwise. After stirring at room temperature for overnight, the reaction mixture was quenched with ice water containing ether, and the aqueous layers were collected. The organic layer was washed one time with water, and the aqueous layer was combined with previous aq. layers. The combined aqueous layers were acidified with 2N HCl (pH=1), and extracted four times with ether. The ether extracts were brined, dried over MgSO$_4$, filtered, and concentrated giving 3.3 g (83%) of 4-benzyloxy-1-methyl-cyclohexanecarboxylic acid as an off white solid. M−H=247.

Example 188

4-Benzyloxy-1-methyl-cyclohexanecarbonyl chloride

A solution of 4-benzyloxy-1-methyl-cyclohexanecarboxylic acid (1.71 g, 6.89 mmol) in thionyl chloride (10 ml) was refluxed for 2 hours. The reaction mixture was concentrated on high vacuum giving 1.84 g (99%) of 4-benzyloxy-1-methyl-cyclohexanecarbonyl chloride as a yellow oil.

Example 189

(4-Benzyloxy-1-methyl-cyclohexyl)-(2-bromo-5H-pyrrolo[2,3-b]pyrazin-7-yl)-methanone A solution of 2-bromo-5H-pyrrolo[2,3-b]pyrazine (531 mg, 2.68 mmol) and 4-benzyloxy-1-methyl-cyclohexanecarbonyl chloride (2.15 g, 8.05 mmol) in anhydrous Toluene (16 ml) was treated with Et$_2$AlCl (1M in Hexanes, 5.36 ml, 5.36 mmol), dropwise. The reaction mixture was stirred at 90° C. for 16 hours. The reaction mixture was cooled to room temperature, quenched with sat. NaHCO$_3$, and extracted with ethyl acetate (3×). The organic layers were collected, dried over MgSO₄, filtered, and concentrated giving a dark brown oil. Silica gel chromatography using 0-50% Et₂O in DCM as eluant provided 205 mg (18%) of (4-benzyloxy-1-methyl-cyclohexyl)-(2-bromo-5H-pyrrolo[2,3-b]pyrazin-7-yl)-methanone as a pale yellow solid. M−H=426.

Example 190

(4-Benzyloxy-1-methyl-cyclohexyl)-[2-(3,4,5-tri-methoxy-phenyl)-5H-pyrrolo[2,3-b]pyrazin-7-yl]-methanone (4-Benzyloxy-1-methyl-cyclohexyl)-[2-(3,4,5-tri-methoxy-phenyl)-5H-pyrrolo[2,3-b]pyrazin-7-yl]-methanone was prepared starting from (4-benzyloxy-1-methyl-cyclohexyl)-(2-bromo-5H-pyrrolo[2,3-b]pyrazin-7-yl)-methanone and 3,4,5-trimethoxybenzeneboronic acid following general procedures as described in these Examples. M+H=516.

Example 191

(4-Hydroxy-1-methyl-cyclohexyl)-[2-(3,4,5-tri-methoxy-phenyl)-5H-pyrrolo[2,3-b]pyrazin-7-yl]-methanone A solution of (4-benzyloxy-1-methyl-cyclohexyl)-[2-(3,4,5-trimethoxy-phenyl)-5H-pyrrolo[2,3-b]pyrazin-7-yl]-methanone (36 mg, 0.070 mmol) and 10% Pd/C (10 mg), in THF (10 ml) and EtOH (8 ml), was hydrogenated for 5 days under a 60 psi H₂ atmosphere. The reaction mixture was vacuum purged with argon (3×), and filtered through a plug of celite using THF and DCM. The filtrate was concentrated giving an opaque oil which was purified by silica gel chromatography using 0-10% MeOH in EtOAc as eluant provided 39 mg (36%) of (4-hydroxy-1-methyl-cyclohexyl)-[2-(3,4,5-trimethoxy-phenyl)-5H-pyrrolo[2,3-b]pyrazin-7-yl]-methanone as a pale yellow solid. MP 242-244° C. M+H=426.

Example 192

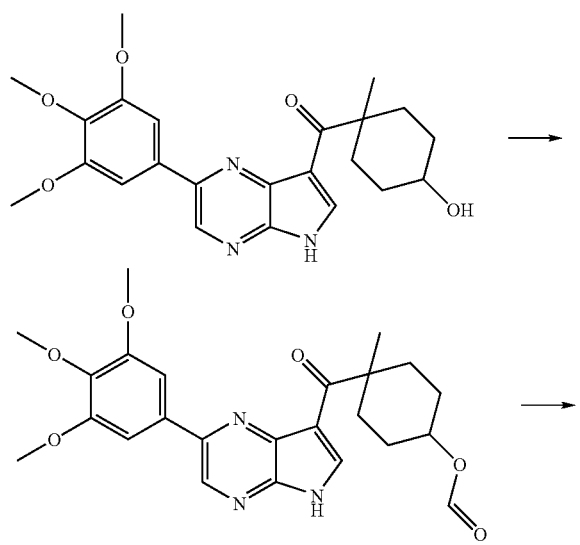

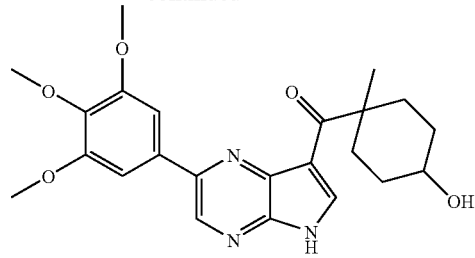

Formic acid 4-methyl-4-[2-(3,4,5-trimethoxy-phenyl)-5H-pyrrolo[2,3-b]pyrazine-7-carbonyl]-cyclohexyl ester A solution of (4-hydroxy-1-methyl-cyclohexyl)-[2-(3,4,5-trimethoxy-phenyl)-5H-pyrrolo[2,3-b]pyrazin-7-yl]-methanone (19 mg, 0.045 mmol), triphenyl phosphine (23 mg, 0.088 mmol), and formic acid (0.003 ml, 0.087 mmol), in THF (0.4 ml), was treated with diethyl azodicarboxylate (0.01 ml, 0.092 mmol). After stirring at room temperature for 2 days, the reaction mixture was purified by preparative thin layer chromatography using 70% EtOAc in Hexanes as eluant providing 12 mg (59%) of formic acid 4-methyl-4-[2-(3,4,5-trimethoxy-phenyl)-5H-pyrrolo[2,3-b]pyrazine-7-carbonyl]-cyclohexyl ester as a white solid. M+H=454.

Example 193

(4-Hydroxy-1-methyl-cyclohexyl)-[2-(3,4,5-tri-methoxy-phenyl)-5H-pyrrolo[2,3-b]pyrazin-7-yl]-methanone A solution of formic acid 4-methyl-4-[2-(3,4,5-trimethoxy-phenyl)-5H-pyrrolo[2,3-b]pyrazine-7-carbonyl]-cyclohexyl ester (12 mg, 0.026 mmol) in MeOH (1 ml) was treated with 2N NaOH aq. (0.2 ml, 0.4 mmol) and allowed to stir at 50° C. for overnight. The reaction mixture was partitioned between EtOAc/sat. NH₄Cl aq., and the organic layers were collected and concentrated. Silica gel chromatography using 0-10% {5% NH₄OH:MeOH} in DCM as eluant gave 10 mg (89%) of (4-hydroxy-1-methyl-cyclohexyl)-[2-(3,4,5-trimethoxy-phenyl)-5H-pyrrolo[2,3-b]pyrazin-7-yl]-methanone as a white solid. M+H=426.

Example 194

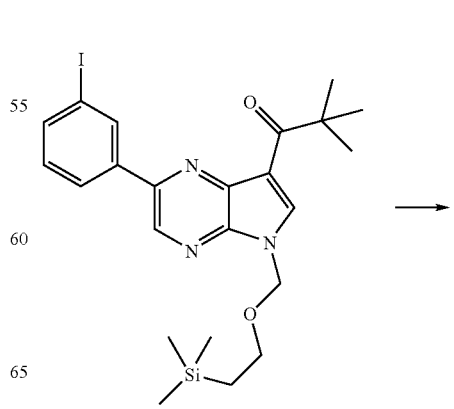

-continued

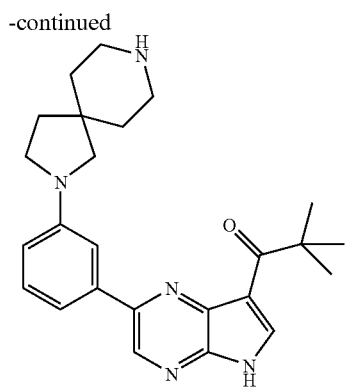

1-{2-[3-(2,8-Diaza-spiro[4.5]dec-2-yl)-phenyl]-5H-pyrrolo[2,3-b]pyrazin-7-yl}-2,2-dimethyl-propan-1-one A solution of 1-[2-(3-iodo-phenyl)-5-(2-trimethylsilanyl-ethoxymethyl)-5H-pyrrolo[2,3-b]pyrazin-7-yl]-2,2-dimethyl-propan-1-one (321 mg, 0.59 mmol), CuI (17 mg, 0.089 mmol), proline (21 mg, 0.18 mmol), $K_2CO_3$ (182 mg, 1.3 mmol), and 2,8-diaza-spiro[4.5]decane-8-carboxylic acid tert-butyl ester (500 mg, 2.1 mmol), in DMSO (3 ml), was stirred in a sealed tube at 100° C. for 16 hours. The reaction mixture was partitioned between EtOAc/Water. The organic layer were collected, dried over $MgSO_4$, filtered, and concentrated. Silica gel chromatography using 10-70% EtOAc in hexane as eluant gave 406 mg (100%) of an orange oil which was dissolved in DCM (5 ml) and treated with TFA (1.2 ml, 16 mmol) for 3 hours. The reaction mixture was stripped down and partitioned between EtOAc/sat. $Na_2CO_3$. The organic layers were collected, dried over $MgSO_4$, filtered, and concentrated. The residue was dissolved in THF (10 ml) and treated with 1N NaOH aq. (until pH=12). After stirring overnight at room temperature, the reaction mixture was made acidic by addition of 1N HCl, and then partitioned between EtOAc/sat. $NaHCO_3$ (3×). The organic layers were collected, dried over $MgSO_4$, filtered, and concentrated. Silica gel chromatography using 0-10% {5% $NH_4OH$:MeOH} in DCM as eluant gave 62 mg (26%) of 1-{2-[3-(2,8-diaza-spiro[4.5]dec-2-yl)-phenyl]-5H-pyrrolo[2,3-b]pyrazin-7-yl}-2,2-dimethyl-propan-1-one as a brown solid. M+H=418.

Example 195

1-{2-[3-(2,7-Diaza-spiro[4.5]dec-2-yl)-phenyl]-5H-pyrrolo[2,3-b]pyrazin-7-yl}-2,2-dimethyl-propan-1-one 1-{2-[3-(2,7-Diaza-spiro[4.5]dec-2-yl)-phenyl]-5H-pyrrolo[2,3-b]pyrazin-7-yl}-2,2-dimethyl-propan-1-one was prepared starting from 1-[2-(3-iodo-phenyl)-5-(2-trimethylsilanyl-ethoxymethyl)-5H-pyrrolo[2,3-b]pyrazin-7-yl]-2,2-dimethyl-propan-1-one and 2,7-diaza-spiro[4.5]decane-7-carboxylic acid tert-butyl ester following general procedures as described in these Examples. M+H=418.

Example 196

1-{2-[3-(2,7-Diaza-spiro[4.4]non-2-yl)-phenyl]-5H-pyrrolo[2,3-b]pyrazin-7-yl}-2,2-dimethyl-propan-1-one 1-{2-[3-(2,7-Diaza-spiro[4.4]non-2-yl)-phenyl]-5H-pyrrolo[2,3-b]pyrazin-7-yl}-2,2-dimethyl-propan-1-one was prepared starting from 1-[2-(3-iodo-phenyl)-5-(2-trimethylsilanyl-ethoxymethyl)-5H-pyrrolo[2,3-b]pyrazin-7-yl]-2,2-dimethyl-propan-1-one and 2,7-diaza-spiro[4.4]nonane-2-carboxylic acid tert-butyl ester following general procedures as described in these Examples. M+H=404.

Example 197

1-[2-[3-(2,2-Dimethyl-propylamino)-phenyl]-5-(2-trimethylsilanyl-ethoxymethyl)-5H-pyrrolo[2,3-b]pyrazin-7-yl]-2,2-dimethyl-propan-1-one 1-[2-[3-(2,2-Dimethyl-propylamino)-phenyl]-5-(2-trimethylsilanyl-ethoxymethyl)-5H-pyrrolo[2,3-b]pyrazin-7-yl]-2,2-dimethyl-propan-1-one was prepared starting from 1-[2-(3-iodo-phenyl)-5-(2-trimethylsilanyl-ethoxymethyl)-5H-pyrrolo[2,3-b]pyrazin-7-yl]-2,2-dimethyl-propan-1-one and 2,2-dimethyl-propylamine following general procedures as described in these Examples. M+H=387.

Example 198

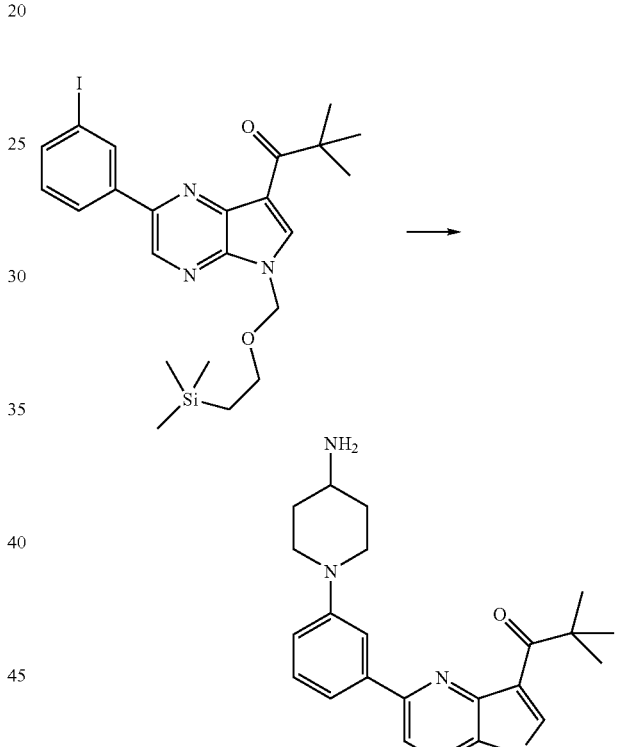

1-{2-[3-(4-Amino-piperidin-1-yl)-phenyl]-5H-pyrrolo[2,3-b]pyrazin-7-yl}-2,2-dimethyl-propan-1-one A solution of 1-[2-(3-iodo-phenyl)-5-(2-trimethylsilanyl-ethoxymethyl)-5H-pyrrolo[2,3-b]pyrazin-7-yl]-2,2-dimethyl-propan-1-one (447 mg, 0.83 mmol), CuI (43 mg, 0.23 mmol), proline (52 mg, 0.45 mmol), $K_2CO_3$ (340 mg, 2.5 mmol), and piperidin-4-yl-carbamic acid tert-butyl ester (500 mg, 2.1 mmol), in DMSO (3.8 ml), was stirred in a sealed tube at 100° C. for 16 hours. The reaction mixture was partitioned between EtOAc/Water. The organic layer were collected, dried over $MgSO_4$, filtered, and concentrated. Silica gel chromatography using 10-70% EtOAc in hexane as eluant gave 295 mg (58%) of an orange oil which was dissolved in DCM (5 ml) and treated with TFA (5 ml, 66 mmol) for 16 hours. The reaction mixture was stripped down and partitioned between EtOAc/sat. $Na_2CO_3$. The organic layers were collected, dried over MgSO$_4$, filtered, and concentrated. Silica gel chromatography using 3-20% {5% NH$_4$OH:MeOH} in DCM as eluant gave a solid which was triturated with 1:1 Et$_2$O/Hex affording 85 mg (27%) of 1-{2-[3-(4-amino-piperidin-1-yl)-phenyl]-5H-pyrrolo[2,3-b]pyrazin-7-yl}-2,2-dimethyl-propan-1-one as a pale yellow solid. M+H=378.

Example 199

1-{2-[3-(3-Aminomethyl-pyrrolidin-1-yl)-phenyl]-5H-pyrrolo[2,3-b]pyrazin-7-yl}-2,2-dimethyl-propan-1-one 1-{2-[3-(3-Aminomethyl-pyrrolidin-1-yl)-phenyl]-5H-pyrrolo[2,3-b]pyrazin-7-yl}-2,2-dimethyl-propan-1-one was prepared starting from 1-[2-(3-iodo-phenyl)-5-(2-trimethyl-silanyl-ethoxymethyl)-5H-pyrrolo[2,3-b]pyrazin-7-yl]-2,2-dimethyl-propan-1-one and pyrrolidin-3-ylmethyl-carbamic acid tert-butyl ester following general procedures as described in these Examples. M+H=378.

Example 200

1-{2-[3-(3,3-Dimethyl-piperazin-1-yl)-phenyl]-5H-pyrrolo[2,3-b]pyrazin-7-yl}-2,2-dimethyl-propan-1-one 1-{2-[3-(3,3-Dimethyl-piperazin-1-yl)-phenyl]-5H-pyrrolo[2,3-b]pyrazin-7-yl}-2,2-dimethyl-propan-1-one was prepared starting from 1-[2-(3-iodo-phenyl)-5-(2-trimethyl-silanyl-ethoxymethyl)-5H-pyrrolo[2,3-b]pyrazin-7-yl]-2,2-dimethyl-propan-1-one and 2,2-Dimethyl-piperazine-1-carboxylic acid tert-butyl ester following general procedures as described in these Examples. M+H=392.

Example 211

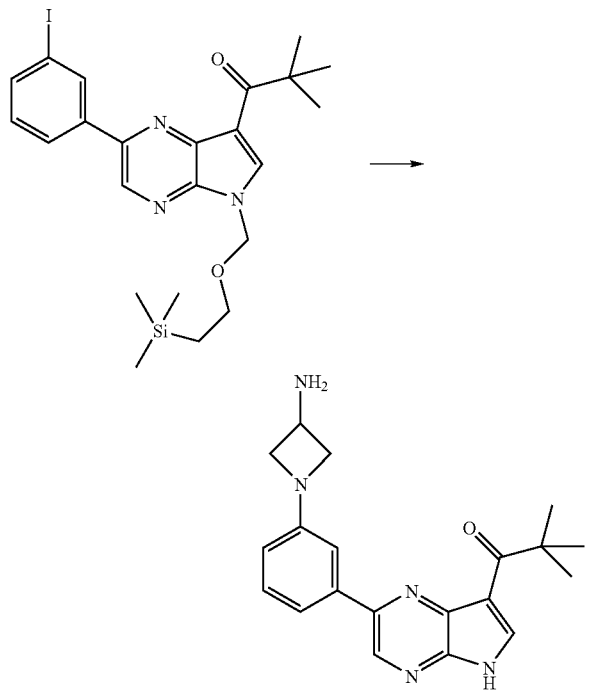

1-{2-[3-(3-Amino-azetidin-1-yl)-phenyl]-5H-pyrrolo[2,3-b]pyrazin-7-yl}-2,2-dimethyl-propan-1-one A solution of 1-[2-(3-iodo-phenyl)-5-(2-trimethylsilanyl-ethoxymethyl)-5H-pyrrolo[2,3-b]pyrazin-7-yl]-2,2-dimethyl-propan-1-one (500 mg, 0.93 mmol), CuI (35 mg, 0.18 mmol), proline (43 mg, 0.37 mmol), K$_2$CO$_3$ (515 mg, 3.7 mmol), and azetidin-3-yl-carbamic acid tert-butyl ester hydrogen chloride (1.364 g, 7.9 mmol), in DMSO (8.5 ml), was stirred in a sealed tube at 100° C. for 2 days. The reaction mixture was partitioned between EtOAc/Water. The organic layer were collected, dried over MgSO$_4$, filtered, and concentrated. Silica gel chromatography using 10-100% EtOAc in hexane as eluant gave 283 mg (52%) of a yellow solid which was dissolved in DCM (4 ml) and treated with TFA (4 ml, 53 mmol) for 16 hours. The reaction mixture was stripped down and partitioned between EtOAc/sat. Na$_2$CO$_3$. The organic layers were collected, dried over MgSO$_4$, filtered, and concentrated. The crude material was dissolved in EtOH (9 ml) and treated with NaOAc (1.271 g, 9.3 mmol) for overnight. The reaction mixture was partitioned between EtOAc/water and the organic layers were collected, dried over MgSO$_4$, filtered, and concentrated. Silica gel chromatography using 0-20% {5% NH$_4$OH:MeOH} in DCM as eluant gave a solid which was triturated with 1:1 Et$_2$O/Hex affording 8 mg (2.4%) of 1-{2-[3-(3-Amino-azetidin-1-yl)-phenyl]-5H-pyrrolo[2,3-b]pyrazin-7-yl}-2,2-dimethyl-propan-1-one as a pale yellow solid. M+H=350.

Example 202

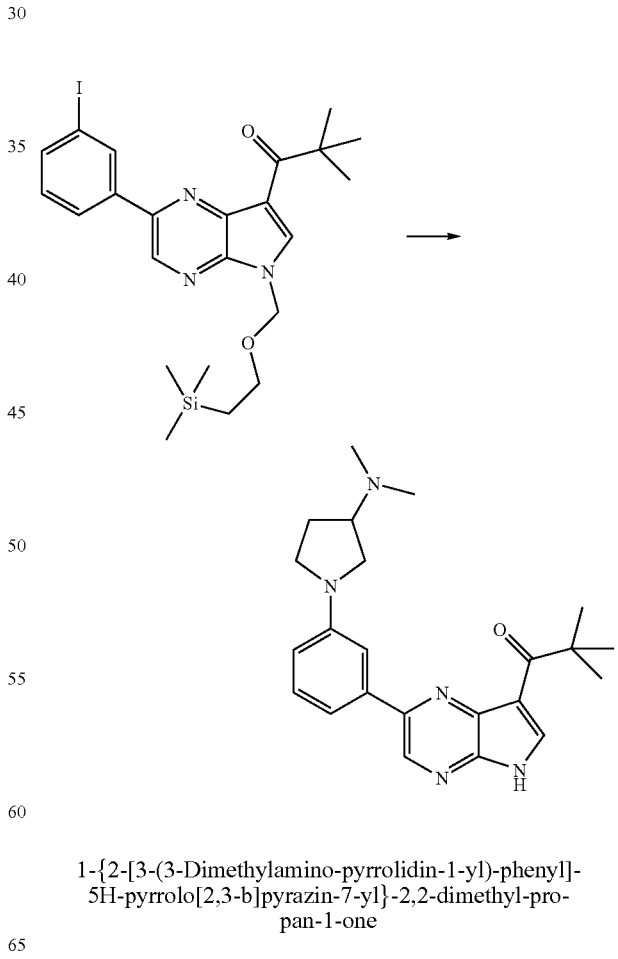

1-{2-[3-(3-Dimethylamino-pyrrolidin-1-yl)-phenyl]-5H-pyrrolo[2,3-b]pyrazin-7-yl}-2,2-dimethyl-propan-1-one A solution of 1-[2-(3-iodo-phenyl)-5-(2-trimethylsilanyl-ethoxymethyl)-5H-pyrrolo[2,3-b]pyrazin-7-yl]-2,2-dimethyl-propan-1-one (285 mg, 0.53 mmol), CuI (40 mg, 0.21 mmol), proline (49 mg, 0.43 mmol), $K_2CO_3$ (367 mg, 2.7 mmol), and dimethyl-pyrrolidin-3-yl-amine (608 mg, 5.3 mmol), in DMSO (1.0 ml), was stirred in a sealed tube at 100° C. for 2 days. The reaction mixture was partitioned between EtOAc/Water. The organic layer were collected, dried over $MgSO_4$, filtered, and concentrated. Silica gel chromatography using 6-100% EtOAc in hexane as eluant gave 221 mg (79%) of a yellow solid which was dissolved in DCM (4 ml) and treated with TFA (4 ml, 53 mmol) for 16 hours. The reaction mixture was stripped down and partitioned between EtOAc/sat. $Na_2CO_3$. The organic layers were collected, dried over $MgSO_4$, filtered, and concentrated. The crude material was dissolved in EtOH (5 ml) and treated with NaOAc (724 mg, 5.3 mmol) for overnight. The reaction mixture was partitioned between EtOAc/water and the organic layers were collected, dried over $MgSO_4$, filtered, and concentrated. Silica gel chromatography using 0-20% {5% $NH_4OH$:MeOH} in DCM as eluant provided 97 mg (47%) of 1-{2-[3-(3-dimethylamino-pyrrolidin-1-yl)-phenyl]-5H-pyrrolo[2,3-b]pyrazin-7-yl}-2,2-dimethyl-propan-1-one a yellow solid. MP 204-206° C., M+H=392.

Example 203

2,2-Dimethyl-1-{2-[3-(3-methyl-piperazin-1-yl)-phenyl]-5H-pyrrolo[2,3-b]pyrazin-7-yl}-propan-1-one 2,2-Dimethyl-1-{2-[3-(3-methyl-piperazin-1-yl)-phenyl]-5H-pyrrolo[2,3-b]pyrazin-7-yl}-propan-1-one was prepared starting from 1-[2-(3-iodo-phenyl)-5-(2-trimethylsilanyl-ethoxymethyl)-5H-pyrrolo[2,3-b]pyrazin-7-yl]-2,2-dimethyl-propan-1-one and 2-methyl-piperazine-1-carboxylic acid tert-butyl ester following general procedures as described in these Examples. M+H=378.

Example 204

1-{2-[3-(2-Hydroxy-2-methyl-propylamino)-phenyl]-5H-pyrrolo[2,3-b]pyrazin-7-yl}-2,2-dimethyl-propan-1-one A solution of 1-[2-(3-iodo-phenyl)-5-(2-trimethylsilanyl-ethoxymethyl)-5H-pyrrolo[2,3-b]pyrazin-7-yl]-2,2-dimethyl-propan-1-one (294 mg, 0.55 mmol), CuI (42 mg, 0.22 mmol), proline (51 mg, 0.44 mmol), $K_2CO_3$ (379 mg, 2.7 mmol), and 1-amino-2-methyl-propan-2-ol (489 mg, 5.5 mmol), in DMSO (1 ml), was stirred in a sealed tube at 100° C. for 16 hours. The reaction mixture was partitioned between EtOAc/water. The organic layer were collected, dried over $MgSO_4$, filtered, and concentrated. Silica gel chromatography using 6-50% EtOAc in hexane as eluant gave 265 mg (97%) of an orange oil which was dissolved in THF (10 ml) and treated with TBAF (1M in THF, 3 ml, 3 mmol) for 16 hours. The reaction mixture was stripped down and partitioned between EtOAc/sat. $NH_4Cl$. The organic layers were collected, dried over $MgSO_4$, filtered, and concentrated. The resulting oil was dissolved in EtOH (5 ml) and treated with sodium acetate (724 mg, 8.8 mmol) and allowed to stir overnight. The reaction mixture was partitioned between EtOAc/Water, and the organic layers were collected, dried over $MgSO_4$, filtered, and concentrated. Silica gel chromatography using 0-10% {5% $NH_4OH$:MeOH} in DCM as eluant gave 107 mg (53%) of 1-{2-[3-(2-hydroxy-2-methyl-propylamino)-phenyl]-5H-pyrrolo[2,3-b]pyrazin-7-yl}-2,2-dimethyl-propan-1-one as a yellow solid. M+H=367.

Example 205

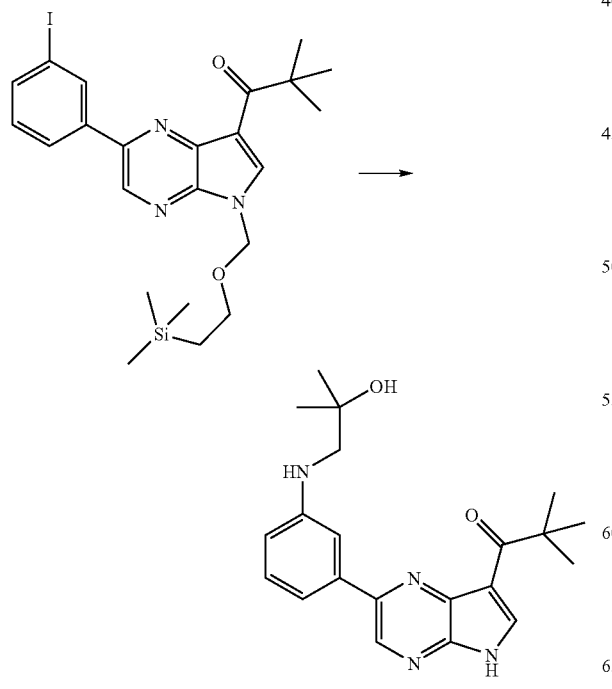

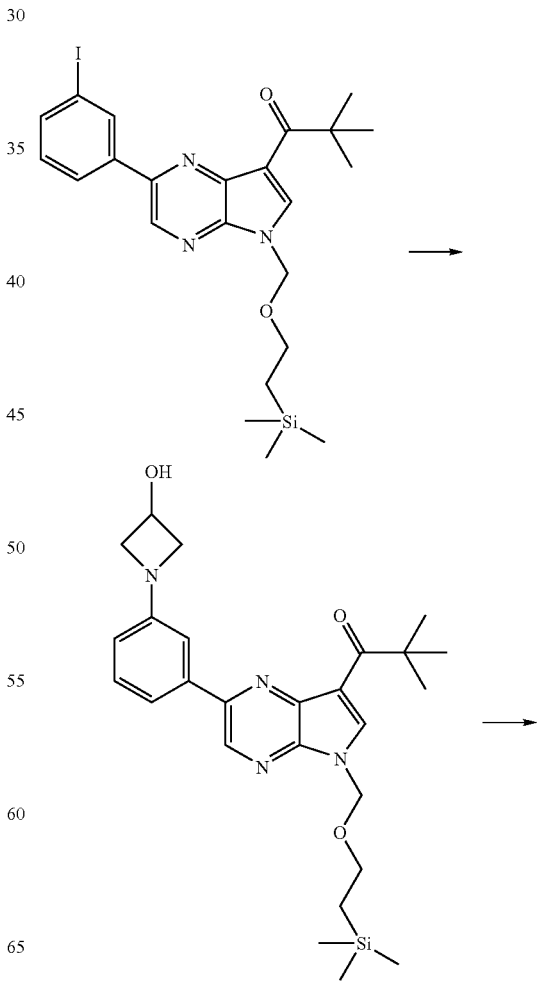

-continued

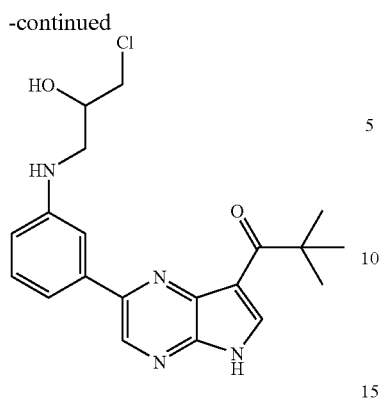

1-[2-[3-(3-Hydroxy-azetidin-1-yl)-phenyl]-5-(2-trimethylsilanyl-ethoxymethyl)-5H-pyrrolo[2,3-b]pyrazin-7-yl]-2,2-dimethyl-propan-1-one 1-[2-[3-(3-Hydroxy-azetidin-1-yl)-phenyl]-5-(2-trimethylsilanyl-ethoxymethyl)-5H-pyrrolo[2,3-b]pyrazin-7-yl]-2,2-dimethyl-propan-1-one was prepared starting from 1-[2-(3-iodo-phenyl)-5-(2-trimethylsilanyl-ethoxymethyl)-5H-pyrrolo[2,3-b]pyrazin-7-yl]-2,2-dimethyl-propan-1-one and azetidin-3-ol hydrogen chloride following the same procedure of RO5364753. M+H=481.

Example 206

1-{2-[3-(3-Chloro-2-hydroxy-propylamino)-phenyl]-5H-pyrrolo[2,3-b]pyrazin-7-yl}-2,2-dimethyl-propan-1-one A solution of 1-[2-[3-(3-hydroxy-azetidin-1-yl)-phenyl]-5-(2-trimethylsilanyl-ethoxymethyl)-5H-pyrrolo[2,3-b]pyrazin-7-yl]-2,2-dimethyl-propan-1-one (36 mg, 0.075 mmol), in MeOH (1 ml), was treated with 18.5% HCl aq (1.75 ml). The reaction mixture was capped and heated to 90° C. for 1.5 hours. The reaction mixture was concentrated to dryness, and the resulting residue was taken up in 10 ml of EtOAc and 5 ml of sat. NaHCO₃ aq. The reaction mixture was allowed to stir for 15 minutes and then extracted into EtOAc. The organic layers were collected, dried over MgSO₄, filtered, concentrated. Silica gel chromatography using 0-10% MeOH in EtOAc as eluant gave 10 mg (35%) of 1-{2-[3-(3-chloro-2-hydroxy-propylamino)-phenyl]-5H-pyrrolo[2,3-b]pyrazin-7-yl}-2,2-dimethyl-propan-1-one as a yellow solid. M+H=387.

Example 207

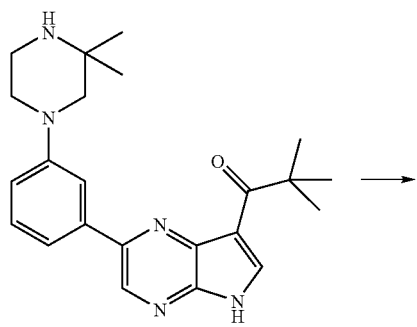

-continued

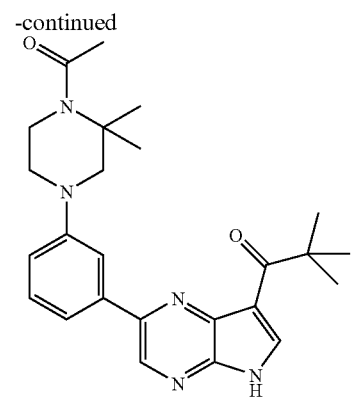

1-{2-[3-(4-Acetyl-3,3-dimethyl-piperazin-1-yl)-phenyl]-5H-pyrrolo[2,3-b]pyrazin-7-yl}-2,2-dimethyl-propan-1-one A solution of 1-{2-[3-(3,3-dimethyl-piperazin-1-yl)-phenyl]-5H-pyrrolo[2,3-b]pyrazin-7-yl}-2,2-dimethyl-propan-1-one (28 mg, 0.07 mmol), in DCM (5 ml), was treated with pyridine (5 drops from Pasteur pipet), followed by acetic anhydride (4 drops from Pasteur pipet). The reaction mixture was allowed to stir at room temperature for overnight. The reaction mixture was partitioned between EtOAc/Water, and the organic layers were collected, dried over MgSO₄, filtered, and concentrated. The residue was dissolved in THF (5 ml) and treated with 1N NaOH (0.3 ml, 0.3 mmol). After stirring for approximately 3 hours, the reaction mixture was partitioned between EtOAc/1N HCl, and the organic layer were collected, washed with sat. NaHCO₃, dried over MgSO₄, filtered, and concentrated. Silica gel chromatography using 0-10% {5% NH₄OH:MeOH} in DCM as eluant gave 22 mg (72%) of 1-{2-[3-(4-acetyl-3,3-dimethyl-piperazin-1-yl)-phenyl]-5H-pyrrolo[2,3-b]pyrazin-7-yl}-2,2-dimethyl-propan-1-one as yellow solid. M+H=434.

Example 208

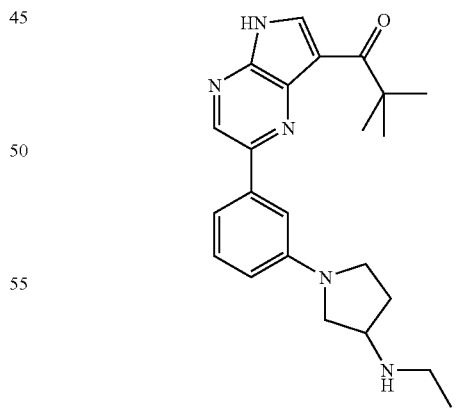

1-{2-[3-(3-Ethylamino-pyrrolidin-1-yl)-phenyl]-5H-pyrrolo[2,3-b]pyrazin-7-yl}-2,2-dimethyl-propan-1-one was obtained by heating 1-[2-(3-iodo-phenyl)-5H-pyrrolo[2,3-b]pyrazin-7-yl]-2,2-dimethyl-propan-1-one and 3-ethylaminopyrrolidine (TCI-US) with 15 mol % copper (I) iodide, 30 mol % proline, and excess potassium carbonate in dimethylsulfoxide with purification by silica gel chromatography (eluant: 0 to 10% ethanol in ethyl acetate): m.p. 200-202° C.; MS m/z 392 (M+H)

Example 209

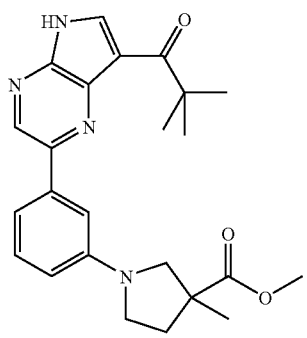

1-{3-[7-(2,2-Dimethyl-propionyl)-5H-pyrrolo[2,3-b]pyrazin-2-yl]-phenyl}-3-methyl-pyrrolidine-3-carboxylic acid methyl ester was obtained according to the copper catalyzed process described immediately above by replacing 3-ethylaminopyrrolidine with methyl 3-methylpyrrolidine 3-carboxylate: m.p. 198-200° C.; MS m/z 421 (M+H)

Example 210

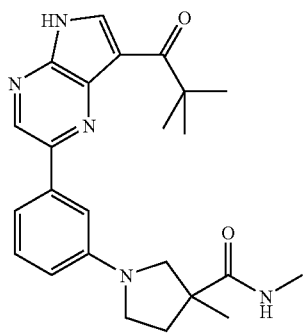

1-{3-[7-(2,2-Dimethyl-propionyl)-5H-pyrrolo[2,3-b]pyrazin-2-yl]-phenyl}-3-methyl-pyrrolidine-3-carboxylic acid methylamide was prepared by treating 1-{3-[7-(2,2-dimethyl-propionyl)-5H-pyrrolo[2,3-b]pyrazin-2-yl]-phenyl}-3-methyl-pyrrolidine-3-carboxylic acid methyl ester (190 mg, 0.3 mmol) with methanol (3 mL) and potassium hydroxide (2 mL, 0.5 M aqueous). Upon partitioning the mixture between 10% aqueous acetic acid and ethyl acetate, the desired acid (110 mg, 0.27 mmol) was dissolved in N,N-dimethylformamide (3 mL) and treated with carbonyl diimidazole (46 mg, 0.28 mmol) and heated to 65° C. for 2 hours. Methylamine (2 mL) was condensed at −20° C. in heavy-walled vessel. The mixture above was added and the vessel was immediately sealed and heated to 50° C. for 5 days. Upon cooling, the volatiles were removed in vacuo and the residue partitioned between 2% aqueous acetic acid and ethyl acetate. The combined organic layers were aged over anhydrous sodium sulfate. The title compound was obtained as a powder (26 mg) following silica gel chromatography (eluant: 40 to 100% ethyl acetate-hexanes): m.p. 252-254° C.; MS m/z 419 (M+H).

Example 211

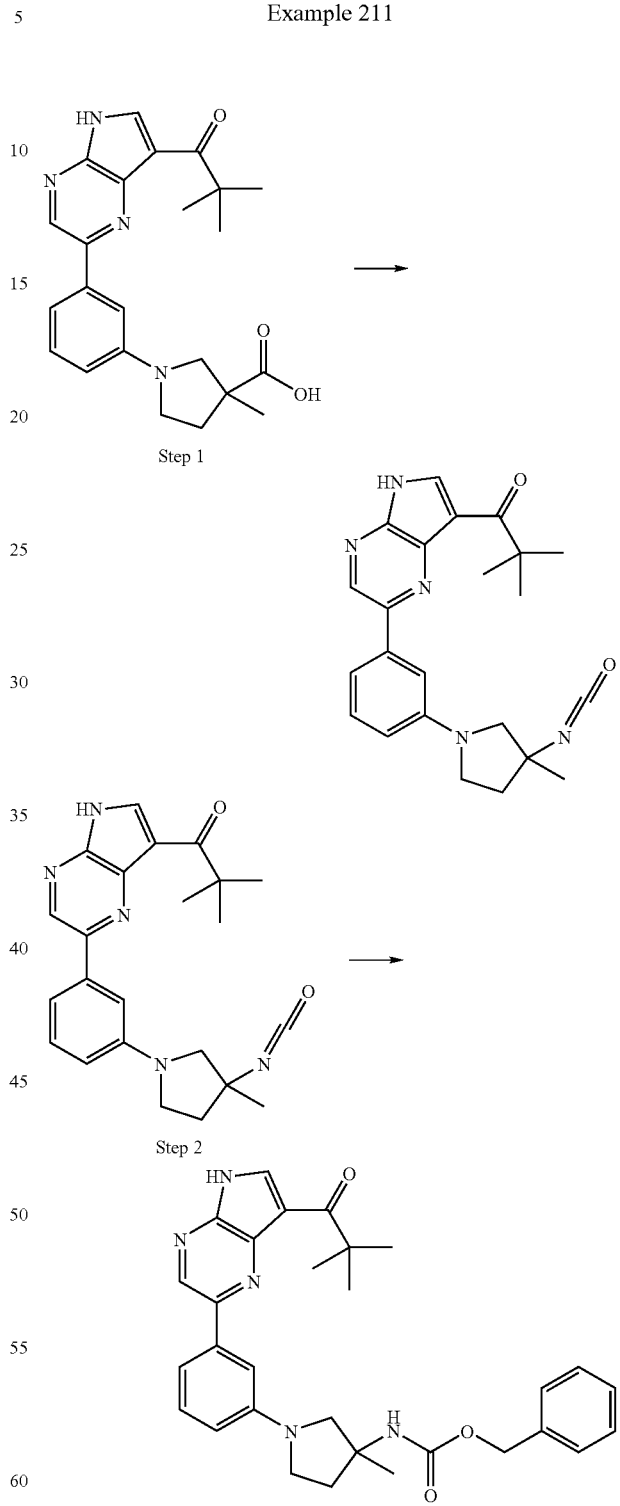

Step 1: (1-{3-[7-(2,2-Dimethyl-propionyl)-5H-pyrrolo[2,3-b]pyrazin-2-yl]-phenyl}-3-methyl-pyrrolidin-3-yl)-carbamic acid benzyl ester was obtained by treating 1-{3-[7-(2,2-dimethyl-propionyl)-5H-pyrrolo[2,3-b]pyrazin-2-yl]-phenyl}-3-methyl-pyrrolidine-3-carboxylic acid (following the general procedures described in these Examples, 105 mg, 0.26 mmol) with diphenylphosphoryl azide (0.06 mL, 0.27 mmol) in toluene (5 mL) and triethylamine (0.07 mL, 0.52 mmol). The resulting solution was heated to 70° C. for 18 hours.

Step 2: The solution was then treated with benzyl alcohol (0.5 mL) and heated to reflux for 20 hours. The mixture was directly loaded onto silica gel. The title compound was eluted with 50 to 80% ethyl acetate-hexanes (20 mg as a foam): MS m/z 512 (M$^{+H}$)

Example 212

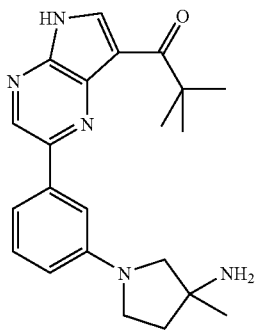

1-{2-[3-(3-Amino-3-methyl-pyrrolidin-1-yl)-phenyl]-5H-pyrrolo[2,3-b]pyrazin-7-yl}-2,2-dimethyl-propan-1-one was obtained by removing the volatiles from step 1 with a rotary evaporator and conducting step 2 in the following manner: Dissolve the residue (approx. 0.4 mmol) from step 1 in 1,4-dioxane (7 mL) and add to a refluxing solution of 35% aqueous hydrochloric acid (7 mL). Cool after 40 minutes and remove the volatiles. Partition the residue between pH 9 buffer and ethyl acetate (5×25 mL). The combined organic extracts were stored over anhydrous sodium sulfate and then the volatiles were removed. The title compound was isolated (36 mg, powder) by silica gel chromatography (eluant: 0.1% iso-propylamine in ethyl acetate, 0 to 5% ethanol gradient): m.p. 216-218° C.; MS m/z 378 (M$^{+H}$).

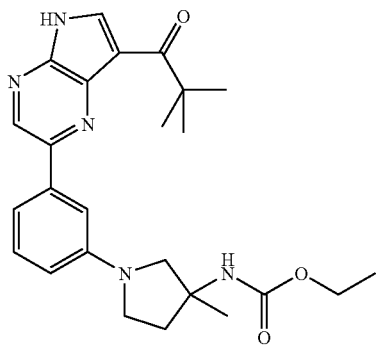

(1-{3-[7-(2,2-Dimethyl-propionyl)-5H-pyrrolo[2,3-b]pyrazin-2-yl]-phenyl}-3-methyl-pyrrolidin-3-yl)-carbamic acid ethyl ester was obtained (21 mg, foam) by replacing benzyl alcohol with ethanol in step 2: MS m/z 450 (M$^{+H}$)

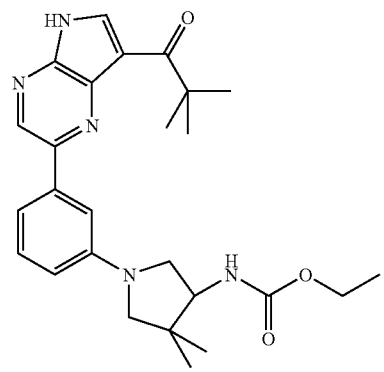

(1-{3-[7-(2,2-Dimethyl-propionyl)-5H-pyrrolo[2,3-b]pyrazin-2-yl]-phenyl}-4,4-dimethyl-pyrrolidin-3-yl)-carbamic acid ethyl ester was prepared by the general amination procedure used to prepare 1-{2-[3-(3-ethylamino-pyrrolidin-1-yl)-phenyl]-5H-pyrrolo[2,3-b]pyrazin-7-yl}-2,2-dimethyl-propan-1-one by replacing 3-ethylaminopyrrolidine with 4,4-dimethylpyrrolidine 3-carboxylic acid (Tyger) and purified by silica gel chromatography (eluant: 25 to 100% ethyl acetate-hexanes). The resulting acid replaced 1-{3-[7-(2,2-dimethyl-propionyl)-5H-pyrrolo[2,3-b]pyrazin-2-yl]-phenyl}-3-methyl-pyrrolidine-3-carboxylic acid in step 1 above and ethanol replaced benzyl alcohol in step 2 above. The title compound (11 mg) was obtained as a foam: m.p. 118-120° C.; MS m/z 464 (M$^{+H}$).

Example 213

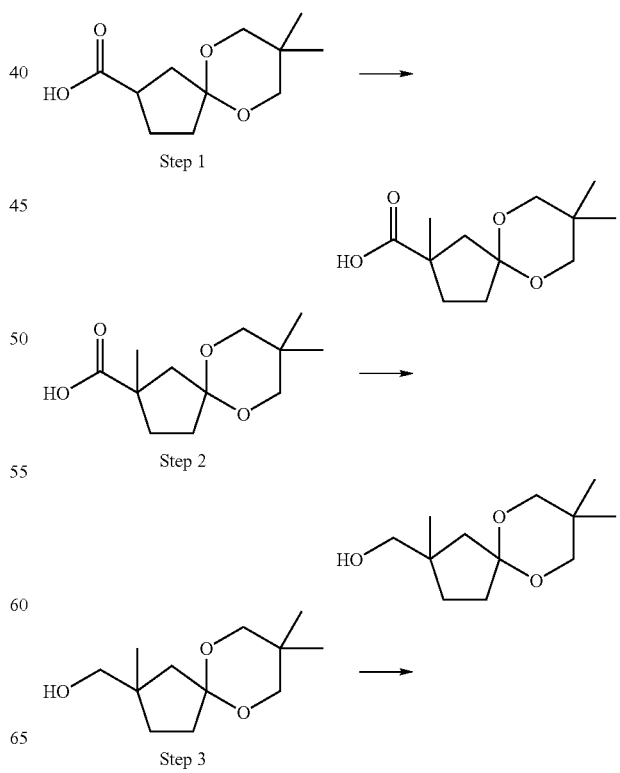

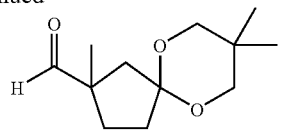

2,8,8-Trimethyl-6,10-dioxa-spiro[4.5]decane-2-carbaldehyde

Step 1: 8,8-Dimethyl-6,10-dioxa-spiro[4.5]decane-2-carboxylic acid (3.5 g, 16.4 mmol, German application DE 4312832) was dissolved in tetrahydrofuran (20 mL) and added to a 0° C. solution of lithium diethylamide (36 mmol in 100 mL of tetrahydrofuran) and then warmed to 50° C. for 2 hours. The resulting solution was allowed to cool to ambient temperature and treated with iodomethane (1.1 mL, 18.2 mmol). After stirring for 4 hours, the mixture was poured into ammonium chloride (2.2 g dissolved in 50 mL of water) and toluene. The mixture was extracted with ethyl acetate (2×100 mL) and the combined organic layers were stored over anhydrous sodium sulfate. The crude acid was obtained upon filtration and removal of volatiles and used directly in the next step.

Step 2: The acid (approx. 15 mmol) was dissolved in tetrahydrofuran (60 mL) and cooled to 0° C. under a nitrogen atmosphere. Lithium aluminumhydride (11 mL, 44 mmol, 4M in ether) was added dropwise and the mixture was heated to reflux for 20 hours. Upon cooling to 0° C., the mixture was treated with Glouber's salt (approx. 10 g), then water (30 mL), and aqueous sodium hydroxide (30 mL, 30 mmol, 1 M) were added. The mixture was allowed to warm to rt and filtered through Celite. The filter cake was washed with THF-toluene and combined with the filtrate. That mixture was extracted with ethyl acetate (3×50 mL) and the combined organic extracts were stored over anhydrous sodium sulfate. An oil (480 mg) was purified by silica gel chromatography (eluant: 25 to 75% ethyl acetate in hexanes) and the spectroscopic properties are consistent with the desired alcohol (480 mg).

Step 3: Dimethyl sulfoxide (anhydrous, 0.34 mL, 4.4 mmol) was dissolved in dichloromethane (20 mL) and cooled to −70° C. Oxalyl chloride (1.44 mL, 2.9 mmol, 2 M dichloromethane) was added dropwise and the bubbling solution was stirred for 10 minutes. A dichloromethane (10 mL) solution of the alcohol above (475 mg, 2.2 mmol) was then added to the −70° C. reagent. After 20 minutes, triethylamine (0.76 mL, 5.5 mmol) was added rapidly and the cooling bath removed. The mixture was quenched after 45 minutes total with aqueous potassium bicarbonate and stirred vigorously for 10 minutes. The mixture was extracted with dichloromethane (3×30 mL) and the combined organic layers were stored over anhydrous sodium sulfate. An oil (550 mg, 2.2 mmol, impure with DMSO) resulted upon removal of the volatiles and spectroscopic properties were consistent with the desired aldehyde.

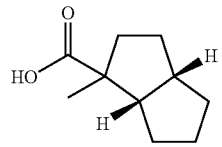

(3aS,6aS)-1-Methyl-octahydro-pentalene-1-carboxylic acid was obtained according to this example by replacing 8,8-dimethyl-6,10-dioxa-spiro[4.5]decane-2-carboxylic acid with (3aS,6aS)-octahydro-pentalene-1-carboxylic acid (*Tetrahedron* 1964, 20, 1843) in step 1 and not conducting steps 2 and 3.

Example 214

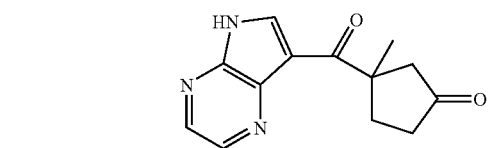

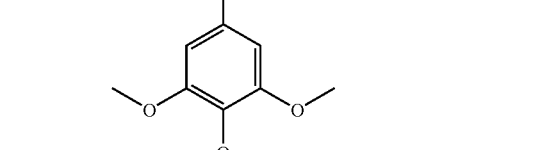

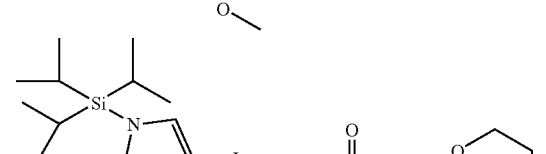

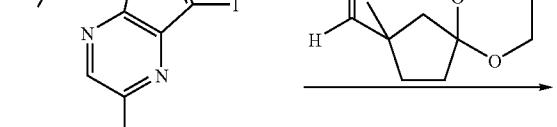

Step 1

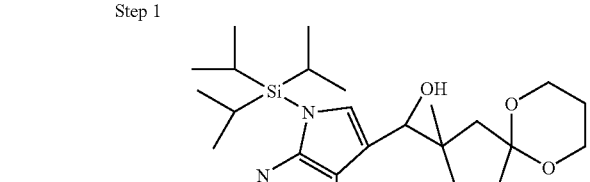

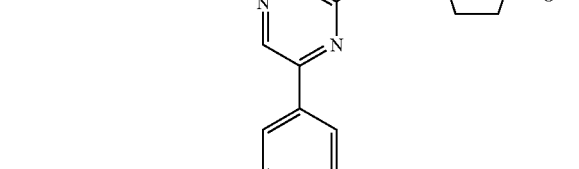

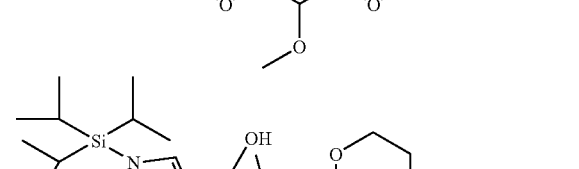

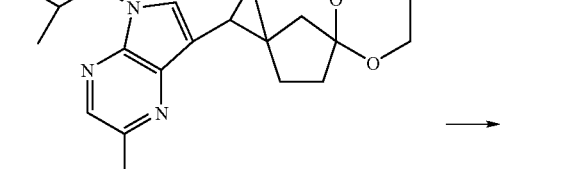

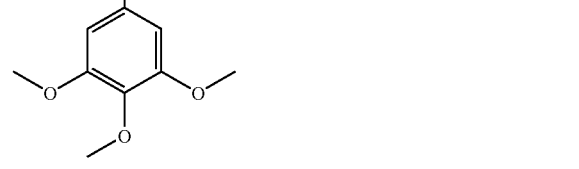

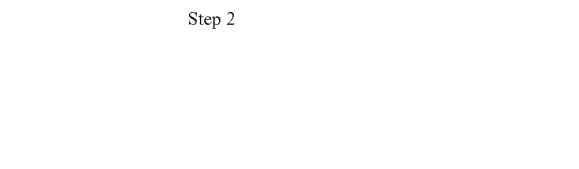

Step 2

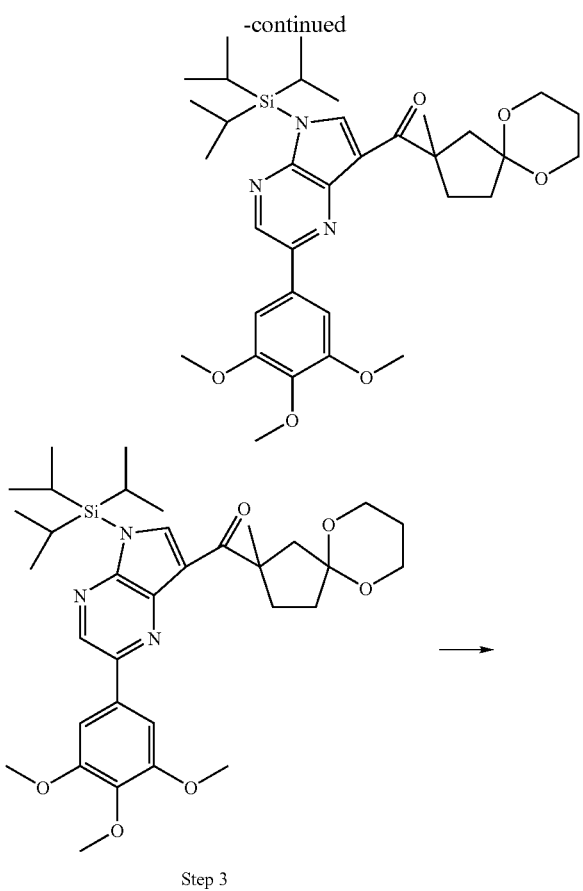

Step 3

3-Methyl-3-[2-(3,4,5-trimethoxy-phenyl)-5H-pyrrolo[2,3-b]pyrazine-7-carbonyl]-cyclopentanone was prepared by the following steps:

Step 1: 7-Iodo-5-triisopropylsilanyl-2-(3,4,5-trimethoxyphenyl)-5H-pyrrolo[2,3-b]pyrazine (830 mg, 1.47 mmol) was dissolved in anhydrous tetrahydrofuran (15 mL) and cooled to −70° C. Iso-propylmagnesium chloride-lithium chloride complex (3.5 mL, 4.5 mmol, 1.3 M tetrahydrofuran) solution was added dropwise and after 10 minutes from the start of the addition, a tetrahydrofuran (3 mL) solution of the aldehyde produced above (550 mg, 2.2 mmol) was then added rapidly. The golden solution was warmed to 0° C. after 1 hour and held at 0° C. for another hour. It was then quenched with aqueous potassium bicarbonate and toluene. The mixture was extracted with ethyl acetate (3×50 mL) and stored over anhydrous sodium sulfate. The volatiles were removed resulting in an oil and LCMS suggests the major products are the desired MW (alcohols) and the loss of TIPS (alcohol).

Step 2: The mixture of alcohols (approx. 1.47 mmol) was dissolved in dichloromethane (12 mL) and treated with sodium bicarbonate (380 mg, 4.5 mmol). With vigorous stirring, Dess-Martin periodinane (685 mg, 1.6 mmol, Aldrich) was added in one portion and stirring continued for 40 minutes. The mixture was poured into water (10 mL) and 5% aqueous sodium thiosulfate (10 mL). The mixture was extracted with dichloromethane (3×25 mL) and stored over anhydrous sodium sulfate.

Step 3: The oxidized mixture was dissolved in acetone (3 mL) at ambient temperature and treated with aqueous hydrochloric acid (1.5 mL, 1.5 mmol, 1 M). The yellow solution gave a precipitate after 5 minutes and stirring was continued for 16 hours. The mixture was quenched with aqueous potassium bicarbonate and extracted with ethyl acetate (3×30 mL). The combined organic extracts were stored over anhydrous sodium sulfate. The title compound (153 mg) was isolated by silica gel chromatography (eluant: 10 to 90% ethyl acetate in hexanes) as a white powder: m.p. 238-240° C.; MS m/z 410 $(M^{+H})$.

Example 215

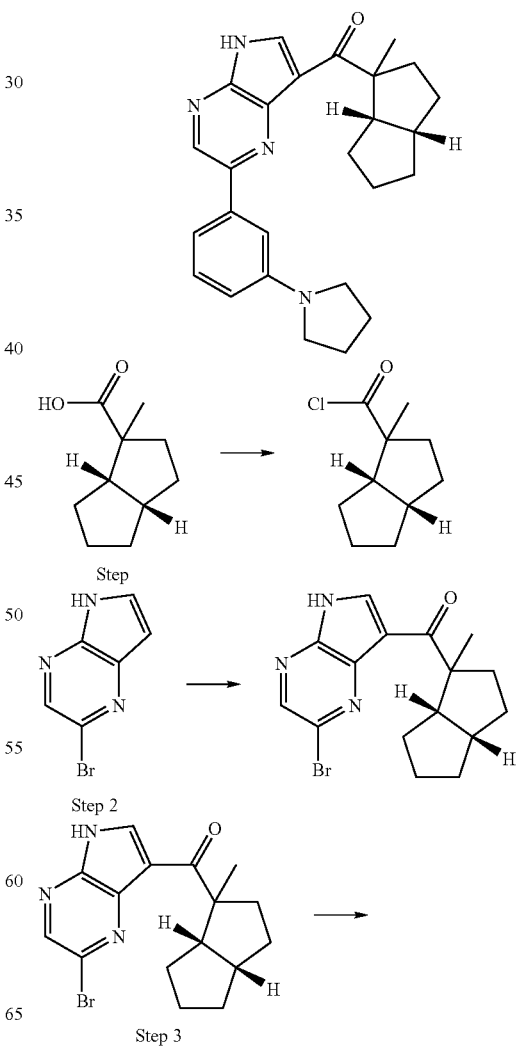

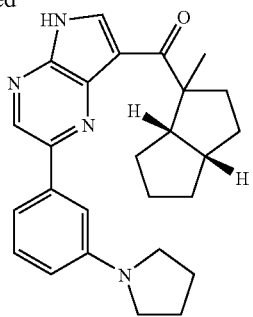

((3aS,6aS)-1-Methyl-octahydro-pentalen-1-yl)-[2-(3-pyrrolidin-1-yl-phenyl)-5H-pyrrolo[2,3-b]pyrazin-7-yl]-methanone was prepared by:

Step 1: (3aS,6aS)-1-Methyl-octahydro-pentalene-1-carboxylic acid (315 mg, 1.9 mmol) was dissolved in 1,2-dichloroethane (3 mL) at ambient temperature and treated with oxalyl chloride (1.9 mL, 2 M in dichloromethane) followed by one drop of N,N-dimethylformamide. The bubbling solution was heated to 50° C. for 2 hours and then the volatiles were removed under vacuum. The crude acid chloride was used without delay.

Step 2: The acid chloride was used directly by dissolving in 1,2-dichloroethane (3 mL) under Argon. The solution was treated with 2-bromo-5H-pyrrolo[2,3-b]pyrazine (45 mg, 0.23 mmol) and diethylaluminum chloride (0.7 mL, 0.7 mmol, 1 M hexane). The mixture gave a solution upon heating to 85° C. It was cooled after 24 hours and partitioned between 2 M dipotassium hydrogen phosphate and dichloromethane (4×20 mL). The combined organic extracts were stored over anhydrous sodium sulfate. The desired ketone was purified by silica gel chromatography (eluant: 10 to 40% ethyl acetate in hexanes) and obtained as a powder (55 mg). The tan powder has spectroscopic properties consistent with the desired ketone.

Step 3: The ketone (45 mg, 0.10 mmol) was dissolved in 1,4-dioxane (2 mL) and potassium carbonate (38 mg, 0.3 mmol, dissolved in 0.2 mL of water) in a microwave reaction vial. The solution was purged with a stream of argon gas. 3-(1-Pyrrolidino)phenyl boronic acid (30 mg, 0.15 mmol) and 1,1'-bis(diphenylphosphino)-ferrocene) palladium dichloride (1:1 dichloromethane complex, 85 mg, 0.10 mmol) were added. The vial was sealed, placed in a microwave reactor and run at 150° C. for 30 min. The reaction mixture was cooled and directly loaded onto a column of silica gel. The desired biphenyl (27 mg, eluant: 40 to 80% ethyl acetate in hexane) was obtained as a yellow solid: m.p. 200-202° C.; MS m/z 415 ($M^{+H}$).

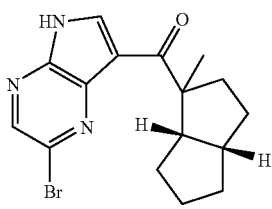

(2-Bromo-5H-pyrrolo[2,3-b]pyrazin-7-yl)-((3aS,6aS)-1-methyl-octahydro-pentalen-1-yl)-methanone was obtained following step 2 and not conducting step 3 of the example above: m.p. foam; MS m/z 348 ($M^{+H}$) and 350 ($M^{+H}$).

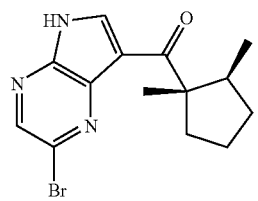

(2-Bromo-5H-pyrrolo[2,3-b]pyrazin-7-yl)-(cis-1,2-dimethyl-cyclopentyl)-methanone was prepared as the racemate according to the example above by replacing (3aS,6aS)-1-methyl-octahydro-pentalene-1-carboxylic acid with racemic cis-1,2-dimethyl-cyclopentanecarboxylic acid (520 mg, 3.7 mmol, *J. Org. Chem.* 1969, 34, 1103) in step 1 and not conducting step 3: m.p. 178-180° C.; MS m/z 322 ($M^{+H}$) and 324 ($M^{+H}$).

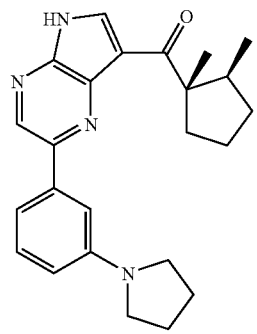

(cis-1,2-Dimethyl-cyclopentyl)-[2-(3-pyrrolidin-1-yl-phenyl)-5H-pyrrolo[2,3-b]pyrazin-7-yl]-methanone according to the example above by replacing (3aS,6aS)-1-methyl-octahydro-pentalene-1-carboxylic acid with racemic cis-1,2-dimethyl-cyclopentanecarboxylic acid (*J. Org. Chem.* 1969, 34, 1103) in step 1: m.p. foam; MS m/z 389 ($M^{+H}$).

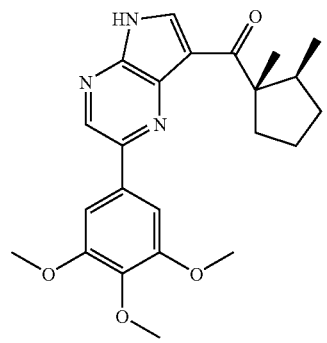

(cis-1,2-Dimethyl-cyclopentyl)-[2-(3,4,5-trimethoxyphenyl)-5H-pyrrolo[2,3-b]pyrazin-7-yl]-methanone according to the example above by replacing (3aS,6aS)-1-methyl-octahydro-pentalene-1-carboxylic acid with racemic cis-1,2-dimethyl-cyclopentanecarboxylic acid (*J. Org. Chem.* 1969, 34, 1103) in step 1 and replacing 3-(1-pyrrolidino)phenyl boronic acid with 3,4,5-trimethoxyphenyl boronic acid in step 3: m.p. 234-236° C.; MS m/z 450 ($M^{+H}$).

Example 216

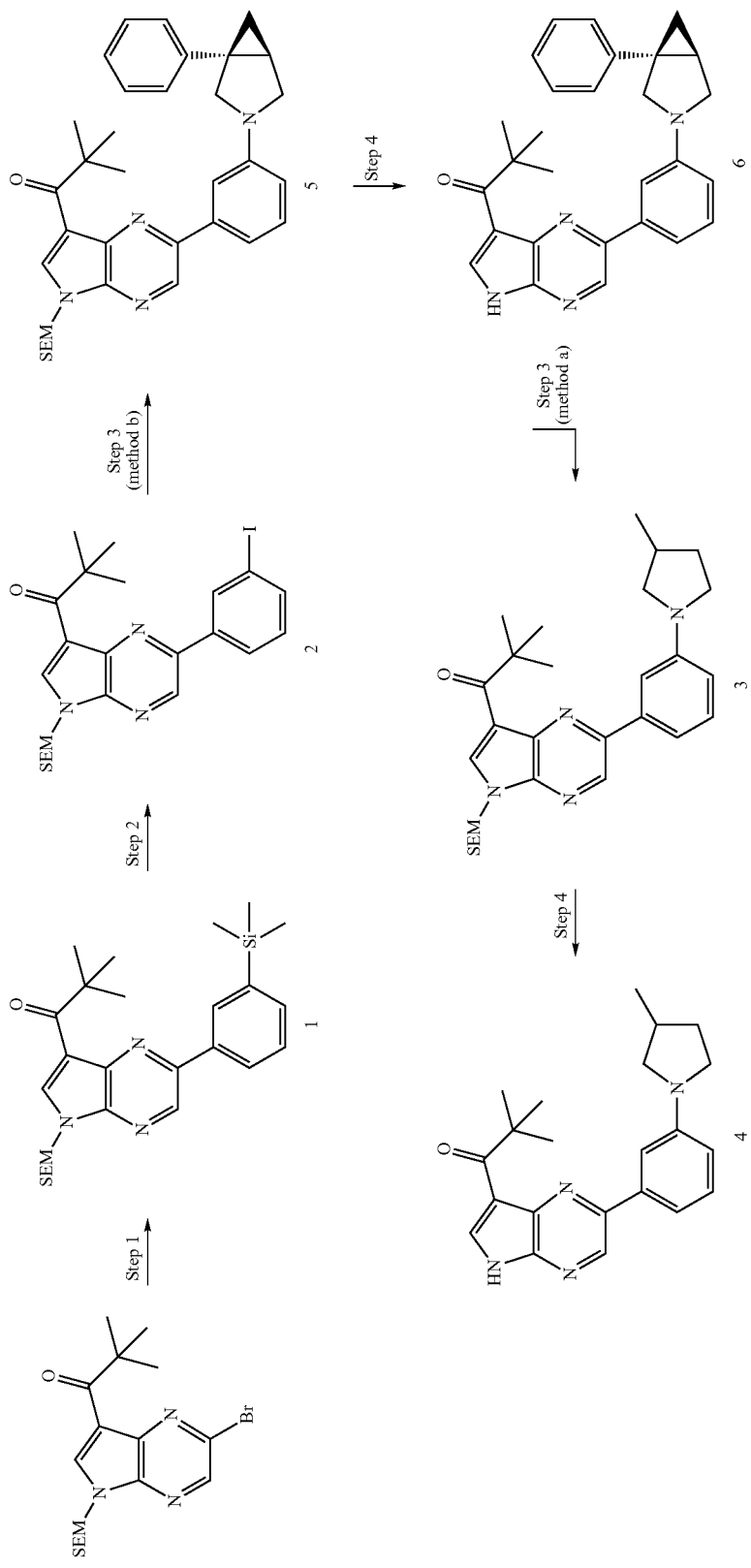

Step 1—4.4 mL of degassed 2M aqueous K$_2$CO$_3$ (8.8 mmol) were added under argon to a mixture of 1-[2-bromo-5-(2-trimethylsilanyl-ethoxymethyl)-5H-pyrrolo[2,3-b]pyrazin-7-yl]-2,2-dimethyl-propan-1-one (1.2 g, 2.91 mmol), 3-trimethylsilylphenylboronic acid (0.85 g, 4.379 mmol) and tetrakis(triphenylphosphine)palladium (0.5 g, 0.433 mmol) in 25 mL of degassed 1,4-dioxane. The resulting yellow solution was stirred at 80° C. overnight before being cooled to RT and filtered through a Varian Chem Elut cartridge. The cartridge was eluted twice with 1,4-dioxane and the filtrate was evaporated. The residue was purified by SiO$_2$ chromatography (hexanes/[hexanes/toluene/EtOAc 6/3.8/0.2] 100-0% hexanes) to give 1.15 g of 1 (82% yield)

Methyl-cyclopentyl-[5-(2-trimethylsilanyl-ethoxymethyl)-2-(3-trimethylsilanyl-phenyl)-5H-pyrrolo[2,3-b]pyrazin-7-yl]-methanone was prepared following the same procedure but using (2-bromo-5H-pyrrolo[2,3-b]pyrazin-7-yl)-(1-methyl-cyclopentyl)-methanone as starting material. The product was isolated in 93% yield after purification by SiO$_2$ chromatography (hexanes/EtOAc 0-5% EtOAc).

Methyl-cyclohexyl-[5-(2-trimethylsilanyl-ethoxymethyl)-2-(3-trimethylsilanyl-phenyl)-5H-pyrrolo[2,3-b]pyrazin-7-yl]-methanone was prepared following the same procedure but using (2-bromo-5H-pyrrolo[2,3-b]pyrazin-7-yl)-(1-methyl-cyclohexyl)-methanone as starting material. The product was isolated in 52% yield after purification by SiO$_2$ chromatography (hexanes/EtOAc 0-5% EtOAc).

Step 2-Iodine monochloride 1M in DCM (9 mL, 9 mmol) was added dropwise at 0° C. and under argon to a mixture of 1 (1.1 g, 2.283 mmol) and K$_2$CO$_3$ (1.26 g, 9.116 mmol) in 50 mL of degassed DCM. The resulting mixture was stirred at 0° C. to RT for two hours before being quenched by addition of 10% aqueous sodium thiosulfate. The aqueous phase was back extracted three times with DCM. Combined organic layers were dried over Na$_2$SO$_4$, filtered and evaporated. The residue was purified by SiO$_2$ chromatography (hexanes/[hexanes/toluene/EtOAc 6/3.8/0.2] 10/0 to 0/10) to give 1.2 g of 2 (>95% yield).

[2-(3-Iodo-phenyl)-5-(2-trimethylsilanyl-ethoxymethyl)-5H-pyrrolo[2,3-b]pyrazin-7-yl]-(1-methyl-cyclopentyl)-methanone was prepared following the same procedure but using (1-methyl-cyclopentyl)-[5-(2-trimethylsilanyl-ethoxymethyl)-2-(3-trimethylsilanyl-phenyl)-5H-pyrrolo[2,3-b]pyrazin-7-yl]-methanone as starting material. The product was isolated in 11% yield along with 50% of [2-(3-iodo-phenyl)-5H-pyrrolo[2,3-b]pyrazin-7-yl]-(1-methyl-cyclopentyl)-methanone by SiO$_2$ chromatography (hexanes/EtOAc 0-10% EtOAc).

[2-(3-Iodo-phenyl)-5-(2-trimethylsilanyl-ethoxymethyl)-5H-pyrrolo[2,3-b]pyrazin-7-yl]-(1-methyl-cyclohexyl)-methanone was prepared following the same procedure but using (1-methyl-cyclohexyl)-[5-(2-trimethylsilanyl-ethoxymethyl)-2-(3-trimethylsilanyl-phenyl)-5H-pyrrolo[2,3-b]pyrazin-7-yl]-methanone as starting material. The product was isolated in 70% yield by SiO$_2$ chromatography (hexanes/EtOAc 0-7% EtOAc).

Step 3 Method a: A mixture of 2 (0.1 g, 0.187 mmol), 3 (0.032 g, 0.374 mol), copper iodide (0.004 g, 18.67 μmol), DL-proline (0.004 g, 37.35 μmol), and K$_2$CO$_3$ (0.052 g, 0.374 mmol) in 0.5 mL of DMSO was degassed for five minutes by bubbling argon through the mixture. The resulting was stirred at 90° C. overnight before being cooled to RT and partitioned between H$_2$O and Et$_2$O. The aqueous layer was back extracted twice with Et$_2$O. Combined organic layers were dried over magnesium sulfate, filtered and evaporated. The residue was purified by SiO$_2$ chromatography (hexanes/EtOAc 0-15% EtOAc) to give 0.075 g of 4 (61% yield)

1-[2-[3-((1S,5R,6R)-6-methanesulfonylmethyl-3-aza-bicyclo[3.1.0]hex-3-yl)-phenyl]-5-(2-trimethylsilanyl-ethoxymethyl)-5H-pyrrolo[2,3-b]pyrazin-7-yl]-2,2-dimethyl-propan-1-one was prepared following the same procedure using (1S,5R,6R)-6-methanesulfonylmethyl-3-aza-bicyclo[3.1.0]hexane (26% yield).

1-[2-[(3aR,6aS)-3-(Hexahydro-cyclopenta[c]pyrrol-2-yl)-phenyl]-5-(2-trimethylsilanyl-ethoxymethyl)-5H-pyrrolo[2,3-b]pyrazin-7-yl]-2,2-dimethyl-propan-1-one was prepared following the same procedure using the commercially available 3-azabiclyclo[3,3,0]octane hydrochloride (44% yield).

1-[2-[3-((1S,5R,6R)-6-Methoxymethyl-3-aza-bicyclo[3.1.0]hex-3-yl)-phenyl]-5-(2-trimethylsilanyl-ethoxymethyl)-5H-pyrrolo[2,3-b]pyrazin-7-yl]-2,2-dimethyl-propan-1-one was prepared following the same procedure using 2 and (1S,5R,6R)-6-methoxymethyl-3-aza-bicyclo[3.1.0]hexane (28% yield).

1-[2-[3-(4-Hydroxy-piperidin-1-yl)-phenyl]-5-(2-trimethylsilanyl-ethoxymethyl)-5H-pyrrolo[2,3-b]pyrazin-7-yl]-2,2-dimethyl-propan-1-one was prepared following the same procedure using 2 and the commercially available piperidin-4-ol.

1-[2-[3-(4-hydroxyl-4-methyl-piperidin-1-yl)-phenyl]-5-(2-trimethylsilanyl-ethoxymethyl)-5H-pyrrolo[2,3-b]pyrazin-7-yl]-2,2-dimethyl-propan-1-one was prepared following the same procedure using 2 and the commercially available 4-methyl-piperidin-4-ol hydrochloride (69% yield). In this reaction, six equivalents of K$_2$CO$_3$ were used instead of two.

N-(1-{3-[7-(2,2-Dimethyl-propionyl)-5-(2-trimethylsilanyl-ethoxymethyl)-5H-pyrrolo[2,3-b]pyrazin-2-yl]-phenyl}-3-methyl-pyrrolidin-3-ylmethyl)-acetamide was prepared the same way using 2 and N-(3-methyl-pyrrolidin-3-ylmethyl)-acetamide (57% yield). In this reaction 3 equivalents of amine, 0.2 equivalents of copper iodide and 0.4 equivalents of DL-proline were used.

N-(1-{3-[7-(2,2-Dimethyl-propionyl)-5-(2-trimethylsilanyl-ethoxymethyl)-5H-pyrrolo[2,3-b]pyrazin-2-yl]-phenyl}-3-methyl-pyrrolidin-3-ylmethyl)-methanesulfonamide was prepared following the same procedure using 2 and N-(3-methyl-pyrrolidin-3-ylmethyl)-methanesulfonamide (40% yield). In this reaction 3 equivalents of amine, 0.2 equivalents of copper iodide and 0.4 equivalents of DL-proline were used.

(1-{3-[7-(2,2-Dimethyl-propionyl)-5-(2-trimethylsilanyl-ethoxymethyl)-5H-pyrrolo[2,3-b]pyrazin-2-yl]-phenyl}-3-methyl-pyrrolidin-3-ylmethyl)-carbamic acid methyl ester was prepared following the same procedure using 2 and (3-methyl-pyrrolidin-3-ylmethyl)-carbamic acid methyl ester (42% yield). In this reaction 3 equivalents of amine, 0.2 equivalents of copper iodide and 0.4 equivalents of DL-proline were used.

Acetic acid 1-{3-[7-(2,2-dimethyl-propionyl)-5-(2-trimethylsilanyl-ethoxymethyl)-5H-pyrrolo[2,3-b]pyrazin-2-yl]-phenyl}-3-methyl-pyrrolidin-3-ylmethyl ester was prepared following the same procedure but using acetic acid 3-methyl-pyrrolidin-3-ylmethyl ester as amine (40% yield).

1-[2-[3-((1S,5R,6R)-6-Hydroxymethyl-3-aza-bicyclo[3.1.0]hex-3-yl)-phenyl]-5-(2-trimethylsilanyl-ethoxymethyl)-5H-pyrrolo[2,3-b]pyrazin-7-yl]-2,2-dimethyl-propan-1-one was prepared using a similar procedure using 2 and (1S,5R,6R)-1-(3-aza-bicyclo[3.1.0]hex-6-yl)-methanol (47% yield). In this reaction, no ligand was used and cesium acetate (2.25 equivalent) was used instead of $K_2CO_3$ (1S,5R,6R)-1-(3-Aza-bicyclo[3.1.0]hex-6-yl)-MeOH was prepared according to the synthesis described in European Patent 0413455B1.

[2-[3-((1S,5R,6R)-6-Hydroxymethyl-3-aza-bicyclo[3.1.0]hex-3-yl)-phenyl]-5-(2-trimethylsilanyl-ethoxymethyl)-5H-pyrrolo[2,3-b]pyrazin-7-yl]-(1-methyl-cyclopentyl)-methanone was prepared following the same procedure but using [2-(3-iodo-phenyl)-5-(2-trimethylsilanyl-ethoxymethyl)-5H-pyrrolo[2,3-b]pyrazin-7-yl]-(1-methyl-cyclopentyl)-methanone and (1S,5R,6R)-1-(3-aza-bicyclo[3.1.0]hex-6-yl)-MeOH as starting materials. In this reaction, the reaction mixture was stirred at 90° C. for 72 hours. The product was obtained in 43% yield by $SiO_2$ chromatography (hexanes/EtOAc 0-30% EtOAc).

[2-[3-((1S,5R,6R)-6-Hydroxymethyl-3-aza-bicyclo[3.1.0]hex-3-yl)-phenyl]-5-(2-trimethylsilanyl-ethoxymethyl)-5H-pyrrolo[2,3-b]pyrazin-7-yl]-(1-methyl-cyclohexyl)-methanone was prepared following the same procedure but using [2-(3-iodo-phenyl)-5-(2-trimethylsilanyl-ethoxymethyl)-5H-pyrrolo[2,3-b]pyrazin-7-yl]-(1-methyl-cyclohexyl)-methanone and (1S,5R,6R)-1-(3-aza-bicyclo[3.1.0]hex-6-yl)-MeOH as starting materials. In this reaction, the reaction mixture was stirred at 90° C. for 24 hours before being cooled to RT. 2.2 equivalents of $K_2CO_3$, 3 equivalents of amine, 0.15 equivalents of CuI and 0.3 equivalents of DL-proline were added and the resulting mixture was stirred at 120° C. overnight. The product was obtained in 15% yield by $SiO_2$ chromatography (hexanes/EtOAc 0-30% EtOAc).

Step 3—Method b: A mixture of 1-[2-(3-iodo-phenyl)-5-(2-trimethylsilanyl-ethoxymethyl)-5H-pyrrolo[2,3-b]pyrazin-7-yl]-2,2-dimethyl-propan-1-one (0.13 g, 0.243 mmol), commercially available (±)-1-phenylazabicyclo[3.1.0]hexane hydr°Chloride, xantphos (0.028 g, 49 μmol), and tris(dibenzylideneacetone)dipalladium(0) (0.022 g, 2.4 μmol) in 1.3 mL of toluene was stirred at 80° C. for 3 hours before being cooled to RT, filtered through celite. The filtrate was evaporated and the residue was purified by $SiO_2$ chromatography (hexanes/EtOAc 0-10% EtOAc) to give 0.065 g of 5 (47% yield).

1-[2-[3-(3,3-Diethyl-pyrrolidin-1-yl)-phenyl]-5-(2-trimethylsilanyl-ethoxymethyl)-5H-pyrrolo[2,3-b]pyrazin-7-yl]-2,2-dimethyl-propan-1-one was prepared following the same procedure but using commercially available 3,3-diethyl-pyrrolidine as starting material. The product was obtained in 69% yield after purification by $SiO_2$ chromatography (hexanes/EtOAc 0-10% EtOAc).

1-[2-[3-(3-Methoxymethyl-3-methyl-pyrrolidin-1-yl)-phenyl]-5-(2-trimethylsilanyl-ethoxymethyl)-5H-pyrrolo[2,3-b]pyrazin-7-yl]-2,2-dimethyl-propan-1-one was prepared following a similar procedure but starting from 3-methoxymethyl-3-methyl-pyrrolidine monohydrochloride. In this instance, the reaction mixture was stirred at 70° C. for 2 hours before being worked up. The product was obtained in 70% yield after $SiO_2$ chromatography (hexanes/EtOAc 15% EtOAc).

1-[2-[(1S,5R)-3-(3-Aza-bicyclo[3.1.0]hex-3-yl)-phenyl]-5-(2-trimethylsilanyl-ethoxymethyl)-5H-pyrrolo[2,3-b]pyrazin-7-yl]-2,2-dimethyl-propan-1-one was prepared following the same procedure using (1S,5R)-3-aza-bicyclo[3.1.0]hexane monohydrochloride as starting material.

(1-{3-[7-(2,2-Dimethyl-propionyl)-5-(2-trimethylsilanyl-ethoxymethyl)-5H-pyrrolo[2,3-b]pyrazin-2-yl]-phenyl}-3-methyl-pyrrolidin-3-ylmethyl)-carbamic acid tert-butyl ester was prepared following the same procedure but using (3-methyl-pyrrolidin-3-ylmethyl)-carbamic acid tert-butyl ester as starting material. The product was obtained in 62% yield after $SiO_2$ chromatography (hexanes/EtOAc 20% EtOAc).

Step 4—A solution of 4 (0.075 g, 0.152 mmol) in 3 mL of a 2/1 mixture of DCM and trifluoroacetic acid was stirred at RT overnight before being evaporated and coevaporated with toluene. The residue was taken into 1.5 mL of EtOH, KOAc (0.12 g, 1.218 mmol) was added and the resulting mixture was stirred at RT for 24 hours before being evaporated. The residue was taken into $H_2O$ and the insoluble yellow material was filtered and thoroughly rinsed with $H_2O$. The residue (adsorbed onto silica) was purified twice by $SiO_2$ chromatography (hexanes/EtOAc 6/4) to give 0.02 g of 5: 2,2-Dimethyl-1-{2-[3-(3-methyl-pyrrolidin-1-yl)-phenyl]-5H-pyrrolo[2,3-b]pyrazin-7-yl}-propan-1-one (36% yield)

1-{2-[3-((1S,5R,6R)-6-Methanesulfonylmethyl-3-aza-bicyclo[3.1.0]hex-3-yl)-phenyl]-5H-pyrrolo[2,3-b]pyrazin-7-yl}-2,2-dimethyl-propan-1-one was prepared following the same procedure using 1-[2-[3-((1S,5R,6R)-6-methanesulfonylmethyl-3-aza-bicyclo[3.1.0]hex-3-yl)-phenyl]-5-(2-trimethylsilanyl-ethoxymethyl)-5H-pyrrolo[2,3-b]pyrazin-7-yl]-2,2-dimethyl-propan-1-one as starting material (39% yield).

1-{2-[(3aR,6aS)-3-(Hexahydro-cyclopenta[c]pyrrol-2-yl)-phenyl]-5H-pyrrolo[2,3-b]pyrazin-7-yl}-2,2-dimethyl-propan-1-one was prepared following the same procedure using 1-[2-[(3aR,6aS)-3-(hexahydro-cyclopenta[c]pyrrol-2-yl)-phenyl]-5-(2-trimethylsilanyl-ethoxymethyl)-5H-pyrrolo[2,3-b]pyrazin-7-yl]-2,2-dimethyl-propan-1-one as starting material (31% yield).

1-{2-[3-((1S,5R,6R)-6-Methoxymethyl-3-aza-bicyclo[3.1.0]hex-3-yl)-phenyl]-5H-pyrrolo[2,3-b]pyrazin-7-yl}-2,2-dimethyl-propan-1-one was prepared following the same procedure using 1-[2-[3-((1S,5R,6R)-6-methoxymethyl-3-aza-bicyclo[3.1.0]hex-3-yl)-phenyl]-5-(2-trimethylsilanyl-ethoxymethyl)-5H-pyrrolo[2,3-b]pyrazin-7-yl]-2,2-dimethyl-propan-1-one as starting material (73% yield).

1-{2-[3-(3-Methoxymethyl-3-methyl-pyrrolidin-1-yl)-phenyl]-5H-pyrrolo[2,3-b]pyrazin-7-yl}-2,2-dimethyl-propan-1-one was prepared following the same procedure using 1-[2-[3-(3-Methoxymethyl-3-methyl-pyrrolidin-1-yl)-phenyl]-5-(2-trimethylsilanyl-ethoxymethyl)-5H-pyrrolo[2,3-b]pyrazin-7-yl]-2,2-dimethyl-propan-1-one as starting material. The product was obtained in 50% yield by $SiO_2$ chromatography (DCM/MeOH 0-5% MeOH).

1-{2-[(1S,5R)-3-(3-Aza-bicyclo[3.1.0]hex-3-yl)-phenyl]-5H-pyrrolo[2,3-b]pyrazin-7-yl}-2,2-dimethyl-propan-1-one was prepared following the same procedure using 1-[2-[(1S,5R)-3-(3-Aza-bicyclo[3.1.0]hex-3-yl)-phenyl]-5-(2-trimethylsilanyl-ethoxymethyl)-5H-pyrrolo[2,3-b]pyrazin-7-yl]-2, 2-dimethyl-propan-1-one as starting material.

1-{2-[3-(4-Hydroxy-piperidin-1-yl)-phenyl]-5H-pyrrolo [2,3-b]pyrazin-7-yl}-2,2-dimethyl-propan-1-one was prepared following the same procedure using 1-[2-[3-(4-hydroxy-piperidin-1-yl)-phenyl]-5-(2-trimethylsilanyl-ethoxymethyl)-5H-pyrrolo[2,3-b]pyrazin-7-yl]-2,2-dimethyl-propan-1-one as starting material (54% yield).

1-{2-[3-(4-Hydroxyl-4-methyl-piperidin-1-yl)-phenyl]-5H-pyrrolo[2,3-b]pyrazin-7-yl}-2,2-dimethyl-propan-1-one was prepared following the same procedure using 1-[2-[3-(4-hydroxyl-4-methyl-piperidin-1-yl)-phenyl]-5-(2-trimethylsilanyl-ethoxymethyl)-5H-pyrrolo[2,3-b]pyrazin-7-yl]-2,2-dimethyl-propan-1-one as starting material (54% yield).

N-(1-{3-[7-(2,2-Dimethyl-propionyl)-5H-pyrrolo[2,3-b]pyrazin-2-yl]-phenyl}-3-methyl-pyrrolidin-3-ylmethyl)-acetamide was prepared following the same procedure using N-(1-{3-[7-(2,2-dimethyl-propionyl)-5-(2-trimethylsilanyl-ethoxymethyl)-5H-pyrrolo[2,3-b]pyrazin-2-yl]-phenyl}-3-methyl-pyrrolidin-3-ylmethyl)-acetamide as starting material (63% yield).

N-(1-{3-[7-(2,2-Dimethyl-propionyl)-5H-pyrrolo[2,3-b]pyrazin-2-yl]-phenyl}-3-methyl-pyrrolidin-3-ylmethyl)-methanesulfonamide was prepared following the same procedure using N-(1-{3-[7-(2,2-dimethyl-propionyl)-5-(2-trimethylsilanyl-ethoxymethyl)-5H-pyrrolo[2,3-b]pyrazin-2-yl]-phenyl}-3-methyl-pyrrolidin-3-ylmethyl)-methanesulfonamide as starting material (59% yield).

(1-{3-[7-(2,2-Dimethyl-propionyl)-5H-pyrrolo[2,3-b]pyrazin-2-yl]-phenyl}-3-methyl-pyrrolidin-3-ylmethyl)-carbamic acid methyl ester was prepared following the same procedure using (1-{3-[7-(2,2-Dimethyl-propionyl)-5-(2-trimethylsilanyl-ethoxymethyl)-5H-pyrrolo[2,3-b]pyrazin-2-yl]-phenyl}-3-methyl-pyrrolidin-3-ylmethyl)-carbamic acid methyl ester as starting material (75% yield).

1-{2-[3-(3-Hydroxymethyl-3-methyl-pyrrolidin-1-yl)-phenyl]-5H-pyrrolo[2,3-b]pyrazin-7-yl}-2,2-dimethyl-propan-1-one was prepared following a similar procedure but using acetic acid 1-{3-[7-(2,2-dimethyl-propionyl)-5-(2-trimethylsilanyl-ethoxymethyl)-5H-pyrrolo[2,3-b]pyrazin-2-yl]-phenyl}-3-methyl-pyrrolidin-3-ylmethyl ester as starting material. In this reaction, the acetate was hydrolysed at the same time of the second step of the SEM hydrolysis by heated at reflux the hydrolysis intermediate in a 8/1/1 mixture of MeOH, H₂O, and Et₃N over the weekend. The product was obtained in 15% yield after SiO₂ chromatography (hexanes/EtOAc 0-30% EtOAc).

1-{2-[3-((1S,5R,6R)-6-Hydroxymethyl-3-aza-bicyclo[3.1.0]hex-3-yl)-phenyl]-5H-pyrrolo[2,3-b]pyrazin-7-yl}-2,2-dimethyl-propan-1-one was prepared following the same procedure using 1-[2-[3-((1S,5R,6R)-6-hydroxymethyl-3-aza-bicyclo[3.1.0]hex-3-yl)-phenyl]-5-(2-trimethylsilanyl-ethoxymethyl)-5H-pyrrolo[2,3-b]pyrazin-7-yl]-2,2-dimethyl-propan-1-one as starting material (38% yield).

{2-[3-((1S,5R,6R)-6-Hydroxymethyl-3-aza-bicyclo[3.1.0]hex-3-yl)-phenyl]-5H-pyrrolo[2,3-b]pyrazin-7-yl}-(1-methyl-cyclopentyl)-methanone was prepared following the same procedure but using [2-[3-((1S,5R,6R)-6-hydroxymethyl-3-aza-bicyclo[3.1.0]hex-3-yl)-phenyl]-5-(2-trimethylsilanyl-ethoxymethyl)-5H-pyrrolo[2,3-b]pyrazin-7-yl]-(1-methyl-cyclopentyl)-methanone as starting material. The product was obtained in 69% yield after purification by SiO₂ preparative TLC (DCM/MeOH 7% MeOH).

{2-[3-((1S,5R,6R)-6-Hydroxymethyl-3-aza-bicyclo[3.1.0]hex-3-yl)-phenyl]-5H-pyrrolo[2,3-b]pyrazin-7-yl}-(1-methyl-cyclohexyl)-methanone was prepared following the same procedure but using [2-[3-((1S,5R,6R)-6-hydroxymethyl-3-aza-bicyclo[3.1.0]hex-3-yl)-phenyl]-5-(2-trimethylsilanyl-ethoxymethyl)-5H-pyrrolo[2,3-b]pyrazin-7-yl]-(1-methyl-cyclohexyl)-methanone as starting material. The product was obtained in 35% yield after purification by SiO₂ preparative TLC (DCM/[DCM/MeOH/NH₄OH 60/10/1] 50% DCM).

Racemic 2,2-dimethyl-1-{2-[3-((1S,5R)-1-phenyl-3-aza-bicyclo[3.1.0]hex-3-yl)-phenyl]-5H-pyrrolo[2,3-b]pyrazin-7-yl}-propan-1-one was prepared following the same procedure but using racemic 2,2-dimethyl-1-[2-[3-((1S,5R)-1-phenyl-3-aza-bicyclo[3.1.0]hex-3-yl)-phenyl]-5-(2-trimethylsilanyl-ethoxymethyl)-5H-pyrrolo[2,3-b]pyrazin-7-yl]-propan-1-one as starting material. The product was obtained in 32% yield after purification by SiO₂ chromatography (DCM/MeOH 0-4% MeOH), followed by a SiO₂ preparative TLC (DCM/MeOH 5% MeOH).

1-{2-[3-(3,3-Diethyl-pyrrolidin-1-yl)-phenyl]-5H-pyrrolo[2,3-b]pyrazin-7-yl}-2,2-dimethyl-propan-1-one was prepared following the same procedure but using 1-[2-[3-(3,3-diethyl-pyrrolidin-1-yl)-phenyl]-5-(2-trimethylsilanyl-ethoxymethyl)-5H-pyrrolo[2,3-b]pyrazin-7-yl]-2,2-dimethyl-propan-1-one as starting material. The product was obtained in 69% yield after two purification by SiO₂ chromatography (DCM/MeOH 0-4% MeOH).

1-{2-[3-(3-Aminomethyl-3-methyl-pyrrolidin-1-yl)-phenyl]-5H-pyrrolo[2,3-b]pyrazin-7-yl}-2,2-dimethyl-propan-1-one was prepared following a similar procedure but using (1-{3-[7-(2,2-dimethyl-propionyl)-5-(2-trimethylsilanyl-ethoxymethyl)-5H-pyrrolo[2,3-b]pyrazin-2-yl]-phenyl}-3-methyl-pyrrolidin-3-ylmethyl)-carbamic acid tert-butyl ester as starting material. In this instance the starting material was taken into a 4/1 mixture of MeOH and acetyl chloride and the reaction mixture was stirred at RT for 2 hours before being evaporated. The residue was taken into 2 mL of concentrated HCl and stirred at RT for 1 hour before being diluted with H₂O and neutralized by addition of solid NaOH. The product was obtained in 44% yield after SiO₂ chromatography (DCM/[DCM/MeOH/NH₄OH 60/10/1] 100-60% DCM).

Example 217

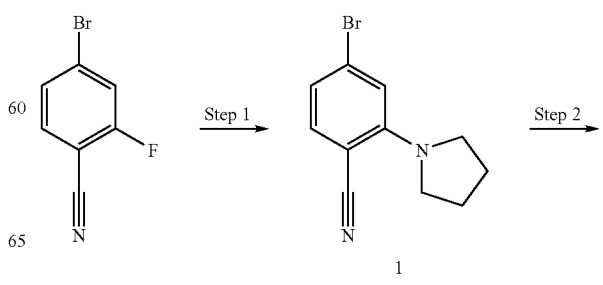

-continued

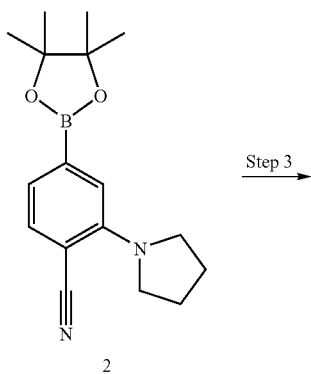

2

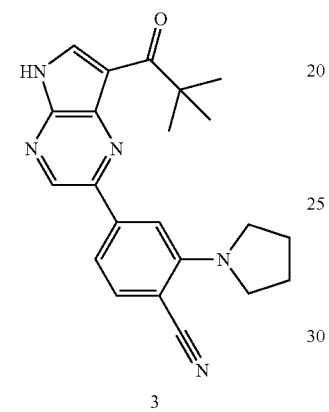

3

Step 1—Pyrrolidine (0.62 mL, 7.424 mmol) was added to a mixture of commercially available 4-bromo-2-fluorobenzonitrile (1 g, 5 mmol) and K₂CO₃ (0.76 g, 5.5 mmol) in 3 mL of DMSO. The resulting mixture was stirred at 100° C. for four hours before being cooled to RT. 10 mL of H₂O were added and the white precipitate that formed was filtered and thoroughly rinsed with H₂O before being dried to give 1.2 g of 1 (>95% yield)

Step 2—A mixture of 1 (0.25 g, 0.996 mmol), bis(pinacolato)diboron (0.28 g, 1.103 mmol), KOAc (0.29 g, 2.955 mmol) and [1,1'-bis(diphenylphosphino)-ferrocene]dichloride palladium(II) DCM complex (0.081 g, 95.55 µmol) in 4 mL of DMSO was degassed for 15 minutes by bubbling argon through the mixture, before being stirred at 80° C. for an hour before being cooled to RT, diluted with H₂O and back extracted three times with Et₂O. Combined organic layers were dried over magnesium sulfate, filtered and evaporated to give crude 2 which was used in step 3 without purification.

Step 3—A mixture of 1-(2-bromo-5H-pyrrolo[2,3-b]pyrazin-7-yl)-2,2-dimethyl-propan-1-one (0.1 g, 0.354 mmol), 2 (theoretically 0.996 mmol), K₂CO₃ (0.150 g, 1.085 mmol), and [1,1'-bis(diphenylphosphine)ferrocene]dichloridepalladium(II) DCM complex (0.030 g, 36.74 µmol) in 3 mL of a 4/1 mixture of 1,4-dioxane and H₂O was degassed for 20 minutes by bubbling argon though the mixture. The resulting mixture was stirred under microwave irradiation at 120° C. for 50 minutes before being cooled to RT. The organic layer was separated and the aqueous layer was back extracted twice with EtOAc. combined organic layers were dried over Na₂SO₄, filtered and evaporated. The residue was purified by SiO₂ chromatography (hexanes/EtOAc 30% EtOAc), followed by a second Chromatography (DCM/acetone 9/1) to give 0.03 g of 3: 4-[7-(2,2-dimethyl-propionyl)-5H-pyrrolo[2,3-b]pyrazin-2-yl]-2-pyrrolidin-1-yl-benzonitrile (23% yield).

Example 218

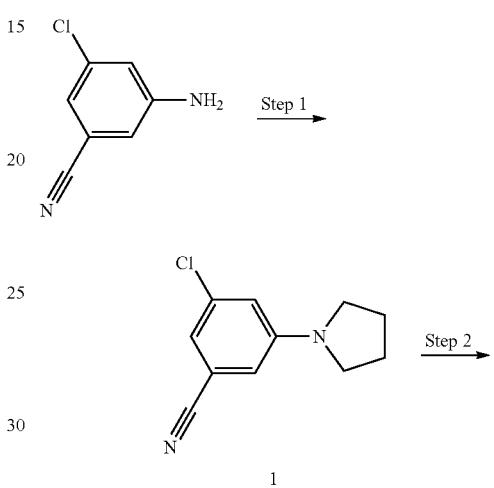

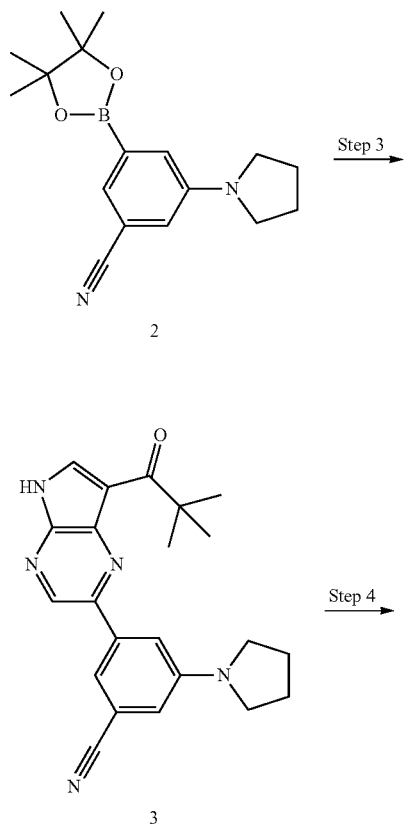

-continued

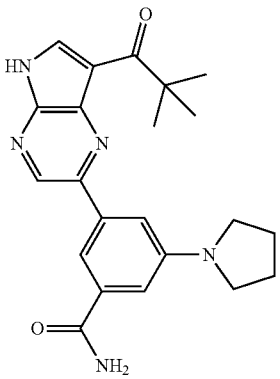

Step 1—A mixture of commercially available 3-amino-5-chlorobenzonitrile (0.7 g, 4.588 mmol), 1,4-dibromobutane (0.57 mL, 4.817 mmol) and $K_2CO_3$ (0.697 g, 5.046 mmol) in 20 mL of $H_2O$ was stirred for 40 minutes at 120° C. under microwave irradiation before being cooled to RT and extracted twice with DCM. The combined organic layers were dried ($Na_2SO_4$), filtered, and evaporated. The residue was purified by $SiO_2$ chromatography (hexanes/EtOAc 0-8% EtOAc) to give 0.295 g of 1 (31% yield).

Step 2—A mixture of 1 (0.43 g, 2.081 mmol), bis(pinacolato)diboron (1.057 g, 4.161 mmol), KOAc (0.613 g, 6.242 mmol), XPhos (0.099 g, 0.208 mmol) and tris(dibenzylideneacetone)dipalladium(0) (0.095 g, 0.104 mmol) in 5 mL of 1,4-dioxane was digassed by bubbling argon through the mixture. It was then stirred 2 hours at 120° C. under microwave irradiation before being cooled to RT, filtered through celite, and partitioned between $H_2O$ and EtOAc. The aqueous layer was back extracted with EtOAc. The combined organic layers were dried ($Na_2SO_4$), filtered, and evaporated. 2 was used in the next reaction without purification.

3-(3,3-Dimethyl-pyrrolidin-1-yl)-5-(4,4,5,5-tetramethyl-[1,3,2]dioxaborolan-2-yl)-benzonitrile was prepared following the same procedure but using commercially available 3,3-dimethyl-pyrrolidine as starting material. In this reaction, the reaction mixture was stirred at 120° C. without microwave irradiation for 2 hours. The product was used in the next reaction without purification.

Step 3—A mixture of 1-(2-bromo-5H-pyrrolo[2,3-b]pyrazin-7-yl)-2,2-dimethyl-propan-1-one (0.3 g, 1.063 mmol), 2 (theoretically 2.081 mmol), $K_2CO_3$ (0.441 g, 3.19 mmol) and tetrakis(triphenylphosphine)palladium(0) (0.123 g, 0.106 mmol) in 8 mL of 1,4-dioxane and 2 ml of $H_2O$ was degassed by bubbling argon through the mixture. It was then stirred 40 minutes at 120° C. under microwave irradiation before being cooled to RT and partitioned between $H_2O$ and EtOAc. The aqueous layer was extracted with EtOAc. He combined organic layers were dried ($Na_2SO_4$), filtered, and evaporated. The residue was adsorbed onto $SiO_2$ and purified three times by $SiO_2$ chromatography (hexanes/EtOAc 0-40% EtOAc, toluene/EtOAc 0-50% EtOAc, and finally DCM/MeOH 0-2% MeOH) to give 0.035 g of 3:3-[7-(2,2-Dimethyl-propionyl)-5H-pyrrolo[2,3-b]pyrazin-2-yl]-5-pyrrolidin-1-yl-benzonitrile (9% yield)

3-[3-(2,2-Dimethyl-propionyl)-1H-indol-5-yl]-5-(3,3-dimethyl-pyrrolidin-1-yl)-benzonitrile was prepared following the same procedure but using 3-(3,3-dimethyl-pyrrolidin-1-yl)-5-(4,4,5,5-tetramethyl-[1,3,2]dioxaborolan-2-yl)-benzonitrile as starting material. In this reaction a 3/1 mixture of DCM and MeOH was used as solvent and the reaction mixture was stirred at 110° C. under microwave irradiation for 25 minutes before being worked up. The product was obtained in 14% yield after two purification by $SiO_2$ chromatography (hexanes/EtOAc 0-40%, followed by DCM/MeOH 0-3% MeOH).

Step 4—A solution of $LiOH·H_2O$ (0.007 g, 0.161 mmol) in 0.3 mL of $H_2O$ and 0.02 mL of $H_2O_2$ 30 wt % in $H_2O$ was added to a suspension of 3 (0.02 g, 54 μmol) in 0.8 mL of THF. The resulting clear solution was stirred at RT overnight before being evaporated. The residue was taken into $H_2O$. After sonication, the insoluble was filtered, rinsed with $H_2O$, and dried under vacuum to give 0.01 g of 4: 3-[7-(2,2-dimethyl-propionyl)-5H-pyrrolo[2,3-b]pyrazin-2-yl]-5-pyrrolidin-1-yl-benzamide (47% yield).

3-[3-(2,2-Dimethyl-propionyl)-1H-indol-5-yl]-5-(3,3-dimethyl-pyrrolidin-1-yl)-benzamide was prepared following the same procedure but using 3-[3-(2,2-dimethyl-propionyl)-1H-indol-5-yl]-5-(3,3-dimethyl-pyrrolidin-1-yl)-benzonitrile as starting material. The product was obtained in 11% yield after purification by $SiO_2$ chromatography (DCM/MeOH 0-5% MeOH).

Example 219

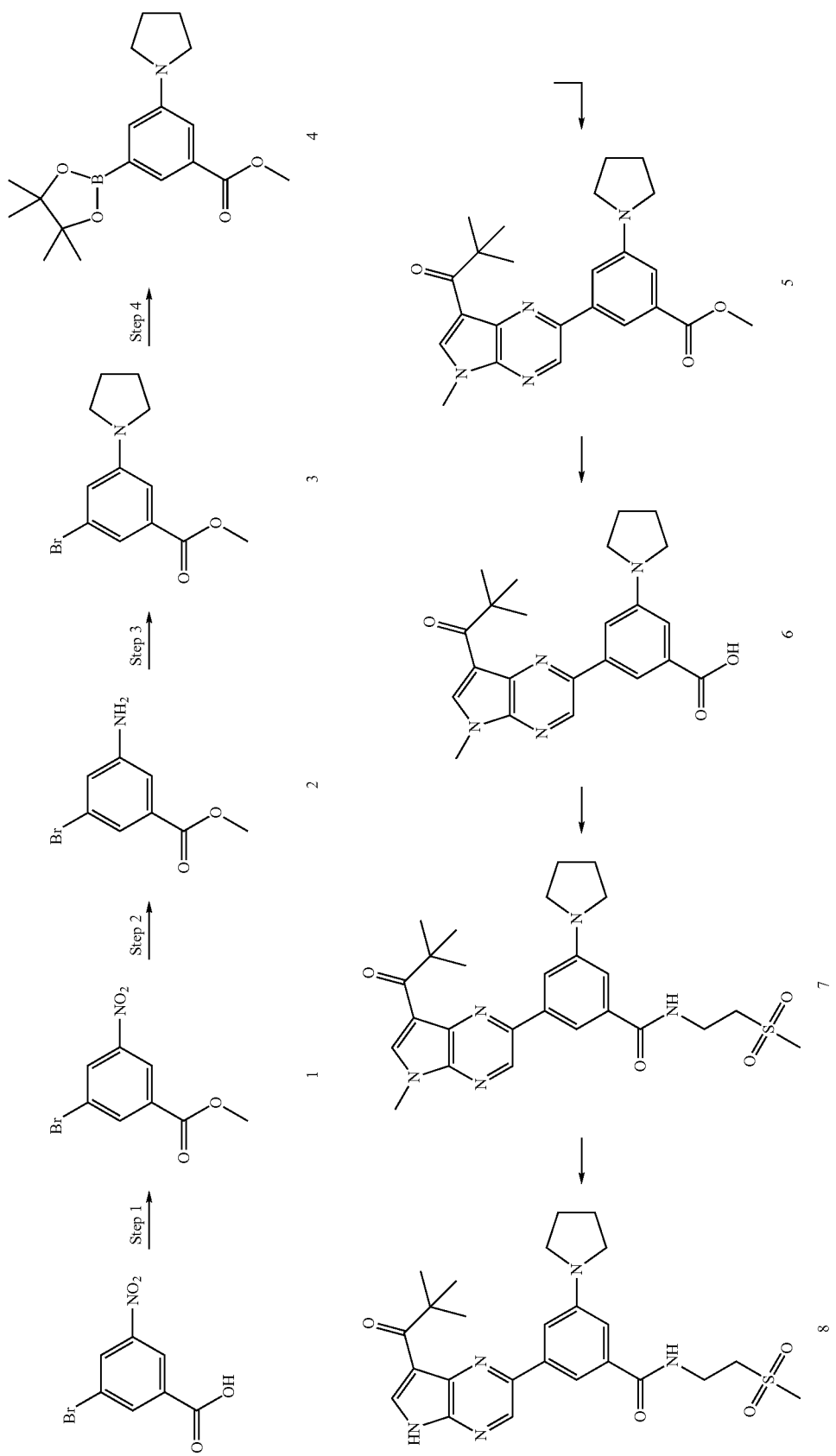

Step 1—(Trimethylsilyl)diazomethane 2M in Et$_2$O (8.13 mL, 16.259 mmol) was added dropwise to a solution of commercially available 3-bromo-5-nitrobenzoic acid (2 g, 8.129 mmol) in 40 mL of DCM and 40 mL of MeOH. The resulting mixture was stirred at RT for 1 hour before being evaporated to give 1: 3-bromo-5-nitro-benzoic acid methylester quantitatively.

Step 2—NH$_4$Cl (4.348 g, 81.29 mmol), followed by iron powder (2.179 g, 39.019 mmol) were added to a solution of 1 (2.11 g, 8.129 mmol) in 40 mL of MeOH and 40 mL of H$_2$O. The resulting mixture was stirred at reflux overnight before being cooled to RT, filtered through celite. The filtrate was evaporated and the residue was partitioned between H$_2$O and DCM. The aqueous layer was back extracted with DCM. The combined organic layers were washed twice with 1M HCl. The combined acidic aqueous layers were basified to pH10 by addition of solid NaOH. The precipitate was filtered, washed with H$_2$O and dried under vacuum to give 1.02 g of 2: 3-mino-5-bromo-benzoic acid methyl ester (55% yield).

Step 3—A mixture of 2 (0.9 g, 3.912 mmol), K$_2$CO$_3$ (0.595 g, 4.303 mmol) and 1,4-dibromobutane (0.49 mL, 4.108 mmol) in 14 mL of CH$_3$CN and 1 mL of H$_2$O was stirred at 110° C. for 30 minutes under microwave irradiation before being cooled to RT. 0.5 more equivalents of 1,4-dibromobutane were added and the resulting mixture was stirred at 110° C. for 30 minutes under microwave irradiation a second time before being cooled to RT. The reaction mixture was extracted twice with DCM. The combined organic layers were dried (Na$_2$SO$_4$), filtered, and evaporated. The residue was purified by SiO$_2$ chromatography (hexanes/EtOAc 0-8% EtOAc) to give 0.25 g of 3: 3-bromo-5-pyrrolidin-1-yl-benzoic acid methyl ester (22% yield).

Step 4—A mixture of 3 (0.25 g, 0.88 mmol), bis(pinacolato)diboron (0.268 g, 1.056 mmol), KOAc (0.259 g, 2.639 mmol), and [1,1'-is(diphenylphosphine)ferrocene]dichloridepalladium(II) DCM complex (0.072 g, 88 µmol) in 5 mL of DMSO was degassed by bubbling argon through the mixture before being stirred at 90° C. for 4 hours before being cooled to RT. The reaction mixture was filtered though celite and the filtrate was partitioned between H$_2$O and EtOAc. The aqueous layer was back extracted with EtOAc. The combined organic layers were dried (Na$_2$SO$_4$), filtered, and evaporated. The boronic ester 4: 3-pyrrolidin-1-yl-5-(4,4,5,5-tetramethyl-[1,3,2]dioxaborolan-2-yl)-benzoic acid methyl ester was used crude in the next reaction.

Step 5—A mixture of (1-[2-bromo-5-(2-trimethylsilanyl-ethoxymethyl)-5H-pyrrolo[2,3-b]pyrazin-7-yl]-2,2-dimethyl-propan-1-one (0.15 g, 0.364 mmol), 4 (theoretically 0.88 mmol), K$_2$CO$_3$ (0.151 g, 1.091 mmol), and tetrakis(triphenylphosphine)palladium(0) (0.042 g, 36 µmol) in 2.8 mL of 1,4-dioxane and 0.7 mL of H$_2$O was degassed by bubbling argon through the mixture before being stirred at 120° C. for 40 minutes under microwave irradiation. The reaction mixture was cooled to RT and partitioned between H$_2$O and EtOAc. The aqueous layer was back extracted with EtOAc. The combined organic layers were dried (Na$_2$SO$_4$), filtered, and evaporated. The residue was purified by SiO$_2$ chromatography (hexanes/EtOAc 0-15% EtOAc) to give 0.205 g of 5: 3-[7-(2,2-dimethyl-propionyl)-5-methyl-5H-pyrrolo[2,3-b]pyrazin-2-yl]-5-pyrrolidin-1-yl-benzoic acid methyl ester (84% yield).

Step 6—0.6 mL of 1M LiOH.H$_2$O (0.6 mmol) were added at RT to a solution of 5 (0.2 g, 0.298 mmol) in 3 mL of THF. The resulting mixture was stirred at RT for 4 days before being partitioned between saturated NH$_4$Cl and EtOAc. The aqueous layer was back extracted with EtOAc. The combined organic layers were dried (Na$_2$SO$_4$), filtered, and evaporated to give 6: 3-[7-(2,2-dimethyl-propionyl)-5-methyl-5H-pyrrolo[2,3-b]pyrazin-2-yl]-5-pyrrolidin-1-yl-benzoic acid quantitatively. The product was used in the next reaction without purification.

Step 7—Commercially available 2-aminoethylmethylsulfone hydrochloride (0.039 g, 0.244 mmol), EDCI (0.041 g, 0.215 mmol), and HOBt.H$_2$O (0.029 g, 0.215 mmol) were added to a solution of 6 (0.075 g, 0.143 mmol) in 1.5 mL of DCM and 0.09 mL of DIPEA. The resulting mixture was stirred at 45° C. overnight before being cooled to RT and partitioned H$_2$O and DCM. The organic layer was washed with saturated NH$_4$Cl. The aqueous layers were extracted with DCM. The combined organic layers were dried (Na$_2$SO$_4$), filtered, and evaporated. The residue was purified by SiO$_2$ chromatography (DCM/MeOH 0-2% MeOH) to give 0.057 g of 7: 3-[7-(2,2-dimethyl-propionyl)-5-methyl-5H-pyrrolo[2,3-b]pyrazin-2-yl]-N-(2-methanesulfonyl-ethyl)-5-pyrrolidin-1-yl-benzamide (63% yield).

3-[7-(2,2-Dimethyl-propionyl)-5-(2-trimethylsilanyl-ethoxymethyl)-5H-pyrrolo[2,3-b]pyrazin-2-yl]-N-(2-hydroxy-ethyl)-5-pyrrolidin-1-yl-benzamide was prepared following the same procedure but using ethanolamine as amine. In this reaction, 1 more equivalent of each reagent and 3 equivalents of amine were added again after 2 days at 45° C. The product was obtained in 30% yield by SiO$_2$ chromatography (DCM/MeOH 0-2% MeOH).

2,2-Dimethyl-1-[2-[3-(4-methyl-piperazine-1-carbonyl)-5-pyrrolidin-1-yl-phenyl]-5-(2-trimethylsilanyl-ethoxymethyl)-5H-pyrrolo[2,3-b]pyrazin-7-yl]-propan-1-one was prepared following the same procedure but using 1-methylpiperazine as amine. In this reaction, 1 more equivalent of each reagent and 3 equivalents of amine were added again after 2 days at 45° C. The product was obtained in 18% yield by SiO$_2$ chromatography (DCM/MeOH 0-2% MeOH).

Step 8—0.4 mL of TFA were added at RT to a solution of 7 (0.055 g, 88 µmol) in 0.6 mL of DCM. The resulting mixture was stirred at RT for 2 hours before being evaporated and coevaporated twice with toluene. The residue was taken into 1 mL of EtOH and NaOAc (0.072 g, 0.876 mmol) was added. The resulting mixture was stirred at RT overnight before being evaporated. The residue was taken into H$_2$O. After sonication, the insoluble was filtered, rinse with H$_2$O, and dried under vacuum. The residue was adsorbed onto SiO$_2$ and purified by SiO$_2$ chromatography (DCM/MeOH 0-3% MeOH) to give 0.037 g of 8: 3-[7-(2,2-dimethyl-propionyl)-5H-pyrrolo[2,3-b]pyrazin-2-yl]-N-(2-methanesulfonyl-ethyl)-5-pyrrolidin-1-yl-benzamide (85% yield).

3-[7-(2,2-Dimethyl-propionyl)-5H-pyrrolo[2,3-b]pyrazin-2-yl]-N-(2-hydroxy-ethyl)-5-pyrrolidin-1-yl-benzamide was prepared following the same procedure but using 3-[7-(2,2-dimethyl-propionyl)-5-(2-trimethylsilanyl-ethoxymethyl)-5H-pyrrolo[2,3-b]pyrazin-2-yl]-N-(2-hydroxy-ethyl)-5-pyrrolidin-1-yl-benzamide as starting material. The product was obtained in 83% yield after SiO$_2$ chromatography (DCM/MeOH 0-5% MeOH).

2,2-Dimethyl-1-{2-[3-(4-methyl-piperazine-1-carbonyl)-5-pyrrolidin-1-yl-phenyl]-5H-pyrrolo[2,3-b]pyrazin-7-yl}-propan-1-one was prepared following the same procedure but using 2,2-dimethyl-1-[2-[3-(4-methyl-piperazine-1-carbonyl)-5-pyrrolidin-1-yl-phenyl]-5-(2-trimethylsilanyl-ethoxymethyl)-5H-pyrrolo[2,3-b]pyrazin-7-yl]-propan-1-one as starting material. The produce was obtained in 71% yield after purification by SiO$_2$ chromatography (DCM/MeOH 0-4% MeOH).

3-[7-(2,2-Dimethyl-propionyl)-5H-pyrrolo[2,3-b]pyrazin-2-yl]-5-pyrrolidin-1-yl-benzoic acid was prepared following the same procedure but using 6: 3-[7-(2,2-dimethyl-propionyl)-5-(2-trimethylsilanyl-ethoxymethyl)-5H-pyrrolo[2,3-b]pyrazin-2-yl]-5-pyrrolidin-1-yl-benzoic acid as starting material. The product was obtained in 12% yield after purification by SiO₂ chromatography (DCM/MeOH 0-4% MeOH).

Example 220 of MeOH and 5 mL of DCM was degassed by bubbling argon through the mixture. The reaction mixture was then stirred at 110° C. for 25 minutes before being cooled to RT and filtered through celite. The filtrate was evaporated, the residue was partitioned between H₂O and DCM. The aqueous layer was back extracted with DCM. The combined organic layers were dried (Na₂SO₄), filtered, and evaporated. The residue was

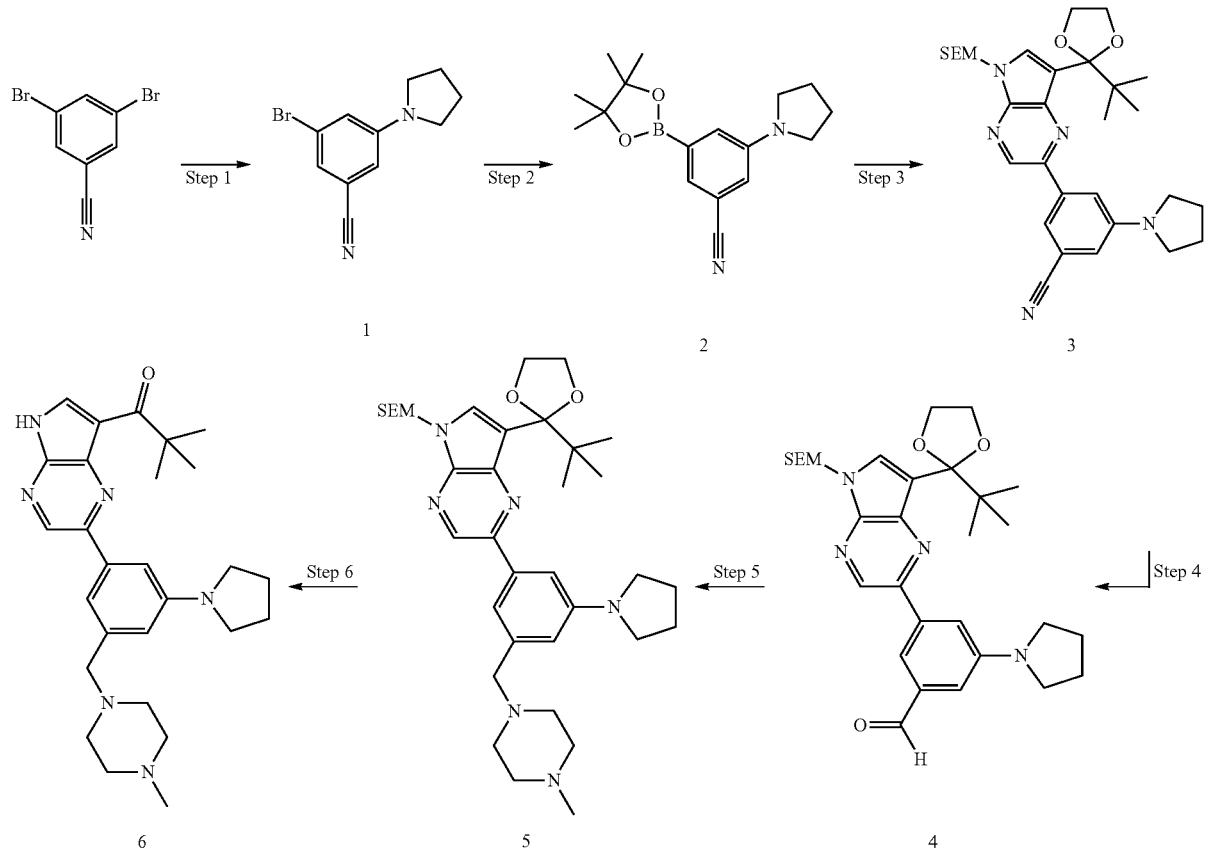

Step 1—A mixture of commercially available 3,5-dibromobenzonitrile (1.3 g, 4.982 mmol), pyrrolidine (0.42 mL, 4.982 mmol), NaOtBu (0.575 g, 5.979 mmol), racemic BINAP (0.621 g, 0.966 mmol) and tris(dibenzylideneacetone)dipalladium(0) (0.456 g, 0.498 mmol) in 25 mL of toluene was stirred at 89° C. for 1 hour before being cooled to RT. The reaction mixture was purified as is by SiO₂ chromatography (hexanes/EtOAc 0-8% EtOAc) to give 0.689 g of 1 (55% yield).

Step 2—A mixture of 1 (0.685 g, 2.728 mmol), bis(pinacolato)diboron (1.039 g, 4.092 mmol), KOAc (0.803 g, 8.183 mmol), and [1,1'-is(diphenylphosphine)ferrocene]dichloridepalladium(II) DCM complex (0.223 g, 0.273 mmol) in 25 ml, of degassed DMSO was stirred at 90° C. for 2 hours before being cooled to RT. H₂O was added and the insoluble material was filtered. The remaining solid was washed off the filter with EtOAc. The filtrated was dried (Na₂SO₄), filtered, and evaporated to give 2. The residue was used in the next reaction without purification.

Step 3—A mixture of 2-bromo-7-(2-tert-butyl-[1,3]dioxolan-2-yl)-5-(2-trimethylsilanyl-ethoxymethyl)-5H-pyrrolo[2,3-b]pyrazine (0.8 g, 1.753 mmol), 2 (theoretically 2.728 mmol), K₂CO₃ (0.727 g, 5.258 mmol) and tetrakis(triphenylphosphine)palladium(0) (0.203 g, 0.175 mmol) in 15 mL purified by SiO₂ chromatography (hexanes/EtOAc 0-25% EtOAc) to give 0.64 g of 3 (67% yield).

Step 4—DIBAL-H 1M in DCM (1.17 mL, 1.17 mmol) was added dropwise at −78° C. to a solution of 3 (0.32 g, 0.584 mmol) in 5 mL of DCM. The resulting mixture was stirred at −78° C. for 2 hours before being quenched by adding saturated R°Chelle salt. The aqueous layer was back extracted twice with DCM. The combined organic layers were dried (Na₂SO₄), filtered, and evaporated to give 4 quantitatively.

Step 5—NaBH(OAc)₃ (0.055 g, 0.248 mmol) was added at RT to a mixture of 4 (0.105 g, 0.191 mmol), N-methylpiperazine (0.02 mL, 0.229 mmol) and 3 Å molecular sieves in 2 ml, of DCM. The resulting mixture was stirred at RT for 3 hours before being diluted with DCM and washed with saturated NaHCO₃. The aqueous layer was back extracted with DCM. The combined organic layers were dried (Na₂SO₄), filtered, and evaporated. The residue was purified by SiO₂ chromatography (DCM/MeOH 0-6% MeOH) to give 0.069 g of 5 (57% yield).

{3-[7-(2-tert-Butyl-[1,3]dioxolan-2-yl)-5-(2-trimethylsilanyl-ethoxymethyl)-5H-pyrrolo[2,3-b]pyrazin-2-yl]-5-pyrrolidin-1-yl-benzyl}-(2-methanesulfonyl-ethyl)-amine was prepared following the same procedure but using 2-methanesulfonyl-ethylamine as amine.

Step 6—0.2 mL of acetyl chloride were added dropwise at 0° C. to a solution of 5 (0.065 g, 0.102 mmol) in 0.8 mL of MeOH. The resulting mixture was allowed to reach RT before being stirred at 40° C. for 2 hours, cooled to RT, and evaporated. The procedure was repeated 3 times before TLC (DCM/[DCM/MeOH/NH$_4$OH 60/10/1] 80% DCM) showed complete consumption of the starting material. The final reaction mixture was cooled to RT and evaporated. The residue was taken in 1 mL of a 8/1/1 mixture of MeOH, H$_2$O, and Et$_3$N and the resulting mixture was stirred at RT for 1 hour before being evaporated. The residue was purified by SiO$_2$ chromatography (DCM/MeOH 0-4% MeOH) and then by SiO$_2$ preparative TLC (DCM/[DCM/MeOH/NH$_4$OH 60/10/1] 80% DCM) to give 0.025 g of 6: 2,2-dimethyl-1-{2-[3-(4-methyl-piperazin-1-ylmethyl)-5-pyrrolidin-1-yl-phenyl]-5H-pyrrolo[2,3-b]pyrazin-7-yl}-propan-1-one (53% yield).

1-(2-{3-[(2-Methanesulfonyl-ethylamino)-methyl]-5-pyrrolidin-1-yl-phenyl}-5H-pyrrolo[2,3-b]pyrazin-7-yl)-2,2-dimethyl-propan-1-one was prepared following the same procedure but using {3-[7-(2-tert-butyl-[1,3]dioxolan-2-yl)-5-(2-trimethylsilanyl-ethoxymethyl)-5H-pyrrolo[2,3-b]pyrazin-2-yl]-5-pyrrolidin-1-yl-benzyl}-(2-methane sulfonyl-ethyl)-amine as starting material.

Example 221 mL of EtOH was stirred under hydrogen (1 atm) for 24 hours before being filtered. The cake was rinsed with MeOH and the filtrate was evaporated. The residue was purified by SiO$_2$ chromatography (hexanes/EtOAc 0-15% EtOAc) to give 4.66 g of 2 (89% yield)

Step 3—Diisobutylaluminium hydride 1M in DCM (17 mL, 17 mmol) was added dropwise at –78° C. to a solution of 2 (2 g, 8.22 mmol) in 50 mL of DCM. The resulting mixture was stirred at –78° C. to 0° C. over 6 hours before being quenched at 0° C. by addition of 15% aqueous NaOH. The reaction mixture was extracted twice with EtOAc. Combined organic layers were dried over Na$_2$SO$_4$, filtered and evaporated. The residue was purified by SiO$_2$ chromatography (hexanes/EtOAc 50% EtOAc) to give 1.4 g of 3 (79% yield)

Step 4—NaH 60% dispersion in oil (0.19 g, 2.322 mmol) was added at 0° C. to a solution of 3 (0.5 g, 2.322 mmol) and iodomethane (0.36 mL, 5.784 mmol) in 10 mL of DMF. The resulting mixture was stirred at 0° C. to RT overnight before being quenched by addition of H$_2$O, and extracted three times with EtOAc. Combined organic layers were dried over Na$_2$SO$_4$, filtered and evaporated. The residue was purified by SiO$_2$ chromatography (hexanes/EtOAc 20% EtOAc) to give 0.38 g of 4 (71% yield)

Step 5—2 mL of HCl 4M in 1,4-dioxane were added at RT to a solution of 4 (0.4 g, 1.858 mmol) in 2 mL of Et$_2$O. The

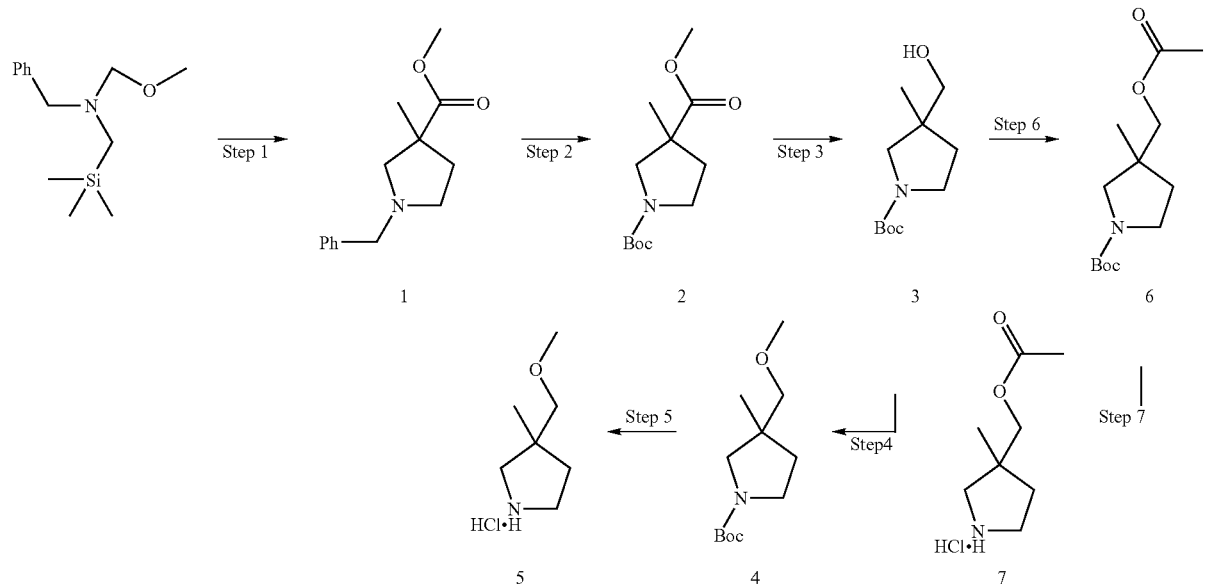

Step 1—Trifluoroacetic acid (0.08 mL, 1.035 mmol) in 5 mL of DCM was added dropwise at 0° C. to a solution of methyl methacrylate (8.8 g, 82.27 mmol) and benzyl-methoxymethyl-trimethylsilanylmethyl-amine (21 mL, 82.26 mmol) in 100 mL of DCM. The resulting mixture was stirred at 0° C. to RT overnight before being washed with saturated aqueous NaHCO$_3$. The aqueous layer was back extracted once with DCM. Combined organic layers were dried over Na$_2$SO$_4$, filtered and evaporated. The residue was purified by SiO$_2$ chromatography (hexanes/EtOAc 0-30% EtOAc) to give 15.72 g of 1 (82% yield)

Benzyl-3-methyl-pyrrolidine-3-carbonitrile was prepared using the same procedure but using methacrylonitrile as dipolarophile (82% yield).

Step 2—A mixture of 1 (5 g, 21.43 mmol), BOC$_2$O (5.6 g, 25.66 mmol) and 2.5 g of Pd(OH)$_2$ 20 wt % on carbon in 50 resulting mixture was stirred at RT overnight before being evaporated. The residue was taken into Et$_2$O a couple of times and evaporated to give 0.274 g of 5 as a monohydrochloride salt.

Step 6—Acetic anhydride (0.21 mL, 2.224 mmol) was added at RT to a mixture of 3 (0.31 g, 1.44 mmol) and pyridine (0.23 mL, 2.844 mmol) in 5 mL of DCM. The resulting mixture was stirred at RT for 24 hours before being quenched with MeOH. The reaction mixture was stirred at RT for 1 hour before being evaporated and coevaporated with toluene. The residue was purified by SiO$_2$ chromatography (hexanes/EtOAc 20% EtOAc) to give 0.3 g of 8 (81% yield).

Step 7—2 mL of HCl 4M in 1,4-dioxane were added at RT to a solution of 8 (0.3 g, 1.166 mmol) in 2 mL of DCM. The resulting mixture was stirred at RT overnight before being evaporated and coevaporated with toluene to give 9: 3-methoxymethyl-3-methyl-pyrrolidine quantitatively as a monohydrochloride salt.

Acetic acid 3-methyl-pyrrolidin-3-ylmethyl ester monohydrochloride was prepared following the same procedure but using 3-acetoxymethyl-3-methyl-pyrrolidine-1-carboxylic acid tert-butyl ester as starting material.

Example 222

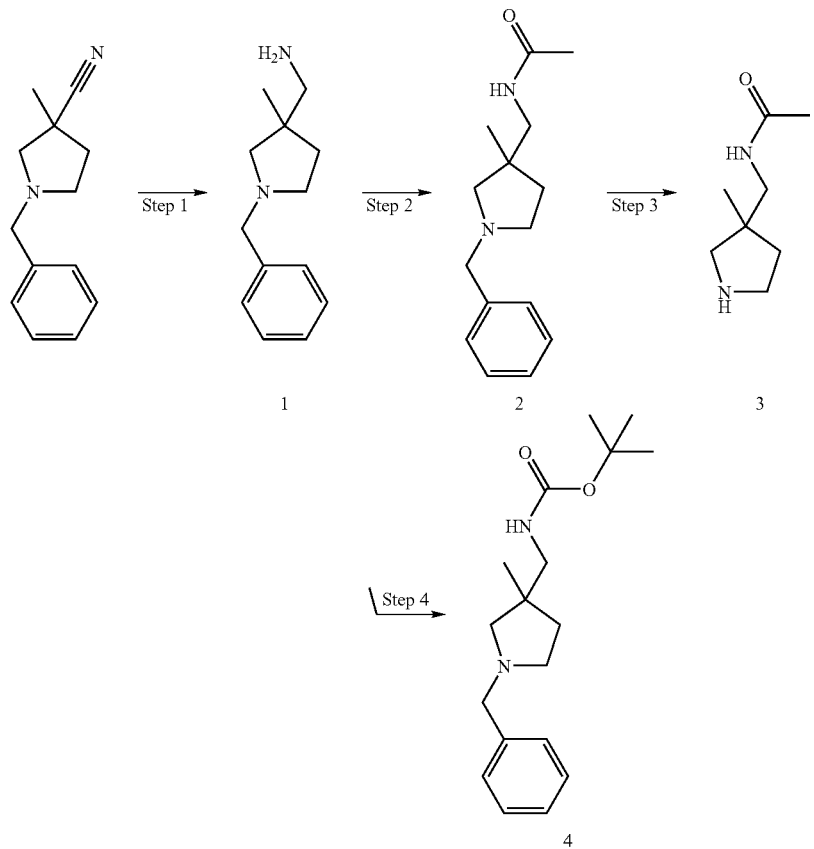

Step 1—LAH 1M in THF (10 mL, 10 mmol) was added at RT to a solution of 1-benzyl-3-methyl-pyrrolidine-3-carbonitrile (2 g, 9.99 mmol) in 50 mL of THF. The resulting mixture was stirred at RT for 6 hours before being quenched at 0° C. by successive addition of 0.38 mL of $H_2O$, 0.38 mL of 15% NaOH and finally by 1.14 mL of $H_2O$. Two scoops of celite were added and the slurry was filtered. After rinsing the insoluble material with THF, the filtrate was evaporated to give 1 quantitatively.

Step 2—Acetic anhydride (0.7 mL, 7.405 mmol) was added at RT to a solution of 1 (1 g, 4.894 mmol) and pyridine (0.8 mL, 9.886 mmol) in 25 mL of DCM. The resulting mixture was stirred at RT for 4 hours before being quenched by addition of 10 mL of MeOH. The reaction mixture was stirred at RT for 1 hour before being evaporated and coevaporated with toluene. The residue was partitioned between $H_2O$ and EtOAc. The aqueous layer was back extracted with EtOAc. The combined organic layers were dried ($Na_2SO_4$), filtered, and evaporated to give 2 quantitatively.

N-(1-Benzyl-3-methyl-pyrrolidin-3-ylmethyl)-methanesulfonamide was prepared following the same procedure but using MsCl as electrophile.

Benzyl-3-methyl-pyrrolidin-3-ylmethyl)-carbamic acid methyl ester was prepared following the same procedure but using methylchloroformate as electrophile.

Step 3—A mixture of 2 (0.260 g, 1.059 mmol) and $Pd(OH)_2$ 20% on carbon (0.125 g) in 50 mL of EtOH was stirred under an atmosphere of hydrogen (1 atm) overnight before being filtered. The filtrate was evaporated to give 3: N-(3-methyl-pyrrolidin-3-ylmethyl)-acetamide quantitatively.

N-(3-Methyl-pyrrolidin-3-ylmethyl)-methanesulfonamide was prepared following the same procedure but using N-(1-benzyl-3-methyl-pyrrolidin-3-ylmethyl)-methanesulfonamide as starting material.

Methyl-pyrrolidin-3-ylmethyl)-carbamic acid methyl ester was prepared following the same procedure but using (1-benzyl-3-methyl-pyrrolidin-3-ylmethyl)-carbamic acid methyl ester as starting material.

Methyl-pyrrolidin-3-ylmethyl)-carbamic acid tert-butyl ester prepared following the same procedure but using (1-benzyl-3-methyl-pyrrolidin-3-ylmethyl)-carbamic acid tert-butyl ester as starting material. The product was obtained in 82% yield after $SiO_2$ chromatography (DCM/MeOH 50% MeOH).

Step 4—$BOC_2O$ (1.18 g, 5.407 mmol) was added at RT to a mixture of 1 (1 g, 4.894 mmol) and $K_2CO_3$ (0.8 g, 5.788 mmol) in 25 mL of THF. The resulting mixture was stirred at RT over the weekend before being filtered. The filtrate was evaporated and the residue was purified (hexanes/EtOAc 0-30% EtOAc) to give 1 g of 4: (1-benzyl-3-methyl-pyrrolidin-3-ylmethyl)-carbamic acid tert-butyl ester (67% yield).

Example 223

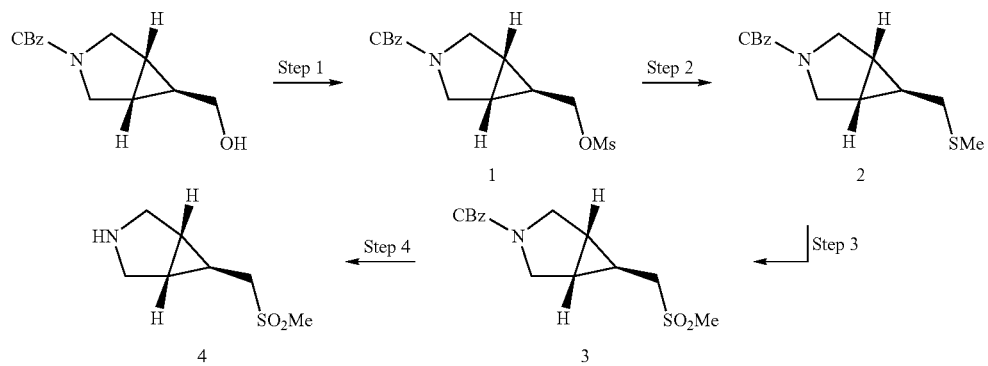

Step 1—Pyridine (0.5 mL, 6.167 mmol) followed by MsCl (0.24 mL, 3.033 mmol) were added at 0° C. to a solution of (1S,5R,6R)-6-hydroxymethyl-3-aza-bicyclo[3.1.0]hexane-3-carboxylic acid benzyl ester (0.5 g, 2.022 mmol) in 15 mL of DCM. The resulting mixture was allowed to reach RT overnight before being partitioned between a saturated aqueous solution of NH$_4$Cl and EtOAc. The aqueous layer was back extracted with EtOAc. The combined organic layers were dried (Na$_2$SO$_4$), filtered, and evaporated. The residue was purified by SiO$_2$ chromatography (hexanes/EtOAc 0 to 60% EtOAc) to give 0.345 g of 1 (52% yield).

(1S,5R,6R)-6-Hydroxymethyl-3-aza-bicyclo[3.1.0]hexane-3-carboxylic acid benzyl ester was prepared according to the procedure in Synlett 1996, 11, 1097-1099.

Step 2—Sodium thiomethoxide (0.111 g, 1.498 mmol) was added at RT to a solution of 1 (0.375 g, 1.152 mmol) in 10 mL of DMF. The resulting mixture was stirred at 50° C. overnight before being cooled to RT and partitioned between H$_2$O and Et$_2$O. The aqueous layer was back extracted twice with Et$_2$O. The organic layers were dried (Na$_2$SO$_4$), filtered, and evaporated to give 0.283 g of 2 (89% yield) that was used in the next step without purification.

Step 3—Oxone (0.465 g, 0.757 mmol) was added at RT to a solution of 2 (0.14 g, 0.505 mmol) in 5 mL of MeOH and 0.5 mL of H$_2$O. The resulting mixture was stirred at RT for three hours before being evaporated. The residue was partitioned between aqueous NaOH and EtOAc. The aqueous layer was extracted with EtOAc. The combined organic layers were dried (Na$_2$SO$_4$), filtered, and evaporated to give 3 quantitatively.

Step 4—A suspension of 3 (0.155 g, 0.501 mmol) and Pd 10 wt % on carbon (0.02 g) in 5 mL of EtOH was stirred under an hydrogen atmosphere (1 atm) for 1 hour before being filtered. The filtrate was evaporated to give 4: (1S,5R,6R)-6-methanesulfonylmethyl-3-aza-bicyclo[3.1.0]hexane quantitatively.

Example 224

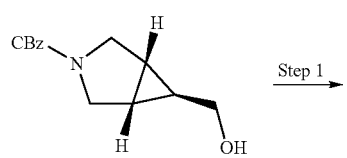

-continued

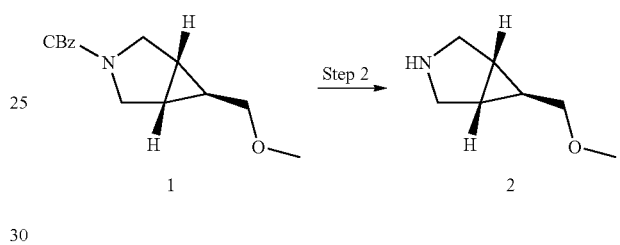

Step 1—A solution of (1S,5R,6R)-6-hydroxymethyl-3-aza-bicyclo[3.1.0]hexane-3-carboxylic acid benzyl ester (0.4 g, 1.617 mmol) in 2.5 mL of DMF was added at 0° C. to a suspension of NaH 60% dispersion in oil (0.078 g, 1.941 mmol). The resulting mixture was stirred at 0° C. for 40 minutes before adding iodomethane (0.11 mL, 1.779 mmol). The reaction mixture was allowed to reach RT overnight before being evaporated. The residue was partitioned between H$_2$O and EtOAc. The aqueous layer was back extracted twice with EtOAc. The combined organic layer were dried (MgSO$_4$), filtered, and evaporated. The residue was purified by SiO$_2$ chromatography (hexanes/EtOAc 30% EtOAc) to give 0.3 g of 1 (71% yield).

Step 2—A suspension of 1 (0.3 g, 1.148 mmol), ammonium formate (0.289 g, 4.592 mmol) and Pd 10 wt % on carbon (0.07 g) was stirred at 65° C. for two hours before being cooled to RT and filtered. The filtrate was evaporated to give 0.11 g of 2: (1S,5R,6R)-6-methoxymethyl-3-aza-bicyclo[3.1.0]hexane (75% yield).

Example 225

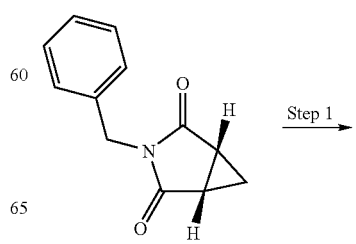

-continued

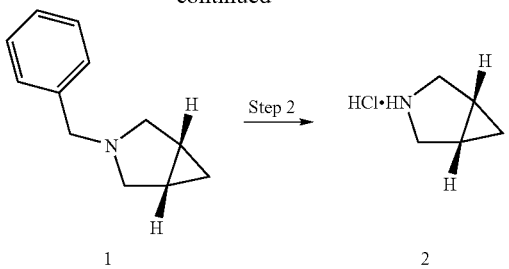

Step 1—LAH 1M in THF was added at RT to a solution of commercially available 3-benzyl-3-aza-bicyclo[3.1.0]hexane-2,4-dione (5 g, 24.85 mmol) in 100 mL of THF. The resulting mixture was stirred at reflux overnight before being cooled to 0° C., and quenched by successive addition of 1.5 mL of $H_2O$, 1.5 mL of 15% NaOH and finally 4.5 mL of $H_2O$. 5 g of celite were added, the reaction mixture was filtered, and the filtrate was evaporated to give 1 quantitatively.

Step 2—A mixture of 1 (1.35 g, 4.434 mmol) and $Pd(OH)_2$ 20 wt % on carbon (1 g) in 50 ml, of EtOH was stirred under hydrogen (1 atm) for 24 hours before being filtered. The cake was rinsed with MeOH. 10 mL of concentrated HCl were added to the filtrate and the filtrate was evaporated and coevaporated with toluene. The crystalline pink residue was triturated with cold iPrOH, and the insoluble residue was filtered, rinsed with acetone, and dried under vacuum to give 1.35 g of 2 (45% yield as the monohydrochloride salt.

Example 226

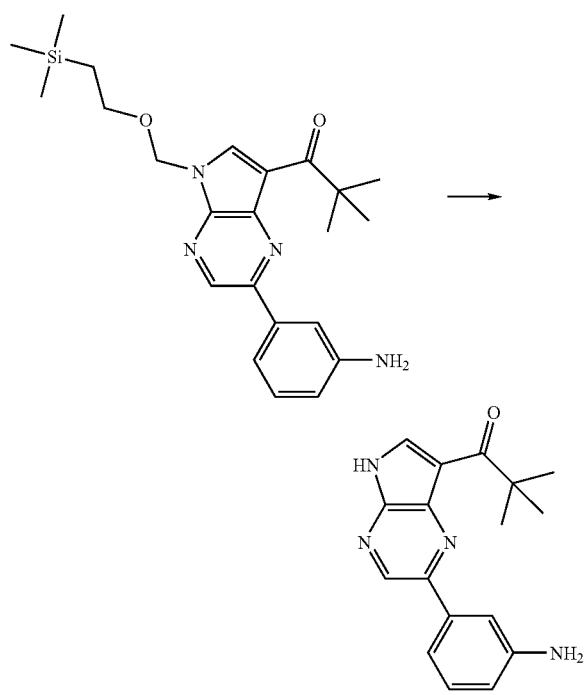

1-[2-(3-Amino-phenyl)-5H-pyrrolo[2,3-b]pyrazin-7-yl]-2,2-dimethyl-propan-1-one

To a microwave vial was added 0.032 gm (0.075 mM) 1-[2-(3-Amino-phenyl)-5-(2-trimethylsilanyl-ethoxymethyl)-5H-pyrrolo[2,3-b]pyrazin-7-yl]-2,2-dimethyl-propan-1-one followed by 0.75 ml of 1M tetrabutylammonium fluoride in THF. The vial was sealed and placed in a 80° C. oil bath for two hours then stirred at room temperature overnight. The mixture was diluted with 10 ml ethyl acetate, rinsed (3×50 ml) water, dried over magnesium sulfate, filtered and concentrated on a rotary evaporator. Purification on a preparative silica gel thin layer chromatography plate (5/95 MeOH/$CH_2Cl_2$) gave 0.014 gm (64% yield) of 1-[2-(3-Amino-phenyl)-5H-pyrrolo[2,3-b]pyrazin-7-yl]-2,2-dimethyl-propan-1-one, M+1 295, M.P. 239-241° C.

Example 227

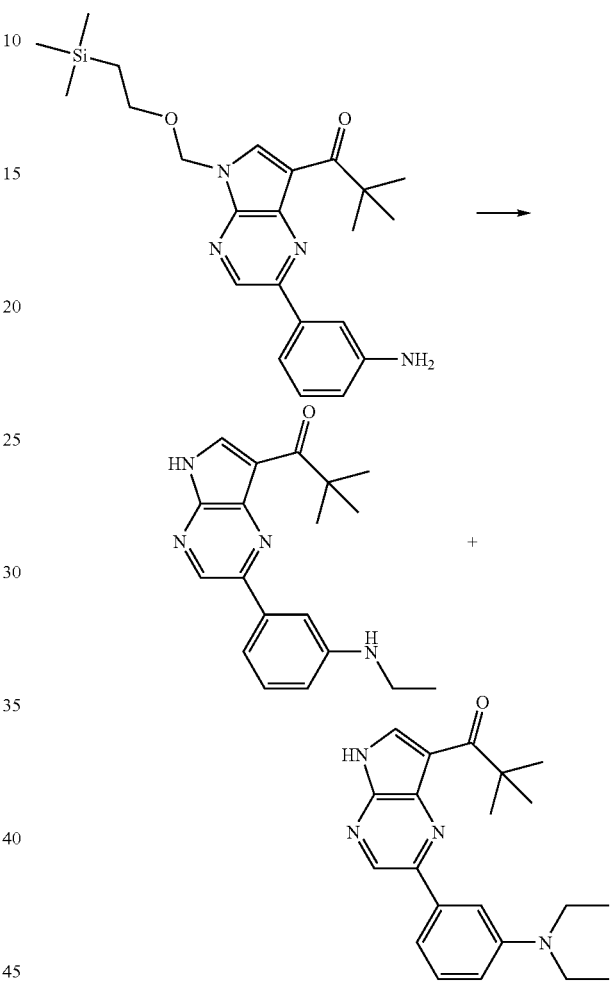

1-[2-(3-Ethylamino-phenyl)-5H-pyrrolo[2,3-b]pyrazin-7-yl]-2,2-dimethyl-propan-1-one To a microwave vial was added 0.050 gm (0.118 mM) 1-[2-(3-Amino-phenyl)-5-(2-trimethylsilanyl-ethoxymethyl)-5H-pyrrolo[2,3-b]pyrazin-7-yl]-2,2-dimethyl-propan-1-one along with 2.0 ml water, 0.2 ml (1.88 mM) ethyl mesylate and 0.138 gm (1.0 mM) potassium carbonate and the mixture sealed and heated to 100° C. for 10 minutes. For five additional times ethyl mesylate and potassium carbonate was added followed by heating for a total of 1.8 ml (17 mM) ethyl mesylate and 1.38 gm (10.0 mM) potassium carbonate. The mixture was diluted with water, extracted three times with ethyl acetate, dried over magnesium sulfate and purified by column chromatography to give the mono and diethyl compounds. The SEM protecting group was removed using the general procedures described in these Examples to give 1-[2-(3-Ethylamino-phenyl)-5H-pyrrolo[2,3-b]pyrazin-7-yl]-2,2-dimethyl-propan-1-one M+1 323, M.P. 189-191° C. and 1-[2-(3-Diethylamino-phenyl)-5H-pyrrolo[2,3-b]pyrazin-7-yl]-2,2-dimethyl-propan-1-one, M+1 351, M.P. 216-217° C.

Example 228

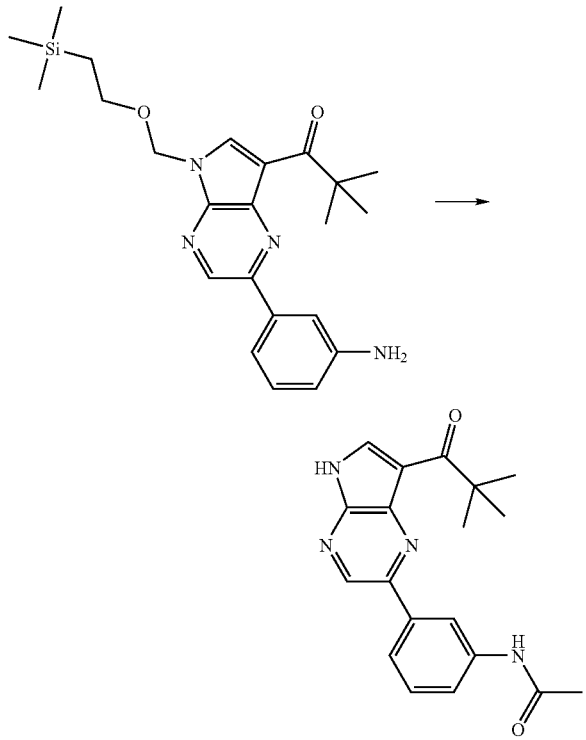

N-{3-[7-(2,2-Dimethyl-propionyl)-5H-pyrrolo[2,3-b]pyrazin-2-yl]-phenyl}-acetamide In a vial was added 0.030 gm (0.071 mM) 1-[2-(3-Aminophenyl)-5H-pyrrolo[2,3-b]pyrazin-7-yl]-2,2-dimethyl-propan-1-one, 0.2 ml THF, 0.008 ml (0.1 mM) pyridine and 0.008 ml (0.085 mM) acetic anhydride. After stirring overnight at room temperature the mixture was concentrated and purified on a preparative TLC plate to give 0.028 gm (0.060 mM) of the acetyl derivative. The SEM protecting group was removed as described previously to give N-{3-[7-(2,2-Dimethyl-propionyl)-5H-pyrrolo[2,3-b]pyrazin-2-yl]-phenyl}-acetamide, M+1 337, M.P. 249-250° C.

Example 229

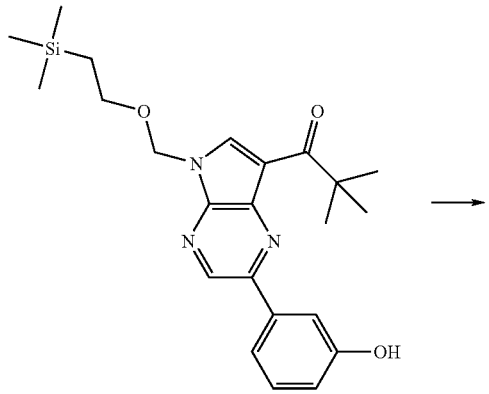

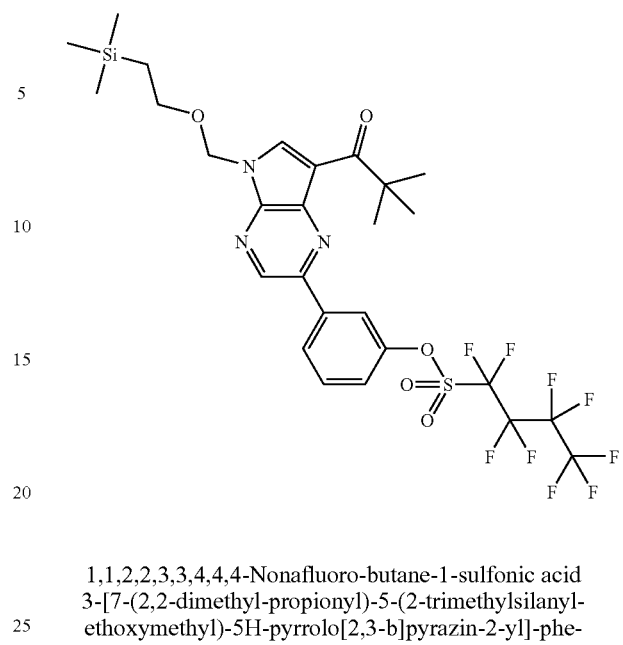

1,1,2,2,3,3,4,4,4-Nonafluoro-butane-1-sulfonic acid 3-[7-(2,2-dimethyl-propionyl)-5-(2-trimethylsilanyl-ethoxymethyl)-5H-pyrrolo[2,3-b]pyrazin-2-yl]-phenyl ester In a flask 0.11 gm (0.259 mM) 1-[2-(3-Hydroxy-phenyl)-5-(2-trimethylsilanyl-ethoxymethyl)-5H-pyrrolo[2,3-b]pyrazin-7-yl]-2,2-dimethyl-propan-1-one, 5 ml dichloromethane, 0.055 ml (0.316 mM) diisopropylethylamine and 0.0015 gm (0.012 mM) 4-dimethylaminopyridine were added. The mixture was chilled in an ice bath and 0.087 ml (0.285 mM) nonafluorobutanesulfonic anhydride was added. The mixture was allowed to warm to room temperature and stir over night. The mixture was diluted with additional dichloromethane, rinsed two times with water, dried over magnesium sulfate and purified by column chromatography (ethyl acetate/hexane) to give 0.15 gm (0.21 mM, 82% yield) 1,1,2,2,3,3,4,4,4-Nonafluoro-butane-1-sulfonic acid 3-[7-(2,2-dimethyl-propionyl)-5-(2-trimethylsilanyl-ethoxymethyl)-5H-pyrrolo[2,3-b]pyrazin-2-yl]-phenyl ester M+1 708.

Example 230

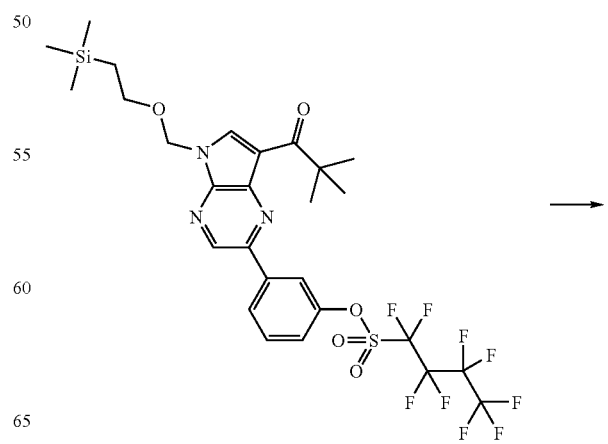

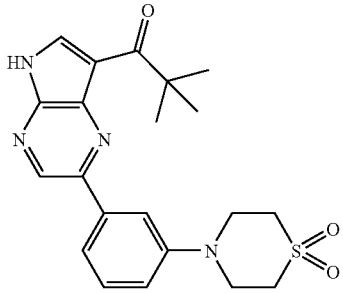

1-{2-[3-(1,1-Dioxo-1lambda*6*-thiomorpholin-4-yl)-phenyl]-5H-pyrrolo[2,3-b]pyrazin-7-yl}-2,2-dimethyl-propan-1-one In a microwave vial was added 0.12 gm (0.17 mM) 1,1,2,2,3,3,4,4,4-Nonafluoro-butane-1-sulfonic acid 3-[7-(2,2-dimethyl-propionyl)-5-(2-trimethylsilanyl-ethoxymethyl)-5H-pyrrolo[2,3-b]pyrazin-2-yl]-phenyl ester, 1.5 ml toluene, 0.035 gm (0.26 mM) Thiomorpholine 1,1-dioxide, 0.0039 gm (0.0085 mM) tris(dibenzylideneacetone)dipalladium(0), 0.0108 gm (0.019 mM) 9,9-dimethyl-4,5-bis(diphenylphosphino)xanthene, and 0.072 gm (0.34 mM) potassium phosphate. The vial is sealed, evacuated and refilled three times with argon then heated in a 115° C. oil bath for 43 hours. The mixture was cooled to room temperature, filtered, solids rinsed with ethyl acetate and the filtrate and rinse concentrated and purified by column chromatography (ethyl acetate/hexane to give 0.062 gm (0.114 mM, 67% yield) of the adduct. The SEM protecting group was removed using the general procedures described in these Examples to give 0.033 gm (0.080 mM) of 1-{2-[3-(1,1-Dioxo-1lambda*6*-thiomorpholin-4-yl)-phenyl]-5H-pyrrolo[2,3-b]pyrazin-7-yl}-2,2-dimethyl-propan-1-one M+1 413, M.P. 279-280° C.

Using this Procedure the Following Compounds were Prepared:

1-{2-[3-(3-Hydroxy-pyrrolidin-1-yl)-phenyl]-5H-pyrrolo[2,3-b]pyrazin-7-yl}-2,2-dimethyl-propan-1-one, M+1 365, M.P. 245-248° C.

1-[2-(3-Azetidin-1-yl-phenyl)-5H-pyrrolo[2,3-b]pyrazin-7-yl]-2,2-dimethyl-propan-1-one M+1 413, M.P. 279-280° C.

1-{2-[3-(2-Methanesulfonyl-ethylamino)-phenyl]-5H-pyrrolo[2,3-b]pyrazin-7-yl}-2,2-dimethyl-propan-1-one M+1 401, m.p. 205-206° C.

5-{3-[7-(2,2-dimethyl-propionyl)-5H-pyrrolo[2,3-b]pyrazin-2-yl]-phenyl}-octahydro-pyrrolo[3,4-c]pyrrol-2-ium trifluoro-acetate (Boc protecting group removed using procedure in example 49) M+1 390

Example 231

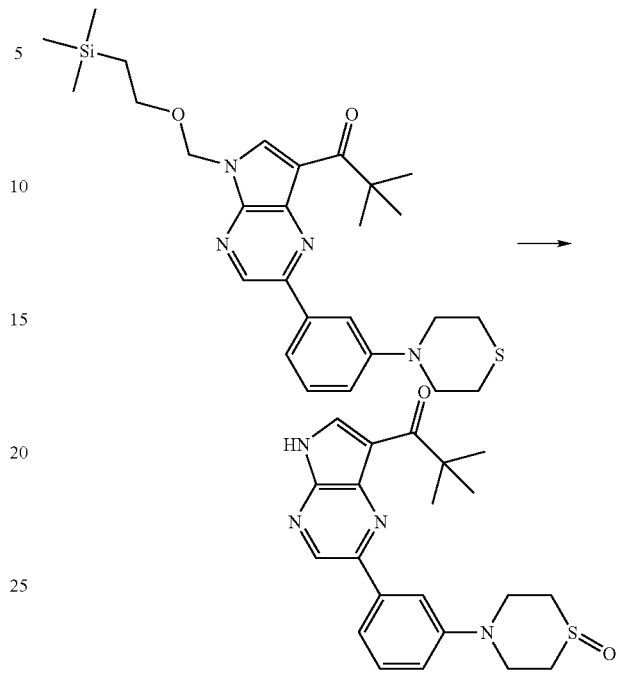

2,2-Dimethyl-1-{2-[3-(1-oxo-1lambda*4*-thiomorpholin-4-yl)-phenyl]-5H-pyrrolo[2,3-b]pyrazin-7-yl}-propan-1-one To a flask was added 2,2-Dimethyl-1-[2-(3-thiomorpholin-4-yl-phenyl)-5-(2-trimethylsilanyl-ethoxymethyl)5H-pyrrolo[2,3-b]pyrazin-7-yl]-propan-1-one (prepared using general procedures described in these Examples) 0.030 gm (0.059 mM), 3-chloroperbenzoic acid (77%) 0.015 gm (0.067 mM), dichloromethane, stirred over night, rinsed with saturated aqueous sodium bicarbonate and purified on preparative TLC plate (3:1 ethyl acetate/hexane) tog give 0.019 gm (0.036 mM, 61% yield) of the sulfoxide. The SEM protecting group was removed following general procedures as described in these Examples to give 2,2-Dimethyl-1-{2-[3-(1-oxo-1lambda*4*-thiomorpholin-4-yl)-phenyl]-5H-pyrrolo[2,3-b]pyrazin-7-yl}-propan-1-one, 0.0025 gm, (0.006 mM) M+1 397.

Example 232

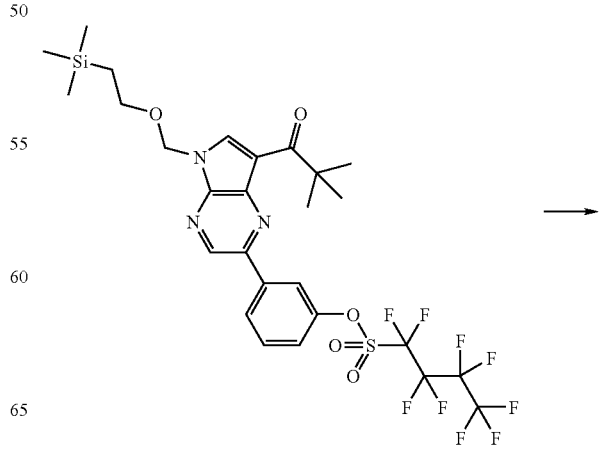

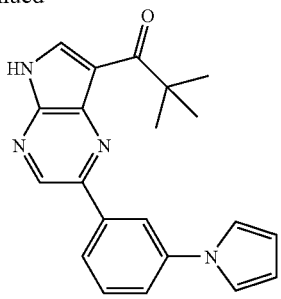

2,2-Dimethyl-1-[2-(3-pyrrol-1-yl-phenyl)-5H-pyrrolo[2,3-b]pyrazin-7-yl]-propan-1-one To a microwave vial was added 1,1,2,2,3,3,4,4,4-Nonafluoro-butane-1-sulfonic acid 3-[7-(2,2-dimethyl-propionyl)-5-(2-trimethylsilanyl-ethoxymethyl)-5H-pyrrolo[2,3-b]pyrazin-2-yl]-phenyl ester 0.20 gm (0.28 mM), pyrrole 0.048 ml (0.69 mM), 2-(dicyclohexylphosphino)-2'-(N,N-dimethylamino)biphenyl 0.011 gm (0.028 mM), tris(dibenzylideneacetone)dipalladium(0) 0.010 gm (0.022 mM), potassium phosphate 0.120 gm (0.565 mM) and 0.8 ml toluene. The vial was sealed, evacuated and refilled three times with argon and placed in a 90° C. oil bath for 16 hours. The vial was cooled to room temperature, filtered, the solids rinsed with ethyl acetate. The filtrate and rinse was concentrated and purified by column chromatography to give the coupled product 0.034 gm (0.072 mM, 26% yield). The SEM protecting group was removed using general procedures described in these Examples to give 2,2-Dimethyl-1-[2-(3-pyrrol-1-yl-phenyl)-5H-pyrrolo[2,3-b]pyrazin-7-yl]-propan-1-one 0.012 gm (0.035 mM, 12% yield over both steps) M+1 345, m.p. 220-222° C.

Example 233

1-{2-[3-((R)-2-Hydroxymethyl-pyrrolidin-1-yl)-phenyl]-5H-pyrrolo[2,3-b]pyrazin-7-yl}-2,2-dimethyl-propan-1-one To a microwave vial was added 1-[2-(3-Iodo-phenyl)-5-(2-trimethylsilanyl-ethoxymethyl)-5H-pyrrolo[2,3-b]pyrazin-7-yl]-2,2-dimethyl-propan-1-one 0.060 gm (0.112 mM), (R)-1-Pyrrolidin-2-yl-methanol 0.034 gm (0.336 mM), copper(1) iodide 0.0021 gm (0.011 mM), potassium phosphate 0.0476 gm (0.224 mM) and 0.3 ml 2-dimethylaminoethanol. The vial was sealed, evacuated and refilled three times with argon and place in a 80° C. oil bath for 35 hours. The vial was cooled to room temperature, 10 ml water was added and the mixture extracted with three 10 ml portions of ethyl acetate. The ethyl acetate was dried over magnesium sulfate, filtered, stripped and purified by column chromatography to give the adduct 0.030 gm (0.059 mM, 53% yield. The SEM protecting group was removed using general procedures described in these Examples to give 1-{2-[3-((R)-2-Hydroxymethyl-pyrrolidin-1-yl)-phenyl]-5H-pyrrolo[2,3-b]pyrazin-7-yl}-2,2-dimethyl-propan-1-one M+1 379.

With this Procedure was Also Prepared:

1-{2-[3-((S)-2-Hydroxymethyl-pyrrolidin-1-yl)-phenyl]-5H-pyrrolo[2,3-b]pyrazin-7-yl}-2,2-dimethyl-propan-1-one, M+1 379.

1-{2-[3-(3-Hydroxy-3-methyl-pyrrolidin-1-yl)-phenyl]-5H-pyrrolo[2,3-b]pyrazin-7-yl}-2,2-dimethyl-propan-1-one M+1 379 m.p. 237-239.

Example 234

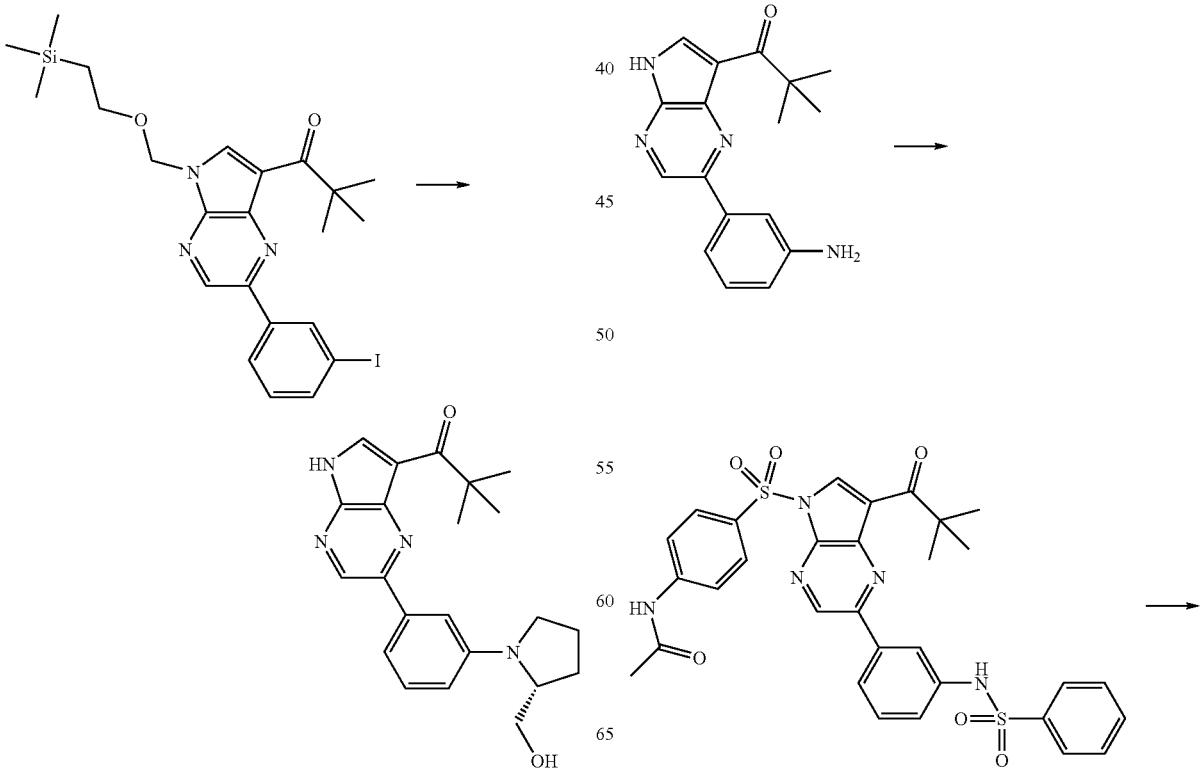

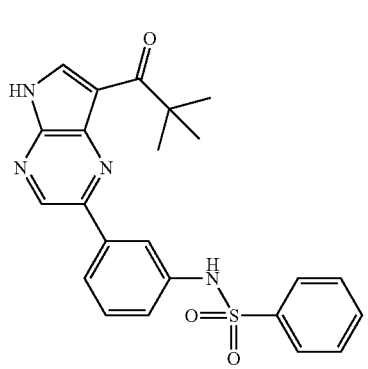

N-{3-[7-(2,2-Dimethyl-propionyl)-5H-pyrrolo[2,3-b]pyrazin-2-yl]-phenyl}-benzenesulfonamide

To a flask was added 1-[2-(3-Amino-phenyl)-5H-pyrrolo[2,3-b]pyrazin-7-yl]-2,2-dimethyl-propan-1-one 0.027 gm (0.092 mM), 1 ml dichloromethane, diisopropylethylamine 0.040 ml (0.23 mM) and benzenesulfonyl chloride 0.026 ml (0.204 mM). The mixture was stirred over night. Additional benzenesulfonyl chloride 0.0095 ml (0.074 mM) and diisopropylethylamine 0.015 ml (0.086 mM) was added and the mixture stirred overnight. The mixture was concentrated, 10 ml water and a few drops 1 M hydrochloric acid were added and it was extracted with ethyl acetate (3×30 ml). The ethyl acetate was dried over magnesium sulfate, stripped and purified on a preparative TLC plate (35:65 ethyl acetate/hexane) to give the diadduct 0.035 gm (0.061 mM, 66% yield). The diadduct was dissolved in a mixture of 3 ml THF and 6 ml MeCN. To this was added 0.4 ml 3M aqueous sodium hydroxide and the mixture heated to 55° C. for 4 hours. To this was added 50 ml water and concentrated on a rotary evaporator to remove the THF and MeCN. To the mixture was added 1M hydrochloric acid till neutral (solid forms) and extracted with ethyl acetate (3×50 ml). The solution was dried over magnesium sulfate and purified by preparative TLC (50:50 ethyl acetate/hexane) to give N-{3-[7-(2,2-Dimethyl-propionyl)-5H-pyrrolo[2,3-b]pyrazin-2-yl]-phenyl}-benzenesulfonamide 0.015 gm (0.035 mM, 38% overall yield) M+1 435, m.p. 217-219° C.

Using this Procedure the Following Compounds were Made:
N-{3-[7-(2,2-Dimethyl-propionyl)-5H-pyrrolo[2,3-b]pyrazin-2-yl]-phenyl}-methanesulfonamide M+1 373 m.p. 216-218° C.

N-(4-{3-[7-(2,2-Dimethyl-propionyl)-5H-pyrrolo[2,3-b]pyrazin-2-yl]-phenylsulfamoyl}-phenyl)-acetamide M+1 492 m.p. 226-228° C.

N-(4-{5-[7-(2,2-Dimethyl-propionyl)-5H-pyrrolo[2,3-b]pyrazin-2-yl]-2-methyl-phenylsulfamoyl}-phenyl)-acetamide M+1 506 m.p. 274-276° C.

Example 235

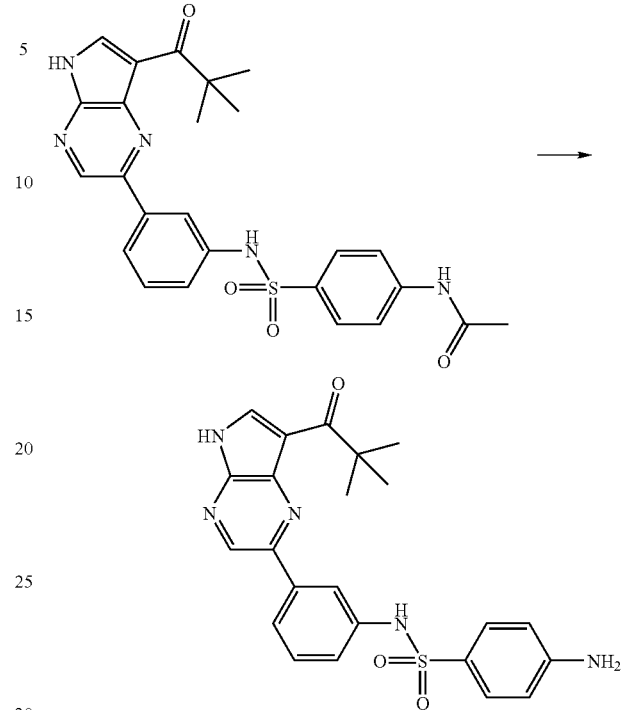

4-Amino-N-{3-[7-(2,2-dimethyl-propionyl)-5H-pyrrolo[2,3-b]pyrazin-2-yl]-phenyl}-benzenesulfonamide

In a flask N-(4-{3-[7-(2,2-Dimethyl-propionyl)-5H-pyrrolo[2,3-b]pyrazin-2-yl]-phenylsulfamoyl}-phenyl)-acetamide 0.034 gm (0.069 mM), 1 ml water and 10 drops 3M aqueous sodium hydroxide was added and the mixture heated to 100° C. for two hours. Water (20 ml) was added and the pH adjusted to 8 with hydrochloric acid and much solid formed. The mixture was extracted three times with ethyl acetate, the ethyl acetate dried over magnesium sulfate to give 4-Amino-N-{3-[7-(2,2-dimethyl-propionyl)-5H-pyrrolo[2,3-b]pyrazin-2-yl]-phenyl}-benzenesulfonamide 0.023 gm (0.051 mM, 74% yield) M+1 450 m.p. 285-286° C.

Using this Procedure the Following Compounds were Made:
4-Amino-N-{5-[7-(2,2-dimethyl-propionyl)-5H-pyrrolo[2,3-b]pyrazin-2-yl]-2-methyl-phenyl}-benzenesulfonamide M+1 464, m.p. 264-266° C.

Example 236

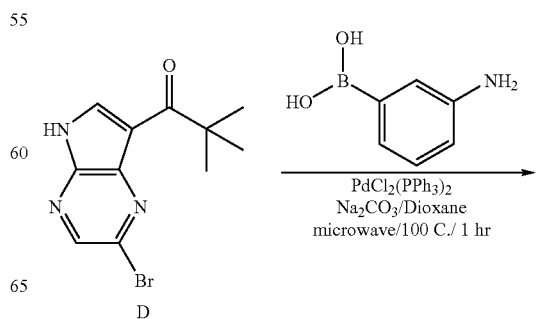

-continued

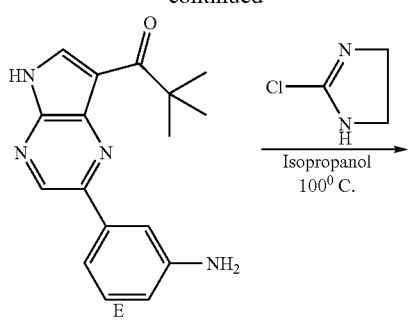

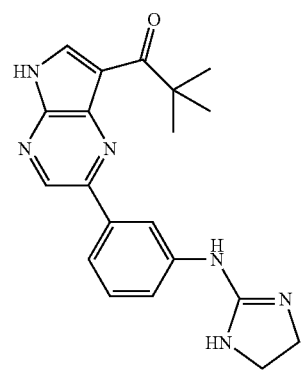

Preparation of E:

A stirred solution of D (1.41 g, 5 mmol) and 3-aminobenzeneboronic acid hydrate (1.03 g, 7.5 mmol) in dry 1,4-dioxane (10 ml) and 2 Molar sodium carbonate aqueous solution (7.5 ml) in a seal tube was purged with Argon for 2 min., then dichloro bis(triphenyl phosphine) palladium(II) (0.35 g, 0.5 mmol) was added and reaction mixture was again deoxygenated and subjected to microwave irradiation at 150 degree Celsius for 1 hr. The cooled mixture was partitioned between water and ethyl acetate, the organic layer was washed with brine, dried over sodium sulphate, and concentrated in vacuo. The residual oil was heated with ether, solid formed was filtered, washed with ether, dried to obtain E as light brown powder (1.45 g, 98% yield) mp 215-218° C.

Preparation of 1-{2-[3-(4,5-Dihydro-1H-imidazol-2-ylamino)-phenyl]-5H-pyrrolo[2,3-b]pyrazin-7-yl}-2,2-dimethyl-propan-1-one Chloroamidine sulfate (0.62 g, 3.1 mmol) was dissolved in cold water (10 ml), while at zero degree Celsius, basified with 10% NaOH aqueous solution, extracted quickly with DCM, dried over potassium carbonate and filtered into a solution of 4 (0.3 g, 1.02 mmol) in isopropanol (15 ml). More than half of the solvent was removed in vacuo and additional 5 ml of isopropanol was added and reaction mixture was heated at 100 degree Celsius under reflux for 1 hr. After cooling, the solvent removed in vacuo. The residue was loaded on silicagel column and eluted with 2.5% methanol-dichloromethane to afford the desired product 1-{2-[3-(4,5-Dihydro-1H-imidazol-2-ylamino)-phenyl]-5H-pyrrolo[2,3-b]pyrazin-7-yl}-2,2-dimethyl-propan-1-one as light yellow powder (0.088 g, 24% yield) mp 228-230° C.

Example 237

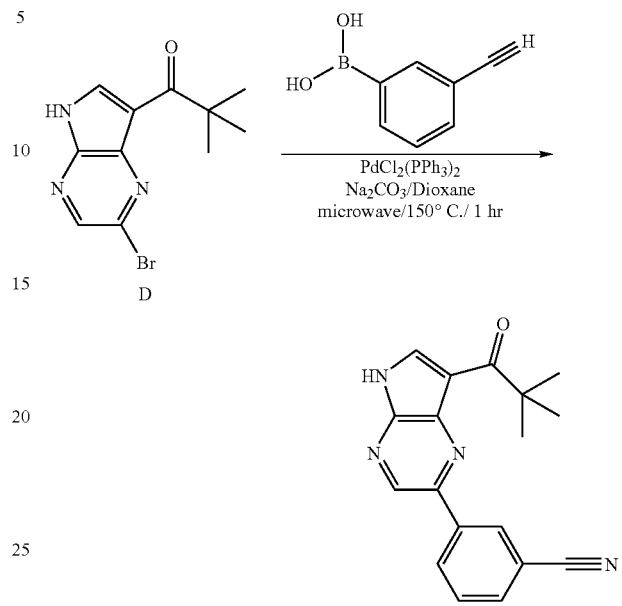

Preparation of 3-[7-(2,2-Dimethyl-propionyl)-5H-pyrrolo[2,3-b]pyrazin-2-yl]-benzonitrile A stirred solution of D (0.28 g, 1 mmol) and 3-cyanophenylboronic acid (0.22 g, 1.5 mmol) in dry 1,4-dioxane (4 ml) and 2 Molar sodium carbonate aqueous solution (1.5 ml) in a seal tube was purged with Argon for 2 min., then dichloro bis(triphenyl phosphine) palladium(II) (0.07 g, 0.1 mmol) was added and reaction mixture was again deoxygenated and subjected to microwave irradiation at 150 degree Celsius for 45 min. The cooled mixture was partitioned between water and ethyl acetate, the organic layer was washed with brine, dried over sodium sulphate, and concentrated in vacuo. The residual oil was loaded on silicagel column and eluted with DCM:1% NH$_4$OH-MeOH (10:0.25) to afford the desired product 3-[7-(2,2-Dimethyl-propionyl)-5H-pyrrolo[2,3-b]pyrazin-2-yl]-benzonitrile as a light yellow powder (0.228 g, 75%) mp 248-249° C.

Example 238

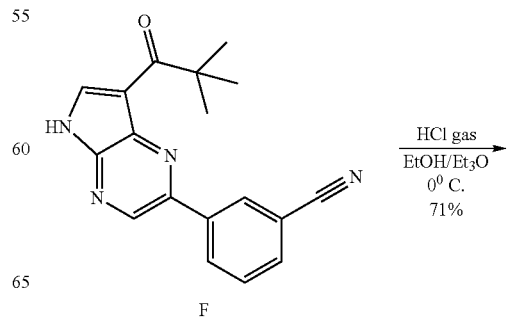

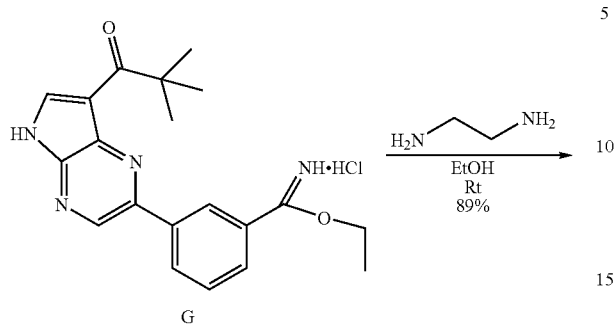

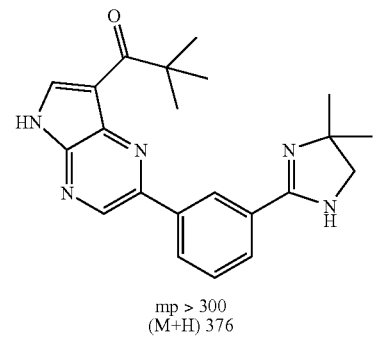

mp > 300
(M+H) 376

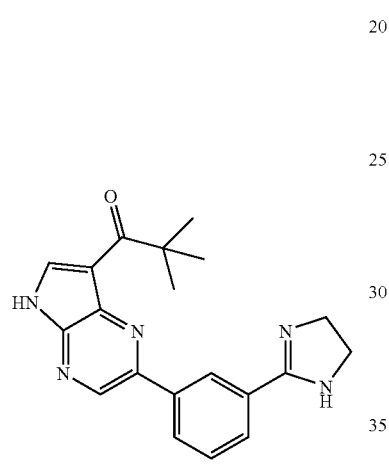

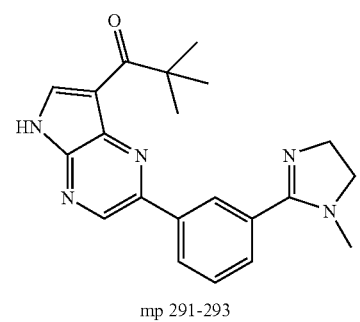

mp 291-293
(M+H) 362

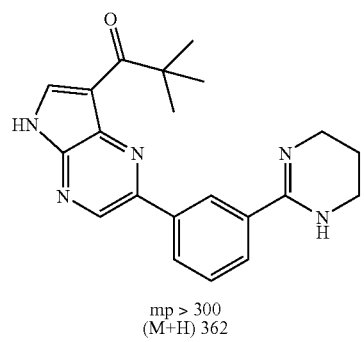

mp > 300
(M+H) 362

Preparation of G:

To a cooled suspension of F (0.27 g, 0.89 mmol) at zero degree Celsius in Et$_2$O (10 ml) and abs. EtOH (5 ml) under dry condition, bubble HCl gas gently for 1 hr. Solvent removed in vacuo to obtain light yellow powder G (0.24 g, 71%) mp 173-175° C.

Example 239

General Procedure for the Preparation of Cyclic Amidine:

To a suspension of G (0.08 g, 0.21 mmol) in EtOH (5 ml) stirring at room temp was added ethylenediamine (0.2 g, 0.31 mmol). After 30 min. of stirring reaction mixture becomes clear. Solvent removed in vacuo, the residual light yellow solid was loaded on silica gel column and eluted with DCM: 1% NH$_4$OH-MeOH (4:1) to afford as a white powder (0.065 g, 89%) mp 240-242° C.

Following compounds were synthesized using above procedure.

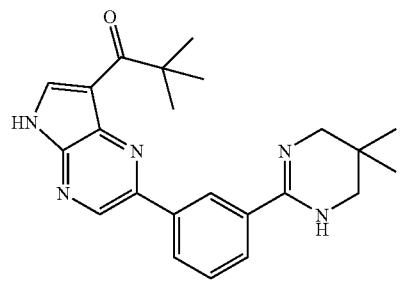

mp 272-274
(M+H) 390

Example 240

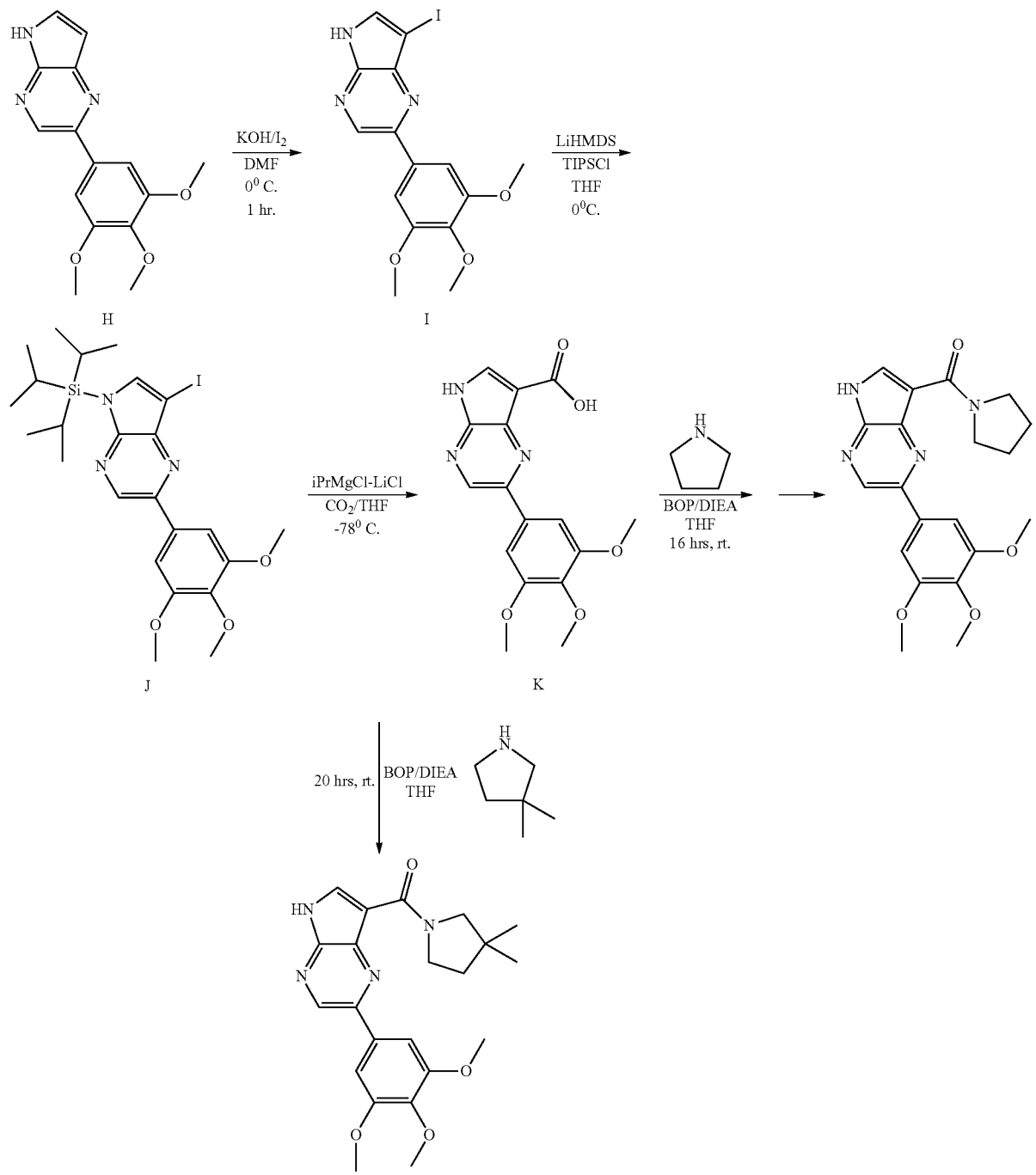

Preparation of I:

To a cooled solution of H (2.0 g, 7 mmol) in DMF (25 ml), add KOH pellets and stirred for 30 min. at zero degree Celsius, then a solution of iodine (2.66 g, 10.5 mmol) in DMF was added dropwise over 20 min. The resulting reaction mixture was allowed to stir at zero degree Celsius for 1 hr. The reaction mixture was poured into ice-cold satd. $Na_2S_2O_3$ aqueous solution. Additional ice-cold water was added to crash out the product, light brown solid formed was filtered, dried to obtain I (2.51 g, 87%) mp 244-246° C.

Preparation of J:

To a suspension of I (0.3 g, 0.73 mmol) in dry THF (10 ml) at zero degree Celsius, add 1 Molar solution of LiHMDS in THF (0.8 ml) under Argon and let it stir at room temp. for 30 min. Replace ice-bath and then add TIPSCl (0.15 g, 0.8 mmol) at zero degree Celsius, following addition, ice-bath removed and reaction mixture was stirred at room temp. for 30 min. Solvent removed in vacuo at room temp. to obtain light brown solid, it was triturated with hexane, filter and washed with hexane, dried to yield J, as a light brown powder (0.38 g, 92%) mp 154-156° C.

Preparation of K:

To a solution of J (1.12 g, 1.97 mmol) in dry THF (10 ml) at −78° C. under Argon, add 1.3 Molar solution of i-PrMgCl—LiCl complex in THF (4.55 ml, 5.92 mmol) dropwise, stir for 10 min., then bubble $CO_2$ gas at −78° C., allow to warm at room temp. while under $CO_2$ atmosphere. Reaction mixture was quenched with 1 Molar Citric acid aqueous solution while stirring, light yellow solid formed was filtered, washed with water, dried to obtain K (0.51 g, 79%) mp 236-237° C.

Preparation of Pyrrolidin-1-yl-[2-(3,4,5-trimethoxy-phenyl)-5H-pyrrolo[2,3-b]pyrazin-7-yl]-methanone To a suspension of D (0.15 g, 0.45 mmol) in THF 910 ml) add BOP (0.3 g, 0.68 mmol) and DIEA (0.09 g, 0.68 mmol), followed by pyrrolidine (0.049 g, 0.68 mmol). Reaction mixture stirred at room temp. for 16 hrs. Solvent removed in vacuo, the residue partitioned between water and DCM, the organic layer was washed with brine, dried over sodium sulphate, and concentrated in vacuo. The residual oil was loaded on silicagel column and eluted with DCM:1% $NH_4OH$-MeOH (10:0.25) to afford Pyrrolidin-1-yl-[2-(3,4,5-trimethoxy-phenyl)-5H-pyrrolo[2,3-b]pyrazin-7-yl]-methanone as a light yellow powder (0.079 g, 36%) mp 210-212° C.

Preparation of (3,3-Dimethyl-pyrrolidin-1-yl)-[2-(3,4,5-trimethoxy-phenyl)-5H-pyrrolo[2,3-b]pyrazin-7-yl]-methanone To a suspension of D (0.15 g, 0.45 mmol) in THF 910 ml) add BOP (0.3 g, 0.68 mmol) and DIEA (0.09 g, 0.68 mmol), followed by 3,3-dimethylpyrrolidine (0.067 g, 0.68 mmol). Reaction mixture stirred at room temp. for 16 hrs. Solvent removed in vacuo, the residue partitioned between water and DCM, the organic layer was washed with brine, dried over sodium sulphate, and concentrated in vacuo. The residual oil was loaded on silicagel column and eluted with DCM:1% $NH_4OH$-MeOH (10:0.25) to afford (3,3-Dimethyl-pyrrolidin-1-yl)-[2-(3,4,5-trimethoxy-phenyl)-5H-pyrrolo[2,3-b]pyrazin-7-yl]-methanone as a off-white powder (0.144 g, 78%%) mp 228-230° C.

Example 241

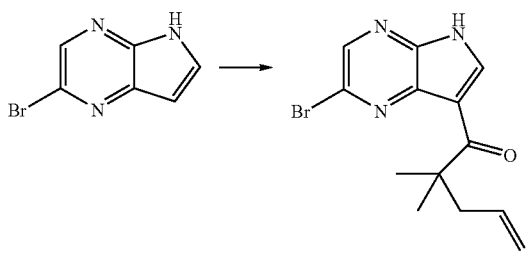

2,2-dimethyl-1-[2-(3,4,5-trimethoxy-phenyl)-5H-pyrrolo[2,3-b]pyrazin-7-yl]-pent-4-en-1-one; 2,2-dimethyl-1-[2-(3,4,5-trimethoxy-phenyl)-5H-pyrrolo[2,3-b]pyrazin-7-yl]-pentan-1-one; 2,2-dimethyl-4-morpholin-4-yl-1-[2-(3,4,5-trimethoxy-phenyl)-5H-pyrrolo[2,3-b]pyrazin-7-yl]-butan-1-one Oxalyl chloride (5.1 mL, 58 mmol) was added to a 0-5° C. solution of 2,2-dimethyl-4-pentenoic acid (5.00 g, 39.0 mmol) in 25 mL of dichloromethane. The mixture was stirred for 3 h, then concentrated to afford crude 2,2-dimethyl-4-pentenoyl chloride, which was dissolved in 10 mL of dichloromethane for use in the next step.

Diethylaluminum chloride (1.0 M in $CH_2Cl_2$, 23.4 mL, 23.4 mmol) was added to a 0-5° C. mixture of 2-bromo-5H-pyrrolo[2,3-b]pyrazine (1.55 g, 7.80 mmol) and 30 mL of dichloromethane in a sealed tube, and the mixture was stirred at 0-5° C. for 20 min. The solution of crude 2,2-dimethyl-4-pentenoyl chloride prepared in the previous step was added dropwise. The resulting mixture was stirred at 60° C. for 64 h, then cooled to 0-5° C. A sat. aq. $NaHCO_3$ solution (50 mL) was carefully added, and the mixture was extracted with three 100 mL portions of ethyl acetate. The combined organic layers were dried over $MgSO_4$, filtered and concentrated to a residue. Column chromatography (0→50% EtOAc/hexanes) afforded 1.033 g (43%) of impure 1-(2-bromo-5H-pyrrolo[2,3-b]pyrazin-7-yl)-2,2-dimethyl-pent-4-en-1-one as a brown solid, which was used without further purification. The major impurity is s.m. (typically 15-30% of the mixture).

Example 242

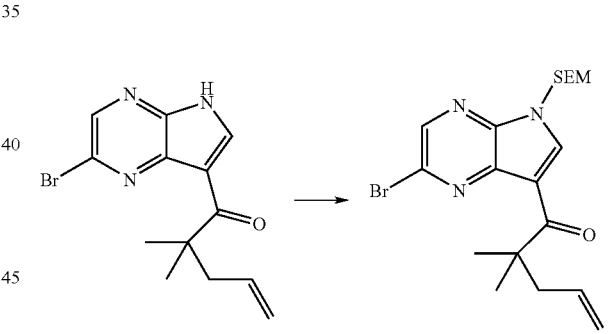

Sodium hydride (60% in mineral oil, 0.161 g, 4.02 mmol) was added to a 0-5° C. solution of impure 1-(2-bromo-5H-pyrrolo[2,3-b]pyrazin-7-yl)-2,2-dimethyl-pent-4-en-1-one (1.03 g, "3.35 mmol") in 10 mL of N,N-dimethylformamide. The mixture was stirred for 30 min., then SEMCl (0.71 mL, 4.02 mmol) was added. The mixture was allowed to warm to RT and stirred for 19 h, then quenched with 100 mL of water. The mixture was extracted with three 100 mL portions of ethyl acetate, and the combined organic layers were dried over $MgSO_4$, filtered and concentrated to a residue. Column chromatography (0→20% EtOAc/hexanes) afforded 1.38 g (69%) of impure 1-[2-bromo-5-(2-trimethylsilanyl-ethoxymethyl)-5H-pyrrolo[2,3-b]pyrazin-7-yl]-2,2-dimethyl-pent-4-en-1-one, which was used without further purification. The major impurity is the 3-H compound, from SEM protection of the impurity carried through from the previous reaction.

Example 243

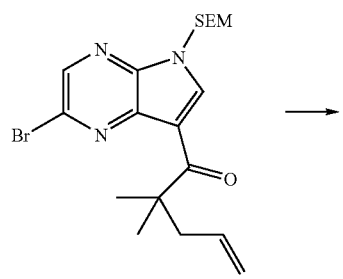

A mixture of impure 1-[2-bromo-5-(2-trimethylsilanyl-ethoxymethyl)-5H-pyrrolo[2,3-b]pyrazin-7-yl]-2,2-dimethyl-pent-4-en-1-one (0.900 g, "2.05 mmol), 3,4,5-trimethoxyphenyl boronic acid (0.479 g, 2.26 mmol), potassium carbonate (0.850 g, 6.15 mmol) and Pd(dppf)Cl₂.CH₂Cl₂ (0.171 g, 0.21 mmol) in 15 mL of 1,4-dioxane and 4 mL of water was stirred at 120° C. in a microwave for 1 h. The resulting mixture was partitioned between 300 mL of ethyl acetate and 200 mL of water. The organic layer was dried over MgSO₄, filtered and concentrated to a residue. Column chromatography (0→35% EtOAc/hexanes) afforded 0.777 g (29% for three steps from 2-bromo-5H-pyrrolo[2,3-b]pyrazine) of 2,2-dimethyl-1-[2-(3,4,5-trimethoxy-phenyl)-5-(2-trimethylsilanyl-ethoxymethyl)-5H-pyrrolo[2,3-b]pyrazin-7-yl]-pent-4-en-1-one.

Example 244

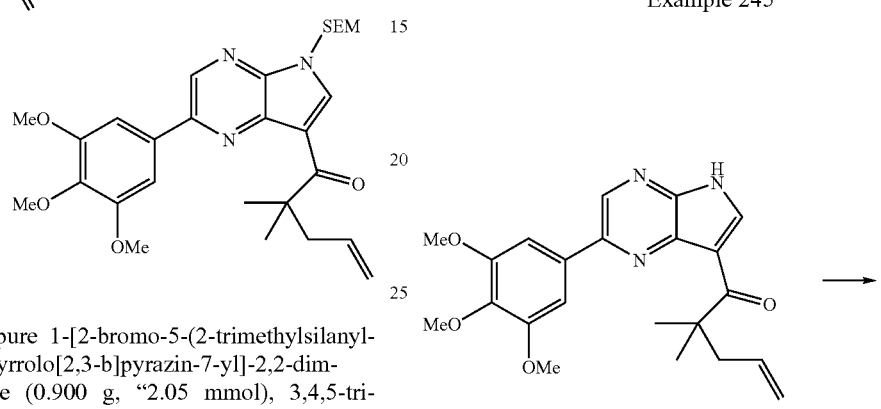

A solution of 2,2-dimethyl-1-[2-(3,4,5-trimethoxy-phenyl)-5-(2-trimethylsilanyl-ethoxymethyl)-5H-pyrrolo[2,3-b]pyrazin-7-yl]-pent-4-en-1-one (0.127 g, 0.242 mmol) in 4 mL of dichloromethane and 1 mL of trifluoroacetic acid was stirred for 3 h, then concentrated. The residue was taken up in 2 mL of ethanol (not all dissolves) and treated with sodium acetate trihydrate (0.329 g, 2.42 mmol). The mixture was stirred for 4 d, then concentrated to a residue. Column chromatography (0→5% MeOH/CH₂Cl₂) afforded 0.048 g (50%) of 2,2-dimethyl-1-[2-(3,4,5-trimethoxy-phenyl)-5H-pyrrolo[2,3-b]pyrazin-7-yl]-pent-4-en-1-one as a white solid.

Example 245

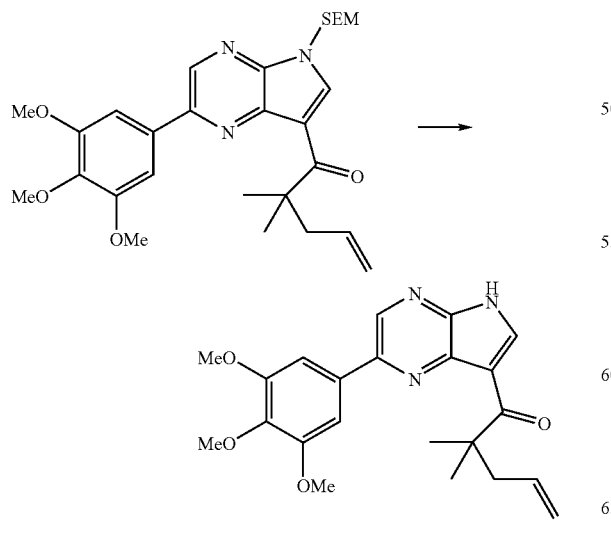

A mixture of 2,2-dimethyl-1-[2-(3,4,5-trimethoxy-phenyl)-5H-pyrrolo[2,3-b]pyrazin-7-yl]-pent-4-en-1-one (0.036 g, 0.091 mmol), 3 mL of ethanol (a small amount of methanol was also added to help solubility) and 10% Pd/C (10 mg) was stirred under a hydrogen atmosphere (balloon) for 3 d, then filtered through Celite and concentrated to afford 0.019 g (53%) of 2,2-dimethyl-1-[2-(3,4,5-trimethoxy-phenyl)-5H-pyrrolo[2,3-b]pyrazin-7-yl]-pentan-1-one as a yellow solid.

Example 246

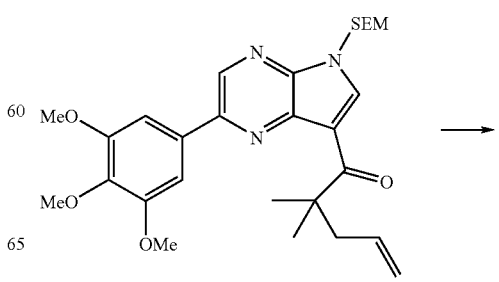

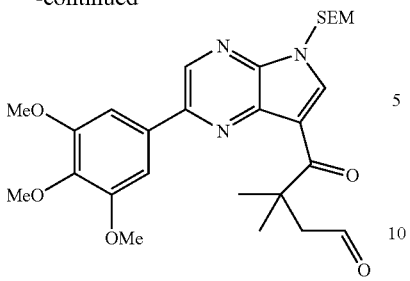

Osmium tetroxide (2.5% solution in water, 0.18 mL, 0.017 mmol) then sodium periodate (0.932 g, 4.36 mmol) were added to a solution of 2,2-dimethyl-1-[2-(3,4,5-trimethoxy-phenyl)-5-(2-trimethylsilanyl-ethoxymethyl)-5H-pyrrolo[2,3-b]pyrazin-7-yl]-pent-4-en-1-one (0.458 g, 0.871 mmol) in 18 mL of t-butanol and 9 mL of water. The mixture was stirred for 18 h, then partitioned between 100 ml of water and 100 mL of ethyl acetate. The organic layer was sequentially washed with a sat. aq. NaHCO₃ solution, water and a sat. aq. NaCl solution, dried over MgSO₄, filtered and concentrated to 0.444 g (99%) of crude 3,3-dimethyl-4-oxo-4-[2-(3,4,5-trimethoxy-phenyl)-5-(2-trimethylsilanyl-ethoxymethyl)-5H-pyrrolo[2,3-b]pyrazin-7-yl]-butyraldehyde as a brown oil, which was used without further purification.

Example 247

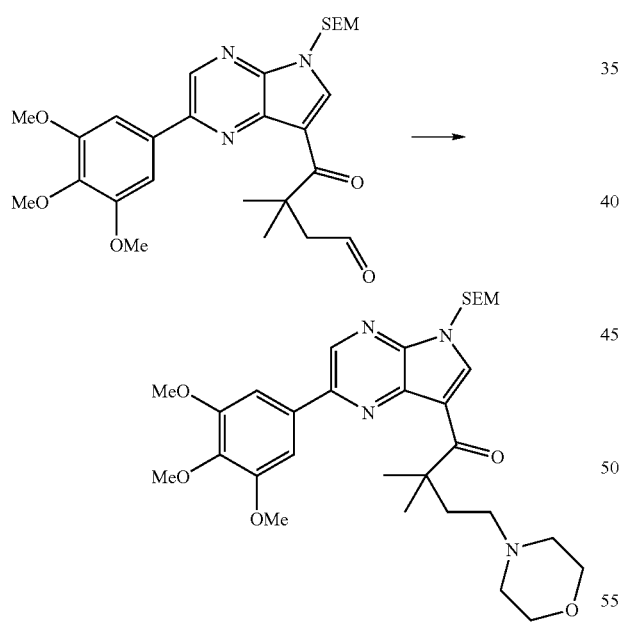

A mixture of crude 3,3-dimethyl-4-oxo-4-[2-(3,4,5-trimethoxy-phenyl)-5-(2-trimethylsilanyl-ethoxymethyl)-5H-pyrrolo[2,3-b]pyrazin-7-yl]-butyraldehyde (0.161 g, 0.305 mmol), morpholine (0.029 mL, 0.34 mmol), and sodium triacetoxyborohydride (0.129 g, 0.610 mmol) in 3 mL of 1,2-dichloroethane was stirred for 15 h. A sat. aq. NaHCO₃ solution (10 mL) was added, and the mixture stirred for 10 min. The layers were separated, and the aqueous layer was extracted with two 20 mL portions of ethyl acetate. The three combined organic layers were dried over MgSO₄, filtered, and concentrated to a residue. Column chromatography (0→10% MeOH/CH₂Cl₂) afforded 0.024 g (13%) of 2,2-dimethyl-4-morpholin-4-yl-1-[2-(3,4,5-trimethoxy-phenyl)-5-(2-trimethylsilanyl-ethoxymethyl)-5H-pyrrolo[2,3-b]pyrazin-7-yl]-butan-1-one as a brown oil.

Example 248

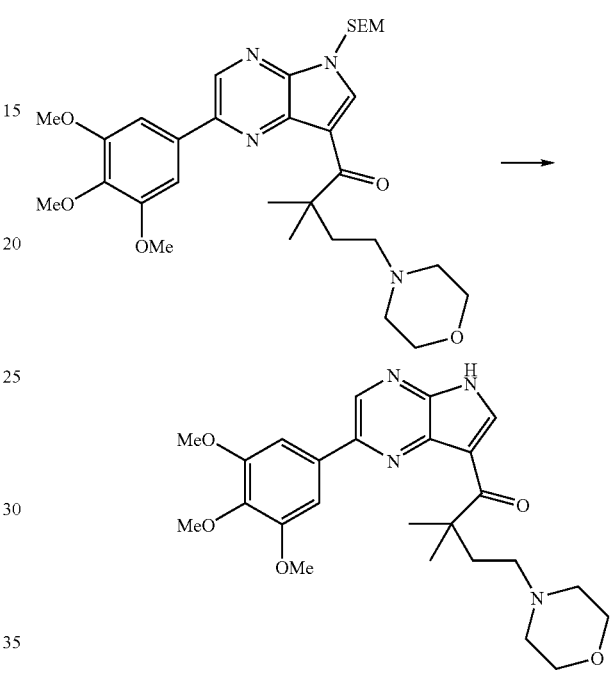

A solution of 2,2-dimethyl-4-morpholin-4-yl-1-[2-(3,4,5-trimethoxy-phenyl)-5-(2-trimethylsilanyl-ethoxymethyl)-5H-pyrrolo[2,3-b]pyrazin-7-yl]-butan-1-one (0.024 g, 0.040 mmol) in 1 mL of dichloromethane and 0.5 mL of trifluoroacetic acid was stirred for 3 h, then concentrated. The resulting residue was dissolved in 1 mL of ethanol and treated with sodium acetate trihydrate (0.054 g, 0.40 mmol). The mixture was stirred for 16 h, then concentrated to a residue. Column chromatography (0→10% MeOH/CH₂Cl₂) afforded 0.014 g (75%) of 2,2-dimethyl-4-morpholin-4-yl-1-[2-(3,4,5-trimethoxy-phenyl)-5H-pyrrolo[2,3-b]pyrazin-7-yl]-butan-1-one as a brown solid.

Example 249

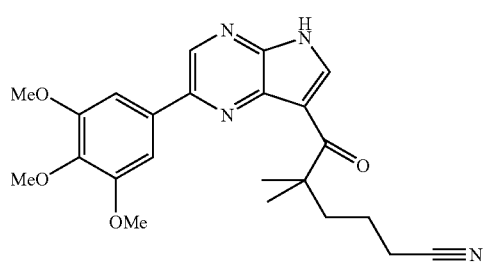

521

5,5-dimethyl-6-oxo-6-[2-(3,4,5-trimethoxy-phenyl)-5H-pyrrolo[2,3-b]pyrazin-7-yl]-hexanenitrile

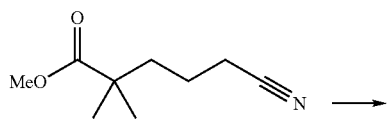

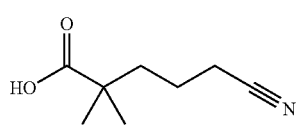

A mixture of 5-cyano-2,2-dimethyl-pentanoic acid methyl ester (4.50 g, 27 mmol) and 2 M aq. LiOH solution (40 mL, 80 mmol) in 30 mL of a 3:2:1 tetrahydrofuran/methanol/water solution was rapidly stirred overnight, then concentrated to approximately half volume. The mixture was extracted with ethyl acetate, then acidified with conc. HCl solution and extracted three times with ethyl acetate. The final three organic layers were combined and sequentially washed with sat. aq. NaHCO₃ solution and sat. aq. NaCl solution, dried over MgSO₄, filtered and concentrated to afford 2.77 g (67%) of 5-cyano-2,2-dimethyl-pentanoic acid as a brown oil, which was used without further purification.

Example 250

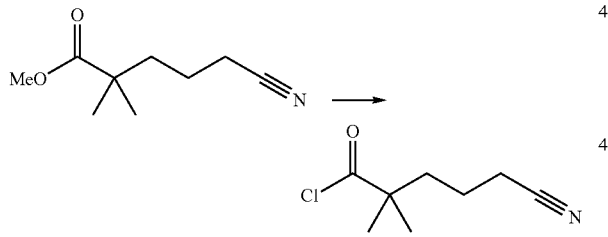

Oxalyl chloride (0.39 mL, 4.5 mmol) was added to a 0-5° C. solution of 5-cyano-2,2-dimethyl-pentanoic acid (0.462 g, 2.98 mmol) in 3 mL of dichloromethane, and the mixture was stirred for 3 h then concentrated to afford crude 5-cyano-2,2-dimethyl-pentanoyl chloride as a yellow oil, which was immediately used in the next step.

Example 251

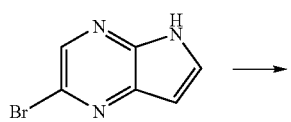

522

-continued

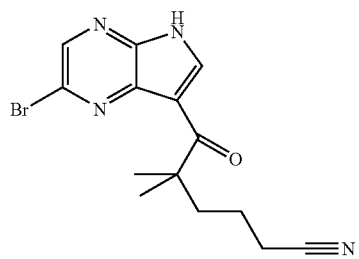

Diethylaluminum chloride (1.0 M in CH₂Cl₂, 3.6 mL, 3.6 mmol) was added to a 0-5° C. mixture of 2-bromo-5H-pyrrolo[2,3-b]pyrazine (0.237 g, 1.20 mmol) and 5 mL of dichloromethane in a sealed tube, and the mixture was stirred at 0-5° C. for 30 min. Crude 5-cyano-2,2-dimethyl-pentanoyl chloride from the previous step ("2.98 mmol") dissolved in 3 mL of dichloromethane was added, and the mixture was stirred at 60° C. for 16 h. A sat. aq. NaHCO₃ solution (50 mL) was carefully added, followed by 50 mL of ethyl acetate. The mixture was filtered through Celite, and the layers separate. The aqueous layer was extracted with 50 mL of ethyl acetate. The combined organic layers were dried over MgSO₄, filtered and concentrated to a residue. Column chromatography (0→80% EtOAc/hexanes) afforded 0.079 g (20%) of 6-(2-bromo-5H-pyrrolo[2,3-b]pyrazin-7-yl)-5,5-dimethyl-6-oxo-hexanenitrile as a yellow liquid.

Example 252

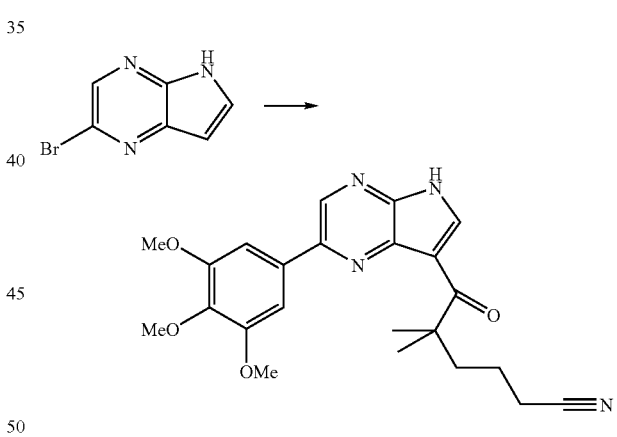

A mixture of 6-(2-bromo-5H-pyrrolo[2,3-b]pyrazin-7-yl)-5,5-dimethyl-6-oxo-hexanenitrile (0.079 g, 0.236 mmol), 3,4,5-trimethoxyphenylboronic acid (0.055 g, 0.26 mmol), potassium carbonate (0.098 g, 0.71 mmol) and Pd(dppf)Cl₂·CH₂Cl₂ (0.019 g, 0.024 mmol) in 2.4 mL of 1,4-dioxane and 0.4 mL of water was stirred at 120° C. in a microwave for 1 h, then at 130° C. in a microwave for 1 h. The resulting mixture was partitioned between 50 mL of ethyl acetate and 25 mL of water. The organic layer was dried over MgSO₄, filtered, and concentrated to a residue. Column chromatography (0→100% EtOAc/hexanes) afforded 0.004 g (4%) of 5,5-dimethyl-6-oxo-6-[2-(3,4,5-trimethoxy-phenyl)-5H-pyrrolo[2,3-b]pyrazin-7-yl]-hexanenitrile as a white solid.

Example 253

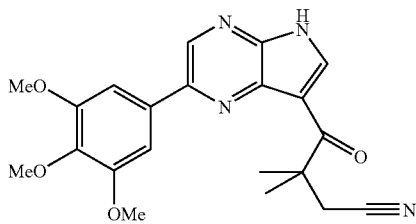

3,3-dimethyl-4-oxo-4-[2-(3,4,5-trimethoxy-phenyl)-5H-pyrrolo[2,3-b]pyrazin-7-yl]-butyronitrile

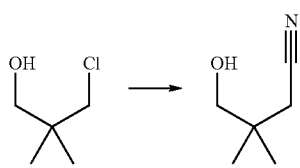

A mixture of 3-chloro-2,2-dimethyl-1-propanol (1.23 g, 10 mmol) and sodium cyanide (0.980 g, 20 mmol) in 4 mL of dimethylsulfoxide was stirred at 140° C. for 63 h, allowed to cool, diluted with 100 mL and acidified to pH 3 with a conc. HCl solution. The mixture was extracted with two 100 mL portions of ethyl acetate. The combined organic layers were dried over MgSO$_4$, filtered and concentrated to afford 0.670 g (59%) of crude 4-hydroxy-3,3-dimethyl-butyronitrile as a brown oil, which was used without further purification.

Example 254

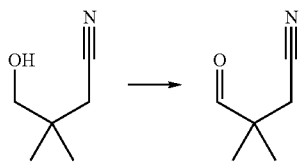

A mixture of crude 4-hydroxy-3,3-dimethyl-butyronitrile (0.444 g, 3.92 mmol) and Dess-Martin periodinane (2.16 g, 5.1 mmol) in 39 mL of dichloromethane was stirred for 4 h, then quenched with a sat. aq. NaHCO$_3$ solution and extracted with 50 mL of dichloromethane. The organic layer was dried over MgSO$_4$, filtered and concentrated to a yellow solid. The solid was taken up in 20 mL of dichloromethane, and insoluble impurities removed by filtration. The filtrate was concentrated to a residue. Column chromatography (0→60% EtOAc/hexanes) afforded 0.241 g (55%) of 3,3-dimethyl-4-oxo-butyronitrile as a colorless oil.

Example 255

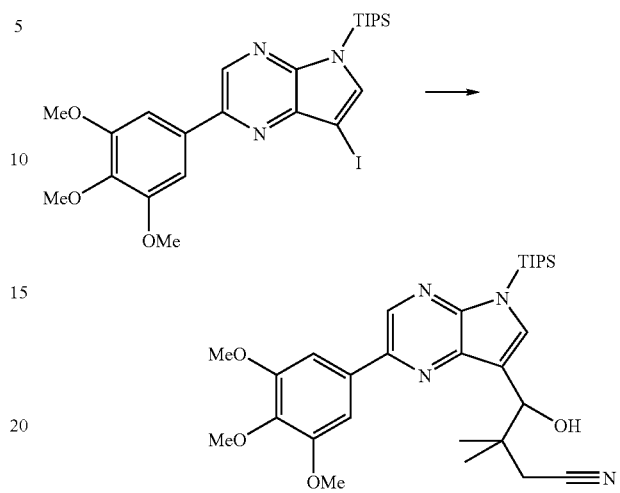

Propyl magnesium chloride lithium chloride (1.3 M solution in THF, 1.7 mL, 2.2 mmol) was added to 3 mL of tetrahydrofuran cooled to −78° C. A solution of 7-iodo-5-triisopropylsilanyl-2-(3,4,5-trimethoxy-phenyl)-5H-pyrrolo[2,3-b]pyrazine (0.250 g, 0.440 mmol) in 2 mL of tetrahydrofuran was slowly added, and the mixture was stirred at −78° C. for 2 h. A solution of 3,3-dimethyl-4-oxo-butyronitrile (0.241 g, 2.17 mmol) in 2 mL of tetrahydrofuran was added dropwise, and the mixture was stirred, allowing to slowly warm to RT, for 19 h, then quenched with 100 mL of a sat. aq. NaHCO$_3$ solution. The resulting mixture was extracted with 100 mL of ethyl acetate, and the organic layer was dried over MgSO$_4$, filtered and concentrated to a residue. Column chromatography (0→50% EtOAc/hexanes) afforded 0.152 g (62%) of 4-hydroxy-3,3-dimethyl-4-[5-triisopropylsilanyl-2-(3,4,5-trimethoxy-phenyl)-5H-pyrrolo[2,3-b]pyrazin-7-yl]-butyronitrile as a yellow oil.

Example 256

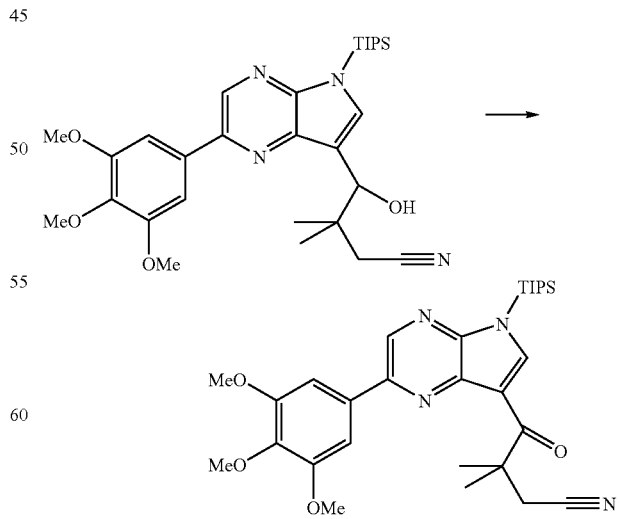

Dess-Martin periodinane (0.122 g, 0.289 mmol) was added to a 0-5° C. solution of 4-hydroxy-3,3-dimethyl-4-[5-triisopropylsilanyl-2-(3,4,5-trimethoxy-phenyl)-5H-pyrrolo[2,3-b]pyrazin-7-yl]-butyronitrile (0.152 g, 0.275 mmol) in 2 mL of dichloromethane. The mixture was stirred at 0-5° C. for 3 h, then quenched with water and a sat. aq. NaHCO₃ solution and extracted with 30 mL of dichloromethane. The organic layer was dried over MgSO₄, filtered and concentrated to a residue. Column chromatography (0→50% EtOAc/hexanes) afforded 0.093 g (61%) of 3,3-dimethyl-4-oxo-4-[5-triisopropylsilanyl-2-(3,4,5-trimethoxy-phenyl)-5H-pyrrolo[2,3-b]pyrazin-7-yl]-butyronitrile as a white solid.

Example 257

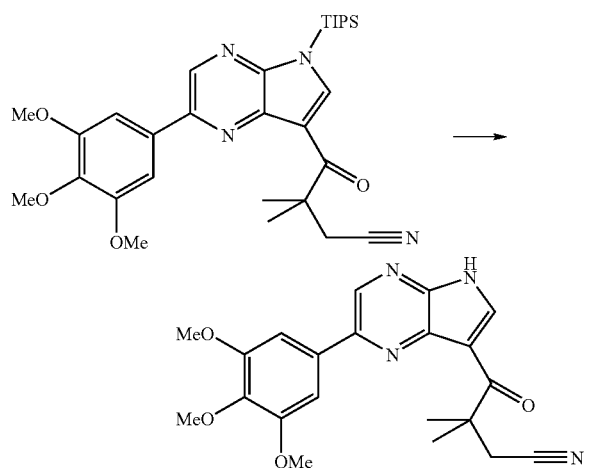

A solution of 3,3-dimethyl-4-oxo-4-[5-triisopropylsilanyl-2-(3,4,5-trimethoxy-phenyl)-5H-pyrrolo[2,3-b]pyrazin-7-yl]-butyronitrile (0.093 g, 0.17 mmol) and 0.3 mL of trifluoroacetic acid in 2 mL of dichloromethane was stirred for 15 h, then concentrated. The resulting residue was redissolved in dichloromethane and washed with a sat. aq. NaHCO₃ solution, dried over MgSO₄, filtered and concentrated to a residue. Column chromatography (0->100% EtOAc/hexanes) afforded 0.006 g (9%) of 3,3-dimethyl-4-oxo-4-[2-(3,4,5-trimethoxy-phenyl)-5H-pyrrolo[2,3-b]pyrazin-7-yl]-butyronitrile as a white solid.

Compound prepared in similar fashion as 3,3-dimethyl-4-oxo-4-[2-(3,4,5-trimethoxy-phenyl)-5H-pyrrolo[2,3-b]pyrazin-7-yl]-butyronitrile:

4,4-Dimethyl-5-oxo-5-[2-(3,4,5-trimethoxy-phenyl)-5H-pyrrolo[2,3-b]pyrazin-7-yl]-pentanenitrile

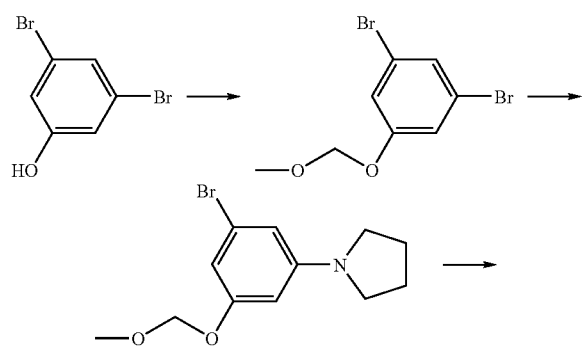

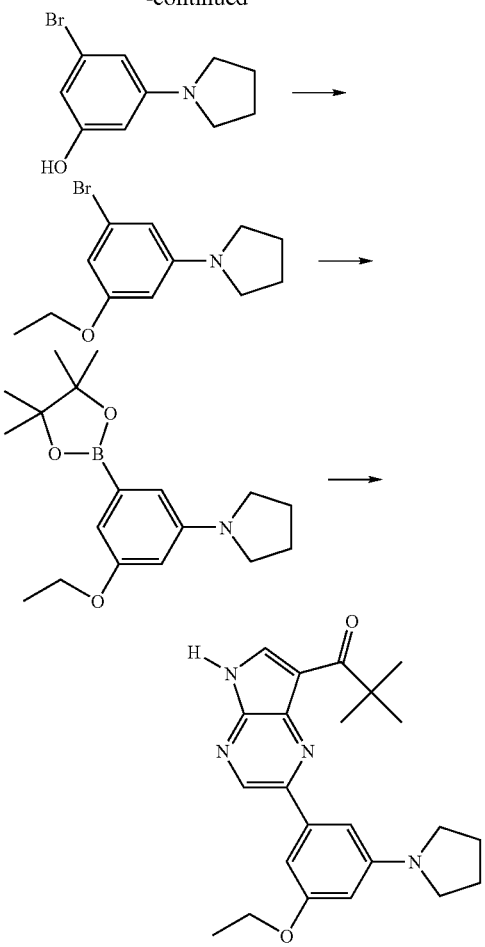

Example 258

1,3-Dibromo-5-methoxymethoxy-benzene. A flask was charged with sodium hydride (953 mg, 23.8 mmol, 60% in oil), in dry DMF (30 ml) and cooled to 0° C. (ice bath) under nitrogen atmosphere. 3,5-Dibromophenol (5 g, 19.9 mmol) was added in 4 equal portions over 10 minutes. After complete addition the cooling bath was removed and the mixture allowed to warm to ambient temperature over 20 minutes. Chloromethyl methyl ether (1.8 ml, 21.8 mmol) was added slowly, via syringe over about 5 minutes. The mixture was stirred over night. The material was quenched via the addition of saturated aqueous NH4Cl (20 ml) and all volatiles were stripped (rotovap/mechanical pump). The remainder was taken up in water (80 ml) and ethyl acetate (80 ml) and the material shaken in a separtatory funnel. The ethyl acetate phase was collected and washed with an equal volume of brine solution. The aqueous phases were back extracted with ethyl acetate (2×50 ml), the organics combined, dried (MgSO4), filtered and stripped to provide a crude oil. The oil was purified by silica gel chromatography using 4%-6% EtOAc in hexanes as eluant to provide 5.74 g of 1,3-dibromo-5-methoxymethoxy-benzene as a light yellow oil.

Example 259

1-(3-Bromo-5-methoxymethoxy-phenyl)-pyrrolidine. A solution of pyrrolidine (1.66 g, 23.27 mmol), in dry tetrahydrofuran (20 ml) was cooled to −78° C. under argon atmosphere. A solution of n-BuLi (15.5 ml, 1.5 M in hexanes) was added via slow drop-wise addition over 5 minutes. After complete addition the cooling bath was removed and the mixture allowed to warm to ice bath temperature over 30 minutes. A second oven dried flask was charged with 1,3-dibromo-5-methoxymethoxy-benzene (5.74 g, 19.4 mmol) and lithium bromide (1.68 g, 19.4 mmol) and taken up in dry tetrahydrofuran (10 ml). This flask was then cooled to 78° C. under argon. The contents of the first flask (slurry containing the lithio salt of pyrrolidine) was taken up in a syringe with wide bore needle and added via drop-wise addition to the second flask (over 10 minutes). The mixture was allowed to slowly warm to ambient temperature over night. The mixture was quenched via the addition of 1 N HCl (23 ml), saturated aqueous NH4Cl (34 ml) and water (40 ml). Ethyl acetate (80 ml) was added and the material shaken in a separatory funnel. The ethyl acetate phase was collected and washed with an equal volume of 50% diluted brine solution. The aqueous phases were back extracted with ethyl acetate (2×50 ml), the organics combined, dried (MgSO4), filtered and stripped to provide a yellow remainder. The oil was purified by silica gel chromatography using 4%-8% EtOAc in hexanes as eluant to provide 930 mg of 1-(3-Bromo-5-methoxymethoxy-phenyl)-pyrrolidine as a light yellow mobile oil.

Example 260

1-(3-Bromo-5-ethoxy-phenyl)-pyrrolidine. A flask was charged with 1-(3-bromo-5-methoxymethoxy-phenyl)-pyrrolidine (206 mg, 0.72 mmol) and a solution of 10% ethanolic hydrogen chloride (5 ml, dry) was added. The flask was capped and stirred for 45 minutes. The volatile material was stripped (rotovap) and methylene chloride (10 ml) was added. This was again stripped. The remainder was taken up in methylene chloride (10 ml). To this stirred material was added a 5% solution of ammonium hydroxide in methanol (20 drops). This material was stripped and the procedure repeated once more. The stripped remainder was taken up in dry DMF (3 ml) and K₂CO₃ (348 mg, 2.52 mmol) was added. Ethyl iodide (0.07 ml, 0.9 mmol) was added and the mixture was capped and stirred for 2.5 hours. Additional ethyl iodide (0.15 ml, 1.9 mmol) was added and the material was capped and heated (60° C.) over night. Ethyl iodide (0.15 ml, 1.9 mmol) was again added and the mixture capped and heated (100° C.) for 12 hours. The volatiles were removed (rotovap/pump) and the remainder was taken up in water (25 ml) and ethyl acetate (25 ml) and the material shaken in a separtatory funnel. The organic phase was collected and the aqueous phase was back extracted with ethyl acetate (2×20 ml), the organics combined, dried (MgSO4), filtered and stripped to provide a crude oil. The oil was purified by preparative TLC using 7% EtOAc in hexanes as eluant to provide 86 mg of 1-(3-bromo-5-ethoxy-phenyl)-pyrrolidine as a golden brown semi-viscous oil.

Example 261

1-[3-Ethoxy-5-(4,4,5,5-tetramethyl-[1,3,2]dioxaborolan-2-yl)-phenyl]-pyrrolidine. A flask was charged with 1-(3-bromo-5-ethoxy-phenyl)-pyrrolidine (86 mg, 0.32 mmol), bis(pinacolato)diboron (97 mg, 0.38 mmol), and KOAc (94 mg, 0.96 mmol). DMSO (2 ml) was added, and the solution was vacuum degassed under argon. Bis(diphenylphosphino)ferrocene]palladium(ll) dichloride dichloromethane complex (8 mg, 0.01 mmol) was added, and the reaction mixture was heated (80° C.) in a oil bath for 4 hours. The reaction mixture was filtered through a plug of celite using ethyl acetate. The filtrate was transferred to a separatory funnel and shaken with water (25 ml). The organic phase was collected and the aqueous phase back extracted with ethyl acetate (2×20 ml). The organic phases were combined, dried (MgSO4), filtered and stripped to provide a crude oil. This material was purified by preparative TLC, eluting with 17% ethyl acetate in hexanes to afford 54 mg of 1-[3-ethoxy-5-(4,4,5,5-tetramethyl-[1,3,2]dioxaborolan-2-yl)-phenyl]-pyrrolidine as a light purple viscous oil.

Example 262

1-[2-(3-Ethoxy-5-pyrrolidin-1-yl-phenyl)-5H-pyrrolo[2,3-b]pyrazin-7-yl]-2,2-dimethyl-propan-1-one. A microwave flask was charged with 1-(2-bromo-5H-pyrrolo[2,3-b]pyrazin-7-yl)-2,2-dimethyl-propan-1-one (48 mg, 0.17 mmol), 1-[3-ethoxy-5-(4,4,5,5-tetramethyl-[1,3,2]dioxaborolan-2-yl)-phenyl]-pyrrolidine (54 mg, 0.17 mmol), and K₂CO₃ (59 mg, 0.43 mmol). Dioxane (2.1 ml) and water (0.5 ml) were added, and the solution was vacuum degassed under argon. [1,1'-Bis(diphenylphosphino)ferrocene]palladium(ll) dichloride dichloromethane complex (14 mg, 0.02 mmol) was added, and the reaction mixture was heated (150° C.) in a microwave reactor for 45 minutes. The reaction mixture was filtered through a plug of celite using ethyl acetate. The filtrate was transferred to a separatory funnel and shaken with water (20 ml). The organic phase was collected and the aqueous phase back extracted with ethyl acetate (2×15 ml). The organic phases were combined, dried (MgSO4), filtered and stripped to provide a viscous semi-solid. This material was purified by preparative TLC, eluting with 4.8% methanol in methylene chloride to afford 31 mg of 1-[2-(3-ethoxy-5-pyrrolidin-1-yl-phenyl)-5H-pyrrolo[2,3-b]pyrazin-7-yl]-2,2-dimethyl-propan-1-one as a yellow powder. MP 236-237° C., M+H=393.

Other Compounds Prepared Using This General Procedure:

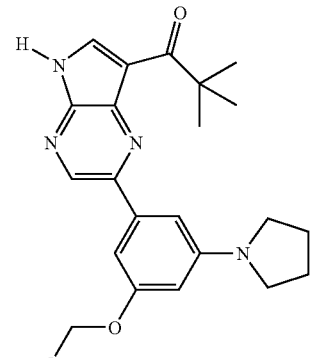

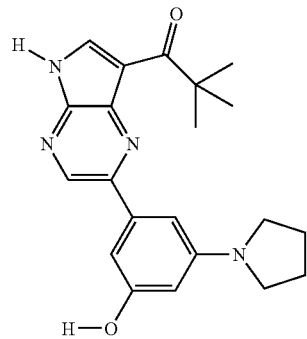

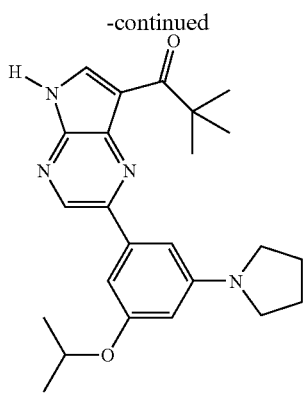

1-[2-(3-Methoxymethoxy-5-pyrrolidin-1-yl-phenyl)-5H-pyrrolo[2,3-b]pyrazin-7-yl]-2,2-dimethyl-propan-1-one, MP=229-230, (M+H)⁺=409.

1-[2-(3-Hydroxy-5-pyrrolidin-1-yl-phenyl)-5H-pyrrolo[2,3-b]pyrazin-7-yl]-2,2-dimethyl-propan-1-one. (Prepared via standard MOM deprotection in final step), MP>300, (M+H)⁺=365.

1-[2-(3-Isopropoxy-5-pyrrolidin-1-yl-phenyl)-5H-pyrrolo[2,3-b]pyrazin-7-yl]-2,2-dimethyl-propan-1-one. (Prepared, respectively, from 1-(3-bromo-5-isopropyloxy-phenyl)-pyrrolidine, which was synthesized via Mitsunobu chemistry from 1-(3-bromo-5-hydroxy-phenyl)-pyrrolidine, following the general procedures described in these Examples, MP=233-235, (M+H)⁺=407.

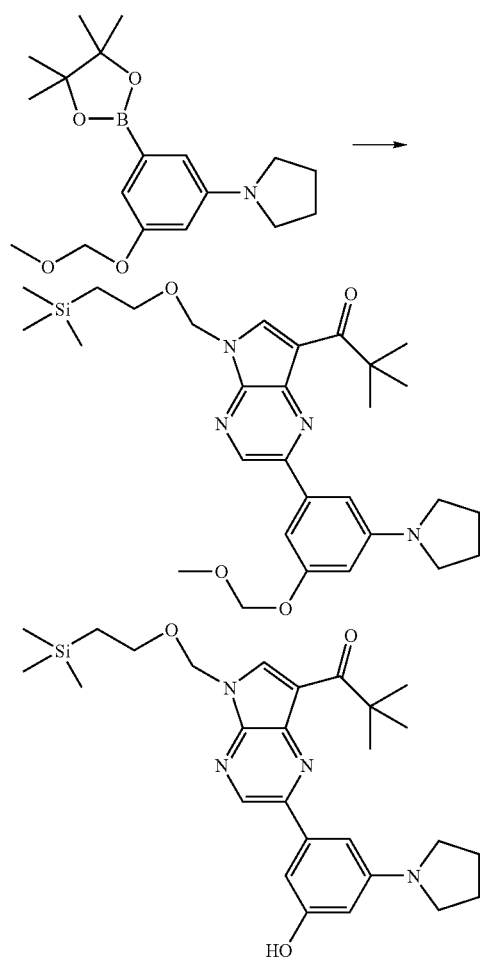

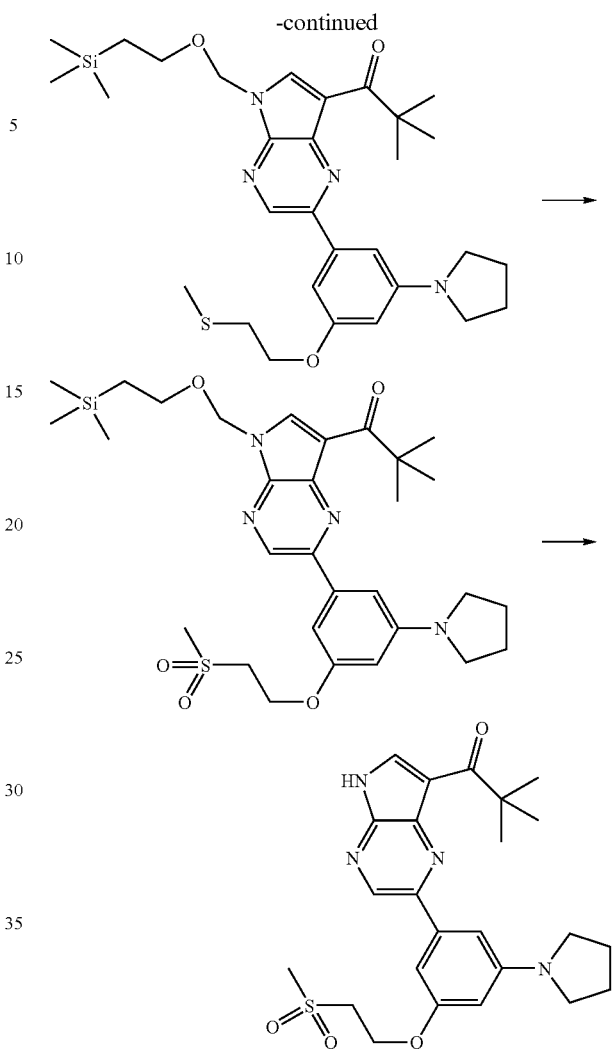

1-[3-Methoxymethoxy-5-(4,4,5,5-tetramethyl-[1,3,2]dioxaborolan-2-yl)-phenyl]-pyrrolidine was prepared from 1-(3-Bromo-5-methoxymethoxy-phenyl)-pyrrolidine. General procedures described in these Examples were followed.

1-[2-(3-Methoxymethoxy-5-pyrrolidin-1-yl-phenyl)-5-(2-trimethylsilanyl-ethoxymethyl)-5H-pyrrolo[2,3-b]pyrazin-7-yl]-2,2-dimethyl-propan-1-one. A microwave flask was charged with 1-[2-bromo-5-(2-trimethylsilanyl-ethoxymethyl)-5H-pyrrolo[2,3-b]pyrazin-7-yl]-2,2-dimethyl-propan-1-one (705 mg, 1.71 mmol, following the general procedures described in these Examples), 1-[3-methoxymethoxy-5-(4,4,5,5-tetramethyl-[1,3,2]dioxaborolan-2-yl)-phenyl]-pyrrolidine (570 mg, 1.71 mmol), and K₂CO₃ (591 mg, 4.28 mmol). Dioxane (13 ml) and water (3.2 ml) were added, and the solution was vacuum degassed under argon. [1,1'-Bis(diphenylphosphino)ferrocene]palladium(II) dichloride dichloromethane complex (140 mg, 0.17 mmol) was added, and the reaction mixture was heated (150° C.) in a microwave reactor for 45 minutes. The reaction mixture was filtered through a plug of celite using ethyl acetate. The filtrate was transferred to a reparatory funnel and shaken with water (60 ml). The organic phase was collected and the aqueous phase back extracted with ethyl acetate (2×50 ml). The organic phases were combined, dried (MgSO4), filtered and stripped to provide a viscous semi-solid. This material was purified by preparative TLC, eluting with 24% ethyl acetate in hexanes to afford 492 mg of 1-[2-

(3-Methoxymethoxy-5-pyrrolidin-1-yl-phenyl)-5-(2-trimethylsilanyl-ethoxymethyl)-5H-pyrrolo[2,3-b]pyrazin-7-yl]-2,2-dimethyl-propan-1-one as a red-brown viscous oil.

Example 264

1-[2-(3-Hydroxy-5-pyrrolidin-1-yl-phenyl)-5-(2-trimethylsilanyl-ethoxymethyl)-5H-pyrrolo[2,3-b]pyrazin-7-yl]-2,2-dimethyl-propan-1-one. To a solution of 1-[2-(3-methoxymethoxy-5-pyrrolidin-1-yl-phenyl)-5-(2-trimethylsilanyl-ethoxymethyl)-5H-pyrrolo[2,3-b]pyrazin-7-yl]-2,2-dimethyl-propan-1-one (492 mg, 0.91 mmol) in $CH_2Cl_2$ (1.5 ml) was added a solution of 10% ethanolic hydrogen chloride (4 ml, dry). The flask was capped and stirred for 2.5 hours. The volatile material was stripped (rotovap). Ethyl acetate (25 ml) and aqueous 5% $Na_2CO_3$ (25 ml) was added and the 2 phase system vigorously stirred for 3 minutes. The material was partitioned and the organic phase collected and washed with brine (25 ml). The aqueous phases were back extracted with EtOAc (2×20 ml). The organics were combined, dried (MgSO4), filtered and stripped to provide a crude semi-solid. The material was purified by preparative TLC, eluting with 38% ethyl acetate in hexanes to afford 326 mg of 1-[2-(3-hydroxy-5-pyrrolidin-1-yl-phenyl)-5-(2-trimethylsilanyl-ethoxymethyl)-5H-pyrrolo[2,3-b]pyrazin-7-yl]-2,2-dimethyl-propan-1-one as a yellow-brown solid.

Example 265

2,2-Dimethyl-1-[2-[3-(2-methylsulfanyl-ethoxy)-5-pyrrolidin-1-yl-phenyl]-5-(2-trimethylsilanyl-ethoxymethyl)-5H-pyrrolo[2,3-b]pyrazin-7-yl]-propan-1-one. A flask was charged with 1-[2-(3-hydroxy-5-pyrrolidin-1-yl-phenyl)-5-(2-trimethylsilanyl-ethoxymethyl)-5H-pyrrolo[2,3-b]pyrazin-7-yl]-2,2-dimethyl-propan-1-one (140 mg, 0.28 mmol), 2-methylsulfanyl-ethanol (reagent A, 0.03 ml, 0.34 mmol), triphenylphosphine (reagent B, 89 mg, 0.34 mmol). THF (1.5 ml) was added and the mixture cooled (ice bath) under nitrogen atmosphere. Diisopropyl azodicarboxylate (reagent C, 0.07 ml, 0.34 mmol) was added via syringe and the material was warmed to ambient. After 1 hour a further 1.2 equivalents each of reagents A, B and C were added. After 2 hours repeat. The mixture was stirred overnight. The crude was loaded onto 2 preparative TLC plates eluting with 20% EtOAc in hexanes. The product band was collected providing 2,2-dimethyl-1-[2-[3-(2-methylsulfanyl-ethoxy)-5-pyrrolidin-1-yl-phenyl]-5-(2-trimethylsilanyl-ethoxymethyl)-5H-pyrrolo[2,3-b]pyrazin-7-yl]-propan-1-one, 82 mg as a yellow viscous oil.

Example 266

1-[2-[3-(2-Methanesulfonyl-ethoxy)-5-pyrrolidin-1-yl-phenyl]-5-(2-trimethylsilanyl-ethoxymethyl)-5H-pyrrolo[2,3-b]pyrazin-7-yl]-2,2-dimethyl-propan-1-one. To a solution of 2,2-dimethyl-1-[2-[3-(2-methylsulfanyl-ethoxy)-5-pyrrolidin-1-yl-phenyl]-5-(2-trimethylsilanyl-ethoxymethyl)-5H-pyrrolo[2,3-b]pyrazin-7-yl]-propan-1-one (82 mg, 0.14 mmol) in 20% water/acetone (3 ml) was added 4-methylmorpholine n-oxide (50 mg, 0.43 mmol) followed by addition of aqueous OsO4 solution (0.01 ml, catalytic). After 8 hours stirring a solution of 5% aqueous sodium bisulfite (25 ml) was added followed by $CH_2Cl_2$ (25 ml). The material was partitioned and the organic phase collected and then washed with brine (25 ml). The aqueous phases were back-extracted with methylene chloride (2×25 ml), the organic phases combined, dried (MgSO$_4$), filtered and stripped to provide a crude remainder. The material was loaded onto 1 preparative TLC plate, eluting with 40% ethyl acetate in hexanes. The product band was collected to afford 75 mg of 1-[2-[3-(2-methanesulfonyl-ethoxy)-5-pyrrolidin-1-yl-phenyl]-5-(2-trimethylsilanyl-ethoxymethyl)-5H-pyrrolo[2,3-b]pyrazin-7-yl]-2,2-dimethyl-propan-1-one as a yellow viscous oil.

Example 267

1-{2-[3-(2-Methanesulfonyl-ethoxy)-5-pyrrolidin-1-yl-phenyl]-5H-pyrrolo[2,3-b]pyrazin-7-yl}-2,2-dimethyl-propan-1-one. To a flask containing 1-[2-[3-(2-methanesulfonyl-ethoxy)-5-pyrrolidin-1-yl-phenyl]-5-(2-trimethylsilanyl-ethoxymethyl)-5H-pyrrolo[2,3-b]pyrazin-7-yl]-2,2-dimethyl-propan-1-one (75 mg, 0.13 mmol) was added methanol (1 ml) and aqueous 6N HCl (1.5 ml). The flask was capped and placed in a heated oil bath (90° C.). After stirring for 50 minutes the mixture was cooled to ambient and the volatiles were stripped (rotovap/pump). The remainder was taken up in EtOAc (15 ml) and 5% aqueous NaHCO$_3$ (15 ml) and stirred for 5 minutes. The material was partitioned and the organic phase collected and washed with brine (15 ml). The aqueous phases were back extracted with EtOAc (2×15 ml). The organics were combined, dried (MgSO4), filtered and stripped to provide a crude semi-solid. The material was purified by crystallization from hot $CH_2Cl_2$/hexanes (containing 4 drops of methanol) to afford 38 mg of 1-{2-[3-(2-methanesulfonyl-ethoxy)-5-pyrrolidin-1-yl-phenyl]-5H-pyrrolo[2,3-b]pyrazin-7-yl}-2,2-dimethyl-propan-1-one as a yellow solid. MP 230-232° C., M+H=471.

The general procedures described in these Examples were followed for synthesis of the following compound:

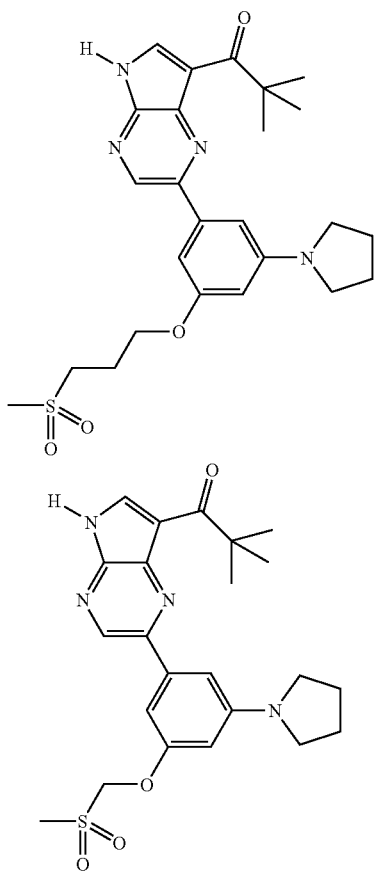

1-{2-[3-(3-Methanesulfonyl-propoxy)-5-pyrrolidin-1-yl-phenyl]-5H-pyrrolo[2,3-b]pyrazin-7-yl}-2,2-dimethyl-propan-1-one, (prepared via alkylation of "sodium phenoxide"

derivative of "1-[2-(3-hydroxy-5-pyrrolidin-1-yl-phenyl)-5-(2-trimethylsilanyl-ethoxymethyl)-5H-pyrrolo[2,3-b]pyrazin-7-yl]-2,2-dimethyl-propan-1-one" with "1-chloro-3-methanesulfonyl-propane" [instead of Mitsunobu alkylation—as key step] MP=232-233, (M+H)+=485.

1-[2-(3-Methanesulfonylmethoxy-5-pyrrolidin-1-yl-phenyl)-5H-pyrrolo[2,3-b]pyrazin-7-yl]-2,2-dimethyl-propan-1-one, (prepared via alkylation of "sodium phenoxide" derivative of "1-[2-(3-hydroxy-5-pyrrolidin-1-yl-phenyl)-5-(2-trimethylsilanyl-ethoxymethyl)-5H-pyrrolo[2,3-b]pyrazin-7-yl]-2,2-dimethyl-propan-1-one" with "chloromethylmethylsulfide" [instead of Mitsunobu alkylation—as key step], and subsequent oxidation to sulfone via procedure similar as described above (M+H)+=587.

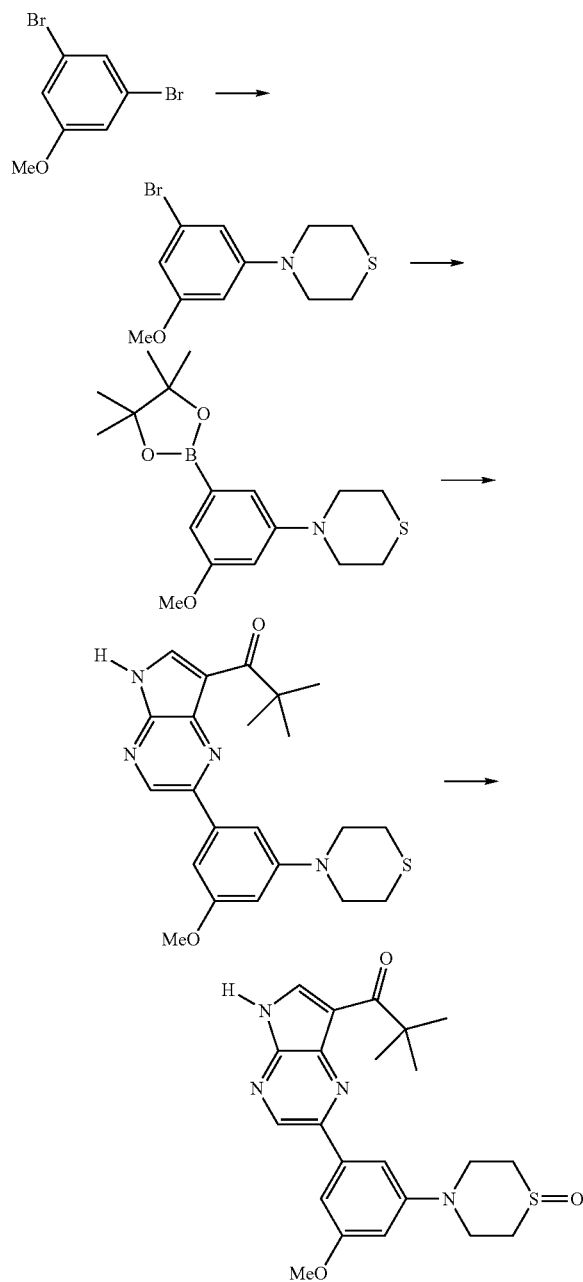

4-(3-Bromo-5-methoxy-phenyl)-thiomorpholine. This material was prepared starting from 1,3-dibromo-5-methoxy-benzene following general procedures described in these Examples, but using thiomorpholine instead of pyrrolidine.

Example 268

4-[3-Methoxy-5-(4,4,5,5-tetramethyl-[1,3,2]dioxaborolan-2-yl)-phenyl]-thiomorpholine. A solution of 4-(3-bromo-5-methoxy-phenyl)-thiomorpholine (785 mg, 2.72 mmol) in dry tetrahydrofuran (15 ml) was cooled to −78° C. under argon. A solution of t-BuLi (4 ml, 1.5 M in pentane) was added via slow drop-wise addition. After 15 minutes stirring 2-isopropoxy-4,4,5,5-tetramethyl-1,2-dioxaborolane (1.1 ml, 5.44 mmol) was added via syringe. The material was allowed to slowly warm to ambient over 3 hours. The mixture was quenched via the addition of a saturated solution of aqueous ammonium chloride (20 ml) followed by water (60 ml). Ethyl acetate (75 ml) was added and the material was shaken in a reparatory funnel. The organic phase was collected and washed with an equal volume of brine. The aqueous phases were back extracted with ethyl acetate (2×50 ml) and the organics combined, dried (MgSO4), filtered and stripped to provide a crude remainder. This material was purified by preparative TLC, eluting with 18% ethyl acetate in hexanes to afford 456 mg of 4-[3-methoxy-5-(4,4,5,5-tetramethyl-[1,3,2]dioxaborolan-2-yl)-phenyl]-thiomorpholine as a light pink viscous oil.

1-[2-(3-methoxy-5-thiomorpholin-4-yl-phenyl)-5H-pyrrolo[2,3-b]pyrazin-7-yl]-2,2-dimethyl-propan-1-one; this material was prepared starting from 4-[3-methoxy-5-(4,4,5,5-tetramethyl-[1,3,2]dioxaborolan-2-yl)-phenyl]-thiomorpholine following the general procedures described in these Examples.

Example 269

1-{2-[3-Methoxy-5-(1-oxo-1lambda*4*-thiomorpholin-4-yl)-phenyl]-5H-pyrrolo[2,3-b]pyrazin-7-yl}-2,2-dimethyl-propan-1-one To a solution of 1-[2-(3-methoxy-5-thiomorpholin-4-yl-phenyl)-5H-pyrrolo[2,3-b]pyrazin-7-yl]-2,2-dimethyl-propan-1-one (80 mg, 0.195 mmol) in methylene chloride (5 ml) and methanol (5 drops) was added m-CPBA (44 mg, 0.195 mmol). After 1 hour the crude material was loaded onto 2 preparative TLC plates, eluting with 10% methanol in methylene chloride. The product band was collected to afford 61 mg of 1-{2-[3-methoxy-5-(1-oxo-1lambda*4*-thiomorpholin-4-yl)-phenyl]-5H-pyrrolo[2,3-b]pyrazin-7-yl}-2,2-dimethyl-propan-1-one as a light yellow-brown solid. MP 259-260° C., M+H=427.

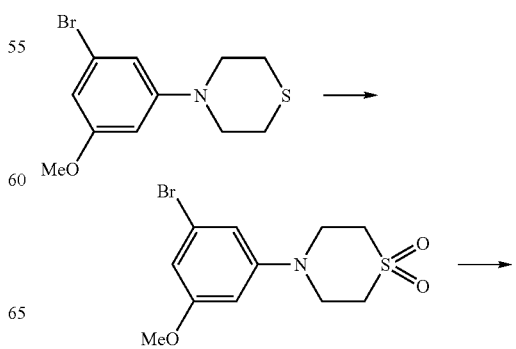

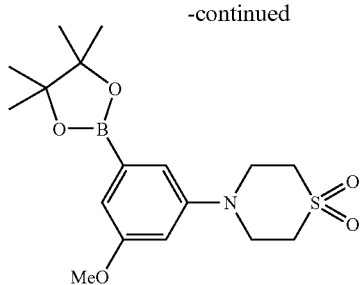

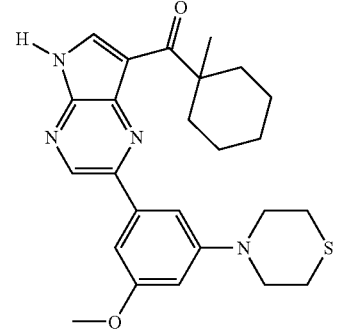

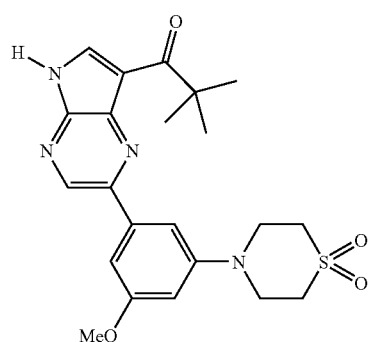

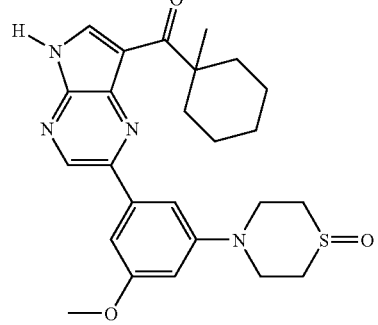

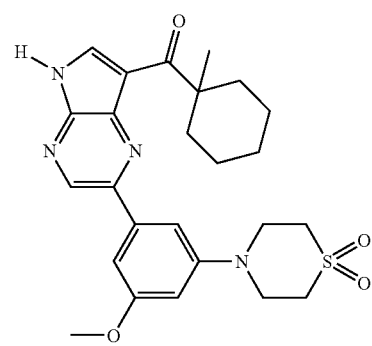

Example 270

4-(3-Bromo-5-methoxy-phenyl)-thiomorpholine 1,1-dioxide. To a mixture of 4-(3-bromo-5-methoxy-phenyl)-thiomorpholine (239 mg, 0.83 mmol) in methylene chloride (10 ml) and methanol (5 drops) was added m-CPBA (409 mg, 1.83 mmol). After 1 hour methanol (10 drops) was added to enhance solubility. The mixture was stirred another 3 hours. Methylene chloride (25 ml) and a 10% solution of aqueous sodium metabisulfite (35 ml) were added and the material was shaken in a reparatory funnel. The organic phase was collected and washed consecutively with equal volumes of 5% aqueous sodium bicarbonate and then brine solution. The aqueous phases were back-extracted with methylene chloride (2×25 ml), the organic phases combined, dried (MgSO4), filtered and stripped to a crude residue. The material was loaded onto 2 preparative TLC plates, eluting with 40% ethyl acetate in hexanes. The product band was collected to afford 76 mg of 4-(3-bromo-5-methoxy-phenyl)-thiomorpholine 1,1-dioxide as a off-white solid.

4-[3-Methoxy-5-(4,4,5,5-tetramethyl-[1,3,2]dioxaborolan-2-yl)-phenyl]-thiomorpholine 1,1-dioxide. This material was prepared starting from 4-(3-bromo-5-methoxy-phenyl)-thiomorpholine 1,1-dioxide following the general procedures described in these Examples.

1-{2-[3-(1,1-Dioxo-1lambda*6*-thiomorpholin-4-yl)-5-methoxy-phenyl]-5H-pyrrolo[2,3-b]pyrazin-7-yl}-2,2-dimethyl-propan-1-one; This material was prepared starting from 4-[3-methoxy-5-(4,4,5,5-tetramethyl-[1,3,2]dioxaborolan-2-yl)-phenyl]-thiomorpholine 1,1-dioxide following the general procedures described in these Examples. MP 275-277° C., M+H=443.

The general procedures described in these Examples were followed for synthesis of the following compounds:

[2-(3-Methoxy-5-thiomorpholin-4-yl-phenyl)-5H-pyrrolo[2,3-b]pyrazin-7-yl]-(1-methyl-cyclohexyl)-methanone. MP=212-214, (M+H)+=451; {2-[3-Methoxy-5-(1-oxo-1lambda*4*-thiomorpholin-4-yl)-phenyl]-5H-pyrrolo[2,3-b]pyrazin-7-yl}-(1-methyl-cyclohexyl)-methanone. MP=270-271, (M+H)+=467; {2-[3-(1,1-Dioxo-1lambda*6*-thiomorpholin-4-yl)-5-methoxy-phenyl]-5H-pyrrolo[2,3-b]pyrazin-7-yl}-(1-methyl-cyclohexyl)-methanone. MP=245-247, (M+H)+=483.

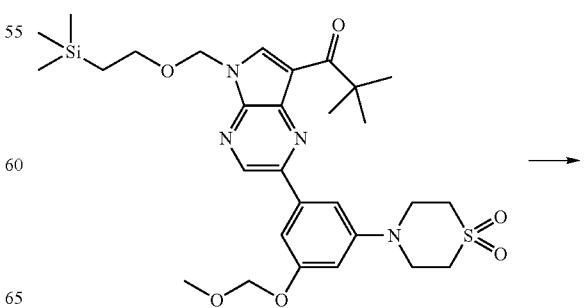

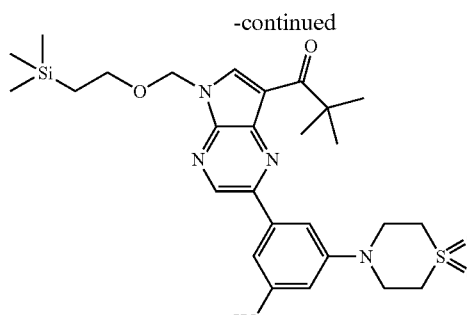

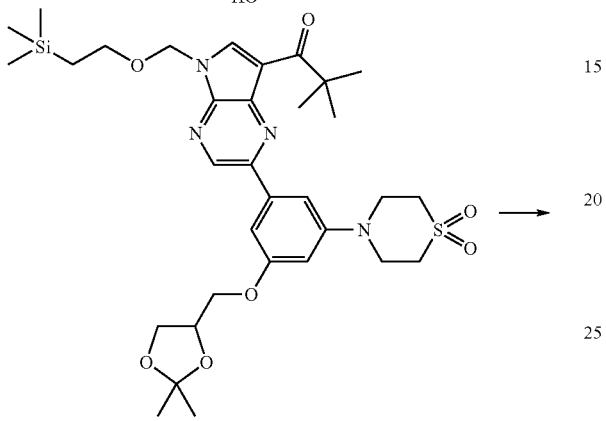

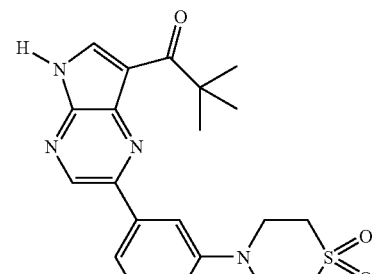

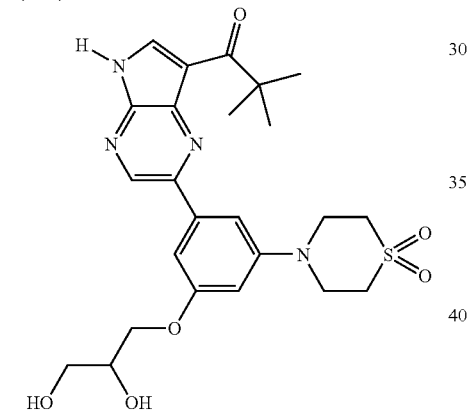

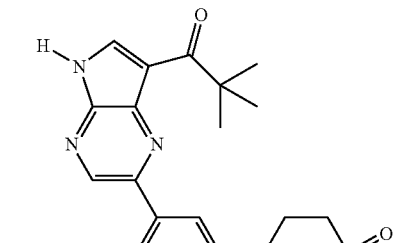

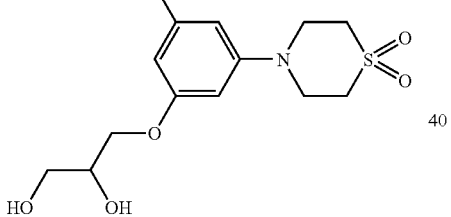

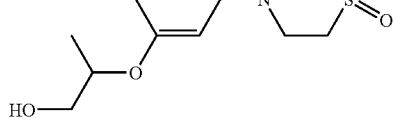

1-[2-[3-(1,1-Dioxo-1lambda*6*-thiomorpholin-4-yl)-5-methoxymethoxy-phenyl]-5-(2-trimethylsilanyl-ethoxymethyl)-5H-pyrrolo[2,3-b]pyrazin-7-yl]-2,2-dimethyl-propan-1-one. This material was prepared via Suzuki coupling protocol similar to that which was described as above, but using "5-thiomorpholine-dioxide" in place of "5-pyrrolidine".

1-[2-[3-(1,1-Dioxo-1lambda*6*-thiomorpholin-4-yl)-5-hydroxy-phenyl]-5-(2-trimethylsilanyl-ethoxymethyl)-5H-pyrrolo[2,3-b]pyrazin-7-yl]-2,2-dimethyl-propan-1-one. This material was prepared from 1-[2-[3-(1,1-dioxo-1lambda*6*-thiomorpholin-4-yl)-5-methoxymethoxy-phenyl]-5-(2-trimethylsilanyl-ethoxymethyl)-5H-pyrrolo[2,3-b]pyrazin-7-yl]-2,2-dimethyl-propan-1-one via "MOM" protecting group cleavage according to general procedures described in these Examples.

1-[2-[3-(2,2-Dimethyl-[1,3]dioxolan-4-ylmethoxy)-5-(1,1-dioxo-1lambda*6*-thiomorpholin-4-yl)-phenyl]-5-(2-trimethylsilanyl-ethoxymethyl)-5H-pyrrolo[2,3-b]pyrazin-7-yl]-2,2-dimethyl-propan-1-one. This material was prepared from 1-[2-[3-(1,1-dioxo-1lambda*6*-thiomorpholin-4-yl)-5-hydroxy-phenyl]-5-(2-trimethylsilanyl-ethoxymethyl)-5H-pyrrolo[2,3-b]pyrazin-7-yl]-2,2-dimethyl-propan-1-one via Mitsunobu type alkylation similar to that which was described as above, but using "(2,2-Dimethyl-[1,3]dioxolan-4-yl)-methanol" in place of "2-methylsulfanyl-ethanol".

1-{2-[3-(2,3-Dihydroxy-propoxy)-5-(1,1-dioxo-1lambda*6*-thiomorpholin-4-yl)-phenyl]-5H-pyrrolo[2,3-b]pyrazin-7-yl}-2,2-dimethyl-propan-1-one. This material was prepared from 1-[2-[3-(2,2-dimethyl-[1,3]dioxolan-4-ylmethoxy)-5-(1,1-dioxo-1lambda*6*-thiomorpholin-4-yl)-phenyl]-5-(2-trimethylsilanyl-ethoxymethyl)-5H-pyrrolo[2,3-b]pyrazin-7-yl]-2,2-dimethyl-propan-1-one following general procedures described in these Examples. M+H=503.

Other Compounds Prepared Using this General Procedure:

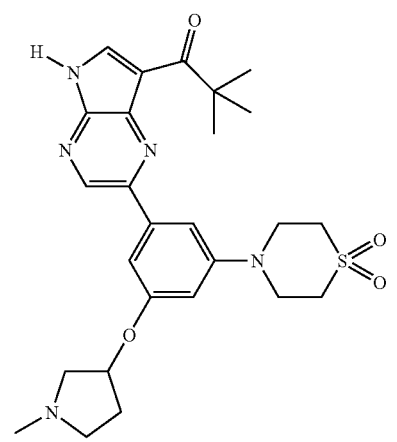

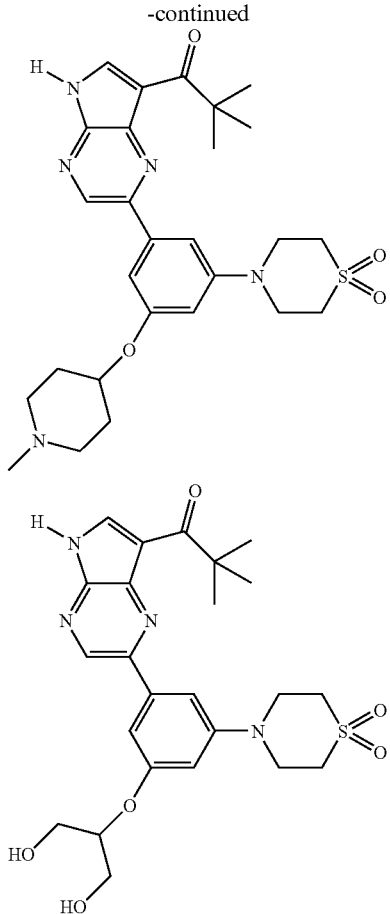

1-{2-[(2E,4E)-5-(2-Dimethylamino-ethoxy)-3-(1,1-dioxo-1lambda*6*-thiomorpholin-4-yl)-hepta-2,4,6-trienyl]-5H-pyrrolo[2,3-b]pyrazin-7-yl}-2,2-dimethyl-propan-1-one, MP=225-227, (M+H)$^+$=500; 1-{2-[(2E,4E)-3-(1,1-Dioxo-1lambda*6*-thiomorpholin-4-yl)-5-(2-hydroxy-1-methyl-ethoxy)-hepta-2,4,6-trienyl]-5H-pyrrolo[2,3-b]pyrazin-7-yl}-2,2-dimethyl-propan-1-one. (Racemic), MP=137-139, (M+H)$^+$=487; 1-{2-[(2E,4E)-3-(1,1-Dioxo-1lambda*6*-thiomorpholin-4-yl)-5-(1-methyl-pyrrolidin-3-yloxy)-hepta-2,4,6-trienyl]-5H-pyrrolo[2,3-b]pyrazin-7-yl}-2,2-dimethyl-propan-1-one. (Racemic). MP=260-262, (M+H)$^+$=512; 1-{2-[(2E,4E)-3-(1,1-Dioxo-1lambda*6*-thiomorpholin-4-yl)-5-(1-methyl-piperidin-4-yloxy)-hepta-2,4,6-trienyl]-5H-pyrrolo[2,3-b]pyrazin-7-yl}-2,2-dimethyl-propan-1-one. MP=250-252, (M+H)$^+$32 526; 1-{2-[(2E,4E)-3-(1,1-Dioxo-1lambda*6*-thiomorpholin-4-yl)-5-(2-hydroxy-1-hydroxymethyl-ethoxy)-hepta-2,4,6-trienyl]-5H-pyrrolo[2,3-b]pyrazin-7-yl}-2,2-dimethyl-propan-1-one. (M+H)$^+$32 503.

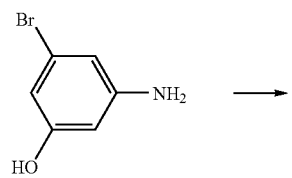

commercially available - but I made it via patent procedure(s) [CAS 116632-23-6]

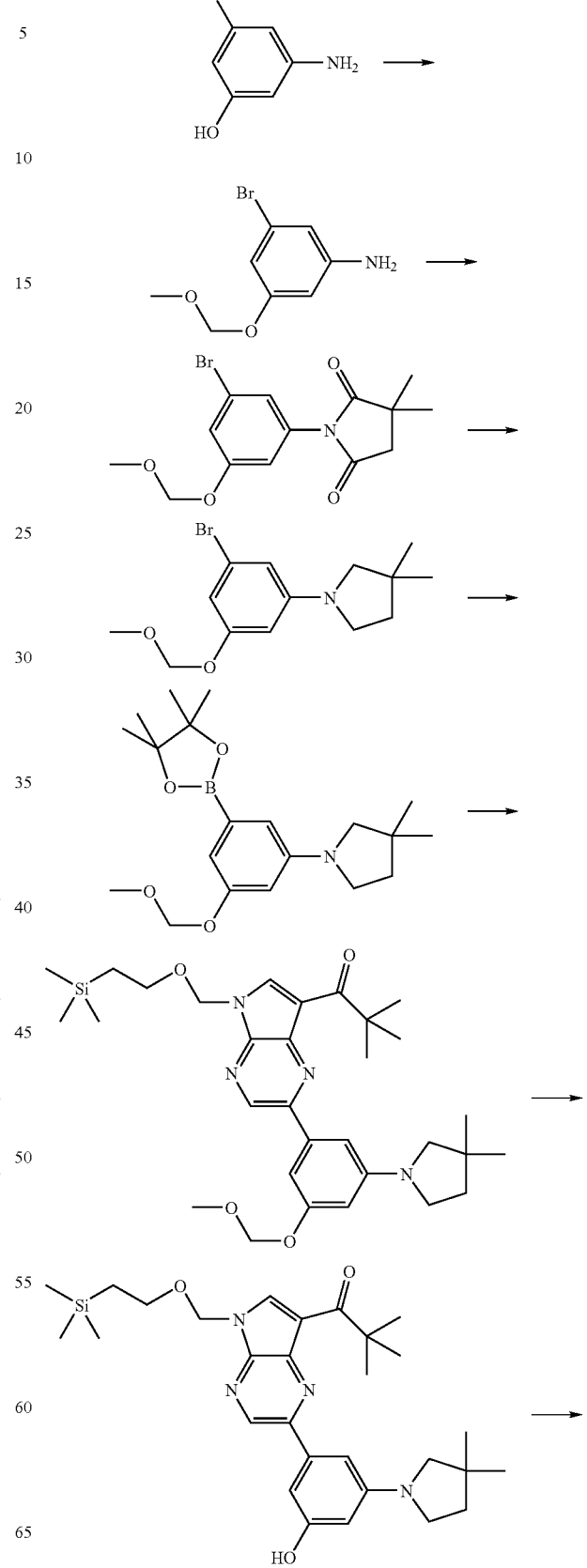

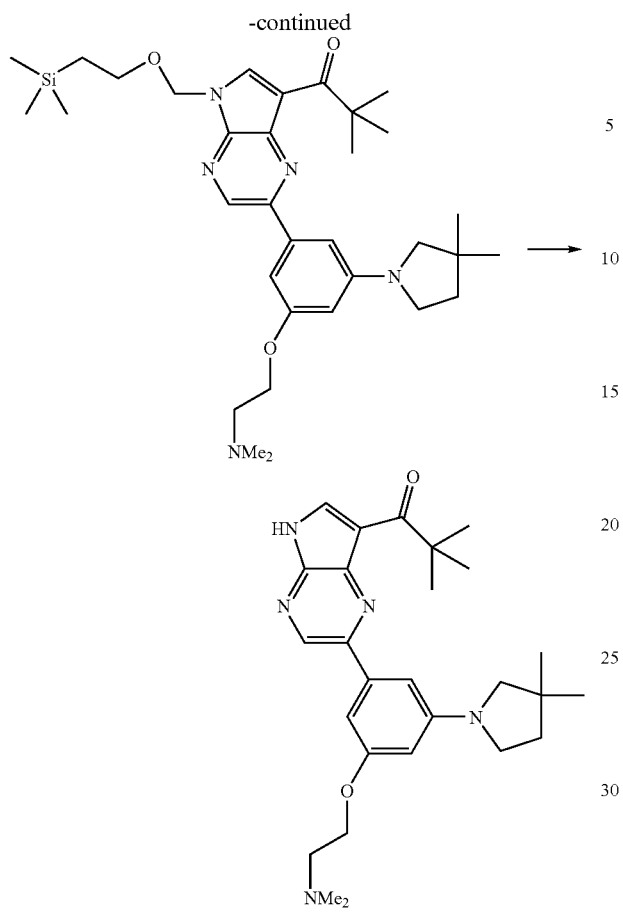

Example 271

3-Amino-5-bromo-phenol. To a solution of 3-bromo-5-nitro-phenol (16.9 g, 77.52 mmol, commercially available [CAS 116632-23-6 {Specs}]) in ethanol (300 ml) and water (100 ml) was added solid ammonium chloride (16.59 g, 310 mmol) and then powdered electrolytic iron (34.4 g, 698 mmol). The material was heated from ambient to reflux temperature (oil bath). The material was refluxed for 3 hours and then filtered, hot, through a plug of celite, washing well with several volumes of hot EtOAc. The solvent was stripped and the remainder was taken up in EtOAc (150 ml) and water (150 ml) and the material shaken. The organic phase was collected and washed with brine (150 ml). The aqueous phases were back extracted with EtOAc (2×100 ml). The organics were combined, dried (MgSO4), filtered and stripped to provide a crude oil. The material was adsorbed onto silica (50 g) and purified by silica gel chromatography, eluting with 15% to 50% ethyl acetate in hexanes to afford 10.35 g of 3-amino-5-bromo-phenol as a dark golden-brown viscous oil.

Example 272

3-Bromo-5-methoxymethoxy-phenylamine. A solution of 3-amino-5-bromo-phenol (3.0 g, 15.96 mmol) in dry DMF (35 ml) was cooled (ice bath) under nitrogen. Sodium hydride (732 g, 18.36 mmol, 60% in oil) was added in 2 equal portions over 5 minutes. After 10 minutes stirring the material was warmed to ambient. Chloromethylmethyl ether (1.38 ml, 18.4 mmol) was added slowly, via syringe. The material was stirred for 2 hours. The solvent was stripped (rotovap/pump) providing a crude remainder which was treated with a solution of saturated aqueous NH4Cl (25 ml), water (35 ml) and ethyl acetate (60 ml). The material was shaken in a reparatory funnel and the organic phase was collected and washed with an equal volume of brine. The aqueous phases were back extracted with ethyl acetate (2×50 ml) and the organics combined, dried (MgSO4), filtered and stripped to provide a viscous oil. The crude was purified by silica gel chromatography using 4%-30% EtOAc in hexanes as eluant to provide 3.50 g of 3-bromo-5-methoxymethoxy-phenylamine as a light yellow mobile oil.

Example 273

1-(3-Bromo-5-methoxymethoxy-phenyl)-3,3-dimethyl-pyrrolidine-2,5-dione. To a solution of 3-bromo-5-methoxymethoxy-phenylamine (1.0 g, 4.31 mmol) in methylene chloride (25 ml) was added 2,2-dimethylsuccinic anhydride (580 mg, 0.195 mmol). The mixture was heated to 50° C. (oil bath) for 1 hour and then stirred over night at ambient at which point a large amount of precipitate had formed. Carbonyldiimidazole (839 mg, 5.17 mmol) was added and within 2 minutes a homogeneous solution was obtained. The material was stirred over night and then the crude was adsorbed onto silica gel (12 g). Purification by silica gel chromatography eluting with 6%-45% EtOAc in hexanes afforded 1.57 g of 1-(3-bromo-5-methoxymethoxy-phenyl)-3,3-dimethyl-pyrrolidine-2,5-dione as a viscous yellow-white oil.

Example 274

1-(3-Bromo-5-methoxymethoxy-phenyl)-3,3-dimethyl-pyrrolidine. To a solution of 1-(3-bromo-5-methoxymethoxy-phenyl)-3,3-dimethyl-pyrrolidine-2,5-dione (643 mg, 1.88 mmol) in dry THF (8 ml) (under nitrogen) was added a solution of borane-dimethylsulfide complex (1.7 ml, 16.9 mmol, 10.1M) via slow drop-wise addition. The material was stirred for 12 hours. The mixture was cooled (ice bath) and carefully quenched via the slow drop-wise addition of water (10 ml). Methylene chloride (60 ml), and water (50 ml) were added and the material shaken. The organic phase was collected and washed with brine (60 ml). The aqueous phases were back extracted with methylene chloride (2×50 ml). The organics were combined, dried (MgSO4), filtered and stripped to provide a crude oil. The material was adsorbed onto silica (12 g) and purified by silica gel chromatography, eluting with 5% to 9% ethyl acetate in hexanes to afford 517 mg of 1-(3-bromo-5-methoxymethoxy-phenyl)-3,3-dimethyl-pyrrolidine as a clear oil.

1-[3-Methoxymethoxy-5-(4,4,5,5-tetramethyl-[1,3,2]dioxaborolan-2-yl)-phenyl]-3,3-dimethyl-pyrrolidine. This material was prepared starting from 1-(3-bromo-5-methoxymethoxy-phenyl)-3,3-dimethyl-pyrrolidine following the general procedures described in these Examples.

1-[2-[3-(3,3-Dimethyl-pyrrolidin-1-yl)-5-methoxymethoxy-phenyl]-5-(2-trimethylsilanyl-ethoxymethyl)-5H-pyrrolo[2,3-b]pyrazin-7-yl]-2,2-dimethyl-propan-1-one. This material was prepared starting from 1-[3-methoxymethoxy-5-(4,4,5,5-tetramethyl-[1,3,2]dioxaborolan-2-yl)-phenyl]-3,3-dimethyl-pyrrolidine following the general procedures described in these Examples.

1-[2-[3-(3,3-Dimethyl-pyrrolidin-1-yl)-5-hydroxy-phenyl]-5-(2-trimethylsilanyl-ethoxymethyl)-5H-pyrrolo[2,3-b]pyrazin-7-yl]-2,2-dimethyl-propan-1-one. This material was prepared starting from 1-[2-[3-(3,3-dimethyl-pyrrolidin-1-yl)-5-methoxymethoxy-phenyl]-5-(2-trimethylsilanyl-ethoxymethyl)-5H-pyrrolo[2,3-b]pyrazin-7-yl]-2,2-dimethyl-propan-1-one following the general procedures described in these Examples.

Example 275

1-[2-[3-(2-Dimethylamino-ethoxy)-5-(3,3-dimethyl-pyrrolidin-1-yl)-phenyl]-5-(2-trimethylsilanyl-ethoxymethyl)-

5H-pyrrolo[2,3-b]pyrazin-7-yl]-2,2-dimethyl-propan-1-one. A flask was charged with 1-[2-[3-(3,3-dimethyl-pyrrolidin-1-yl)-5-methoxymethoxy-phenyl]-5-(2-trimethylsilanyl-ethoxymethyl)-5H-pyrrolo[2,3-b]pyrazin-7-yl]-2,2-dimethyl-propan-1-one (90 mg, 0.17 mmol), 2-dimethylamino-ethanol (reagent A, 0.04 ml, 0.34 mmol) and triphenylphosphine (reagent B, 90 mg, 0.34 mmol). THF (2 ml) was added under nitrogen atmosphere. Diisopropyl azodicarboxylate (reagent C, 0.07 ml, 0.34 mmol) was added via syringe and the material was stirred. After 1 hour a further 2 equivalents each of reagents A, B and C were added. The mixture was stirred overnight. The crude was loaded onto 2 preparative TLC plates eluting with 3% MeOH in dichloromethane. The plates were dried and re-developed with the solvent system. This process was repeated once more and then product band was collected providing 1-[2-[3-(2-dimethylamino-ethoxy)-5-(3,3-dimethyl-pyrrolidin-1-yl)-phenyl]-5-(2-trimethylsilanyl-ethoxymethyl)-5H-pyrrolo[2,3-b]pyrazin-7-yl]-2,2-dimethyl-propan-1-one, 56 mg, as a golden yellow viscous oil.

1-{2-[3-(2-Dimethylamino-ethoxy)-5-(3,3-dimethyl-pyrrolidin-1-yl)-phenyl]-5H-pyrrolo[2,3-b]pyrazin-7-yl}-2,2-dimethyl-propan-1-one. This material was prepared starting from 1-[2-[3-(2-dimethylamino-ethoxy)-5-(3,3-dimethyl-pyrrolidin-1-yl)-phenyl]-5-(2-trimethylsilanyl-ethoxymethyl)-5H-pyrrolo[2,3-b]pyrazin-7-yl]-2,2-dimethyl-propan-1-one following the general procedures described in these Examples. MP=240-242

The general procedures described in these Examples were followed for synthesis of the following compound:

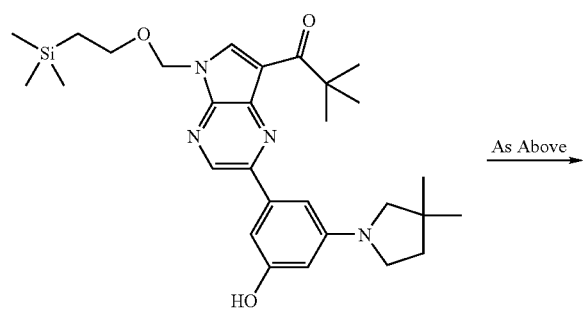

As Above

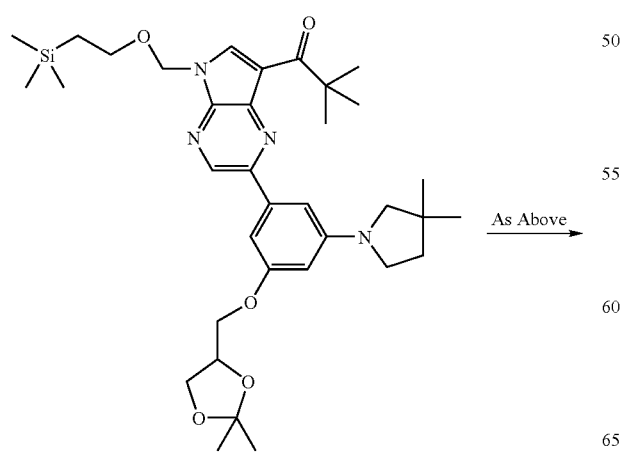

As Above

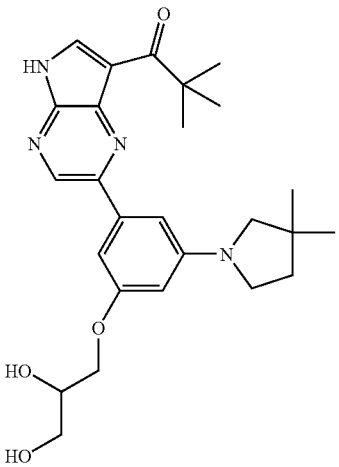

1-[2-[3-(2,2-Dimethyl-[1,3]dioxolan-4-ylmethoxy)-5-(3,3-dimethyl-pyrrolidin-1-yl)-phenyl]-5-(2-trimethylsilanyl-ethoxymethyl)-5H-pyrrolo[2,3-b]pyrazin-7-yl]-2,2-dimethyl-propan-1-one. This material was prepared starting from 1-[2-[3-(3,3-dimethyl-pyrrolidin-1-yl)-5-hydroxy-phenyl]-5-(2-trimethylsilanyl-ethoxymethyl)-5H-pyrrolo[2,3-b]pyrazin-7-yl]-2,2-dimethyl-propan-1-one via Mitsunobu type alkylation similar to that which was described above, but using "(2,2-dimethyl-[1,3]dioxolan-4-yl)-methanol" in place of "2-methylsulfanyl-ethanol".

1-{2-[3-(2,3-Dihydroxy-propoxy)-5-(3,3-dimethyl-pyrrolidin-1-yl)-phenyl]-5H-pyrrolo[2,3-b]pyrazin-7-yl}-2,2-dimethyl-propan-1-one. This material was prepared from 1-[2-[3-(2,2-dimethyl-[1,3]dioxolan-4-ylmethoxy)-5-(3,3-dimethyl-pyrrolidin-1-yl)-phenyl]-5-(2-trimethylsilanyl-ethoxymethyl)-5H-pyrrolo[2,3-b]pyrazin-7-yl]-2,2-dimethyl-propan-1-one via a similar procedure to that which was described above. M+H=466.

The general procedures described in these Examples were followed for synthesis of the following compound:

1-{2-[3-(3,3-Dimethyl-pyrrolidin-1-yl)-5-(1-methyl-piperidin-4-yloxy)-phenyl]-5H-pyrrolo[2,3-b]pyrazin-7-yl}-2,2-dimethyl-propan-1-one.

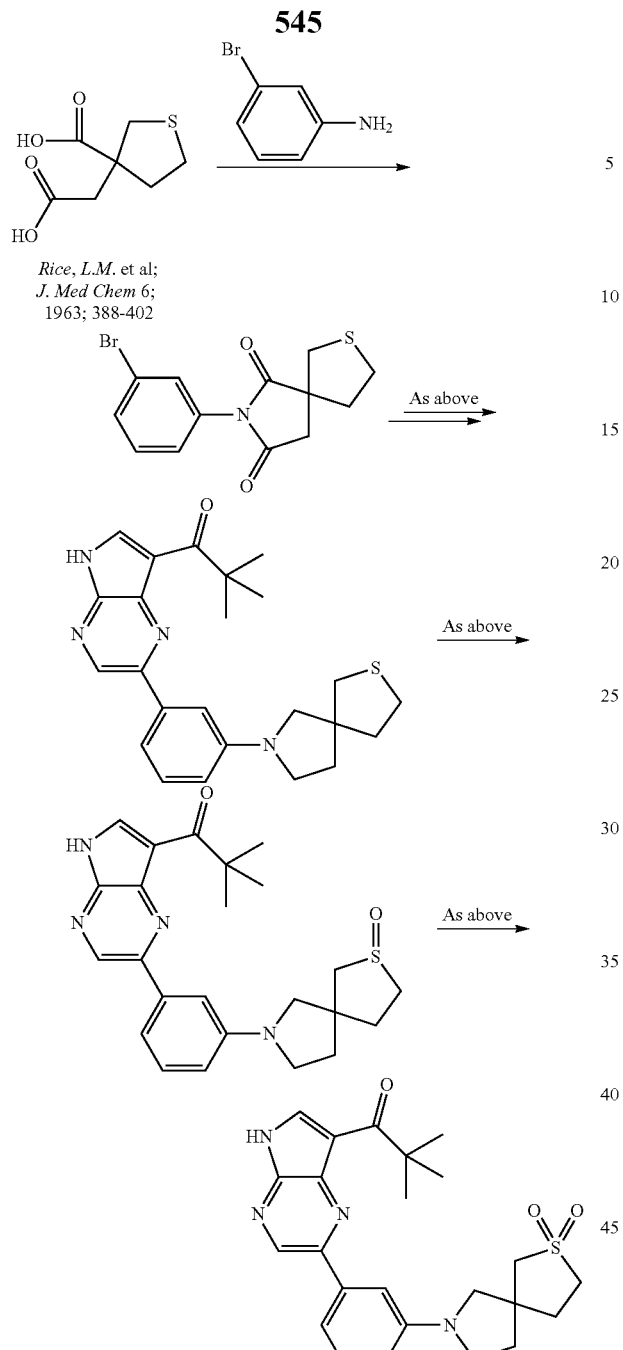

Example 276

7-(3-Bromo-phenyl)-2-thia-7-aza-spiro[4.4]nonane-6,8-dione. A solution of 3-bromo-phenylamine (1.0 g, 5.81 mmol) and 3-carboxymethyl-tetrahydro-thiophene-3-carboxylic acid (1.15 g, 6.05 mmol, [Rice, L. M. et al; J. Med Chem; 6; 1963; 388-402]) in xylene (10 ml) was heated for 2 hours (oil bath, 180° C.) with fitted Dean-Stark trap to remove water. The material was cooled to ambient and the xylene stripped (rotovap/pump). The material was covered with dry $CH_2Cl_2$ (10 ml). Carbonyldiimidazole (1.18 g, 7.26 mmol) was added with vigorous stirring and a homogeneous solution was rapidly obtained. After over night stirring the material was adsorbed onto silica (12 g). The crude was purified by chromatography on silica gel, eluting with a gradient of 100% $CH_2Cl_2$ to 0.12% $MeOH/CH_2Cl_2$, to afford 1.76 g of 7-(3-bromo-phenyl)-2-thia-7-aza-spiro[4.4]nonane-6,8-dione as a light yellow solid.

2,2-Dimethyl-1-{2-[3-(2-thia-7-aza-spiro[4.4]non-7-yl)-phenyl]-5H-pyrrolo[2,3-b]pyrazin-7-yl}-propan-1-one. This material was prepared starting from 7-(3-bromo-phenyl)-2-thia-7-aza-spiro[4.4]nonane-6,8-dione, using the general procedures described in these Examples. MP=239-241, $(M+H)^+=421$.

2,2-Dimethyl-1-{2-[3-(2-oxo-2lambda*4*-thia-7-aza-spiro[4.4]non-7-yl)-phenyl]-5H-pyrrolo[2,3-b]pyrazin-7-yl}-propan-1-one. This material was prepared starting from 2,2-dimethyl-1-{2-[3-(2-thia-7-aza-spiro[4.4]non-7-yl)-phenyl]-5H-pyrrolo[2,3-b]pyrazin-7-yl}-propan-1-one, using the general procedures described in these Examples. MP=148-150, $(M+H)^+=437$.

1-{2-[3-(2,2-Dioxo-2lambda*6*-thia-7-aza-spiro[4.4]non-7-yl)-phenyl]-5H-pyrrolo[2,3-b]pyrazin-7-yl}-2,2-dimethyl-propan-1-one. This material was prepared starting from 2,2-dimethyl-1-{2-[3-(2-oxo-2lambda*4*-thia-7-aza-spiro[4.4]non-7-yl)-phenyl]-5H-pyrrolo[2,3-b]pyrazin-7-yl}-propan-1-one, using the general procedures as described above. MP=237-239, $(M+H)^+=453$.

The general procedures described in these Examples were followed for synthesis of the following compounds:

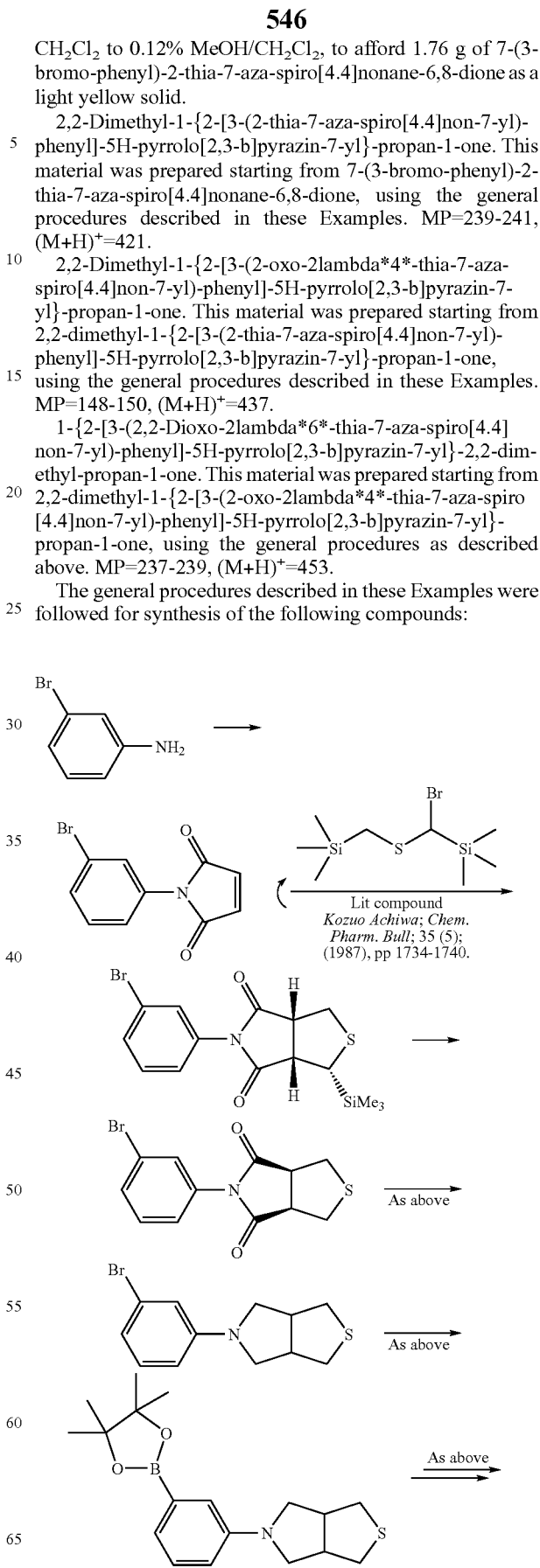

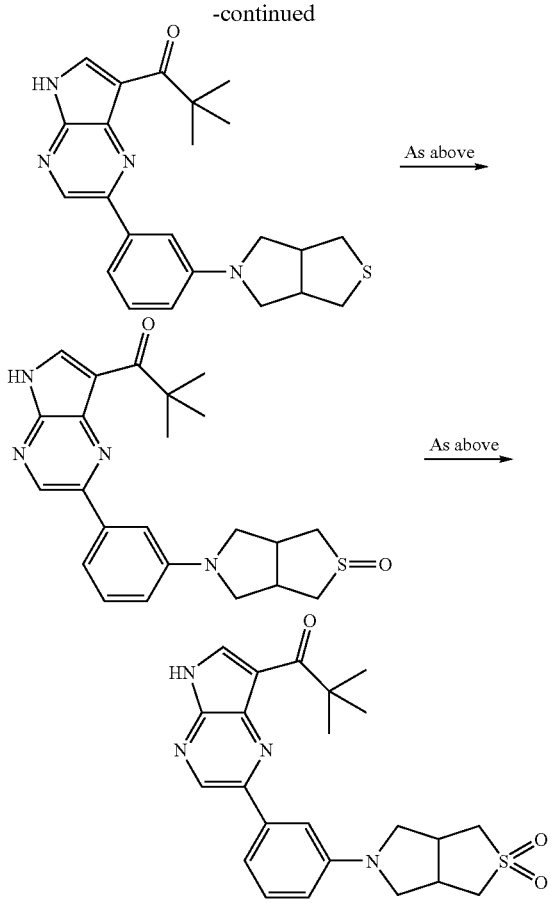

Example 277

1-(3-Bromo-phenyl)-pyrrole-2,5-dione. To a solution of maleic anhydride (1.71 g, 17.4 mmol) in dry ether (25 ml) was added a solution of 3-bromo-phenylamine (3.0 g, 17.4 mmol) in ether (5 ml), via slow drop-wise addition. The material was stirred for 1 hour at ambient Sodium acetate (721 mg, 8.8 mmol) and then acetic anhydride (6 ml, 63 mmol) were added and the mixture was heated for 2 hours (oil bath, 100° C.). The material was cooled to ambient and then in an ice bath. Water (50 ml) was added with vigorous stirring and the resultant precipitate was collected by filtration. The precipitate was washed with several volumes of water and finally with hexane (30 ml). The material was dried over night in the vacuum oven to afford 2.84 g of 1-(3-bromo-phenyl)-pyrrole-2,5-dione as a light yellow-white powder.

Example 278

(3S,3aS,6aR)-5-(3-Bromo-phenyl)-3-trimethylsilanyl-tetrahydro-thieno[3,4-c]pyrrole-4,6-dione. A flask was charged with 1-(3-bromo-phenyl)-pyrrole-2,5-dione (800 mg, 3.17 mmol) and bromo-trimethylsilanyl-trimethylsilanylmethyl-sulfanyl-methane (1.36 g, 4.76 mmol, [literature compound]) in dry DMF (3 ml) under nitrogen atmosphere. The material was heated at 110° C. (oil bath) for 2 hours and then cooled to ambient. The solvent was stripped (rotovap/pump) and the remainder taken up in benzene (30 ml) and brine (30 ml). The material was shaken and the organic phase collected. The aqueous phase was back-extracted with benzene (2×20 ml) and the organic phases combined, dried (MgSO$_4$), filtered and stripped. The crude was purified by chromatography on silica gel eluting with 5% to 40% EtOAc in hexanes, providing 1.04 g of (3S,3aS,6aR)-5-(3-bromo-phenyl)-3-trimethylsilanyl-tetrahydro-thieno[3,4-c]pyrrole-4,6-dione as a light white-yellow solid.

Example 279

(3aR,6aS)-5-(3-Bromo-phenyl)-tetrahydro-thieno[3,4-c]pyrrole-4,6-dione. To a solution of (3S,3aS,6aR)-5-(3-bromo-phenyl)-3-trimethylsilanyl-tetrahydro-thieno[3,4-c]pyrrole-4,6-dione (637 mg, 1.66 mmol) in HMPA (5 ml) and water (2 drops) was added powdered cesium fluoride (254 mg, 1.66 mmol). The mixture was heated (80° C., oil bath) for 8 hours and then stirred over night at ambient. Water (50 ml) and benzene (60 ml) were added and the material was shaken. The organic phase was collected and washed with brine (50 ml). The benzene phase was collected and the aqueous phase was back-extracted (2×40 ml) with benzene. The organics were combined, dried (MgSO4), filtered and stripped. The remainder was purified by silica gel chromatography eluting with 4% to 45% ethyl acetate in hexanes to afford 290 mg of (3aR,6aS)-5-(3-bromo-phenyl)-tetrahydro-thieno[3,4-c]pyrrole-4,6-dione, as a brown-yellow solid.

2,2-Dimethyl-1-{2-[3-(tetrahydro-thieno[3,4-c]pyrrol-5-yl)-phenyl]-5H-pyrrolo[2,3-b]pyrazin-7-yl}-propan-1-one. This material was prepared starting from (3aR,6aS)-5-(3-bromo-phenyl)-tetrahydro-thieno[3,4-c]pyrrole-4,6-dione, following the general procedures as described in these Examples.

2,2-Dimethyl-1-{2-[3-(2-oxo-hexahydro-2lambda*4*-thieno[3,4-c]pyrrol-5-yl)-phenyl]-5H-pyrrolo[2,3-b]pyrazin-7-yl}-propan-1-one. This material was prepared starting from 2,2-Dimethyl-1-{2-[3-(tetrahydro-thieno[3,4-c]pyrrol-5-yl)-phenyl]-5H-pyrrolo[2,3-b]pyrazin-7-yl}-propan-1-one, following the general procedures as described in these Examples.

1-{2-[3-(2,2-Dioxo-hexahydro-2lambda*6*-thieno[3,4-c]pyrrol-5-yl)-phenyl]-5H-pyrrolo[2,3-b]pyrazin-7-yl}-2,2-dimethyl-propan-1-one. This material was prepared starting from 2,2-Dimethyl-1-{2-[3-(tetrahydro-thieno[3,4-c]pyrrol-5-yl)-phenyl]-5H-pyrrolo[2,3-b]pyrazin-7-yl}-propan-1-one using the general procedures as described above.

Example 280

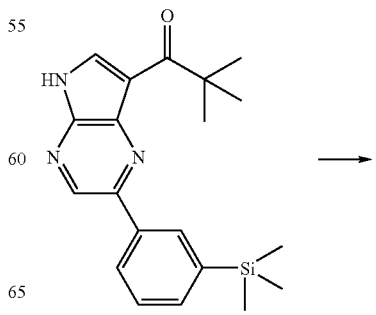

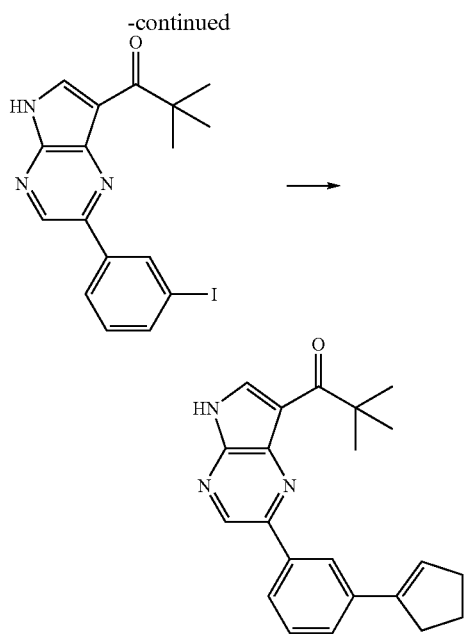

2,2-Dimethyl-1-[2-(3-trimethylsilanyl-phenyl)-5H-pyrrolo[2,3-b]pyrazin-7-yl]-propan-1-one (250 mg, 0.71 mmol) was suspended in 7 ml of methylene chloride and potassium carbonate (393 mg, 2.8 mmol) was added. The flask was wrapped in aluminum foil and iodine monochloride (2.5 ml of a 1M solution in methylene chloride) was added dropwise. The mixture was stirred in the dark at room temperature for one hour. The reaction was quenched with 10% aqueous sodium thiosulfate, extracted into methylene chloride, and washed with water two times. The organic layer was dried with sodium sulfate, concentrated, triturated with ethyl ether, filtered and dried in a vacuum oven to give 232 mg (81%) of 1-[2-(3-iodo-phenyl)-5H-pyrrolo[2,3-b]pyrazin-7-yl]-2,2,-dimethyl-propan-1-one as a yellow solid. (M+H)$^+$=406.

The iodo intermediate (150 mg, 0.37 mmol) was combined with potassium carbonate (179 mg, 1.3 mmol), cyclopenten-1-ylboronic acid (50 mg, 0.44 mmol) and Pd(dppf)Cl$_2$-DCM (30 mg, 0.037 mmol) in a microwave vial which was capped and purged with nitrogen. Solvent was added (3.7 ml of 20% aqueous dioxane) and the flask was purged with nitrogen again two times. The reaction was heated in a microwave reactor at 125° C. for 30 minutes. Ethyl acetate and water were added to the reaction mixture and the layers were separated. The organic layer was washed with water and brine and concentrated. The crude product was purified by flash chromatography using a gradient of 0% to 30% ethyl acetate in hexanes to give 1-[2-(3-cyclopent-1-enyl-phenyl)-5H-pyrrolo[2,3-b]pyrazin-7-yl]-2,2,-dimethyl-propan-1-one (58 mg, 45%) as a white solid. (M+H)$^+$=346.

Other compounds prepared using this route:
2,2-Dimethyl-1-{2-[3-(5-trifluoromethyl-2H-pyrazol-3-yl)-phenyl]-5H-pyrrolo[2,3-b]pyrazin-7-yl}-propan-1-one (M+H)$^+$=414;
1-[2-(3-Cyclohex-1-enyl-phenyl)-5H-pyrrolo[2,3-b]pyrazin-7-yl]-2,2-dimethyl-propan-1-one (M+H)$^+$=360; MP=188.0-190.0° C.;
2,2-Dimethyl-1-[2-(3-thiophen-2-yl-phenyl)-5H-pyrrolo[2,3-b]pyrazin-7-yl]-propan-1-one (M+H)$^+$=362;
1-[2-(3-Cyclopentyl-phenyl)-5H-pyrrolo[2,3-b]pyrazin-7-yl]-2,2-dimethyl-propan-1-one (M+H)$^+$=348;
2,2-Dimethyl-1-{2-[3-(1H-pyrazol-4-yl)-phenyl]-5H-pyrrolo[2,3-b]pyrazin-7-yl}-propan-1-one (M+H)$^+$=346; MP>300° C.; except the starting material was SEM-protected, and the SEM protecting group was removed by treating the Suzuki product with a 1M solution of tetrabutylammonium fluoride in THF and heating the solution at 75° C. for one hour.

The above general procedure was followed for the synthesis of the following compounds:
2,2-Dimethyl-1-{2-[4-(4-methyl-piperazin-1-yl)-phenylamino]-5H-pyrrolo[2,3-b]pyrazin-7-yl}-propan-1-one (M+H)$^+$=393; MP>300° C.
2,2-Dimethyl-1-{2-[3-(4-methyl-piperazin-1-yl)-phenylamino]-5H-pyrrolo[2,3-b]pyrazin-7-yl}-propan-1-one (M−H)$^-$=391

Example 281

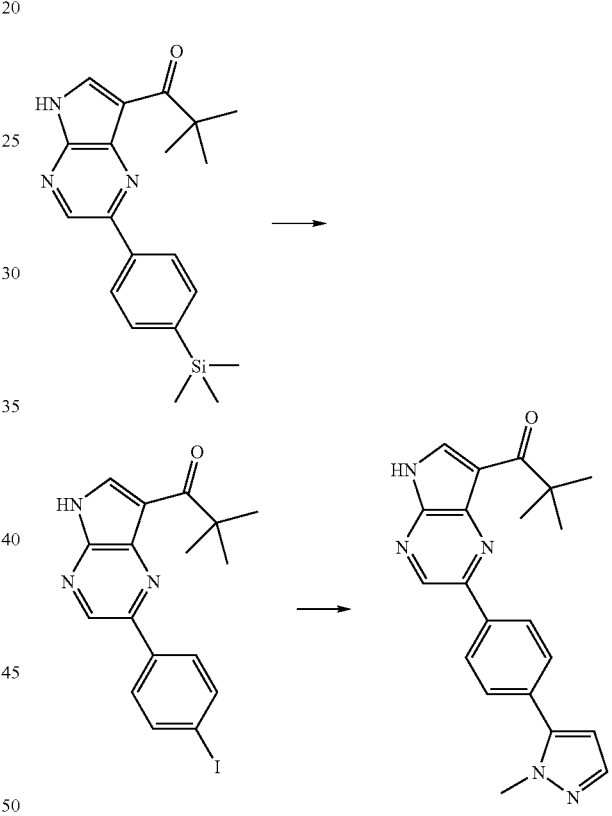

1-[2-(4-Iodo-phenyl)-5H-pyrrolo[2,3-b]pyrazin-7-yl]-2,2,-dimethyl-propan-1-one was synthesized from 2,2-Dimethyl-1-[2-(4-trimethylsilanyl-phenyl)-5H-pyrrolo[2,3-b]pyrazin-7-yl]-propan-1-one following general procedures as described in these Examples. (M+H)$^+$=406; MP=262.0-263.0° C.

2,2-Dimethyl-1-{2-[4-(2-methyl-2H-pyrazol-3-yl)-phenyl]-5H-pyrrolo[2,3-b]pyrazin-7-yl}-propan-1-one was synthesized from the iodo intermediate, following the general procedures as described in these Examples.
(M+H)$^+$=360; MP=257.0-258.0° C.

Other compounds prepared using this route:
1-{2-[4-(3,5-Dimethyl-isoxazol-4-yl)-phenyl]-5H-pyrrolo[2,3-b]pyrazin-7-yl}-2,2-dimethyl-propan-1-one (M+H)$^+$=375; MP=254.0-255.0° C.

Example 282

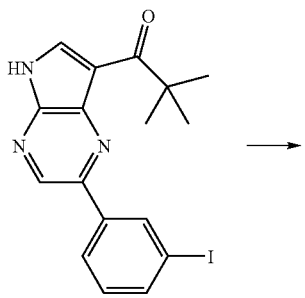

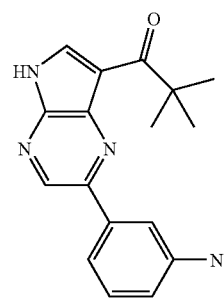

1-[2-(3-Iodo-phenyl)-5H-pyrrolo[2,3-b]pyrazin-7-yl]-2,2,-dimethyl-propan-1-one (150 mg, 0.37 mmol), the oxalate salt of 2-oxa-6-aza-spiro[3.3]heptane (267 mg, 0.93 mmol), potassium carbonate (255 mg, 1.85 mmol), copper iodide (14 mg, 0.074 mmol), and d,l-proline (17 mg, 0.148 mmol) were added to a microwave vial. The vial was capped and purged with nitrogen. DMSO (3.7 ml) was added and the vial was purged with nitrogen again. The reaction was heated in a sand bath at 100° C. for 72 hours. The reaction was poured into ice water, extracted into ethyl acetate, washed with water and brine, dried with sodium sulfate and concentrated. The crude product was purified by flash chromatography using a gradient of 30% to 50% ethyl acetate in hexanes to yield 35 mg (25%) of 2,2-dimethyl-1-{2-[3-(2-oxa-6-aza-spiro[3.3]hept-6-yl)-phenyl]-5H-pyrrolo[2,3-b]pyrazin-7-yl}-propan-1-one as a yellow solid. (M+H)$^+$=377; MP=260.0-262.0° C.

Other compounds prepared using this route:

1-{3-[7-(2,2-Dimethyl-propionyl)-5H-pyrrolo[2,3-b]pyrazin-2-yl]-phenyl}-pyrrolidine-3-carbonitrile
(M+H)$^+$=374

1-{2-[3-(3-Dimethylamino-azetidin-1-yl)-phenyl]-5H-pyrrolo[2,3-b]pyrazin-7-yl}-2,2-dimethyl-propan-1-one
(M+H)$^+$=378

Except that the starting material was SEM-protected, and the SEM protecting group was removed with TFA in DCM:

1-[2-(3-Imidazol-1-yl-phenyl)-5H-pyrrolo[2,3-b]pyrazin-7-yl]-2,2-dimethyl-propan-1-one
(M+H)$^+$=346.

1-{2-[3-((R)-3-Hydroxymethyl-pyrrolidin-1-yl)-phenyl]-5H-pyrrolo[2,3-b]pyrazin-7-yl}-2,2-dimethyl-propan-1-one (M+H)$^+$=379. After the TFA step, NMR analysis showed that part of the SEM protecting group had been transferred to the alcohol. Tetrabutylammonium fluoride (room temperature for 1.5 hours) was used to complete the deprotection.

1-{2-[3-((S)-3-Hydroxymethyl-pyrrolidin-1-yl)-phenyl]-5H-pyrrolo[2,3-b]pyrazin-7-yl}-2,2-dimethyl-propan-1-one (M+H)$^+$=379. Tetrabutylammonium fluoride (80° C. for 1 hour) was used to remove the SEM group.

1-{2-[3-(3,3-Dimethyl-pyrrolidin-1-yl)-phenyl]-5H-pyrrolo[2,3-b]pyrazin-7-yl}-2,2-dimethyl-propan-1-one (M+H)$^+$=377; MP=233.0-235.0° C. 1M NaOH in THF was used instead of sodium acetate to complete the deprotection.

1-{2-[3-(3,3-Difluoro-azetidin-1-yl)-phenyl]-5H-pyrrolo[2,3-b]pyrazin-7-yl}-2,2-dimethyl-propan-1-one (M+H)$^+$=371. 1M NaOH in THF was used instead of sodium acetate to complete the deprotection.

1-{2-[3-(3,3-Dimethyl-azetidin-1-yl)-phenyl]-5H-pyrrolo[2,3-b]pyrazin-7-yl}-2,2-dimethyl-propan-1-one (M+H)$^+$=363; MP=227.0-229.0° C. 1M NaOH in THF was used instead of sodium acetate to complete the deprotection.

Example 283

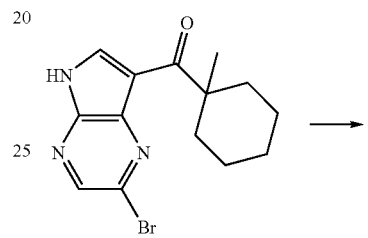

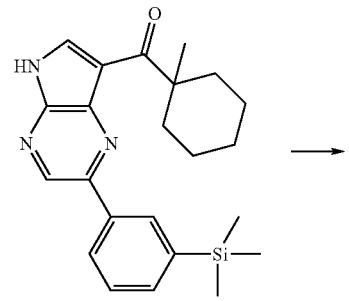

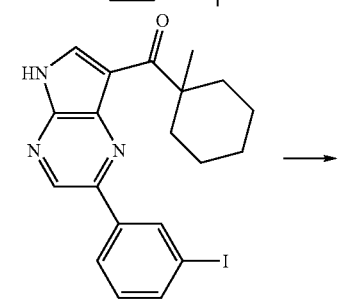

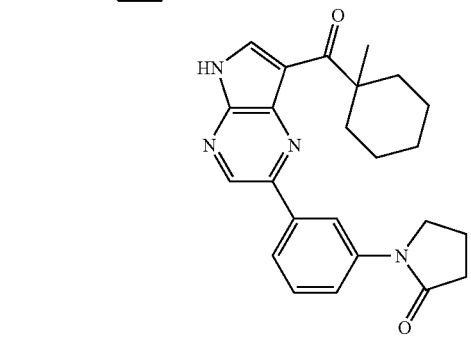

Methyl-cyclohexyl)-[2-(3-trimethylsilanyl-phenyl)-5H-pyrrolo[2,3-b]pyrazin-7-yl]methanone was prepared, following the general procedures as described in these Examples.

This compound was converted to [2-(3-iodo-phenyl)-5H-pyrrolo[2,3-b]pyrazin-7-yl]-(1-methyl-cyclohexyl)-methanone, following the general procedures as described in these Examples.

General procedures as described in these Examples were used to prepare 1-{3-[7-(1-methyl-cyclohexanecarbonyl)-5H-pyrrolo[2,3-b]pyrazin-2-yl]-phenyl}-pyrrolidin-2-one. (M+H)⁺=403; MP=215.0-217.0° C.

Other compounds prepared using part of this route:

Methyl-cyclohexyl)-[2-(3-pyrrol-1-yl-phenyl)-5H-pyrrolo[2,3-b]pyrazin-7-yl]methanone, (M+H)⁺=385, was prepared from [2-(3-iodo-phenyl)-5H-pyrrolo[2,3-b]pyrazin-7-yl]-(1-methyl-cyclohexyl)-methanone, protected with a SEM group added as above, using the general procedure described above. Deprotection was carried using TFA as above except that 1M NaOH in THF was used instead of sodium acetate to complete the deprotection.

Example 284

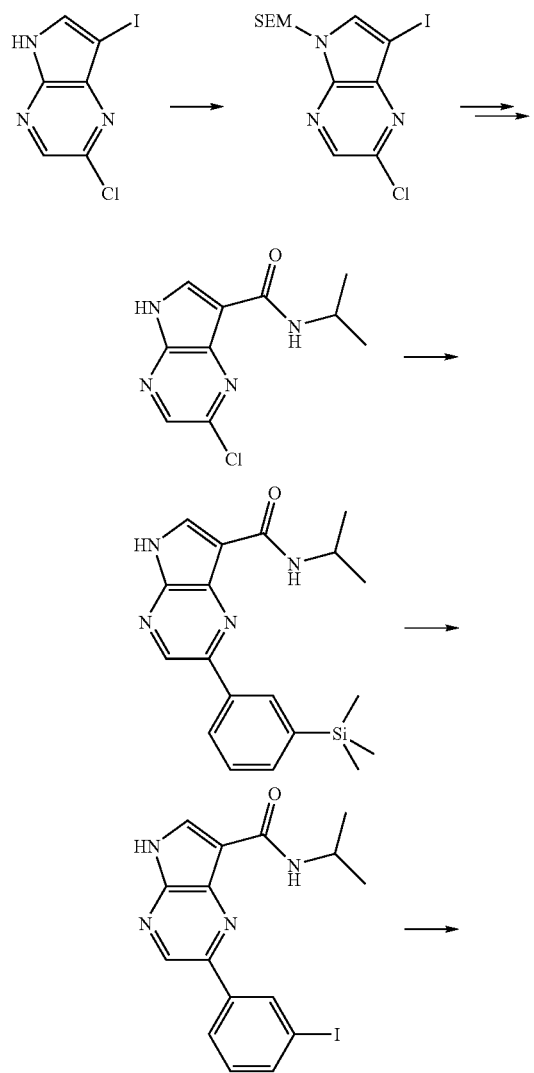

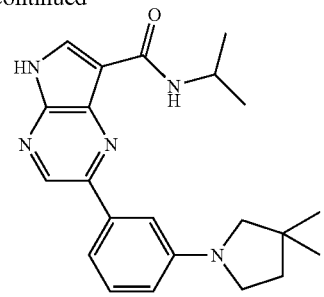

2-Chloro-7-iodo-5H-pyrrolo[2,3-b]pyrazine was SEM protected following general procedures as described in these Examples.

2-Chloro-5H-pyrrolo[2,3-b]pyrazine-7-carboxylic acid isopropylamide was prepared following general procedures as described in these Examples followed by SEM removal using TFA as above except that 1M NaOH in THF was used instead of sodium acetate to complete the deprotection.

2-(3-Trimethylsilanyl-phenyl)-5H-pyrrolo[2,3-b]pyrazine-7-carboxylic acid isopropylamide was prepared using general procedures described in these Examples.

2-(3-Iodo-phenyl)-5H-pyrrolo[2,3-b]pyrazine-7-carboxylic acid isopropylamide was prepared using general procedures described in these Examples.

2-[3-(3,3-Dimethyl-pyrrolidin-1-yl)-phenyl]-5H-pyrrolo[2,3-b]pyrazine-7-carboxylic acid isopropylamide, (M+H)⁺=378, was prepared using general procedures described in these Examples.

Example 285

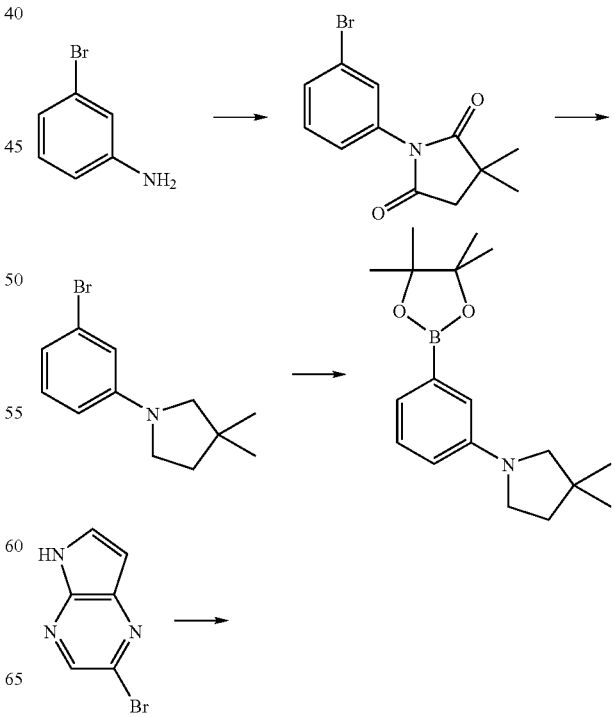

-continued

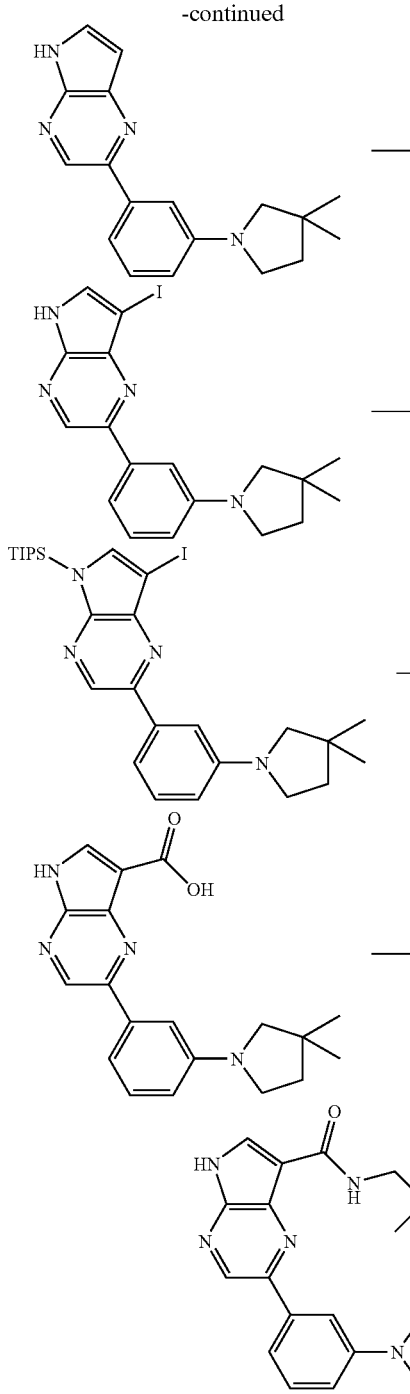

3-Bromo-phenylamine (10.0 g, 58.1 mmol) and 3,3-dimethyl-dihydro-furan-2,5-dione (8.2 g, 63.9 mmol) were suspended in 387 ml of methylene chloride and heated at 50° C. for 3 hours. Carbonyldiimidazole (11.3 g, 69.7 mmol) was added in portions and the reaction was heated at 50° C. overnight. Most of the solvent was removed on a rotary evaporator. The solid residue was triturated with 20% ethyl acetate in hexanes, filtered and dried to give 15 g (92%) of somewhat impure 1-(3-bromo-phenyl)-3,3-dimethyl-pyrrolidine-2,5-dione which was used without further purification.

1-(3-Bromo-phenyl)-3,3-dimethyl-pyrrolidine-2,5-dione (2.5 g, 8.9 mmol) suspended in 45 ml of THF. Borane (7.9 ml of a 10.1M solution in methyl sulfide) was added and the reaction was stirred at room temperature for 3 hours. The reaction was cooled to 0° C. in an ice bath and 20 ml of methanol was added dropwise, then 60 ml of water. The mixture was transferred to a separatory funnel and methylene chloride was added. The organic phase was washed with water and brine, filtered through celite and concentrated. The crude product was purified by flash chromatography using a gradient of 0% to 5% ethyl acetate in hexanes to give 1.7 g (75%) of 1-(3-bromo-phenyl)-3,3-dimethyl-pyrrolidine.

Other compounds prepared using this route:

2-[3-(3,3-Dimethyl-pyrrolidin-1-yl)-phenyl]-5-H-pyrrolo[2,3-b]pyrazine-7-carboxylic acid tert-butylamide (M+H)$^+$= 392; MP=205.0-207.0° C.;

2-[3-(3,3-Dimethyl-pyrrolidin-1-yl)-phenyl]-5-H-pyrrolo[2,3-b]pyrazine-7-carboxylic acid (2-methoxy-propyl)-amide (M+H)$^+$=408;

2-[3-(3,3-Dimethyl-pyrrolidin-1-yl)-phenyl]-5-H-pyrrolo[2,3-b]pyrazine-7-carboxylic acid (tetrahydro-pyran-3-yl)-amide (M+H)$^+$=420; MP=145.0-147.0° C.

Example 286

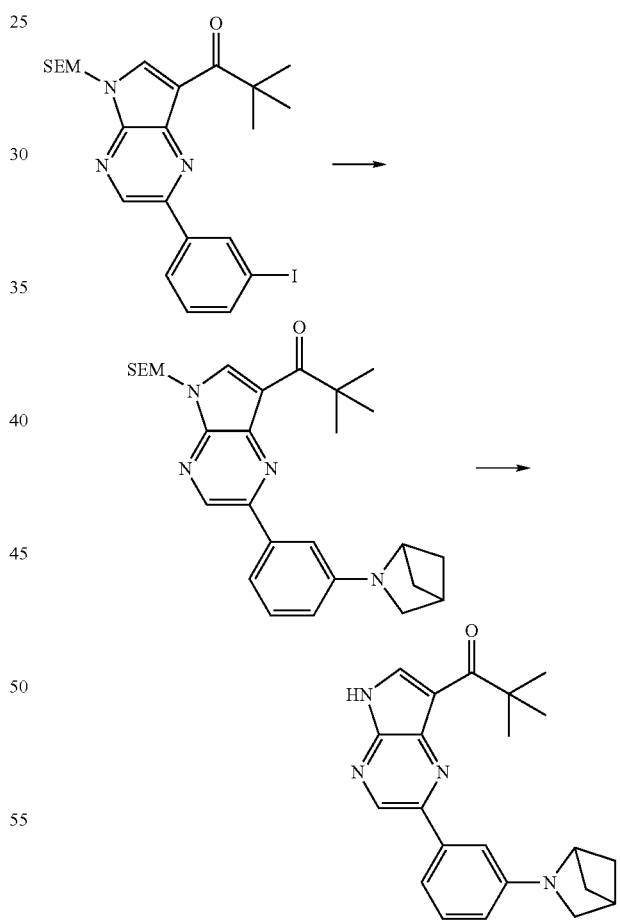

1-{2-[3-(2-Aza-bicyclo[2.1.1]hex-2-yl)-phenyl]-5H-pyrrolo[2,3-b]pyrazin-7-yl}-2,2-dimethyl-propan-1-one 2-Aza-bicyclo[2.1.1]hexane-2-carboxylic acid benzyl ester (1.2 g, 5.57 mmol, prepared as described in: Krow, G. R.; Lin, G.; Rapolu, D.; Fang, Y.; Lester, W. S.; Herzon, S. B.; Sonnet, P. E. J. Org. Chem., 2003, 68, 5292; Krow, G. R.; Lee, Y. B.; Lester; W. S.; Christian, H.; Shaw, D. A.; Yuan, J. J. Org.

Chem., 1998, 63, 8558), dissolved in 2 mL of MeOH, was added to 12 ml of conc. HCl and heated at reflux for 1.5 h. TLC analysis (KMnO$_4$) showed no remaining sm. The reaction mixture was concentrated in vacuo and then concentrated twice from 15 mL of toluene to give 2-azabicyclo[2.1.1] hexane hydrochloride as a dark solid (0.53 g, 79%; $^1$HNMR (DMSO): δ 4.11 (d, 1H, J=6.15 hz), 3.15 (m, 2H), 2.84 (quintet, 1H, J=3.12 hz), 1.98 (s br, 2H), 1.39 (dd, 2H, J=2.16, 5.50 hz) that was used in the next step without further purification.

1-[2-[3-(2-Azabicyclo[2.1.1]hex-2-yl)-phenyl]-5-(2-trimethylsilanyl-ethoxymethyl)-5H-pyrrolo[2,3-b]pyrazin-7-yl]-2,2-dimethyl-propan-1-one was prepared from 1-[2-(3-Iodophenyl)-5-(2-trimethylsilanyl-ethoxymethyl)-5H-pyrrolo[2,3-b]pyrazin-7-yl]-2,2-dimethyl-propan-1-one and 2-azabicyclo[2.1.1]hexane hydrochloride as described above (34%; MS=361 M+H).

JAK Assay Information

Determination of IC$_{50}$ of Janus Kinase (JAK) Inhibition:
  Enzymes and peptide substrate used are described below:
  JAK1: Recombinant human kinase domain from Invitrogen (Cat # PV4774)
  JAK3: Recombinant human kinase domain from Millipore (Cat # 14-629) or prepared.
  JAK2: Recombinant human kinase domain from Millipore (Cat # 14-640)
  Substrate: N-terminally biotinylated 14-mer peptide derived from activation loop of JAK1 with sequence of the peptide substrate: Biotin-KAIETDKEYYTVKD
  Assay conditions_used are described below:
  Assay Buffer: JAK Kinase Buffer: 50 mM Hepes [pH 7.2], 10 mM MgCl$_2$, 1 mM DTT, 1 mg/ml BSA. The assay is carried out in this buffer.
  Assay Format The kinase activity of all three JAK kinases is measured using a radioactive, end-point assay and with trace amounts of $^{33}$P-ATP. The assays are carried out in 96-well polypropylene plates.

Experimental Method:
  All concentrations are final in the reaction mixture and all incubations are carried at room temperature. Assay steps are described below:
  1) Compounds are serially diluted in 100% DMSO typically at a 10× starting concentration of 1 mM. Final concentration of DMSO in the reaction is 10%.
  2) Compounds are preincubated with enzyme (0.5 nM JAK3 (commercially available), 0.2 nM JAK3 (prepared), 1 nM JAK2, 5 nM JAK1) for 10 minutes.
  3) Reactions are initiated by the addition of a cocktail of the two substrates (ATP and peptide premixed in the JAK Kinase Buffer). In the JAK2/JAK3 assays, ATP and the peptide are used at concentrations of 1.5 uM and 50 uM, respectively. JAK1 assay is carried out at an ATP concentration of 10 uM and a peptide concentration of 50 uM.
  4) The duration of the assay for JAK2 and JAK3 is 20 minutes. JAK1 assay is carried out for 40 minutes. With all three enzymes, reactions are terminated by the addition of 0.5M EDTA to a final concentration of 100 mM.
  5) 25 ul of terminated reactions are transferred to 150 ul of a 7.5% (v/v) slurry of streptavidin-coated sepharose beads in MgCl$_2$- and CaCl$_2$-free 1× Phosphate Buffered Saline containing 50 mM of EDTA in 96-well, 1.2 um MultiScreen-BV filter plates.
  6) After a 30-minute incubation, the beads are washed under vacuum with the following buffers:
    a. 3 to 4 washes with 200 ul of 2M NaCl.
    b. 3 to 4 washes with 200 ul of 2M NaCl plus 1% (v/v) phosphoric acid.
    c. 1 wash with water.
  7) Washed plates are dried in a 60° C. oven for between 1 to 2 hours.
  8) 70 ul of Microscint 20 scintillation fluid is added to each well of filter plates and after at least 30 minutes of incubation, radioactive counts are measured in a Perkinelmer microplate scintillation counter.

Representative IC$_{50}$ results are in Table II below:

TABLE II

| Compound | IC$_{50}$ h-jak2-sf21-c | IC$_{50}$ h-jak3-sf21-c | IC$_{50}$ h-jak1-sf21-c | IC$_{50}$ h-syk (360-635)-baculovirus-c |
|---|---|---|---|---|
| I-12 | 0.4548 | 0.0561 | | 0.317 |
| I-64 | 3.4396 | 0.0241 | 2.1 | 1.314 |
| I-82 | 0.0108 | 0.0046 | 0.09 | 0.036 |
| I-117 | 0.107 | 0.0068 | | 0.162 |

SYK Assay Information

Determination of IC$_{50}$ of Spleen Tyrosine Kinase (SYK) Inhibition:

SYK kinase assay is a standard kinase assay adapted to a 96 well plate format. This assay is performed in 96-well format for IC$_{50}$ determination with 8 samples which represented 10 half log dilutions and a 40 µL reaction volume. The assay measures the incorporation of radiolabeled $^{33}$P γATP into an N-terminally biotinylated peptide substrate, derived from naturally occurring phosphoacceptor consensus sequence (Biotin-11aa DY*E). Phosphorylated products were detected upon termination of reactions with EDTA and the addition of Streptavidin coated beads. Representative results are in Table II above.

Assay plates: 96-well MultiScreen 0.65 um filter plates (Millipore Cat. No.: MADVNOB10)
  Streptavidin coated beads: Streptavidin Sepharose™, suspension 5.0 mL, in 50 mM
  EDTA/PBS diluted (1:100), (Amersham, Cat. No.: 17-5113-01)
  Compounds: 10 mM in 100% dimethylsulfoxide (DMSO), final conc.: compound 0.003-100 uM in 10% DMSO
  Enzyme: SYK RPA purified, truncated construct of Spleen Tyrosine Kinase aa 360-635, stock solution 1 mg/mL, MW: 31.2 KDa, final conc.:0.0005 µM.
  Peptide 1: biotinylated peptide is derived from a naturally occurring phosphor-acceptor consensus sequence (Biotin-EPEGDYEEVLE), special order from QCB, stock solution 20 mM, final conc.: 5.0 µM.
  ATP: Adenosine-5'-triphosphate 20 mM, (ROCHE Cat. No.: 93202720), final concentration: 20 µM
  Buffer: HEPES: 2-Hydroxyethyl piperazine-2-ethane-sulfonic acid (Sigma™, Cat. No.: H-3375) final concentration: 50 mM HEPES pH7.5
  BSA: Bovine Serum Albumin Fraction V, fatty acid free (Roche Diagnostics GmbH, Cat. No. 9100221) diluted to a final concentration of 0.1%
  EDTA: EDTA stock solution 500 mM, (GIBCO, Cat. No.: 15575-038) final concentration: 0.1 mM
  DTT: 1,4-Dithiothreitol (Roche Diagnostics GmbH, Cat. No.: 197777), final conc.: 1 mM
  MgCl$_2$×6H$_2$O: MERCK, Cat. No.: 105833.1000, final concentration: 10 mM
  Assay Dilution Buffer (ADB): 50 mM HEPES, 0.1 mM EGTA, 0.1 mM Na Vanadate, 0.1 mM β-glycerophosphate, 10 mM MgCl$_2$, 1 mM DTT, 0.1% BSA, pH 7.5
  Bead wash buffer: 10 g/L PBS (Phosphate buffered saline) with 2M NaCl+1% phosphoric acid.

Experimental Method:
  In 40 4 volume, 26 µL ADB diluted, purified recombinant human SYK360-635 [0.5 nM] was mixed with 4 µL of 10× concentrations of the test compounds, [usually 100 µM-0.003 µM] in [10%] DMSO and the mixture was incubated for 10 min at RT.

The kinase reaction was initiated by the addition of 10 µL 4× substrate cocktail containing the DYE peptide substrate [0 or 5 µM], ATP [20 µM] and $^{33}$PγATP [2 µCi/r×n]. After incubation at 30° C. for 15 min, the reaction was terminated by the transfer of 25 µL of the reaction sample to a 96 well 0.65 gm Millipore MADVNOB membrane/plate containing 200 µL 5 mM EDTA and 20% Streptavidine coated beads in PBS.

The unbound radionucleotides were washed under vacuum with 3×250 µL 2M NaCl; 2×250 µL 2M NaCl+1% phosphoric acid; 1×250 µL H$_2$O. After the last wash membrane/plates were transferred to an adaptor plate, heat dried for 15 min at 60° C., and 50 µL scintillation cocktail was added to each well and 4 h later the amount of radioactivity was counted in a top counter.

The percent inhibition was calculated based on the uninhibited enzyme rate:

% Inhibition=100/(1+(IC$_{50}$/Inhibitor conc)$^n$)

The IC$_{50}$ was calculated using a non-linear curve fit with XLfit software (ID Business Solution Ltd., Guilford, Surrey, UK).

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:
1. A compound of Formula I

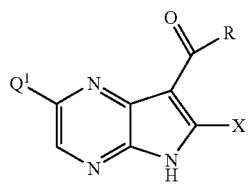

wherein:
R is R$^1$, R$^2$, R$^3$, or R$^4$;
R$^1$ is lower alkyl, lower alkoxy, phenyl, benzyl, heteroaryl, cycloalkyl, heterocycloalkyl, or cycloalkylalkyl, optionally substituted with one or more R$^{1a}$;
R$^{1a}$ is R$^{1b}$ or R$^{1c}$;
each R$^{1b}$ is independently halogen, oxo, hydroxy, or —CN;
each R$^{1c}$ is independently —C(=O)O(R$^{1f}$), —C(=O)CH$_2$(R$^{1e}$), —S(R$^{1f}$), —S(O)$_2$(R$^{1f}$), —S(=O)(R$^{1f}$), lower alkyl, lower alkoxy, amino, amido, lower haloalkyl, phenyl, heteroaryl, cycloalkyl, heterocycloalkyl, cycloalkyloxy, or heterocycloalkyloxy optionally substituted with one or more R$^{1d}$;
each R$^{1d}$ is independently H, halogen, hydroxy, lower alkyl, lower alkoxy, or lower haloalkyl;
each R$^{1e}$ is independently H, lower alkyl, lower alkoxy, —CN, lower haloalkyl, phenyl, heteroaryl, cycloalkyl, or heterocycloalkyl;
each R$^{1f}$ is independently H, lower alkyl, lower haloalkyl, phenyl, heteroaryl, cycloalkyl, or heterocycloalkyl;
R$^2$ is N(R$^{2a}$)$_2$;
each R$^{2a}$ is independently H or R$^{2b}$;
each R$^{2b}$ is independently lower alkyl, phenyl, heteroaryl, cycloalkyl, heterocycloalkyl, or heterocycloalkyl alkylene, optionally substituted with one or more R$^{2c}$;
R$^{2c}$ is R$^{2d}$ or R$^{2e}$;
each R$^{2d}$ is independently halogen, oxo, or hydroxy;
each R$^{2e}$ is independently —N(R$^{2g}$)$_2$, —C(=O) (R$^{2g}$), —C(=O)O(R$^{2g}$), —C(=O)N(R$^{2g}$)$_2$, —N(R$^{2g}$)C(=O)(R$^{2g}$), —S(=O)$_2$(R$^{2g}$), —S(O)$_2$N(R$^{2g}$)$_2$, lower alkyl, lower alkoxy, lower haloalkyl, phenyl, heteroaryl, heteroaryloxy, cycloalkyl, or heterocycloalkyl, optionally substituted with one or more R$^{2f}$;
each R$^{2f}$ is independently H, halogen, lower alkyl, lower alkoxy, or lower haloalkyl;
each R$^{2g}$ is independently H, lower alkyl, lower alkoxy, lower haloalkyl, or phenyl;
R$^3$ is —C(=O)R$^{3a}$;
R$^{3a}$ is lower alkyl, lower alkoxy, phenyl, or N(R$^{3b}$)$_2$;
each R$^{3b}$ is independently H or lower alkyl;
R$^4$ is —O(R$^{4a}$);
R$^{4a}$ H or R$^{4b}$;
R$^{4b}$ is lower alkyl, phenyl, benzyl, lower haloalkyl, cycloalkyl, heterocycloalkyl, heteroaryl, optionally substituted with one or more R$^{4c}$;
each R$^{4c}$ is independently halogen, hydroxy, lower alkyl, lower haloalkyl, or lower alkoxy;
Q$^1$ is phenyl optionally substituted with one or more Q$^{1a}$;
each Q$^{1a}$ is independently Q$^{1b}$ or Q$^{1c}$;
each Q$^{1b}$ is independently halogen, hydroxy, —CN, —S(Q$^{1c}$, —S(O)$_2$(Q$^{1c}$), or —S(=O)(Q$^{1e}$);
each Q$^{1c}$ is independently Q$^{1d}$ or Q$^{1e}$;
each Q$^{1d}$ is independently —O(Q$^{1e}$), —S(=O)$_2$ (Q$^{1e}$), —C(=O)(Q$^{1e}$), —C(=O)O(Q$^{1e}$), -(Q$^{1e}$)$_2$, —N(Q$^{1e}$)C(=O)(Q$^{1e}$), —N(Q$^{1e}$)C(=O)O(Q$^{1e}$), or —N(Q$^{1e}$)C(=O)N(Q$^{1e}$)$_2$;
each Q$^{1e}$ is independently or Q$^{1e'}$;
each Q$^{1e'}$ is independently lower alkyl, phenyl, benzyl, lower haloalkyl, cycloalkyl, heterocycloalkyl, or heteroaryl, optionally substituted with one or more Q$^{1f}$;
each Q$^{1f}$ is independently Q$^{1g}$ or Q$^{1h}$;
each Q$^g$ is independently halogen, hydroxy, oxo, or C(=O)(Q$^{1h}$);
each Q$^{1h}$ is independently
lower alkyl, lower alkoxy, phenyl, benzyl, cycloalkyl, heterocycloalkyl, or heteroaryl, optionally substituted with one or more Q$^{1i}$;
each Q$^{1i}$ is independently halogen, hydroxy, lower alkyl, lower haloalkyl, or lower alkoxy;
X is H;
or a pharmaceutically acceptable salt thereof.

2. The compound of claim 1, wherein $R^1$ is cycloalkyl.

3. The compound of claim 1, wherein $R^1$ is heterocycloalkyl.

4. The compound of claim 1, wherein $R^1$ is benzyl.

5. The compound of claim 1, wherein $R^1$ is phenyl.

6. The compound of claim 1, wherein $Q^{1c}$ is $Q^{1d}$, $Q^{1d}$ is $Q^{1d}$ is $-O(Q^{1e})$, $Q^{1e}$ is $Q^{1e'}$, and $Q^{1e'}$ is lower alkyl.

7. The compound of claim 6, wherein $Q^{1e'}$ is methyl.

8. The compound of claim 1, wherein $Q^{1c}$ is $Q^{1e}$, $Q^{1e}$ is $Q^{1e'}$, and $Q^{1e'}$ is heterocycloalkyl.

9. The compound of claim 8, wherein $Q^{1e'}$ pyrrolidine is pyrrolidine.

10. The compound of claim 1, wherein $Q^{1a}$ is $Q^{1b}$.

11. The compound of claim 10, wherein $Q^{1b}$ is halogen.

12. The compound of claim 10, wherein $Q^{1b}$ is hydroxy.

13. The compound of claim 1, wherein R is $R^1$ and $R^1$ is lower alkyl.

14. The compound of claim 13, wherein $R^1$ is $-CHC(CH_3)_3$.

15. The compound of claim 13, wherein $R^1$ is iso-butyl.

16. The compound of claim 13, wherein $R^1$ is iso-propyl.

17. The compound of claim 13, wherein $R^1$ is tert-butyl.

18. The compound of claim 17, wherein $Q^{1a}$ is $Q^{1c}$, $Q^{1c}$ is $Q^{1e}$, $Q^{1e}$, is $Q^{1e'}$, and $Q^{1e'}$ is pyrrolidine.

19. The compound of claim 1, wherein R is $R^2$.

20. The compound of claim 19, wherein $R^2$ is $NH(R^{2a})$ and $R^{2a}$ is $R^{2b}$.

21. The compound of claim 20, wherein $R^{2b}$ is heterocycloalkyl.

22. The compound of claim 20, wherein $R^{2b}$ is cycloalkyl.

23. The compound of claim 20, wherein $R^{2b}$ is lower alkyl.

24. The compound of claim 23, wherein $R^{2b}$ is iso-propyl.

25. The compound of claim 20, wherein $R^{2b}$ is heterocycloalkyl alkylene.

26. The compound of claim 25, wherein $R^{2b}$ is pyrrolidinyl methylene.

27. The compound of claim 20, wherein $R^{2b}$ is pyrrolidine.

28. The compound of claim 1, wherein $Q^{1a}$ is $Q^{1c}$.

29. The compound of claim 28, wherein $Q^{1c}$ is $Q^{1d}$, $Q^{1d}$ is $-C(=O)(Q^{1e})$, $Q^{1e}$ is $Q^{1e'}$, and $Q^{1e'}$ is heterocycloalkyl, optionally substituted with one or more $Q^{1f}$.

30. The compound of claim 28, wherein $Q^{1c}$ is $Q^{1d}$, $Q^{1d}$ is $-O(Q^{1e})$, $Q^{1e}$ is $Q^{1e'}$, and $Q^{1e'}$ is lower alkyl, optionally substituted with one or more $Q^{1f}$.

31. The compound of claim 30, wherein $Q^{1e'}$ is methyl.

32. The compound of claim 30, wherein $Q^{1f}$ is $Q^{1h}$ and $Q^{1h}$ is heterocycloalkyl.

33. The compound of claim 32, wherein $Q^{1h}$ is morpholine.

34. The compound of claim 28, wherein $Q^{1e}$ is $Q^{1e'}$, $Q^{1e'}$, and $(Q^{1e}$ is heterocycloalkyl, optionally substituted with one or more $Q^{1f}$.

35. The compound of claim 34, wherein $Q^{1e'}$ is pyrrolidine, optionally substituted with one or more $Q^{1f}$.

36. The compound of claim 34, wherein $Q^{1e'}$ is piperazine, optionally substituted with one or more $Q^{1f}$.

37. The compound of claim 34, wherein $Q^{1e'}$ is piperidine, optionally substituted with one or more $Q^{1f}$.

38. The compound of claim 34, wherein $Q^{1e'}$ is morpholine, optionally substituted with one or more $Q^{1f}$.

39. The compound of claim 34, wherein $Q^{1e'}$ is pyrrolidinone, optionally substituted with one or more $Q^{1f}$.

40. A pharmaceutical composition comprising the compound of claim 1, admixed with at least one pharmaceutically acceptable carrier, excipient or diluent.

41. A compound of claim 1, selected from the group consisting of:

Phenyl-[2-(3,4,5-trimethoxy-phenyl)-5H-pyrrolo[2,3-b]pyrazin-7-yl]-methanone;

3-Methyl-1-[2-(3,4,5-trimethoxy-phenyl)-5H-pyrrolo[2,3-b]pyrazin-7-yl]-butan-1-one;

1-[2-(3,4,5-Trimethoxy-phenyl)-5H-pyrrolo[2,3-b]pyrazin-7-yl]-ethanone;

1-[2-(3,4-Dimethoxy-phenyl)-5H-pyrrolo[2,3-b]pyrazin-7-yl]-3-methyl-butan-1-one;

1-[2-(5-Fluoro-2-methoxy-phenyl)-5H-pyrrolo[2,3-b]pyrazin-7-yl]-3-methyl-butan-1-one;

3-Methyl-1-[2-(3-pyrrolidin-1-yl-phenyl)-5H-pyrrolo[2,3-b]pyrazin-7-yl]-butan-1-one;

4-[7-(3-Methyl-butyryl)-5H-pyrrolo[2,3-b]pyrazin-2-yl]-benzamide;

3-[7-(3-Methyl-butyryl)-5H-pyrrolo[2,3-b]pyrazin-2-yl]-benzamide;

N-Methyl-3-[7-(3-methyl-butyryl)-5H-pyrrolo[2,3-b]pyrazin-2-yl]-benzamide;

2-(3,4,5-Trimethoxy-phenyl)-5H-pyrrolo[2,3-b]pyrazine-7-carboxylic acid isopropylamide;

1-[2-(3,4-Dimethoxy-phenyl)-5H-pyrrolo[2,3-b]pyrazin-7-yl]-4-methyl-pentan-1-one;

2,2-Dimethyl-1-[2-(3,4,5-trimethoxy-phenyl)-5H-pyrrolo[2,3-b]pyrazin-7-yl]-propan-1-one;

N,N-Dimethyl-3-[7-(3-methyl-butyryl)-5H-pyrrolo[2,3-b]pyrazin-2-yl]-benzamide;

3-Methyl-1-(2-phenyl-5H-pyrrolo[2,3-b]pyrazin-7-yl)-butan-1-one;

2-(3,4,5-Trimethoxy-phenyl)-5H-pyrrolo[2,3-b]pyrazine-7-carboxylic acid (2-methoxy-1-methyl-ethyl)-amide;

2-Methyl-1-[2-(3,4,5-trimethoxy-phenyl)-5H-pyrrolo[2,3-b]pyrazin-7-yl]-propan-1-one;

2-(3,4-Dimethoxy-phenyl)-5H-pyrrolo[2,3-b]pyrazine-7-carboxylic acid isopropylamide;

2-(3,4,5-Trimethoxy-phenyl)-5H-pyrrolo[2,3-b]pyrazine-7-carboxylic acid (tetrahydro-pyran-4-yl)-amide;

2-(3,4-Dimethoxy-phenyl)-5H-pyrrolo[2,3-b]pyrazine-7-carboxylic acid pyrrolidin-3-ylamide;

2-(3,4-Dimethoxy-phenyl)-5H-pyrrolo[2,3-b]pyrazine-7-carboxylic acid cyclobutylamide;

2-(3,4-Dimethoxy-phenyl)-5H-pyrrolo[2,3-b]pyrazine-7-carboxylic acid (2-methoxy-1-methoxymethyl-ethyl)-amide;

2-(3,4-Dimethoxy-phenyl)-5H-pyrrolo[2,3-b]pyrazine-7-carboxylic acid isopropyl-methyl-amide;

2-(3,4-Dimethoxy-phenyl)-5H-pyrrolo[2,3-b]pyrazine-7-carboxylic acid tert-butylamide;

2-(3,4-Dimethoxy-phenyl)-5H-pyrrolo[2,3-b]pyrazine-7-carboxylic acid (2-methoxy-1-methyl-ethyl)-amide;

1-[2-(3,4-Dimethoxy-phenyl)-5H-pyrrolo[2,3-b]pyrazin-7-yl]-3,3-dimethyl-butan-1-one;

2-(3,4-Dimethoxy-phenyl)-5H-pyrrolo[2,3-b]pyrazine-7-carboxylic acid (2-hydroxy-1-hydroxymethyl-ethyl)-amide;

(2-{([2-(3,4-Dimethoxy-phenyl)-5H-pyrrolo[2,3-b]pyrazine-7-carbonyl]-amino}-2-methyl-propyl)-carbamic acid tert-butyl ester;

2-(3,4-Dimethoxy-phenyl)-5H-pyrrolo[2,3-b]pyrazine-7-carboxylic acid (2-hydroxy-1-methyl-ethyl)-amide;

2-(3,4-Dimethoxy-phenyl)-5H-pyrrolo[2,3-b]pyrazine-7-carboxylic acid (2-amino-1,1-dimethyl-ethyl)-amide;

2-(3-Pyrrolidin-1-yl-phenyl)-5H-pyrrolo[2,3-b]pyrazine-7-carboxylic acid tert-butylamide;

2-(3,4-Dimethoxy-phenyl)-5H-pyrrolo[2,3-b]pyrazine-7-carboxylic acid(1S,2R)-2-carbamoyl-cyclopentyl)-amide;
2-(3,4-Dimethoxy-phenyl)-5H-pyrrolo[2,3-b]pyrazine-7-carboxylic acid (tetrahydro-pyran-4-yl)-amide;
2-(3,4-Dimethoxy-phenyl)-5H-pyrrolo[2,3-b]pyrazine-7-carboxylic acid piperidin-4-ylamide;
6-Methyl-2-(3,4,5-trimethoxy-phenyl)-5H-pyrrolo[2,3-b]pyrazine-7-carboxylic acid tert-butylamide;
1-[2-(3,4-Dimethoxy-phenyl)-5H-pyrrolo[2,3-b]pyrazin-7-yl]-2,2-dimethyl-propan-1-one;
2-Cyclohexyl-1-[2-(3,4,5-trimethoxy-phenyl)-5H-pyrrolo[2,3-b]pyrazin-7-yl]-ethanone;
2-(3-Methanesulfonyl-phenyl)-5H-pyrrolo[2,3-b]pyrazine-7-carboxylic acid isopropylamide;
2-(2-Methoxy-phenyl)-5H-pyrrolo[2,3-b]pyrazine-7-carboxylic acid isopropylamide;
1-Phenyl-2-[2-(3,4,5-trimethoxy-phenyl)-5H-pyrrolo[2,3-b]pyrazin-7-yl]-ethane-1,2-dione;
2,2-Dimethyl-1-{2-[4-(2-morpholin-4-yl-ethoxy)-phenyl]-5H-pyrrolo[2,3-b]pyrazin-7-yl}-propan-1-one;
2,2-Dimethyl-1-{2-[3-(2-morpholin-4-yl-ethoxy)-phenyl]-5H-pyrrolo[2,3-b]pyrazin-7-yl}-propan-1-one;
4-{4-[7-(2,2-Dimethyl-propionyl)-5H-pyrrolo[2,3-b]pyrazin-2-yl]-phenyl}-piperazine-1-carboxylic acid tert-butyl ester;
Pyrrolidin-3-yl-[2-(3,4,5-trimethoxy-phenyl)-5H-pyrrolo[2,3-b]pyrazin-7-yl]-methanone; compound with trifluoro-acetic acid;
4-{3-[7-(2,2-Dimethyl-propionyl)-5H-pyrrolo[2,3-b]pyrazin-2-yl]-phenyl}-piperazine-1-carboxylic acid tert-butyl ester;
2,2-Dimethyl-1-[2-(4-piperazin-1-yl-phenyl)-5H-pyrrolo[2,3-b]pyrazin-7-yl]-propan-1-one;
2,2-Dimethyl-1-[2-(3-piperazin-1-yl-phenyl)-5H-pyrrolo[2,3-b]pyrazin-7-yl]-propan-1-one;
2-(3-Methylcarbamoyl-phenyl)-5H-pyrrolo[2,3-b]pyrazine-7-carboxylic acid isopropylamide;
2-[3-(1-Hydroxy-1-methyl-ethyl)-phenyl]-5H-pyrrolo[2,3-b]pyrazine-7-carboxylic acid isopropylamide;
2-Phenyl-1-[2-(3,4,5-trimethoxy-phenyl)-5H-pyrrolo[2,3-b]pyrazin-7-yl]-ethanone;
(1-Methyl-cyclopropyl)-[2-(3,4,5-trimethoxy-phenyl)-5H-pyrrolo[2,3-b]pyrazin-7-yl]-methanone;
2-(3,4,5-Trimethoxy-phenyl)-5H-pyrrolo[2,3-b]pyrazine-7-carboxylic acid (3-hydroxy-2,2-dimethyl-propyl)-amide;
(3-Methyl-oxetan-3-yl)-[2-(3,4,5-trimethoxy-phenyl)-5H-pyrrolo[2,3-b]pyrazin-7-yl]-methanone;
(4-Methyl-tetrahydro-pyran-4-yl)-[2-(3,4,5-trimethoxy-phenyl)-5H-pyrrolo[2,3-b]pyrazin-7-yl]-methanone;
[2-(3,4,5-Trimethoxy-phenyl)-5H-pyrrolo[2,3-b]pyrazin-7-yl]-(2,2,5-trimethyl-[1,3]dioxan-5-yl)-methanone;
3-Hydroxy-2-hydroxymethyl-2-methyl-1-[2-(3,4,5-trimethoxy-phenyl)-5H-pyrrolo[2,3-b]pyrazin-7-yl]-propan-1-one;
2,2-Diethoxy-1-[2-(3,4,5-trimethoxy-phenyl)-5H-pyrrolo[2,3-b]pyrazin-7-yl]-propan-1-one;
2-(3-Methoxy-phenyl)-5H-pyrrolo[2,3-b]pyrazine-7-carboxylic acid isopropylamide;
2-(5-Chloro-2-methoxy-phenyl)-5H-pyrrolo[2,3-b]pyrazine-7-carboxylic acid isopropylamide;
3,3-Dimethyl-1-[2-(3-morpholin-4-yl-phenyl)-5H-pyrrolo[2,3-b]pyrazin-7-yl]-butan-1-one;
3,3-Dimethyl-1-[2-(3-pyrrolidin-1-yl-phenyl)-5H-pyrrolo[2,3-b]pyrazin-7-yl]-butan-1-one;
2-[3-(Pyrrolidine-1-carbonyl)-phenyl]-5H-pyrrolo[2,3-b]pyrazin-7-carboxylic acid isopropylamide;
2-(2-Chloro-phenyl)-5H-pyrrolo[2,3-b]pyrazine-7-carboxylic acid isopropylamide;
1-[2-(3,4,5-Trimethoxy-phenyl)-5H-pyrrolo[2,3-b]pyrazin-7-yl]-propane-1,2-dione;
2,2-Dimethyl-1-[2-(3-pyrrolidin-1-yl-phenyl)-5H-pyrrolo[2,3-b]pyrazin-7-yl]-propan-1-one;
3-Methyl-3-[2-(3,4,5-trimethoxy-phenyl)-5H-pyrrolo[2,3-b]pyrazine-7-carbonyl]-piperidine-1-carboxylic acid tert-butyl ester;
2-(2-Trifluoromethoxy-phenyl)-5H-pyrrolo[2,3-b]pyrazine-7-carboxylic acid isopropylamide;
(3-Methyl-piperidin-3-yl)-[2-(3,4,5-trimethoxy-phenyl)-5H-pyrrolo[2,3-b]pyrazin-7-yl]-methanone;
2-(3,4,5-Trimethoxy-phenyl)-5H-pyrrolo[2,3-b]pyrazine-7-carboxylic acid phenylamide;
3-[7-(2,2-Dimethyl-propionyl)-5H-pyrrolo[2,3-b]pyrazin-2-yl]-benzoic acid tert-butyl ester;
3-(7-Isopropylcarbamoyl-5H-pyrrolo[2,3-b]pyrazin-2-yl)-benzoic acid tert-butyl ester;
3-{3-Methyl-3-[2-(3,4,5-trimethoxy-phenyl)-5H-pyrrolo[2,3-b]pyrazine-7-carbonyl]-piperidin-1-yl}-3-oxo-propionitrile;
2-(3,4-Dimethoxy-phenyl)-5H-pyrrolo[2,3-b]pyrazine-7-carboxylic acid amide;
2-(3,4,5-Trimethoxy-phenyl)-5H-pyrrolo[2,3-b]pyrazine-7-carboxylic acid (2-hydroxy-propyl)-amide;
2-(2,5-Dimethoxy-phenyl)-5H-pyrrolo[2,3-b]pyrazine-7-carboxylic acid isopropylamide;
3,3-Dimethyl-1-[2-(3-morpholin-4-ylmethyl-phenyl)-5H-pyrrolo[2,3-b]pyrazin-7-yl]-butan-1-one;
2-(3-Methylcarbamoyl-phenyl)-5H-pyrrolo[2,3-b]pyrazine-7-carboxylic acid (2-methoxy-1-methyl-ethyl)-amide;
2-(3-Methylcarbamoyl-phenyl)-5H-pyrrolo[2,3-b]pyrazine-7-carboxylic acid ((S)-2-methoxy-1-methyl-ethyl)-amide;
(4-Methyl-tetrahydro-thiopyran-4-yl)-[2-(3,4,5-trimethoxy-phenyl)-5H-pyrrolo[2,3-b]pyrazin-7-yl]-methanone;
2-(2,4-Dimethoxy-phenyl)-5H-pyrrolo[2,3-b]pyrazine-7-carboxylic acid isopropylamide;
(4-Methyl-1,1-dioxo-hexahydro-1$\lambda^6$-thiopyran-4-yl)-[2-(3,4,5-trimethoxy-phenyl)-5H-pyrrolo[2,3-b]pyrazin-7-yl]-methanone;
2-(3,4-Dimethoxy-phenyl)-5H-pyrrolo[2,3-b]pyrazine-7-carboxylic acid (1-acetyl-pyrrolidin-3-yl)-amide;
2-(3,4,5-Trimethoxy-phenyl)-5H-pyrrolo[2,3-b]pyrazine-7-carboxylic acid (2-methoxy-propyl)-amide;
2-({[2-(3,4,5-Trimethoxy-phenyl)-5H-pyrrolo[2,3-b]pyrazine-7-carbonyl]-amino}-methyl)-pyrrolidine-1-carboxylic acid tert-butyl ester;
2-(3,4-Dimethoxy-phenyl)-5H-pyrrolo[2,3-b]pyrazine-7-carboxylic acid (1-acetyl-piperidin-4-yl)-amide;
2-(3,4-Dimethoxy-phenyl)-5H-pyrrolo[2,3-b]pyrazine-7-carboxylic acid (1-methyl-pyrrolidin-3-yl)-amide;
2-[3-(3-Methoxy-pyrrolidin-1-yl)-phenyl]-5H-pyrrolo[2,3-b]pyrazine-7-carboxylic acid tert-butylamide;
2-[3-(3-Methoxy-pyrrolidin-1-yl)-phenyl]-5H-pyrrolo[2,3-b]pyrazine-7-carboxylic acid ((S)-2-methoxy-1-methyl-ethyl)-amide;
2-(3,4,5-Trimethoxy-phenyl)-5H-pyrrolo[2,3-b]pyrazine-7-carboxylic acid (tetrahydro-pyran-3-yl)-amide;
2-Methyl-2-[2-(3,4,5-trimethoxy-phenyl)-5H-pyrrolo[2,3-b]pyrazine-7-carbonyl]-pyrrolidine-1-carboxylic acid tert-butyl ester;

(2-Methyl-pyrrolidin-2-yl)-[2-(3,4,5-trimethoxy-phenyl)-5H-pyrrolo[2,3-b]pyrazin-7-yl]-methanone;

2-Phenyl-1-[2-(3,4,5-trimethoxy-phenyl)-5H-pyrrolo[2,3-b]pyrazin-7-yl]-propan-1-one;

2-(3,4,5-Trimethoxy-phenyl)-5H-pyrrolo[2,3-b]pyrazine-7-carboxylic acid (4-hydroxy-cyclohexyl)-amide;

2-(3,4,5-Trimethoxy-phenyl)-5H-pyrrolo[2,3-b]pyrazine-7-carboxylic acid (1,1-dioxo-tetrahydro-1$\lambda^6$-thiophen-3-yl)-amide;

2-(3,4,5-Trimethoxy-phenyl)-5H-pyrrolo[2,3-b]pyrazine-7-carboxylic acid (pyrrolidin-2-ylmethyl)-amide;

2-(3,4,5-Trimethoxy-phenyl)-5H-pyrrolo[2,3-b]pyrazine-7-carboxylic acid (1-acetyl-pyrrolidin-2-ylmethyl)-amide;

3-({[2-(3,4,5-Trimethoxy-phenyl)-5H-pyrrolo[2,3-b]pyrazine-7-carbonyl]-amino}-methyl)-pyrrolidine-1-carboxylic acid tea-butyl ester;

2-(3,4,5-Trimethoxy-phenyl)-5H-pyrrolo[2,3-b]pyrazine-7-carboxylic acid (pyrrolidin-3-ylmethyl)-amide;

2-(3,4,5-Trimethoxy-phenyl)-5H-pyrrolo[2,3-b]pyrazine-7-carboxylic acid (1-acetyl-pyrrolidin-3-ylmethyl)-amide;

1-{2-[4-(4-Acetyl-piperazin-1-yl)-phenyl]-5H-pyrrolo[2,3-b]pyrazin-7-yl}-2,2-dimethyl-propan-1-one;

1-{2-[3-(4-Acetyl-piperazin-1-yl)-phenyl]-5H-pyrrolo[2,3-b]pyrazin-7-yl}-2,2-dimethyl-propan-1-one;

2-(3-Dimethylamino-phenyl)-5H-pyrrolo[2,3-b]pyrazine-7-carboxylic acid isopropylamide;

2-Methyl-2-(tetrahydro-pyran-2-yloxy)-1-[2-(3,4,5-trimethoxy-phenyl)-5H-pyrrolo[2,3-b]pyrazin-7-yl]-propan-1-one;

3,3-Dimethyl-1-[2-(3,4,5-trimethoxy-phenyl)-5H-pyrrolo[2,3-b]pyrazin-7-yl]-butan-1-one;

2-[3-(2-Oxo-pyrrolidin-1-yl)-phenyl]-5H-pyrrolo-[2,3-b]pyrazine-7-carboxylic acid tert-butylamide;

2-(3,4,5-Trimethoxy-phenyl)-5H-pyrrolo[2,3-b]pyrazine-7-carboxylic acid (1-ethylcarbamoyl-pyrrolidin-3-ylmethyl)-amide;

2-(3,4,5-Trimethoxy-phenyl)-5H-pyrrolo[2,3-b]pyrazine-7-carboxylic acid (piperidin-4-ylmethyl)-amide;

2-(3,4,5-Trimethoxy-phenyl)-5H-pyrrolo[2,3-b]pyrazine-7-carboxylic acid (1-acetyl-piperidin-4-ylmethyl)-amide;

2-(3,4,5-Trimethoxy-phenyl)-5H-pyrrolo[2,3-b]pyrazine-7-carboxylic acid isobutyl-amide;

2-(3,4,5-Trimethoxy-phenyl)-5H-pyrrolo[2,3-b]pyrazine-7-carboxylic acid (2-methanesulfonyl-ethyl)-amide;

2-(3,4,5-Trimethoxy-phenyl)-5H-pyrrolo[2,3-b]pyrazine-7-carboxylic acid (2-sulfamoyl-ethyl)-amide 2-(3,4,5-Trimethoxy-phenyl)-5H-pyrrolo[2,3-b]pyrazine-7-carboxylic acid (2,3-dihydroxy-propyl)-amide 2-(3,4,5-Trimethoxy-phenyl)-5H-pyrrolo[2,3-b]pyrazine-7-carboxylic acid (tetrahydro-furan-3-yl)-amide;

1-{2-Methyl-2-[2-(3,4,5-trimethoxy-phenyl)-5H-pyrrolo[2,3-b]pyrazine-7-carbonyl]-pyrrolidin-1-yl}-ethanone;

2,2-Dimethyl-1-[2-(3,4,5-trimethoxy-phenyl)-5H-pyrrolo[2,3-b]pyrazin-7-yl]-butan-1-one;

2,2-Dimethyl-1-[2-(3-pyrazol-1-yl-phenyl)-5H-pyrrolo[2,3-b]pyrazin-7-yl]-propan-1-one;

2-(3-Chloro-5-fluoro-phenyl)-5H-pyrrolo[2,3-b]pyrazine-7-carboxylic acid isopropylamide;

(1-Methyl-cyclohexyl)-[2-(3,4,5-trimethoxy-phenyl)-5H-pyrrolo[2,3-b]pyrazin-7-yl]-methanone;

3,3,3-Trifluoro-2-methyl-2-trifluoromethyl-1-[2-(3,4,5-trimethoxy-phenyl)-5H-pyrrolo[2,3-b]pyrazin-7-yl]-propan-1-one;

1-[2-(3-Fluoro-phenyl)-5H-pyrrolo[2,3-b]pyrazin-7-yl]-2,2-dim ethyl-propan-1-one;

2-(3,4,5-Trimethoxy-phenyl)-5H-pyrrolo[2,3-b]pyrazine-7-carboxylic acid (2 methoxy-ethyl)-amide;

2,2-Dimethyl-1-{2-[3-(5-methyl-[1,3,4]oxadiazol-2-yl)-phenyl]-5-pyrrolo[2,3-b]pyrazin-7-yl}-propan-1-one;

2-(3,4,5-Trimethoxy-phenyl)-5H-pyrrolo[2,3-b]pyrazine-7-carboxylic acid (2,2-dimethyl-propyl)-amide;

2-(3,4,5-Trimethoxy-phenyl)-5H-pyrrolo[2,3-b]pyrazine-7-carboxylic acid (2-methoxy-2-methyl-propyl)-amide;

2,2-Dimethyl-1-[2-(4-pyrrolidin-1-yl-phenyl)-5H-pyrrolo[2,3-b]pyrazin-7-yl]-propan-1-one;

1-[2-(3-Dimethylamino-phenyl)-5H-pyrrolo[2,3-b]pyrazin-7-yl]-2,2-dimethyl-propan-1-one;

2,2-Dimethyl-1-{2-[3-(2H-pyrazol-3-yl)-phenyl]-5H-pyrrolo[2,3-b]pyrazin-7-yl}-propan-1-one;

2-(3,4,5-Trimethoxy-phenyl)-5H-pyrrolo[2,3-b]pyrazine-7-carboxylic acid (3-methoxy-propyl)-amide;

1-[2-(4-Methoxy-phenyl)-5H-pyrrolo[2,3-b]pyrazin-7-yl]-2,2-dimethyl-propan-1-one;

3-[7-(2,2-Dimethyl-propionyl)-5H-pyrrolo[2,3-b]pyrazin-2-yl]-N-methyl-benzamide;

1-[2-(3-Methoxymethyl-phenyl)-5H-pyrrolo[2,3-b]pyrazin-7-yl]-2,2-dimethyl propan-1-one;

(1-Methyl-cyclohexyl)-[2-(3-pyrrolidin-1-yl-phenyl)-5H-pyrrolo[2,3-b]pyrazin-7-yl]-methanone;

1-[2-(4-Methoxymethyl-phenyl)-5H-pyrrolo[2,3-b]pyrazin-7-yl]-2,2-dimethyl-propan-1-one;

1-[2-(2-Methoxy-phenyl)-5H-pyrrolo[2,3-b]pyrazin-7-yl]-2,2-dimethyl-propan-1-one;

1-[2-(3-Methoxy-phenyl)-5H-pyrrolo[2,3-b]pyrazin-7-yl]-2,2-dimethyl-propan-1-one;

2,2-Dimethyl-1-(2-phenyl-5H-pyrrolo[2,3-b]pyrazin-7-yl)-propan-1-one;

N-Cyclopentyl-3-[7-(2,2-dimethyl-propionyl)-5H-pyrrolo[2,3-b]pyrazin-2-yl]-benzamide;

2,2-Dimethyl-1-[2-(3-piperidin-1-yl-phenyl)-5H-pyrrolo[2,3-b]pyrazin-7-yl]-propan-1-one;

2,2-Dimethyl-1-[2-(3-morpholin-4-yl-phenyl)-5H-pyrrolo[2,3-b]pyrazin-7-yl]-propan-1-one;

3-[7-(2,2-Dimethyl-propionyl)-5H-pyrrolo[2,3-b]pyrazin-2-yl]-benzoic acid;

1-[2-(3-Isopropenyl-phenyl)-5H-pyrrolo[2,3-b]pyrazin-7-yl]-2,2-dimethyl propan-1-one;

1-[2-(3-Hydroxy-phenyl)-5H-pyrrolo[2,3-b]pyrazin-7-yl]-2,2-dimethyl-propan-1-one;

(1-Methyl-cyclopentyl)-[2-(3-pyrrolidin-1-yl-phenyl)-5H-pyrrolo[2,3-b]pyrazin-7-yl]-methanone;

4-Methoxy-1-[2-(3,4,5-trimethoxy-phenyl)-5H-pyrrolo[2,3-b]pyrazin-7-yl]-pentan-1-one;

(1-Methyl-cycloheptyl)-[2-(3-pyrrolidin-1-yl-phenyl)-5H-pyrrolo[2,3-b]pyrazin-7-yl]-methanone;

1-[2-(3-Ethylamino-phenyl)-5H-pyrrolo[2,3-b]pyrazin-7-yl]-2,2-dimethyl-propan-1-one;

1-[2-(3-Diethylamino-phenyl)-5H-pyrrolo[2,3-b]pyrazin-7-yl]-2,2-dimethyl-propan-1-one;

1-[2-(3-Amino-phenyl)-5H-pyrrolo[2,3-b]pyrazin-7-yl]-2,2-dimethyl-propan-1-one;

1-[2-(3-Methoxy-5-thiomorpholin-4-yl-phenyl)-5H-pyrrolo[2,3-b]pyrazin-7-yl]-2,2-dimethyl-propan-1-one;

1-{2-[3-Methoxy-5-(1-oxo-1$\lambda^4$-thiomorpholin-4-yl)-phenyl]-5H-pyrrolo[2,3-b]pyrazin-7-yl}-2,2-dimethyl-propan-1-one;

1-{2-[3-(1,1-Dioxo-1$\lambda^6$-thiomorpholin-4-yl)-5-methoxy-phenyl]-5H-pyrrolo[2,3-b]pyrazin-7-yl}-2,2-dimethyl-propan-1-one;

1-[2-(3-Methoxymethoxy-5-pyrrolidin-1-yl-phenyl)-5H-pyrrolo[2,3-b]pyrazin-7-yl]-2,2-dimethyl-propan-1-one;

1-[2-(3-Isopropoxy-5-pyrrolidin-1-yl-phenyl)-5H-pyrrolo[2,3-b]pyrazin-7-yl]-2,2-dimethyl-propan-1-one;

1-[2-(3-Ethoxy-5-pyrrolidin-1-yl-phenyl)-5H-pyrrolo[2,3-b]pyrazin-7-yl]-2,2-dimethyl-propan-1-one;

1-[2-(3-Hydroxy-5-pyrrolidin-1-yl-phenyl)-5H-pyrrolo[2,3-b]pyrazin-7-yl]-2,2-dimethyl-propan-1-one;

[2-(3-Methoxy-5-thiomorpholin-4-yl-phenyl)-5H-pyrrolo[2,3-b]pyrazin-7-yl]-(1-methyl-cyclohexyl)-methanone;

{2-[3-(1,1-Dioxo-1$\lambda^6$-thiomorpholin-4-yl)-5-methoxy-phenyl]-5H-pyrrolo[2,3-b]pyrazin-7-yl}-(1-methyl-cyclohexyl)-methanone;

{2-[3-Methoxy-5-(1-oxo-1$\lambda^4$-thiomorpholin-4-yl)-phenyl]-5H-pyrrolo[2,3-b]pyrazin-7-yl}-(1-methyl-cyclohexyl)-methanone;

1-{2-[3-(2,3-Dihydroxy-propoxy)-5-(1,1-dioxo-1$\lambda^6$-thiomorpholin-4-yl)-phenyl]-5H-pyrrolo[2,3-b]pyrazin-7-yl}-2,2-dimethyl-propan-1-one;

1-{2-[3-(3-Methanesulfonyl-propoxy)-5-pyrrolidin-1-yl-phenyl]-5H-pyrrolo[2,3-b]pyrazin-7-yl}-2,2-dimethyl-propan-1-one;

1-{2-[3-(2-Dimethylamino-ethoxy)-5-(1,1-dioxo-1$\lambda^6$-thiomorpholin-4-yl)-phenyl]-5H-pyrrolo[2,3-b]pyrazin-7-yl}-2,2-dimethyl-propan-1-one;

1-{2-[3-(1,1-Dioxo-1$\lambda^6$-thiomorpholin-4-yl)-5-(2-hydroxy-1-methyl-ethoxy)-phenyl]-5H-pyrrolo[2,3-b]pyrazin-7-yl}-2,2-dimethyl-propan-1-one;

1-{2-[3-(2-Methanesulfonyl-ethoxy)-5-pyrrolidin-1-yl-phenyl]-5H-pyrrolo[2,3-b]pyrazin-7-yl}-2,2-dimethyl-propan-1-one;

1-{2-[3-(1,1-Dioxo-1$\lambda^6$-thiomorpholin-4-yl)-5-(1-methyl-pyrrolidin-3-yloxy)-phenyl]-5H-pyrrolo[2,3-b]pyrazin-7-yl}-2,2-dimethyl-propan-1-one;

1-{2-[3-(1,1-Dioxo-1$\lambda^6$-thiomorpholin-4-yl)-5-(1-methyl-piperidin-4-yloxy)-phenyl]-5H-pyrrolo[2,3-b]pyrazin-7-yl}-2,2-dimethyl-propan-1-one;

1-{2-[3-(1,1-Dioxo-1$\lambda^6$-thiomorpholin-4-yl)-5-(2-hydroxy-1-hydroxymethyl-ethoxy)-phenyl]-5H-pyrrolo[2,3-b]pyrazin-7-yl}-2,2-dimethyl-propan-1-one;

1-{2-[3-(2-Dimethylamino-ethoxy)-5-(3,3-dimethyl-pyrrolidin-1-yl)-phenyl]-5H-pyrrolo[2,3-b]pyrazin-7-yl}-2,2-dimethyl-propan-1-one;

1-{2-[3-(2,3-Dihydroxy-propoxy)-5-(3,3-dimethyl-pyrrolidin-1-yl)-phenyl]-5H-pyrrolo[2,3-b]pyrazin-7-yl}-2,2-dimethyl-propan-1-one;

2,2-Dimethyl-1-{2-[3-(2-thia-7-aza-spiro[4.4]non-7-yl))-phenyl]-5H-pyrrolo[2,3-b]pyrazin-7-yl}-propan-1-one;

1-{2-[3-(2,2-Dioxo-2$\lambda^6$-thia-7-aza-spiro[4.4]non-7-yl)-phenyl]-5H-pyrrolo[2,3-b]pyrazin-7-yl}-2,2-dimethyl-propan-1-one;

2,2-Dimethyl-1-{2-[3-(2-oxo-2$\lambda^4$-thia-7-aza-spiro[4.4]non-7-yl)-phenyl]-5H-pyrrolo[2,3-b]pyrazin-7-yl}-propan-1-one;

2,2-Dimethyl-1-[2-[3-(3-trifluoromethyl-5,6-dihydro-8H-[1,2,4]triazolo[4,3-a]pyrazin-7-ylmethyl)-phenyl]-5H-pyrrolo[2,3-b]pyrazin-7-yl]-propan-1-one;

1-{2-[3-(5,6-Dihydro-8H-[1,2,4]triazolo[4,3-a]pyrazin-7-ylmethyl)-phenyl]-5H-pyrrolo[2,3-b]pyrazin-7-yl}-2,2-dimethyl-propan-1-one;

2,2-Dimethyl-1-{2-[4-(3-trifluoromethyl-5,6-dihydro-8H-[1,2,4]-triazolo[4,3-a]pyrazin-7-ylmethyl)-phenyl]-5H-pyrrolo[2,3-b]pyrazin-7-yl}-propan-1-one;

4-{3-[7-(2,2-Dimethyl-propionyl)-5H-pyrrolo[2,3-b]pyrazin-2-yl]-phenyl}1,5-dimethyl-piperazin-2-one;

[2-(3-Cyclopentylamino-phenyl)-5H-pyrrolo[2,3-b]pyrazin-7-yl]-(1-methyl-cyclohexyl)-methanone;

{2-[3-(Cyclopentyl-methyl-amino)-phenyl]-5H-pyrrolo[2,3-b]pyrazin-7-yl}-(1-methyl-cyclohexyl)-methanone;

1-[2-(3-Cyclopentylamino-phenyl)-5H-pyrrolo[2,3-b]pyrazin-7-yl]-2,2-dimethyl-propan-1-one;

1-{2-[3-(2-Hydroxy-cyclopentylamino)-phenyl]-5H-pyrrolo[2,3-b]pyrazin-7-yl}-2,2-dimethyl-propan-1-one;

3-Methyl-4-{3-[7-(1-methyl-cyclohexanecarbonyl)-5H-pyrrolo[2,3-b]pyrazin-2-yl]-phenyl}-piperazin-2-one;

1-(2-{3-[4-(2-Hydroxy-acetyl)-piperazin-yl]-phenyl}-5H-pyrrolo[2,3-b]pyrazin-7-yl)-2,2-dimethyl-propan-1-one;

2,2-Dimethyl-1-{2-[3-(1-methyl-pyrrolidin-3-ylamino)-phenyl]-5H-pyrrolo[2,3-b]pyrazin-7-yl}-propan-1-one;

2,2-Dimethyl-1-{2-[3-(tetrahydro-furan-3-ylamino)-phenyl]-5H-pyrrolo[2,3-b]pyrazin-7-yl}-propan-1-one;

1-(2-{3-[4-(2-Hydroxy-acetyl)-piperazin-1-yl]-phenyl}-5H-pyrrolo[2,3-b]pyrazin-7-yl)-2,2-dimethyl-propan-1-one;

1-(2-{4-[4-(2-Hydroxy-ethyl)-piperazin-1-yl]-phenyl}-5H-pyrrolo[2,3-b]pyrazin-7-yl)-2,2-dimethyl-propan-1-one;

1-[2-(3-Isopropylamino-phenyl)-5H-pyrrolo[2,3-b]pyrazin-7-yl]-2,2-dimethyl-propan-1-one;

1-{2-[3-(4-Methanesulfonyl-piperazin-1-yl)-phenyl]-5H-pyrrolo[2,3-b]pyrazin-7-yl}-2,2-dimethyl-propan-1-one;

1-{2-[4-(4-Methanesulfonyl-piperazin-1-yl)-phenyl]-5H-pyrrolo[2,3-b]pyrazin-7-yl}-2,2-dimethyl-propan-1-one;

1-(2-{3-[4-(2-Hydroxy-ethyl)-piperazin-1-yl]-phenyl}-5H-pyrrolo[2,3-b]pyrazin-7-yl)-2,2-dimethyl-propan-1-one;

1-{2-[3-((1R,2S)-2-Hydroxy-cyclopentylamino)-phenyl]-5H-pyrrolo[2,3-b]pyrazin-7-yl}-2,2-dimethyl-propan-1-one;

1-{2-[3-(1-Methanesulfonyl-piperidin-4-ylamino)-phenyl]-5H-pyrrolo[2,3-b]pyrazin-7-yl}-2,2-dimethyl-propan-1-one;

3-(4-{3-[7-(2,2-Dimethyl-propionyl)-5H-pyrrolo[2,3-b]pyrazin-2-yl]-phenyl}-piperazin-1-yl)-3-oxo-propionitrile;

2,2-Dimethyl-3-oxo-3-[2-(3,4,5-trimethoxy-phenyl)-5H-pyrrolo[2,3-b]pyrazin-7-yl]-propionitrile;

2,2-Dimethyl-3-oxo-3-[2-(3-pyrrolidin-1-yl-phenyl)-5H-pyrrolo[2,3-b]pyrazin-7-yl]-propionitrile;

2,2-Dimethyl-3-phenyl-1-[2-(3-pyrrolidin-1-yl-phenyl)-5H-pyrrolo[2,3-b]pyrazin-7-yl]-propan-1-one;

1-[2-(3-Pyrrolidin-1-yl-phenyl)-5H-pyrrolo[2,3-b]pyrazine-7-carbonyl]-cyclohexanecarbonitrile;

2,2-Dimethyl-3-oxo-3-[2-(3-piperazin-1-yl-phenyl)-5H-pyrrolo[2,3-b]pyrazin-7-yl]-propionitrile;

1-{2-[3-(5,6-Dihydro-8H-[1,2,4]triazolo[4,3-a]pyrazin-7-yl)-phenyl]-5H-pyrrolo[2,3-b]pyrazin-7-yl}-2,2-dimethyl-propan-1-one;

2,2-Dimethyl-1-{2-[3-(3-trifluoromethyl-5,6-dihydro-8H-[1,2,4]triazolo[4,3-a]pyrazin-7-yl)-phenyl]-5H-pyrrolo[2,3-b]pyrazin-7-yl}-propan-1-one;

N-Allyl-N-{2,2-dimethyl-3-oxo-3-[2-(3-pyrrolidin-1-yl-phenyl)-5H-pyrrolo[2,3-b]pyrazin-7-yl]-propyl}-benzenesulfonamide;

2,2-Dimethyl-3-phenyl-1-[2-(3,4,5-trimethoxy-phenyl)-5H-pyrrolo[2,3-b]pyrazin-7-yl]-propan-1-one;
1-[6-Bromo-2-(3-pyrrolidin-1-yl-phenyl)-5H-pyrrolo[2,3-b]pyrazin-7-yl]-2,2-dimethyl-propan-1-one;
1-[2,6-Bis-(3-pyrrolidin-1-yl-phenyl)-5H-pyrrolo[2,3-b]pyrazin-7-yl]-2,2-dimethyl-propan-1-one;
1-[6-Chloro-2-(3-pyrrolidin-1-yl-phenyl)-5H-pyrrolo[2,3-b]pyrazin-7-yl]-2,2-dimethyl-propan-1-one;
2,2-Dimethyl-1-[2-(3,4,5-trimethoxy-phenyl)-5H-pyrrolo[2,3-b]pyrazin-7-yl]-pent-4-yn-1-one;
2,2-Dimethyl-1-[2-(3-piperazin-1-yl-phenyl)-5H-pyrrolo[2,3-b]pyrazin-7-yl]-propan-1-one;
2-{2-Benzenesulfonylamino-4-[7-(2,2-dimethyl-propionyl)-5H-pyrrolo[2,3-b]pyrazin-2-yl]-phenoxy}-2-methyl-propionic acid ethyl ester;
2-(3,4,5-Trimethoxy-phenyl)-5H-pyrrolo[2,3-b]pyrazine-7-carboxylic acid isobutyl-amide;
2-(3,4,5-Trimethoxy-phenyl)-5H-pyrrolo[2,3-b]pyrazine-7-carboxylic acid (2-methanesulfonyl-ethyl)-amide;
2-(3,4,5-Trimethoxy-phenyl)-5H-pyrrolo[2,3-b]pyrazine-7-carboxylic acid (2-sulfamoyl-ethyl)-amide;
2-(3,4,5-Trimethoxy-phenyl)-5H-pyrrolo[2,3-b]pyrazine-7-carboxylic acid (2,3-dihydroxy-propyl)-amide;
2-(3,4,5-Trimethoxy-phenyl)-5H-pyrrolo[2,3-b]pyrazine-7-carboxylic acid (tetrahydro-furan-3-yl)-amide;
2-(3,4,5-Trimethoxy-phenyl)-5H-1-pyrrolo[2,3-b]pyrazine-7-carboxylic acid (2-methoxy-ethyl)-amide;
2-(3,4,5-Trimethoxy-phenyl)-5H-pyrrolo[2,3-b]pyrazine-7-carboxylic acid (2,2-dimethyl-propyl)-amide;
2-(3,4,5-Trimethoxy-phenyl)-5H-pyrrolo[2,3-b]pyrazine-7-carboxylic acid (2-methoxy-2-methyl-propyl)-amide;
2-(3,4,5-Trimethoxy-phenyl)-5H-pyrrolo[2,3-b]pyrazine-7-carboxylic acid (3-methoxy-propyl)-amide;
1-[2-(4-Methoxy-phenyl)-5H-pyrrolo[2,3-b]pyrazin-7-yl]-2,2-dimethyl-propan-1-one;
1-[2-(2-Methoxy-phenyl)-5H-pyrrolo[2,3-b]pyrazin-7-yl]-2,2-dimethyl-propan-1-one;
1-[2-(3-Methoxy-phenyl)-5H-pyrrolo[2,3-b]pyrazin-7-yl]-2,2-dimethyl-propan-1one;
1-[2-(4-Methoxy-3-pyrrolidin-1-yl-phenyl)-5H-pyrrolo[2,3-b]pyrazin-7-yl]-2,2-dimethyl-propan-1-one;
1-[2-(3-Methoxy-5-pyrrolidin-yl-phenyl)-5H-pyrrolo[2,3-b]pyrazin-7-yl]-2,2-dimethyl-propan-1-one;
2,2-Dimethyl-1-[2-(4-methylsulfanyl-3-pyrrolidin-1-yl-phenyl)-5H-pyrrolo[2,3-b]pyrazin-7-yl]-propan-1-one;
1-[2-(4-Methanesulfinyl-3-pyrrolidin-1-yl-phenyl)-5H-pyrrolo[2,3-b]pyrazin-7-yl]-2,2-dimethyl-propan-1-one;
1-{2-[3-(3-Methanesulfonyl-pyrrolidin-1-yl)-phenyl]-5H-pyrrolo[2,3-b]pyrazin-7-yl}-2,2-dimethyl-propan-1-one;
1-{2-[3-(3,3-Dimethyl-pyrrolidin-1-yl)-phenyl]-5H-pyrrolo[2,3-b]pyrazin-7-yl}-2,2-dimethyl-propan-1-one;
1-{2-[3-(3-(3-Methoxy-azetidin-1-yl)-phenyl]-5H-pyrrolo[2,3-b]pyrazin-7-yl}-2,2-dimethyl-propan-1-one;
(4-Methyl-piperidin-4-yl)-[2-(3,4,5-trimethoxy-phenyl)-5H-pyrrolo[2,3-b]pyrazin-7-yl]-methanone;
2-(3-Chloro-5-fluoro-phenyl)-5H-pyrrolo[2,3-b]pyrazine-7-carboxylic acid isopropylamide;
2-[3-(4-Methoxy-benzyloxy)-phenyl]-5H-pyrrolo[2,3-b]pyrazine-7-carboxylic acid isopropylamide;
2-[3-(2-Methoxymethyl-pyrrolidin-1-yl)-phenyl]-5H-pyrrolo[2,3-b]pyrazine-7-carboxylic acid isopropylamide;
1-{2-[3-(3-Methoxy-pyrrolidin-1-yl)-phenyl]-5H-pyrrolo[2,3-b]pyrazin-7-yl}-2,2-dimethyl-propan-1-one;
1-{2-[3-(4-Methoxy-benzyloxy)-phenyl]-5H-pyrrolo[2,3-b]pyrazin-7-yl}-2,2-dimethyl-propan-1-one;
1-[2-(3-Iodo-phenyl)-5H-pyrrolo[2,3-b]pyrazin-7-yl]-2,2-dimethyl-propan-1-one;
1-{2-[3-(3-Ethylamino-pyrrolidin-1-yl)-phenyl]-5H-pyrrolo[2,3-b]pyrazin-7-yl}-2,2-dimethyl-propan-1-one;
((3aS,6aS)-1-Methyl-octahydro-pentalen-1-yl)-[2-(3-pyrrolidin-1-yl-phenyl)-5H-pyrrolo[2,3-b]pyrazin-7-yl]-methanone;
1-{3-[7-(2,2-Dimethyl-propionyl)-5H-pyrrolo[2,3-b]pyrazin-2-yl]-phenyl}-3-methyl-pyrrolidine-3-carboxylic acid methyl ester;
(1-{3-[7-(2,2-Dimethyl-propionyl)-5H-pyrrolo[2,3-b]pyrazin-2-yl]-phenyl}-3-methyl-pyrrolidin-3-yl)-carbamic acid benzyl ester;
1-{3-[7-(2,2-Dimethyl-propionyl)-5H-pyrrolo[2,3-b]pyrazin-2-yl]-phenyl}-3-methyl-pyrrolidine-3-carboxylic acid methylamide;
[2-(3-Iodo-phenyl)-5H-pyrrolo[2,3-b]pyrazin-7-yl]-(1-methyl-cyclohexy)-methanone;
((1S,2S)-1,2-Dimethyl-cyclopentyl)-[2-(3,4,5-trimethoxy-phenyl)-5H-pyrrolo[2,3-b]pyrazin-7-yl]-methanone;
1-{2-[3-(3-Amino-3-methyl-pyrrolidin-1-yl)-phenyl]-5H-pyrrolo[2,3-b]pyrazin-7-yl}-2,2-dimethyl-propan-1-one;
(1-{3-[7-(2,2-Dimethyl-propionyl)-5H-pyrrolo[2,3-b]pyrazin-2-yl]-phenyl}-3-methyl-pyrrolidin-3-yl)-carbamic acid ethyl ester;
(1-{3-[7-(2,2-Dimethyl-propionyl)-5H-pyrrolo[2,3-b]pyrazin-2-yl]-phenyl}-4,4-dimethyl-pyrrolidin-3-yl)-carbamic acid ethyl ester;
3-Methyl-3-[2-(3,4,5-trimethoxy-phenyl)-5H-pyrrolo[2,3-b]pyrazine-7-carbonyl]-cyclopentanone;
1-{2-Methyl-2-[2-(3,4,5-trimethoxy-phenyl)-5H-pyrrolo[2,3-b]pyrazine-7-carbonyl]-pyrrolidin-1-yl}-ethanone;
(1-Methyl-cyclohexyl)-[2-(3,4,5-trimethoxy-phenyl)-5H-pyrrolo[2,3-b]pyrazin-7-yl]-methanone;
(1-Methyl-cyclohexyl)-[2-(3-pyrrolidin-1-yl-phenyl)-5H-pyrrolo[2,3-b]pyrazin-7-yl]-methanone;
3-[7-(2,2-Dimethyl-propionyl)-5H-pyrrolo[2,3-b]pyrazin-2-yl]-benzoic acid;
(1-Methyl-cyclopentyl)-[2-(3-pyrrolidin-1-yl-phenyl)-5H-pyrrolo[2,3-b]pyrazin-7-yl]-methanone;
4-Methoxy-1-[2-(3,4,5-trimethoxy-phenyl)-5H-pyrrolo[2,3-b]pyrazin-7-yl]-pentan-1-one;
(1-Methyl-cycloheptyl)-[2-(3-pyrrolidin-1-yl-phenyl)-5H-pyrrolo[2,3-b]pyrazin-7-yl]-methanone;
2-Methoxy-2-methyl-1-[2-(3,4,5-trimethoxy-phenyl)-5H-pyrrolo[2,3-b]pyrazin-7-yl]-propan-1-one;
2-Methoxy-1-[2-(3,4,5-trimethoxy-phenyl)-5H-pyrrolo[2,3-b]pyrazin-7-yl]-ethanone;
1-[2-(3-Benzyloxy-phenyl)-5H-pyrrolo[2,3-b]pyrazin-7-yl]-2,2-dimethyl-propan-1-one;
1-[2-(3-Ethoxy-phenyl)-5H-pyrrolo[2,3-b]pyrazin-7-yl]-2,2-dimethyl-propan-1-one;
1-[2-(3-Isobutoxy-phenyl)-5H-pyrrolo[2,3-b]pyrazin-7-yl]-2,2-dimethyl-propan-1-one;
1-[2-(3-Isopropoxy-phenyl)-5H-pyrrolo[2,3-b]pyrazin-7-yl]-2,2-dimethyl-propan-1-one;
2,2-Dimethyl-1-[2-(3-propoxy-phenyl)-5H-pyrrolo[2,3-b]pyrazin-7-yl]-propan-1-one;
Adamantan-1-yl-[2-(3,4,5-trimethoxy-phenyl)-5H-pyrrolo[2,3-b]pyrazin-7-yl]-methanone;
3-Methoxy-2,2-dimethyl-1-[2-(3,4,5-trimethoxy-phenyl)-5H-pyrrolo[2,3-b]pyrazin-7-yl]-propan-1-one;

1-[2-(3-Ethyl-phenyl)-5H-pyrrolo[2,3-b]pyrazin-7-yl]-2,
2-dimethyl-propan-1-one;
1-[2-(3,5-Dimethoxy-phenyl)-5H-pyrrolo[2,3-b]pyrazin-
7-yl]-2,2-dimethyl-propan-1-one;
1-{2-[3-(3-Hydroxy-propyl)-phenyl]-5H-pyrrolo[2,3-b]
pyrazin-7-yl}-2,2-dimethyl-propan-1-one;
1-[2-(3-Aminomethyl-phenyl)-5H-pyrrolo[2,3-b]pyrazin-
7-yl]-2,2-dimethyl-propan-1-one;
1-{2-[3-(2-Hydroxy-ethyl)-phenyl]-5H-pyrrolo[2,3-b]
pyrazin-7-yl}-2,2-dimethyl-propan-1-one;
3-Hydroxy-2,2-dimethyl-1-[2-(3,4,5-trimethoxy-phenyl)-
5H-pyrrolo[2,3-b]pyrazin-7-yl]-propan-1-one;
2,2-Dimethyl-1-[2-(3-piperidin-1-ylmethyl-phenyl)-5H-
pyrrolo[2,3-b]pyrazin-7-yl]-propan-1-one;
4-[7-(2,2-Dimethyl-propionyl)-5H-pyrrolo[2,3-b]
pyrazin-2-yl]-benzoic acid;
(1-Methyl-cyclopentyl)-[2-(3,4,5-trimethoxy-phenyl)-
5H-pyrrolo[2,3-b]pyrazin-7-yl]-methanone;
(1-Methyl-cyclohexyl)-[2-(3-morpholin-4-yl-phenyl)-
5H-pyrrolo[2,3-b]pyrazin-7-yl]-ethanone;
4-{3-[7-(1-Methyl-cyclohexanecarbonyl)-5H-pyrrolo[2,
3-b]pyrazin-2-yl]-phenyl}-piperazine-1-carboxylic
acid tert-butyl ester;
(1-Methyl-cyclohexyl)-[2-(3-piperazin-1-yl-phenyl)-5H-
pyrrolo[2,3-b]pyrazin-7-yl]-methanone;
(1-Methyl-cyclopentyl)-[2-(3-morpholin-4-yl-phenyl)-
5H-pyrrolo[2,3-b]pyrazin-7-yl]-methanone;
1-[2-(2-Fluoro-phenyl)-5H-pyrrolo[2,3-b]pyrazin-7-yl]-
2,2-dimethyl-propan-1-one;
1-(4-{3-[7-(1-Methyl-cyclohexanecarbonyl)-5H-pyrrolo
[2,3-b]pyrazin-2-yl]-phenyl}-piperazin-1-yl)-etha-
none;
(1-Methyl-cyclohexyl)-{2-[3-(5-methyl-[1,3,4]oxadia-
zol-2-yl)-phenyl]-5H-pyrrolo[2,3-b]pyrazin-7-yl}-
methanone;
{2-[3-(3-Hydroxy-propyl)-phenyl]-5H-pyrrolo[2,3-b]
pyrazin-7-yl}-(1-methyl-cyclohexyl)-methanone;
4-{4-[7-(1-Methyl-cyclohexanecarbonyl)-5H-pyrrolo[2,
3-b]pyrazin-2-yl]-phenyl}-piperazine-1-carboxylic
acid tert-butyl ester;
[2-(3-Methoxy-phenyl)-5H-pyrrolo[2,3-b]pyrazin-7-yl]-
(1-methyl-cyclohexyl)-methanone;
(1-Methyl-cyclohexyl)-[2-(4-piperazin-1-yl-phenyl)-5H-
pyrrolo[2,3-b]pyrazin-7-yl]-methanone;
1-(4-{4-[7-(1-Methyl-cyclohexanecarbonyl)-5H-pyrrolo
[2,3-b]pyrazin-2-yl]-phenyl}-piperazin-1-yl)-etha-
none;
1-[2-(2-Hydroxy-phenyl)-5H-pyrrolo[2,3-b]pyrazin-7-
yl]-2,2-dimethyl-propan-1-one;
(4-Hydroxy-1-methyl-cyclohexyl)-[2-(3,4,5-trimethoxy-
phenyl)-5H-pyrrolo[2,3-b]pyrazin-7-yl]-methanone;
[2-(4-Dimethylamino-phenyl)-5H-pyrrolo pyrazin-7-yl]-
(1-methyl-cyclohexyl)-methanone;
3-(4-{3-[7-(1-Methyl-cyclohexanecarbonyl)-5H-pyrrolo
[2,3-b]pyrazin-2-yl]-phenyl}-piperazin-1-yl)-3-oxo-
propionitrile;
4-(4-{3-[7-(1-Methyl-cyclohexanecarbonyl)-5H-pyrrolo
[2,3-b]pyrazin-2-yl]-phenyl}-piperazine-1-carbonyl)-
piperidine-1-carboxylic acid tert-butyl ester;
4-{3-[7-(1-Methyl-cyclohexanecarbonyl)-5H-pyrrolo[2,
3-b]pyrazin-2-yl]-phenyl}-piperazine-1-sulfonyl car-
bamic acid tert-butyl ester
{2-[3-(4-Methanesulfonyl-piperazin-1-yl)-phenyl]-5H-
pyrrolo[2,3-b]pyrazin-7-yl}-(1-methyl-cyclohexyl)-
methanone;
4-{3-[7-(1-Methyl-cyclohexanecarbonyl)-5H-pyrrolo[2,
3-b]pyrazin-2-yl]-phenyl}-piperazine-1-sulfonic acid
amide;
(1-Methyl-cyclohexyl)-(2-{3-[4-(piperidine-4-carbonyl-
piperazin-1-yl]-phenyl}-5H-pyrrolo[2,3-b]pyrazin-7-
yl)-methanone;
(1-Methyl-cyclohexyl)-[2-(4-piperidin-1-yl-phenyl)-5H-
pyrrolo[2,3-b]pyrazin-7-yl]-methanone;
[2-(4-Diethylamino-phenyl)-5H-pyrrolo[2,3-b]pyrazin-7-
yl]-(1-methyl-cyclohexyl)-methanone;
(1,3-Dimethyl-cyclohexyl)-[2-(3,4,5-trimethoxy-phenyl)-
5H-pyrrolo[2,3-b]pyrazin-7-yl]-methanone;
(1-Methyl-cyclohexyl)-[2-(4-morpholin-4-yl-phenyl)-
5H-pyrrolo[2,3-b]pyrazin-7-yl]-methanone;
(1-Methyl-cyclohexyl)-{2-[4-(4-methyl-piperazin-1-yl)-
phenyl]-5H-pyrrolo[2,3-b]pyrazin-7-yl}-methanone;
[2-(4-Methylamino-phenyl)-5H-pyrrolo[2,3-b]pyrazin-7-
yl]-(1-methyl-cyclohexyl)-methanone;
(4-Hydroxy-1-methyl-cyclohexyl)-[2-(3,4,5-trimethoxy-
phenyl)-5H-pyrrolo[2,3-b]pyrazin-7-yl]-methanone;
4-[7-(2,2-Dimethyl-propionyl)-5H-pyrrolo[2,3-b]
pyrazin-2-yl]-N-methyl-benzenesulfonamide;
4-[7-(2,2-Dimethyl-propionyl)-5H-pyrrolo[2,3-b]
pyrazin-2-yl]-benzenesulfonamide;
3-[7-(2,2-Dimethyl-propionyl)-5H-pyrrolo[2,3-b]
pyrazin-2-yl]-benzene sulfonamide;
3-[7-(2,2-Dimethyl-propionyl)-5H-pyrrolo[2,3-b]
pyrazin-2-yl]-N-methyl-benzenesulfonamide;
1-{2-[3-(2,8-Diaza-spiro[4.5]dec-2-yl)-phenyl]-5H-pyr-
rolo[2,3-b]pyrazin-7-yl}-2,2-dimethyl-propan-1-one;
1-{2-[3-(2,7-Diaza-spiro[4.4]non-2-yl)-phenyl]-5H-pyr-
rolo[2,3-b]pyrazin-7-yl}-2,2-dimethyl-propan-1-one;
1-{2-[3-(3-Aminomethyl-pyrrolidin-1-yl)-phenyl]-5H-
pyrrolo[2,3-b]pyrazin-7-yl}-2,2-dimethyl-propan-1-
one;
1-{2-[3-(3,3-Dimethyl-piperazin-1-yl)-phenyl]-5H-pyr-
rolo[2,3-b]pyrazin-7-yl}-2,2-dimethyl-propan-1-one;
1{-2-[3-(2,7-Diaza-spiro[4.5]dec-2-yl)-phenyl]-5H-pyr-
rolo[2,3-b]pyrazin-7-yl}-2,2-dimethyl-propan-1-one;
1-{2-[3-(3-Dimethylamino-pyrrolidin-1-yl)-phenyl]-5H-
pyrrolo[2,3-b]pyrazin-7-yl}-2,2-dimethyl-propan-1-
one;
1-{2-[3-(2-Hydroxy-2-methyl-propylamino)-phenyl]-5H-
pyrrolo[2,3-b]pyrazin-7-yl}-2,2-dimethyl-propan-1-
one;
1-{2-[3-(4-Amino-piperidin-1-yl)-phenyl]-5H-pyrrol[2,
3-b]pyrazin-7-yl}-2,2-dimethyl-propan-1-one;
2,2-Dimethyl-1-{2-[3-(3-methyl-piperazin-1-yl)-phenyl]-
5H-pyrrolo[2,3-b]pyrazin-7-yl}-propan-1-one;
1-{2-[3-(4-Acetyl-3,3-dimethyl-piperazin-1-yl)-phenyl]-
5H-pyrrolo[2,3-b]pyrazin-7-yl}-2,2-dimethyl-propan-
1-one;
1-{2-[3-(3-Amino-azetidin-1-yl)-phenyl]-5H-pyrrolo[2,
3-b]pyrazin-7-yl}-2,2-dimethyl-propan-1-one;
1-{2-[3-(3-Chloro-2-hydroxy-propylamino)-phenyl]-5H-
pyrrolo[2,3-b]pyrazin-7-yl}-2,2-dimethyl-propan-1-
one;
1-{2-[3-(2,2-Dimethyl-propylamino)-phenyl]-5H-pyrrolo
[2,3-b]pyrazin-7-yl}-2,2-dimethyl-propan-1-one;
2,2-Dimethyl-1-[2-(3-pyrrolidin-1-yl-phenyl)-5H-pyrrolo
[2,3-b]pyrazin-7-yl]-propan-1-one;
(1-Methyl-cyclohexyl)-[2-(3,4,5-trimethoxy-phenyl)-5H-
pyrrolo[2,3-b]pyrazin-7-yl]-methanone;
1-[2-(3-Fluoro-phenyl)-5H-pyrrolo[2,3-b]pyrazin-7-yl]-
2,2-dimethyl-propan-1-one;
(1-Methyl-cyclohexyl)-[2-(3-pyrrolidin-1-yl-phenyl)-5H-
pyrrolo[2,3-b]pyrazin-7-yl]-methanone;

2,2-Dimethyl-1-(2-phenyl-5H-pyrrolo[2,3-b]pyrazin-7-yl)-propan-1-one;
2,2-Dimethyl-1-[2-(3,4,5-trimethoxy-phenyl)-5H-pyrrolo[2,3-b]pyrazin-7-yl]-pent-4-en-1-one;
2,2-Dimethyl-1-[2-(3,4,5-trimethoxy-phenyl)-5H-pyrrolo[2,3-b]pyrazin-7-yl]-pentan-1-one,
2,2-Dimethyl-4-morpholin-4-yl-1-[2-(3,4,5-trimethoxy-phenyl)-5H-pyrrolo[2,3-b]pyrazin-7-yl]-butan-1-one;
4,4-Dimethyl-5-oxo-5-[2-(3,4,5-trimethoxy-phenyl)-5H-pyrrolo[2,3-b]pyrazin-7-yl]-pentanenitrile;
5,5-Dimethyl-6-oxo-6-[2-(3,4,5-trimethoxy-phenyl)-5H-pyrrolo[2,3-b]pyrazin-7-yl]-hexanenitrile;
2,2-Dimethyl-1-[2-(3-pyrazol-1-yl-phenyl)-5H-pyrrolo[2,3-b]pyrazin-7-yl]-propan-1-one;
2,2-Dimethyl-1-{2-[3-(5-methyl-[1,3,4]oxadiazol-2-yl)-phenyl]-5H-pyrrolo[2,3-b]pyrazin-7-yl}-propan-1-one;
2,2-Dimethyl-1-{2-[3-(2H-pyrazol-3-yl)-phenyl]-5H-pyrrolo[2,3-b]pyrazin-7-yl}-propan-1-one;
3-[7-(2,2-Dimethyl-propionyl)-5H-pyrrolo[2,3-b]pyrazin-2-yl]-N-methyl-benzamide;
1-[2-(3-Methoxymethyl-phenyl)-5H-pyrrolo[2,3-b]pyrazin-7-yl]-2,2-dimethyl-propan-1-one;
1-[2-(4-Methoxymethyl-phenyl)-5H-pyrrolo[2,3-b]pyrazin-7-yl]-2,2-dimethyl-propan-1-one;
N-Cyclopentyl-3-[7-(2,2-dimethyl-propionyl)-5H-pyrrolo[2,3-b]pyrazin-2-yl]-benzamide;
3-[7-(2,2-Dimethyl-propionyl)-5H-pyrrolo[2,3-b]pyrazin-2-yl]-benzoic acid;
1-[2-(3-Isopropenyl-phenyl)-5H-pyrrolo[2,3-b]pyrazin-7-yl]-2,2-dimethyl-propan-1-one;
1-[2-(3-Hydroxy-phenyl)-5H-pyrrolo[2,3-b]pyrazin-7-yl]-2,2-dimethyl-propan-1-one;
1-[2-(3-tert-Butyl-5-methyl-phenyl)-5H-pyrrolo[2,3-b]pyrazin-7-yl]-2,2-dimethyl-propan-1-one;
1-(2-Biphenyl-3-yl-5H-pyrrolo[2,3-b]pyrazin-7-yl)-2,2-dimethyl-propan-1-one;
1-[2-(3-tert-Butoxymethyl-phenyl)-5H-pyrrolo[2,3-b]pyrazin-7-yl]-2,2-dimethyl-propan-1-one;
1-[2-(3-Isopropyl-phenyl)-5H-pyrrolo[2,3-b]pyrazin-7-yl]-2,2-dimethyl-propan-1-one;
1-{2-[3-(3,5-Dimethyl-isoxazol-4-yl)-phenyl]-5H-pyrrolo[2,3-b]pyrazin-7-yl}-2,2-dimethyl-propan-1-one;
1-[2-(3-Bromo-phenyl)-5H-pyrrolo[2,3-b]pyrazin-7-yl]-2,2-dimethyl-propan-1-one;
2,2-Dimethyl-1-{2-[3-(2-methyl-2H-pyrazol-3-yl)-phenyl]-5H-pyrrolo[2,3-b]pyrazin-7-yl}-propan-1-one;
1-[2-(3-Chloro-4-fluoro-phenyl)-5H-pyrrolo[2,3-b]pyrazin-7-yl]-2,2-dimethyl-propan-1-one;
2,2-Dimethyl-1-[2-(2'-methyl-biphenyl-3-yl)-5H-pyrrolo[2,3-b]pyrazin-7-yl]-propan-1-one;
1-[2-(3-Hydroxymethyl-phenyl)-5H-pyrrolo[2,3-b]pyrazin-7-yl]-2,2-dimethyl-propan-1-one;
1-[2-(3-Cyclopent-1-enyl-phenyl)-5H-pyrrolo[2,3-b]pyrazin-7-yl]-2,2-dimethyl-propan-1-one;
1-[2-(3-Acetyl-4-hydroxy-phenyl)-5H-pyrrolo[2,3-b]pyrazin-7-yl]-2,2-dimethyl-propan-1-one;
1-{2-[3-(3H-Imidazol-4-yl-phenyl]-5H-pyrrolo[2,3-b]pyrazin-7-yl}-2,2-dimethyl-propan-1-one;
2,2-Dimethyl-1-[2-(3-oxazol-5-yl-phenyl)-5H-pyrrolo[2,3-b]pyrazin-7-yl]-propan-1-one;
2,2-Dimethyl-1-[2-(3-trimethylsilanyl-phenyl)-5H-pyrrolo[2,3-b]pyrazin-7-yl]-propan-1-one;
3-{3-[7-(2,2-Dimethyl-propionyl)-5H-pyrrolo[2,3-b]pyrazin-2-yl]-phenyl}-3-oxo-propionitrile;
1-[2-(3-Iodo-phenyl)-5H-pyrrolo[2,3-b]pyrazin-7-yl]-2,2-dimethyl-propan-1-one;
2,2-Dimethyl-1-{2-[3-(5-trifluoromethyl-2H-pyrazol-3-yl)-phenyl]-5H-pyrrolo[2,3-b]pyrazin-7-yl}-propan-1-one;
1-[2-(3-Cyclohex-1-enyl-phenyl)-5H-pyrrolo[2,3-b]pyrazin-7-yl]-2,2-dimethyl-propan-1-one;
2,2-Dimethyl-1-[2-(3-thiophen-2-yl-phenyl)-5H-pyrrolo[2,3-b]pyrazin-7-yl]-propan-1-one;
1-[2-(3-Cyclopentyl-phenyl)-5H-pyrrolo[2,3-b]pyrazin-7-yl]-2,2-dimethyl-propan-1-one;
1-(2-Biphenyl-4-yl-5H-pyrrolo[2,3-b]pyrazin-7-yl)-2,2-dimethyl-propan-1-one;
1-[2-(3-Imidazol-1-yl-phenyl)-5H-pyrrolo[2,3-b]pyrazin-7-yl]-2,2-dimethyl-propan-1-one;
2,2-Dimethyl-1-{2-[4-(5-methyl-[1,3,4]oxadiazol-2-yl)-phenyl]-5H-pyrrolo[2,3-b]pyrazin-7-yl}-propan-1-one;
2,2-Dimethyl-1-[2-(4-trimethylsilanyl-phenyl)-5H-pyrrolo[2,3-b]pyrazin-7-yl]-propan-1-one;
1-[2-(4-Iodo-phenyl)-5H-pyrrolo[2,3-b]pyrazin-7-yl]-2,2-dimethyl-propan-1-one;
1-{2-[4-(3,5-Dimethyl-isoxazol-4-yl)-phenyl]-5H-pyrrolo[2,3-b]pyrazin-7-yl}-2,2-dimethyl-propan-1-one;
2,2-Dimethyl-1-{2-[4-(2-methyl-2H-pyrazol-3-yl)-phenyl]-5H-pyrrolo[2,3-b]pyrazin-7-yl}-propan-1-one;
1-{2-[4-(3H-Imidazol-4-yl)-phenyl]-5H-pyrrolo[2,3-b]pyrazin-7-yl}-2,2-dimethyl-propan-1-one;
2,2-Dimethyl-1-{2-[4-(2-piperidin-1-yl-ethoxy)-phenyl]-5H-pyrrolo[2,3-b]pyrazin-7-yl}-propan-1-one;
1-{2-[3-(3,3-Dimethyl-pyrrolidin-1-yl)-phenyl]-5H-pyrrolo[2,3-b]pyrazin-7-yl}-2,2-dimethyl-propan-1-one;
3-[7-(2,2-Dimethyl-propionyl)-5H-pyrrolo[2,3-b]pyrazin-2-yl]-N-ethyl-benzamide;
1-{2-[3-((R)-3-Hydroxymethyl-pyrrolidin-1-yl)-phenyl]-5H-pyrrolo[2,3-b]pyrazin-7-yl}-2,2-dimethyl-propan-1-one;
1-{2-[3-((S)-3-Hydroxymethyl-pyrrolidin-1-yl)-phenyl]-5H-pyrrolo[2,3-b]pyrazin-7-yl}-2,2-dimethyl-propan-1-one;
(1-Methyl-cyclohexyl)-{2-[4-(2-piperidin-1-yl-ethoxy)-phenyl]-5H-pyrrolo[2,3b]pyrazin-7-yl}-methanone;
2,2-Dimethyl-1-{2-[3-(1H-pyrazol-4-yl)-phenyl]-5H-pyrrolo[2,3-b]pyrazin-7-yl}-propan-1-one;
1-{2-[3-(3,3-Difluoro-azetidin-1-yl)-phenyl]-5H-pyrrolo[2,3-b]pyrazin-7-yl}-2,2-dimethyl-propan-1-one;
2,2-Dimethyl-1-{2-[3-(2-oxa-6-aza-spiro[3.3]hept-6-yl)-phenyl]-5H-pyrrolo[2,3-b]pyrazin-7-yl}-propan-1-one;
1-{3-[7-(2,2-Dimethyl-propionyl)-5H-pyrrolo[2,3-b]pyrazin-2-yl]-phenyl}pyrrolidin-2-one;
1-{3-[7-(1-Methyl-cyclohexanecarbonyl)-5H-pyrrolo[2,3-b]pyrazin-2-yl]-phenyl}-pyrrolidin-2-one;
(1-Methyl-cyclohexyl)-[2-(3-pyrrol-1-yl-phenyl)-5H-pyrrolo[2,3-b]pyrazin-7-yl]-methanone;
2-[3-(3,3-Dimethyl-pyrrolidin-1-yl)-phenyl]-5H-pyrrolo[2,3-b]pyrazine-7-carboxylic acid isopropylamide;
1-{3-[7-(2,2-Dimethyl-propionyl)-5H-pyrrolo[2,3-b]pyrazin-2-yl]-phenyl}-pyrrolidine-3-carbonitrile;
1-{2-[3-(3-Dimethylamino-azetidin-1-yl)-phenyl]-5H-pyrrolo[2,3-b]pyrazin-7-yl}-2,2-dimethyl-propan-1-one;
2-[3-(3,3-Dimethyl-pyrrolidin-1-yl)-phenyl]-5H-pyrrolo[2,3-b]pyrazine-7-carboxylic acid (3-hydroxy-2,2-dimethyl-propyl)-amide;
1-{2-[3-(3,3-Dimethyl-azetidin-1-yl)-phenyl]-5H-pyrrolo[2,3-b]pyrazin-7-yl}-2,2-dimethyl-propan-1-one;
2-[3-(3,3-Dimethyl-pyrrolidin-1-yl)-phenyl]-5H-pyrrolo[2,3-b]pyrazine-7-carboxylic acid tert-butylamide;

2-[3-(3,3-Dimethyl-pyrrolidin-1-yl)-phenyl]-5H-pyrrolo[2,3-b]pyrazine-7-carboxylic acid (2-methoxy-propyl)-amide;
2-[3-(3,3-Dimethyl-pyrrolidin-1-yl)-phenyl]-5H-pyrrolo[2,3-b]pyrazine-7-carboxylic acid (tetrahydro-pyran-3-yl)-amide;
2-Methyl-2-phenyl-1-[2-(3,4,5-methoxy-phenyl)-5H-pyrrolo[2,3-b]pyrazin-7-yl]-propan-1-one;
1-[2-(3,5-Di-pyrrolidin-1-yl-phenyl)-5H-pyrrolo[2,3-b]pyrazin-7-yl]-2,2-dimethyl-propan-1-one;
3-[7-(2,2-Dimethyl-propionyl)-5H-pyrrolo[2,3-b]pyrazin-2-yl]-benzonitrile;
3-[7-(1-Methyl-cyclohexanecarbonyl)-5H-pyrrolo[2,3-b]pyrazin-2-yl]-benzaldehyde;
(1-Methyl-cyclohexyl)-[2-(3-pyrrolidin-1-ylmethyl-phenyl)-5H-pyrrolo[2,3-b]pyrazin-7-yl]-methanone;
1-{2-[3-(4,5-Dihydro-1H-imidazol-2-ylamino)-phenyl]-5H-pyrrolo[2,3-b]pyrazin-7-yl}-2,2-dimethyl-propan-1-one;
1-{2-[3-(4,5-Dihydro-1H-imidazol-2-yl)-phenyl]-5H-pyrrolo[2,3-b]pyrazin-7-yl}-2,2-dimethyl-propan-1-one;
2,2-Dimethyl-1-{2-[3-(1,4,5,6-tetrahydro-pyrimidin-2-yl)-phenyl]-5H-pyrrolo[2,3-b]pyrazin-7-yl}-propan-1-one;
1-{2-[3-(5,5-Dimethyl-1,4,5,6-tetrahydro-pyrimidin-2-yl)-phenyl]-5H-pyrrolo[2,3-b]pyrazin-7-yl}-2,2-dimethyl-propan-1-one;
1-{2-[3-(4,4-Dimethyl-4,5-dihydro-1H-imidazol-2-yl)-phenyl]-5H-pyrrolo[2,3-b]pyrazin-7-yl}-2,2-dimethyl-propan-1-one;
2,2-Dimethyl-1-{2-[3-(1-methy-4,5-dihydro-1H-imidazol-2-yl)-phenyl]-5H-pyrrolo[2,3-b]pyrazin-7-yl}-propan-1-one;
Pyrrolidin-1-yl-[2-(3,4,5-trimethoxy-phenyl)-5H-pyrrolo[2,3-b]pyrazin-7-yl]-methanone,
(3,3-Dimethyl-pyrrolidin-1-yl)-[2-(3,4,5-trimethoxy-phenyl)-5H-pyrrolo[2,3-b]pyrazin-7-yl]-methanone;
2,2-Dimethyl-1-[2-(3,4,5-trimethoxy-phenyl)-5H-pyrrolo[2,3-b]pyrazin-7-yl]-butan-1-one;
3,3,3-Trifluoro-2-methyl-2-trifluoromethyl-1-[2-(3,4,5-trimethoxy-phenyl)-5H-pyrrolo[2,3-b]pyrazin-7-yl]-propan-1-one;
1-[2-(3-Ethylamino-phenyl)-5H-pyrrolo[2,3-b]pyrazin-7-yl]-2,2-dimethyl-propan-1-one;
1-[2-(3-Diethylamino-phenyl)-5H-pyrrolo[2,3-b]pyrazin-7-yl]-2,2-dimethyl-propan-1-one;
1-[2-(3-Amino-phenyl)-5H-pyrrolo[2,3-b]pyrazin-7-yl]-2,2-dimethyl-propan-1-one;
N-{3-[7-(2,2-Dimethyl-propionyl)-5H-pyrrolo[2,3-b]pyrazin-2-yl]-phenyl}-acetamide;
1-{2-[3-(3-Hydroxy-pyrrolidin-1-yl)-phenyl]-5H-pyrrolo[2,3-b]pyrazin-7-yl}-2,2-dimethyl-propan-1-one;
1-{2-[3-(1,1-Dioxo-1λ6-thiomorpholin-4-yl)-phenyl]-5H-pyrrolo[2,3-b]pyrazin-7-yl}-2,2-dimethyl-propan-1-one;
1-[2-(3-Azetidin-1-yl-phenyl)-5H-pyrrolo[2,3-b]pyrazin-7-yl]-2,2-dimethyl-propan-1-one;
2,2-Dimethyl-1-{2-[3-(1-oxo-1λ4-thiomorpholin-4-yl)-phenyl]-5H-pyrrolo[2,3-b]pyrazin-7-yl}-propan-1-one;
2,2-Dimethyl-1-[2-(3-pyrrol-1-yl-phenyl)-5H-pyrrolo[2,3-b]pyrazin-7-yl]-propan-1-one;
1-{2-[3-(2-Methanesulfonyl-ethylamino)-phenyl]-5H-pyrrolo[2,3-b]pyrazin-7-yl}-2,2-dimethyl-propan-1-one;
1-{2-[(3aS,6aR)-3-(Hexahydro-pyrrolo[3,4-c]pyrrol-2-yl)-phenyl]-5H-pyrrolo[2,3-b]pyrazin-7-yl}-2,2-dimethyl-propan-1-one;
1-{2-[3-((S)-2-Hydroxymethyl-pyrrolidin-1-yl)-phenyl]-5H-pyrrolo[2,3-b]pyrazin-7-yl}-2,2-dimethyl-propan-1-one;
1-{2-[3-((R)-2-Hydroxymethyl-pyrrolidin-1-yl)-phenyl]-5H-pyrrolo[2,3-b]pyrazin-7-yl}-2,2-dimethyl-propan-1-one;
N-{3-[7-(2,2-Dimethyl-propionyl)-5H-pyrrolo[2,3-b]pyrazin-2-yl]-phenyl}-methanesulfonamide;
N-(4-{3-[7-(2,2-Dimethyl-propionyl)-5H-pyrrolo[2,3-b]pyrazin-2-yl]-phenylsulfamoyl}-phenyl)-acetamide;
4-Amino-N-{3-[7-(2,2-dimethyl-propionyl)-5H-pyrrolo[2,3-b]pyrazin-2-yl]-phenyl}-benzenesulfonamide;
N-{3-[7-(2,2-Dimethyl-propionyl)-5H-pyrrolo[2,3-b]pyrazin-2-yl]-phenyl}-benzenesulfonamide;
N-(4-{5-[7-(2,2-Dimethyl-propionyl)-5H-pyrrolo[2,3-b]pyrazin-2-yl]-2-methyl-phenylsulfamoyl}-phenyl)-acetamide;
4-Amino-N-{5-[7-(2,2-dimethyl-propionyl)-5H-pyrrolo[2,3-b]pyrazin-2-yl]-2-methyl-phenyl}-benzenesulfonamide;
1-{2-[3-(3-Hydroxy-3-methyl-pyrrolidin-1-yl)-phenyl]-5H-pyrrolo[2,3-b]pyrazin-7-yl}-2,2-dimethyl-propan-1-one;
1-{2-[3-(3-Hydroxy-3-methyl-pyrrolidin-1-yl)-phenyl]-5H-pyrrolo[2,3-b]pyrazin-7-yl}-2,2-dimethyl-propan-1-one;
3-[7-(2,2-Dimethyl-propionyl)-5H-pyrrolo[2,3-b]pyrazin-2-yl]-benzaldehyde;
2,2-Dimethyl-1-[2-(3-pyrrolidin-1-ylmethyl-phenyl)-5H-pyrrolo[2,3-b]pyrazin-7-yl]-propan-1-one;
1-{2-[3-(4-Dimethyl amino-piperidin-1-ylmethyl)-phenyl]-5H-pyrrolo[2,3-b]pyrazin-7-yl}-2,2-dimethyl-propan-1-one;
2,2-Dimethyl-1-{2-[3-(4-methyl-piperazin-1-ylmethyl)-phenyl]-5H-pyrrolo[2,3-b]pyrazin-7-yl}-propan-1-one;
1-[2-(4-Aminomethyl-phenyl)-5H-pyrrolo[2,3-b]pyrazin-7-yl]-2,2-dimethyl-propan-1-one;
2,2-Dimethyl-1-{2-[3-(4-methylsulfanyl-piperidin-1-ylmethyl)-phenyl]-1-5H-pyrrolo[2,3-b]pyrazin-7-yl}-propan-1-one;
1-{2-[3-(3-Hydroxy-pyrrolidin-1-ylmethyl)-phenyl]-5H-pyrrolo[2,3-b]pyrazin-7-yl}-2,2-dimethyl-propan-1-one;
1-{2-[3-((S)-2-Hydroxymethyl-pyrrolidin-1-ylmethyl)-phenyl]-5H-pyrrolo[2,3-b]pyrazin-7-yl}-2,2-dimethyl-propan-1-one;
1-{2-[3-((R)-2-Hydroxymethyl-pyrrolidin-1-ylmethyl)-phenyl]-5H-pyrrolo[2,3-b]pyrazin-7-yl}-2,2-dimethyl-propan-1-one;
(1-{3-[7-(2,2-Dimethyl-propionyl)-5H-pyrrolo[2,3-b]pyrazin-2-yl]-benzyl}-pyrrolidin-3-yl)-carbamic acid tert-butyl ester;
1-[2-(3-{[Bis-(2-hydroxy-ethyl)-amino]-methyl}-phenyl)-5H-pyrrolo[2,3-b]pyrazin-7-yl]-2,2-dimethyl-propan-1-one;
1-[2-(3-{[Ethyl-(4-hydroxy-butyl)-amino]-methyl}-phenyl)-5H-pyrrolo[2,3-b]pyrazin-7-yl]-2,2-dimethyl-propan-1-one;
(S)-1-{3-[7-(2,2-Dimethyl-propionyl)-5H-pyrrolo[2,3-b]pyrazin-2-yl]-benzyl}-pyrrolidine-2-carboxylic acid amide;
(R)-1-{3-[7-(2,2-Dimethyl-propionyl)-5H-pyrrolo[2,3-b]pyrazin-2-yl]-benzyl}-pyrrolidine-2-carboxylic acid amide;
1-{2-[3-(4-Hydroxymethyl-piperidin-1-ylmethyl)-phenyl]-5H-pyrrolo[2,3-b]pyrazin-7-yl}-2,2-dimethyl-propan-1-one;

1-{2-[3-(3-Hydroxymethyl-pyrrolidin-1-ylmethyl)-phenyl]-5H-pyrrolo[2,3-b]pyrazin-7-yl}-2,2-dimethyl-propan-1-one;
1-{2-[3-(3-Amino-pyrrolidin-1-ylmethyl)-phenyl]-5H-pyrrolo[2,3-b]pyrazin-7-yl}-2,2-dimethyl-propan-1-one;
2,2-Dimethyl-1-{2-[3-(3-methylamino-pyrrolidin-1-ylmethyl)-phenyl]-5H-pyrrolo[2,3-b]pyrazin-7-yl}-propan-1-one;
1-{2-[3-(1H-Imidazol-2-yl)-phenyl]-5H-pyrrolo[2,3-b]pyrazin-7-yl}-2,2-dimethyl-propan-1-one,
1-{2-[3-(3-Benzyl-pyrrolidin-1-ylmethyl)-phenyl]-5H-pyrrolo[2,3-b]pyrazin-7-yl}-2,2-dimethyl-propan-1-one;
N-(1-{3-[7-(2,2-Dimethyl-propionyl)-5H-pyrrolo[2,3-b]pyrazin-2-yl]-benzyl}-pyrrolidin-3-yl)-N-methyl-methanesulfonamide;
N-(1-{3-[7-(2,2-Dimethyl-propionyl)-5H-pyrrolo[2,3-b]pyrazin-2-yl]-benzyl}-pyrrolidin-3-yl)-methane-sulfonamide;
4-[7-(2,2-Dimethyl-propionyl)-5H-pyrrolo[2,3-b]pyrazin-2-yl]-2-pyrrolidin-1-yl-benzonitrile;
2,2-Dimethyl-1-{2-[3-(3-methyl-pyrrolidin-1-yl)-phenyl]-5H-pyrrolo[2,3-b]pyrazin-7-yl}-propan-1-one;
1-{2-[3-(3-Methoxymethyl-3-methyl-pyrrolidin-1-yl)-phenyl]-5H-pyrrolo[2,3-b]pyrazin-7-yl}-2,2-dimethyl-propan-1-one;
1-{2-[(1S,5R)-3-(3-Aza-bicyclo[3.1.0]hex-3-yl)-phenyl]-5H-pyrrolo[2,3-b]pyrazin-7-yl}-2,2-dimethyl-propan-1-one;
2,2-Dimethyl-1-[2-(3-piperidin-1-yl-phenyl)-5H-pyrrolo[2,3-b]pyrazin-7-yl]-propan-1-one;
2,2-Dimethyl-1-[2-(3-morpholin-4-yl-phenyl)-5H-pyrrolo[2,3-b]pyrazin-7-yl]-propan-1-one;
1-{2-[3-((1S,5R,6R)-6-Methanesulfonylmethyl-3-aza-bicyclo[3.1.0]hex-3-yl)-phenyl]-5H-pyrrolo[2,3-b]pyrazin-7-yl}-2,2-dimethyl-propan-1-one;
3-[7-(2,2-Dimethyl-propionyl)-5H-pyrrolo[2,3-b]pyrazin-2-yl]-5-pyrrolidin-1-yl-benzonitrile;
3-[7-(2,2-Dimethyl-propionyl)-5H-pyrrolo[2,3-b]pyrazin-2-yl]-N-(2-methanesulfonyl-ethyl)-5-pyrrolidin-1-yl-benzamide;
3-[7-(2,2-Dimethyl-propionyl)-5H-pyrrolo[2,3-b]pyrazin-2-yl]-5-pyrrolidin-1-yl-benzamide;
3-[7-(2,2-Dimethyl-propionyl)-5H-pyrrolo[2,3-b]pyrazin-2-yl]-N-(2-hydroxy-ethyl)-5-pyrrolidin-1-yl-benzamide;
2,2-Dimethyl-1-{2-[3-(4-methyl-piperazine-1-carbonyl)-5-pyrrolidin-1-phenyl]5H-pyrrolo[2,3-b]pyrazin-7-yl}-propan-1-one;
1-{2-[(3aS,6aR)-3-(Hexahydro-cyclopenta[c]pyrrol-2-yl)-phenyl]-5H-pyrrolo[2,3-b]pyrazin-7-yl}-2,2-dimethyl-propan-1-one;
3-[7-(2,2-Dimethyl-propionyl)-5H-pyrrolo[2,3-b]pyrazin-2-yl]-5-pyrrolidin-1-yl-benzoic acid;
3-[7-(2,2-Dimethyl-propionyl)-5H-pyrrolo[2,3-b]pyrazin-2-yl]-5-(3,3-dimethyl-pyrrolidin-1-yl)-benzamide;
2,2-Dimethyl-1-{2-[3-((1S,5R)-1-phenyl-3-aza-bicyclo[3.1.0]hex-3-yl)-phenyl]-5H-pyrrolo[2,3-b]pyrazin-7-yl}-propan-1-one;
1-{2-[3-(3,3-Diethyl-pyrrolidin-1-yl)-phenyl]-5H-pyrrolo[2,3-b]pyrazin-7-yl}-2,2-dimethyl-propan-1-one;
2,2-Dimethyl-1-{2-[3-(4-methyl-piperazin-1-ylmethyl)-5-pyrrolidin-1-yl-phenyl]-5H-pyrrolo[2,3-b]pyrazin-7-yl}-propan-1-one;
1-{2-[3-((1S,5R,6R)-6-Hydroxymethyl-3-aza-bicyclo[3.1.0]hex-3-yl)-phenyl]-5H-pyrrol[2,3-b]pyrazin-7-yl}-2,2-dimethyl-propan-1-one;
{2-[3-(1S,5R,6R)-6-Hydroxymethyl-3-aza-bicyclo[3.1.0]hex-3-yl)-phenyl]-5H-pyrrol[2,3-b]pyrazin-7-yl}-(1-methyl-cyclohexyl)-methanone;
1-{2-[3-((1R,5S,6R)-6-Methoxymethyl-3-aza-bicyclo[3.1.0]hex-3-yl)-phenyl]-5H-pyrrolo[2,3-b]pyrazin-7-yl}-2,2-dimethyl-propan-1-one;
{2-[3-((1R,5S,6R)-6-Hydroxymethyl-3-aza-bicyclo[3.1.0]hex-3-yl)-phenyl]-5H-pyrrolo[2,3-b]pyrazin-7-yl}-(1-methyl-cyclopentyl)-methanone;
1-{2-[3-(4-Hydroxy-piperidin-1-yl)-phenyl]-5H-pyrrolo[2,3-b]pyrazin-7-yl}-2,2-dimethyl-propan-1-one;
1-{2-[3-(4-Hydroxy-4-methyl-piperidin-1-yl)-phenyl]-5H-pyrrolo[2,3-b]pyrazin-7-yl}-2,2-dimethyl-propan-1-one;
1-{2-[3-(3-Hydroxymethyl-3-methyl-pyrrolidin-1-yl)-phenyl]-5H-pyrrolo[2,3-b]pyrazin-7-yl}-2,2-dimethyl-propan-1-one;
N-(1-{3-[7-(2,2-Dimethyl-propionyl)-5H-pyrrolo[2,3-b]pyrazin-2-yl]-phenyl}-3-methyl-pyrrolidin-3-ylmethyl)-acetamide;
N-(1-{3-[7-(2,2-Dimethyl-propionyl)-5H-pyrrolo[2,3-b]pyrazin-2-yl]-phenyl}-3-methyl-pyrrolidin-3-ylmethyl)-methanesulfonamide;
(1-{3-[7-(2,2-Dimethyl-propionyl)-5H-pyrrolo[2,3-b]pyrazin-2-yl]-phenyl}-3-methyl-pyrrolidin-3-ylmethyl)-carbamic acid methyl ester;
2,2-Dimethyl-1-[2-(4-pyrrolidin-1-yl-phenyl)-5H-pyrrolo[2,3-b]pyrazine-7-yl]-2,2-dimethyl-propan-1-one;
1-[2-(3-Dimethylamino-phenyl)-5H-pyrrolo[2,3-b]pyrazin-7-yl]-2,2-dimethyl-propan-1-one;
N-{3-[7-(2,2-Dimethyl-propionyl)-5H-pyrrolo[2,3-b]pyrazin-2-yl]-benzyl}methanesulfonamide;
N-{3-[7-(2,2-Dimethyl-propionyl)-5H-1-pyrrolo[2,3-b]pyrazin-2-yl]-benzyl}-phenyl-methanesulfonamide;
Cyclopropanesulfonic acid 3-[7-(2,2-dimethyl-propionyl)-5H-pyrrolo[2,3-b]pyrazin-2-yl]-benzylamide;
N-{3-[7-(2,2-Dimethyl-propionyl)-5H-pyrrolo[2,3-b]pyrazin-2-yl]-benzyl}-benzenesulfonamide;
N-{4-[7-(2,2-Dimethyl-propionyl)-5H-pyrrolo[2,3-b]pyrazin-2-yl]-benzyl}-C-phenyl-methanesulfonamide;
Cyclopropanesulfonic acid 4-[7-(2,2-dimethyl-propionyl)-5H-pyrrolo[2,3-b]pyrazin-2-yl]-benzylamide;
Propane-1-sulfonic acid 3-[7-(2,2-dimethyl-propionyl)-5H-pyrrolo[2,3-b]pyrazin-2-yl]-benzylamide;
1-{2-[3-(2-tert-Butyl-pyrrolidin-1-ylmethyl)-phenyl]-5H-pyrrolo[2,3-b]pyrazin-7-yl}-2,2-dimethyl-propan-1-one;
1-(2-{3-[(Cyclohexyl-methyl-amino)-methyl]-phenyl}-5H-pyrrolo[2,3-b]pyrazin-7-yl)-2,2-dimethyl-propan-1-one;
1-{2-[3-(3-Dimethylamino-pyrrolidin-1-ylmethyl)-phenyl]-5H-pyrrolo[2,3-b]pyrazin-7-yl}-2,2-dimethyl-propan-1-one;
2,2-Dimethyl-1-{2-[3-((S)-2-methyl-pyrrolidin-1-ylmethyl)-phenyl]-5H-pyrrolo[2,3-b]pyrazin-7-yl}-propan-1-one;
1-{2-[3-(3-Methoxy-pyrrolidin-1-ylmethyl)-phenyl]-5H-pyrrolo[2,3-b]pyrazin-7-yl}-2,2-dimethyl-propan-1-one;
1-(2-{3-[(Cyclopropylmethyl-propyl-amino)-methyl]-phenyl}-5H-pyrrolo[2,3-b]pyrazin-7-yl)-2,2-dimethyl-propan-1-one;
1-{2-[3-((R)-2-Methoxymethyl-pyrrolidin-1-ylmethyl)-phenyl]-5H-pyrrolo[2,3-b]pyrazin-7-yl}-2,2-dimethyl-propan-1-one;
1-(2-{3-[(4,5-Dihydro-1H-imidazol-2-ylamino)-methyl]-phenyl}-5H-pyrrolo[2,3-b]pyrazin-7-yl)-2,2-dimethyl-propan-1-one;

1-{2-[3-(3,3-Dimethyl-pyrrolidin-1-ylmethyl)-phenyl]-5H-pyrrolo[2,3-b]pyrazin-7-yl}-2,2-dimethyl-propan-1-one;
3-(4-{3-[7-(2,2-Dimethyl-propionyl)-5H-pyrrolo[2,3-b]pyrazin-2-yl]-benzyl}-piperazin-1-yl)-3-oxo-propionitrile;
2-(3,4,5-Trimethoxy-phenyl)-5H-pyrrolo[2,3-b]pyrazine-7-carboxylic acid (2-methoxy-1-methyl-ethyl)-amide;
2-Phenyl-1-[2-(3,4,5-trimethoxy-phenyl)-5H-pyrrolo[2,3-b]pyrazin-7-yl]-propan-1-one;
2-(3,4,5-Trimethoxy-phenyl)-5H-pyrrolo[2,3-b]pyrazine-7-carboxylic acid;
2-(3,4,5-Trimethoxy-phenyl)-5H-pyrrolo[2,3-b]pyrazine-7-carboxylic acid (1-acetyl-pyrrolidin-3-ylmethyl)-amide;
2-(3,4,5-Trimethoxy-phenyl)-5H-pyrrolo[2,3-b]pyrazine-7-carboxylic acid (1-ethylcarbamoyl-pyrrolidin-3-ylmethyl)-amide;
2-(3,4,5-Trimethoxy-phenyl)-5H-pyrrolo[2,3-b]pyrazine-7-carboxylic acid (pipeddin-4-ylmethyl)-amide;
2-(3,4,5-Trimethoxy-phenyl)-5H-pyrrolo[2,3-b]pyrazine-7-carboxylic acid (1-acetyl-piperidin-4-ylmethyl)-amide;
1-{2-[3-(3,3-Dimethyl-pyrrolidin-1-yl)-5-(1-methyl-piperidin-4-yloxy)-phenyl]-5H-pyrrolo[2,3-b]pyrazin-7-yl}-2,2-dimethyl-propan-1-one;
2,2-Dimethyl-1-{2-[(3aR,6aS)-3-(tetrahydro-thieno[3,4-c]pyrrol-5-yl)-phenyl]-5H-pyrrolo[2,3-b]pyrazin-7-yl}-1-propan-1-one;
1-{2-[3-((1S,2S)-2-Hydroxy-cyclopentylamino)-phenyl]-5H-pyrrolo[2,3-b]pyrazin-7-yl}-2,2-dimethyl-propan-1-one;
1-(2-{3-[(2-Methanesulfonyl-ethylamino)-methyl]-5-pyrrolidin-1-yl-phenyl}-5H-pyrrolo[2,3-b]pyrazin-7-yl)-2,2-dimethyl-propan-1-one;
1-{2-[3-(3,3-Dimethyl-azetidin-1-yl)-phenyl]-5H-pyrrolo[2,3-b]pyrazin-7-yl}-2,2-dimethyl-propan-1-one;
1-{2-[3-(3-Aminomethyl-3-methyl-pyrrolidin-1-yl)-phenyl]-5H-pyrrolo[2,3-b]pyrazin-7-yl}-2,2-dimethyl-propan-1-one;
1-{2-[3-((3aR,6aS)-2,2-Dioxo-hexahydro-2λ6-thieno[3,4-c]pyrrol-5-yl)-phenyl]-5H-pyrrolo[2,3-b]pyrazin-7-yl}-2,2-dimethyl-propan-1-one,
2,2-Dimethyl-1-{2-[3-(3aR,6aS)-2-oxo-hexahydro-2λ4-thieno[3,4-c]pyrrol-5-yl)-phenyl]-5H-pyrrol[2,3-b]pyrazin-7-yl}-propan-1-one;
2-Oxo-2,3-dihydro-benzooxazole-6-sulfonic acid {6-[7-(2,2-dimethyl-propionyl)-5H-pyrrolo[2,3-b]pyrazin-2-yl]-1H-indol-4-yl}-amide;
2-Methyl-2-phenyl-1-[2-(3,4,5-trimethoxy-phenyl)-5H-pyrrolo[2,3-b]pyrazin-7-yl]-propan-1-one;
1-{2-[3-(2-Amino-1,1-dimethyl-ethylamino)-phenyl]-5H-pyrrolo[2,3-b]pyrazin-7-yl}-2,2-dimethyl-propan-1-one;
1H-Indazole-5-sulfonic acid {6-[7-(2,2-dimethyl-propionyl)-5H-pyrrolo[2,3-b]pyrazin-2-yl]-1H-indol-4-yl}-amide;
(4-{3-[7-(2,2-Dimethyl-propionyl)-5H-pyrrolo[2,3-b]pyrazin-2-yl]-phenyl}-piperazin-1-yl)-acetic acid;
4-Amino-3-chloro-N-{6-[7-(2,2-dimethyl-propionyl)-5H-pyrrolo[2,3-b]pyrazin-2-yl]-1H-indol-4-yl}-benzenesulfonamide;
1-{2-[3-(2-Methoxy-2-methyl-propylamino)-phenyl]-5H-pyrrolo[2,3-b]pyrazin-7-yl}-2,2-dimethyl-propan-1-one;
2-[3-(3,3-Dimethyl-pyrrolidin-1-yl)-phenyl]-5H-pyrrolo[2,3-b]pyrazine-7-carboxylic acid tert-butylamide;
3,3-Dimethyl-4-oxo-4-[2-(3,4,5-trimethoxy-phenyl)-5H-pyrrolo[2,3-b]pyrazin-7-yl]-butyronitrile;
1-{2-[3-(3-Hydroxy-azetidin-1-yl)-phenyl]-5H-pyrrolo[2,3-b]pyrazin-7-yl}-2,2-dimethyl-propan-1-one;
1-[2-(3-Methanesulfonyl methoxy-5-pyrrolidin-1-yl-phenyl)-5H-pyrrolo[2,3-b]pyrazin-7-yl]-2,2-dimethyl-propan-1-one;
N-{6-[7-(2,2-Dimethyl-propionyl)-5H-pyrrolo[2,3-b]pyrazin-2-yl]-1H-indol-4-yl}-3-methoxy-benzenesulfonamide;
2-[3-(3,3-Dimethyl-pyrrolidin-1-yl)-phenyl]-5H-pyrrolo[2,3-b]pyrazine-7-carboxylic acid (2-methoxy-propyl)-amide;
(1-{3-[7-(2,2-Dimethyl-propionyl)-5H-pyrrolo[2,3-b]pyrazin-2-yl]-phenyl}-4,4-dimethyl-pyrrolidin-3-yl)-carbamic acid ethyl ester;
3-Methyl-3-[2-(3,4,5-trimethoxy-phenyl)-5H-pyrrolo[2,3-b]pyrazine-7-carbonyl]-cyclopentanone;
2-[3-(3,3-Dimethyl-pyrrolidin-1-yl)-phenyl]-5H-pyrrolo[2,3-b]pyrazine-7-carboxylic acid(tetrahydro-pyran-3-yl)-amide;
4-(4-Hydroxy-piperidin-1-yl)-2,2-dimethyl-1-[2-(3,4,5-trimethoxy-phenyl)-5H-pyrrolo[2,3b]pyrazin-7-yl]-butan-1-one;
4-[(2-Hydroxy-ethyl)-methyl-amino]-2,2-dimethyl-1-[2-(3,4,5-trimethoxy-phenyl)-5H-pyrrolo[2,3-b]pyrazin-7-yl]-butan-1-one;
2,2-Dimethyl-1-{2-[3-(tetrahydro-pyran-4-ylamino)-phenyl]-5H-pyrrolo[2,3-b]pyrazin-7-yl}-propan-1-one;
3-Amino-N-{6-[7-(2,2-dimethyl-propionyl)-5H-pyrrolo[2,3-b]pyrazin-2-yl]-1H-indol-4-yl}-benzenesulfonamide;
2-[3-(3,3-Dimethyl-pyrrolidin-1-yl)-phenyl]-5H-pyrrolo[2,3-b]pyrazine-7-carboxylic acid ((S)-2-hydroxy-1,2-dimethyl-propyl)-amide;
1-[2-(3-Fluoro-phenyl)-5H-pyrrolo[2,3-b]pyrazin-7-yl]-2,2-dimethyl-propan-1-one;
(3-Hydroxy-1-methyl-cyclopentyl)-[2-(3,4,5-trimethoxy-phenyl)-5H-pyrrolo[2,3-b]pyrazin-7-yl]-methanone;
4-Amino-N-{6-[7-(2,2-dimethyl-propionyl)-5H-pyrrolo[2,3-b]pyrazin-2-yl]-1H-indol-4-yl}-3-fluoro-benzenesulfonamide;
2-{4-Methyl-4-[2-(3,4,5-trimethoxy-phenyl)-5H-pyrrolo[2,3-b]pyrazine-7-carbonyl-piperidin]-1-yl}-acetamide;
1-{4-Methyl-4-[2-(3,4,5-trimethoxy-phenyl)-5H-pyrrolo[2,3-b]pyrazine-7-carbonyl]-piperidin-1-yl}-ethanone;
6-Oxo-1,6-dihydro-pyridine-3-sulfonic acid {6-[7-(2,2-dimethyl-propionyl)-5H-pyrrolo[2,3-b]pyrazin-2-yl]-1H-indol-4-yl}-amide;
4-Amino-N-{6-[7-(2,2-dimethyl-propionyl)-5H-pyrrolo[2,3-b]pyrazin-2-yl]-1H-indol-4-yl}-3-trifluoromethyl-benzenesulfonamide;
1-{2-[3-(3,3-Dimethyl-pyrrolidin-1-yl)-5-(3-methanesulfonyl-propoxy)-phenyl]-5H-pyrrolo[2,3-b]pyrazin-7-yl}-2,2-dimethyl-propan-1-one;
N-{6-[7-(2,2-Dimethyl-propionyl)-5H-pyrrolo[2,3-b]pyrazin-2-yl]-1H-indol-4-yl}-4-hydroxy-benzenesulfonamide;
((1S,3S)-3-Hydroxy-1-methyl-cyclopentyl)-[2-(3,4,5-trimethoxy-phenyl)-5H-pyrrolo[2,3-b]pyrazin-7-yl]-methanone;
1-{2-[3-(2-Aza-bicyclo[2.1.1]hex-2-yl)-phenyl]-5H-pyrrolo[2,3-b]pyrazin-7-yl}-2,2-dimethyl-propan-1-one;
((1S,2R)-1,2-Dimethyl-cyclopentyl)-[2-(3-pyrrolidin-1-yl-phenyl)-5H-pyrrolo[2,3-b]pyrazin-7-yl]-methanone;
1-{2-[3-(3,3-Dimethyl-pyrrolidin-1-yl)-5-(2-hydroxy-propoxy)-phenyl]-5H-pyrrolo[2,3-b]pyrazin-7-yl}-2,2-dimethyl-propan-1-one;
1-{2-[3-(4,5-Dihydro-1H-imidazol-2-ylamino)-5-(3,3-dimethyl-pyrrolidin-1-yl)-phenyl]-5H-pyrrolo[2,3-b]pyrazin-7-yl}-2,2-dim ethyl-propan-1-one;

2-[3-(3,3-Dimethyl-pyrrolidin-1-yl)-phenyl]-5H-pyrrolo[2,3-b]pyrazine-7-carboxylic acid phenylamide;
2-[3-(3,3-Dimethyl-pyrrolidin-1-yl)-phenyl]-5H-pyrrolo[2,3-b]pyrazine-7-carboxylic acid (2-hydroxy-1,1-dimethyl-ethyl)-amide;
2,2-Dimethyl-1-[2-(3-methylsulfanyl-5-pyrrolidin-1-yl-phenyl)-5H-pyrrolo[2,3-b]pyrazin-7-yl]-propan-1-one;
1-[2-(3-Methanesulfinyl-5-pyrrolidin-1-yl-phenyl)-5H-pyrrolo[2,3-b]pyrazin-7-yl]-2,2-dimethyl-propan-1-one;
1-[2-(3-Methanesulfonyl-5-pyrrolidin-1-yl-phenyl)-5H-pyrrolo[2,3-b]pyrazin-7-yl]-2,2-dimethyl-propan-1-one;
2,2-Dimethyl-1-{2-[3-(3-pyridin-4-yl-pyrrolidin-1-yl)-phenyl]-5H-pyrrolo[2,3-b]pyrazin-7-yl}-propan-1-one;
2,2-Dimethyl-1-{2-[3-(3-pyridin-2-yl-pyrrolidin-1-yl)-phenyl]-5H-pyrrolo[2,3-b]pyrazin-7-yl}-propan-1-one;
1-{2-[3-(1,7-Diaza-spiro[4.4]non-7-yl)-phenyl]-5H-pyrrolo[2,3-b]pyrazin-7-yl}-2,2-dimethyl-propan-1-one;
2,2-Dimethyl-1-{2-[3-(3-pyridin-3-yl-pyrrolidin-1-yl)-phenyl]-5H-pyrrolo[2,3-b]pyrazin-7-yl}-propan-1-one;
{4-Methyl-4-[2-(3,4,5-trimethoxy-phenyl)-5H-pyrrolo[2,3-b]pyrazine-7-carbonyl]-piperidin-1-yl}-acetonitrile;
2,2-Dimethyl-3-methylsulfanyl-1-[2-(3,4,5-trimethoxy-phenyl)-5H-pyrrolo[2,3-b]pyrazin-7-yl]-propan-1-one;
3-Methanesulfonyl-2,2-dimethyl-1-[2-(3,4,5-trimethoxy-phenyl)-5H-pyrrolo[2,3-b]pyrazin-7-yl]-propan-1-one;
2-[3-(2-Dimethylamino-ethoxy)-5-(3,3-dimethyl-pyrrolidin-1-yl)-phenyl]-5H-pyrrolo[2,3-b]pyrazine-7-carboxylic acid (3-hydroxy-2,2-dimethyl-propyl)-amide;
1-[2-(3-tert-Butylamino-phenyl)-5H-pyrrolo[2,3-b]pyrazin-7-yl]-2,2-dimethyl-propan-1-one; and
1-(2-{3-[3-(2,3-Dihydroxy-propyl)-3-methyl-pyrrolidin-1-yl]-phenyl}-5H-pyrrolo[2,3-b]pyrazin-7-yl)-2,2-dimethyl-propan-1-one.

42. A compound of Formula I

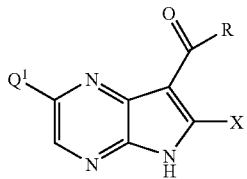

I wherein:
R is $R^1$, $R^2$, $R^3$, or $R^4$;
  $R^1$ is lower alkyl, lower alkoxy, phenyl, benzyl, heteroaryl, cycloalkyl, heterocycloalkyl, or cycloalkyl alkylene, optionally substituted with one or more $R^{1a}$;
  $R^{1a}$ is $R^{1b}$ or $R^{1c}$;
    each $R^{1b}$ is independently halogen, oxo, hydroxy, or —CN;
    each $R^{1c}$ is independently —C(=O)O($R^{1f}$), —C(=O)($R^{1e}$), —C(=O)CH$_2$($R^{1e}$), —S($R^{1f}$), —S(O)$_2$($R^{1f}$), —N($R^{1f}$)S(O)$_2$($R^{1f}$), —S(=O)($R^{1f}$), lower alkyl, lower alkoxy, amino, amido, lower haloalkyl, phenyl, heteroaryl, cycloalkyl, heterocycloalkyl, cycloalkyloxy, or heterocycloalkyloxy optionally substituted with one or more $R^{1d}$;
      each $R^{1d}$ is independently halogen, hydroxy, lower alkyl, lower alkoxy, lower hydroxyalkyl, amino, amido, cyano, or lower haloalkyl;
      each $R^{1e}$ is independently H, lower alkyl, lower alkoxy, —CN, lower haloalkyl, phenyl, heteroaryl, cycloalkyl, or heterocycloalkyl;
      $R^{1f}$ is independently H, lower alkyl, lower haloalkyl, lower alkenyl, phenyl, heteroaryl, cycloalkyl, or heterocycloalkyl;
$R^2$ is N($R^{2a}$)$_2$;
  each $R^{2a}$ is independently H or $R^{2b}$;
    each $R^{2b}$ is independently lower alkyl, lower alkoxy, phenyl, heteroaryl, cycloalkyl, heterocycloalkyl, or heterocycloalkyl alkylene, optionally substituted with one or more $R^{2c}$;
    $R^{2c}$ is $R^{2d}$ or $R^{2e}$;
      each $R^{2d}$ is independently halogen, oxo, or hydroxy;
      each $R^{2e}$ is independently —N($R^{2g}$)$_2$, —C(=O)($R^{2g}$), —C(=O)O($R^{2g}$), —C(=O)N($R^{2g}$)$_2$, —N($R^{2g}$)C(=O)($R^{2g}$), —S(=O)$_2$($R^{2g}$), —S(O)$_2$N($R^{2g}$)$_2$, lower alkyl, lower alkoxy, lower haloalkyl, phenyl, heteroaryl, heteroaryloxy, cycloalkyl, or heterocycloalkyl, optionally substituted with one or more $R^{2f}$;
        each $R^{2f}$ is independently H, halogen, lower alkyl, lower alkoxy, or lower haloalkyl;
        each $R^{2g}$ is independently H, lower alkyl, lower alkoxy, lower haloalkyl, or phenyl;
$R^3$ is —C(=O)$R^{3a}$,
  $R^{3a}$ is lower alkyl, lower alkoxy, phenyl, or N($R^{3b}$)$_2$;
  each $R^{3b}$ is independently H or lower alkyl;
$R^4$ is —O($R^{4a}$);
  $R^{4a}$ is H or $R^{4b}$;
    $R^{4b}$ is lower alkyl, phenyl, benzyl, lower haloalkyl, cycloalkyl, heterocycloalkyl, heteroaryl, optionally substituted with one or more $R^{4c}$;
      each $R^{4c}$ is independently halogen, hydroxy, lower alkyl, lower haloalkyl, or lower alkoxy;
$Q^1$ is phenyl, optionally substituted with one or more $Q^{1a}$,
  each $Q^{1a}$ is independently $Q^{1b}$ or $Q^{1c}$,
    each $Q^{1b}$ is independently halogen, hydroxy, —CN, —S($Q^{1e}$), —S(O)$_2$($Q^{1e}$), or —S(=O)($Q^{1e}$);
    each $Q^{1c}$ is independently $Q^{1d}$ or $Q^{1e}$;
      each $Q^{1d}$ is independently —O($Q^{1e}$), —S(=O)$_2$($Q^{1e}$), —C(=O)N($Q^{1e}$)$_2$, —S(=O)($Q^{1e}$), —N($Q^{1e}$)S(=O)$_2$($Q^{1e}$), —C(=O)($Q^{1e}$), —C(=O)O($Q^{1e}$), —N($Q^{1e}$)C(=O)($Q^{1e}$), —N($Q^{1e}$)C(=O)O($Q^{1e}$), —Si($Q^{1e}$)$_3$, or —N($Q^{1e}$)C(=O)N($Q^{1e}$)$_2$;
      each $Q^{1e}$ is independently H or $Q^{1e'}$;
        each $Q^{1e'}$ is independently lower alkenyl, phenyl, lower haloalkyl, lower thioalkyl, cycloalkyl, cycloalkenyl, heterocycloalkyl, heterocycloalkyl alkylene, or heteroaryl, optionally substituted with one or more $Q^{1f}$;
        each $Q^{1f}$ is independently $Q^{1g}$ or $Q^{1h}$;
        each $Q^{1g}$ is independently halogen, hydroxy, oxo, —(C($Q^{1h}$)$_2$)$_m$S(O)$_2$($Q^{1h}$), —(C($Q^{1h}$)$_2$)$_m$N($Q^{1h}$)(C($Q^{1h}$)$_2$)$_m$S(O)$_2$($Q^{1h}$), —(C($Q^{1h}$)$_2$)$_m$N($Q^{1h}$)$_2$, —(C($Q^{1h}$)$_2$)$_m$C(=O)($Q^{1h}$), or —N($Q^{1h}$)C(=O)($Q^{1h}$);
        each m is independently 0, 1, or 2;
        each $Q^{1h}$ is independently $Q^{1i}$ or $Q^{1j}$;
        each $Q^{1i}$ is independently H or hydroxy;
        each $Q^{1j}$ is independently lower alkyl, lower haloalkyl, lower alkoxy, lower thioalkyl, cyano, amino, phenyl, benzyl, cycloalkyl, heterocycloalkyl, or heteroaryl, optionally substituted with one or more $Q^{1k}$;
        each $Q^{1k}$ is independently halogen, hydroxy, lower alkyl, lower haloalkyl, lower hydroxyalkyl, amino, lower thioalkyl, lower alkoxy, or cyano;

X is $X^1$ or $X^2$;

$X^1$ is H, halogen, or hydroxy;

$X^2$ is lower alkyl, lower alkoxy, lower haloalkyl, phenyl, cycloalkyl, heterocycloalkyl, or heteroaryl, optionally substituted with one or more $X^{2'}$;

each $X^{2'}$ is independently hydroxy, halogen, lower alkyl, lower alkoxy, lower haloalkyl, cycloalkyl, heterocycloalkyl, or heteroaryl;

or a pharmaceutically acceptable salt thereof.

* * * * *

UNITED STATES PATENT AND TRADEMARK OFFICE
CERTIFICATE OF CORRECTION

PATENT NO. : 8,008,298 B2
APPLICATION NO. : 12/378977
DATED : August 30, 2011
INVENTOR(S) : Bamberg et al.

It is certified that error appears in the above-identified patent and that said Letters Patent is hereby corrected as shown below:

Claim 1, column 560, line 49, delete "–C(=O)(Q$^{1e}$)"
and insert -- –C(=O)N(Q$^{1e}$)$_2$, –C(=O)(Q$^{1e}$), --

Claim 1, column 560, line 50, at the beginning of the line insert -- –N --

Claim 1, column 560, line 52, delete "or" and insert -- H or --

Claim 6, column 561, line 6, delete "Q$^{1c}$ is Q$^{1d}$, Q$^{1d}$ is Q$^{1d}$"
and insert -- Q$^{1c}$ is Q$^{1d}$, Q$^{1d}$ is --

Claim 6, column 561, line 7, delete "–O(Q$^{1e}$), Q$^{1e}$" and insert -- –O(Q$^{1e}$), Q$^{1e}$ --

Claim 9, column 561, line 11, delete "pyrrolidine"

Claim 27, column 561, line 39, delete "20" and insert -- 25 --

Claim 34, column 561, line 51, delete "Q$^{1e}$ is Q$^{1e}$, Q$^{1e}$,"
and insert -- Q$^{1c}$ is Q$^{1e}$, Q$^{1e}$ is Q$^{1e'}$, --

Claim 34, column 561, line 52, delete "(Q$^{1e}$" and insert -- Q$^{1e'}$ --

Claim 41, column 562, line 59, delete "(2-[([2" and insert -- (2-{[2 --

Claim 41, column 563, line 2, delete "acid(1S,2R)" and insert -- acid ((1S,2R) --

Claim 41, column 565, line 17, delete "tea-butyl" and insert -- tert-butyl --

Claim 41, column 567, line 50, at the end of the line, delete "non-7-yl))-"
and insert -- non-7-yl)- --

Signed and Sealed this
Eighth Day of November, 2011

David J. Kappos
*Director of the United States Patent and Trademark Office*

CERTIFICATE OF CORRECTION (continued)
U.S. Pat. No. 8,008,298 B2

Claim 41, column 567, line 59, delete "2,2-Dimethyl-1-[2-"
and insert -- 2,2-Dimethyl-1-{2- --

Claim 41, column 567, line 61, delete "-7-yl]" and insert -- -7-yl} --

Claim 41, column 568, line 2, delete "phenyl}1,5" and insert -- phenyl}-1,5 --

Claim 41, column 569, line 27, delete "5H-1-pyrrolo" and insert -- 5H-pyrrolo --

Claim 41, column 571, line 54 delete "pyrrolo pyrazin"
and insert -- pyrrolo[2,3-b]pyrazin --

Claim 41, column 572, line 38, delete "1{-2-" and insert -- 1-{2- --

Claim 41, column 575, line 7, delete "(3,4,5-methoxy-phenyl)"
and insert -- (3,4,5-trimethoxy-phenyl) --

Claim 41, column 577, line 48, delete "1-phenyl]" and insert -- 1-yl-phenyl] --

Claim 41, column 578, line 1, delete "{2-[3-(1S,5R,6R)"
and insert -- (2-[3-((1S,5R,6R) --

Claim 41, column 578, line 28, delete "-2,2-dimethyl"

Claim 41, column 578, line 33, delete "5H-1-pyrrolo" and insert -- 5H-pyrrolo --

Claim 41, column 578, line 34, delete "-phenyl" and insert -- -C-phenyl --

Claim 41, column 579, line 20, delete "(pipeddin" and insert -- (piperidin --

Claim 42, column 582, line 2, delete "heteroatyl" and insert -- heteroaryl --